(12) United States Patent
Yednock et al.

(10) Patent No.: US 7,605,166 B2
(45) Date of Patent: *Oct. 20, 2009

(54) METHODS AND COMPOSITIONS FOR TREATING RHEUMATOID ARTHRITIS

(75) Inventors: Theodore A. Yednock, Forest Knolls, CA (US); Stephen B. Freedman, San Francisco, CA (US); Ivan Lieberburg, Berkeley, CA (US); Michael A. Pleiss, Sunnyvale, CA (US); Andrei W. Konradi, San Francisco, CA (US); George Shopp, South San Francisco, CA (US); Elizabeth Messersmith, El Cerrito, CA (US)

(73) Assignee: Elan Pharmaceuticals Inc., South San Francisco, CA (US)

( * ) Notice: Subject to any disclaimer, the term of this patent is extended or adjusted under 35 U.S.C. 154(b) by 464 days.

This patent is subject to a terminal disclaimer.

(21) Appl. No.: 10/875,282

(22) Filed: Jun. 25, 2004

(65) Prior Publication Data

US 2005/0065192 A1 Mar. 24, 2005

Related U.S. Application Data

(60) Provisional application No. 60/482,211, filed on Jun. 25, 2003.

(51) Int. Cl.
*A61K 31/24* (2006.01)
*A61K 31/255* (2006.01)
*A61K 31/195* (2006.01)
*C07D 239/50* (2006.01)
*C07C 69/75* (2006.01)
*C07C 229/36* (2006.01)
*C07C 229/40* (2006.01)

(52) U.S. Cl. .................. 514/275; 514/533; 514/534; 514/561; 514/518; 544/297; 560/1; 562/561

(58) Field of Classification Search .............. 514/275, 514/533, 534
See application file for complete search history.

(56) References Cited

U.S. PATENT DOCUMENTS

| | | | |
|---|---|---|---|
| 6,270,766 B1 | 8/2001 | Feldman et al. | |
| 6,489,300 B1 | 12/2002 | Thorsett et al. | |
| 6,953,802 B2* | 10/2005 | Konradi et al. | 514/256 |
| 7,008,949 B2* | 3/2006 | Konradi et al. | 514/275 |
| 7,135,477 B2* | 11/2006 | Konradi et al. | 514/275 |
| 2002/0198172 A1 | 12/2002 | Sandage, Jr. et al. | |
| 2004/0142954 A1* | 7/2004 | Konradi et al. | 514/275 |

FOREIGN PATENT DOCUMENTS

| | | | |
|---|---|---|---|
| GB | 1080503 | * | 8/1967 |
| WO | 97/18838 A1 | | 5/1997 |
| WO | WO00/43372 | * | 7/2000 |
| WO | WO 03/072040 | | 9/2003 |

OTHER PUBLICATIONS

Kraan et al., "Modulation of Inflammation and Metalloproteinase Expression in Synovial Tissue by Leflunomide and Methotrexate in Patients with Active Rheumatoid Arthritis" Arthritis and Rheumatism (2000) vol. 43, No. 8, pp. 1820-1830.*
The Merck Manual of Diagnosis and Therapy, seventeenth edition, published 199 by Merck Research Laboratories, ed. by Beers and Berkow, p. 419.*
Barbadillo et al., "Anti-integrin immunotherapy in rheumatoid arthritis: protective effect of anti-α4 antibody in adjuvant arthritis," *Springer Semin Immunopathol.*, 1995, pp. 427-436, vol. 16, No. 4, Springer-Verlag.
Barbadillo et al., "Anti-VLA4 mAb prevents adjuvant arthritis in Lewis rats," *Arthr. Rheuma.*, 1993, vol. 36, No. 95.
Issekutz et al., "Monocyte Migration to Arthritis in the Rat Utilizes both CD11/CD18 and Very Late Activation Antigen 4 Integrin Mechanisms," *J. Exp. Med.*, Mar. 1995, pp. 1197-1203, vol. 181, No. 3, The Rockefeller University Press.
Seiffge, "Protective Effects of Monoclonal Antibody to VLA-4 on Leukocyte Adhesion and Course of Disease in Adjuvant Arthritis in Rats," *The Journal of Rheumatology*, 1996, pp. 2086-2091, vol. 23, No. 12.
Zeidler et al., "Therapeutic Effects of Antibodies Against Adhesion Molecules in Murine Collagen Type II-Induced Arthritis," *Autoimmunity*, 1995, pp. 245-252, VI. 21, No. 4, Amsterdam B.V., The Netherlands.
FDA Alert for Healthcare Professionals, "Natalizumab (marketed as Tysabri)," Apr. 8, 2005.
International Search Report dated Oct. 3, 2005 (1 pp.).
Sobera L A, et al., "Natalizumab. Treatment of IBD, treatment of multiple sclerosis: AN 100226, AntegrenTM" Drugs of the Future, Barcelona, ES, vol. 25, No. 9, Sep. 9, 2000, pp. 917-921.
Tilley J W: "VLA-4 Antagonists" Expert Opinion on Therapeutic Patents, Ashley Publications, GB, vol. 12, No. 7, 2002, pp. 991-1008.
Maini R, et al., "Infliximab (chimeric anti-tumor necrosis factor alpha monoclonal antibody) versus placebo in rheumatoid arthritis patients receiving comcomitant methotrexate: a tamdomised phase III trial" Lancet the, Lancet Limited. London, GB, vol. 354, No. 9194, Dec. 4, 1999, pp. 1932-1939.

* cited by examiner

*Primary Examiner*—Shaojia Anna Jiang
*Assistant Examiner*—Eric S Olson
(74) *Attorney, Agent, or Firm*—Crowell & Moring LLP

(57) ABSTRACT

This application relates to methods and compositions for treating rheumatoid arthritis by administering a combination therapy comprising methotrexate and an antibody to alpha-4 integrin or an immunologically active antigen binding fragment in therapeutically effective amounts. The application also relates generally to methods and compositions for treating rheumatoid arthritis by administering a combination therapy comprising methotrexate and small molecule alpha-4 integrin antagonist that inhibits the alpha-4 integrin (α4 integrin) interaction with VCAM-1. The invention further relates to methods of preparing the compounds and methods of using the compounds and compositions.

19 Claims, 11 Drawing Sheets

Figure 1:
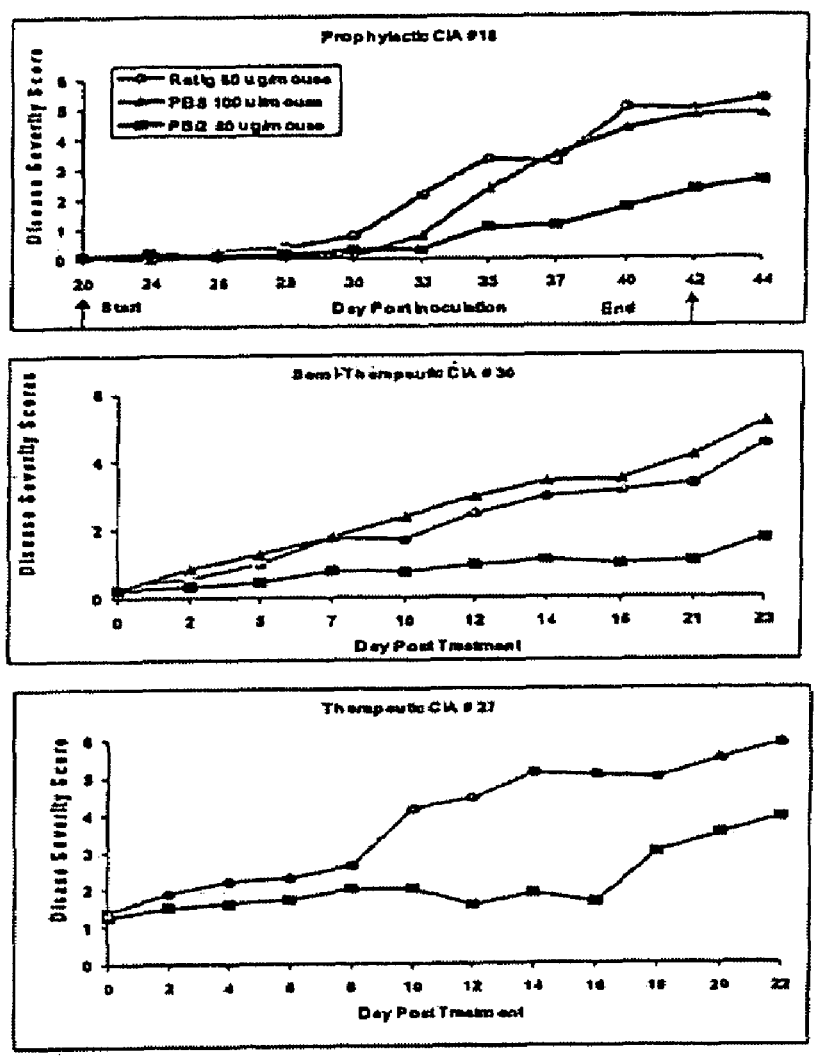

B.2) Effects of anti-VLA-4, VCAM-1, LPAM-1 antibodies on CIA, Semi-Therapeutic

SEQUENCE LISTING

```
<160> NUMBER OF SEQ ID NOS: 24

<210> SEQ ID NO 1
<211> LENGTH: 360
<212> TYPE: DNA
<213> ORGANISM: Homo sapiens
<220> FEATURE:
<221> NAME/KEY: CDS
<222> LOCATION: (1)...(360)

<400> SEQUENCE: 1 gtc aaa ctg cag cag tct ggg gca gag ctt gtg aag cca ggg gcc tca        48
Val Lys Leu Gln Gln Ser Gly Ala Glu Leu Val Lys Pro Gly Ala Ser
1               5                   10                  15 gtc aag ttg ttc tgc aca gct tct ggc ttc aac att aaa gac acc tat        96
Val Lys Leu Phe Cys Thr Ala Ser Gly Phe Asn Ile Lys Asp Thr Tyr
            20                  25                  30 atg cac tgg gtg aag cag agg cct caa cag ggc ctg gag tgg att gga       144
Met His Trp Val Lys Gln Arg Pro Gln Gln Gly Leu Glu Trp Ile Gly
        35                  40                  45 agg att gat cct gcg agt ggc gat act aaa tat gac ccg aag ttc cag       192
Arg Ile Asp Pro Ala Ser Gly Asp Thr Lys Tyr Asp Pro Lys Phe Gln
```

```
gtc aag gcc act att aca gcg gac acg tcc tcc aac aca gcc tgg ctg      240
Val Lys Ala Thr Ile Thr Ala Asp Thr Ser Ser Asn Thr Ala Trp Leu
 65                  70                  75                  80 cag ctc agc agc ctg aca tct gag gac act gcc gtc tac tac tgt gca      288
Gln Leu Ser Ser Leu Thr Ser Glu Asp Thr Ala Val Tyr Tyr Cys Ala
             85                  90                  95 gac gga atg tgg gta tca acg gga tat gct ctg gac ttc tgg ggc caa      336
Asp Gly Met Trp Val Ser Thr Gly Tyr Ala Leu Asp Phe Trp Gly Gln
        100                 105                 110 ggg acc acg gtc acc gtc tcc tca                                      360
Gly Thr Thr Val Thr Val Ser Ser
        115                 120
```

<210> SEQ ID NO 2
<211> LENGTH: 120
<212> TYPE: PRT
<213> ORGANISM: Homo sapiens

<400> SEQUENCE: 2

```
Val Lys Leu Gln Gln Ser Gly Ala Glu Leu Val Lys Pro Gly Ala Ser
 1               5                  10                  15

Val Lys Leu Phe Cys Thr Ala Ser Gly Phe Asn Ile Lys Asp Thr Tyr
            20                  25                  30

Met His Trp Val Lys Gln Arg Pro Gln Gln Gly Leu Glu Trp Ile Gly
         35                 40                  45

Arg Ile Asp Pro Ala Ser Gly Asp Thr Lys Tyr Asp Pro Lys Phe Gln
 50                  55                  60

Val Lys Ala Thr Ile Thr Ala Asp Thr Ser Ser Asn Thr Ala Trp Leu
 65                  70                  75                  80

Gln Leu Ser Ser Leu Thr Ser Glu Asp Thr Ala Val Tyr Tyr Cys Ala
             85                  90                  95

Asp Gly Met Trp Val Ser Thr Gly Tyr Ala Leu Asp Phe Trp Gly Gln
        100                 105                 110

Gly Thr Thr Val Thr Val Ser Ser
        115                 120
```

<210> SEQ ID NO 3
<211> LENGTH: 318
<212> TYPE: DNA
<213> ORGANISM: Homo sapiens
<220> FEATURE:
<221> NAME/KEY: CDS
<222> LOCATION: (1)...(318)

<400> SEQUENCE: 3

```
agt att gtg atg acc cag act ccc aaa ttc ctg ctt gtt tca gca gga       48
Ser Ile Val Met Thr Gln Thr Pro Lys Phe Leu Leu Val Ser Ala Gly
 1               5                  10                  15 gac agg gtt acc ata acc tgc aag gcc agt cag agt gtg act aat gat       96
Asp Arg Val Thr Ile Thr Cys Lys Ala Ser Gln Ser Val Thr Asn Asp
            20                  25                  30 gta gct tgg tac caa cag aag cca ggg cag tct cct aaa ctg ctg ata      144
Val Ala Trp Tyr Gln Gln Lys Pro Gly Gln Ser Pro Lys Leu Leu Ile
         35                 40                  45 tat tat gca tcc aat cgc tac act gga gtc cct gat cgc ttc act ggc      192
Tyr Tyr Ala Ser Asn Arg Tyr Thr Gly Val Pro Asp Arg Phe Thr Gly
 50                  55                  60 agt gga tat ggg acg gat ttc act ttc acc atc agc act gtg cag gct      240
Ser Gly Tyr Gly Thr Asp Phe Thr Phe Thr Ile Ser Thr Val Gln Ala
```

```
                65                  70                  75                  80
gaa gac ctg gca gtt tat ttc tgt cag cag gat tat agc tct ccg tac         288
Glu Asp Leu Ala Val Tyr Phe Cys Gln Gln Asp Tyr Ser Ser Pro Tyr
                85                  90                  95 acg ttc gga ggg ggg acc aag ctg gag atc                                 318
Thr Phe Gly Gly Gly Thr Lys Leu Glu Ile
            100                 105

<210> SEQ ID NO 4
<211> LENGTH: 106
<212> TYPE: PRT
<213> ORGANISM: Homo sapiens

<400> SEQUENCE: 4

Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Thr Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
 50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile
            100                 105

<210> SEQ ID NO 5
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 5 atg gac tgg acc tgg agg gtc ttc tgc ttg ctg gct gta gca cca ggt         48
Met Asp Trp Thr Trp Arg Val Phe Cys Leu Leu Ala Val Ala Pro Gly
 1               5                  10                  15 gcc cac tcc cag gtc caa ctg cag gag tcc ggt gct gaa gtt gtt aaa         96
Ala His Ser Gln Val Gln Leu Gln Glu Ser Gly Ala Glu Val Val Lys
                20                  25                  30 ccg ggt tcc tcc gtt aaa ctg tcc tgc aaa gct tcc ggt ttc aac atc        144
Pro Gly Ser Ser Val Lys Leu Ser Cys Lys Ala Ser Gly Phe Asn Ile
            35                  40                  45 aaa gac acc tac atg cac tgg gtt aaa cag cgt ccg ggt cag ggt ctg        192
Lys Asp Thr Tyr Met His Trp Val Lys Gln Arg Pro Gly Gln Gly Leu
 50                  55                  60 gaa tgg atc ggt cgt atc gac ccg gct tcc ggt gac acc aaa tac gac        240
Glu Trp Ile Gly Arg Ile Asp Pro Ala Ser Gly Asp Thr Lys Tyr Asp
65                  70                  75                  80 ccg aaa ttc cag gtt aaa gct acc atc acc gct gac gaa tcc acc tcc        288
Pro Lys Phe Gln Val Lys Ala Thr Ile Thr Ala Asp Glu Ser Thr Ser
                85                  90                  95 acc gct tac ctg gaa ctg tcc tcc ctg cgt tcc gaa gac acc gct gtt        336
Thr Ala Tyr Leu Glu Leu Ser Ser Leu Arg Ser Glu Asp Thr Ala Val
            100                 105                 110 tac tac tgc gct gac ggt atg tgg gtt tcc acc ggt tac gct ctg gac        384
Tyr Tyr Cys Ala Asp Gly Met Trp Val Ser Thr Gly Tyr Ala Leu Asp
```

```
Tyr Tyr Cys Ala Asp Gly Met Trp Val Ser Thr Gly Tyr Ala Leu Asp
            115                 120                 125 ttc tgg ggt cag ggt acc acg gtc acc gtc tcc tca ggt gag tcc        429
Phe Trp Gly Gln Gly Thr Thr Val Thr Val Ser Ser Gly Glu Ser
        130                 135                 140

<210> SEQ ID NO 6
<211> LENGTH: 143
<212> TYPE: PRT
<213> ORGANISM: Homo sapiens

<400> SEQUENCE: 6

Met Asp Trp Thr Trp Arg Val Phe Cys Leu Leu Ala Val Ala Pro Gly
1               5                   10                  15

Ala His Ser Gln Val Gln Leu Gln Glu Ser Gly Ala Glu Val Val Lys
            20                  25                  30

Pro Gly Ser Ser Val Lys Leu Ser Cys Lys Ala Ser Gly Phe Asn Ile
        35                  40                  45

Lys Asp Thr Tyr Met His Trp Val Lys Gln Arg Pro Gly Gln Gly Leu
    50                  55                  60

Glu Trp Ile Gly Arg Ile Asp Pro Ala Ser Gly Asp Thr Lys Tyr Asp
65                  70                  75                  80

Pro Lys Phe Gln Val Lys Ala Thr Ile Thr Ala Asp Glu Ser Thr Ser
                85                  90                  95

Thr Ala Tyr Leu Glu Leu Ser Ser Leu Arg Ser Glu Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140

<210> SEQ ID NO 7
<211> LENGTH: 383
<212> TYPE: DNA
<213> ORGANISM: Homo sapiens
<220> FEATURE:
<221> NAME/KEY: CDS
<222> LOCATION: (1)...(375)

<400> SEQUENCE: 7 atg ggt tgg tcc tgc atc atc ctg ttc ctg gtt gct acc gct acc ggt        48
Met Gly Trp Ser Cys Ile Ile Leu Phe Leu Val Ala Thr Ala Thr Gly
1               5                   10                  15 gtt cac tcc atc gtt atg acc cag tcc ccg gac tcc ctg gct gtt tcc        96
Val His Ser Ile Val Met Thr Gln Ser Pro Asp Ser Leu Ala Val Ser
            20                  25                  30 ctg ggt gaa cgt gtt acc atc aac tgc aaa gct tcc cag tcc gtt acc       144
Leu Gly Glu Arg Val Thr Ile Asn Cys Lys Ala Ser Gln Ser Val Thr
        35                  40                  45 aac gac gtt gct tgg tac cag cag aaa ccg ggt cag tcc ccg aaa ctg       192
Asn Asp Val Ala Trp Tyr Gln Gln Lys Pro Gly Gln Ser Pro Lys Leu
    50                  55                  60 ctg atc tac tac gct tcc aac cgt tac acc ggt gtt ccg gac cgt ttc       240
Leu Ile Tyr Tyr Ala Ser Asn Arg Tyr Thr Gly Val Pro Asp Arg Phe
65                  70                  75                  80 tcc ggt tcc ggt tac ggt acc gac ttc acc ttc acc atc tcc tcc gtt       288
Ser Gly Ser Gly Tyr Gly Thr Asp Phe Thr Phe Thr Ile Ser Ser Val
                85                  90                  95 cag gct gaa gac gtt gct gtt tac tac tgc cag cag gac tac tcc tcc       336
Gln Ala Glu Asp Val Ala Val Tyr Tyr Cys Gln Gln Asp Tyr Ser Ser
```

```
                    100              105              110
ccg tac acc ttc ggt ggt ggt acc aaa ctg gag atc taa ggatcctc           383
Pro Tyr Thr Phe Gly Gly Gly Thr Lys Leu Glu Ile *
            115              120
```

<210> SEQ ID NO 8
<211> LENGTH: 124
<212> TYPE: PRT
<213> ORGANISM: Homo sapiens

<400> SEQUENCE: 8

```
Met Gly Trp Ser Cys Ile Ile Leu Phe Leu Val Ala Thr Ala Thr Gly
 1               5                  10                  15

Val His Ser Ile Val Met Thr Gln Ser Pro Asp Ser Leu Ala Val Ser
            20                  25                  30

Leu Gly Glu Arg Val Thr Ile Asn Cys Lys Ala Ser Gln Ser Val Thr
        35                  40                  45

Asn Asp Val Ala Trp Tyr Gln Gln Lys Pro Gly Gln Ser Pro Lys Leu
    50                  55                  60

Leu Ile Tyr Tyr Ala Ser Asn Arg Tyr Thr Gly Val Pro Asp Arg Phe
65                  70                  75                  80

Ser Gly Ser Gly Tyr Gly Thr Asp Phe Thr Phe Thr Ile Ser Ser Val
                85                  90                  95

Gln Ala Glu Asp Val Ala Val Tyr Tyr Cys Gln Gln Asp Tyr Ser Ser
            100                 105                 110

Pro Tyr Thr Phe Gly Gly Gly Thr Lys Leu Glu Ile
        115                 120
```

<210> SEQ ID NO 9
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 9

```
atg gac tgg acc tgg agg gtc ttc tgc ttg ctg gct gta gca cca ggt        48
Met Asp Trp Thr Trp Arg Val Phe Cys Leu Leu Ala Val Ala Pro Gly
 1               5                  10                  15 gcc cac tcc cag gtc caa ctg cag gag agc ggt cca ggt ctt gtg aga        96
Ala His Ser Gln Val Gln Leu Gln Glu Ser Gly Pro Gly Leu Val Arg
            20                  25                  30 cct agc cag acc ctg agc ctg acc tgc acc gtg tct ggc ttc aac att       144
Pro Ser Gln Thr Leu Ser Leu Thr Cys Thr Val Ser Gly Phe Asn Ile
        35                  40                  45 aaa gac acc tat atg cac tgg gtg aga cag cca cct gga cga ggt ctt       192
Lys Asp Thr Tyr Met His Trp Val Arg Gln Pro Pro Gly Arg Gly Leu
    50                  55                  60 gag tgg att gga agg att gat cct gcg agt ggc gat act aaa tat gac       240
Glu Trp Ile Gly Arg Ile Asp Pro Ala Ser Gly Asp Thr Lys Tyr Asp
65                  70                  75                  80 ccg aag ttc cag gtc aga gtg aca atg ctg gta gac acc agc agc aac       288
Pro Lys Phe Gln Val Arg Val Thr Met Leu Val Asp Thr Ser Ser Asn
                85                  90                  95 aca gcc tgg ctg aga ctc agc agc gtg aca gcc gcc gac acc gcg gtc       336
Thr Ala Trp Leu Arg Leu Ser Ser Val Thr Ala Ala Asp Thr Ala Val
            100                 105                 110 tat tat tgt gca gac gga atg tgg gta tca acg gga tat gct ctg gac       384
Tyr Tyr Cys Ala Asp Gly Met Trp Val Ser Thr Gly Tyr Ala Leu Asp
```

```
            115                 120                 125
ttc tgg ggc caa ggg acc acg gtc acc gtc tcc tca ggt gag tcc      429
Phe Trp Gly Gln Gly Thr Thr Val Thr Val Ser Ser Gly Glu Ser
    130                 135                 140

<210> SEQ ID NO 10
<211> LENGTH: 143
<212> TYPE: PRT
<213> ORGANISM: Homo sapiens

<400> SEQUENCE: 10

Met Asp Trp Thr Trp Arg Val Phe Cys Leu Leu Ala Val Ala Pro Gly
  1               5                  10                  15

Ala His Ser Gln Val Gln Leu Gln Glu Ser Gly Pro Gly Leu Val Arg
             20                  25                  30

Pro Ser Gln Thr Leu Ser Leu Thr Cys Thr Val Ser Gly Phe Asn Ile
         35                  40                  45

Lys Asp Thr Tyr Met His Trp Val Arg Gln Pro Pro Gly Arg Gly Leu
     50                  55                  60

Glu Trp Ile Gly Arg Ile Asp Pro Ala Ser Gly Asp Thr Lys Tyr Asp
 65                  70                  75                  80

Pro Lys Phe Gln Val Arg Val Thr Met Leu Val Asp Thr Ser Ser Asn
                 85                  90                  95

Thr Ala Trp Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140

<210> SEQ ID NO 11
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 11 atg gac tgg acc tgg agg gtc ttc tgc ttg ctg gct gta gca cca ggt       48
Met Asp Trp Thr Trp Arg Val Phe Cys Leu Leu Ala Val Ala Pro Gly
  1               5                  10                  15 gcc cac tcc cag gtc caa ctg cag gag agc ggt cca ggt ctt gtg aga       96
Ala His Ser Gln Val Gln Leu Gln Glu Ser Gly Pro Gly Leu Val Arg
             20                  25                  30 cct agc cag acc ctg agc ctg acc tgc acc gtg tct ggc ttc aac att      144
Pro Ser Gln Thr Leu Ser Leu Thr Cys Thr Val Ser Gly Phe Asn Ile
         35                  40                  45 aaa gac acc tat atg cac tgg gtg aga cag cca cct gga cga ggt ctt      192
Lys Asp Thr Tyr Met His Trp Val Arg Gln Pro Pro Gly Arg Gly Leu
     50                  55                  60 gag tgg att gga agg att gat cct gcg agt ggc gat act aaa tat gac      240
Glu Trp Ile Gly Arg Ile Asp Pro Ala Ser Gly Asp Thr Lys Tyr Asp
 65                  70                  75                  80 ccg aag ttc cag gtc aaa gcg aca att acg gca gac acc agc agc aac      288
Pro Lys Phe Gln Val Lys Ala Thr Ile Thr Ala Asp Thr Ser Ser Asn
                 85                  90                  95 cag ttc agc ctg aga ctc agc agc gtg aca gcc gcc gac acc gcg gtc      336
Gln Phe Ser Leu Arg Leu Ser Ser Val Thr Ala Ala Asp Thr Ala Val
            100                 105                 110
```

```
tat tat tgt gca gac gga atg tgg gta tca acg gga tat gct ctg gac      384
Tyr Tyr Cys Ala Asp Gly Met Trp Val Ser Thr Gly Tyr Ala Leu Asp
        115                 120                 125 ttc tgg ggc caa ggg acc acg gtc acc gtc tcc tca ggt gag tcc          429
Phe Trp Gly Gln Gly Thr Thr Val Thr Val Ser Ser Gly Glu Ser
130                 135                 140

<210> SEQ ID NO 12
<211> LENGTH: 143
<212> TYPE: PRT
<213> ORGANISM: Homo sapiens

<400> SEQUENCE: 12

Met Asp Trp Thr Trp Arg Val Phe Cys Leu Leu Ala Val Ala Pro Gly
1               5                   10                  15

Ala His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Phe Asn Ile
        35                  40                  45

Lys Asp Thr Tyr Met His Trp Val Arg Gln Pro Pro Gly Arg Gly Leu
50                  55                  60

Glu Trp Ile Gly Arg Ile Asp Pro Ala Ser Gly Asp Thr Lys Tyr Asp
65                  70                  75                  80

Pro Lys Phe Gln Val Lys Ala Thr Ile Thr Ala Asp Thr Ser Ser Asn
                85                  90                  95

Gln Phe Ser Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140

<210> SEQ ID NO 13
<211> LENGTH: 372
<212> TYPE: DNA
<213> ORGANISM: Homo sapiens
<220> FEATURE:
<221> NAME/KEY: CDS
<222> LOCATION: (1)...(372)

<400> SEQUENCE: 13 cag gtc caa ctg cag gag agc ggt cca ggt ctt gtg aga cct agc cag      48
Gln Val Gln Leu Gln Glu Ser Gly Pro Gly Leu Val Arg Pro Ser Gln
1               5                   10                  15 acc ctg agc ctg acc tgc acc gtg tct ggc ttc aac att aaa gac acc      96
Thr Leu Ser Leu Thr Cys Thr Val Ser Gly Phe Asn Ile Lys Asp Thr
            20                  25                  30 tat atg cac tgg gtg aga cag cca cct gga cga ggt ctt gag tgg att     144
Tyr Met His Trp Val Arg Gln Pro Pro Gly Arg Gly Leu Glu Trp Ile
        35                  40                  45 gga agg att gat cct gcg agt ggc gat act aaa tat gac ccg aag ttc     192
Gly Arg Ile Asp Pro Ala Ser Gly Asp Thr Lys Tyr Asp Pro Lys Phe
    50                  55                  60 cag gtc aga gtg aca atg ctg gta gac acc agc agc aac cag ttc agc     240
Gln Val Arg Val Thr Met Leu Val Asp Thr Ser Ser Asn Gln Phe Ser
65                  70                  75                  80 ctg aga ctc agc agc gtg aca tct gag gac acc gcg gtc tat tat tgt     288
Leu Arg Leu Ser Ser Val Thr Ser Glu Asp Thr Ala Val Tyr Tyr Cys
                85                  90                  95
```

```
gca gac gga atg tgg gta tca acg gga tat gct ctg gac ttc tgg ggc      336
Ala Asp Gly Met Trp Val Ser Thr Gly Tyr Ala Leu Asp Phe Trp Gly
            100                 105                 110 caa ggg acc acg gtc acc gtc tcc tca ggt gag tcc                      372
Gln Gly Thr Thr Val Thr Val Ser Ser Gly Glu Ser
        115                 120

<210> SEQ ID NO 14
<211> LENGTH: 124
<212> TYPE: PRT
<213> ORGANISM: Homo sapiens

<400> SEQUENCE: 14

Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Asn Ile Lys Asp Thr
            20                  25                  30

Tyr Met His Trp Val Arg Gln Pro Gly Arg Gly Leu Glu Trp Ile
        35                  40                  45

Gly Arg Ile Asp Pro Ala Ser Gly Asp Thr Lys Tyr Asp Pro Lys Phe
 50                  55                  60

Gln Val Arg Val Thr Met Leu Val Asp Thr Ser Ser Asn Gln Phe Ser
65                   70                  75                  80

Leu Arg Leu Ser Ser Val Thr Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Thr Val Thr Val Ser Ser Gly Glu Ser
        115                 120

<210> SEQ ID NO 15
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 15 atg gac tgg acc tgg agg gtc ttc tgc ttg ctg gct gta gca cca ggt      48
Met Asp Trp Thr Trp Arg Val Phe Cys Leu Leu Ala Val Ala Pro Gly
 1               5                  10                  15 gcc cac tcc cag gtc caa ctg cag gag agc ggt cca ggt ctt gtg aga      96
Ala His Ser Gln Val Gln Leu Gln Glu Ser Gly Pro Gly Leu Val Arg
            20                  25                  30 cct agc cag acc ctg agc ctg acc tgc acc gtg tct ggc ttc aac att      144
Pro Ser Gln Thr Leu Ser Leu Thr Cys Thr Val Ser Gly Phe Asn Ile
        35                  40                  45 aaa gac acc tat atg cac tgg gtg aaa cag cga cct gga cga ggt ctt      192
Lys Asp Thr Tyr Met His Trp Val Lys Gln Arg Pro Gly Arg Gly Leu
 50                  55                  60 gag tgg att gga agg att gat cct gcg agt ggc gat act aaa tat gac      240
Glu Trp Ile Gly Arg Ile Asp Pro Ala Ser Gly Asp Thr Lys Tyr Asp
65                   70                  75                  80 ccg aag ttc cag gtc aga gtg aca atg ctg gta gac acc agc agc aac      288
Pro Lys Phe Gln Val Arg Val Thr Met Leu Val Asp Thr Ser Ser Asn
                85                  90                  95 cag ttc agc ctg aga ctc agc agc gtg aca gcc gcc gac acc gcg gtc      336
Gln Phe Ser Leu Arg Leu Ser Ser Val Thr Ala Ala Asp Thr Ala Val
            100                 105                 110
```

```
tat tat tgt gca gac gga atg tgg gta tca acg gga tat gct ctg gac        384
Tyr Tyr Cys Ala Asp Gly Met Trp Val Ser Thr Gly Tyr Ala Leu Asp
        115                 120                 125 ttc tgg ggc caa ggg acc acg gtc acc gtc tcc tca ggt gag tcc            429
Phe Trp Gly Gln Gly Thr Thr Val Thr Val Ser Ser Gly Glu Ser
130                 135                 140

<210> SEQ ID NO 16
<211> LENGTH: 143
<212> TYPE: PRT
<213> ORGANISM: Homo sapiens

<400> SEQUENCE: 16

Met Asp Trp Thr Trp Arg Val Phe Cys Leu Leu Ala Val Ala Pro Gly
1               5                   10                  15

Ala His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Phe Asn Ile
        35                  40                  45

Lys Asp Thr Tyr Met His Trp Val Lys Gln Arg Pro Gly Arg Gly Leu
    50                  55                  60

Glu Trp Ile Gly Arg Ile Asp Pro Ala Ser Gly Asp Thr Lys Tyr Asp
65                  70                  75                  80

Pro Lys Phe Gln Val Arg Val Thr Met Leu Val Asp Thr Ser Ser Asn
                85                  90                  95

Gln Phe Ser Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140

<210> SEQ ID NO 17
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 17 atg gac tgg acc tgg agg gtc ttc tgc ttg ctg gct gta gca cca ggt         48
Met Asp Trp Thr Trp Arg Val Phe Cys Leu Leu Ala Val Ala Pro Gly
1               5                   10                  15 gcc cac tcc cag gtc caa ctg cag gag agc ggt cca ggt ctt gtg aga         96
Ala His Ser Gln Val Gln Leu Gln Glu Ser Gly Pro Gly Leu Val Arg
            20                  25                  30 cct agc cag acc ctg agc ctg acc tgc acc gcg tct ggc ttc aac att        144
Pro Ser Gln Thr Leu Ser Leu Thr Cys Thr Ala Ser Gly Phe Asn Ile
        35                  40                  45 aaa gac acc tat atg cac tgg gtg aga cag cca cct gga cga ggt ctt        192
Lys Asp Thr Tyr Met His Trp Val Arg Gln Pro Pro Gly Arg Gly Leu
    50                  55                  60 gag tgg att gga agg att gat cct gcg agt ggc gat act aaa tat gac        240
Glu Trp Ile Gly Arg Ile Asp Pro Ala Ser Gly Asp Thr Lys Tyr Asp
65                  70                  75                  80 ccg aag ttc cag gtc aga gtg aca atg ctg gta gac acc agc agc aac        288
Pro Lys Phe Gln Val Arg Val Thr Met Leu Val Asp Thr Ser Ser Asn
                85                  90                  95 cag ttc agc ctg aga ctc agc agc gtg aca gcc gcc gac acc gcg gtc        336
```

```
Gln Phe Ser Leu Arg Leu Ser Ser Val Thr Ala Ala Asp Thr Ala Val
            100                 105                 110
tat tat tgt gca gac gga atg tgg gta tca acg gga tat gct ctg gac    384
Tyr Tyr Cys Ala Asp Gly Met Trp Val Ser Thr Gly Tyr Ala Leu Asp
        115                 120                 125
ttc tgg ggc caa ggg acc acg gtc acc gtc tcc tca ggt gag tcc        429
Phe Trp Gly Gln Gly Thr Thr Val Thr Val Ser Ser Gly Glu Ser
    130                 135                 140
```

<210> SEQ ID NO 18
<211> LENGTH: 143
<212> TYPE: PRT
<213> ORGANISM: Homo sapiens

<400> SEQUENCE: 18

```
Met Asp Trp Thr Trp Arg Val Phe Cys Leu Leu Ala Val Ala Pro Gly
  1               5                  10                  15

Ala His Ser Gln Val Gln Leu Gln Glu Ser Gly Pro Gly Leu Val Arg
                 20                  25                  30

Pro Ser Gln Thr Leu Ser Leu Thr Cys Thr Ala Ser Gly Phe Asn Ile
             35                  40                  45

Lys Asp Thr Tyr Met His Trp Val Arg Gln Pro Pro Gly Arg Gly Leu
 50                  55                  60

Glu Trp Ile Gly Arg Ile Asp Pro Ala Ser Gly Asp Thr Lys Tyr Asp
 65                  70                  75                  80

Pro Lys Phe Gln Val Arg Val Thr Met Leu Val Asp Thr Ser Ser Asn
                 85                  90                  95

Gln Phe Ser Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140
```

<210> SEQ ID NO 19
<211> LENGTH: 386
<212> TYPE: DNA
<213> ORGANISM: Homo sapiens
<220> FEATURE:
<221> NAME/KEY: CDS
<222> LOCATION: (1)...(386)

<400> SEQUENCE: 19

```
atg ggt tgg tcc tgc atc atc ctg ttc ctg gtt gct acc gct acc ggt    48
Met Gly Trp Ser Cys Ile Ile Leu Phe Leu Val Ala Thr Ala Thr Gly
  1               5                  10                  15 gtt cac tcc gac atc cag ctg acc cag agc cca agc agc ctg agc gcc    96
Val His Ser Asp Ile Gln Leu Thr Gln Ser Pro Ser Ser Leu Ser Ala
                 20                  25                  30 agc gtg ggt gac aga gtg acc atc acc tgt aag gcc agt cag agt gtg   144
Ser Val Gly Asp Arg Val Thr Ile Thr Cys Lys Ala Ser Gln Ser Val
             35                  40                  45 act aat gat gta gct tgg tac cag cag aag cca ggt aag gct cca aag   192
Thr Asn Asp Val Ala Trp Tyr Gln Gln Lys Pro Gly Lys Ala Pro Lys
 50                  55                  60 ctg ctg atc tac tat gca tcc aat cgc tac act ggt gtg cca agc aga   240
Leu Leu Ile Tyr Tyr Ala Ser Asn Arg Tyr Thr Gly Val Pro Ser Arg
 65                  70                  75                  80 ttc agc ggt agc ggt agc ggt acc gac ttc acc ttc acc atc agc agc   288
Phe Ser Gly Ser Gly Ser Gly Thr Asp Phe Thr Phe Thr Ile Ser Ser
```

```
                        85                  90                  95
ctc cag cca gag gac atc gcc acc tac tac tgc cag cag gat tat agc    336
Leu Gln Pro Glu Asp Ile Ala Thr Tyr Tyr Cys Gln Gln Asp Tyr Ser
                100                 105                 110 tct ccg tac acg ttc ggc caa ggg acc aag gtg gaa atc aaa cgt aag    384
Ser Pro Tyr Thr Phe Gly Gln Gly Thr Lys Val Glu Ile Lys Arg Lys
        115                 120                 125 tg                                                                 386

<210> SEQ ID NO 20
<211> LENGTH: 128
<212> TYPE: PRT
<213> ORGANISM: Homo sapiens

<400> SEQUENCE: 20

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
                20                  25                  30

Ser Val Gly Asp Arg Val Thr Ile Thr Cys Lys Ala Ser Gln Ser Val
            35                  40                  45

Thr Asn Asp Val Ala Trp Tyr Gln Gln Lys Pro Gly Lys Ala Pro Lys
        50                  55                  60

Leu Leu Ile Tyr Tyr Ala Ser Asn Arg Tyr Thr Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Asp Tyr Ser
                100                 105                 110

Ser Pro Tyr Thr Phe Gly Gln Gly Thr Lys Val Glu Ile Lys Arg Lys
        115                 120                 125

<210> SEQ ID NO 21
<211> LENGTH: 386
<212> TYPE: DNA
<213> ORGANISM: Homo sapiens
<220> FEATURE:
<221> NAME/KEY: CDS
<222> LOCATION: (1)...(386)

<400> SEQUENCE: 21 atg ggt tgg tcc tgc atc atc ctg ttc ctg gtt gct acc gct acc ggt    48
Met Gly Trp Ser Cys Ile Ile Leu Phe Leu Val Ala Thr Ala Thr Gly
1               5                   10                  15 gtc cac tcc agc atc gtg atg acc cag agc cca agc agc ctg agc gcc    96
Val His Ser Ser Ile Val Met Thr Gln Ser Pro Ser Ser Leu Ser Ala
                20                  25                  30 agc gtg ggt gac aga gtg acc atc acc tgt aag gcc agt cag agt gtg    144
Ser Val Gly Asp Arg Val Thr Ile Thr Cys Lys Ala Ser Gln Ser Val
            35                  40                  45 act aat gat gta gct tgg tac cag cag aag cca ggt aag gct cca aag    192
Thr Asn Asp Val Ala Trp Tyr Gln Gln Lys Pro Gly Lys Ala Pro Lys
        50                  55                  60 ctg ctg atc tac tat gca tcc aat cgc tac act ggt gtg cca gat aga    240
Leu Leu Ile Tyr Tyr Ala Ser Asn Arg Tyr Thr Gly Val Pro Asp Arg
65                  70                  75                  80 ttc agc ggt agc ggt tat ggt acc gac ttc acc ttc acc atc agc agc    288
Phe Ser Gly Ser Gly Tyr Gly Thr Asp Phe Thr Phe Thr Ile Ser Ser
                85                  90                  95
```

```
ctc cag cca gag gac atc gcc acc tac tac tgc cag cag gat tat agc        336
Leu Gln Pro Glu Asp Ile Ala Thr Tyr Tyr Cys Gln Gln Asp Tyr Ser
        100                 105                 110 tct ccg tac acg ttc ggc caa ggg acc aag gtg gaa atc aaa cgt aag        384
Ser Pro Tyr Thr Phe Gly Gln Gly Thr Lys Val Glu Ile Lys Arg Lys
        115                 120                 125 tg                                                                     386
```

<210> SEQ ID NO 22
<211> LENGTH: 128
<212> TYPE: PRT
<213> ORGANISM: Homo sapiens

<400> SEQUENCE: 22

```
Met Gly Trp Ser Cys Ile Ile Leu Phe Leu Val Ala Thr Ala Thr Gly
 1               5                  10                  15

Val His Ser Ser Ile Val Met Thr Gln Ser Pro Ser Ser Leu Ser Ala
            20                  25                  30

Ser Val Gly Asp Arg Val Thr Ile Thr Cys Lys Ala Ser Gln Ser Val
        35                  40                  45

Thr Asn Asp Val Ala Trp Tyr Gln Gln Lys Pro Gly Lys Ala Pro Lys
    50                  55                  60

Leu Leu Ile Tyr Tyr Ala Ser Asn Arg Tyr Thr Gly Val Pro Asp Arg
65                  70                  75                  80

Phe Ser Gly Ser Gly Tyr Gly Thr Asp Phe Thr Phe Thr Ile Ser Ser
                85                  90                  95

Leu Gln Pro Glu Asp Ile Ala Thr Tyr Tyr Cys Gln Gln Asp Tyr Ser
            100                 105                 110

Ser Pro Tyr Thr Phe Gly Gln Gly Thr Lys Val Glu Ile Lys Arg Lys
        115                 120                 125
```

<210> SEQ ID NO 23
<211> LENGTH: 386
<212> TYPE: DNA
<213> ORGANISM: Homo sapiens
<220> FEATURE:
<221> NAME/KEY: CDS
<222> LOCATION: (1)...(386)

<400> SEQUENCE: 23

```
atg ggt tgg tcc tgc atc atc ctg ttc ctg gtt gct acc gct acc ggt         48
Met Gly Trp Ser Cys Ile Ile Leu Phe Leu Val Ala Thr Ala Thr Gly
 1               5                  10                  15 gtc cac tcc gac atc cag atg acc cag agc cca agc agc ctg agc gcc        96
Val His Ser Asp Ile Gln Met Thr Gln Ser Pro Ser Ser Leu Ser Ala
            20                  25                  30 agc gtg ggt gac aga gtg acc atc acc tgt aag gcc agt cag agt gtg       144
Ser Val Gly Asp Arg Val Thr Ile Thr Cys Lys Ala Ser Gln Ser Val
        35                  40                  45 act aat gat gta gct tgg tac cac cag aag cca ggt aag gct cca aag       192
Thr Asn Asp Val Ala Trp Tyr His Gln Lys Pro Gly Lys Ala Pro Lys
    50                  55                  60 ctg ctg atc tac tat gca tcc aat cgc tac act ggt gtg cca gat aga       240
Leu Leu Ile Tyr Tyr Ala Ser Asn Arg Tyr Thr Gly Val Pro Asp Arg
65                  70                  75                  80 ttc agc ggt agc ggt tat ggt acc gac ttc acc ttc acc atc agc agc       288
Phe Ser Gly Ser Gly Tyr Gly Thr Asp Phe Thr Phe Thr Ile Ser Ser
                85                  90                  95 ctc cag cca gag gac atc gcc acc tac tac tgc cag cag gat tat agc       336
Leu Gln Pro Glu Asp Ile Ala Thr Tyr Tyr Cys Gln Gln Asp Tyr Ser
```

```
                      100              105             110
tct ccg tac acg ttc ggc caa ggg acc aag gtg gaa atc aaa cgt aag        384
Ser Pro Tyr Thr Phe Gly Gln Gly Thr Lys Val Glu Ile Lys Arg Lys
        115              120             125 tg                                                                     386

<210> SEQ ID NO 24
<211> LENGTH: 128
<212> TYPE: PRT
<213> ORGANISM: Homo sapiens

<400> SEQUENCE: 24

Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
                20                  25                  30

Ser Val Gly Asp Arg Val Thr Ile Thr Cys Lys Ala Ser Gln Ser Val
             35                  40                  45

Thr Asn Asp Val Ala Trp Tyr His Gln Lys Pro Gly Lys Ala Pro Lys
 50                  55                  60

Leu Leu Ile Tyr Tyr Ala Ser Asn Arg Tyr Thr Gly Val Pro Asp Arg
65                  70                  75                  80

Phe Ser Gly Ser Gly Tyr Gly Thr Asp Phe Thr Phe Thr Ile Ser Ser
                85                  90                  95

Leu Gln Pro Glu Asp Ile Ala Thr Tyr Tyr Cys Gln Gln Asp Tyr Ser
            100                 105                 110

Ser Pro Tyr Thr Phe Gly Gln Gly Thr Lys Val Glu Ile Lys Arg Lys
        115                 120                 125
```

METHODS AND COMPOSITIONS FOR TREATING RHEUMATOID ARTHRITIS

FIELD OF THE INVENTION

This application relates to methods and compositions for treating rheumatoid arthritis by administering a combination therapy comprising methotrexate and an antibody to alpha-4 integrin or an immunologically active antigen binding fragment in therapeutically effective amounts. The application also relates generally to methods and compositions for treating rheumatoid arthritis by administering a combination therapy comprising methotrexate and small molecule alpha-4 integrin antagonist that inhibits the alpha-4 integrin (α4 integrin) interaction with VCAM-1. The invention further relates to methods of preparing the compounds and methods of using the compounds and compositions.

BACKGROUND OF THE INVENTION

Inflammation

Inflammation is a response of vascularized tissues to infection or injury and is affected by adhesion of leukocytes to the endothelial cells of blood vessels and their infiltration into the surrounding tissues. In normal inflammation, infiltrating leukocytes release toxic mediators to kill invading organisms, phagocytize debris and dead cells, and play a role in tissue repair and the immune response. However, in pathologic inflammation, infiltrating leukocytes are over-responsive and can cause serious or fatal damage. See, e.g., Hickey, *Psychoneuroimmunology II* (Academic Press 1990).

The integrins are a family of cell-surface glycoproteins involved in cell-adhesion, immune cell migration and activation. Alpha-4 (α4) integrin is expressed by all circulating leukocytes except neutrophils, and forms heterodimeric receptors in conjunction with either the beta1 (β1) or beta7 (β7) integrin subunits. Both alpha-4 beta-1 (α4β1) and alpha-4 beta-7 (α4β7) play a role in the migration of leukocytes across the vascular endothelium (Springer et al., *Cell*, 1994 76: 301-14; Butcher et al., *Science*, 1996, 272: 60-6) and contribute to cell activation and survival within the parenchyma (Damle et al., *J. Immunol.*, 1993; 151: 2368-79; Koopman et al., *J. Immunol.*, 1994, 152: 3760-7; Leussink et al., *Acta Neuropathol.*, 2002, 103: 131-136). α4β1 is constitutively expressed on lymphocytes, monocytes, macrophages, mast cells, basophils and eosinophils.

α4β1 (also known as very late antigen-4, VLA-4), binds to vascular cell adhesion molecule-1 (VCAM-1) (Lobb et al., *J. Clin. Invest.*, 1994, 94: 1722-8), which is expressed by the vascular endothelium at many sites of chronic inflammation (Bevilacqua et al., 1993 *Annu. Rev. Immunol.*, 11: 767-804; Postigo et al., 1993 *Res. Immunol.*, 144: 723-35). α4β1 has other ligands, including fibronectin and other extracellular matrix (ECM) components.

Intercellular adhesion mediated by α4β1 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection.

Rheumatoid Arthritis

Rheumatoid arthritis ("RA") is a chronic inflammatory disease that causes pain, swelling, stiffness, and loss of function, primarily the joints. RA is estimated to affect approximately 1 percent of the world's population. In the U.S. alone, an estimated 2.1 million people suffer from the disease. This relatively high frequency suggests a complex etiology and pathogenesis.

The disease process leading to RA begins in the synovium, the membrane that surrounds a joint creating a protective sac. In healthy individuals, the synovium produces synovial fluid that lubricates, nourishes and protects joint tissues. This clear fluid lubricates and nourishes the cartilage and bones inside the joint capsule. In individuals suffering from RA, the immune system, for unknown reasons, attacks the cells inside synovium. Leukocytes infiltrate from the circulation into the synovium causing continuous abnormal inflammation (i.e., synovitis). Consequently, the synovium becomes inflamed, causing warmth, redness, swelling, and pain. The collagen in the cartilage is gradually destroyed, narrowing the joint space and eventually damaging bone. The inflammation causes erosive bone damage in the affected area. During this process, the cells of the synovium grow and divide abnormally, making the normally thin synovium thick and resulting in a joint that is swollen and puffy to the touch. See, e.g., Paul, *Immunology* (3d ed., Raven Press, 1993).

It is believed that bone damage begins during the first year or two that a person has the disease. This is one reason why early diagnosis and treatment are important in the management of RA. As the disease progresses, abnormal synovial cells begin to invade and destroy the cartilage and bone within the joint. The surrounding muscles, ligaments, and tendons that support and stabilize the joint become weak and unable to work normally. RA also causes more generalized bone loss that may lead to osteoporosis, making bones fragile and more prone to fracture. All of these effects cause the pain, impairment and deformities associated with RA.

Although RA almost always develops in the wrists and knuckes, some patients experience the effects of the disease in places other than the joints. For instance, the knees and the ball of the foot are often affected as well. Often, many joints may be involved, and even the spine can be affected. In about 25% of people with RA, inflammation of small blood vessels can cause rheumatoid nodules, or lumps, under the skin. These are bumps under the skin that often form close to the joints. As the disease progresses, fluid may also accumulate, particularly in the ankles. Many patients with RA also develop anemia, or a decrease in the normal number of red blood cells. Other less prevalent effects include neck pain, dry eyes and dry mouth. On rare occasions, patients may also develop inflammation of the-blood vessels, the lining of the lungs, or the sac enclosing the heart.

RA has several special features that differentiate it from other types of arthritis. For example, RA generally occurs in a symmetrical pattern—if one knee or hand is involved, the other one is also. The disease often affects the wrist joints and the finger joints closest to the hand. RA usually first affects the small joints of the hands and feet, but may also involve the wrists, elbows, ankles and knees. It can also affect other parts of the body besides the joints. In addition, patients with the disease may have fatigue, occasional fever, and a general sense of not feeling well (malaise).

Another distinct feature of RA is the variance between individuals. For some, it lasts only a few months or a year or two and subsides without causing any noticeable damage. Other people have mild or moderate disease, with periods of worsening symptoms (flares) and periods in which they feel better (remissions). In severe cases, the disease is chronically active most of the time, lasting for many years, and leading to serious joint damage and disability.

RA encompasses a number of disease subtypes, such as Felty's syndrome, seronegative RA, "classical" RA, progressive and/or relapsing RA, and RA with vasculitis. Some experts classify the disease into type 1 or type 2. Type 1, the less common form, lasts a few months at most and leaves no permanent disability. Type 2 is chronic and lasts for years, sometimes for life.

RA is believed to be one of several "autoimmune" diseases ("auto" means self), so-called because a person's immune system attacks his or her own body tissues. Although much has been learned about the process leading to RA, researchers have yet to uncover all of the factors that lead to this disease. One prevalent theory is that a combination of factors trigger RA, including an abnormal autoimmune response, genetic susceptibility, environmental, biologic factors, hormonal, and reproductive factors. Nonetheless, despite intensive research, the cause of RA remains obscure. See El-Gabalawy et al., ARTHRITIS RES. 4(suppl 3):S297-S301 (2002).

RA occurs across all races and ethnic groups. Although the disease often begins in middle age and occurs with increased frequency in older people, children and young adults may also develop juvenile RA. Like other forms of arthritis, RA exhibits a clear gender bias: approximatley two to three times as many women as men have the disease (Lawrence et al., *Arthritis Rheum.*, 1998, 41:778-799). However, a genetic predisposition has been identified and, in white populations, localized to a pentapeptide in the HLA-DR1 locus of class II histocompatibility genes. Environmental factors may also play a role. Immunologic changes may be initiated by multiple factors.

Prominent immunologic abnormalities that may be important in pathogenesis include immune complexes found in joint fluid cells and in vasculitis. Plasma cells produce antibodies that contribute to these complexes. Lymphocytes that infiltrate the synovial tissue are primarily T helper cells, which can produce pro-inflammatory cytokines. Increased adhesion molecules contribute to inflammatory cell emigration and retention in the synovial tissue.

The onset is usually insidious, with progressive joint involvement, but may be abrupt, with simultaneous inflammation in multiple joints. Tenderness in nearly all inflamed joints and synovial thickening are common. Initial manifestations may occur in any joint.

Stiffness lasting less than 30 minutes on arising in the morning or after prolonged inactivity is common. Subcutaneous rheumatoid nodules are not usually an early manifestation. Visceral nodules, vasculitis causing leg ulcers or mononeuritis multiplex, pleural or pericardial effusions, lymphadenopathy, Felty's syndrome, Sjögren's syndrome, and episcleritis are other manifestations. As many as 75% of patients improve symptomatically with conservative treatment during the first year of disease. However, less than 10% are eventually severely disabled despite full treatment. The disease greatly affects the lives of most RA patients. Complete bed rest is occasionally indicated for a short period during the most active, painful stage of severe disease. In less severe cases, regular rest should be prescribed.

Nonsteroidal anti-inflammatory drugs may provide important symptomatic relief and may be adequate as simple therapy for mild RA, but they do not appear to alter the long-term course of disease. Salicylates, such as aspirin, may be used for treatment.

Gold compounds usually are given in addition to salicylates or other NSAIDs if the latter do not sufficiently relieve pain or suppress active joint inflammation. In some patients, gold may produce clinical remission and decrease the formation of new bony erosions. Parenteral preparations include gold sodium thiomalate or gold thioglucose. Gold should be discontinued when any of the above manifestations appear. Minor toxic manifestations (e.g., mild pruritus, minor rash) may be eliminated by temporarily withholding gold therapy, then resuming it cautiously about 2 wk after symptoms have subsided. However, if toxic symptoms progress, gold should be withheld and the patient given a corticosteroid. A topical corticosteroid or oral prednisone 15 to 20 mg/day in divided doses is given for mild gold dermatitis; larger doses may be needed for hematologic complications. A gold chelating drug, dimercaprol 2.5 mg/kg IM, may be given up to four to six times/day for the first 2 days and bid for 5 to 7 days after a severe gold reaction.

Hydroxychloroquine can also control symptoms of mild or moderately active RA. Toxic effects usually are mild and include dermatitis, myopathy, and generally reversible corneal opacity. However, irreversible retinal degeneration has been reported. Sulfasalazine may also be used for treatment of RA.

Oral penicillamine may have a benefit similar to gold and may be used in some cases if gold fails or produces toxicity in patients with active RA. Side effects requiring discontinuation are more common than with gold and include marrow suppression, proteinuria, nephrosis, other serious toxic effects (eg, myasthenia gravis, pemphigus, Goodpasture's syndrome, polymyositis, a lupuslike syndrome), rash, and a foul taste.

Steroids are the most effective short-term anti-inflammatory drugs. However, their clinical benefit for RA often diminishes with time. Steroids do not predictably prevent the progression of joint destruction. Furthermore, severe rebound follows the withdrawal of corticosteroids in active disease. Contraindications to steroid use include peptic ulcer, hypertension, untreated infections, diabetes mellitus, and glaucoma.

Immunosuppressive drugs are increasingly used in management of severe, active RA. However, major side effects can occur, including liver disease, pneumonitis, bone marrow suppression, and, after long-term use of azathioprine and malignancy.

Whatever may be the actual cause, there is no cure for RA, and although the disease is not fatal, disease complications and symptoms may persist throughout an individual's lifetime, and may even shorten survival by a few years. Affected joints may become deformed, and the performance of even ordinary tasks may be very difficult or impossible.

SUMMARY OF THE INVENTION

Based on the above, new compositions and methods of preventing rheumatoid arthritis and treating the symptoms of rheumatoid arthritis are needed such that patients can have better quality of life.

The invention relates to combination therapies comprising methotrexate and an antibody to alpha-4 integrin or an immunologically active antigen binding fragment thereof or a small molecule alpha-4 integrin antagonist for use in a subject in need thereof. Preferably, the subject is a mammal. More preferably, the mammal is human.

The invention also relates to methods of treating rheumatoid arthritis in a subject in need thereof comprising administering in therapeutically effective amounts, a combination therapy comprising methotrexate and an antibody to alpha-4 integrin or an immunologically active antigen binding fragment thereof or a small molecule alpha-4 integrin antagonist. Preferably, the subject is a mammal. More preferably, the mammal is human.

The invention further relates to regimes for the treatment of rheumatoid arthritis which comprises administering to a subject in need thereof about 2 mg to about 20 mg of methotrexate and a therapeutically effective amount of a methotrexate and an antibody to alpha-4 integrin or an immunologically active antigen binding fragment thereof or a small molecule alpha-4 integrin antagonist. Preferably, the subject is a mammal. More preferably, the mammal is human.

In yet another embodiment, the invention relates to the use of the combination therapies as described herein in the preparation of a medicament for the treatment of rheumatoid arthritis.

These and other objects, advantages, and features of the invention will become apparent to those persons skilled in the art upon reading the details of the methods and formulations as more fully described below.

BRIEF DESCRIPTIONS OF THE DRAWINGS

FIG. 1. FIG. 1 shows the effect of anti-alpha 4-integrin antibody in vivo prophylactically (upper panel), semi-therapeutic dosing (middle panel) and therapeutic dosing (lower panel).

Figure 2:
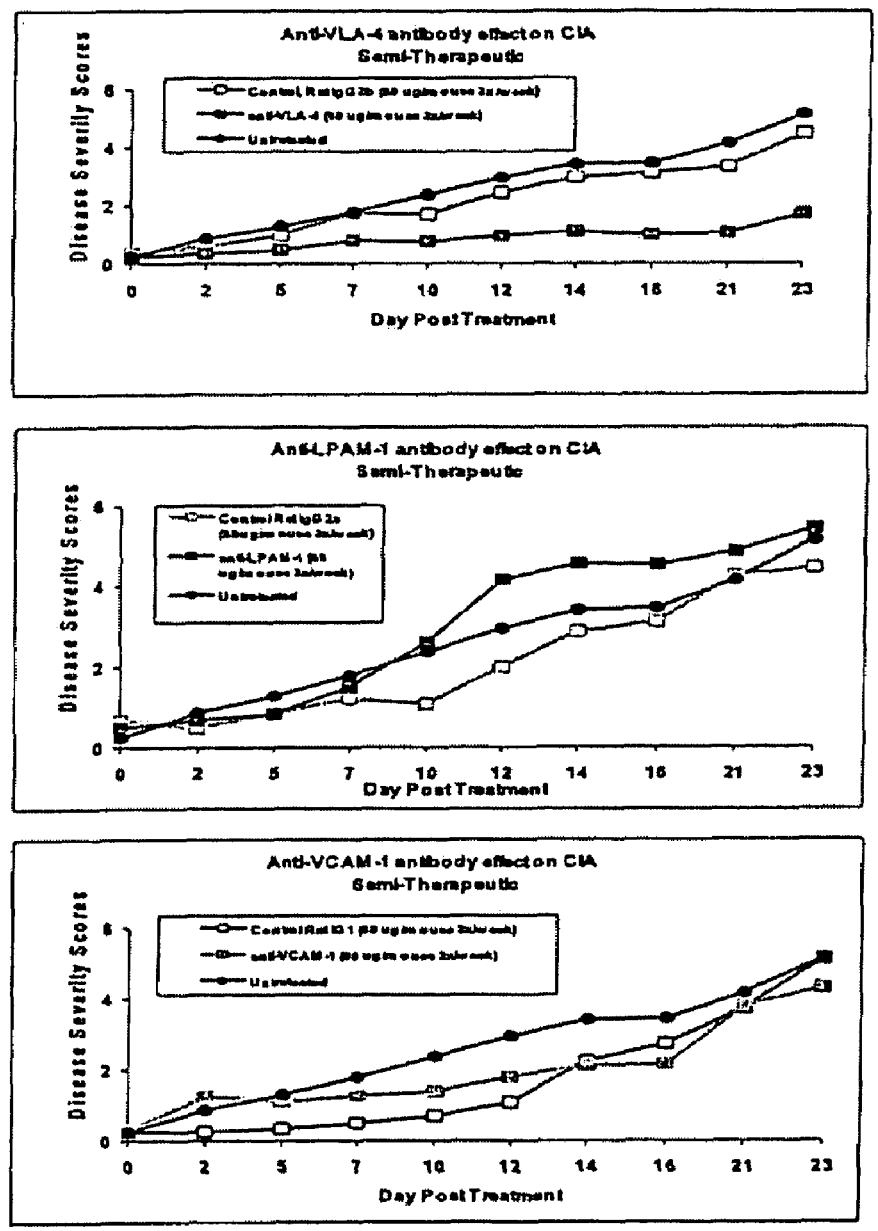

FIG. 2. FIG. 2 shows the effect of anti-alpha4 antibodies (upper panel), anti-α4β7 (LPAM-1) antibodies (middle panel) and anti-VACM-1 antibodies in vivo using CIA models (lower panel).

Figure 3:
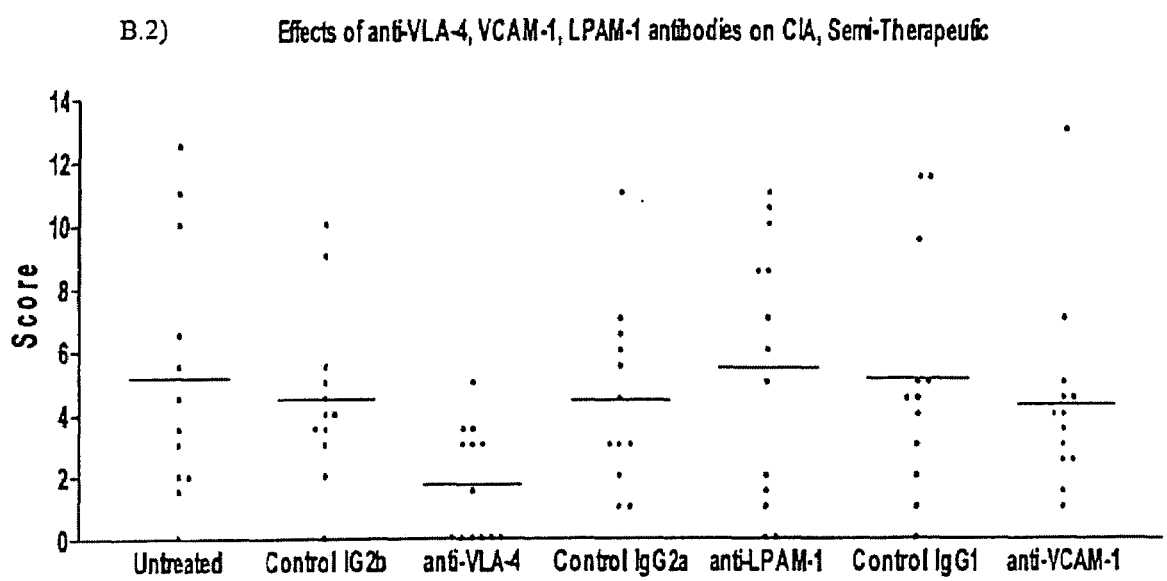

FIG. 3. FIG. 3 shows the effects of anti-VLA-4, anti-VCAM-2 and anti-LPAM-1 antibodies in vivo in CIA models at semi-therapeutic dosing.

Figure 4:
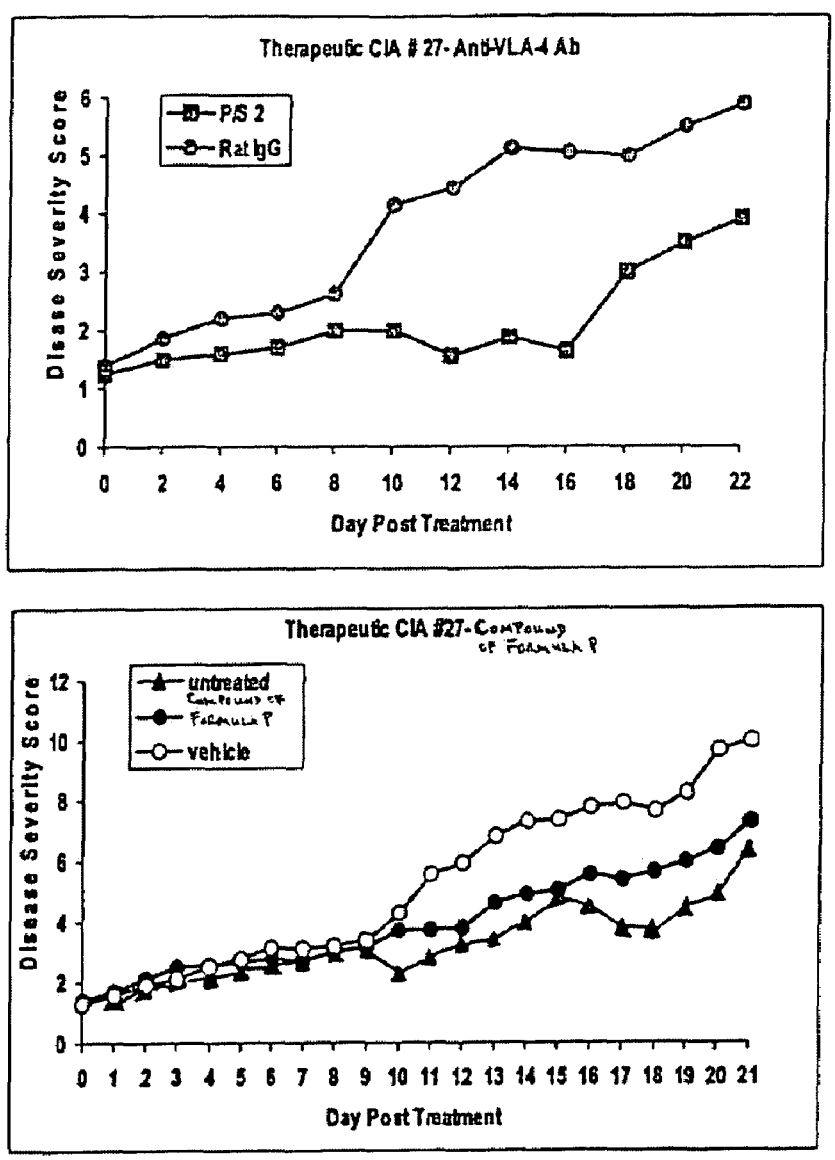

FIG. 4. FIG. 4 shows the effect of anti-VLA-4 antibody in vivo in CIA model at therapeutic dosing-(upper panel). Effect of the compound of Formula P in vivo in CIA model at therapeutic dosing (lower panel).

Figure 5:
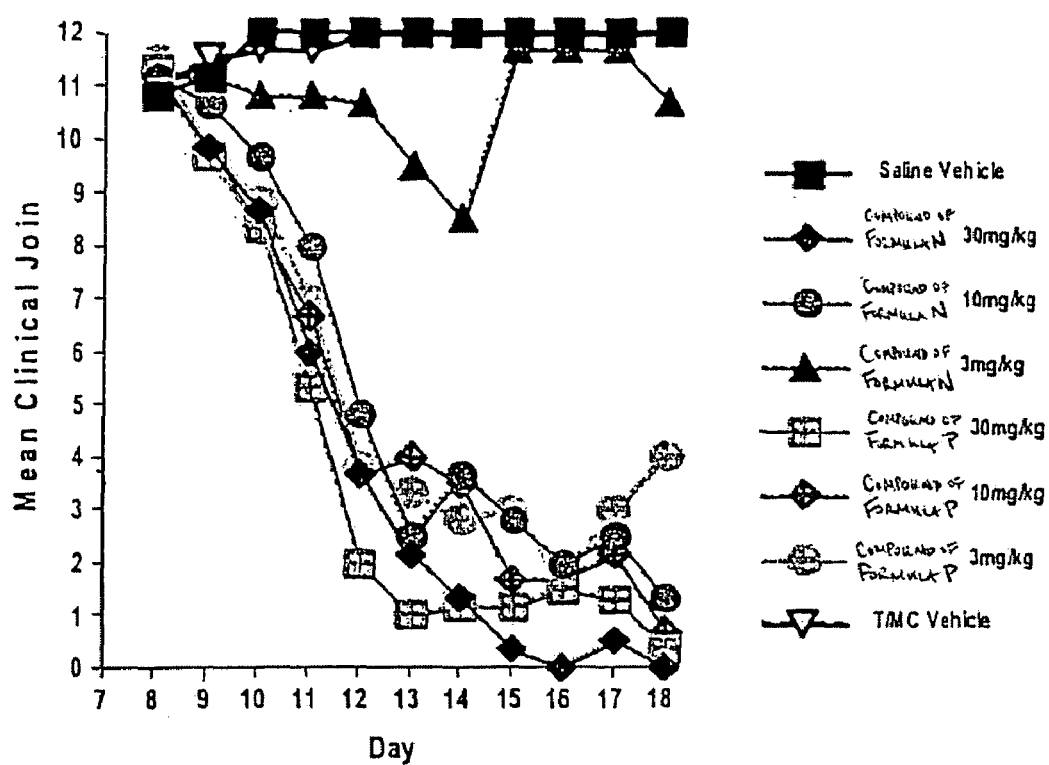

FIG. 5. FIG. 5 shows the valuation of compounds in AIA Animal Model.

Figure 6:
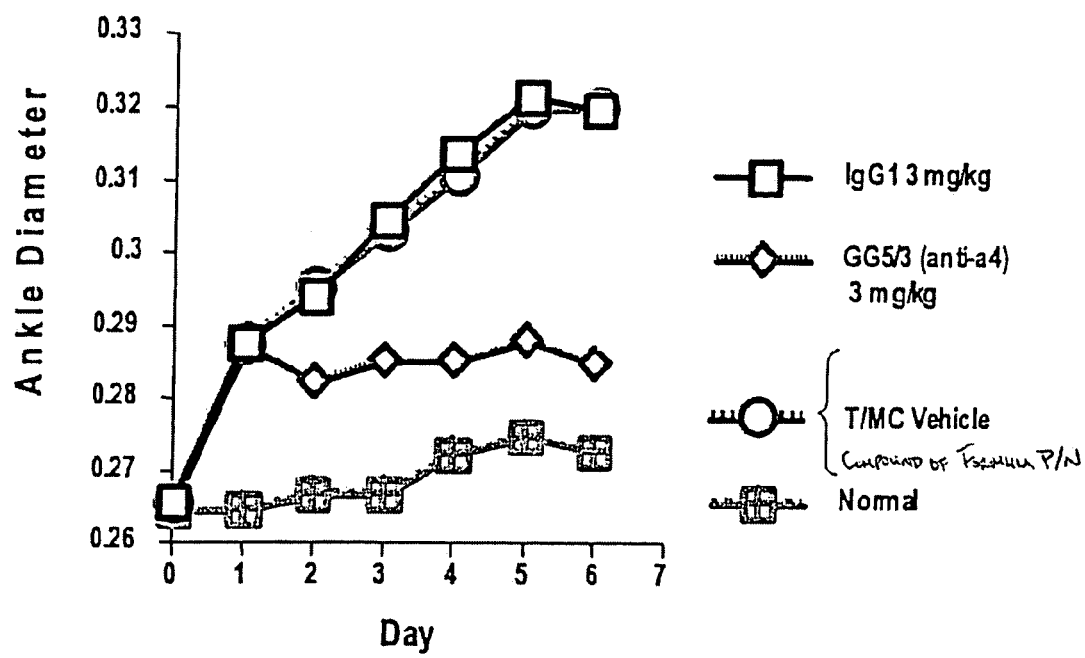

FIG. 6. FIG. 6 shows comparative effects of anti-alpha 4 antibodies and the compounds of Formulae W and Y in rat CIA model.

Figure 7:
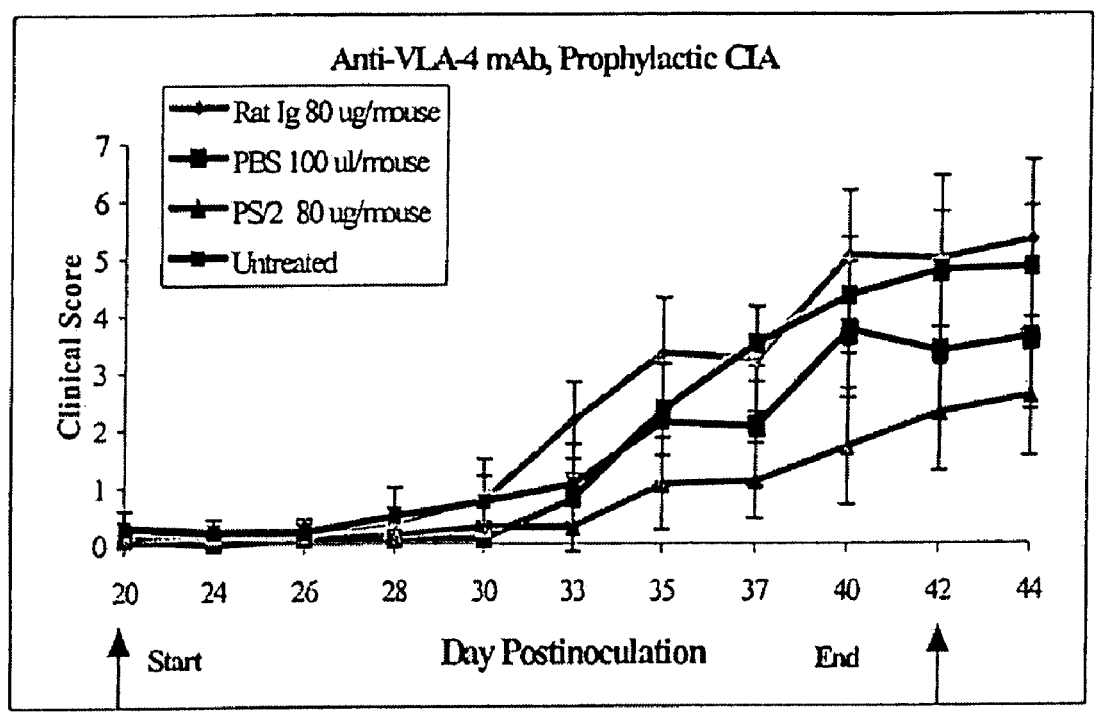

FIG. 7. FIG. 7 shows prophylactic treatment with anti-alpha 4 antibodies (PS/2) in the CIA Animal Model.

Figure 8:
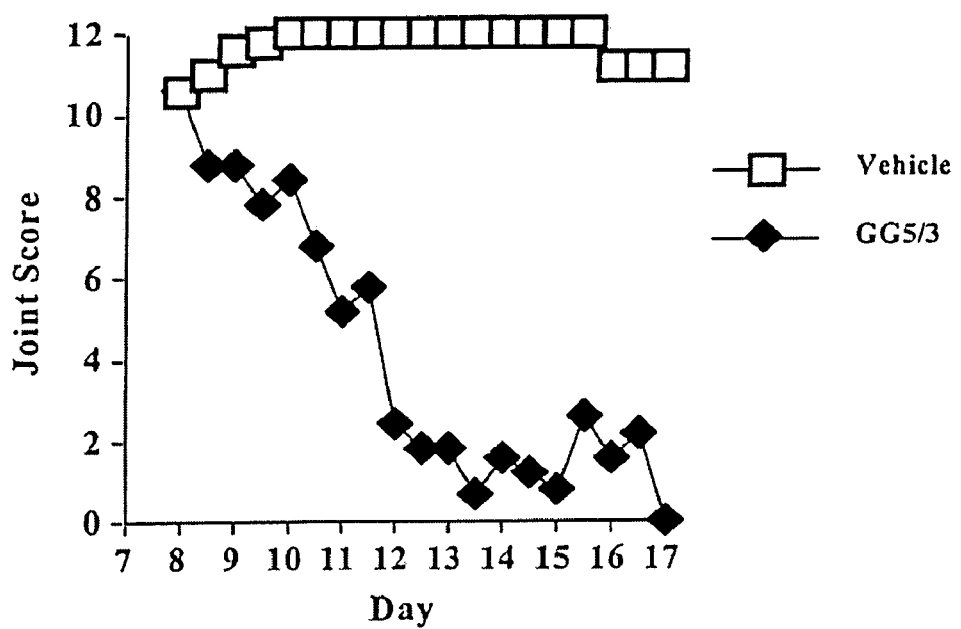

FIG. 8. FIG. 8 shows the therapeutic treatment with anti-alpha 4 antibody (GG5/3) in the AIA Animal Model.

Figure 9:
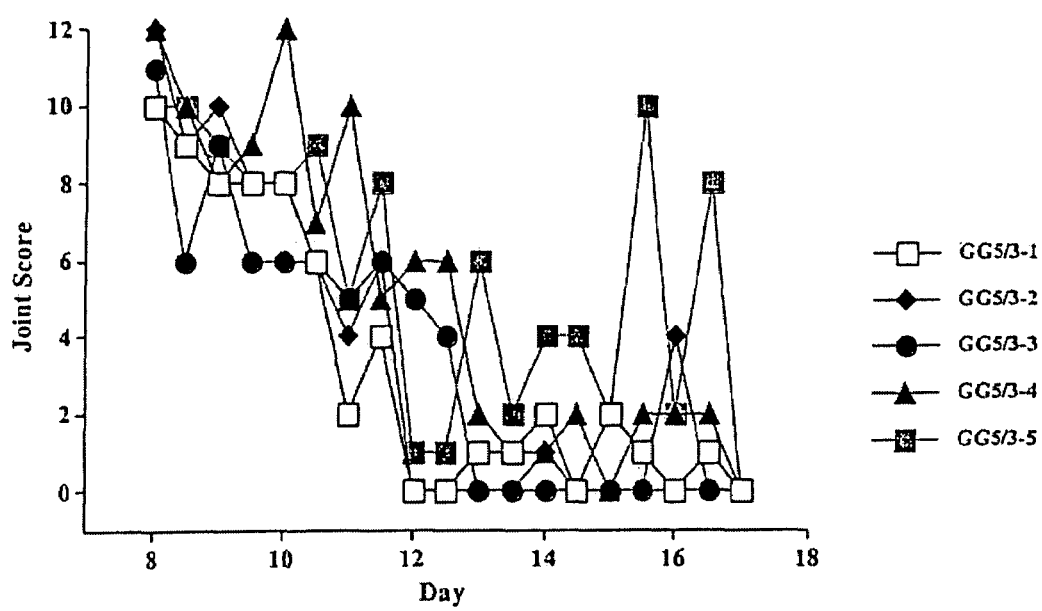

FIG. 9. FIG. 9 shows the therapeutic treatment with anti-alpha 4 antibody (GG5/3) in the AIA Animal Model.

Figure 10:
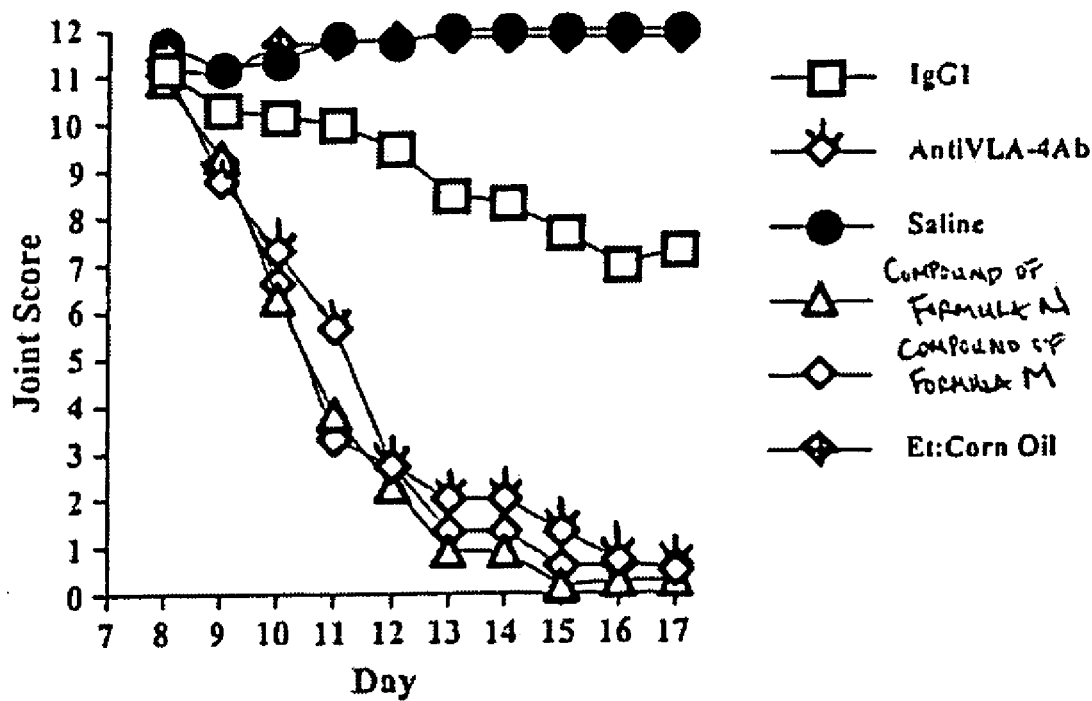

FIG. 10. FIG. 10 shows the results of dosage regimen for therapeutic treatment with small molecule alpha-4 antagonists in the AIA Animal Model.

Figure 11:
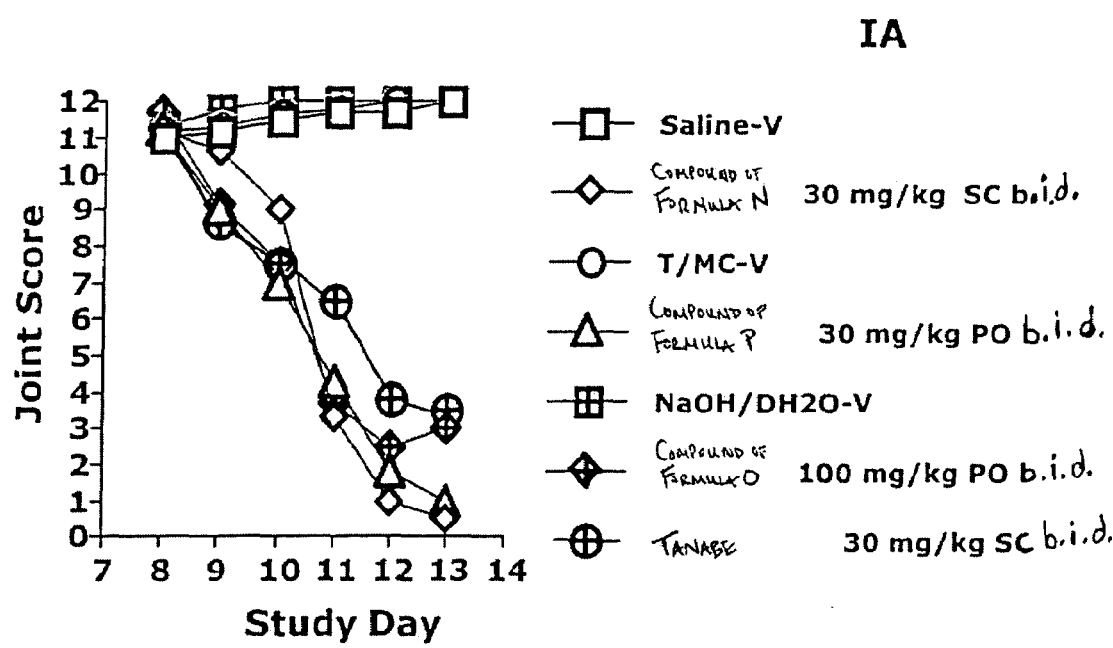

FIG. 11. FIG. 11 shows the potency and specificity of compounds in the AIA Animal Model.

DETAILED DESCRIPTION OF THE INVENTION

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller, subject to any specifically excluded limit in the stated range. Where the stated range includes one or both of the limits, ranges excluding either both of those included limits are also included in the invention. Also contemplated are any values that fall within the cited ranges.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

DEFINITIONS

By "protein" is meant to include but is not limited to immunoglobulins, enzymes, receptor, and fragments thereof. Although discussion of the formulation is provided in reference to an antibody or immunoglobulin, other proteins are contemplated as interchangeable in the formulations disclosed.

By "immunoglobulin" is meant to include, but is not limited to, an antibody and antibody fragment (such as scFv, Fab, Fc, F(ab')$_2$), and other genetically engineered portions of antibodies. Depending on the amino acid sequence of the constant domain of their heavy chains, immunoglobulins can be assigned to different classes. There are five major classes of immunoglobulins: IgA, IgD, IgE, IgG and IgM. Several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha (α), delta (Δ), epsilon (ε), gamma (γ), and mu (μ), respectively. The subunit structures and three-dimensional configurations of different classes of immunoglobulins are well known. Preferably, the immunoglobulin recognizes and binds to alpha-4 integrin.

The term "antibody" is used in the broadest sense and includes monoclonal antibodies (including agonist and antagonist antibodies), antibody compositions with polyepitopic specificity, and antibody fragments (e.g., Fab, F(ab')$_2$, scFv and Fv), so long as they exhibit the desired biological activity. "Antibody" is meant to include polyclonal antibodies, monoclonal antibodies, humanized antibodies, human antibodies, Primatized® antibodies and other antibodies produced via genetic engineering.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975 Nature 256: 495 or by the many improvements thereon derived in the intervening period. Some of these are discussed for instance in, Harlow et al., USING ANTIBODIES: A LABORATORY MANUAL— PORTABLE PROTOCOL NO. 1 (Cold Spring Harbor Press, NY 1998); Harlow et al., ANTIBODIES: A LABORATORY MANUAL (Cold Spring Harbor Press, NY 1988); and Shepherd et al., MONOCLONAL ANTIBODIES: A PRACTICAL APPROACH (Oxford University Press, 2000).

The term "monoclonal antibodies" also includes "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. For example, the ability to bind to alpha-4 integrin. The "monoclonal antibodies" may also be isolated from phage antibody libraries using the techniques described for example in Clackson et al., 1991 Nature 352: 624-628 and Marks et al., 1991 J. Mol. Biol., 222: 581-597.

"Humanized" forms of non-human (e.g., murine, rabbit, bovine, equine, porcine, and the like) antibodies are chimeric immunoglobulins, immunoglobulin chains or fragments thereof (such as Fv, Fab, Fab', F(ab')$_2$ or other antigen-binding subsequences of-antibodies), which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

The expression "linear antibodies" are also included by the general term "antibody" and are a pair of tandem Fd segments ($V_H$-$C_H$1-$V_H$-$C_H$1), which form a pair of antigen binding regions. Linear antibodies can be bispecific or monospecific.

A "variant antibody" (also included by the generic term "antibody") is a molecule which differs in amino acid sequence from a "parent" antibody's amino acid sequence by virtue of addition, deletion and/or substitution of one or more amino acid residue(s) in the parent antibody sequence. In the preferred embodiment, the variant comprises one or more amino acid substitution(s) in one or more hypervariable region(s) of the parent antibody. For example, the variant may comprise at least one substitution, e.g., from about one to about ten, and preferably from about two to about five, in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of the N-terminal, C-terminal, or internal extensions, deletions, or insertions into the antibody sequence should be construed as affecting sequence identity or homology.

To analyze such properties, one should compare a Fab form of the variant to a Fab form of the parent antibody or a full length form of the variant to a full length form of the parent antibody, for example, because it has been found that the format of the antibody impacts its activity in the biological activity assays disclosed herein. The variant antibody of particular interest is one which displays at least about 10 fold, preferably at least about 20 fold, and most preferably at least about 50 fold, enhancement in biological activity when compared to the parent antibody. The "parent" antibody is one which is encoded by an amino acid sequence used for the preparation of the variant. Preferably, the parent antibody has a human framework region and has human antibody constant region(s). For example, the parent antibody may be a humanized or a human antibody.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Antibody fragments" comprise a portion of an intact antibody, generally the antigen binding or variable region of the intact antibody. Examples of antibody fragments include Fab, Fab', F(ab')$_2$, and Fv fragments; diabodies; linear antibodies; single-chain antibody molecules; and multispecific antibodies formed from antibody fragments.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_H$ domains which enables the sFv to form the desired structure for antigen binding.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites.

The route of antibody administration is in accord with welll known methods, and may include injection or infusion by intravenous, intraperitoneal, intracerebral, intramuscular, intraocular, intraarterial, or intralesional routes, or by sustained release systems. The antibody can be administered continuously by infusion or by bolus injection. Therapeutic antibody compositions generally are placed into a container having a sterile access port, for example, an intravenous solution bag or vial having a stopper pierceable by a hypodermic injection needle.

A "stable" formulation is one in which the protein therein essentially retains its physical stability and/or chemical stability and/or biological activity upon storage. Various analytical techniques for measuring protein stability are available in the art and are reviewed in PEPTIDE AND PROTEIN DRUG DELIVERY, 247-301 (Vincent Lee ed., New York, N.Y., 1991) and Jones, 1993 Adv. Drug Delivery Rev. 10: 29-90, for examples. Stability can be measured at a selected temperature for a selected time period as exemplified by the provided examples.

A protein, such as an antibody or fragment thereof, "retains its physical stability" in a pharmaceutical formulation if it shows no signs of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity. Chemical stability can be assessed by detecting and quantifying chemically altered forms of the protein. Chemical alteration may involve size modification (e.g., clipping), which can be evaluated using size exclusion chromatography, SDS-PAGE and/or matrix-assisted laser desorption ionization/time-of-flight mass spectrometry (MALDI/TOF MS), for examples. Other types of chemical alteration include charge alteration (e.g., occurring as a result of deamidation), which can be evaluated by ion-exchange chromatography, for example.

An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention has a pH in the range from about 3.0 to about 7.5; preferably from about pH 4.0 to about 7.0; more preferably from about pH 5.0 to about 6.5; and most preferably has a pH of about 6.0±0.5. A pH of any point in between the above ranges is also contemplated.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

By "patient" or "subject" is meant to include any mammal. A "mammal", for purposes of treatment, refers to any animal classified as a mammal, including but not limited to humans, domestic and farm animals, and zoo, sports, or pet animals, such as dogs, horses, cats, cows, and the like. Preferably, the mammal is human.

By "Antegren™" is meant to include the antibody also known as AN100226 (antibody code number) or natalizumab (USAN name). Antegren™ is a recombinant, humanized anti-alpha-4 integrin antibody. Preferably the disease or condition being treated in the mammal is one which is modulated when a therapeutically effective dose of Antegren™ is administered.

The terms "small molecule alpha-4-integrin antagonists" (i.e., anti-alpha-4 agents and small molecule compounds) as used herein refer to any agent that binds specifically to an integrin comprising an alpha-4 subunit and inhibits activity of the integrin. Preferably such molecules bind to alpha-4 in a manner that prevents its interaction with VCAM 1 and thereby VCAM-1 signaling. This also includes agents that specifically bind to alpha-4 integrin as well as agents that bind to an integrin dimer that comprises the alpha-4 integrin, e.g., alpha-4 beta-1 (i.e., $\alpha 4\beta 1$ integrin) or alpha-4 beta-7 (i.e., $\alpha 4\beta 7$ integrin). Preferably, the agent is one that binds to alpha-4 in a manner, which inhibits VLA4 (alpha-4) from interacting with its cognate ligand, i.e., beta-7 or beta-1. More preferably, the anti-alpha-4 agent inhibits VLA4 from interacting with VCAM-1.

The term "agent" is meant to include synthetic molecules (e.g., antibodies, small molecules, peptides, or other synthetically produced molecules or compounds, as well as recombinantly produced gene products) as well as naturally occurring compounds (e.g., polypeptides, antibodies, antibody fragments and the like). Preferably the agent is an antagonist of alpha-4 beta-1 integrin interaction with its cognate ligand. Thus, the agent preferably binds to either VCAM-1 or to alpha-4 beta-1 integrin in a manner so as to inhibit or prevent VCAM-1 interaction with alpha-4 beta-1 integrin. The agent also inhibits VLA-4 recruitment of immune cells inhibiting an inflammatory response, which is responsible for the disease or condition being treated in the subject.

The term "efficacy" as used herein in the context of a chronic dosage regime refers to the effectiveness of a particular treatment regime. Efficacy can be measured based on change the course of the disease in response to an agent of the present invention.

The term "success" as used herein in the context of a chronic treatment regime refers to the effectiveness of a particular treatment regime. This includes a balance of efficacy, toxicity (e.g., side effects and patient tolerance of a formulation or dosage unit), patient compliance, and the like. For a chronic administration regime to be considered "successful"

it must balance different aspects of patient care and efficacy to produce the most favorable patient outcome.

The terms "specifically binds" or "binds specifically" as used herein refer to the situation in which one member of a specific binding pair will not show any significant binding to molecules other than its specific binding partner (e.g., an affinity of about 1000 times or more for its binding partner). In the present invention, the small compounds, such as N-[N-(3-pyridinesulfonyl)-L-3,3-dimethyl-4-thiaprolyl]-O-[1-methylpiperzain-4-ylcarbonyl]-L-tyrosine isopropyl ester, will not show significant binding to any polypeptide other than an alpha-4 integrin or a receptor comprising an alpha-4 integrin. For example, the small compounds used in the methods of the invention that bind to an alpha-4 integrin with a binding affinity of greater than 0.3 nM are said to bind specifically to an alpha-4 integrin.

The term "substantially similar" as used herein is intended to mean any polypeptide that has an alteration in the sequence such that a functionally equivalent amino acid is substituted for one or more amino acids in the polypeptide, thus producing a change that has no or relatively little effect on the binding properties of the polypeptide. For example, one or more amino acid residues within the sequence can be substituted by another amino acid of a similar polarity or similar size.

The terms "elicits an immune response" and "elicits a host immune response" as used herein refer to the production of an immune response to a receptor comprising an alpha-4 integrin in a subject upon introduction of an agent of the invention to the subject. An immune response in the subject can be characterized by a serum reactivity with an alpha-4 integrin receptor that is at least twice that of an untreated subject, more preferably three times the reactivity of an untreated subject, and even more preferably at least four times the reactivity of an untreated subject, with serum immunoreactivity measured using a serum dilution of approximately 1:100.

The terms "treating", "treatment", and the like are used herein to refer to obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment", as used herein, covers any treatment of a disease in a mammal, particularly a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; or (c) relieving the disease, i.e., causing regression of the disease and/or its symptoms or conditions. The invention is directed towards treating a patient's suffering from disease related to pathological inflammation. The present invention is involved in preventing, inhibiting, or relieving adverse effects attributed to pathological inflammation over long periods of time and/or are such caused by the physiological responses to inappropriate inflammation present in a biological system over long periods of time.

As used herein, "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenoxy" refers to the group "alkenyl-O-".

"Substituted alkenoxy" refers to the group "substituted alkenyl-O-".

"Alkenyl" refers to alkenyl group preferably having from 2 to 10 carbon atoms and more preferably 2 to 6 carbon atoms and having at least 1 and preferably from 1-2 sites of alkenyl unsaturation.

"Lower alkenyl" refers to an alkenyl group preferably having from 2 to 6 carbon atoms and having at least 1 site and preferably only 1 site of alkenyl unsaturation (i.e., >C=C<). This term is exemplified by groups such as allyl, ethenyl, propenyl, butenyl, and the like.

"Substituted alkenyl" refers to alkenyl groups having from 1 to 5 substituents independently selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, cycloalkyloxy, substituted cycloalkyloxy, heteroaryloxy, substituted heteroaryloxy, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$- alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

Preferably, the substituents are independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Alkoxy" refers to the group "alkyl-O-" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O-".

"Alkyl" refers to linear or branched alkyl groups preferably having from 1 to 10 carbon atoms and more preferably 1 to 6 carbon atoms. This term is exemplified by groups such as methyl, t-butyl, n-heptyl, octyl and the like.

"Lower alkyl" refers to monovalent alkyl groups having from 1 to 5 carbon atoms including straight and branched chain alkyl groups. This term is exemplified by groups such as methyl, ethyl, iso-propyl, n-propyl, n-butyl, iso-butyl, sec-butyl, t-butyl, n-pentyl and the like. "Lower alkyl" may be optionally substituted with a halogen, such as chloro, fluoro, bromo and the like.

"Substituted alkyl" refers to an alkyl group, of from 1 to 10 carbon atoms, having from 1 to 5 substituents independently selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, cycloalkyloxy, substituted cycloalkyloxy, heteroaryloxy, substituted heteroaryloxy, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

Preferably, the substituents are independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Alkylene" refers to linear and branched divalent alkyl groups having from 1 to 10 carbon atoms and more preferably 1 to 6 carbon atoms. This term is exemplified by groups such as methylene (—CH₂—), 1,6-heptylene, 1,8-octylene, ethylene (—CH₂CH₂—), the propylene isomers (e.g., —CH₂CH₂CH₂— and —CH(CH₃)CH₂—) and the like.

"Lower alkylene" refers to divalent alkylene groups of from 1 to 4 carbon atoms including straight and branched chain alkylene groups. This term is exemplified by groups such as methylene, ethylene, n-propylene, iso-propylene (—CH₂CH(CH₃)— and —CH(CH₃)CH₂—) and the like.

"Substituted alkylene" refers to alkylene groups having from 1 to 5 substituents independently selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl , —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynyl" refers to alkynyl group preferably having from 2 to 10 carbon atoms and more preferably 3 to 6 carbon atoms and having at least 1 and preferably from 1-2 sites of alkynyl unsaturation.

"Lower alkynyl" refers to an alkynyl group preferably having from 2 to 6 carbon atoms and having at least 1 site and preferably only 1 site of alkynyl unsaturation (i.e., —C≡C—). This term is exemplified by groups such as acetyl (—C≡CH), propargyl (—CH$_2$—C≡CH), 3-butynyl (—CH$_2$CH$_2$C≡CH$_3$) and the like.

"Substituted alkynyl" refers to alkynyl groups having from 1 to 5 substituents independently selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$— substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic, substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Amidino" refers to the group H$_2$NC(=NH)— and the term "alkylamidino" refers to compounds having 1 to 3 alkyl groups (e.g., alkylHNC(=NH)—).

"Amino" refers to the group —NH$_2$.

"Substituted amino" refers to the group —NRR, where each R group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, provided that both R groups are not hydrogen; or the R groups can be joined together with the nitrogen atom to form a heterocyclic or substituted heterocyclic ring.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the groups —NRSO$_2$alkyl, —NRSO$_2$substituted alkyl, —NRSO$_2$cycloalkyl, —NRSO$_2$substituted cycloalkyl, —NRSO$_2$alkenyl, —NRSO$_2$substituted alkenyl, —NRSO$_2$alkynyl, —NRSO$_2$substituted alkynyl, —NRSO$_2$aryl, —NRSO$_2$substituted aryl, —NRSO$_2$heteroaryl, —NRSO$_2$substituted heteroaryl, —NRSO$_2$heterocyclic, and —NRSO$_2$substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the groups —NRSO$_2$NRR, —NRSO$_2$NR-alkyl, —NRSO$_2$NR-substituted alkyl, —NRSO$_2$NR-alkenyl, —NRSO$_2$NR-substituted alkenyl, —NRSO$_2$NR-alkynyl, —NRSO$_2$NR-substituted alkynyl, —NRSO$_2$NR-aryl, —NRSO$_2$NR-substituted aryl, —NRSO$_2$NR-cycloalkyl, —NRSO$_2$NR-substituted cycloalkyl, —NRSO$_2$NR-heteroaryl, and—NRSO$_2$NR-substituted heteroaryl, —NRSO$_2$NR-heterocyclic, and —NRSO$_2$NR-substituted heterocyclic, where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the groups —NRSO$_2$O-alkyl, —NRSO$_2$O-substituted alkyl, —NRSO$_2$O-alkenyl, —NRSO$_2$O-substituted alkenyl, —NRSO$_2$O-alkynyl, —NRSO$_2$O-substituted alkynyl, —NRSO$_2$O-cycloalkyl, —NRSO$_2$O-substituted cycloalkyl, —NRSO$_2$O-aryl, —NRSO$_2$O-substituted aryl, —NRSO$_2$O-heteroaryl, —NRSO$_2$O-substituted heteroaryl, —NRSO$_2$O-heterocyclic, and —NRSO$_2$O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like) provided that the point of attachment is through an aromatic ring atom. Preferred aryls include phenyl, naphthyl and 5,6,7,8-tetrahydronaphth-2-yl.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —OS(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

Preferred substituents are selected from the group consisting of hydroxy, acyl, acylamino, acyloxy, alkyl, substituted alkyl, alkoxy, substituted alkoxy, alkenyl, substituted alkenyl, amino, substituted amino, aminoacyl, aminocarbonyloxy, aminocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, cycloalkyl, substituted cycloalkyl, halo, nitro, heteroaryl, substituted heteroaryl, heterocyclic, substituted heterocyclic, and oxycarbonylamino.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkyl, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aralkoxy" refers to aryl-alkylene-O— groups.

"Substituted aralkoxy" refers to substituted aryl-alkylene-O— groups.

"Carboxyl" refers to the group —COOH and pharmaceutically acceptable salts thereof "Carboxyl esters" refers —C(O)O-alkyl, —C(O)O-substituted alkyl, —C(O)O-alkenyl, —C(O)O-substituted alkenyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic.

"Cycloalkenyl" refers to cyclic alkenyl groups of from 3 to 8 carbon atoms having single or multiple unsaturation but which are not aromatic.

"Cycloalkoxy" refers to —O-cycloalkyl groups.

"Substituted cycloalkoxy" refers to —O-substituted cycloalkyl groups.

"Cycloalkyl", with regard to the compounds of Formulae I and II and the PEG derivatives, refers to cyclic alkyl groups of from 3 to 12 carbon atoms having a single or multiple condensed rings including, by way of example, adamantyl, cyclopropyl, cyclobutyl, cyclopentyl, cyclohexyl, cyclooctyl and the like. Preferably "cycloalkyl" refers to cyclic alkyl groups of from 3 to 8 carbon atoms having a single cyclic ring.

"Cycloalkyl", with regards to the compounds of Formulae III-IX, refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Lower cycloalkyl" refers to cyclic alkyl groups of from 3 to 6 carbon atoms having a single cyclic ring including, by way of example, cyclopropyl, cyclobutyl, cyclopentyl and cyclohexyl.

"Substituted cycloalkyl" and "substituted cycloalkenyl" refers to a cycloalkyl or cycloalkenyl group, preferably of from 3 to 8 carbon atoms, having from 1 to 5 substituents independently selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Preferred substituents are selected from the group consisting of oxo (=O), thioxo (=S), alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is fluoro, chloro or bromo.

"Heteroaryl" refers to an aromatic carbocyclic group of from 2 to 10 carbon atoms and 1 to 4 heteroatoms selected from the group consisting of oxygen, nitrogen and sulfur within the ring or oxides thereof. Such heteroaryl groups can have a single ring (e.g., pyridyl or furyl) or multiple condensed rings (e.g., indolizinyl or benzothienyl) wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Additionally, the carbon atoms of the ring may be substituted with an oxo (=O). Preferred heteroaryls include pyridyl, pyrrolyl, indolyl, furyl, pyridazinyl, pyrimidinyl, pyrazinyl, 1-oxo-1,2,5-thiadiazolyl and 1,1-dioxo-1,2,5-thiadiazolyl. The term "heteroaryl having two nitrogen atoms in the heteroaryl ring" refers to a heteroaryl group having two, and only two, nitrogen atoms in the heteroaryl ring and optionally containing 1 or 2 other heteroatoms in the heteroaryl ring, such as oxygen or sulfur.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl-, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

Preferably the substituents are selected from the group consisting of those defined above as preferred for substituted aryl.

"Heteroaryloxy" refers to the group —O-heteroaryl and "substituted heteroaryloxy" refers to the group —O-substituted heteroaryl.

"Heteroaralkoxy" refers to the group heteroaryl-alkylene-O—.

"Substituted heteroaralkoxy" refers to the group substituted heteroaryl-alkylene-O—.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl; —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Preferably, the substituents are selected from the group consisting of the preferred substitutents defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, morpholinyl, thiomorpholino, thiomorpholinyl (also referred to as thiamorpholinyl), piperidinyl, pyrrolidine, tetrahydrofuranyl, and the like.

"Heterocyclyloxy" refers to the group —O-heterocyclic arid "substituted heterocyclyloxy" refers to the group —O-substituted heterocyclic.

"Lower alkylenecycloalkyl" refers to the group consisting of a lower alkylene-lower cycloalkyl, as defined herein. Such groups are exemplified by methylenecyclopropyl (—CH$_2$-cyclopropyl), ethylenecyclopropyl and the like.

"N,N-Dimethylcarbamyloxy" refers to the group —OC(O)N(CH$_3$)$_2$.

"Oxo" refers to (=O).

"Oxyalkylene" refers to —OCH$_2$CHR$^d$— where R$^d$ is alkyl.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonyl" refers to the groups alkyl-SO$_2$O—, substituted alkyl-SO$_2$O—, alkenyl-SO$_2$O—, substituted alkenyl-SO$_2$O—, alkynyl-SO$_2$O—, substituted alkynyl-SO$_2$O—, aryl-SO$_2$O—, substituted aryl-SO$_2$O—, cycloalkyl-SO$_2$O—, substituted cycloalkyl-SO$_2$O—, heteroaryl-SO$_2$O—, substituted heteroaryl-SO$_2$O—, heterocyclic-SO$_2$O—, and substituted heterocyclic-SO$_2$O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonylamino" refers to the groups —OSO$_2$NH$_2$, —OSO$_2$NRR, —OSO$_2$NR-alkyl, —OSO$_2$NR-substituted alkyl, —OSO$_2$NR-alkenyl, —OSO$_2$NR-substituted alkenyl, —OSO$_2$NR-alkynyl, —OSO$_2$NR-substituted alkynyl, —OSO$_2$NR-cycloalkyl, —OSO$_2$NR-substituted cycloalkyl, —OSO$_2$NR-aryl, —OSO$_2$NR-substituted aryl, —OSO$_2$NR-heteroaryl, —OSO$_2$NR-substituted heteroaryl, —OSO$_2$NR-heterocyclic, and —OSO$_2$NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioalkyl" refers to the groups —S-alkyl.

"Substituted thioalkyl" refers to the group —S-substituted alkyl.

"Thioamidino" refers to the group RSC(=NH)— where R is hydrogen or alkyl.

"Thioaryl" refers to the group —S-aryl and "substituted thioaryl" refers to the group —S-substituted aryl.

"Thiocarbonylamino" refers to the group —C(S)NRR where each R is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as-defined herein.

"Thiocycloalkyl" refers to the groups —S-cycloalkyl.

"Substituted thiocycloalkyl" refers to the group —S-substituted cycloalkyl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Thiol" refers to the group —SH.

"Optionally substituted" means that the recited group may be unsubstituted or the recited group may be substituted.

"Pharmaceutically acceptable carrier" means a carrier that is useful in preparing a pharmaceutical composition or formulation that is generally safe, non-toxic and neither biologically nor otherwise undesirable, and includes a carrier that is acceptable for veterinary use as well as human pharmaceutical use. A pharmaceutically acceptable carrier or excipient as used in the specification and claims includes both one or more than one of such carriers.

"Pharmaceutically-acceptable cation" refers to the cation of a pharmaceutically-acceptable salt.

"Pharmaceutically acceptable salt" refers to salts which retain the biological effectiveness and properties of the compounds of this invention and which are not biologically or otherwise undesirable. Pharmaceutically acceptable salts refer to pharmaceutically acceptable salts of the compounds, which salts are derived from a variety of organic and inorganic counter ions well known in the art and include, by way of example only, sodium, potassium, calcium, magnesium, ammonium, tetraalkylammonium- and the like; and when the molecule contains a basic functionality, salts of organic or inorganic acids, such as hydrochloride, hydrobromide, tartrate, mesylate, acetate, maleate, oxalate and the like.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

A "therapeutically effective amount" means the amount of a compound or antibody that, when administered to a mammal for treating a disease, is sufficient to effect such treatment for the disease. The "therapeutically effective amount" will vary depending on the compound, the disease and its severity and the age, weight, etc., of the mammal to be treated.

As used herein, the following abbreviations have the following meanings. If an abbreviation is not defined, it has its generally accepted meaning.

AC=acid ceramidase
CAN=acetonitrile
AcOH=acetic acid
ACTH=adrenocorticotropic hormone
ADEM=acute disseminated encephalomyelitis
ANA=Anti-nuclear antibodies
aq or aq.=aqueous
AUC=Area under the curve
BBB=blood brain barrier
bd=broad doublet
bm=broad multiplet
Bn=benzyl
Boc=tert-butoxycarbonyl
$Boc_2O$=di-tert-butyl dicarbonate
BOP=benzotriazol-1-yloxy-tris(dimethylamino)phosphonium hexafluorophosphate
bs=broad singlet
BSA=bovine serum albumin
C constant region of an immunoglobulin
Cbz=carbobenzyloxy
cDNA complementary deoxyribnucleic acid
CDR=complementarity determining region
CDR1=complementarity determining region 1
CDR2=complementarity determining region 2
CDR3=complementarity determining region 3
CFA=complete Freund's adjuvant
$CHCl_3$=chloroform
$CH_2Cl_2$ dichloromethane
CIDP=chronic immune demyelinating polyneuropathy
CNS central nervous system
$(COCl)_2$=oxalyl chloride
COX-2=cyclooxygenase-2
CRP=C-Reactive Protein
CS=Cockayne's syndrome
CSF=colony stimulating factor
d=doublet
DBU=1,8-diazabicyclo[5.4.0]undec-7-ene
DCC=1,3-dicyclohexylcarbodiimide
dd=doublet of doublets
DMAP=4-N,N-dimethylaminopyridine ethylcarbodiimide hydrochloride
DME=ethylene glycol dimethyl ether
DMF=N,N-dimethylformamide
DMSO=dimethylsulfoxide
DNA=deoxyribonucleic acid
dt=doublet of triplets
EAE-=experimental autoimmune encephalomyelitis
EBNA2=Epstein-Barr virus nuclear antigen 2
ECM=extracellular matrix
EDC=1'-(3-'dimethylaminopropyl)-3-ethylcarbodiimide hydrochloride
EDTA=Ethylenediamine tetraacetic acid
ELAMS=endothelial adhesion molecules
EM=electron microscopy
$Et_3N$=triethylamine
$Et_2O$=diethyl ether
EtOAc=ethyl acetate
EtOH=ethanol
eq or eq. =equivalent
FACS=Fluorescence activated Cell Sorter
FITC=Fluorescein isothiocyanate
FmocO=N-(9-fluorenylmethoxycarbonyl)
FmocONSu=N-(9-fluorenylmethoxycarbonyl)-succinimide
FR=framework region
FR1=framework region 1
FR2=framework region 2
FR3=framework region 3
g=grams
GA=glatiramer acetate
GM-CSF=granulocyte monocyte colony stimulating factor
h or hr=hour
H=heavy chain of an immunoglobulin
HAMA=human anti-mouse antibody
HB or Hb=hemoglobin
HBr=hydrobromic acid
HBSS=Hank's Balanced Saline Solution
HCl=hydrochloric acid
Hct=hematocrit, or measurement of packed red blood cells obtained by centrifugation in a volume of a blood sample
H-E=hematoxylin-eosin
HEPES=4-(2-hydroxyethyl)-1-piperazine-ethanesulfonic acid
hex A=hexoaminidase A
HIC=Hydrophobic interaction chromatography
HIG=human immunoglobulin
$H_2O$=water
HOBT=1-hydroxybenzotriazole hydrate
HUVEC=human umbilical vascular endothelial cells
IgG Fc=a binding domain of the immunoglobulin
i.p.=intraperitoneal
ICAM-1=intercellular adhesion molecule 1
Ig=immunoglobulin
IgG=immunoglobulin G
IgM=immunoglobulin M
IL=interleukin
IL-1=interleukin-1
IL-2=interleukin-2
IL-8=interleukin-8

IBD=inflammatory bowel disease
IBDQ=inflammatory bowel disease questionairre
ITT=Intention-to-treat (including all subjects randomized, regardless of whether dosed)
$K_2CO_3$=potassium carbonate
kg=kilogram
L=liter
LCMS=Liquid chromatography Mass Spectroscopy
LFA-1=lymphocyte function-related antigen 1-(also known as $\beta_2$ integrin, CD11a/CD18 and $\alpha_L\beta_2$)
m=multiplet (when used with NMR data)
M=Molar
MAbs=monoclonal antibodies
Mac-1=$\alpha_M\beta_2$ integrin (also known as CD11b/CD18)
MAdCAM-1=mucosal addressin cell adhesion molecule
MALDI/TOF MS matrix-assisted laser desorption ionization/time-of-flight mass spectrometry
MALDI/TOF MS=matrix-assisted laser desorption ionization/time-of-flight mass spectrometry
MBP=myelin basic protein
MCH=Mean Corpuscular Hemoglobin; Hb/RBC
MCHC=mean corpuscular hemoglobin count expressed as a percentage; Hb/Hct.
MCP-1=monocyte chemotactic protein 1
MCV=mean corpuscular volume; the avg. volume of erythrocytes, conventionally expressed in cubic micrometers per red cell.
MeOH=methanol
MES=2-(N-morpholino)ethanesulfonic acid
mg=milligram
$MgSO_4$=magnesium sulfate
min.=minute
MIP-1$\alpha$=macrophage inflammatory protein 1 alpha
MIP-1$\beta$=macrophage inflammatory protein 1 beta
mL=milliliter
MLD=metachromatic leukodystrophy
mm=millimeter
mM=millimolar
MOG=myelin-oligodendrocyte glycoprotein
mol=moles
mmol=millimol
mp=melting point
mpk=milligrams per killogram
MS=multiple sclerosis
N=normal
NaCl=sodium chloride
$Na_2CO_3$=sodium carbonate
$NaHCO_3$=sodium bicarbonate
NaOEt=sodium ethoxide
NaOH=sodium hydroxide
ng=nanograms
$NH_4Cl$=ammonium chloride
NMM=N-methylmorpholine
NSAID=nonsteroidal anti-inflammatory
OtBu=tert-butoxy
PBS++=Phosphate buffered saline
PCR=poly erase chain reaction
PEG=polyethylene glycol
Phe=L-phenylalanine
PKU=phenylketonuria
PLP=proteolipid protein
POEMS=polyneuropathy organomegaly endocrinopathy, M-protein and skin changes
PMSF=phenylmethylsulfonylfluoride
Pro=L-proline
PRP=prion related protein
psi=pounds per square inch
$PtO_2$=platinum oxide
q=quartet
quint.=quintet
q.s. or Q.S.=bring to volume
RA=rheumatoid arthritis
RANTES=regulated upon activation, normal T-cell expressed and secreted chemokine (also known as small inducible cytokine A5)
RBC=red blood cell count
Rfs or $R_f$=retention factor
RNA=ribonucleic acid
rpm=rotations per minute
rt or RT=room temperature
RT-PCR=reverse transcription polymerase chain reaction
s=singlet
SAE=Serious adverse event
SAMIs=selective adhesion molecule inhibitors
sat or sat.=saturated
scFv=single chain Fv fragment
SCR=solochrome-R-cyanlin
SDS=sodium dodecyl sulfate
SDS-PAGE=sodium dodecyl sulfate polyacrylamide gel electrophoresis
t=triplet
t-BuOH=tert-butanol
TFA=trifluoroacetic acid
TGF-$\beta$=tumor growth factor beta
THF=tetrahydrofuran
TLC or tlc=thin layer chromatography
TNF=tumor necrosis factor
TNF-$\alpha$=tumor necrosis factor alpha
TNF-$\beta$=tumor necrosis factor beta
Ts=tosyl
TsCl=tosyl chloride
TsOH=tosylate
TYR=tyrosine
µg=microgram
µL=microliter
µM=micromolar
µm=microns
UV=ultraviolet
VCAM-1=vascular cell adhesion molecule 1
$V_H$=heavy chain of the variable domain
$V_L$=light chain of the variable domain
VLA-4=very late antigen 4 (also known as alpha-4 beta-1, $\alpha_4\beta_1$)
$V_t$=Total volume
WBC=White Blood Cells
w/w=weight to weight
w/v=weight to volume
v/v=volume to volume
φ=phenyl

GENERAL ASPECTS OF THE INVENTION

The present invention is based on the surprising result that combination therapies of methotrexate and antibodies to alpha-4 integrin, such as Antegren™, as well as combination therapies of methotrexate and small molecule alpha-4 antagonists effectively suppress the deleterious effects of RA.

Methotrexate

Methotrexate (Amethopterin®, Mexate®, Folex® and Rheumatrex®) interferes with the production and maintenance of DNA. It is not understood exactly how methotrexate works in rheumatoid arthritis, but reduces inflammation and slow worsening of the disease. Methotrexate is considered a disease-modifying antirheumatic drug (DMARD). It is effective in the early stages of rheumatoid arthritis to prevent disease progression, especially in combination with other medications.

Methotrexate is effective in relieving joint inflammation, slowing disease progression, and preventing disability by delaying joint destruction. Patients with rheumatoid arthritis may be more likely to continue treatment with methotrexate than with other DMARDs because of favorable results and tolerable side effects. Physicians often recommend that methotrexate be used with one or more combination therapy.

Combination therapy may allow for lower doses of an individual drug to be used, which may reduce the risk of adverse effects that can occur with higher doses. Methotrexate combined with hydroxychloroquine and sulfasalazine may be more effective that methotrexate alone.

Whatever may be the actual cause, there is no cure for RA, and although the disease is not fatal, disease complications and symptoms may persist throughout an individual's lifetime, and may even shorten survival by a few years. Affected joints may become deformed, and the performance of even ordinary tasks may be very difficult or impossible.

Notwithstanding what has been previously reported in the literature, new compounds, compositions and methods for using these compounds and compositions to inhibit rheumatoid arthritis are needed.

In a general sense, the method of the invention does not involve any particular mode of administration, since the mode of administration is dependent upon the form of the active agent and the formulation developed to administer the active agent. Modes of administration include, but are not limited to, oral, parenteral (e.g., subcutaneous, subdural, intravenous, intramuscular, intrathecal, intraperitoneal, intracerebral, intraarterial, or intralesional routes of administration), topical, localized (e.g., surgical application or surgical suppository), rectal, and pulmonary (e.g., aerosols, inhalation, or powder). The route of administration would be based on the composition being administered (e.g., immunoglobulin being administered intravenously versus small compound being administered orally), tissue targeting (e.g., intrathecal administration to target the site of a spinal cord injury), and the like, as would be known to the artisan of ordinary skill.

Additionally, the anti-alpha-4 agents (e.g., anti-alpha-4-antibodies, small compound alpha-4-integrin antagonists, and the like) can be combined with other compounds or compostions used to treat, ameliorate or palliate symptoms associated with rheumatoid arthritis. Furthermore, the compounds disclosed herein can be administered alone or in combination with other agents, such as alpha-4 integrin inhibitors, including anti-alpha-4 integrin antibodies and immunologically active fragments thereof (e.g., natalizumab). When administered in combination, the small compound alpha-4-integrin antagonists may be administered in the same formulation as these other compounds or compositions, or in a separate formulation. When administered in combination, the anti-alpha-4-antibodies are generally administered in a separate formulation than the small compound alpha-4-integrin antagonists, other compounds, and compositions. When administered in combinations, the anti-alpha-4 agents may be administered prior to, following, or concurrently with the other compounds and compositions used to treat, ameliorate, or palliate symptoms. The invention relates to introducing relatively constant amounts of an active agent to a patient's circulatory system over a period of months or years. This chronic introduction of an agent that selectively binds to alpha-4 integrin or a dimer comprising alpha-4 integrin (e.g. alpha-4-beta-1) results in suppression of pathological inflammation being maintained at a constant level over a period of time. By maintaining therapeutic levels of an active agent for a period of time, pathological inflammation can be chronically suppressed in the patient.

Compounds of Formulae I and II

In one aspect, the compounds that can be utilized as combination therapies with methotrexate for the treatment of RA are compounds of Formulae I, IA, IB, IC, and II.

In one aspect, the compounds that can be utilized as combination therapies with methotrexate for the treatment of RA are compounds defined by Formula I below. These compounds have a binding affinity to VLA-4 as expressed by an $IC_{50}$ of about 15 μM or less (measured as described in Example A below):

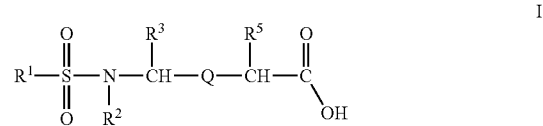

I wherein $R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;

$R^5$ is —$(CH_2)_x$—Ar—$R^{5'}$ where $R^{5'}$ is selected from the group consisting of —O-Z-$NR^8R^{8'}$ and —O-Z-$R^{8''}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a heterocycle or a substituted heterocycle, $R^{8''}$ is selected from the group consisting of heterocycle and substituted heterocycle, and Z is selected from the group consisting of —C(O)— and —$SO_2$—;

Ar is aryl, heteroaryl, substituted aryl or substituted heteroaryl;

x is an integer of from 1 to 4;

Q is —$C(X)NR^7$— wherein $R^7$ is selected from the group consisting of hydrogen and alkyl; and X is selected from the group consisting of oxygen and sulfur;

and pharmaceutically acceptable salts thereof.

In another embodiment, the compounds can be provided as prodrugs which convert (e.g., hydrolyze, metabolize, etc.) in vivo to a compound of Formula I above. In a preferred example of such an embodiment, the carboxylic acid group of the compound of Formula I is modified into a group which, in vivo, will convert to a carboxylic acid group (including salts thereof). In a particularly preferred embodiment, such prodrugs are represented by compounds of Formula IA:

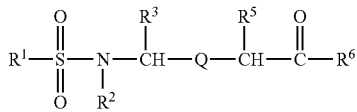

wherein:

R$^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;

R$^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and R$^1$ and R$^2$ together with the nitrogen atom bound to R$^2$ and the SO$_2$ group bound to R$^1$ can form a heterocyclic or a substituted heterocyclic group;

R$^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when R$^2$ does not form a heterocyclic group with R$^1$, R$^2$ and R$^3$ together with the nitrogen atom bound to R$^2$ and the carbon atom bound to R$^3$ can form a heterocyclic or a substituted heterocyclic group;

R$^5$ is —(CH$_2$)$_x$—Ar—R$^{5'}$ where R$^{5'}$ is selected from the group consisting of —O-Z-NR$^8$R$^{8'}$ and —O-Z-R$^{8'}$ wherein R$^8$ and R$^{8'}$ are independently selected from the group consisting of hydrogen, alkyl, substituted alkyl, cycloalkyl, substituted cycloalkyl, heterocyclic, substituted heterocyclic, and where R$^8$ and R$^{8'}$ are joined to form a heterocycle or a substituted heterocycle, R$^{8''}$ is selected from the group consisting of heterocycle and substituted heterocycle, and Z is selected from the group consisting of —C(O)— and —SO$_2$—;

Ar is aryl, heteroaryl, substituted aryl or substituted heteroaryl;

x is an integer of from 1 to 4;

R$^6$ is selected from the group consisting of 2,4-dioxotetrahydrofuran-3-yl (3,4-enol), amino, alkoxy, substituted alkoxy, cycloalkoxy, substituted cycloalkoxy, —O—(N-succinimidyl), —NH-adamantyl, —O-cholest-5-en-3-β-yl, —NHOY where Y is hydrogen, alkyl, substituted alkyl, aryl, and substituted aryl, —NH(CH$_2$)$_p$COOY where p is an integer of from 1 to 8 and Y is as defined above, —OCH$_2$NR$^9$R$^{10}$ where R$^9$ is selected from the group consisting of —C(O)-aryl and —C(O)-substituted aryl and R$^{10}$ is selected from the group consisting of hydrogen and —CH$_2$COOR$^{11}$ where R$^{11}$ is alkyl, and —NHSO$_2$Z' where Z' is alkyl, substituted alkyl, cycloalkyl, substituted cycloalkyl, aryl, substituted aryl, heteroaryl, substituted heteroaryl, heterocyclic and substituted heterocyclic;

Q is —C(X)NR$^7$— wherein R$^7$ is selected from the group consisting of hydrogen and alkyl; and X is selected from the group consisting of oxygen and sulfur;

and pharmaceutically acceptable salts thereof with the following provisos (A) when R$^1$ and R$^2$ together with the SO$_2$ group pendent to R$^1$ and the nitrogen pendent to R$^2$ form a saccharin-2-yl group, R$^3$ is —CH$_3$, R$^5$ is p-[(CH$_3$)$_2$NC(O)O—]benzyl and Q is —C(O)NH— then R$^6$ is not —OC(CH$_3$)$_3$;

(B) when R$^1$ is p-methylphenyl, R$^2$ and R$^3$ together with the nitrogen atom pendent to R$^2$ and the carbon atom pendent to R$^3$ form a pyrrodinyl ring derived from D-proline; R$^5$ is p-[(4-methylpiperazin-1-yl)NC(O)O—]benzyl derived from D-phenylalanine and Q is —C(O)NH—then R$^6$ is not —OC(CH$_3$)$_3$;

(C) when R$^1$ is pyrimidin-2-yl, R$^2$ and R$^3$ together with the nitrogen atom bound to R$^2$ and the carbon atom bound to R$^3$ form a pyrrolidinyl ring, R$^5$ is p-[(CH$_3$)$_2$NC(O)O—]benzyl and Q is —C(O)NH— then R$^6$ is not —OC(CH$_3$)$_3$; and (D) when R$^1$ is p-methylphenyl, R$^2$ and R$^3$ together with the nitrogen atom pendent to R$^2$ and the carbon atom pendent to R$^3$ form a (2S)-piperazin-2-carbonyl ring; R$^5$ is p-[(CH$_3$)$_2$NC(O)O—]benzyl and Q is —C(O)NH— then R$^6$ is not —OC(CH$_3$)$_3$.

Further description of the compounds of the above Formulae I and IA and procedures and reaction conditions for preparing these compounds are described in U.S. Ser. No. 09/126,958 (filed Jul. 31, 1998 and issued as U.S. Pat. No. 6,489,300), herein incorporated by reference in its entirety.

Preferably, in the compounds of Formulae I and IA above, R$^1$ is selected from the group consisting of alkyl, substituted alkyl, aryl, substituted aryl, heterocyclic, substituted heterocylic, heteroaryl and substituted heteroaryl. More preferably R$^1$ is selected from the group consisting of aryl, substituted aryl, heteroaryl and substituted heteroaryl.

Preferably R$^1$, in the compounds of Formulae I and IA above is selected from the group consisting of phenyl, 4-methylphenyl, 4-t-butylphenyl, 2,4,6-trimethylphenyl, 2-fluorophenyl, 3-fluorophenyl, 4-fluorophenyl, 2,4-difluorophenyl, 3,4-difluorophenyl, 3,5-difluorophenyl, 2-chlorophenyl, 3-chlorophenyl, 4-chlorophenyl, 3,4-dichlorophenyl, 3,5-dichlorophenyl, 3-chloro-4-fluorophenyl, 4-bromophenyl, 2-methoxyphenyl, 3-methoxyphenyl, 4-methoxyphenyl, 3,4-dimethoxyphenyl, 4-t-butoxyphenyl, 4-(3'-dimethylamino-n-propoxy)-phenyl, 2-carboxyphenyl, 2-(methoxycarbonyl) phenyl, 4-(H$_2$NC(O)—)phenyl, 4-(H$_2$NC(S)—)phenyl, 4-cyanophenyl, 4-trifluoromethylphenyl, 4-trifluoromethoxyphenyl, 3,5-di-(trifluoromethyl)phenyl, 4-nitrophenyl, 4-aminophenyl, 4-(CH$_3$C(O)NH—) phenyl, 4-(PhNHC(O)NH—)phenyl, 4-amidinophenyl, 4-methylamidinophenyl, 4-(CH$_3$SC(=NH)-)phenyl, 4-chloro-3-(H$_2$NS(O)$_2$—)phenyl, 1-naphthyl, 2-naphthyl, pyridin-2-yl, pyridin-3-yl, pyrimidin-2-yl, quinolin-8-yl, 2-(trifluoroacetyl)-1,2,3,4-tetrahydroisoquinolin-7-yl, morpholin-4-yl, 2-thienyl, 5-chloro-2-thienyl, 2,5-dichloro-4-thienyl, 1-N-methylimidazol-4-yl, 1-N-methylpyrazol-3-yl, 1-N-methylpyrazol-4-yl, 1-N-butylpyrazol-4-yl, 1-N-methyl-3-methyl-5-chloropyrazol-4-yl, 1-N-methyl-5-methyl-3-chloropyrazol-4-yl, 2-thiazolyl and 5-methyl-1,3,4-thiadiazol-2-yl.

Preferably, R$^2$, in the compounds of Formulae I and IA above is selected from the group consisting of methyl, benzyl, —(CH$_2$)$_2$-2-thienyl, and —(CH$_2$)$_2$—φ.

In one preferred embodiment, R$^2$ and R$^3$, in the compounds of Formulae I and IA above together with the nitrogen atom bound to the R$^2$ substituent and the carbon bound to the R$^3$ substituent form a heterocyclic group or a substituted heterocyclic group of 4 to 6 ring atoms having 1 to 2 heteroatoms in the ring selected from the group consisting of nitrogen, oxygen and sulfur which ring is optionally substituted with 1 to 2 substituents selected from the group consisting of fluoro, methyl, hydroxy, oxo (=O), amino, phenyl, thiophenyl, thiobenzyl, (thiomorpholin-4-yl)C(O)O—, CH$_3$S(O)$_2$— and CH$_3$S(O)$_2$O—, or can be fused to another ring such as a phenyl or cycloalkyl ring to provide for a fused ring heterocycle of from 10 to 14 ring atoms having 1 to 2 heteroatoms in the ring selected from the group consisting of nitrogen, oxygen and sulfur. Such heterocyclic rings include azetidinyl (e.g., L-azetidinyl), thiazolidinyl (e.g., L-thiazolidinyl), piperidinyl (e.g., L-piperidinyl), piperazinyl (e.g., L-piperazinyl), dihydroindolyl (e.g., L-2,3-dihydroindol-2-yl), tetrahydroquinolinyl (e.g., L-1,2,3,4-tetrahydroquinolin-2-yl), thiomorpholinyl (e.g., L-thiomorpholin-3-yl), pyrrolidinyl (e.g., L-pyrrolidinyl), substituted pyrrolidinyl such as 4-hydroxypyrrolidinyl (e.g., 4-α-(or β-)hydroxy-L-pyrrolidinyl), 4-oxopyrrolidinyl (e.g., 4-oxo-L-pyrolidinyl), 4-fluoropyrrolidinyl (e.g., 4-α-(or β-)fluoro-L-pyrrolidinyl), 4,4-difluoropyrrolidinyl (e.g., 4,4-difluoro-L-pyrrolidinyl), 4-(thiomorpholin-4-ylC(O)O—)pyrrolidinyl (e.g., 4-α-(or β-)-(thiomorpholin-4-ylC(O)O—)-L-pyrrolidinyl, 4-($CH_3S(O)_2$O—)pyrrolidinyl (e.g., 4-α-(or β-)($CH_3S(O)_2$O—)-L-pyrrolidinyl, 3-phenylpyrrolidinyl (e.g., 3-α-(or β-)phenyl-L-pyrrolidinyl), 3-thiophenylpyrrolidinyl (e.g., 3-α-(or β-)-thiophenyl-L-pyrrolidinyl), 4-aminopyrrolidinyl (e.g., 4-α-(or β-)amino-L-pyrrolidinyl), 3-methoxypyrrolidinyl (e.g., 3-α-(or β-)methoxy-L-pyrrolidinyl), 4,4-dimethylpyrrolidinyl, substituted piperazinyl such as 4-N-Cbz-piperazinyl and 4-($CH_3S(O)_2$—)piperazinyl, substituted thiazolidinyl such as 5,5-dimethylthiazolindin-4-yl, 1,1-dioxo-thiazolidinyl (e.g., L-1,1-dioxo-thiazolidin-2-yl), substituted 1,1-dioxo-thiazolidinyl such as L-1,1-dioxo-5,5-dimethylthiazolidin-2-yl, 1,1-dioxothiomorpholinyl (e.g., L-1,1-dioxo-thiomorpholin-3-yl) and the like.

Q, in the compounds of Formulae I and IA above, is preferably —C(O)NH— or —C(S)NH—.

In the compounds of Formulae I and IA above, Ar is preferably aryl or substituted aryl and, even more preferably, is phenyl or substituted phenyl. Preferably, x is 1.

In the compounds of Formulae I and IA above, $R^5$ is preferably selected from all possible isomers arising by substitution with the following groups:

3-[$(CH_3)_2$NC(O)O—]benzyl,
4-[$(CH_3)_2$NC(O)O—]benzyl,
4-[(piperidin-1'-yl)C(O)O—]benzyl,
4-[(piperidin-4'-yl)C(O)O—]benzyl,
4-[(1'-methylpiperidin-4'-yl)C(O)O—]benzyl,
4-[(4'-hydroxypiperidin-1-yl)C(O)O—]benzyl,
4-[(4'-formyloxypiperidin-1'-yl)C(O)O—]benzyl,
4-[(4'-ethoxycarbonylpiperidin-1-yl)C(O)O—]benzyl,
4-[(4'-carboxylpiperidin-1-yl)C(O)O—]benzyl,
4-[(3'-hydroxymethylpiperidin-1-yl)C(O)O—]benzyl,
4-[(4'-hydroxymethylpiperidin-1-yl)C(O)O—]benzyl,
4-[(4'-phenyl-1'-Boc-piperidin-4'-yl)-C(O)O—]benzyl,
4-[(4'-piperidon-1-yl ethylene ketal]C(O)O—]benzyl,
4-[(piperazin-4'-yl)-C(O)O—]benzyl,
4-[(1'-Boc-piperazin-4'-yl)-C(O)O—]benzyl,
4-[(4'-methylpiperazin-1'-yl)C(O)O—]benzyl,
4-[(4'-methylhomopiperazin-1-yl)C(O)O—]benzyl,
4-[(4'-(2-hydroxyethyl)piperazin-1'-yl)C(O)O—]benzyl,
4-[(4'-phenylpiperazin-1'-yl)C(O)O—]benzyl,
4-[(4'-(pyridin-2-yl)piperazin-1'-yl)C(O)O—]benzyl,
4-[(4'-(4-trifluoromethylpyridin-2-yl)piperazin-1'-yl)C(O)O—]benzyl,
4-[(4'-(pyrimidin-2-yl)piperazin-1'-yl)C(O)O—]benzyl,
4-[(4'-acetylpiperazin-1-yl)C(O)O—]benzyl,
4-[(4'-(phenylC(O)—)piperazin-1'-yl)C(O)O—]benzyl,
4-[(4'-(pyridin-4-ylC(O)—)piperazin-1'-yl)C(O)O—]benzyl,
4-[(4'-(phenylNHC(O)—)piperazin-1-yl)C(O)O—]benzyl,
4-[(4'-(phenyNHC(S)—)piperazin-1-yl)C(O)O—]benzyl,
4-[(4'-methanesulfonylpiperazin-1'-yl-C(O)O—)benzyl,
4-[(4'-trifluoromethanesulfonylpiperazin-1'-yl-C(O)O—)benzyl,
4-[(morpholin-4'-yl)C(O)O—]benzyl,
3-nitro-4-[(morpholin-4'-yl)-C(O)O—]benzyl,
4-[(thiomorpholin-4'-yl)C(O)O—]benzyl,
4-[(thiomorpholin-4'-yl sulfone)-C(O)O—]benzyl (alternative nomenclature 4-[(1,1-dioxothiomorpholin-4-yl)-C(O)O—]benzyl),
4-[(pyrrolidin-1-yl)C(O)O—]benzyl,
4-[(2'-methylpyrrolidin-1-yl)C(O)O—]benzyl,
4-[(2'-(methoxycarbonyl)pyrrolidin-1'-yl)C(O)O—]benzyl,
4-[(2'-(hydroxymethyl)pyrrolidin-1'-yl)C(O)O—]benzyl,
4-[(2'-(N,N-dimethylamino)ethyl)($CH_3$)NC(O)O—]benzyl,
4-[(2'-(N-methyl-N-toluene-4-sulfonylamino)ethyl)($CH_3$)N—C(O)O—]benzyl,
4-[(2'-(morpholin-4'-yl)ethyl)($CH_3$)NC(O)O—]benzyl,
4-[(2'-(hydroxy)ethyl)($CH_3$)NC(O)O—]benzyl,
4-[bis(2'-(hydroxy)ethyl)NC(O)O—]benzyl,
4-[(2'-(formyloxy)ethyl)($CH_3$)NC(O)O—]benzyl,
4-[($CH_3$OC(O)$CH_2$)HNC(O)O—]benzyl,
4-[2'-(phenylNHC(O)O—)ethyl-]HNC(O)O—]benzyl,
3-chloro-4-[($CH_3$)$_2$NC(O)O—]benzyl,
3-chloro-4-[(4'-methylpiperazin-1'-yl)C(O)O—]benzyl,
3-chloro-4-[(4'-(pyridin-2-yl)piperazin-1'-yl)C(O)O—]benzyl,
3-chloro-4-[(thiomorpholin-4'-yl)C(O)O—]benzyl, and
3-fluoro-4-[($CH_3$)$_2$NC(O)O—]benzyl.

In the compounds of Formula IA, $R^6$ is preferably 2,4-dioxo-tetrahydrofuran-3-yl (3,4-enol), methoxy, ethoxy, n-propoxy, isopropoxy, n-butoxy, t-butoxy, cyclopentoxy, cyclopropylmethoxy, neopentoxy, 2-α-isopropyl-4-β-methylcyclohexoxy, 2-β-isopropyl-4-β-methylcyclohexoxy, 2-methoxyphenoxy, 2-(morpholin-4-yl)ethoxy, —O($CH_2CH_2O)_2CH_3$, 2-(phenoxy)ethoxy, —$OCH_2$C$(CH_3)_2$NHBoc, —$NH_2$, benzyloxy, —$NHCH_2COOH$, —$NHCH_2CH_2COOH$, —NH-adamantyl, —$NHSO_2$-p-$CH_3$—φ, —$NHCH_2CH_2COOCH_2CH_3$—NHOY' where Y' is hydrogen, methyl, iso-propyl or benzyl, O—(N-succinimidyl), —O-cholest-5-en-3-β-yl, —$OCH_2$—OC(O)C$(CH_3)_3$, —O($CH_2)_z$NHC(O)W where z is 1 or 2 and W is selected from the group consisting of pyrid-3-yl, N-methylpyridyl, and N-methyl-1,4-dihydro-pyrid-3-yl, —NR"C(O)—R' where R' is aryl, heteroaryl or heterocyclic and R" is hydrogen or —$CH_2C(O)OCH_2CH_3$.

Even more preferably, $R^6$ in the compounds of Formula IA is selected from the group consisting of methoxy, ethoxy, n-propoxy, isopropoxy, n-butoxy, t-butoxy, cyclopentoxy, cyclopropylmethoxy, neopentoxy, 2-α-isopropyl-4-β-methylcyclohexoxy, 2-β-isopropyl-4-β-methylcyclohexoxy, 2-methoxyphenoxy, 2-(morpholin-4-yl)ethoxy, —O($CH_2CH_2O)_2CH_3$, 2-(phenoxy)ethoxy, —$OCH_2$C$(CH_3)_2$NHBoc, and benzyloxy.

Preferred compounds within the scope of Formulae I and IA above include by way of example:

N-(toluene-4-sulfonyl)-L-prolyl-L-4-(4-methylpiperazin-1-ylcarbonyloxy)phenylalanine ethyl ester
N-(toluene-4-sulfonyl)-L-prolyl-L-4-(N,N-dimethylcarbamyloxy)phenylalanine ethyl ester
N-(toluene-4-sulfonyl)-L-prolyl-L-4-(4-methylpiperazin-1-ylcarbonyloxy)phenylalanine isopropyl ester
N-(toluene-4-sulfonyl)-L-prolyl-L-4-(4-methylpiperazin-1-ylcarbonyloxy)phenylalanine n-butyl ester
N-(toluene-4-sulfonyl)-L-prolyl-L-4-(4-methylpiperazin-1-ylcarbonyloxy)phenylalanine cyclopentyl ester
N-(toluene-4-sulfonyl)-L-prolyl-L-4-(4-methylpiperazin-1-ylcarbonyloxy)phenylalanine tert-butyl ester
N-(toluene-4-sulfonyl)-L-prolyl-L-4-(4-methylpiperazin-1-ylcarbonyloxy)phenylalanine N-(toluene-4-sulfonyl)-L-prolyl-L-4-(N,N-dimethylcarbamyloxy)phenylalanine isopropyl ester
N-(toluene-4-sulfonyl)-L-prolyl-L-4-(N,N-dimethylcarbamyloxy)phenylalanine n-butyl ester
N-(toluene-4-sulfonyl)-L-prolyl-L-4-(N,N-dimethylcarbamyloxy)phenylalanine cyclopentyl ester
N-(toluene-4-sulfonyl)-L-prolyl-L-4-(N,N-dimethylcarbamyloxy)phenylalanine tert-butyl ester
N-(toluene-4-sulfonyl)-L-prolyl-L-4-(N,N-dimethylcarbamyloxy)phenylalanine
N-(toluene-4-sulfonyl)-L-prolyl-L-4-(isonipecotoyloxy)phenylalanine ethyl ester
N-(α-toluenesulfonyl)-L-prolyl-L-4-(N-methylisonipecotoyloxy)phenylalanine ethyl ester
N-(α-toluenesulfonyl)-L-prolyl-L-4-(4-methylpiperazin-1-ylcarbonyloxy)phenylalanine
N-(toluene-4-sulfonyl)-L-prolyl-L-3-(N,N-dimethylcarbamyloxy)phenylalanine ethyl ester
N-(toluene-4-sulfonyl)-L-prolyl-L-4-(1-tert-butylcarbonyloxy-4-phenylpiperidin-4-ylcarbonyloxy)phenylalanine ethyl ester
N-(toluene-4-sulfonyl)-L-(5,5-dimethyl)thiaprolyl-L-4-(N,N-dimethylcarbamyloxy)phenylalanine isopropyl ester
N-(toluene-4-sulfonyl)-L-(5,5-dimethyl)thiaprolyl-L-4-(N,N-dimethylcarbamyloxy)phenylalanine tert-butyl ester
N-(toluene-4-sulfonyl)-L-(5,5-dimethyl)thiaprolyl-L-4-(N,N-dimethylcarbamyloxy)phenylalanine
N-(toluene-4-sulfonyl)-L-[(1,1-dioxo)thiamorpholin-3-carbonyl]-L-4-(N,N-dimethylcarbamyloxy)phenylalanine tert-butyl ester
N-(toluene-4-sulfonyl)-L-[(11,1-dioxo)thiamorpholin-3-carbonyl]-L-4-(N,N-dimethylcarbamyloxy)phenylalanine
N-(toluene-4-sulfonyl)-L-(5,5-dimethyl)thiaprolyl-L-4-(4-methylpiperazin-1-ylcarbonyloxy)phenylalanine tert-butyl ester
N-(toluene-4-sulfonyl)-L-(5,5-dimethyl)thiaprolyl-L-4-(4-methylpiperazin-1-ylcarbonyloxy)phenylalanine
N-(toluene-4-sulfonyl)sarcosyl-L-4-(N,N-dimethylcarbamyloxy)phenylalanine isopropyl ester
N-(toluene-4-sulfonyl)sarcosyl-L-4-(N,N-dimethylcarbamyloxy)phenylalanine tert-butyl ester
N-(toluene-4-sulfonyl)sarcosyl-L-4-(N,N-dimethylcarbamyloxy)phenylalanine
N-(toluene-4-sulfonyl)-L-prolyl-L-4-(N,N-dimethylaminosulfonyloxy)phenylalanine tert-butyl ester
N-(toluene-4-sulfonyl)-L-prolyl-L-4-(N,N-dimethylaminosulfonyloxy)phenylalanine
N-(1-methylimidazole-4-sulfonyl)-L-prolyl-L-4-(N,N-dimethylcarbamyloxy)phenylalanine tert-butyl ester
N-(4-aminobenzenesulfonyl)-L-prolyl-L-4-(N,N-dimethylcarbamyloxy)phenylalanine tert-butyl ester
N-(toluene-4-sulfonyl)sarcosyl-L-4-(morpholin-4-ylcarbonyloxy)phenylalanine tert-butyl ester
N-(toluene-4-sulfonyl)-L-prolyl-L-4-(morpholin-4-ylcarbonyloxy)phenylalanine tert-butyl ester
N-(α-toluenesulfonyl)-L-(5,5-dimethyl)thiaprolyl-L-4-(N,N-dimethylcarbamyloxy)phenylalanine
N-(toluene-4-sulfonyl)-L-(piperazin-2-carbonyl)-L-4-(N,N-dimethylcarbamyloxy)phenylalanine
N-(α-toluenesulfonyl)-t-(5,5-dimethyl)thiaprolyl-L-4-(N,N-dimethylcarbamyloxy)phenylalanine tert-butyl ester
N-(toluene-4-sulfonyl)-L-prolyl-L-4-(N,N-dimethylcarbamyloxy)phenylalanine N-adamantyl amide
N-(toluene-4-sulfonyl)-L-prolyl-L-4-(N,N-dimethylcarbamyloxy)phenylalanylglycine
N-(toluene-4-sulfonyl)-L-prolyl-L-4-(N,N-dimethylaminosulfonyloxy)phenylalanine methyl ester
N-(toluene-4-sulfonyl)-L-(piperazin-2-carbonyl)-L-4-(N,N-dimethylcarbamyloxy)phenylalanine tert-butyl ester
N-(toluene-4-sulfonyl)-L-(4-benzyloxycarbonylpiperazin-2-carbonyl)-L-4-(N,N-dimethylcarbamyloxy)phenylalanine tert-butyl ester
N-(toluene-4-sulfonyl)sarcosyl-L-4-(isonipecotoyloxy)phenylalanine
N-(toluene-4-sulfonyl)-L-[(1,1-dioxo)thiamorpholin-3-carbonyl]-L-4-(morpholin-4-ylcarbonyloxy)phenylalanine tert-butyl ester
N-(toluene-4-sulfonyl)-L-[(1,1-dioxo)thiamorpholin-3-carbonyl]-L-4-(morpholin-4-ylcarbonyloxy)phenylalanine
N-(1-methylpyrazole-4-sulfonyl)-L-prolyl-L-4-(N,N-dimethylcarbamyloxy)phenylalanine tert-butyl ester
N-(4-fluorobenzenesulfonyl)-L-prolyl-L-4-(N,N-dimethylcarbamyloxy)phenylalanine tert-butyl ester
N-(toluene-4-sulfonyl)sarcosyl-L-4-(4-methylpiperazin-1-ylcarbonyloxy)phenylalanine tert-butyl ester
N-(toluene-4-sulfonyl)-L-(1,1-dioxo-5,5-dimethyl)thiaprolyl-L-4-(N,N-dimethylcarbamyloxy)phenylalanine tert-butyl ester
N-(1-methylimidazole-4-sulfonyl)-L-prolyl-L-4-(N,N-dimethylcarbamyloxy)phenylalanine
2-(saccharin-2-yl)propionoyl-L-4-(N,N-dimethylcarbamyloxy)phenylalanine tert-butyl ester
N-(toluene-4-sulfonyl)-L-(1,1-dioxo-5,5-dimethyl)thiaprolyl-L-4-(N,N-dimethylcarbamyloxy)phenylalanine
N-(4-fluorobenzenesulfonyl)-L-prolyl-L-4-(N,N-dimethylcarbamyloxy)phenylalanine
N-(pyridine-3-sulfonyl)-L-prolyl-L-4-(N,N-dimethylcarbamyloxy)phenylalanine
N-(toluene-4-sulfonyl)-D-prolyl-L-4-(4-methylpiperazin-1-ylcarbonyloxy)phenylalanine tert-butyl ester
N-(toluene-4-sulfonyl)-L-N-methylalanyl-L-4-(4-methylpiperazin-1-ylcarbonyloxy)phenylalanine tert-butyl ester
N-(4-nitrobenzenesulfonyl)-L-prolyl-L-4-(N,N-dimethylcarbamyloxy)phenylalanine tert-butyl ester
N-(toluene-4-sulfonyl)-L-[(1,1-dioxo)thiamorpholin-3-carbonyl]-L-4-(N,N-dimethylaminosulfonyloxy)phenylalanine tert-butyl ester
N-(toluene-4-sulfonyl)sarcosyl-L-4-(thiomorpholin-4-ylcarbonyloxy)phenylalanine tert-butyl ester
N-(toluene-4-sulfonyl)-L-N-methylalanyl-L-4-(4-methylpiperazin-1-ylcarbonyloxy)phenylalanine
N-(toluene-4-sulfonyl)-L-prolyl-L-4-(1,1-dioxothiomorpholin-4-ylcarbonyloxy)phenylalanine
N-(toluene-4-sulfonyl)-L-prolyl-L-4-(thiomorpholin-4-ylcarbonyloxy)phenylalanine
N-(toluene-4-sulfonyl)-4-prolyl-L-4-(isonipecotoyloxy)phenylalanine
N-(toluene-4-sulfonyl)-L-prolyl-L-4-(pyrrolidin-1-ylcarbonyloxy)phenylalanine
N-(toluene-4-sulfonyl)-L-prolyl-L-4-(morpholin-4-ylcarbonyloxy)phenylalanine
N-(toluene-4-sulfonyl)-L-prolyl-L-4-(4-methylpiperazin-1-ylcarbonyloxy)phenylalanine neopentyl ester
N-(toluene-4-sulfonyl)-L-prolyl-L-4-(N,N-dimethylcarbamyloxy)phenylalanine neopentyl ester
N-(toluene-4-sulfonyl)-L-prolyl-L-4-(4-tert-butyloxycarbonylpiperazin-1-ylcarbonyloxy)phenylalanine ethyl ester N-(toluene-4-sulfonyl)-L-prolyl-L-4-(morpholin-4-ylcarbonyloxy)phenylalanine ethyl ester
2-(saccharin-2-yl)propionoyl-L-4-(4-methylpiperazin-1-ylcarbonyloxy)phenylalanine tert-butyl ester
2-(saccharin-2-yl)propionoyl-L-4-(N,N-dimethylcarbamyloxy)phenylalanine
N-(toluene-4-sulfonyl)sarcosyl-L-4-(,1-dioxothiomorpholin-4-ylcarbonyloxy)phenylalanine tert-butyl ester
N-(toluene-4-sulfonyl)sarcosyl-L-4-(thiomorpholin-4-ylcarbonyloxy)phenylalanine
N-(toluene-4-sulfonyl)-L-N-methylalanyl-L-4-(N,N-dimethylcarbamyloxy)phenylalanine tert-butyl ester
N-(toluene-4-sulfonyl)-L-(thiamorpholin-3-carbonyl)-L-4-(N,N-dimethylcarbamyloxy)phenylalanine tert-butyl ester
N-(toluene-4-sulfonyl)sarcosyl-L-4-(1,1-dioxothiomorpholin-4-ylcarbonyloxy)phenylalanine
N-(toluene-4-sulfonyl)-L-(1,1-dioxothiamorpholin-3-carbonyl)-L-4-(N,N-dimethylcarbamyloxy)phenylalanine tert-butyl ester
N-(toluene-4-sulfonyl)-L-(1,1-dioxothiamorpholin-3-carbonyl)-L-4-(morpholin-4-ylcarbonyloxy)phenylalanine tert-butyl ester
N-(toluene-4-sulfonyl)-L-N-methylalanyl-L-4-(N,N-dimethylcarbamyloxy)phenylalanine
N-(4-fluorobenzenesulfonyl)-L-(thiamorpholin-3-carbonyl)-L-4-(N,N-dimethylcarbamyloxy)phenylalanine tert-butyl ester
N-(4-fluorobenzenesulfonyl)-L-(1,1-dioxothiamorpholin-3-carbonyl)-L-4-(N,N-dimethylcarbamyloxy)phenylalanine tert-butyl ester
N-(pyridine-3-sulfonyl)-L-prolyl-L-4-(N,N-dimethylcarbamyloxy)phenylalanine tert-butyl ester
N-(pyrimidine-2-sulfonyl)-L-prolyl-L-4-(N,N-dimethylcarbamyloxy)phenylalanine tert-butyl ester
N-(4-nitrobenzenesulfonyl)-L-prolyl-L-4-(N,N-dimethylcarbamyloxy)phenylalanine
N-(4-cyanobenzenesulfonyl)-L-prolyl-L-4-(N,N-dimethylcarbamyloxy)phenylalanine tert-butyl ester
N-(toluene-4-sulfonyl)-L-(1,1-dioxothiamorpholin-3-carbonyl)-L-4-(N,N-dimethylaminosulfonyloxy)phenylalanine
N-(toluene-4-sulfonyl)-L-(1,1-dioxothiamorpholin-3-carbonyl)-L-4-(N,N-dimethylcarbamyloxy)phenylalanine
N-(toluene-4-sulfonyl)-L-(1,1-dioxo)thiaprolyl-L-4-(N,N-dimethylcarbamyloxy)phenylalanine tert-butyl ester
N-(4-fluorobenzenesulfonyl)-L-prolyl-L-4-(N,N-dimethylcarbamyloxy)phenylalanine tert-butyl ester
N-(1-methylpyrazole-4-sulfonyl)-L-prolyl-L-4-(N,N-dimethylcarbamyloxy)phenylalanine
N-(toluene-4-sulfonyl)-L-(1,1-dioxo)thiaprolyl-L-4-(N,N-dimethylcarbamyloxy)phenylalanine
N-(4-fluorobenzenesulfonyl)-L-thiaprolyl-L-4-(N,N-dimethylcarbamyloxy)phenylalanine
N-(toluene-4-sulfonyl)-L-prolyl-L-4-(piperazin-1-ylcarbonyloxy)phenylalanine
N-(toluene-4-sulfonyl)-L-prolyl-L-4-(1-tert-butyloxycarbonylpiperazin-1-ylcarbonyloxy)phenylalanine tert-butyl ester
N-(toluene-4-sulfonyl)-L-prolyl-L-4-(piperazin-1-ylcarbonyloxy)phenylalanine ethyl ester
N-(toluene-4-sulfonyl)-L-prolyl-L-4-(4-acetylpiperazin-1-ylcarbonyloxy)phenylalanine ethyl ester
N-(toluene-4-sulfonyl)-L-prolyl-L-4-(4-methanesulfonylpiperazin-1-ylcarbonyloxy)phenylalanine ethyl ester
N-(toluene-4-sulfonyl)-L-prolyl-L-4-(morpholin-4-ylcarbonyloxy)-3-nitrophenylalanine
N-(toluene-4-sulfonyl)-L-prolyl-L-4-(1-tert-butyloxycarbonylpiperazin-1-ylcarbonyloxy)phenylalanine
N-(toluene-4-sulfonyl)-L-N-methyl-2-(tert-butyl)glycinyl-L-4-(4-methylpiperazin-1-ylcarbonyloxy)phenylalanine tert-butyl ester
N-(4-fluorobenzenesulfonyl)-L-(5,5-dimethyl)thiaprolyl-L-4-(N,N-dimethylcarbamyloxy)phenylalanine tert-butyl ester
N-(4-fluorobenzenesulfonyl)-L-(1,1-dioxothiamorpholin-3-carbonyl)-L-4-(1,1-dioxothiomorpholin-4-ylcarbonyloxy)phenylalanine tert-butyl ester
N-(toluene-4-sulfonyl)-L-(1,1-dioxothiamorpholin-3-carbonyl)-L-4-(1,1-dioxothiomorpholin-4-ylcarbonyloxy)phenylalanine tert-butyl ester
N-(4-fluorobenzenesulfonyl)-L-prolyl-L-4-(1,1-dioxothiomorpholin-4-ylcarbonyloxy)phenylalanine tert-butyl ester
N-(4-fluorobenzenesulfonyl)-L-prolyl-L-4-(thiomorpholin-4-ylcarbonyloxy)phenylalanine tert-butyl ester
N-(4-fluorobenzenesulfonyl)-L-prolyl-L-4-(morpholin-4-ylcarbonyloxy)phenylalanine tert-butyl ester
N-(4-fluorobenzenesulfonyl)-L-(5,5-dimethyl)thiaprolyl-L-4-(N,N-dimethylcarbamyloxy)phenylalanine
N-(4-fluorobenzenesulfonyl)-L-(1,1-dioxothiamorpholin-3-carbonyl)-L-4-(morpholin-4-ylcarbonyloxy)phenylalanine tert-butyl ester
N-(4-trifluoromethoxybenzenesulfonyl)-L-prolyl-L-4-(N,N-dimethylcarbamyloxy)phenylalanine tert-butyl ester
N-(toluene-4-sulfonyl)-L-(1,1-dioxothiamorpholin-3-carbonyl)-L-4-(N,N-dimethylcarbamyloxy)phenylalanine isopropyl ester
3-[N-(toluene-4-sulfonyl)-N-methylamino]-1-[1-tert-butyloxycarbonyl-2-(N,N-dimethylcarbamyloxy)phenylethyl]azetidin-2-one
N-(4-fluorobenzenesulfonyl)-L-(1,1-dioxo-5,5-dimethyl)thiaprolyl-L-4-(N,N-dimethylcarbamyloxy)phenylalanine tert-butyl ester
N-(toluene-4-sulfonyl)-L-(1,1-dioxo-5,5-dimethyl)thiaprolyl-L-4-(N,N-s dimethylcarbamyloxy)phenylalanine isopropyl ester
N-(toluene-4-sulfonyl)-L-(1,1-dioxothiamorpholin-3-carbonyl)-L-4-(morpholin-4-ylcarbonyloxy)phenylalanine
N-(4-fluorobenzenesulfonyl)-L-(5,5-dimethyl)thiaprolyl-L-4-(N,N-dimethylcarbamyloxy)phenylalanine
N-(pyrimidine-2-sulfonyl)-L-prolyl-L-4-(N,N-dimethylcarbamyloxy)phenylalanine
N-(toluene-4-sulfonyl)-L-(1,1-dioxothiamorpholin-3-carbonyl)-L-4-(4-methylpiperazin-1-ylcarbonyloxy)phenylalanine tert-butyl ester
3-[N-(toluene-4-sulfonyl)-N-methylamino]-1-[1-carboxy-2-(N,N-dimethylcarbamyloxy)phenylethyl]azetidin-2-one
N-(1-methylpyrazole-4-sulfonyl)-L-prolyl-L-4-(4-methylpiperazin-1-ylcarbonyloxy)phenylalanine tert-butyl ester
N-(4-fluorobenzenesulfonyl)-L-(1,1-dioxo)thiaprolyl-L-4-(N,N-dimethylcarbamyloxy)phenylalanine
N-(toluene-4-sulfonyl)-L-prolyl-L-4-(isonipecotoyloxy)phenylalanine tert-butyl ester
N-(toluene-4-sulfonyl)-L-prolyl-L-4-(1,1-dioxothiomorpholin-4-ylcarbonyloxy)phenylalanine tert-butyl ester
N-(toluene-4-sulfonyl)-L-prolyl-L-4-(thiomorpholin-4-ylcarbonyloxy)phenylalanine tert-butyl ester N-(toluene-4-sulfonyl)-L-prolyl-L-4-(pyrrolidin-1-ylcarbonyloxy)phenylalanine tert-butyl ester
N-(4-fluorobenzenesulfonyl)-L-thiaprolyl-L-4-(N,N-dimethylcarbamyloxy)phenylalanine tert-butyl ester
N-(4-fluorobenzenesulfonyl)-L-(1,1-dioxo)thiaprolyl-L-4-(N,N-dimethylcarbamyloxy)phenylalanine tert-butyl ester
N-(2,5-dichlorothiophene-3-sulfonyl)-L-prolyl-L-4-(N,N-dimethylcarbamyloxy)phenylalanine tert-butyl ester
N-(4-acetamidobenzenesulfonyl)-L-prolyl-L-4-(N,N-dimethylcarbamyloxy)phenylalanine tert-butyl ester
N-(4-tert-butylbenzenesulfonyl)-L-(1,1-dioxothiamorpholin-3-carbonyl)-L-4-(N,N-dimethylcarbamyloxy)phenylalanine tert-butyl ester
N-(pyridine-2-sulfonyl)-L-prolyl-L-4-(N,N-dimethylcarbamyloxy)phenylalanine
N-(2-fluorobenzenesulfonyl)-L-(1,1-dioxothiamorpholin-3-carbonyl)-L-4-(N,N-dimethylcarbamyloxy)phenylalanine tert-butyl ester
N-(3-fluorobenzenesulfonyl)-L-(1,1-dioxothiamorpholin-3-carbonyl)-L-4-(N,N-dimethylcarbamyloxy)phenylalanine tert-butyl ester
N-(2,4-difluorobenzenesulfonyl)-L-(1,1-dioxothiamorpholin-3-carbonyl)-L-4-(N,N-dimethylcarbamyloxy)phenylalanine tert-butyl ester
N-(4-acetamidobenzenesulfonyl)-L-prolyl-L-4-(N,N-dimethylcarbamyloxy)phenylalanine
N-(4-trifluoromethoxybenzenesulfonyl)-L-prolyl-L-4-(NW-dimethylcarbamyloxy)phenylalanine
N-(4-fluorobenzenesulfonyl)-L-(5,5-dimethyl)thiaprolyl-L-4-(N,N-dimethylcarbamyloxy)phenylalanine tert-butyl ester
N-(4-cyanobenzenesulfonyl)-L-prolyl-L-4-(N,N-dimethylcarbamyloxy)phenylalanine
N-(toluene-4-sulfonyl)-L-(3,3-dimethyl)prolyl-L-4-(N,N-dimethylcarbamyloxy)phenylalanine tert-butyl ester
N-(toluene-4-sulfonyl)-L-(3,3-dimethyl)prolyl-L-4-(N,N-dimethylcarbamyloxy)phenylalanine isopropyl ester
N-(1-methylpyrazole-4-sulfonyl)-L-prolyl-L-4-(N,N-dimethylcarbamyloxy)phenylalanine isopropyl ester
N-(1-methylpyrazole-4-sulfonyl)-L-(5,5-dimethyl)thiaprolyl-L-4-(N,N-dimethylcarbamyloxy)phenylalanine tert-butyl ester
N-(1-methylpyrazole-4-sulfonyl)-L-(5,5-dimethyl)thiaprolyl-L-4-(N,N-dimethylcarbamyloxy)phenylalanine
N-(toluene-4-sulfonyl)-L-prolyl-L-4-(N-(1,4-dioxa-8-aza-spiro[4.5]decan-8-yl)carbonyloxy)phenylalanine ethyl ester
N-(toluene-4-sulfonyl)-L-prolyl-L-4-(N-(1,4-dioxa-8-aza-spiro[4.5]decan-8-yl)carbonyloxy)phenylalanine
N-(toluene-4-sulfonyl)-L-prolyl-L-4-(4'-acetylpiperazin-1-ylcarbonyloxy)phenyl alanine
N-(toluene-4-sulfonyl)-L-prolyl-L-4-(4'-methanesulfonylpiperazin-1-ylcarbonyloxy)phenylalanine
N-(toluene-4-sulfonyl)-L-prolyl-L-4-(4'-phenylpiperazin-1-ylcarbonyloxy)phenylalanine
N-(toluene-4-sulfonyl)-L-prolyl-L-4-(piperazin-1-ylcarbonyloxy)phenylalanine tert-butyl ester
2-(saccharin-2-yl)propionyl-L-4-(4'-methylpiperazin-1-ylcarbonyloxy)phenylalanine
N-(toluene-4-sulfonyl)-L-prolyl-L-4-(4'-methanesulfonylpiperazin-1-ylcarbonyloxy)phenylalanine tert-butyl ester
N-(toluene-4-sulfonyl)-L-prolyl-L-4-(N,N-dimethylcarbamyloxy)phenylalanine (N'-tert-butoxycarbonyl-2-amino-2-methylpropyl) ester
N-(toluene-4-sulfonyl)-L-prolyl-L-4-(4'-acetylpiperazin-1-ylcarbonyloxy)phenylalanine tert-butyl ester
N-(toluene-4-sulfonyl)-L-prolyl-L-4-(4-hydroxypiperidin-1-ylcarbonyloxy)phenylalanine tert-butyl ester
N-(toluene-4-sulfonyl)-L-prolyl-L-4-(N-(2-(morpholin-4'-yl)ethyl)carbamyloxy)phenylalanine tert-butyl ester
N-(toluene-4-sulfonyl)-L—prolyl-L-4-(N-(1,4-dioxa-8-aza-spiro[4.5]decan-8-yl)carbonyloxy)phenylalanine tert-butyl ester
N-(toluene-4-sulfonyl)-L-prolyl-L-4-(N-(2-hydroxyethyl)-N-methylcarbamyloxy)phenylalanine tert-butyl ester
N-(toluene-4-sulfonyl)-L-prolyl-4-(4'-(2-hydroxyethyl)piperazin-1-ylcarbonyloxy)-L-phenylalanine tert-butyl ester
N-(toluene-4-sulfonyl)-L-prolyl-L-4-(N-(2-formyloxyethyl)-N-methylcarbamyloxy)phenylalanine
N-(toluene-4-sulfonyl)-L-prolyl-L-4-(N-(2'-hydroxyethyl)-N-methylcarbamyloxy)phenylalanine isopropyl ester
N-(toulene-4-sulfonyl)-L-prolyl-L-4-(N-(methoxycarbonylmethyl)carbamyloxy)phenylalanine tert-butyl ester
N-(1-methylpyrazole-4-sulfonyl)-L-(5,5-dimethyl)thiaprolyl-L-(4-N,N-dimethylcarbamyloxy)phenylalanine isopropyl ester
N-(toluene-4-sulfonyl)-L-prolyl-L-4-(4'-methoxypiperidin-1-ylcarbonyloxy)phenylalanine isopropyl ester
N-(toluene-4-sulfonyl)-L-prolyl-L-4-(4'-methoxypiperidin-1-ylcarbonyloxy)phenylalanine
N-(toluene-4-sulfonyl)-L-4-oxoprolyl-L-4-(N,N-dimethylcarbamyloxy)phenylalanine tert-butyl ester
N-(toluene-4-sulfonyl)-L-trans-4-hydroxyprolyl-L-4-(N,N-dimethylcarbamyloxy)phenylalanine tert-butyl ester
N-(3-fluorobenzenesulfonyl)-L-prolyl-L-4-(N,N-dimethylcarbamyloxy)phenylalanine tert-butyl ester
N-(morpholino-sulfonyl)-L-prolyl-L-(4-N,N-dimethylcarbamyloxy)phenylalanine tert-butyl ester
N-(morpholino-sulfonyl)-L-prolyl-L-(4-N,N-dimethylcarbamyloxy)phenylalanine
N-(1-methylpyrazole-4-sulfonyl)-L-(1,1-dioxothiamorpholin-3-carbonyl)-L-4-(N,N-dimethylcarbamyloxy)phenylalanine tert-butyl ester
N-(2-fluorobenzenesulfonyl)-L-(1,1-dioxothiamorpholin-3-carbonyl)-L-4-(N,N-dimethylcarbamyloxy)phenylalanine
N-(2,4-difluorobenzenesulfonyl)-L-(1,1-dioxothiamorpholin-3-carbonyl)-L-4-(N,N-dimethylcarbamyloxy)phenylalanine
N-(toluene-4-sulfonyl)-L-(thiamorpholin-3-carbonyl)-L-4-(N,N-dimethylcarbamyloxy)phenylalanine
N-(pyridine-3-sulfonyl)-L-(5,5-dimethyl-thiaprolyl-L-4-(N,N-dimethylcarbamyloxy)phenylalanine isopropyl ester
N-(3-fluorobenzenesulfonyl)-L-(1,1-dioxothiamorpholin-3-carbonyl)-L-4-(N,N-dimethylcarbamyloxy)phenylalanine
N-(1-methylpyrazole-4-sulfonyl)-L-(1,1-dioxothiamorpholin-3-carbonyl)-L-4-(N,N-dimethylcarbamyloxy)phenylalanine
N-(4-tert-butylbenzenesulfonyl)-L-(1,1-dioxothiamorpholin-3-carbonyl)-L-4-(N,N-dimethylcarbamyloxy)phenylalanine
N-(toluene-4-sulfonyl)-(3,3-dimethyl)prolyl-L-4-(N,N-dimethylcarbamyloxy)phenylalanine
N-(2,5-dichlorothiophene-3-sulfonyl)-L-prolyl-L-4-(N,N-dimethylcarbamyloxy)phenylalanine N-(4-methoxybenzenesulfonyl)-L-prolyl-L-4-(N,N-dimethylcarbamyloxy)phenylalanine N-(4-methoxybenzenesulfonyl)-L-prolyl-L-4-(N,N-dimethylcarbamyloxy)phenylalanine isopropyl ester N-(toluene-4-sulfonyl)-L-(1-oxo-thiomorpholin-3-carbonyl)-L-4-(N,N-dimethylcarbamyloxy)phenylalanine N-(toluene-4-sulfonyl)-L-(1-oxo-thiomorpholin-3-carbonyl)-L-4-(N,N-dimethylcarbamyloxy)phenylalanine tert-butyl ester N-(3,4-difluorobenzenesulfonyl)-L-prolyl-4-(N,N-dimethylcarbamyloxy)phenylalanine isopropyl ester N-(3,4-difluorobenzenesulfonyl)-L-prolyl-4-(N,N-dimethylcarbamyloxy)phenylalanine N-(3,4-difluorobenzenesulfonyl)-L-(1,1-dioxothiamorpholin-3-carbonyl)-L-4-(N,N-dimethylcarbamyloxy)phenylalanine tert-butyl ester N-(3,4-difluorobenzenesulfonyl)-L-(1,1-dioxothiamorpholin-3-carbonyl)-L-4-(N,N-dimethylcarbamyloxy)phenylalanine N-(toluene-4-sulfonyl)-L-(5,5-dimethyl)thiaprolyl-L-(thiomorpholin-4-ylcarbonyloxy)phenylalanine tert-butyl ester N-(toluene-4-sulfonyl)-L-(5,5-dimethyl)thiaprolyl-L-(thiomorpholin-4-ylcarbonyloxy)phenylalanine N-(1-methylpyrazole-4-sulfonyl)-L-(5,5-dimethyl)thiaprolyl-L-4-(N,N-dimethylcarbamyloxy)phenylalanine ethyl ester N-(pyridine-3-sulfonyl)-L-(5,5-dimethyl)thiaprolyl-L-4-(N,N-dimethylcarbamyloxy)phenylalanine N-(pyridine-2-sulfonyl)-L-prolyl-L-4-(N,N-dimethylcarbamyloxy)phenylalanine isopropyl ester N-(pyridine-2-sulfonyl)-L-prolyl-L-4-(N,N-dimethylcarbamyloxy)phenylalanine N-(pyridine-2-sulfonyl)-L-(5,5-dimethyl)thiaprolyl-L-4-(N,N-dimethylcarbamyloxy)phenylalanine isopropyl ester N-(pyridine-2-sulfonyl)-L-(5,5-dimethyl)thiaprolyl-L-4-(N,N-dimethylcarbamyloxy)phenylalanine N-(toluene-4-sulfonyl)-L-(thiamorpholin-3-carbonyl)-L-4-(N,N-dimethylcarbamyloxy)phenylalanine isopropyl ester N-(3-fluorobenzenesulfonyl)-L-(5,5-dimethyl)thiaprolyl-L-4-(N,N-dimethylcarbamyloxy)phenylalanine isopropyl ester N-(2-fluorobenzenesulfonyl)-L-(5,5-dimethyl)thiaprolyl-L-4-(N,N-dimethylcarbamyloxy)phenylalanine isopropyl ester N-(3,4-difluorobenzenesulfonyl)-L-(5,5-dimethyl)thiaprolyl-L-4-(N,N-dimethylcarbamyloxy)phenylalanine isopropyl ester N-(3,5-difluorobenzenesulfonyl)-L-(5,5-dimethyl)thiaprolyl-L-4-(N,N-dimethylcarbamyloxy)phenylalanine isopropyl ester N-(2,4-difluorobenzenesulfonyl)-L-(5,5-dimethyl)thiaprolyl-L-4-(N,N-dimethylcarbamyloxy)phenylalanine isopropyl ester N-(4-chlorobenzenesulfonyl)-L-(5,5-dimethyl)thiaprolyl-L-4-(N,N-dimethylcarbamyloxy)phenylalanine isopropyl ester N-(3-chlorobenzenesulfonyl)-L-(5,5-dimethyl)thiaprolyl-L-4-(N,N-dimethylcarbamyloxy)phenylalanine isopropyl ester N-(2-chlorobenzenesulfonyl)-L-(5,5-dimethyl)thiaprolyl-L-4-(N,N-dimethylcarbamyloxy)phenylalanine isopropyl ester N-(3,4-dichlorobenzenesulfonyl)-L-(5,5-dimethyl)thiaprolyl-L-4-(N,N-dimethylcarbamyloxy)phenylalanine isopropyl ester N-(3,5-dichlorobenzenesulfonyl)-L-(5,5-dimethyl)thiaprolyl-L-4-(N,N-dimethylcarbamyloxy)phenylalanine isopropyl ester N-(3-chlorobenzenesulfonyl)-L-(1,1-dioxothiamorpholin-3-carbonyl)-L-4-(N,N-dimethylcarbamyloxy)phenylalanine tert-butyl ester N-(3,4-dichlorobenzenesulfonyl)-L-(1,1-dioxothiamorpholin-3-carbonyl)-L-4-(N,N-dimethylcarbamyloxy)phenylalanine tert-butyl ester N-(4-methoxybenzenesulfonyl)-L-(5,5-dimethyl)thiaprolyl-L-4-(N,N-dimethylcarbamyloxy)phenylalanine isopropyl ester N-(3-methoxybenzenesulfonyl)-L-(5,5-dimethyl)thiaprolyl-L-4-(N,N-dimethylcarbamyloxy)phenylalanine isopropyl ester N-(2-methoxybenzenesulfonyl)-L-(5,5-dimethyl)thiaprolyl-L-4-(N,N-dimethylcarbamyloxy)phenylalanine isopropyl ester N-(3,4-dimethoxybenzenesulfonyl)-L-(5,5-dimethyl)thiaprolyl-L-4-(N,N-dimethylcarbamyloxy)phenylalanine isopropyl ester N-(2,4-difluorobenzenesulfonyl)-L-(thiamorpholin-3-carbonyl)-L-4-(N,N-dimethylcarbamyloxy)phenylalanine isopropyl ester N-(3,4-dichlorobenzenesulfonyl)-L-(1,1-dioxothiamorpholin-3-carbonyl)-L-4-(N,N-dimethylcarbamyloxy)phenylalanine N-(3-chlorobenzenesulfonyl)-L-(1,1-dioxothiamorpholin-3-carbonyl)-L-4-(N,N-dimethylcarbamyloxy)phenylalanine N-(3-chloro-4-fluorobenzenesulfonyl)-L-(1,1-dioxothiamorpholin-3-carbonyl)-L-4-(N,N-dimethylcarbamyloxy)phenylalanine tert-butyl ester N-(1-methylpyrazole-4-sulfonyl)-L-(thiamorpholin-3-carbonyl)-L-4-(N,N-dimethylcarbamyloxy)phenylalanine tert-butyl ester N-(3,4-difluorobenzenesulfonyl)-L-(thiamorpholin-3-carbonyl)-L-4-(N,N-dimethylcarbamyloxy)phenylalanine tert-butyl ester N-(toluene-4-sulfonyl)-L-(5,5-dimethyl)thioprolyl-L-(thiomorpholin-4-ylcarbonyloxy)phenylalanine isopropyl ester N-(3,4-difluorobenzenesulfonyl)-L-(thiamorpholin-3-carbonyl)-L-4-(N,N-dimethylcarbamyloxy)phenylalanine N-(2,5-dichlorothiophene-3-sulfonyl)-L-(5,5-dimethyl)thiaprolyl-L-4-(N,N-dimethylcarbamyloxy)phenylalanine isopropyl ester N-(1-methylpyrazole-4-sulfonyl)-L-(5,5-dimethyl)thiaprolyl-L-4-(thiomorpholin-4-ylcarbonyloxy)phenylalanine isopropyl ester N-(8-quinolinesulfonyl)-L-prolyl-L-4-(N,N-dimethylcarbamyloxy)phenylalanine isopropyl ester N-(8-quinolinesulfonyl)-L-prolyl-L-4-(N,N-dimethylcarbamyloxy)phenylalanine N-(8-quinolinesulfonyl)-L-(5,5-dimethyl)thiaprolyl-L-4-(N,N-dimethylcarbamyloxy)phenylalanine isoproplyl ester N-(8-quinolinesulfonyl)-L-(5,5-dimethyl)thiaprolyl-L-4-(N,N-dimethylcarbamyloxy)phenylalanine N-(toluene-4-sulfonyl)-L-prolyl-L-4-(4-phenylpiperazin-1-ylcarbonyloxy)phenylalanine tert-butyl ester N-(toluene-4-sulfonyl)-L-prolyl-L-4-(4'-(ethoxycarbonyl)piperidin-1-ylcarbonyloxy)phenyl alanine tert-butyl ester N-(pyridine-3-sulfonyl)-L-(5,5-dimethyl)thiaprolyl-L-4-(N,N-dimethylcarbamyloxy)phenylalanine tert-butyl ester N-(3-sulfonamido-4-chloro-benzenesulfonyl)-L-prolyl-L-4-(N,N-dimethylcarbamyloxy)phenylalanine isopropyl ester N-(toluene-4-sulfonyl)-L-(1-oxothiomorpholin-3-carbonyl)-L-4-(N,N-dimethylcarbamyloxy)phenylalanine isopropyl ester N-(2,4-difluorobenzenefulfonyl)-L-(1-oxothiomorpholin-3-carbonyl)-L-4-(N,N-dimethylcarbamyloxy)phenylalanine tert-butyl ester N-(1-methylpyrazol-4-sulfonyl)-L-(5,5-dimethyl)thiaprolyl-L-4-(N,N-dimethylcarbamyloxy)phenylalanine 2,2-dimethylpropyl ester N-(pyridine-3-sulfonyl)-L-(5,5-dimethyl)thiaprolyl-L-4-(N,N-dimethylcarbamyloxy)phenylalanine 2,2-dimethylpropyl ester.

N-(1-methylpyrazole-4-sulfonyl)-L-(5,5-dimethyl)thiaprolyl-L-4-(N,N-dimethylcarbamyloxy)phenylalanine cyclopropylmethyl ester N-(1-methylpyrazole-4-sulfonyl)-L-(5,5-dimethyl)thiaprolyl-L-4-(N,N-dimethylcarbamyloxy)phenylalanine methyl ester N-(pyridine-3-sulfonyl)-L-(5,5-dimethyl)thiaprolyl-L-4-(N,N-dimethylcarbamyloxy)phenylalanine ethyl ester N-(pyridine-3-sulfonyl)-L-(5,5-dimethyl)thiaprolyl-L-4-(N,N-dimethylcarbamyloxy)phenylalanine cyclopropylmethyl ester N-(1-methylpyrazole-4-sulfonyl)-L-(5,5-dimethyl)thiaprolyl-L-4-(N,N-dimethylcarbamyloxy)phenylalanine 2-methoxyphenyl ester N-(1-methylpyrazole-4-sulfonyl)-L-(5,5-dimethyl)thiaprolyl-L-4-(N,N-dimethylcarbamyloxy)phenylalanine n-butyl ester N-(1-methylpyrazole-4-sulfonyl)-L-(5,5-dimethyl)thiaprolyl-L-4-(N,N-dimethylcarbamyloxy)phenylalanine n-propyl ester N-(1-methylpyrazole-4-sulfonyl)-L-(5,5-dimethyl)thiaprolyl-L-4-(N,N-dimethylcarbamyloxy)phenylalanine 2,2-dimethylpropionyloxymethyl ester N-(toluene-4-sulfonyl)-L-prolyl-L-4-(N-(4'-(2'-aminoethyl)morpholino)carbamyloxy)phenylalanine N-(toluene-4-sulfonyl)-L-prolyl-L-4-[4-(carboxy)piperidin-1-ylcarbonyloxy]phenylalanine N-(toluene-4-sulfonyl)-L-prolyl-L-4-(N,N-bis-(2-hydroxyethyl)carbamyloxy)phenylalanine isopropyl ester N-(toluene-4-sulfonyl)-L-prolyl-L-4-[3-(hydroxymethyl)piperidin-1-ylcarbonyloxy]phenylalanine isopropyl ester N-(toluene-4-sulfonyl)-L-prolyl-L-4-(4-trifluoromethanesulfonylpiperazin-1-ylcarbonyloxy)phenylalanine tert-butyl ester N-(4-(N-phenylurea)benzenesulfonyl)-L-prolyl-L-4-(N,N-dimethylcarbamyloxy)phenylalanine tert-butyl ester N-(2-trifluoroacetyl-1,2,3,4-tetrahydroisoquinolin-7-sulfonyl)-L-prolyl-L-4-(N,N-dimethylcarbamyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine N-(pyridine-4-sulfonyl)-L-(5,5-dimethyl)thiaprolyl-L-4-(N,N-dimethylcarbamyloxy)phenylalanine isopropyl ester N-(pyridine-4-sulfonyl)-L-(5,5-dimethyl)thiaprolyl-L-4-(N,N-dimethylcarbamyloxy)phenylalanine N-(toluene-4-sulfonyl)-L-(5,5-dimethyl)thiaprolyl-L-4-(N-methyl-N-(2-dimethylaminoethyl)carbamyloxy)phenylalanine tert-butyl ester N-(toluene-4-sulfonyl)-L-prolyl-L-4-(N-methyl-N-(2-dimethylaminoethyl)carbamyloxy)phenylalanine tert-butyl ester N-(toluene-4-sulfonyl)-L-(5,5-dimethyl)thiaprolyl-L-4-(N-methyl-N-(2-dimethylaminoethyl)carbamyloxy)phenylalanine N-(toluene-4-sulfonyl)-L-prolyl-L-4-(N-methyl-N-(2-dimethylaminoethyl)carbamyloxy)phenylalanine N-(4-fluorobenzenesulfonyl)-L-(5,5-dimethyl)thiaprolyl-L-3-chloro-4-(4-methylpiperazin-1-ylcarbonyloxy)phenylalanine tert-butyl ester N-(4-fluorobenzenesulfonyl)-L-(5,5-dimethyl)thiaprolyl-L-3-chloro-4-(N,N-dimethycarbamyloxy)phenylalanine N-(4-fluorobenzenesulfonyl)-L-(5,5-dimethyl)thiaprolyl-L-3-chloro-4-(thiomorpholin-4-ylcarbonyloxy)phenylalanine tert-butyl ester N-(4-fluorobenzenesulfonyl)-L-(5,5-dimethyl)thiaprolyl-L-3-chloro-4-(thiomorpholin-4-ylcarbonyloxy)phenylalanine isopropyl ester N-(4-fluorobenzenesulfonyl)-L-(5,5-dimethyl)thiaprolyl-L-3-chloro-4-(N,N-dimethylcarbamyloxy)]phenylalanine isopropyl ester N-(toluene-4-sulfonyl)-L-(5,5-dimethyl)thiaprolyl-L-3-chloro-4-(N,N-dimethylcarbamyloxy)phenylalanine isopropyl ester N-(4-fluorobenzenesulfonyl)-L-(5,5-dimethyl)thiaprolyl-L-3-chloro-4-(4-methylpiperazin-1-ylcarbonyloxy)]phenylalanine isopropyl ester N-(toluene-4-sulfonyl)-L-prolyl-L-3-chloro-4-(N,N-dimethylcarbamyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine tert-butyl ester N-(4-nitrobenzenesulfonyl)-L-prolyl-L-4-(N,N-dimethylcarbamyloxy)phenylalanine isopropyl ester N-(4-aminobenzenesulfonyl)-L-prolyl-L-4-(N,N-dimethylcarbamyloxy)phenylalanine isopropyl ester N-(toluene-4-sulfonyl)-L-prolyl-L-4-(thiomorpholin-4-ylcarbonyloxy)phenylalanine isopropyl ester N-(toluene-4-sulfonyl)-L-prolyl-L-4-(4-phenylcarbamylpiperazin-1-ylcarbonyloxy)phenylalanine isopropyl ester N-(toluene-4-sulfonyl)-L-prolyl-L-4-(4-phenylcarbamylpiperazin-1-ylcarbonyloxy)phenylalanine N-(1-n-butylpyrazole-4-sulfonyl)-L-(5,5-dimethyl)thiaprolyl-L-4-(N,N-dimethylcarbamyloxy)phenylalanine isopropyl ester N-(toluene-4-sulfonyl)-L-prolyl-L-4-(pyridin-4-ylcarbonyl)piperazin-1-ylcarbonyloxy)phenylalanine isopropyl ester N-(toluene-4-sulfonyl)-L-4-oxoprolyl-L-4-(N,N-dimethylcarbamyloxy)phenylalanine N-(toluene-4-sulfonyl)-L-trans-4-hydroxyprolyl-L-4-(N,N-dimethylcarbamyloxy)phenylalanine N-(4-cyanobenzenesulfonyl)-L-prolyl-L-4-(N,N-dimethylcarbamyloxy)phenylalanine isopropyl ester
N-(4-aminobenzenesulfonyl)-L-prolyl-L-4-(N,N-dimethylcarbamyloxy)phenylalanine
N-(toluene-4-sulfonyl)-L-4-oxoprolyl-L-4-(4-methylpiperazin-1-ylcarbonyloxy)phenylalanine tert-butyl ester
N-(toluene-4-sulfonyl)-L-prolyl-L-4-[3-(hydroxymethyl)piperidin-1-ylcarbonyloxy]phenylalanine
N-(toluene-4-sulfonyl)-L-(4,4-difluoro)prolyl-L-4-(N,N-dimethylcarbamyloxy)phenylalanine isopropyl ester
N-(toluene-4-sulfonyl)-L-(4,4-difluoro)prolyl-L-4-(N,N-dimethylcarbamyloxy)phenylalanine
N-(toluene-4-sulfonyl)-L-prolyl-L-(4-benzoylpiperazin-1-ylcarbonyloxy)phenylalanine isopropyl ester
N-(1-methyl-1H-imidazole-4-sulfonyl)-L-prolyl-L-4-(N,N-dimethylcarbamyloxy)phenylalanine isopropyl ester
N-(toluene-4-sulfonyl)-L-4-(thiomorpholin-4-ylcarbonyloxy)prolyl-L-4-(thiomorpholin-4-ylcarbonyloxy)phenylalanine
N-(4-cyanobenzenesulfonyl)-L-prolyl-L-4-(thiomorpholin-4-ylcarbonyloxy)phenylalanine isopropyl ester
N-(4-amidinobenzenesulfonyl)-L-prolyl-L-4-(N,N-dimethylcarbamyloxy)phenylalanine methyl ester
N-(toluene-4-sulfonyl)-L-4-oxoprolyl-L-4-(thiomorpholin-4-ylcarbonyloxy)phenylalanine tert-butyl ester
N-(toluene-4-sulfonyl)-L-4-hydroxyprolyl-L-4-(thiomorpholin-4-ylcarbonyloxy)phenylalanine
N-(toluene-4-sulfonyl)-L-prolyl-L-(4-benzoylpiperazin-1-ylcarbonyloxy)phenylalanine
N-(4-amidinobenzenesulfonyl)-L-prolyl-L-4-(thiomorpholin-4-ylcarbonyloxy)phenylalanine methyl ester
N-(3-fluorobenzenesulfonyl)-L-prolyl-L-4-(N,N-dimethylcarbonyloxy)phenylalanine
N-(toluene-4-sulfonyl)-L-prolyl-L-4-[N-methyl-N-(2-(N'-methyl-N'-toluenesulfonyl-amino)ethyl)carbamyloxy]phenylalanine isopropyl ester
N-(toluene-4-sulfonyl)-L-prolyl-L-4-[N-(2-(N'-phenylaminocarbonyloxy)ethyl)carbamyloxy)]phenylalanine isopropyl ester
N-(4-fluorobenzenesulfonyl)-L-4-(trans-hydroxy)prolyl-L-4-(N,N-dimethylcarbamyloxy)phenylalanine isopropyl ester
N-(4-fluorobenzenesulfonyl)-L-4-(trans-hydroxy)prolyl-L-4-(N,N-dimethylcarbamyloxy)phenylalanine tert-butyl ester
N-(4-amidinobenzenesulfonyl)-L-prolyl-L-4-(N,N-dimethylcarbamyloxy)phenylalanine
piperazine-1,4-dicarboxylic acid bis-{4-[(2S)-2-tert-butoxycarbonyl-2-((4R)-5,5-dimethyl-3-(toluene-4-sulfonyl)thiazolidine-4-carboxamido)ethyl]phenyl} ester
piperazine-1,4-dicarboxylic acid bis-{4-[(2S)-2-carboxy-2-((4R)-5,5-dimethyl-3-(toluene-4-sulfonyl)thiazolidine-4-carboxamido)ethyl]phenyl} ester
N-(toluene-4-sulfonyl)-L-(pyrazin-3-carbonyl)-L-4-(N,N-dimethylcarbamyloxy)phenylalanine tert-butyl ester
N-(4-fluorobenzenesulfonyl)-L-(5,5-dimethyl)thiaprolyl-L-4-(2-hydroxymethylpyrrolidin-1-ylcarbonyloxy)phenylalanine tert-butyl ester
N-(4-fluorobenzenesulfonyl)-L-(5,5-dimethyl)thiaprolyl-L-4-(2-hydroxymethylpyrrolidin-1-ylcarbonyloxy)phenylalanine
N-(toluene-4-sulfonyl)-L-prolyl-L-4-(2-methoxycarbonylpyrrolidin-1-ylcarbonyloxy)phenylalanine tert-butyl ester
N-(4-fluorobenzenesulfonyl)-L-(5,5-dimethyl)thiaprolyl-L-3-chloro-4-(thiomorpholin-4-ylcarbonyloxy)phenylalanine
N-(4-fluorobenzenesulfonyl)-L-(5,5-dimethyl)thiaprolyl-L-4-(4-(2-pyridyl)piperazin-1-ylcarbonyloxy)]phenylalanine
N-(4-fluorobenzenesulfonyl)-L-(5,5-dimethyl)thiaprolyl-L-4-(4-(2-pyridyl)piperazin-1-ylcarbonyloxy)]phenylalanine tert-butyl ester
piperazine-1,4-dicarboxylic acid bis-{4-[(2S)-2-isopropoxycarbonyl-2-((2R)-1-(toluene-4-sulfonyl)pyrrolidine-2-carboxamido)ethyl]phenyl} ester
N-(toluene-4-sulfonyl)-L-(4-hydroxy)prolyl-L-4-(thiomorpholin-4-ylcarbonyloxy)phenylalanine tert-butyl ester
N-(toluene-4-sulfonyl)-L-prolyl-L-4-(N,N-dimethylcarbamyloxy)phenylalanine 2-(2-methoxyethoxy)ethyl ester
N-(4-fluorobenzenesulfonyl)-L-(5,5-dimethyl)thiaprolyl-L-4-(4-(2-pyrimidyl)piperazin-1-ylcarbonyloxy)]phenylalanine tert-butyl ester
N-(4-fluorobenzenesulfonyl)-L-(5,5-dimethyl)thiaprolyl-L-3-fluoro-4-(N,N-dimethylcarbamyloxy)phenylalanine isopropyl ester
N-(toluene-4-sulfonyl)-L-(1-methanesulfonylpyrazin-3-carbonyl)-L-4-(N,N-dimethylcarbamyloxy)phenylalanine tert-butyl ester
N-[2-(1,1-dioxo-2,3-dihydro-3,3-dimethyl-1,2-benzisothiazol-2-yl)acetyl]-L-4-(N,N-dimethylcarbamyloxy)phenylalanine
N-[2-(N-2, 10-camphorsultamyl)acetyl]-L-4-(N,N-dimethylcarbamyloxy)phenylalanine tert-butyl ester
N-[2-(N-2, 10-camphorsultamyl)acetyl]-L-4-(N,N-dimethylcarbamyloxy)phenylalanine
N-[2-(N-2, 10-camphorsultamyl)acetyl]-L-3-chloro-4-(N,N-dimethylcarbamyloxy)phenylalanine isopropyl ester
N-(4-bromobenzenesulfonyl)-L-(5,5-dimethyl)thiaprolyl-L-4-(N,N-dimethylcarbamyloxy)phenylalanine tert-butyl ester
N-(4-bromobenzenesulfonyl)-L-(5,5-dimethyl)thiaprolyl-L-4-(N,N-dimethylcarbamyloxy)phenylalanine
N-(toluene-4-sulfonyl)-L-(4-hydroxy)prolyl-L-4-(4-methylpiperazin-1-ylcarbonyloxy)phenylalanine
N-(4-fluorobenzenesulfonyl)-L-(5,5-dimethyl)thiaprolyl-L-4-(4-(2-pyrimidyl)piperazin-1-ylcarbonyloxy)]phenylalanine
piperazine-1,4-dicarboxylic acid bis-{4-[(2S)-2-tert-butoxycarbonyl-2-((2R)-1-(toluene-4-sulfonyl)pyrrolidine-2-carboxamido)ethyl]phenyl} ester
N-(4-fluorobenzenesulfonyl)-L-(5,5-dimethyl)thiaprolyl-L-4-(4-(2-pyridyl)piperazin-1-ylcarbonyloxy)]phenylalanine isopropyl ester
N-(4-fluorobenzenesulfonyl)thiazolidinyl-2-carbonyl-L-4-(N,N-dimethylcarbamyloxy)phenylalanine
N-(4-fluorobenzenesulfonyl)thiazolidinyl-2-carbonyl-L-4-(N,N-dimethylcarbamyloxy)phenylalanine tert-butyl ester
N-(toluene-4-sulfonyl)-L-(4-oxo)prolyl-L-4-(thiomorpholin-4-ylcarbonyloxy)phenylalanine
N-(toluene-4-sulfonyl)-L-(4-oxo)prolyl-L-4-(4-methylpiperazin-1-ylcarbonyloxy)phenylalanine
N-(4-fluorobenzenesulfonyl)thiazolidinyl-2-carbonyl-L-4-(4-(2-pyridyl)piperazin-1-ylcarbonyloxy)]phenylalanine
N-(4-nitrobenzenesulfonyl)-L-prolyl-L-4-(4-(2-pyridyl)piperazin-1-ylcarbonyloxy)]phenylalanine tert-butyl ester
N-(4-fluorobenzenesulfonyl)thiazolidinyl-2-carbonyl-L-4-(4-(2-pyridyl)piperazin-1-ylcarbonyloxy)]phenylalanine tert-butyl ester N-(4-bromobenzenesulfonyl)-L-(5,5-dimethyl)thiaprolyl-L-4-(4-(2-pyridyl)piperazin-1-ylcarbonyloxy)]phenylalanine N-(toluene-4-sulfonyl)-L-prolyl-L-4-(4-(N-phenylthiocarbonyl)piperazin-1-ylcarbonyloxy)]phenylalanine isopropyl ester N-(4-fluorobenzenesulfonyl)thiazolidinyl-2-carbonyl-L-4-(4-methylhomopiperazin-1-ylcarbonyloxy)phenylalanine tert-butyl ester piperazine-1,4-dicarboxylic acid bis-{4-[(2S)-2-carboxyl-2-((2R)-1-(toluene-4-sulfonyl)pyrrolidine-2-carboxamido)ethyl]phenyl} ester N-(toluene-4-sulfonyl)-L-4-(methanesulfonyloxy)prolyl-L-4-(N,N-dimethylcarbamyloxy)phenylalanine tert-butyl ester N-(4-aminocarbonylbenzenesulfonyl)-L-prolyl-L-4-(N,N-dimethylcarbamyloxy)phenylalanine N-(4-aminocarbonylbenzenesulfonyl)-L-prolyl-L-4-(thiomorpholin-4-ylcarbonyloxy)phenylalanine N-(4-amidinobenzenesulfonyl)-L-prolyl-L-4-(thiomorpholin-4-ylcarbonyloxy)phenylalanine N-(4-nitrobenzenesulfonyl)-L-prolyl-L-4-(4-(2-pyridyl)piperazin-1-ylcarbonyloxy)]phenylalanine N-(4-fluorobenzenesulfonyl)-L-(5,5-dimethyl)thiaprolyl-L-3-chloro-4-(4-(2-pyridyl)piperazin-1-ylcarbonyloxy)]phenylalanine ethyl ester N-(4-fluorobenzenesulfonyl)-L-(5,5-dimethyl)thiaprolyl-L-3-chloro-4-(4-(2-pyridyl)piperazin-1-ylcarbonyloxy)phenylalanine N-(4-fluorobenzenesulfonyl)thiazolidinyl-2-carbonyl-L-4-(4-methylhomopiperazin-1-ylcarbonyloxy)phenylalanine N-(1-methylpyrazole-3-sulfonyl)-L-(5,5-dimethyl)thiaprolyl-L-3-chloro-4-(N,N-dimethylcarbamyloxy)phenylalanine isopropyl ester N-(1-methylimidazole-4-sulfonyl)-L-prolyl-L-4-(4-(2-pyridyl)piperazin-1-ylcarbonyloxy)phenylalanine isopropyl ester N-(1-methylimidazole-4-sulfonyl)-L-prolyl-L-4-(4-(2-pyridyl)piperazin-1-ylcarbonyloxy)phenylalanine tert-butyl ester N-(toluene-4-sulfonyl)-L-prolyl-L-4-(4-(2-pyridyl)piperazin-1-ylcarbonyloxy)phenylalanine N-(toluene-4-sulfonyl)-L-prolyl-L-4-(4-(2-pyridyl)piperazin-1-ylcarbonyloxy)phenylalanine tert-butyl ester N-(toluene-4-sulfonyl)-L-prolyl-L-4-(4-(2-pyridyl)piperazin-1-ylcarbonyloxy)phenylalanine isopropyl ester N-(4-fluorobenzenesulfonyl)-L-prolyl-L-4-(4-(2-pyridyl)piperazin-1-ylcarbonyloxy)phenylalanine isopropyl ester N-(4-fluorobenzenesulfonyl)-L-prolyl-L-4-(4-(2-pyridyl)piperazin-1-ylcarbonyloxy)phenylalanine tert-butyl ester N-(toluene-4-sulfonyl)-L-(1-methanesulfonylpyrazin-3-carbonyl)-L-4-(N,N-dimethylcarbamyloxy)phenylalanine N-(toluene-4-sulfonyl)-L-4-(methanesulfonyloxy)prolyl-L-4-(N,N-dimethylcarbamyloxy)phenylalanine N-(methanesulfonyl)-N-benzylglycinyl-L-4-(N,N-dimethylcarbamyloxy)phenylalanine tert-butyl ester N-(4-bromobenzenesulfonyl)-L-(5,5-dimethyl)thiaprolyl-L-4-(4-(2-pyridyl)piperazin-1-ylcarbonyloxy)phenylalanine tert-butyl ester N-(4-trifluoromethoxybenzenesulfonyl)-L-(5,5-dimethyl)thiaprolyl-L-4-(N,N-dimethylcarbamyloxy)phenylalanine N-(4-trifluoromethoxybenzenesulfonyl)-L-(5,5-dimethyl)thiaprolyl-L-4-(N,N-dimethylcarbamyloxy)phenylalanine tert-butyl ester N-(4-trifluoromethoxybenzenesulfonyl)-L-(5,5-dimethyl)thiaprolyl-L-4-(4-(2-pyridyl)piperazin-1-ylcarbonyloxy)phenylalanine tert-butyl ester N-(4-fluorobenzenesulfonyl)-L-prolyl-L-4-(4-(2-pyridyl)piperazin-1-ylcarbonyloxy)phenylalanine N-(4-fluorobenzenesulfonyl)-L-(4-hydroxy)prolyl-L-4-(4-(2-pyridyl)piperazin-1-ylcarbonyloxy)phenylalanine N-(4-trifluoromethoxybenzenesulfonyl)-L-(5,5-dimethyl)thiaprolyl-L-4-(4-(2-pyridyl)piperazin-1-ylcarbonyloxy)phenylalanine N-(1-methylimidazole-4-sulfonyl)-L-prolyl-L-3-chloro-4-(N,N-dimethylcarbamyloxy)phenylalanine N-(1-methylimidazole-4-sulfonyl)-L-prolyl-L-3-chloro-4-(N,N-dimethylcarbamyloxy)phenylalanine isopropyl ester N-(1-methylimidazole-4-sulfonyl)-L-prolyl-L-4-(4-(2-pyridyl)piperazin-1-ylcarbonyloxy)phenylalanine N-(1-methylimidazole-4-sulfonyl)-L-(5,5-dimethyl)thiaprolyl-L-4-(4-(2-pyridyl)piperazin-1-ylcarbonyloxy)phenylalanine N-(1-methylpyrazole-3-sulfonyl)-L-prolyl-L-4-(4-(2-pyridyl)piperazin-1-ylcarbonyloxy)phenylalanine N-(1-methylpyrazole-3-sulfonyl)-L-prolyl-L-4-(4-(2-pyridyl)piperazin-1-ylcarbonyloxy)phenylalanine isopropyl ester N-(1-methylpyrazole-3-sulfonyl)-L-prolyl-L-4-(4-(2-pyridyl)piperazin-1-ylcarbonyloxy)phenylalanine tert-butyl ester N-(1-methylpyrazole-3-sulfonyl)-L-(5,5-dimethyl)thiaprolyl-L-4-(4-(2-pyridyl)piperazin-1-ylcarbonyloxy)phenylalanine tert-butyl ester N-(1-methylimidazole-4-sulfonyl)-L-prolyl-L-3-chloro-4-(4-(2-pyridyl)piperazin-1-ylcarbonyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine 2-phenoxyethyl ester N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine ethyl ester N-(3-chloro-1,5-dimethylpyrazole-3-sulfonyl)-L-(5,5-dimethyl)thiaprolyl-L-3-chloro-4-(4-(5-trifluoromethyl-2-pyridyl)piperazin-1-ylcarbonyloxy)phenylalanine and pharmaceutically acceptable salts thereof as well as any of the ester compounds recited above wherein one ester is replaced with another ester selected from the group consisting of methyl ester, ethyl ester, n-propyl ester, isopropyl ester, n-butyl ester, isobutyl ester, sec-butyl ester, tert-butyl ester and neopentyl ester.

More preferred compounds within the scope of Formulae I and IA and IB (below) include by way of example:

N-(toluene-4-sulfonyl)-L-prolyl-L-4-(4-methylpiperazin-1-ylcarbonyloxy)phenylalanine ethyl ester N-(toluene-4-sulfonyl)-L-prolyl-L-4-(N,N-dimethylcarbamyloxy)phenylalanine ethyl ester N-(toluene-4-sulfonyl)-L-prolyl-L-4-(4-methylpiperazin-1-ylcarbonyloxy)phenylalanine isopropyl ester N-(toluene-4-sulfonyl)-L-prolyl-L-4-(4-methylpiperazin-1-ylcarbonyloxy)phenylalanine n-butyl ester
N-(toluene-4-sulfonyl)-L-prolyl-L-4-(4-methylpiperazin-1-ylcarbonyloxy)phenylalanine cyclopentyl ester
N-(toluene-4-sulfonyl)-L-prolyl-L-4-(4-methylpiperazin-1-ylcarbonyloxy)phenylalanine tert-butyl ester
N-(toluene-4-sulfonyl)-L-prolyl-L-4-(4-methylpiperazin-1-ylcarbonyloxy)phenylalanine
N-(toluene-4-sulfonyl)-L-prolyl-L-4-(N,N-dimethylcarbamyloxy)phenylalanine isopropyl ester
N-(toluene-4-sulfonyl)-L-prolyl-L-4-(N,N-dimethylcarbamyloxy)phenylalanine n-butyl ester
N-(toluene-4-sulfonyl)-L-prolyl-L-4-(N,N-dimethylcarbamyloxy)phenylalanine cyclopentyl ester
N-(toluene-4-sulfonyl)-L-prolyl-L-4-(N,N-dimethylcarbamyloxy)phenylalanine tert-butyl ester
N-(toluene-4-sulfonyl)-L-prolyl-L-4-(N,N-dimethylcarbamyloxy)phenylalanine
N-(toluene-4-sulfonyl)-L-prolyl-L-4-(isonipecotoyloxy)phenylalanine ethyl ester
N-(α-toluenesulfonyl)-L-prolyl-L-4-(N-methylisonipecotoyloxy)phenylalanine ethyl ester
N-(α-toluenesulfonyl)-L-prolyl-L-4-(4-methylpiperazin-1-ylcarbonyloxy)phenylalanine
N-(toluene-4-sulfonyl)-L-prolyl-L-3-(N,N-dimethylcarbamyloxy)phenylalanine ethyl ester
N-(toluene-4-sulfonyl)-L-prolyl-L-4-(1-tert-butylcarbonyloxy-4-phenylpiperidin-4-ylcarbonyloxy)phenylalanine ethyl ester
N-(toluene-4-sulfonyl)-L-(5,5-dimethyl)thiaprolyl-L-4-(N,N-dimethylcarbamyloxy)phenylalanine isopropyl ester
N-(toluene-4-sulfonyl)-L-(5,5-dimethyl)thiaprolyl-L-4-(N,N-dimethylcarbamyloxy)phenylalanine tert-butyl ester
N-(toluene-4-sulfonyl)-L-(5,5-dimethyl)thiaprolyl-L-4-(N,N-dimethylcarbamyloxy)phenylalanine
N-(toluene-4-sulfonyl)-L-[(1,1-dioxo)thiamorpholin-3-carbonyl]-L-4-(N,N-dimethylcarbamyloxy)phenylalanine tert-butyl ester
N-(toluene-4-sulfonyl)-L-[(1,1-dioxo)thiamorpholin-3-carbonyl]-L-4-(N,N-dimethylcarbamyloxy)phenylalanine
N-(toluene-4-sulfonyl)-L-(5,5-dimethyl)thiaprolyl-L-4-(4-methylpiperazin-1-ylcarbonyloxy)phenylalanine tert-butyl ester
N-(toluene-4-sulfonyl)-L-(5,5-dimethyl)thiaprolyl-L-4-(4-methylpiperazin-1-ylcarbonyloxy)phenylalanine
N-(toluene-4-sulfonyl)sarcosyl-L-4-(N,N-dimethylcarbamyloxy)phenylalanine isopropyl ester
N-(toluene-4-sulfonyl)sarcosyl-L-4-(N-N-dimethylcarbamyloxy)phenylalanine tert-butyl ester
N-(toluene-4-sulfonyl)sarcosyl-L-4-(N,N-dimethylcarbamyloxy)phenylalanine
N-(1-methylimidazole-4-sulfonyl)-L-prolyl-L-4-(N,N-dimethylcarbamyloxy)phenylalanine tert-butyl ester
N-(4-aminobenzenesulfonyl)-L-prolyl-L-4-(N,N-dimethylcarbamyloxy)phenylalanine tert-butyl ester
N-(toluene-4-sulfonyl)sarcosyl-L-4-(morpholin-4-ylcarbonyloxy)phenylalanine tert-butyl ester
N-(toluene-4-sulfonyl)-L-prolyl-L-4-(morpholin-4-ylcarbonyloxy)phenylalanine tert-butyl ester
N-α-toluenesulfonyl)-L-(5,5-dimethyl)thiaprolyl-L-4-(N,N-dimethylcarbamyloxy)phenylalanine
N-(toluene-4-sulfonyl)-L-(piperazin-2-carbonyl)-L-4-(N,N-dimethylcarbamyloxy)phenylalanine
N-(α-toluenesulfonyl)-L-(5,5-dimethyl)thiaprolyl-L-4-(N,N-dimethylcarbamyloxy)phenylalanine tert-butyl ester
N-(toluene-4-sulfonyl)-L-(piperazin-2-carbonyl)-L-4-(N,N-dimethylcarbamyloxy)phenylalanine tert-butyl ester
N-(toluene-4-sulfonyl)-L-(4-benzyloxycarbonylpiperazin-2-carbonyl)-L-4-(N,N-dimethylcarbamyloxy)phenylalanine tert-butyl ester
N-(toluene-4-sulfonyl)sarcosyl-L-4-(isonipecotoyloxy)phenylalanine
N-(toluene-4-sulfonyl)-L-[(1,1-dioxo)thiamorpholin-3-carbonyl]-L-4-(morpholin-4-ylcarbonyloxy)phenylalanine tert-butyl ester
N-(toluene-4-sulfonyl)-L-[(1,1-dioxo)thiamorpholin-3-carbonyl]-L-4-(morpholin-4-ylcarbonyloxy)phenylalanine
N-(1-methylpyrazole-4-sulfonyl)-L-prolyl-L-4-(N,N-dimethylcarbamyloxy)phenylalanine tert-butyl ester
N-(4-fluorobenzenesulfonyl)-L-prolyl-L-4-(N,N-dimethylcarbamyloxy)phenylalanine tert-butyl ester
N-(toluene-4-sulfonyl)sarcosyl-L-4-(4-methylpiperazin-1-ylcarbonyloxy)phenylalanine tert-butyl ester
N-(toluene-4-sulfonyl)-L-(1,1-dioxo-5,5-dimethyl)thiaprolyl-L-4-(N,N-dimethylcarbamyloxy)phenylalanine tert-butyl ester
N-(1-methylimidazole-4-sulfonyl)-L-prolyl-L-4-(N,N-dimethylcarbamyloxy)phenylalanine
N-(toluene-4-sulfonyl)-L-(1,1-dioxo-5,5-dimethyl)thiaprolyl-L-4-(N,N-dimethylcarbamyloxy)phenylalanine
N-(4-fluorobenzenesulfonyl)-L-prolyl-L-4-(N,N-dimethylcarbamyloxy)phenylalanine
N-(pyridine-3-sulfonyl)-L-prolyl-L-4-(N,N-dimethylcarbamyloxy)phenylalanine
N-(toluene-4-sulfonyl)-D-prolyl-L-4-(4-methylpiperazin-1-ylcarbonyloxy)phenylalanine tert-butyl ester
N-(toluene-4-sulfonyl)-L-N-methylalanyl-L-4-(4-methylpiperazin-1-ylcarbonyloxy)phenylalanine tert-butyl ester
N-(4-nitrobenzenesulfonyl)-L-prolyl-L-4-(N,N-dimethylcarbamyloxy)phenylalanine tert-butyl ester
N-(toluene-4-sulfonyl)sarcosyl-L-4-(thiomorpholin-4-ylcarbonyloxy)phenylalanine tert-butyl ester
N-(toluene-4-sulfonyl)-L-N-methylalanyl-L-4-(4-methylpiperazin-1-ylcarbonyloxy)phenylalanine
N-(toluene-4-sulfonyl)-L-prolyl-L-4-(1,1-dioxothiomorpholin-4-ylcarbonyloxy)phenylalanine
N-(toluene-4-sulfonyl)-L-prolyl-L-4-(thiomorpholin-4-ylcarbonyloxy)phenylalanine
N-(toluene-4-sulfonyl)-L-prolyl-L-4-(isonipecotoyloxy)phenylalanine
N-(toluene-4-sulfonyl)-L-prolyl-L-4-(pyrrolidin-1-ylcarbonyloxy)phenylalanine
N-(toluene-4-sulfonyl)-L-prolyl-L-4-(morpholin-4-ylcarbonyloxy)phenylalanine
N-(toluene-4-sulfonyl)-L-prolyl-L-4-(4-methylpiperazin-1-ylcarbonyloxy)phenylalanine neopentyl ester
N-(toluene-4-sulfonyl)-L-prolyl-L-4-(N-dimethylcarbamyloxy)phenylalanine neopentyl ester
N-(toluene-4-sulfonyl)-L-prolyl-L-4-(4-tert-butyloxycarbonylpiperazin-1-ylcarbonyloxy)phenylalanine ethyl ester
N-(toluene-4-sulfonyl)-L-prolyl-L-4-(morpholin-4-ylcarbonyloxy)phenylalanine ethyl ester
N-(toluene-4-sulfonyl)sarcosyl-L-4-(1,1-dioxothiomorpholin-4-ylcarbonyloxy)phenylalanine tert-butyl ester N-(toluene-4-sulfonyl)sarcosyl-L-4-(thiomorpholin-4-ylcarbonyloxy)phenylalanine N-(toluene-4-sulfonyl)-L-N-methylalanyl-L-4-(N,N-dimethylcarbamyloxy)phenylalanine tert-butyl ester N-(toluene-4-sulfonyl)-L-(thiamorpholin-3-carbonyl)-L-4-(N,N-dimethylcarbamyloxy)phenylalanine tert-butyl ester N-(toluene-4-sulfonyl)sarcosyl-L-4-(1,1-dioxothiomorpholin-4-ylcarbonyloxy)phenylalanine N-(toluene-4-sulfonyl)-L-(1,1-dioxothiamorpholin-3-carbonyl)-L-4-(N,N-dimethylcarbamyloxy)phenylalanine tert-butyl ester N-(toluene-4-sulfonyl)-L-(1,1-dioxothiamorpholin-3-carbonyl)-L-4-(morpholin-4-ylcarbonyloxy)phenylalanine tert-butyl ester N-(toluene-4-sulfonyl)-L-N-methylalanyl-L-4-(N,N-dimethylcarbamyloxy)phenylalanine N-(4-fluorobenzenesulfonyl)-L-(thiamorpholin-3-carbonyl)-L-4-(N,N-dimethylcarbamyloxy)phenylalanine tert-butyl ester N-(4-fluorobenzenesulfonyl)-L-(1,1-dioxothiamorpholin-3-carbonyl)-L-4-(N,N-dimethylcarbamyloxy)phenylalanine tert-butyl ester N-(pyridine-3-sulfonyl)-L-prolyl-L-4-(N,N-dimethylcarbamyloxy)phenylalanine tert-butyl ester N-(pyrimidine-2-sulfonyl)-L-prolyl-L-4-(N,N-dimethylcarbamyloxy)phenylalanine tert-butyl ester N-(4-nitrobenzenesulfonyl)-L-prolyl-L-4-(N,N-dimethylcarbamyloxy)phenylalanine N-(4-cyanobenzenesulfonyl)-L-prolyl-L-4-(N,N-dimethylcarbamyloxy)phenylalanine tert-butyl ester N-(toluene-4-sulfonyl)-L-(1,1-dioxothiamorpholin-3-carbonyl)-L-4-(N,N-dimethylcarbamyloxy)phenylalanine N-(toluene-4-sulfonyl)-L-(1,1-dioxo)thiaprolyl-L-4-(N,N-dimethylcarbamyloxy)phenylalanine tert-butyl ester N-(4-fluorobenzenesulfonyl)-L-prolyl-L-4-(N,N-dimethylcarbamyloxy)phenylalanine tert-butyl ester N-(1-methylpyrazole-4-sulfonyl)-L-prolyl-L-4-(N,N-dimethylcarbamyloxy)phenylalanine N-(toluene-4-sulfonyl)-L-(1,1-dioxo)thiaprolyl-L-4-(N,N-dimethylcarbamyloxy)phenylalanine N-(4-fluorobenzenesulfonyl)-L-thiaprolyl-L-4-(N,N-dimethylcarbamyloxy)phenylalanine N-(toluene-4-sulfonyl)-L-prolyl-L-4-(piperazin-1-ylcarbonyloxy)phenylalanine N-(toluene-4-sulfonyl)-L-prolyl-L-4-(1-tert-butyloxycarbonylpiperazin-1-ylcarbonyloxy)phenylalanine tert-butyl ester N-(toluene-4-sulfonyl)-L-prolyl-L-4-(piperazin-1-ylcarbonyloxy)phenylalanine ethyl ester N-(toluene-4-sulfonyl)-L-prolyl-L-4-(4-acetylpiperazin-1-ylcarbonyloxy)phenylalanine ethyl ester N-(toluene-4-sulfonyl)-L-prolyl-L-4-(4-methanesulfonylpiperazin-1-ylcarbonyloxy)phenylalanine ethyl ester N-(toluene-4-sulfonyl)-L-prolyl-L-4-(morpholin-4-ylcarbonyloxy)-3-nitrophenylalanine N-(toluene-4-sulfonyl)-L-prolyl-L-4-(1-tert-butyloxycarbonylpiperazin-1-ylcarbonyloxy)phenylalanine N-(toluene-4-sulfonyl)-L-N-methyl-2-(tert-butyl)glycinyl-L-4-(4-methylpiperazin-1-ylcarbonyloxy)phenylalanine tert-butyl ester N-(4-fluorobenzenesulfonyl)-L-(5,5-dimethyl)thiaprolyl-L-4-(N,N-dimethylcarbamyloxy)phenylalanine tert-butyl ester N-(4-fluorobenzenesulfonyl)-L-(1,1-dioxothiamorpholin-3-carbonyl)-L-4-(1,1-dioxothiomorpholin-4-ylcarbonyloxy)phenylalanine tert-butyl ester N-(toluene-4-sulfonyl)-L-(1,1-dioxothiamorpholin-3-carbonyl)-L-4-(1,1-dioxothiomorpholin-4-ylcarbonyloxy)phenylalanine tert-butyl ester N-(4-fluorobenzenesulfonyl)-L-prolyl-L-4-(1,1-dioxothiomorpholin-4-ylcarbonyloxy)phenylalanine tert-butyl ester N-(4-fluorobenzenesulfonyl)-L-prolyl-L-4-(thiomorpholin-4-ylcarbonyloxy)phenylalanine tert-butyl ester N-(4-fluorobenzenesulfonyl)-L-prolyl-L-4-(morpholin-4-ylcarbonyloxy)phenylalanine tert-butyl ester N-(4-fluorobenzenesulfonyl)-L-(5,5-dimethyl)thiaprolyl-L-4-(N,N-dimethylcarbamyloxy)phenylalanine N-(4-fluorobenzenesulfonyl)-L-(1,1-dioxothiamorpholin-3-carbonyl)-L-4-(morpholin-4-ylcarbonyloxy)phenylalanine tert-butyl ester N-(4-trifluoromethoxybenzenesulfonyl)-L-prolyl-L-4-(N,N-dimethylcarbamyloxy)phenylalanine tert-butyl ester N-(toluene-4-sulfonyl)-L-(1,1-dioxothiamorpholin-3-carbonyl)-L-4-(N,N-dimethylcarbamyloxy)phenylalanine isopropyl ester 3-[N-(toluene-4-sulfonyl)-N-methylamino]-1-[1-tert-butyloxycarbonyl-2-(N,N-dimethylcarbamyloxy)phenylethyl]azetidin-2-one N-(4-fluorobenzenesulfonyl)-L-(1,1-dioxo-5,5-dimethyl)thiaprolyl-L-4-(N,N-dimethylcarbamyloxy)phenylalanine tert-butyl ester N-(toluene-4-sulfonyl)-L-(1,1-dioxo-5,5-dimethyl)thiaprolyl-L-4-(N,N-dimethylcarbamyloxy)phenylalanine isopropyl ester N-(toluene-4-sulfonyl)-L-(1,1-dioxothiamorpholin-3-carbonyl)-L-4-(morpholin-4-ylcarbonyloxy)phenylalanine N-(4-fluorobenzenesulfonyl)-L-(5,5-dimethyl)thiaprolyl-L-4-(N,N-dimethylcarbamyloxy)phenylalanine N-(pyrimidine-2-sulfonyl)-L-prolyl-L-4-(N,N-dimethylcarbamyloxy)phenylalanine N-(toluene-4-sulfonyl)-L-(1,1-dioxothiamorpholin-3-carbonyl)-L-4-(4-methylpiperazin-1-ylcarbonyloxy)phenylalanine tert-butyl ester 3-[N-(toluene-4-sulfonyl)-N-methylamino]-1-[1-carboxy-2-(N,N-dimethylcarbamyloxy)phenylethyl]azetidin-2-one N-(1-methylpyrazole-4-sulfonyl)-L-prolyl-L-4-(4-methylpiperazin-1-ylcarbonyloxy)phenylalanine tert-butyl ester N-(4-fluorobenzenesulfonyl)-L-(1,1-dioxo)thiaprolyl-L-4-(N,N-dimethylcarbamyloxy)phenylalanine N-(toluene-4-sulfonyl)-L-prolyl-L-4-(isonipecotoyloxy)phenylalanine tert-butyl ester N-(toluene-4-sulfonyl)-L-prolyl-L-4-(1,1-dioxothiomorpholin-4-ylcarbonyloxy)phenylalanine tert-butyl ester N-(toluene-4-sulfonyl)-L-prolyl-L-4-(thiomorpholin-4-ylcarbonyloxy)phenylalanine tert-butyl ester N-(toluene-4-sulfonyl)-L-prolyl-L-4-(pyrrolidin-1-ylcarbonyloxy)phenylalanine tert-butyl ester N-(4-fluorobenzenesulfonyl)-L-thiaprolyl-L-4-(N,N-dimethylcarbamyloxy)phenylalanine tert-butyl ester N-(4-fluorobenzenesulfonyl)-L-(1,1-dioxo)thiaprolyl-L-4-(N,N-dimethylcarbamyloxy)phenylalanine tert-butyl ester N-(2,5-dichlorothiophene-3-sulfonyl)-L-prolyl-L-4-(N,N-dimethylcarbamyloxy)phenylalanine tert-butyl ester N-(4-acetamidobenzenesulfonyl)-L-prolyl-L-4-(N,N-dimethylcarbamyloxy)phenylalanine tert-butyl ester N-(4-tert-butylbenzenesulfonyl)-L-(1,1-dioxothiamorpholin-3-carbonyl)-L-4-(N,N-dimethylcarbamyloxy)phenylalanine tert-butyl ester N-(pyridine-2-sulfonyl)-L-prolyl-L-4-(N,N-dimethylcarbamyloxy)phenylalanine N-(2-fluorobenzenesulfonyl)-L-(1,1-dioxothiamorpholin-3-carbonyl)-L-4-(N,N-dimethylcarbamyloxy)phenylalanine tert-butyl ester N-(3-fluorobenzenesulfonyl)-L-(1,1-dioxothiamorpholin-3-carbonyl)-L-4-(N,N-dimethylcarbamyloxy)phenylalanine tert-butyl ester N-(2,4-difluorobenzenesulfonyl)-L-(1,1-dioxothiamorpholin-3-carbonyl)-L-4-(N,N-dimethylcarbamyloxy)phenylalanine tert-butyl ester N-(4-acetamidobenzenesulfonyl)-L-prolyl-L-4-(N,N-dimethylcarbamyloxy)phenylalanine N-(4-trifluoromethoxybenzenesulfonyl)-L-prolyl-L-4-(N,N-dimethylcarbamyloxy)phenylalanine N-(4-fluorobenzenesulfonyl)-L-(5,5-dimethyl)thiaprolyl-L-4-(N,N-dimethylcarbamyloxy)phenylalanine tert-butyl ester N-(4-cyanobenzenesulfonyl)-L-prolyl-L-4-(N,N-dimethylcarbamyloxy)phenylalanine N-(toluene-4-sulfonyl)-L-(3,3-dimethyl)prolyl-L-4-(N,N-dimethylcarbamyloxy)phenylalanine tert-butyl ester N-(toluene-4-sulfonyl)-L-(3,3-dimethyl)prolyl-L-4-(N,N-dimethylcarbamyloxy)phenylalanine isopropyl ester N-(1-methylpyrazole-4-sulfonyl)-L-prolyl-L-4-(N,N-dimethylcarbamyloxy)phenylalanine iso-propyl ester N-(1-methylpyrazole-4-sulfonyl)-L-(5,5-dimethyl)thiaprolyl-L-4-(N,N-dimethylcarbamyloxy)phenylalanine tert-butyl ester N-(1-methylpyrazole-4-sulfonyl)-L-(5,5-dimethyl)thiaprolyl-L-4-(N,N-dimethylcarbamyloxy)phenylalanine N-(toluene-4-sulfonyl)-L-prolyl-L-4-(N-(1,4-dioxa-8-aza-spiro[4.5]decan-8-yl)carbonyloxy)phenylalanine ethyl ester N-(toluene-4-sulfonyl)-L-prolyl-L-4-(N-(1,4-dioxa-8-aza-spiro[4.5]decan-8-yl)carbonyloxy)phenylalanine N-(toluene-4-sulfonyl)-L-prolyl-L-4-(4'-acetylpiperazin-1-ylcarbonyloxy)phenylalanine N-(toluene-4-sulfonyl)-L-prolyl-L-4-(4'-methanesulfonylpiperazin-1-ylcarbonyloxy)phenylalanine N-(toluene-4-sulfonyl)-L-prolyl-L-4-(4'-phenylpiperazin-1-ylcarbonyloxy)phenylalanine N-(toluene-4-sulfonyl)-L-prolyl-L-4-(piperazin-1-ylcarbonyloxy)phenylalanine tert-butyl ester N-(toluene-4-sulfonyl)-L-prolyl-L-4-(4'-methanesulfonylpiperazin-1-ylcarbonyloxy)phenylalanine tert-butyl ester N-(toluene-4-sulfonyl)-L-prolyl-L-4-(N,N-dimethylcarbamyloxy)phenylalanine (N'-tert-butoxycarbonyl-2-amino-2-methylpropyl) ester N-(toluene-4-sulfonyl)-L-prolyl-L-4-(4'-acetylpiperazin-1-ylcarbonyloxy)phenylalanine tert-butyl ester N-(toluene-4-sulfonyl)-L-prolyl-L-4-(4'-hydroxypiperidin-1-ylcarbonyloxy)phenylalanine tert-butyl ester N-(toluene-4-sulfonyl)-L-prolyl-L-4-(N-(2'-(morpholin-4'-yl)ethyl)carbamyloxy)phenylalanine tert-butyl ester N-(toluene-4-sulfonyl)-L-prolyl-L-4-(N-(1,4-dioxa-8-aza-spiro[4.5]decan-8-yl)carbonyloxy)phenylalanine tert-butyl ester N-(toluene-4-sulfonyl)-L-prolyl-L-4-(N-(2'-hydroxyethyl)-N-methylcarbamyloxy)phenylalanine tert-butyl ester N-(toluene-4-sulfonyl)-L-prolyl-4-(4'-(2-hydroxyethyl)piperazin-1-ylcarbonyloxy)-L-phenylalanine tert-butyl ester N-(toluene-4-sulfonyl)-L-prolyl-L-4-(N-(2'-formyloxyethyl)-N-methylcarbamyloxy)phenylalanine N-(toluene-4-sulfonyl)-L-prolyl-L-4-(N-(2'-hydroxyethyl)-N-methylcarbamyloxy)phenylalanine isopropyl ester N-(toulene-4-sulfonyl)-L-prolyl-L-4-(N-(methoxycarbonylmethyl)carbamyloxy)phenylalanine tert-butyl ester N-(1-methylpyrazole-4-sulfonyl)-L-(5,5-dimethyl)thiaprolyl-L-(4-N,N-dimethylcarbamyloxy)phenylalanine isopropyl ester N-(toluene-4-sulfonyl)-L-prolyl-L-4-(4'-methoxypiperidin-1-ylcarbonyloxy)phenylalanine isopropyl ester N-(toluene-4-sulfonyl)-L-prolyl-L-4-(4'-methoxypiperidin-1-ylcarbonyloxy)phenylalanine N-(toluene-4-sulfonyl)-L-4-oxoprolyl-L-4-(N,N-dimethylcarbamyloxy)phenylalanine tert-butyl ester N-(toluene-4-sulfonyl)-L-trans-4-hydroxyprolyl-L-4-(N,N-dimethylcarbamyloxy)phenylalanine tert-butyl ester N-(3-fluorobenzenesulfonyl)-L-prolyl-L-4-(N,N-dimethylcarbamyloxy)phenylalanine tert-butyl ester N-(morpholino-sulfonyl)-L-prolyl-L-(4-N,N-dimethylcarbamyloxy)phenylalanine tert-butyl ester N-(morpholino-sulfonyl)-L-prolyl-L-(4-N,N-dimethylcarbamyloxy)phenylalanine N-(1-methylpyrazole-4-sulfonyl)-L-(1,1-dioxothiamorpholin-3-carbonyl)-L-4-(N,N-dimethylcarbamyloxy)phenylalanine tert-butyl ester N-(2-fluorobenzenesulfonyl)-L-(1,1-dioxothiamorpholin-3-carbonyl)-L-4-(N,N-dimethylcarbamyloxy)phenylalanine N-(2,4-difluorobenzenesulfonyl)-L-(1,1-dioxothiamorpholin-3-carbonyl)-L-4-(N,N-dimethylcarbamyloxy)phenylalanine N-(toluene-4-sulfonyl)-L-(thiamorpholin-3-carbonyl)-L-4-(N,N-dimethylcarbamyloxy)phenylalanine N-(pyridine-3-sulfonyl)-L-(5,5-dimethyl-thiaprolyl-L-4-(N,N-dimethylcarbamyloxy)phenylalanine isopropyl ester N-(3-fluorobenzenesulfonyl)-L-(1,1-dioxothiamorpholin-3-carbonyl)-L-4-(N,N-dimethylcarbamyloxy)phenylalanine N-(1-methylpyrazole-4-sulfonyl)-L-(1,1-dioxothiamorpholin-3-carbonyl)-L-4-(N,N-dimethylcarbamyloxy)phenylalanine N-(4-tert-butylbenzenesulfonyl)-L-(1,1-dioxothiamorpholin-3-carbonyl)-L-4-(N,N-dimethylcarbamyloxy)phenylalanine N-(toluene-4-sulfonyl)-(3,3-dimethyl)prolyl-L-4-(N,N-dimethylcarbamyloxy)phenylalanine N-(2,5-dichlorothiophene-3-sulfonyl)-L-prolyl-L-4-(N,N-dimethylcarbamyloxy)phenylalanine N-(4-methoxybenzenesulfonyl)-L-prolyl-L-4-(N,N-dimethylcarbamyloxy)phenylalanine N-(4-methoxybenzenesulfonyl)-L-prolyl-L-4-(N,N-dimethylcarbamyloxy)phenylalanine isopropyl ester N-(toluene-4-sulfonyl)-L-(1-oxo-thiomorpholin-3-carbonyl)-L-4-(N,N-dimethylcarbamyloxy)phenylalanine N-(toluene-4-sulfonyl)-L-(1-oxo-thiomorpholin-3-carbonyl)-L-4-(N,N-dimethylcarbamyloxy)phenylalanine tert-butyl ester N-(3,4-difluorobenzenesulfonyl)-L-prolyl-4-(N,N-dimethylcarbamyloxy)phenylalanine isopropyl ester N-(3,4-difluorobenzenesulfonyl)-L-prolyl-4-(N,N-dimethylcarbamyloxy)phenylalanine N-(3,4-difluorobenzenesulfonyl)-L-(1,1-dioxothiamorpholin-3-carbonyl)-L-4-(N,N-dimethylcarbamyloxy)phenylalanine tert-butyl ester N-(3,4-difluorobenzenesulfonyl)-L-(1,1-dioxothiamorpholin-3-carbonyl)-L-4-(N,N-dimethylcarbamyloxy)phenylalanine N-(toluene-4-sulfonyl)-L-(5,5-dimethyl)thiaprolyl-L-(thiomorpholin-4-ylcarbonyloxy)phenylalanine tert-butyl ester N-(toluene-4-sulfonyl)-L-(5,5-dimethyl)thiaprolyl-L-(thiomorpholin-4-ylcarbonyloxy)phenylalanine N-(1-methylpyrazole-4-sulfonyl)-L-(5,5-dimethyl)thiaprolyl-L-4-(N,N-dimethylcarbamyloxy)phenylalanine ethyl ester N-(pyridine-3-sulfonyl)-L-(5,5-dimethyl)thiaprolyl-L-4-(N,N-dimethylcarbamyloxy)phenylalanine N-(pyridine-2-sulfonyl)-L-prolyl-L-4-(N,N-dimethylcarbamyloxy)phenylalanine isopropyl ester N-(pyridine-2-sulfonyl)-L-prolyl-L-4-(N,N-dimethylcarbamyloxy)phenylalanine N-(pyridine-2-sulfonyl)-L-(5,5-dimethyl)thiaprolyl-L-4-(N,N-dimethylcarbamyloxy)phenylalanine isopropyl ester N-(pyridine-2-sulfonyl)-L-(5,5-dimethyl)thiaprolyl-L-4-(N,N-dimethylcarbamyloxy)phenylalanine N-(toluene-4-sulfonyl)-L-(thiamorpholin-3-carbonyl)-L-4-(N,N-dimethylcarbamyloxy)phenylalanine isopropyl ester N-(3-fluorobenzenesulfonyl)-L-(5,5-dimethyl)thiaprolyl-L-4-(N,N-dimethylcarbamyloxy)phenylalanine isopropyl ester N-(2-fluorobenzenesulfonyl)-L-(5,5-dimethyl)thiaprolyl-L-4-(N,N-dimethylcarbamyloxy)phenylalanine isopropyl ester N-(3,4-difluorobenzenesulfonyl)-L-(5,5-dimethyl)thiaprolyl-L-4-(N,N-dimethylcarbamyloxy)phenylalanine isopropyl ester N-(3,5-difluorobenzenesulfonyl)-L-(5,5-dimethyl)thiaprolyl-L-4-(N,N-dimethylcarbamyloxy)phenylalanine isopropyl ester N-(2,4-difluorobenzenesulfonyl)-L-(5,5-dimethyl)thiaprolyl-L-4-(N,N-dimethylcarbamyloxy)phenylalanine isopropyl ester N-(4-chlorobenzenesulfonyl)-L-(5,5-dimethyl)thiaprolyl-L-4-(N,N-dimethylcarbamyloxy)phenylalanine isopropyl ester N-(3-chlorobenzenesulfonyl)-L-(5,5-dimethyl)thiaprolyl-L-4-(N,N-dimethylcarbamyloxy)phenylalanine isopropyl ester N-(2-chlorobenzenesulfonyl)-L-(5,5-dimethyl)thiaprolyl-L-4-(N,N-dimethylcarbamyloxy)phenylalanine isopropyl ester N-(3,4-dichlorobenzenesulfonyl)-L-(5,5-dimethyl)thiaprolyl-L-4-(N,N-dimethylcarbamyloxy)phenylalanine isopropyl ester N-(3,5-dichlorobenzenesulfonyl)-L-(5,5-dimethyl)thiaprolyl-L-4-(N,N-dimethylcarbamyloxy)phenylalanine isopropyl ester N-(3-chlorobenzenesulfonyl)-L-(1,1-dioxothiamorpholin-3-carbonyl)-L-4-(N,N-dimethylcarbamyloxy)phenylalanine tert-butyl ester N-(3,4-dichlorobenzenesulfonyl)-L-(1,1-dioxothiamorpholin-3-carbonyl)-L-4-(N,N-dimethylcarbamyloxy)phenylalanine tert-butyl ester N-(4-methoxybenzenesulfonyl)-L-(5,5-dimethyl)thiaprolyl-L-4-(N,N-dimethylcarbamyloxy)phenylalanine isopropyl ester N-(3-methoxybenzenesulfonyl)-L-(5,5-dimethyl)thiaprolyl-L-4-(N,N-dimethylcarbamyloxy)phenylalanine isopropyl ester N-(2-methoxybenzenesulfonyl)-L-(5,5-dimethyl)thiaprolyl-L-4-(N,N-dimethylcarbamyloxy)phenylalanine isopropyl ester N-(3,4-dimethoxybenzenesulfonyl)-L-(5,5-dimethyl)thiaprolyl-L-4-(N,N-dimethylcarbamyloxy)phenylalanine isopropyl ester N-(2,4-difluorobenzenesulfonyl)-L-(thiamorpholin-3-carbonyl)-L-4-(N,N-dimethylcarbamyloxy)phenylalanine isopropyl ester N-(3,4-dichlorobenzenesulfonyl)-L-(1,1-dioxothiamorpholin-3-carbonyl)-L-4-(N,N-dimethylcarbamyloxy)phenylalanine N-(3-chlorobenzenesulfonyl)-L-(1,1-dioxothiamorpholin-3-carbonyl)-L-4-(N,N-dimethylcarbamyloxy)phenylalanine N-(3-chloro-4-fluorobenzenesulfonyl)-L-(1,1-dioxothiamorpholin-3-carbonyl)-L-4-(N,N-dimethylcarbamyloxy)phenylalanine tert-butyl ester N-(1-methylpyrazole-4-sulfonyl)-L-(thiamorpholin-3-carbonyl)-L-4-(N,N-dimethylcarbamyloxy)phenylalanine tert-butyl ester N-(3,4-difluorobenzenesulfonyl)-L-(thiamorpholin-3-carbonyl)-L-4-(N,N-dimethylcarbamyloxy)phenylalanine tert-butyl ester N-(toluene-4-sulfonyl)-L-(5,5-dimethyl)thioprolyl-L-(thiomorpholin-4-ylcarbonyloxy)phenylalanine isopropyl ester N-(3,4-difluorobenzenesulfonyl)-L-(thiamorpholin-3-carbonyl)-L-4-(N,N-dimethylcarbamyloxy)phenylalanine N-(2,5-dichlorothiophene-3-sulfonyl)-L-(5,5-dimethyl)thiaprolyl-L-4-(N,N-dimethylcarbamyloxy)phenylalanine isopropyl ester N-(1-methylpyrazole-4-sulfonyl)-L-(5,5-dimethyl)thiaprolyl-L-4-(thiomorpholin-4-ylcarbonyloxy)phenylalanine isopropyl ester N-(8-quinolinesulfonyl)-L-prolyl-L-4-(N,N-dimethylcarbamyloxy)phenylalanine isopropyl ester N-(8-quinolinesulfonyl)-L-prolyl-L-4-(N,N-dimethylcarbamyloxy)phenylalanine N-(8-quinolinesulfonyl)-L-(5,5-dimethyl)thiaprolyl-L-4-(N,N-dimethylcarbamyloxy)phenylalanine isoproplyl ester N-(8-quinolinesulfonyl)-L-(5,5-dimethyl)thiaprolyl-L-4-(N,N-dimethylcarbamyloxy)phenylalanine N-(toluene-4-sulfonyl)-L-prolyl-L-4-(4-phenylpiperazin-1-ylcarbonyloxy)phenylalanine tert-butyl ester N-(toluene-4-sulfonyl)-L-prolyl-L-4-(4'-(ethoxycarbonyl)piperidin-1-ylcarbonyloxy)phenylalanine tert-butyl ester N-(pyridine-3-sulfonyl)-L-(5,5-dimethyl)thiaprolyl-L-4-(N,N-dimethylcarbamyloxy)phenylalanine tert-butyl ester N-(3-sulfonamido-4-chloro-benzenesulfonyl)-L-prolyl-L-4-(N,N-dimethylcarbamyloxy)phenylalanine isopropyl ester N-(toluene-4-sulfonyl)-L-(1-oxothiomorpholin-3-carbonyl)-L-4-(N,N-dimethylcarbamyloxy)phenylalanine isopropyl ester N-(2,4-difluorobenzenefulfonyl)-L-(1-oxothiomorpholin-3-carbonyl)-L-4-(N,N-dimethylcarbamyloxy)phenylalanine tert-butyl ester N-(1-methylpyrazole-4-sulfonyl)-L-(5,5-dimethyl)thiaprolyl-L-4-(N,N-dimethylcarbamyloxy)phenylalanine 2,2-dimethylpropyl ester N-(pyridine-3-sulfonyl)-L-(5,5-dimethyl)thiaprolyl-L-4-(N,N-dimethylcarbamyloxy)phenylalanine 2,2-dimethylpropyl ester N-(1-methylpyrazole-4-sulfonyl)-L-(5,5-dimethyl)thiaprolyl-L-4-(N,N-dimethylcarbamyloxy)phenylalanine cyclopropylmethyl ester N-(1-methylpyrazole-4-sulfonyl)-L-(5,5-dimethyl)thiaprolyl-L-4-(N,N-dimethylcarbamyloxy)phenylalanine methyl ester N-(pyridine-3-sulfonyl)-L-(5,5-dimethyl)thiaprolyl-L-4-(N,N-dimethylcarbamyloxy)phenylalanine ethyl ester N-(pyridine-3-sulfonyl)-L-(5,5-dimethyl)thiaprolyl-L-4-(N,N-dimethylcarbamyloxy)phenylalanine cyclopropylmethyl ester N-(1-methylpyrazole-4-sulfonyl)-L-(5,5-dimethyl)thiaprolyl-L-4-(N,N-dimethylcarbamyloxy)phenylalanine 2-methoxyphenyl ester N-(1-methylpyrazole-4-sulfonyl)-L-(5,5-dimethyl)thiaprolyl-L-4-(N,N-dimethylcarbamyloxy)phenylalanine n-butyl ester N-(1-methylpyrazole-4-sulfonyl)-L-(5,5-dimethyl)thiaprolyl-L-4-(N,N-dimethylcarbamyloxy)phenylalanine n-propyl ester N-(1-methylpyrazole-4-sulfonyl)-L-(5,5-dimethyl)thiaprolyl-L-4-(N,N-dimethylcarbamyloxy)phenylalanine 2,2-dimethylpropionyloxymethyl ester N-(toluene-4-sulfonyl)-L-prolyl-L-4-(N-(4'-(2'-aminoethyl)morpholino)carbamyloxy)phenylalanine N-(toluene-4-sulfonyl)-L-prolyl-L-4-[4-(carboxy)piperidin-1-ylcarbonyloxy]phenylalanine N-(toluene-4-sulfonyl)-L-prolyl-L-4-(N,N-bis-(2-hydroxyethyl)carbamyloxy)phenylalanine isopropyl ester N-(toluene-4-sulfonyl)-L-prolyl-L-4-[3-(hydroxymethyl)piperidin-1-ylcarbonyloxy]phenylalanine isopropyl ester N-(toluene-4-sulfonyl)-L-prolyl-L-4-(4-trifluoromethanesulfonylpiperazin-1-ylcarbonyloxy)phenylalanine tert-butyl ester N-(4-(N-phenylurea)benzenesulfonyl)-L-prolyl-L-4-(N,N-dimethylcarbamyloxy)phenylalanine tert-butyl ester N-(2-trifluoroacetyl-1,2,3,4-tetrahydroisoquinolin-7-sulfonyl)-L-prolyl-L-4-(N,N-dimethylcarbamyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine N-(pyridine-4-sulfonyl)-L-(5,5-dimethyl)thiaprolyl-L-4-(N,N-dimethylcarbamyloxy)phenylalanine isopropyl ester N-(pyridine-4-sulfonyl)-L-(5,5-dimethyl)thiaprolyl-L-4-(N,N-dimethylcarbamyloxy)phenylalanine N-(toluene-4-sulfonyl)-L-(5,5-dimethyl)thiaprolyl-L-4-(N-methyl-N-(2-dimethylaminoethyl)carbamyloxy)phenylalanine tert-butyl ester N-(toluene-4-sulfonyl)-L-prolyl-L-4-(N-methyl-N-(2-dimethylaminoethyl)carbamyloxy)phenylalanine tert-butyl ester N-(toluene-4-sulfonyl)-L-(5,5-dimethyl)thiapropyl-L-4-(N-methyl-N-(2-dimethylaminoethyl)carbamyloxy)phenylalanine N-(toluene-4-sulfonyl)-L-prolyl-L-4-(N-methyl-N-(2-dimethylaminoethyl)carbamyloxy)phenylalanine N-(4-fluorobenzenesulfonyl)-L-(5,5-dimethyl)thiaprolyl-L-3-chloro-4-(4-methylpiperazin-1-ylcarbonyloxy)phenylalanine tert-butyl ester N-(4-fluorobenzenesulfonyl)-L-(5,5-dimethyl)thiaprolyl-L-3-chloro-4-(N,N-dimethycarbamyloxy)phenylalanine N-(4-fluorobenzenesulfonyl)-L-(5,5-dimethyl)thiaprolyl-L-3-chloro-4-(thiomorpholin-4-ylcarbonyloxy)phenylalanine tert-butyl ester N-(4-fluorobenzenesulfonyl)-L-(5,5-dimethyl)thiaprolyl-L-3-chloro-4-(thiomorpholin-4-ylcarbonyloxy)phenylalanine isopropyl ester N-(4-fluorobenzenesulfonyl)-L-(5,5-dimethyl)thiaprolyl-L-3-chloro-4-(N,N-dimethylcarbamyloxy)]phenylalanine isopropyl ester N-(toluene-4-sulfonyl)-L-(5,5-dimethyl)thiaprolyl-L-3-chloro-4-(N,N-dimethylcarbamyloxy)phenylalanine isopropyl ester N-(4-fluorobenzenesulfonyl)-L-(5,5-dimethyl)thiaprolyl-L-3-chloro-4-(4-methylpiperazin-1-ylcarbonyloxy)]phenylalanine isopropyl ester N-(toluene-4-sulfonyl)-L-prolyl-L-3-chloro-4-(N,N-dimethylcarbamyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine tert-butyl ester N-(4-nitrobenzenesulfonyl)-L-prolyl-L-4-(N,N-dimethylcarbamyloxy)phenylalanine isopropyl ester N-(4-aminobenzenesulfonyl)-L-prolyl-L-4-(N,N-dimethylcarbamyloxy)phenylalanine isopropyl ester N-(toluene-4-sulfonyl)-L-prolyl-L-4-(thiomorpholin-4-ylcarbonyloxy)phenylalanine isopropyl ester N-(toluene-4-sulfonyl)-L-prolyl-L-4-(4-phenylcarbamylpiperazin-1-ylcarbonyloxy)phenylalanine isopropyl ester N-(toluene-4-sulfonyl)-L-prolyl-L-4-(4-phenylcarbamylpiperazin-1-ylcarbonyloxy)phenylalanine N-(1-n-butylpyrazole-4-sulfonyl)-L-(5,5-dimethyl)thiaprolyl-L-4-(N,N-dimethylcarbamyloxy)phenylalanine isopropyl ester N-(toluene-4-sulfonyl)-L-prolyl-L-4-(pyridin-4-ylcarbonyl)piperazin-1-ylcarbonyloxy)phenylalanine isopropyl ester N-(toluene-4-sulfonyl)-L-4-oxoprolyl-L-4-(N,N-dimethylcarbamyloxy)phenylalanine N-(toluene-4-sulfonyl)-L-trans-4-hydroxyprolyl-L-4-(N,N-dimethylcarbamyloxy)phenylalanine N-(4-cyanobenzenesulfonyl)-L-prolyl-L-4-(N,N-dimethylcarbamyloxy)phenylalanine isopropyl ester N-(4-aminobenzenesulfonyl)-L-prolyl-L-4-(N,N-dimethylcarbamyloxy)phenylalanine N-(toluene-4-sulfonyl)-L-4-oxoprolyl-L-4-(4-methylpiperazin-1-ylcarbonyloxy)phenylalanine tert-butyl ester N-(toluene-4-sulfonyl)-L-prolyl-L-4-[3-(hydroxymethyl)piperidin-1-ylcarbonyloxy]phenylalanine N-(toluene-4-sulfonyl)-L-(4,4-difluoro)prolyl-L-4-(N,N-dimethylcarbamyloxy)phenylalanine isopropyl ester N-(toluene-4-sulfonyl)-L-(4,4-difluoro)prolyl-L-4-(N,N-dimethylcarbamyloxy)phenylalanine N-(toluene-4-sulfonyl)-L-prolyl-L-(4-benzoylpiperazin-1-ylcarbonyloxy)phenylalanine isopropyl ester N-(1-methyl-1H-imidazole-4-sulfonyl)-L-prolyl-L-4-(N,N-dimethylcarbamyloxy)phenylalanine isopropyl ester N-(toluene-4-sulfonyl)-L-4-(thiomorpholin-4-ylcarbonyloxy)prolyl-L-4-(thiomorpholin-4-ylcarbonyloxy)phenylalanine N-(4-cyanobenzenesulfonyl)-L-prolyl-L-4-(thiomorpholin-4-ylcarbonyloxy)phenylalanine isopropyl ester N-(4-amidinobenzenesulfonyl)-L-prolyl-L-4-(N,N-dimethylcarbamyloxy)phenylalanine methyl ester N-(toluene-4-sulfonyl)-L-4-oxoprolyl-L-4-(thiomorpholin-4-ylcarbonyloxy)phenylalanine tert-butyl ester N-(toluene-4-sulfonyl)-L-4-hydroxyprolyl-L-4-(thiomorpholin-4-ylcarbonyloxy)phenylalanine N-(toluene-4-sulfonyl)-L-prolyl-L-(4-benzoylpiperazin-1-ylcarbonyloxy)phenylalanine N-(4-amidinobenzenesulfonyl)-L-prolyl-L-4-(thiomorpholin-4-ylcarbonyloxy)phenylalanine methyl ester N-(3-fluorobenzenesulfonyl)-L-prolyl-L-4-(N,N-dimethylcarbonyloxy)phenylalanine N-(toluene-4-sulfonyl)-L-prolyl-L-4-[N-methyl-N-(2-(N'-methyl-N'-toluenesulfonyl-amino)ethyl)carbamyloxy]phenylalanine isopropyl ester N-(toluene-4-sulfonyl)-L-prolyl-L-4-[N-(2-(N'-phenylaminocarbonyloxy)ethyl)carbamyloxy)]phenylalanine isopropyl ester N-(4-fluorobenzenesulfonyl)-L-4-(trans-hydroxy)prolyl-L-4-(N,N-dimethylcarbamyloxy)phenylalanine isopropyl ester N-(4-fluorobenzenesulfonyl)-L-4-(trans-hydroxy)prolyl-L-4-(N,N-dimethylcarbamyloxy)phenylalanine tert-butyl ester N-(4-amidinobenzenesulfonyl)-L-prolyl-L-4-(N,N-dimethylcarbamyloxy)phenylalanine N-(toluene-4-sulfonyl)-L-(pyrazin-3-carbonyl)-L-4-(N,N-dimethylcarbamyloxy)phenylalanine tert-butyl ester N-(4-fluorobenzenesulfonyl)-L-(5,5-dimethyl)thiaprolyl-L-4-(2-hydroxymethylpyrrolidin-1-ylcarbonyloxy)phenylalanine tert-butyl ester N-(4-fluorobenzenesulfonyl)-L-(5,5-dimethyl)thiaprolyl-L-4-(2-hydroxymethylpyrrolidin-1-ylcarbonyloxy)phenylalanine N-(toluene-4-sulfonyl)-L-prolyl-L-4-(2-methoxycarbonylpyrrolidin-1-ylcarbonyloxy)phenylalanine tert-butyl ester N-(4-fluorobenzenesulfonyl)-L-(5,5-dimethyl)thiaprolyl-L-3-chloro-4-(thiomorpholin-4-ylcarbonyloxy)phenylalanine N-(4-fluorobenzenesulfonyl)-L-(5,5-dimethyl)thiaprolyl-L-4-(4-(2-pyridyl)piperazin-1-ylcarbonyloxy)]phenylalanine N-(4-fluorobenzenesulfonyl)-L-(5,5-dimethyl)thiaprolyl-L-4-(4-(2-pyridyl)piperazin-1-ylcarbonyloxy)]phenylalanine tert-butyl ester N-(toluene-4-sulfonyl)-L-(4-hydroxy)prolyl-L-4-(thiomorpholin-4-ylcarbonyloxy)phenylalanine tert-butyl ester N-(toluene-4-sulfonyl)-L-prolyl-L-4-(N,N-dimethylcarbamyloxy)phenylalanine 2-(2-methoxyethoxy)ethyl ester N-(4-fluorobenzenesulfonyl)-L-(5,5-dimethyl)thiaprolyl-L-4-(4-(2-pyrimidyl)piperazin-1-ylcarbonyloxy)]phenylalanine tert-butyl ester N-(4-fluorobenzenesulfonyl)-L-(5,5-dimethyl)thiaprolyl-L-3-fluoro-4-(N,N-dimethylcarbamyloxy)phenylalanine isopropyl ester N-(toluene-4-sulfonyl)-L-(1-methanesulfonylpyrazin-3-carbonyl)-L-4-(N,N-dimethylcarbamyloxy)phenylalanine tert-butyl ester N-(4-bromobenzenesulfonyl)-L-(5,5-dimethyl)thiaprolyl-L-4-(N,N-dimethylcarbamyloxy)phenylalanine tert-butyl ester N-(4-bromobenzenesulfonyl)-L-(5,5-dimethyl)thiaprolyl-L-4-(N,N-dimethylcarbamyloxy)phenylalanine N-(toluene-4-sulfonyl)-L-(4-hydroxy)prolyl-L-4-(4-methylpiperazin-1-ylcarbonyloxy)phenylalanine N-(4-fluorobenzenesulfonyl)-L-(5,5-dimethyl)thiaprolyl-L-4-(4-(2-pyrimidyl)piperazin-1-ylcarbonyloxy)]phenylalanine N-(4-fluorobenzenesulfonyl)-L-(5,5-dimethyl)thiaprolyl-L-4-(4-(2-pyridyl)piperazin-1-ylcarbonyloxy)]phenylalanine isopropyl ester N-(4-fluorobenzenesulfonyl)thiazolidinyl-2-carbonyl-L-4-(N,N-dimethylcarbamyloxy)phenylalanine N-(4-fluorobenzenesulfonyl)thiazolidinyl-2-carbonyl-L-4-(N,N-dimethylcarbamyloxy)phenylalanine tert-butyl ester N-(toluene-4-sulfonyl)-L-(4-oxo)prolyl-L-4-(thiomorpholin-4-ylcarbonyloxy)phenyl alanine N-(toluene-4-sulfonyl)-L-(4-oxo)prolyl-L-4-(4-methylpiperazin-1-ylcarbonyloxy)phenylalanine N-(4-fluorobenzenesulfonyl)thiazolidinyl-2-carbonyl-L-4-(4-(2-pyridyl)piperazin-1-ylcarbonyloxy)]phenylalanine N-(4-nitrobenzenesulfonyl)-L-prolyl-L-4-(4-(2-pyridyl)piperazin-1-ylcarbonyloxy)]phenylalanine tert-butyl ester N-(4-fluorobenzenesulfonyl)thiazolidinyl-2-carbonyl-L-4-(4-(2-pyridyl)piperazin-1-ylcarbonyloxy)]phenylalanine tert-butyl ester N-(4-bromobenzenesulfonyl)-L-(5,5-dimethyl)thiaprolyl-L-4-(4-(2-pyridyl)piperazin-1-ylcarbonyloxy)]phenylalanine N-(toluene-4-sulfonyl)-L-prolyl-L-4-(4-(N-phenylthiocarbonyl)piperazin-1-ylcarbonyloxy)]phenylalanine isopropyl ester N-(4-fluorobenzenesulfonyl)thiazolidinyl-2-carbonyl-L-4-(4-methylhomopiperazin-1-ylcarbonyloxy)phenylalanine tert-butyl ester N-(toluene-4-sulfonyl)-L-4-(methanesulfonyloxy)prolyl-L-4-(N,N-dimethylcarbamyloxy)phenylalanine tert-butyl ester N-(4-aminocarbonylbenzenesulfonyl)-L-prolyl-L-4-(N,N-dimethylcarbamyloxy)phenylalanine N-(4-aminocarbonylbenzenesulfonyl)-L-prolyl-L-4-(thiomorpholin-4-ylcarbonyloxy)phenylalanine N-(4-amidinobenzenesulfonyl)-L-prolyl-L-4-(thiomorpholin-4-ylcarbonyloxy)phenylalanine N-(4-nitrobenzenesulfonyl)-L-prolyl-L-4-(4-(2-pyridyl)piperazin-1-ylcarbonyloxy)]phenylalanine N-(4-fluorobenzenesulfonyl)-L-(5,5-dimethyl)thiaprolyl-L-3-chloro-4-(4-(2-pyridyl)piperazin-1-ylcarbonyloxy)]phenylalanine ethyl ester N-(4-fluorobenzenesulfonyl)-L-(5,5-dimethyl)thiaprolyl-L-3-chloro-4-(4-(2-pyridyl)piperazin-1-ylcarbonyloxy)phenylalanine N-(4-fluorobenzenesulfonyl)thiazolidinyl-2-carbonyl-L-4-(4-methylhomopiperazin-1-ylcarbonyloxy)phenylalanine N-(1-methylpyrazole-3-sulfonyl)-L-(5,5-dimethyl)thiaprolyl-L-3-chloro-4-(N,N-dimethylcarbamyloxy)phenylalanine isopropyl ester N-(1-methylimidazole-4-sulfonyl)-L-prolyl-L-4-(4-(2-pyridyl)piperazin-1-ylcarbonyloxy)phenylalanine isopropyl ester N-(1-methylimidazole-4-sulfonyl)-L-prolyl-L-4-(4-(2-pyridyl)piperazin-1-ylcarbonyloxy)phenylalanine tert-butyl ester N-(toluene-4-sulfonyl)-L-prolyl-L-4-(4-(2-pyridyl)piperazin-1-ylcarbonyloxy)phenylalanine N-(toluene-4-sulfonyl)-L-prolyl-L-4-(4-(2-pyridyl)piperazin-1-ylcarbonyloxy)phenylalanine tert-butyl ester N-(toluene-4-sulfonyl)-L-prolyl-L-4-(4-(2-pyridyl)piperazin-1-ylcarbonyloxy)phenylalanine isopropyl ester
N-(4-fluorobenzenesulfonyl)-L-prolyl-L-4-(4-(2-pyridyl)piperazin-1-ylcarbonyloxy)phenylalanine isopropyl ester
N-(4-fluorobenzenesulfonyl)-L-prolyl-L-4-(4-(2-pyridyl)piperazin-1-ylcarbonyloxy)phenylalanine tert-butyl ester
N-(toluene-4-sulfonyl)-L-(1-methanesulfonylpyrazin-3-carbonyl)-L-4-(N,N-dimethylcarbamyloxy)phenylalanine
N-(toluene-4-sulfonyl)-L-4-(methanesulfonyloxy)prolyl-L-4-(N,N-dimethylcarbamyloxy)phenylalanine
N-(4-bromobenzenesulfonyl)-L-(5,5-dimethyl)thiaprolyl-L-4-(4-(2-pyridyl)piperazin-1-ylcarbonyloxy)phenylalanine tert-butyl ester
N-(4-trifluoromethoxybenzenesulfonyl)-L-(5,5-dimethyl)thiaprolyl-L-4-(N,N-dimethylcarbamyloxy)phenylalanine
N-(4-trifluoromethoxybenzenesulfonyl)-L-(5,5-dimethyl)thiaprolyl-L-4-(N,N-dimethylcarbamyloxy)phenylalanine tert-butyl ester
N-(4-trifluoromethoxybenzenesulfonyl)-L-(5,5-dimethyl)thiaprolyl-L-4-(4-(2-pyridyl)piperazin-1-ylcarbonyloxy)phenylalanine tert-butyl ester
N-(4-fluorobenzenesulfonyl)-L-prolyl-L-4-(4-(2-pyridyl)piperazin-1-ylcarbonyloxy)phenylalanine
N-(4-fluorobenzenesulfonyl)-L-(4-hydroxy)prolyl-L-4-(4-(2-pyridyl)piperazin-1-ylcarbonyloxy)phenylalanine
N-(4-trifluoromethoxybenzenesulfonyl)-L-(5,5-dimethyl)thiaprolyl-L-4-(4-(2-pyridyl)piperazin-1-ylcarbonyloxy)phenylalanine
N-(1-methylimidazole-4-sulfonyl)-L-prolyl-L-3-chloro-4-(N,N-dimethylcarbamyloxy)phenylalanine
N-(1-methylimidazole-4-sulfonyl)-L-prolyl-L-3-chloro-4-(N,N-dimethylcarbamyloxy)phenylalanine isopropyl ester
N-(1-methylimidazole-4-sulfonyl)-L-prolyl-L-4-(4-(2-pyridyl)piperazin-1-ylcarbonyloxy)phenylalanine
N-(1-methylimidazole-4-sulfonyl)-L-(5,5-dimethyl)thiaprolyl-L-4-(4-(2-pyridyl)piperazin-1-ylcarbonyloxy)phenylalanine
N-(1-methylpyrazole-3-sulfonyl)-L-prolyl-L-4-(4-(2-pyridyl)piperazin-1-ylcarbonyloxy)phenylalanine
N-(1-methylpyrazole-3-sulfonyl)-L-prolyl-L-4-(4-(2-pyridyl)piperazin-1-ylcarbonyloxy)phenylalanine isopropyl ester
N-(1-methylpyrazole-3-sulfonyl)-L-prolyl-L-4-(4-(2-pyridyl)piperazin-1-ylcarbonyloxy)phenylalanine tert-butyl ester
N-(1-methylpyrazole-3-sulfonyl)-L-(5,5-dimethyl)thiaprolyl-L-4-(4-(2-pyridyl)piperazin-1-ylcarbonyloxy)phenylalanine tert-butyl ester
N-(1-methylimidazole-4-sulfonyl)-L-prolyl-L-3-chloro-4-(4-(2-pyridyl)piperazin-1-ylcarbonyloxy)phenylalanine isopropyl ester
N-(1-methylpyrazole-3-sulfonyl)-L-(5,5-dimethyl)thiaprolyl-L-4-(N,N-dimethylcarbamyloxy)phenylalanine 2-phenoxyethyl ester
N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine
N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine ethyl ester
N-(3-chloro-1,5-dimethylpyrazole-3-sulfonyl)-L-(5,5-dimethyl)thiaprolyl-L-3-chloro-4-(4-(5-trifluoromethyl-2-pyridyl)piperazin-1-ylcarbonyloxy)phenylalanine and pharmaceutically acceptable salts thereof.

Preferred compounds of Formulae I and IA above include those set forth in Table 1 below:

TABLE 1

$$R^1-\underset{\underset{O}{\overset{O}{\|}}}{S}-\underset{R^2}{N}-CH\underset{R^3}{|}-\underset{\|}{\overset{O}{C}}-\underset{H}{N}-CH\underset{R^5}{|}-\overset{O}{\overset{\|}{C}}-R^6$$

| $R^1$ | $R^2$ | $R^3$ | $R^5$ | $R^6$ |
|---|---|---|---|---|
| p-CH$_3$-φ- | $R^2/R^3$ = cyclic 3 carbon atoms (L-pyrrolidinyl) | | p-[(4-methylpiperazin-1-yl)C(O)O-]benzyl- | —OCH$_2$CH$_3$ |
| p-CH$_3$-φ- | $R^2/R^3$ = cyclic 3 carbon atoms (L-pyrrolidinyl) | | p-[(CH$_3$)$_2$NC(O)O-]benzyl- | —OCH$_2$CH$_3$ |
| p-CH$_3$-φ- | $R^2/R^3$ = cyclic 3 carbon atoms (L-pyrrolidinyl) | | p-[(4-methylpiperazin-4-yl)C(O)O-]benzyl- | —OCH(CH$_3$)$_2$ |
| p-CH$_3$-φ- | $R^2/R^3$ = cyclic 3 carbon atoms (L-pyrrolidinyl) | | p-[(4-methylpiperazin-1-yl)C(O)O-]benzyl- | —O-n-butyl |
| p-CH$_3$-φ- | $R^2/R^3$ = cyclic 3 carbon atoms (L-pyrrolidinyl) | | p-[(4-methylpiperazin-1-yl)C(O)O-]benzyl- | —O-cyclopentyl |
| p-CH$_3$-φ- | $R^2/R^3$ = cyclic 3 carbon atoms (L-pyrrolidinyl) | | p-[(4-methylpiperazin-1-yl)C(O)O-]benzyl- | —OC(CH$_3$)$_3$ |
| p-CH$_3$-φ- | $R^2/R^3$ = cyclic 3 carbon atoms (L-pyrrolidinyl) | | p-[(4-methylpiperazin-1-yl)C(O)O-]benzyl- | —OH |
| p-CH$_3$-φ- | $R^2/R^3$ = cyclic 3 carbon atoms (L-pyrrolidinyl) | | p-[(CH$_3$)$_2$NC(O)O-]benzyl- | —OCH(CH$_3$)$_2$ |

TABLE 1-continued

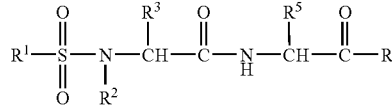

| R$^1$ | R$^2$ | R$^3$ | R$^5$ | R$^6$ |
|---|---|---|---|---|
| p-CH$_3$-φ- | R$^2$/R$^3$ = cyclic 3 carbon atoms (L-pyrrolidinyl) | | p-[(CH$_3$)$_2$NC(O)O-]benzyl- | —O-n-butyl |
| p-CH$_3$-φ- | R$^2$/R$^3$ = cyclic 3 carbon atoms (L-pyrrolidinyl) | | p-[(CH$_3$)$_2$NC(O)O-]benzyl- | —O-cyclopentyl |
| p-CH$_3$-φ- | R$^2$/R$^3$ = cyclic 3 carbon atoms (L-pyrrolidinyl) | | p-[(CH$_3$)$_2$NC(O)O-]benzyl- | —OC(CH$_3$)$_3$ |
| p-CH$_3$-φ- | R$^2$/R$^3$ = cyclic 3 carbon atoms (L-pyrrolidinyl) | | p-[(CH$_3$)$_2$NC(O)O-]benzyl- | —OH |
| p-CH$_3$-φ- | R$^2$/R$^3$ = cyclic 3 carbon atoms (L-pyrrolidinyl) | | p-[(piperidin-4-yl)C(O)O-]benzyl- | —OCH$_2$CH$_3$ |
| φ-CH$_2$— | R$^2$/R$^3$ = cyclic 3 carbon atoms (L-pyrrolidinyl) | | p-[(1-methylpiperidin-4-yl)C(O)O-]benzyl- | —OCH$_2$CH$_3$ |
| φ-CH$_2$— | R$^2$/R$^3$ = cyclic 3 carbon atoms (L-pyrrolidinyl) | | p-[(4-methylpiperazin-1-yl)C(O)O-]benzyl- | —OH |
| p-CH$_3$-φ- | R$^2$/R$^3$ = cyclic 3 carbon atoms (L-pyrrolidinyl) | | m-[(CH$_3$)$_2$NC(O)O-]benzyl- | —OCH$_2$CH$_3$ |
| p-CH$_3$-φ- | R$^2$/R$^3$ = cyclic 3 carbon atoms (L-pyrrolidinyl) | | p-[(1-Boc-4-phenylpiperidin-4-yl)-C(O)O-]benzyl- | —OCH$_2$CH$_3$ |
| p-CH$_3$-φ- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OCH(CH$_3$)$_2$ |
| p-CH$_3$-φ- | R$^2$/R$^3$ = cyclic —CH$_2$—S—C(CH$_3$)$_2$— (L-5 5-dimethylthiazolidin-4-yl) | | p-[(CH$_3$)$_2$NC(O)O-]benzyl- | —OC(CH$_3$)$_3$ |
| p-CH$_3$-φ- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OH |
| p-CH$_3$-φ- | R$^2$/R$^3$ = cyclic —CH$_2$CH$_2$—SO$_2$—CH$_2$— (L-1,1-dioxothiomorpholin-3-yl) | | p-[(CH$_3$)$_2$NC(O)O-]benzyl- | —OC(CH$_3$)$_3$ |
| p-CH$_3$-φ- | R$^2$/R$^3$ = cyclic —CH$_2$CH$_2$—SO$_2$—CH$_2$— (L-1,1-dioxothiomorpholin-3-yl) | | p-[(CH$_3$)$_2$NC(O)O-]benzyl- | —OH |
| p-CH$_3$-φ- | R$^2$/R$^3$ = cyclic —CH$_2$—S—C(CH$_3$)$_2$— (L-5,5-dimethylthiazolidin-4-yl) | | p-[(4-methylpiperazin-1-yl)C(O)O-]benzyl- | —OC(CH$_3$)$_3$ |
| p-CH$_3$-φ- | R$^2$/R$^3$ = cyclic —CH$_2$—S—C(CH$_3$)$_2$— (L-5,5-dimethylthiazolidin-4-yl) | | p-[(4-methylpiperazin-1-yl)C(O)O-]benzyl- | —OH |
| p-CH$_3$-φ- | CH$_3$— | H | p-[(CH$_3$)$_2$NC(O)O-]benzyl- | —OCH(CH$_3$)$_2$ |
| p-CH$_3$-φ- | CH$_3$— | H | p-[(CH$_3$)$_2$NC(O)O-]benzyl- | —OC(CH$_3$)$_3$ |
| p-CH$_3$-φ- | CH$_3$— | H | p-[(CH$_3$)$_2$NC(O)O-]benzyl- | —OH |
| 1-methylimidazol-4-yl | R$^2$/R$^3$ = cyclic 3 carbon atoms (L-pyrrolidinyl) | | p-[(CH$_3$)$_2$NC(O)O-]benzyl- | —OC(CH$_3$)$_3$ |
| p-NH$_2$-φ- | R$^2$/R$^3$ = cyclic 3 carbon atoms (L-pyrrolidinyl) | | p-[(CH$_3$)$_2$NC(O)O-]benzyl- | —OC(CH$_3$)$_3$ |
| p-CH$_3$-φ- | CH$_3$— | H | p-[(morpholin-4-yl)C(O)O-]benzyl- | —OC(CH$_3$)$_3$ |
| p-CH$_3$-φ- | R$^2$/R$^3$ = cyclic 3 carbon atoms (L-pyrrolidinyl) | | p-[(morpholin-4-yl)C(O)O-]benzyl- | —OC(CH$_3$)$_3$ |
| φ-CH$_2$— | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OH |
| p-CH$_3$-φ- | R$^2$/R$^3$ = cyclic —CH$_2$CH$_2$—NH—CH$_2$— (L-piperazinyl) | | p-[(CH$_3$)$_2$NC(O)O-]benzyl- | —OH |
| φ-CH$_2$— | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OC(CH$_3$)$_3$ |

TABLE 1-continued $$R^1-\underset{\underset{O}{\overset{O}{\|}}}{\overset{\|}{S}}-\underset{R^2}{N}-\underset{\underset{R^3}{|}}{CH}-\overset{O}{\overset{\|}{C}}-\underset{H}{N}-\underset{\underset{R^5}{|}}{CH}-\overset{O}{\overset{\|}{C}}-R^6$$

| R¹ | R² | R³ | R⁵ | R⁶ |
|---|---|---|---|---|
| p-CH₃-φ- | R²/R³ = cyclic —CH₂CH₂—NH—CH₂— (L-piperazinyl) | | p-[(CH₃)₂NC(O)O-]benzyl- | —OC(CH₃)₃ |
| p-CH₃-φ- | R²/R³ = cyclic —CH₂CH₂-(Cbz)NHCH₂— [L-4-N-(Cbz)-piperazinyl] | | p-[(CH₃)₂NC(O)O-]benzyl- | —OC(CH₃)₃ |
| p-CH₃-φ- | CH₃— | H | p-[(piperidin-1-yl)C(O)O-]benzyl- | —OH |
| p-CH₃-φ- | R²/R³ = cyclic —CH₂CH₂—SO₂—CH₂— (L-1,1-dioxothiomorpholin-3-yl) | | p-[(morpholin-4-yl)C(O)O-]benzyl- | —OC(CH₃)₃ |
| p-CH₃-φ- | R²/R³ = cyclic —CH₂CH₂—SO₂—CH₂— (L-1,1-dioxothiomorpholin-3-yl) | | p-[(morpholin-4-yl)C(O)O-]benzyl- | —OH |
| 1-methylpyrazol-4-yl | R²/R³ = cyclic 3 carbon atoms (L-pyrrolidinyl) | | p-[(CH₃)₂NC(O)O-]benzyl- | —OC(CH₃)₃ |
| p-F-φ | R²/R³ = cyclic 3 carbon atoms (L-pyrrolidinyl) | | p-[(CH₃)₂NC(O)O-]benzyl- | —OC(CH₃)₃ |
| p-CH₃-φ- | —CH₃ | H | p-[(4-methylpiperazin-1-yl)C(O)O-]benzyl- | —OC(CH₃)₃ |
| p-CH₃-φ- | R²/R³ = cyclic —CH₂—SO₂—C(CH₃)₂— (L-1,1-dioxo-5,5-dimethylthiazolidin-4-yl) | | p-[(CH₃)₂NC(O)O-]benzyl- | —OC(CH₃)₃ |
| 1-methylpyrazol-4-yl | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—SO₂—C(CH₃)₂— (L-1,1-dioxo-5,5-dimethylthiazolidin-4-yl) | | p-[(CH₃)₂NC(O)O-]benzyl- | —OH |
| p-F-φ | R²/R³ = cyclic 3 carbon atoms (L-pyrrolidinyl) | | p-[(CH₃)₂NC(O)O-]benzyl- | —OH |
| 3-pyridyl | R²/R³ = cyclic 3 carbon atoms (L-pyrrolidinyl) | | p-[(CH₃)₂NC(O)O-]benzyl- | —OH |
| p-CH₃-φ- | R²/R³ = cyclic 3 carbon atoms (D-pyrrolidinyl) | | p-[(4-methylpiperazin-1-yl)C(O)O-]benzyl- | —OC(CH₃)₃ |
| p-CH₃-φ- | —CH₃ | —CH₃ | p-[(4-methylpiperazin-1-yl)C(O)O-]benzyl- | —OC(CH₃)₃ |
| p-nitro-φ | R²/R³ = cyclic 3 carbon atoms (L-pyrrolidinyl) | | p-[(CH₃)₂NC(O)O-]benzyl- | —OC(CH₃)₃ |
| p-CH₃-φ- | —CH₃ | H | p-[(thiomorpholin-4-yl)C(O)O-]benzyl- | —OC(CH₃)₃ |
| p-CH₃-φ- | —CH₃ | —CH₃ | p-[(4-methylpiperazin-1-yl)C(O)O-]benzyl- | —OH |
| p-CH₃-φ- | R²/R³ = cyclic 3 carbon atoms (L-pyrrolidinyl) | | p-[(thiomorpholin-4-yl sulfone)-C(O)O-]benzyl- | —OH |
| p-CH₃-φ- | R²/R³ = cyclic 3 carbon atoms (L-pyrrolidinyl) | | p-[(thiomorpholin-4-yl)C(O)O-]benzyl- | —OH |
| p-CH₃-φ- | R²/R³ = cyclic 3 carbon atoms (L-pyrrolidinyl) | | p-[(piperidin-1-yl)C(O)O-]benzyl- | —OH |
| p-CH₃-φ- | R²/R³ = cyclic 3 carbon atoms (L-pyrrolidinyl) | | p-[(pyrrolidin-1-yl)C(O)O-]benzyl- | —OH |
| p-CH₃-φ- | R²/R³ = cyclic 3 carbon atoms (L-pyrrolidinyl) | | p-[(morpholin-4-yl)C(O)O-]benzyl- | —OH |
| p-CH₃-φ- | R²/R³ = cyclic 3 carbon atoms (L-pyrrolidinyl) | | p-[(4-methylpiperazin-1-yl)C(O)O-]benzyl- | —OCH₂C(CH₃)₃ |
| p-CH₃-φ- | R²/R³ = cyclic 3 carbon atoms (L-pyrrolidinyl) | | p-[(CH₃)₂NC(O)O-]benzyl- | —OCH₂C(CH₃)₃ |
| p-CH₃-φ- | R²/R³ = cyclic 3 carbon atoms (L-pyrrolidinyl) | | p-[(1-Boc-piperazin-4-yl)C(O)O-]benzyl- | —OCH₂CH₃ |

TABLE 1-continued $$R^1-\underset{\underset{O}{\overset{O}{\|}}}{S}-\underset{R^2}{N}-\underset{R^3}{CH}-\overset{O}{\overset{\|}{C}}-\underset{H}{N}-\underset{R^5}{CH}-\overset{O}{\overset{\|}{C}}-R^6$$

| R¹ | R² | R³ | R⁵ | R⁶ |
|---|---|---|---|---|
| p-CH₃-φ- | R²/R³ = cyclic 3 carbon atoms (L-pyrrolidinyl) | | p-[(morpholin-4-yl)C(O)O-]benzyl- | —OCH₂CH₃ |
| p-CH₃-φ- | —CH₃ | H | p-[(thiomorpholin-4-yl sulfone)-C(O)O-]benzyl- | —OC(CH₃)₃ |
| p-CH₃-φ- | —CH₃ | H | p-[(thiomorpholin-4-yl)C(O)O-]benzyl- | —OH |
| p-CH₃-φ- | —CH₃ | —CH₃ | p-[(CH₃)₂NC(O)O-]benzyl- | —OC(CH₃)₃ |
| p-CH₃-φ- | R²/R³ = cyclic —CH₂—CH₂—S—CH₂— (L-thiomorpholin-3-yl) | | p-[(CH₃)₂NC(O)O-]benzyl- | —OC(CH₃)₃ |
| p-CH₃-φ- | —CH₃ | H | p-[(thiomorpholin-4-yl sulfone)-C(O)O-]benzyl- | —OH |
| p-CH₃-φ- | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| p-CH₃-φ- | R²/R³ = cyclic —CH₂—CH₂—SO₂—CH₂— (L-1,1-dioxothiomorpholin-3-yl) | | p-[(morpholin-4-yl)C(O)O-]benzyl- | —OC(CH₃)₃ |
| p-CH₃-φ- | —CH₃ | —CH₃ | p-[(CH₃)₂NC(O)O-]benzyl- | —OH |
| p-F-φ | R²/R³ = cyclic —CH₂—CH₂—S—CH₂— (L-thiomorpholin-3-yl) | | p-[(CH₃)₂NC(O)O-]benzyl- | —OC(CH₃)₃ |
| p-F-φ | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| pyridin-3-yl | R²/R³ = cyclic 3 carbon atoms (L-pyrrolidinyl) | | p-[(CH₃)₂NC(O)O-]benzyl- | —OC(CH₃)₃ |
| p-nitro-φ | R²/R³ = cyclic 3 carbon atoms (L-pyrrolidinyl) | | p-[(CH₃)₂NC(O)O-]benzyl- | —OH |
| p-N≡C-φ | R²/R³ = cyclic 3 carbon atoms (L-pyrrolidinyl) | | p-[(CH₃)₂NC(O)O-]benzyl- | —OC(CH₃)₃ |
| p-CH₃-φ | R²/R³ = cyclic —CH₂—CH₂—SO₂—CH₂— (L-1,1-dioxothiomorpholin-3-yl) | | p-[(CH₃)₂NC(O)O-]benzyl- | —OH |
| p-CH₃-φ | R²/R³ = cyclic —CH₂—SO₂—CH₂— (L-1,1-dioxothiazolidin-4-yl) | | p-[(CH₃)₂NC(O)O-]benzyl- | —OC(CH₃)₃ |
| p-F₃C-φ | R²/R³ = cyclic 3 carbon atoms (L-pyrrolidinyl) | | p-[(CH₃)₂NC(O)O-]benzyl- | —OC(CH₃)₃ |
| 1-methylpyrazol-4-yl | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—SO₂—CH₂— (L-1,1-dioxothiazolidin-4-yl) | | p-[(CH₃)₂NC(O)O-]benzyl- | —OH |
| p-F-φ | R²/R³ = cyclic —CH₂—S—CH₂— (L-thiazolidin-4-yl) | | p-[(CH₃)₂NC(O)O-]benzyl- | —OH |
| p-CH₃-φ- | R²/R³ = cyclic 3 carbon atoms (L-pyrrolidinyl) | | p-[(CH₃)₂NC(O)O-]benzyl- | 2,4-dioxo-tetrahydrofuran-3-yl(3,4-enol) |
| p-CH₃-φ- | R²/R³ = cyclic 3 carbon atoms (L-pyrrolidinyl) | | p-[(piperazin-4-yl)C(O)O-]benzyl- | —OH |
| p-CH₃-φ- | R²/R³ = cyclic 3 carbon atoms (L-pyrrolidinyl) | | p-[(1-Boc-piperazin-4-yl)C(O)O-]benzyl- | —OC(CH₃)₃ |
| p-CH₃-φ- | R²/R³ = cyclic 3 carbon atoms (L-pyrrolidinyl) | | p-[(piperazin-4-yl)C(O)O-]benzyl- | —OCH₂CH₃ |
| p-CH₃-φ- | R²/R³ = cyclic 3 carbon atoms (L-pyrrolidinyl) | | p-[(4-acetylpiperazin-1-yl)C(O)O-]benzyl- | —OCH₂CH₃ |
| p-CH₃-φ- | R²/R³ = cyclic 3 carbon atoms (L-pyrrolidinyl) | | p-[(4-methanesulfonylpiperazin-1-yl)-C(O)O-]benzyl- | —OCH₂CH₃ |

TABLE 1-continued

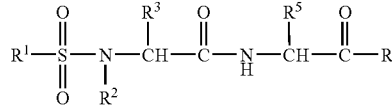

| R¹ | R² | R³ | R⁵ | R⁶ |
|---|---|---|---|---|
| p-CH₃-φ- | R²/R³ = cyclic 3 carbon atoms (L-pyrrolidinyl) | | 3-nitro-4-[(morpholin-4-yl)-C(O)O-]benzyl- | —OH |
| p-CH₃-φ- | R²/R³ = cyclic 3 carbon atoms (L-pyrrolidinyl) | | p-[(1-Boc-piperazin-4-yl)C(O)O-]benzyl- | —OH |
| p-CH₃-φ- | —CH₃ | —C(CH₃)₃ | p[(4-methylpiperazin-1-yl)C(O)O-]benzyl- | —OC(CH₃)₃ |
| p-F-φ | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| p-F-φ | R²/R³ = cyclic —CH₂—CH₂—SO₂—CH₂— (L-1,1-dioxothiomorpholin-3-yl) | | p-[(1,1-dioxothiomorpholin-4-yl)-C(O)O-]benzyl- | —OC(CH₃)₃ |
| p-CH₃-φ- | R²/R³ = cyclic —CH₂—CH₂—SO₂—CH₂— (L-1,1-dioxothiomorpholin-3-yl) | | p-[(1,1-dioxothiomorpholin-4-yl)-C(O)O-]benzyl- | —OC(CH₃)₃ |
| p-F-φ | R²/R³ = cyclic 3 carbon atoms (L-pyrrolidinyl) | | p-[(1,1-dioxothiomorpholin-4-yl)-C(O)O-]benzyl- | —OC(CH₃)₃ |
| p-F-φ | R²/R³ = cyclic 3 carbon atoms (L-pyrrolidinyl) | | p-[(thiomorpholin-4-yl)C(O)O-]benzyl- | —OC(CH₃)₃ |
| p-F-φ | R²/R³ = cyclic 3 carbon atoms (L-pyrrolidinyl) | | p-[(morpholin-4-yl)C(O)O-]benzyl- | —OC(CH₃)₃ |
| p-F-φ | R²/R³ = cyclic —CH₂—S—C(CH₃)₂— (L-5,5-dimethylthiazolidin-4-yl) | | p-[(CH₃)₂NC(O)O-]benzyl- | —OH |
| p-F-φ | R²/R³ = cyclic —CH₂—CH₂—SO₂—CH₂— (L-1,1-dioxothiomorpholin-3-yl) | | p-[(morpholin-4-yl)C(O)O-]benzyl- | —OC(CH₃)₃ |
| p-F₃CO-p | R²/R³ = cyclic 3 carbon atoms (L-pyrrolidinyl) | | p-[(CH₃)₂NC(O)O-]benzyl- | —OC(CH₃)₃ |
| p-CH₃-φ- | R²/R³ = cyclic —CH₂—CH₂—SO₂—CH₂— (L-1,1-dioxothiomorpholin-3-yl) | | p-[(CH₃)₂NC(O)O-]benzyl- | —OCH(CH₃)₂ |
| p-F-φ | R²/R³ = cyclic —CH₂—SO₂—C(CH₃)₂— (L-1,1-dioxo-5,5-dimethylthiazolidin-4-yl) | | p-[(CH₃)₂NC(O)O-]benzyl- | —OC(CH₃)₃ |
| p-CH₃-φ- | R²/R³ = cyclic —CH₂—SO₂—C(CH₃)₂— (L-1,1-dioxo-5,5-dimethylthiazolidin-4-yl) | | p-[(CH₃)₂NC(O)O-]benzyl- | —OCH(CH₃)₂ |
| p-CH₃-φ- | R²/R³ = cyclic —CH₂—CH₂—SO₂—CH₂— (L-1,1-dioxothiomorpholin-3-yl) | | p-[(morpholin-4-yl)C(O)O-]benzyl- | —OH |
| p-F-φ | R²/R³ = cyclic —CH₂—SO₂—C(CH₃)₂— (L-1,1-dioxo-5,5-dimethylthiazolidin-4-yl) | | p-[(CH₃)₂NC(O)O-]benzyl- | —OH |
| pyrimidin-2-yl | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—CH₂—SO₂—CH₂— (L-1,1-dioxothiomorpholin-3-yl) | | p-[(4-methylpiperazin-1-yl)C(O)O-]benzyl- | —OC(CH₃)₃ |
| p-F-φ | R²/R³ = cyclic —CH₂—SO₂—CH₂— (L-1,1-dioxothiazolidin-4-yl) | | p-[(CH₃)₂NC(O)O-]benzyl- | —OC(CH₃)₃ |
| 2,5-dichlorothien-3-yl | R²/R³ = cyclic 3 carbon atoms (L-pyrrolidinyl) | | p-[(CH₃)₂NC(O)O-]benzyl- | —OC(CH₃)₃ |
| p-CH₃C(O)NH-p | R²/R³ = cyclic 3 carbon atoms (L-pyrrolidinyl) | | p-[(CH₃)₂NC(O)O-]benzyl- | —OC(CH₃)₃ |
| p-C(CH₃)₃-φ | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |

TABLE 1-continued $$R^1-\underset{\underset{R^2}{|}}{\overset{\overset{O}{\|}}{\underset{\|}{S}}}-\underset{\underset{}{|}}{N}-\underset{\underset{}{|}}{\overset{R^3}{C}H}-\overset{\overset{O}{\|}}{C}-\underset{\underset{H}{|}}{N}-\underset{\underset{}{|}}{\overset{R^5}{C}H}-\overset{\overset{O}{\|}}{C}-R^6$$

| R¹ | R² | R³ | R⁵ | R⁶ |
|---|---|---|---|---|
| pyridin-2-yl | R²/R³ = cyclic<br>3 carbon atoms<br>(L-pyrrolidinyl) | | p-[(CH₃)₂NC(O)O-]benzyl- | —OH |
| o-F-φ | R²/R³ = cyclic<br>—CH₂—CH₂—SO₂—CH₂—<br>(L-1,1-dioxothiomorpholin-3-yl) | | p-[(CH₃)₂NC(O)O-]benzyl- | —OC(CH₃)₃ |
| m-F-φ | R²/R³ = cyclic<br>—CH₂—CH₂—SO₂—CH₂—<br>(L-1,1-dioxothiomorpholin-3-yl) | | p-[(CH₃)₂NC(O)O-]benzyl- | —OC(CH₃)₃ |
| 2,4-difluoro-φ | R²/R³ = cyclic<br>—CH₂—CH₂—SO₂—CH₂—<br>(L-1,1-dioxothiomorpholin-3-yl) | | p-[(CH₃)₂NC(O)O-]benzyl- | —OC(CH₃)₃ |
| p-CH₃C(O)NH-φ | R²/R³ = cyclic<br>3 carbon atoms<br>(L-pyrrolidinyl) | | p-[(CH₃)₂NC(O)O-]benzyl- | —OH |
| p-C(F)₃O-φ | R²/R³ = cyclic<br>3 carbon atoms<br>(L-pyrrolidinyl) | | p-[(CH₃)₂NC(O)O-]benzyl- | —OH |
| p-F-φ | R²/R³ = cyclic<br>—CH₂S—S—C(CH₃)₂—<br>(L-5,5-dimethylthiazolidin-4-yl) | | p-[(CH₃)₂NC(O)O-]benzyl- | —OCH(CH₃)₂ |
| p-N≡C-φ | R²/R³ = cyclic<br>3 carbon atoms<br>(L-pyrrolidinyl) | | p-[(CH₃)₂NC(O)O-]benzyl- | —OH |
| morpholin-4-yl | R²/R³ = cyclic<br>3 carbon atoms<br>(L-pyrrolidinyl) | | p-[(CH₃)₂NC(O)O-]benzyl- | —OC(CH₃)₃ |
| p-CH₃-φ- | R²/R³ = cyclic<br>—CH₂—CH₂—C(CH₃)₂—<br>(L-4,4-dimethyl pyrrolidinyl) | | p-[(CH₃)₂NC(O)O-]benzyl- | —OC(CH₃)₃ |
| p-CH₃-φ- | R²/R³ = cyclic<br>—CH₂—CH₂—C(CH₃)₂—<br>(L-4,4-dimethyl pyrrolidinyl) | | p-[(CH₃)₂NC(O)O-]benzyl- | —OCH(CH₃)₂ |
| 1-methylpyrazol-4-yl | R²/R³ = cyclic<br>3 carbon atoms<br>(L-pyrrolidinyl) | | p-[(CH₃)₂NC(O)O-]benzyl- | —OCH(CH₃)₂ |
| p-CH₃-φ- | R²/R³ = cyclic<br>—CH₂—S—C(CH₃)₂—<br>(L-5,5-dimethylthiazolidin-4-yl) | | p-[(CH₃)₂NC(O)O-]benzyl- | —OCH(CH₃)₂ |
| p-CH₃-φ- | R²/R³ = cyclic<br>3 carbon atoms<br>(L-pyrrolidinyl) | | p-[(thiomorpholin-4-yl)C(O)O-]benzyl- | —OC(CH₃)₃ |
| 1-methylimidazol-4-yl | R²/R³ = cyclic<br>3 carbon atoms<br>(L-pyrrolidinyl) | | p-[(CH₃)₂NC(O)O-]benzyl- | —OH |
| p-CH₃-φ- | R²/R³ = cyclic<br>—CH₂—CH₂—SO₂—CH₂—<br>(L-1,1-dioxothiomorpholin-3-yl) | | p-[(CH₃)₂NC(O)O-]benzyl- | |
| 1-methylpyrazol-4-yl | R²/R³ = cyclic<br>—CH₂—S—C(CH₃)₂—<br>(L-5,5-dimethylthiazolidin-4-yl) | | p-[(CH₃)₂NC(O)O-]benzyl- | —OC(CH₃)₃ |
| p-CH₃C(O)NH-φ | R²/R³ = cyclic<br>3 carbon atoms<br>(L-pyrrolidinyl) | | p-[(CH₃)₂NC(O)O-]benzyl- | —OC(CH₃)₃ |
| p-(CH₃)₃C-φ- | R²/R³ = cyclic<br>—CH₂—CH₂—SO₂—CH₂—<br>(L-1,1-dioxothiomorpholin-3-yl) | | p-[(CH₃)₂NC(O)O-]benzyl- | —OC(CH₃)₃ |
| 1-methylpyrazol-4-yl | R²/R³ = cyclic<br>—CH₂—S—C(CH₃)₂—<br>(L-5,5-dimethylthiazolidin-4-yl) | | p-[(CH₃)₂NC(O)O-]benzyl- | —OH |
| pyridin-3-yl- | R²/R³ = cyclic<br>3 carbon atoms<br>(L-pyrrolidinyl) | | p-[(CH₃)₂NC(O)O-]benzyl- | —OH |
| p-N≡C-φ- | R²/R³ = cyclic<br>3 carbon atoms<br>(L-pyrrolidinyl) | | p-[(CH₃)₂NC(O)O-]benzyl- | —OH |
| p-F-φ- | R²/R³ = cyclic<br>—CH₂—S—C(CH₃)₂—<br>(L-5,5-dimethylthiazolidin-4-yl) | | p-[(CH₃)₂NC(O)O-]benzyl- | —OCH(CH₃)₂ |

TABLE 1-continued $$R^1-\underset{\underset{O}{\overset{O}{\|}}}{S}-\underset{R^2}{N}-\underset{R^3}{CH}-\overset{O}{\overset{\|}{C}}-\underset{H}{N}-\underset{R^5}{CH}-\overset{O}{\overset{\|}{C}}-R^6$$

| R¹ | R² | R³ | R⁵ | R⁶ |
|---|---|---|---|---|
| p-CH₃-φ- | R²/R³ = cyclic 3 carbon atoms (L-pyrrolidinyl) | | p-[(1,4-dioxa-8-azaspiro[4.5]decan-8-yl)-C(O)O-]benzyl- | —OCH₂CH₃ |
| p-CH₃-φ- | R²/R³ = cyclic 3 carbon atoms (L-pyrrolidinyl) | | p-[(1,4-dioxa-8-azaspiro[4.5]decan-8-yl)-C(O)O-]benzyl- | —OH |
| p-CH₃-φ- | R²/R³ = cyclic 3 carbon atoms (L-pyrrolidinyl) | | p-[(4-acetylpiperazin-1-yl)C(O)O-]benzyl- | —OH |
| p-CH₃-φ- | R²/R³ = cyclic 3 carbon atoms (L-pyrrolidinyl) | | p-[(4-methanesulfonylpiperazin-1-yl)-C(O)O-]benzyl- | —OH |
| p-CH₃-φ- | R²/R³ = cyclic 3 carbon atoms (L-pyrrolidinyl) | | p-[(4-φ-piperazin-1-yl)C(O)(O)-]benzyl- | —OH |
| p-CH₃-φ- | R²/R³ = cyclic 3 carbon atoms (L-pyrrolidinyl) | | p-[(piperazin-1-yl)C(O)O-]benzyl- | —OC(CH₃)₃ |
| p-CH₃-φ- | R²/R³ = cyclic —CH₂CH₂—NH—CH₂— (L-piperazinyl) | | p-[(CH₃)₂NC(O)O-]benzyl- | —OC(CH₃)₃ |
| p-F₃CO-φ- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—CH₂—C(CH₃)₂— (4,4-dimethyl pyrrolidinyl) | | p-[(CH₃)₂NC(O)O-]benzyl- | —OC(CH₃)₃ |
| p-CH₃-φ- | R²/R³ = cyclic —CH₂—CH₂—C(CH₃)₂— (4,4-dimethyl pyrrolidinyl) | | p-[(CH₃)₂NC(O)O-]benzyl- | —OCH(CH₃)₂ |
| p-CH₃C(O)NH-φ- | R²/R³ = cyclic 3 carbon atoms (L-pyrrolidinyl) | | p-[(CH₃)₂NC(O)O-]benzyl- | —OH |
| o-F-φ- | R²/R³ = cyclic (L-1,1-dioxothiomorpholin-3-yl) | | p-[(CH₃)₂NC(O)O-]benzyl- | —OC(CH₃)₃ |
| morpholin-4-yl- | R²/R³ = cyclic 3 carbon atoms (L-pyrrolidinyl) | | p-[(CH₃)₂NC(O)O-]benzyl- | —OC(CH₃)₃ |
| m-F-φ- | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| 2,4-difluoro-φ- | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| morpholin-4-yl- | R²/R³ = cyclic 3 carbon atoms (L-pyrrolidinyl) | | p-[(CH₃)₂NC(O)O-]benzyl- | —OH |
| 1-methylpyrazol-4-yl- | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| o-F-φ- | R²/R³ = cyclic —CH₂—CH₂—SO₂—CH₂— (L-1,1-dioxothiomorpholin-3-yl) | | p-[(CH₃)₂NC(O)O-]benzyl- | —OH |
| 2,4-difluoro-φ- | R²/R³ = cyclic —CH₂—CH₂—SO₂—CH₂— (L-1,1-dioxothiomorpholin-3-yl) | | p-[(CH₃)₂NC(O)O-]benzyl- | —OH |
| p-CH₃-φ- | R²/R³ = cyclic —CH₂—CH₂—S—CH₂— (L-thiomorpholin-3-yl) | | p-[(CH₃)₂NC(O)O-]benzyl- | —OH |
| pyridin-3-yl- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| m-F-φ- | R²/R³ = cyclic —CH₂—CH₂—SO₂—CH₂— (L-1,1-dioxothiomorpholin-3-yl) | | p-[(CH₃)₂NC(O)O-]benzyl- | —OH |
| pyridin-2-yl- | R²/R³ = cyclic 3 carbon atoms (L-pyrrolidinyl) | | p-[(CH₃)₂NC(O)O-]benzyl- | —OCH(CH₃)₂ |

TABLE 1-continued

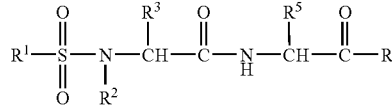

| R¹ | R² | R³ | R⁵ | R⁶ |
|---|---|---|---|---|
| 1-methylpyrazol-4-yl | R²/R³ = cyclic —CH₂—CH₂—SO₂—CH₂— (L-1,1-dioxothiomorpholin-3-yl) | | p-[(CH₃)₂NC(O)O-]benzyl- | —OH |
| p-CH₃-φ- | R²/R³ = cyclic 3 carbon atoms (L-pyrrolidinyl) | | p-[(4-methanesulfonylpiperazin-1-yl)-C(O)O-]benzyl- | —OC(CH₃)₃ |
| p-CH₃-φ- | R²/R³ = cyclic 3 carbon atoms (L-pyrrolidinyl) | | p-[(4-φ-piperazin-1-yl)C(O)(O)-]benzyl- | —OC(CH₃)₃ |
| p-CH₃-φ- | R²/R³ = cyclic 3 carbon atoms | | p-[(CH₃)₂NC(O)O-]benzyl- | —O—CH₂C(CH₃)₂—NHC(O)OC(CH₃)₃ |
| p-CH₃-φ- | R²/R³ = cyclic 3 carbon atoms | | p-[(CH₃)₂NC(O)O-]benzyl- | —O—CH₂CH₂—(morpholin-4-yl) |
| p-CH₃-φ- | R²/R³ = cyclic 3 carbon atoms (L-pyrrolidinyl) | | p-[(4-acetylpiperazin-1-yl)C(O)O-]benzyl- | —OC(CH₃)₃ |
| p-CH₃-φ- | R²/R³ = cyclic 3 carbon atoms (L-pyrrolidinyl) | | p-[(CH₃)₂NCH₂CH₂N(CH₃)C(O)O-]benzyl- | —OC(CH₃)₃ |
| p-CH₃-φ- | R²/R³ = cyclic —CH₂—S—C(CH₃)₂— (L-5,5-dimethylthiazolidin-4-yl) | | p-[(CH₃)₂NCH₂CH₂N(CH₃)C(O)O-]benzyl- | —OC(CH₃)₃ |
| p-CH₃-φ- | R²/R³ = cyclic —CH₂—S—C(CH₃)₂— (L-5,5-dimethylthiazolidin-4-yl) | | p-[(CH₃)₂NCH₂CH₂N(CH₃)C(O)O-]benzyl- | —OH |
| p-CH₃-φ- | R²/R³ = cyclic 3 carbon atoms (L-pyrrolidinyl) | | p-[(CH₃)₂NCH₂CH₂N(CH₃)C(O)O-]benzyl- | —OH |
| p-CH₃-φ- | R²/R³ = cyclic 3 carbon atoms (L-pyrrolidinyl) | | p-[(4-hydroxypiperidin-1-yl)C(O)O-]benzyl- | —OC(CH₃)₃ |
| p-(CH₃)₃C-φ- | R²/R³ = cyclic —CH₂—CH₂—SO₂—CH₂— (L-1,1-dioxothiomorpholin-3-yl) | | p-[(CH₃)₂NC(O)O-]benzyl- | —OH |
| p-CH₃-φ- | R²/R³ = cyclic —CH₂—S—C(CH₃)₂— (L-5,5-dimethylthiazolidin-4-yl) | | p-[(thiomorpholin-4-yl)C(O)O-]benzyl- | —OC(CH₃)₃ |
| 2,5-dichlorothien-3-yl- | R²/R³ = cyclic 3 carbon atoms (L-pyrrolidinyl) | | p-[(CH₃)₂NC(O)O-]benzyl- | —OH |
| p-CH₃O-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic —CH₂—CH₂—C(CH₃)₂— (4,4-dimethyl pyrrolidinyl) | | p-[(CH₃)₂NC(O)O-]benzyl- | —OH |
| p-F-φ- | R²/R³ = cyclic —CH₂—S—C(CH₃)₂— (L-5,5-dimethylthiazolidin-4-yl) | | 3-chloro-4-[(4-methylpiperazin-1-yl)C(O)O-]-benzyl- | —OC(CH₃)₃ |
| p-F-φ- | R²/R³ = cyclic —CH₂—S—C(CH₃)₂— (L-5,5-dimethylthiazolidin-4-yl) | | 3-chloro-4-[(CH₃)₂NC(O)O-]-benzyl- | —OH |
| p-F-φ- | R²/R³ = cyclic (L-5,5-dimethylthiazolidin-4-yl) | benzyl- | 3-chloro-4-[(thiomorpholin-4-yl)C(O)O-]- | —OC(CH₃)₃ |
| p-CH₃-φ- | R²/R³ = cyclic 3 carbon atoms (L-pyrrolidinyl) | | p-[(morpholin-4-yl)-CH₂CH₂NHC(O)O-]benzyl- | —OC(CH₃)₃ |
| p-CH₃-φ- | R²/R³ = cyclic 3 carbon atoms (L-pyrrolidinyl) | | p-[(1,4-dioxa-8-azaspiro[4.5]decan-8-yl)-C(O)O-]benzyl- | —OC(CH₃)₃ |
| p-F-φ- | R²/R³ = cyclic —CH₂—S—C(CH₃)₂— (L-5,5-dimethylthiazolidin-4-yl) | | 3-chloro-4-[(CH₃)₂NC(O)O-]-benzyl- | —OC(CH₃)₃ |
| p-CH₃-φ- | R²/R³ = cyclic —CH₂—S—C(CH₃)₂— (L-5,5-dimethylthiazolidin-4-yl) | | p-[(thiomorpholin-4-yl)C(O)O-]benzyl- | —OH |
| pyridin-2-yl- | R²/R³ = cyclic 3 carbon atoms (L-pyrrolidinyl) | | p-[(CH₃)₂NC(O)O-]benzyl- | —OH |

TABLE 1-continued

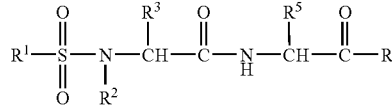

| R¹ | R² | R³ | R⁵ | R⁶ |
|---|---|---|---|---|
| p-CH₃-φ- | R²/R³ = cyclic —CH₂—CH₂—(O)—CH₂— (L-1-oxothiomorpholin-4-yl) | | p-[(CH₃)₂NC(O)O-]benzyl- | —OCH(CH₃)₂ |
| 4-Cl-3-(NH₂—SO₂-)-φ- | R²/R³ = cyclic 3 carbon atoms (L-pyrrolidinyl) | | p-[(CH₃)₂NC(O)O-]benzyl- | —OCH(CH₃)₂ |
| p-F-φ- | R²/R³ = cyclic —CH₂—S—C(CH₃)₂— (L-5,5-dimethylthiazolidin-4-yl) | | 3-chloro-4-[(thiomorpholin-4-yl)C(O)O-]-benzyl- | —OCH(CH₃)₂ |
| p-F-φ- | R²/R³ = cyclic —CH₂—S—C(CH₃)₂— (L-5,5-dimethylthiazolidin-4-yl) | | 3-chloro-4-[(CH₃)₂NC(O)O-]-benzyl- | —OCH(CH₃)₂ |
| p-CH₃-φ- | R²/R³ = cyclic 3 carbon atoms (L-pyrrolidinyl) | | p-[HOCH₂CH₂N(CH₃)C(O)O-]benzyl- | —OC(CH₃)₃ |
| p-F-φ- | R²/R³ = cyclic —CH₂—S—C(CH₃)₂— (L-5,5-dimethylthiazolidin-4-yl) | | p-[(2-(hydroxymethyl)pyrrolidin-1-yl)-C(O)O-]-benzyl- | —OC(CH₃)₃ |
| p-F-φ- | R²/R³ = cyclic —CH₂—S—C(CH₃)₂— (L-5,5-dimethylthiazolidin-4-yl) | | p-[(2-(hydroxymethyl)pyrrolidin-1-yl)-C(O)O-]-benzyl- | —OH |
| p-CH₃-φ- | R²/R³ = cyclic 3 carbon atoms (L-pyrrolidinyl) | | p-[(2-(CH₃OC(O)-)pyrrolidin-1-yl)-C(O)O-]-benzyl- | —OC(CH₃)₃ |
| p-CH₃-φ- | R²/R³ = cyclic 3 carbon atoms (L-pyrrolidinyl) | | p-[(4-(HC(O)O-)piperidin-1-yl)-C(O)O-]-benzyl- | —OH |
| p-CH₃-φ- | R²/R³ = cyclic 3 carbon atoms (L-pyrrolidinyl) | | p-[(4-(hydroxypiperidin-1-yl)-C(O)O-]-benzyl- | —OCH(CH₃)₂ |
| p-F-φ- | R²/R³ = cyclic —CH₂—S—C(CH₃)₂— (L-5,5-dimethylthiazolidin-4-yl) | | 3-chloro-4-[(thiomorpholin-4-yl)C(O)O-]-benzyl- | —OH |
| p-CH₃-φ- | R²/R³ = cyclic 3 carbon atoms (L-pyrrolidinyl) | | p-[(4-(CH₃CH₂OC(O)-)piperidin-1-yl)C(O)O-]-benzyl- | —OC(CH₃)₃ |
| p-CH₃-φ- | R²/R³ = cyclic 3 carbon atoms (L-pyrrolidinyl) | | p-[(4-(HOCH₂CH₂-)piperazin-1-yl)-C(O)O-]benzyl- | —OC(CH₃)₃ |
| p-F-φ- | R²/R³ = cyclic —CH₂—S—C(CH₃)₂— (L-5,5-dimethylthiazolidin-4-yl) | | p-[(4-(pyridin-2-yl)piperazin-1-yl)-C(O)O-]benzyl- | —OH |
| p-F-φ- | R²/R³ = cyclic —CH₂—S—C(CH₃)₂— (L-5,5-dimethylthiazolidin-4-yl) | | p-[(4-(pyridin-2-yl)piperazin-1-yl)-C(O)O-]benzyl | —OC(CH₃)₃ |
| p-CH₃-φ- | R²/R³ = cyclic 3 carbon atoms (L-pyrrolidinyl) | | p-[HC(O)OCH₂CH₂N(CH₃)C(O)O-]benzyl- | —OH |
| p-CH₃-φ- | R²/R³ = cyclic 3 carbon atoms (L-pyrrolidinyl) | | p-[HOCH₂CH₂N(CH₃)C(O)O-]benzyl- | —OCH(CH₃)₂ |
| p-CH₃-φ- | R²/R³ = cyclic 3 carbon atoms (L-pyrrolidinyl) | | p-[CH₃OC(O)CH₂NHC(O)O-]benzyl- | —OC(CH₃)₃ |
| quinolin-8-yl- | R²/R³ = cyclic 3 carbon atoms (L-pyrrolidinyl) | | p-[(CH₃)₂NC(O)O-]benzyl- | —OCH(CH₃)₂ |
| 3,4-difluoro-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(thiomorpholin-4-yl)-C(O)O-]benzyl- | —OCH(CH₃)₂ |
| p-CH₃O-φ- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—CH₂—(O)—CH₂— (L-1-oxothiomorpholin-4-yl) | | p-[(CH₃)₂NC(O)O-]benzyl- | —OH |

TABLE 1-continued $$R^1-\overset{O}{\underset{O}{S}}-\underset{R^2}{N}-\underset{R^3}{CH}-\overset{O}{C}-\underset{H}{N}-\underset{R^5}{CH}-\overset{O}{C}-R^6$$

| R¹ | R² | R³ | R⁵ | R⁶ |
|---|---|---|---|---|
| 3,4-difluoro-φ- | R²/R³ = cyclic —CH₂CH₂—SO₂—CH₂— (L-1,1-dioxothiomorpholin-3-yl) | | p-[(CH₃)₂NC(O)O-]benzyl- | —OC(CH₃)₃ |
| p-H₂N-φ- | R²/R³ = cyclic 3 carbon atoms (L-pyrrolidinyl) | | p-[(CH₃)₂NC(O)O-]benzyl- | —OCH(CH₃)₂ |
| 3,4-difluoro-φ- | R²/R³ = cyclic —CH₂CH₂—SO₂—CH₂— (L-1,1-dioxothiomorpholin-3-yl) | | p-[(CH₃)₂NC(O)O-]benzyl- | —OH |
| 3,4-difluoro-φ- | R²/R³ = cyclic 3 carbon atoms (L-pyrrolidinyl) | | p-[(CH₃)₂NC(O)O-]benzyl- | —OH |
| quinolin-8-yl- | R²/R³ = cyclic 3 carbon atoms (L-pyrrolidinyl) | | p-[(CH₃)₂NC(O)O-]benzyl- | —OH |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| p-CH₃-φ- | R²/R³ = cyclic —CH₂—CH₂—(O)—CH₂— (L-1-oxothiomorpholin-4-yl) | | p-[(CH₃)₂NC(O)O-]benzyl- | —OC(CH₃)₃ |
| 1-n-butylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 1-methylpyrazol-3-yl | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 2-(CF₃C(O)-)-1,2,3,4-tetrahydro-isoquinolin-7-yl | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(4-(φNHC(O)-)-piperazin-1-yl)-C(O)O-]benzyl- | —OH |
| p-CH₃-φ- | R²/R³ = cyclic 3 carbon atoms (L-pyrrolidinyl) | | p-[(4-methoxypiperidin-1-yl)C(O)O-]benzyl- | —OH |
| p-CH₃-φ- | R²/R³ = cyclic 3 carbon atoms (L-pyrrolidinyl) | ]benzyl | p-[(4-(pyndin-4-ylC(O))piperazin-1-yl)-C(O)O-]benzyl- | —OCH(CH₃)₂ |
| p-CH₃-φ- | R²/R³ = cyclic —CH₂—C(O)—CH₂— (L-4-oxopyrrolidinyl) | | p-[(CH₃)₂NC(O)O-]benzyl- | —OC(CH₃)₃ |
| p-CH₃-φ- | R²/R³ = cyclic —CH₂—CH(OH)CH₂— (L-4-hydroxypyrrolidinyl) | | p-[(CH₃)₂NC(O)O-]benzyl- | —OC(CH₃)₃ |
| m-F-φ- | R²/R³ = cyclic 3 carbon atoms (L-pyrrolidinyl) | | p-[(CH₃)₂NC(O)O-]benzyl- | —OC(CH₃)₃ |
| p-CH₃-φ- | R²/R³ = cyclic 3 carbon atoms (L-pyrrolidinyl) | | p-[(4-methoxypiperidin-1-yl)C(O)O-]benzyl- | —OCH(CH₃)₂ |
| p-CH₃-φ- | R²/R³ = cyclic 3 carbon atoms (L-pyrrolidinyl) | | p-[(4-φNHC(O)-)piperazin-1-yl)-C(O)O-]benzyl- | —OCH(CH₃)₂ |
| p-(φNHC(O)NH)φ- | R²/R³ = cyclic 3 carbon atoms (L-pyrrolidinyl) | | p-[(CH₃)₂NC(O)O-]benzyl- | —OC(CH₃)₃ |
| p-F-φ- | R²/R³ = cyclic —CH₂—S—C(CH₃)₂— (L-5,5-dimethylthiazolidin-4-yl) | | 3-chloro-4-[(4-methylpiperidin-1-yl)-C(O)O-]-benzyl- | —OCH(CH₃)₂ |
| p-CH₃-φ- | R²/R³ = cyclic —CH₂—S—C(CH₃)₂— (L-5,5-dimethylthiazolidin-4-yl) | | 3-chloro-4-[(CH₃)₂NC(O)O-]-benzyl- | —OCH(CH₃)₂ |
| p-CH₃-φ- | R²/R³ = cyclic 3 carbon atoms (L-pyrrolidinyl) | | p-[(4-(CH₃SO₂-)piperazin-1-yl)-C(O)O]benzyl- | —OC(CH₃)₃ |
| p-CH₃-φ- | R²/R³ = cyclic 3 carbon atoms (L-pyrrolidinyl) | | p-[(morpholin-4-yl)CH₂CH₂NHC(O)O-]benzyl- | —OH |

TABLE 1-continued

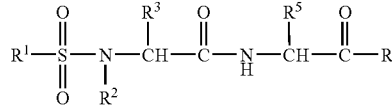

| R¹ | R² | R³ | R⁵ | R⁶ |
|---|---|---|---|---|
| p-CH₃-φ- | R²/R³ = cyclic 3 carbon atoms (L-pyrrolidinyl) | | p-[(4-(HO(O)-)piperidin-1-yl)C(O)O-]benzyl- | —OH |
| p-CH₃-φ- | R²/R³ = cyclic 3 carbon atoms (L-pyrrolidinyl) | | p-[(HOCH₂CH₂)₂NC(O)O-]benzyl- | —OCH(CH₃)₂ |
| p-O₂N-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(4-(HOCH₂-)piperidin-1-yl)-C(O)O-]benzyl- | —OCH(CH₃)₂ |
| p-CH₃-φ- | R²/R³ = cyclic 3 carbon atoms (L-pyrrolidinyl) | | 3-chloro-4-[(CH₃)₂NC(O)O)-]-benzyl- | —OCH(CH₃)₂ |
| p-CH₃-φ- | R²/R³ = cyclic —CH₂—CH₂—S—CH₂— (L-thiomorpholin-3-yl) | | p-[(CH₃)₂NC(O)O-]benzyl- | —OCH(CH₃)₂ |
| 1-methylpyrazol-3-yl- | R²/R³ = cyclic —CH₂—S—C(CH₃)₂— (L-5,5-dimethylthiazolidin-4-yl) | | p-[(CH₃)₂NC(O)O-]benzyl- | —OH |
| m-F-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| o-F-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 3,4-difluoro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 3,5-difluoro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 2,4-difluoro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| p-NH₂-φ- | R²/R³ = cyclic 3 carbon atoms (L-pyrrolidinyl) | | p-[(CH₃)₂NC(O)O-]benzyl- | —OH |
| p-N≡C-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic —CH₂CH(OH)CH₂— (L-4-hydroxypyrrolidinyl) | | p-[(CH₃)₂NC(O)O-]benzyl- | —OH |
| p-CH₃-φ- | R²/R³ = cyclic —CH₂C(O)CH₂— (L-4-oxypyrrolidinyl) | | p-[(CH₃)₂NC(O)O-]benzyl- | —OH |
| pyridin-2-yl- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| p-Cl-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| m-Cl-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| o-Cl-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 3,4-dichloro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 3,5-dichloro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂CH₃ |

TABLE 1-continued $$R^1-\underset{\underset{O}{\overset{O}{\|}}}{\overset{\overset{O}{\|}}{S}}-\underset{R^2}{N}-\underset{R^3}{CH}-\overset{O}{\overset{\|}{C}}-\underset{H}{N}-\underset{R^5}{CH}-\overset{O}{\overset{\|}{C}}-R^6$$

| $R^1$ | $R^2$ | $R^3$ | $R^5$ | $R^6$ |
|---|---|---|---|---|
| pyridin-3-yl- | $R^2/R^3$ = cyclic —$CH_2$—S—$C(CH_3)_2$— (L-5,5-dimethylthiazolidin-4-yl) | | p-[$(CH_3)_2$NC(O)O-]benzyl- | —OH |
| 1-methylpyrazol-4-yl- | $R^2/R^3$ = cyclic —$CH_2$—S—$C(CH_3)_2$— (L-5,5-dimethylthiazolidin-4-yl) | | p-[(thiomorpholin-4-yl)-C(O)O-]benzyl- | —OCH$(CH_3)_2$ |
| quinolin-8-yl | $R^2/R^3$ = cyclic —$CH_2$—S—$C(CH_3)_2$— (L-5,5-dimethylthiazolidin-4-yl) | | p-[$(CH_3)_2$NC(O)O-]benzyl- | —OCH$(CH_3)_2$ |
| m-Cl-φ- | $R^2/R^3$ = cyclic —$CH_2CH_2$—$SO_2$—$CH_2$— (L-1,1-dioxothiomorpholin-3-yl) | | p-[$(CH_3)_2$NC(O)O-]benzyl- | —OC$(CH_3)_3$ |
| pyridin-2-yl | $R^2/R^3$ = cyclic —$CH_2$—S—$C(CH_3)_2$— (L-5,5-dimethylthiazolidin-4-yl) | | p-[$(CH_3)_2$NC(O)O-]benzyl- | —OH |
| 3,4-dichloro-φ- | $R^2/R^3$ = cyclic —$CH_2CH_2$—$SO_2$—$CH_2$— (L-1,1-dioxothiomorpholin-3-yl) | | p-[$(CH_3)_2$NC(O)O-]benzyl- | —OC$(CH_3)_3$ |
| 2,5-dichlorothien-3-yl- | $R^2/R^3$ = cyclic —$CH_2$—S—$C(CH_3)_2$— (L-5,5-dimethylthiazolidin-4-yl) | | p-[$(CH_3)_2$NC(O)O-]benzyl- | —OCH$(CH_3)_2$ |
| p-$CH_3$O-φ- | $R^2/R^3$ = cyclic —$CH_2$—S—$C(CH_3)_2$— (L-5,5-dimethylthiazolidin-4-yl) | | p-[$(CH_3)_2$NC(O)O-]benzyl- | —OCH$(CH_3)_2$ |
| m-$CH_3$O-φ- | $R^2/R^3$ = cyclic —$CH_2$—S—$C(CH_3)_2$— (L-5,5-dimethylthiazolidin-4-yl) | | p-[$(CH_3)_2$NC(O)O-]benzyl- | —OCH$(CH_3)_2$ |
| o-$CH_3$O-φ- | $R^2/R^3$ = cyclic —$CH_2$—S—$C(CH_3)_2$— (L-5,5-dimethylthiazolidin-4-yl) | | p-[$(CH_3)_2$NC(O)O-]benzyl- | —OCH$(CH_3)_2$ |
| 3,4-dimethoxy-φ- | $R^2/R^3$ = cyclic —$CH_2$—S—$C(CH_3)_2$— (L-5,5-dimethylthiazolidin-4-yl) | | p-[$(CH_3)_2$NC(O)O-]benzyl- | —OCH$(CH_3)_2$ |
| 2,4-difluoro-φ- | $R^2/R^3$ = cyclic —$CH_2$—$CH_2$—S—$CH_2$— (L-thiomorpholin-3-yl) | | p-[$(CH_3)_2$NC(O)O-]benzyl- | —OC$(CH_3)_3$ |
| 3,4-dichloro-φ- | $R^2/R^3$ = cyclic —$CH_2CH_2$—$SO_2$—$CH_2$— (L-1,1-dioxothiomorpholin-3-yl) | | p-[$(CH_3)_2$NC(O)O-]benzyl- | —OH |
| m-Cl-φ- | $R^2/R^3$ = cyclic —$CH_2CH_2$—$SO_2$—$CH_2$— (L-1,1-dioxothiomorpholin-3-yl) | | p-[$(CH_3)_2$NC(O)O-]benzyl- | —OH |
| 2,4-difluoro-φ- | $R^2/R^3$ = cyclic —$CH_2$—$CH_2$—S(O)—$CH_2$— (L-1-oxothiomorpholin-4-yl) | | p-[$(CH_3)_2$NC(O)O-]benzyl- | —OC$(CH_3)_3$ |
| p-$CH_3$-φ- | $R^2/R^3$ = cyclic —$CH_2$—C(O)—$CH_2$— (L-4-oxopyrrolidinyl) | | p-[(4-methylpiperzin-1-yl)C(O)O-]benzyl- | —OCH$(CH_3)_2$ |
| p-$CH_3$-φ- | $R^2/R^3$ = cyclic —$CH_2CH(OH)CH_2$— (L-4-hydroxypyrrolidinyl) | | p-[(thiomorpholin-4yl)-C(O)O-]benzyl- | —OC$(CH_3)_3$ |
| p-$CH_3$-φ- | $R^2/R^3$ = cyclic 3 carbon atoms (L-pyrrolidinyl) | | p-[(3-(HOCH$_2$-)piperidin-1-yl)-C(O)O-]benzyl- | —OH |
| p-$CH_3$-φ- | $R^2/R^3$ = cyclic —$CH_2$—$CF_2$—$CH_2$— (L-4,4-difluoro-pyrrolidinyl) | | p-[$(CH_3)_2$NC(O)O-]benzyl- | —OCH$(CH_3)_2$ |
| p-$CH_3$-φ- | $R^2/R^3$ = cyclic 3 carbon atoms (L-pyrrolidinyl) | | p-[$(CH_3)_2$NC(O)O-]benzyl- | —O$(CH_2CH_2O)_2CH_3$ |
| p-$CH_3$-φ- | $R^2/R^3$ = cyclic —$CH_2CH$(—O—C(O)thiornorpholin-4-yl-$CH_2$- (L-4-(thiomorpholin-4-yl)C(O)O-pyrrolidinyl) | | p-[(thiomorpholin-4-yl)-C(O)O-]benzyl- | —OC$(CH_3)_3$ |
| p-$CH_3$-φ- | $R^2/R^3$ = cyclic —$CH_2$—$CF_2$—$CH_2$— (L-4,4-difluoro-pyrolidinyl) | | p-[$(CH_3)_2$NC(O)O-]benzyl- | —OH |

TABLE 1-continued

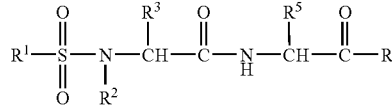

| R$^1$ | R$^2$ | R$^3$ | R$^5$ | R$^6$ |
|---|---|---|---|---|
| p-F-φ- | R$^2$/R$^3$ = cyclic —CH$_2$—S—C(CH$_3$)$_2$— (L-5,5-dimethylthiazolidin-4-yl) | | p-[(4-(pyrimidin-2-yl)piperazin-1-yl)-C(O)O-]benzyl- | —OC(CH$_3$)$_3$ |
| p-CH$_3$-φ- | R$^2$/R$^3$ = cyclic 3 carbon atoms (L-pyrrolidinyl) | | p-[(4-(φC(O)-)piperazin-1-yl)-C(O)O-]benzyl- | —OCH(CH$_3$)$_2$ |
| p-F-φ- | R$^2$/R$^3$ = cyclic —CH$_2$—S—C(CH$_3$)$_2$— (L-5,5-dimethylthiazolidin-4-yl) | | 3-fluoro-4-[(CH$_3$)$_2$NC(O)O-]-benzyl- | —OCH(CH$_3$)$_2$ |
| p-F-φ- | R$^2$/R$^3$ = cyclic (L-5,5-dimethylthiazolidin-4-yl) | | 3-chloro-4-[(4-(pyridin-2-yl)piperazin-1-yl)C(O)O-]-benzyl- | —OCH(CH$_3$)$_2$ |
| p-F-φ- | R$^2$/R$^3$ = cyclic —CH$_2$—S—C(CH$_3$)$_2$— (L-5,5-dimethylthiazolidin-4-yl) | | 3-chloro-4-[(4-(pyridin-2-yl)piperazin-1-yl)C(O)O-]-benzyl- | —OC(CH$_3$)$_3$ |
| p-CH$_3$-φ- | R$^2$/R$^3$ = cyclic —CH$_2$CH$_2$N—(—SO$_2$CH$_3$)—CH$_2$— (L-4-methanesulfonyl-piperazinyl) | | p-[(CH$_3$)$_2$NC(O)O-]benzyl- | —OC(CH$_3$)$_3$ |
| 1-methylimidazol-4-yl- | R$^2$/R$^3$ = cyclic 3 carbon atoms (L-pyrrolidinyl) | | p-[(CH$_3$)$_2$NC(O)O-]benzyl- | —OCH(CH$_3$)$_2$ |
| p-Br-φ- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OC(CH$_3$)$_3$ |
| p-Br-φ- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OH |
| p-NH$_2$C(=N)-φ- | R$^2$/R$^3$ = cyclic 3 carbon atoms (L-pyrrolidinyl) | | p-[(CH$_3$)$_2$NC(O)O-]benzyl- | —OCH$_3$ |
| p-N≡C-φ- | R$^2$/R$^3$ = cyclic 3 carbon atoms (L-pyrrolidinyl) | | p-[(thiomorpholin-4-yl)-C(O)O-]benzyl- | —OCH(CH$_3$)$_2$ |
| p-CH$_3$-φ- | R$^2$/R$^3$ = cyclic —CH$_2$CH(—O—C(O)thiomorpholin-4-yl)-CH$_2$- (L-4-(thiomorpholin-4-yl)C(O)O-pyrrolidinyl) | | p-[(thiomorpholin-4-yl)-C(O)O-]benzyl- | —OH |
| p-CH$_3$-φ- | R$^2$/R$^3$ = cyclic —CH$_2$—C(O)—CH$_2$— (L-4-oxopyrrolidinyl) | | p-[(thiomorpholin-4-yl)-C(O)O-]benzyl- | —OC(CH$_3$)$_3$ |
| p-CH$_3$-φ- | R$^2$/R$^3$ = cyclic —CH$_2$—C(O)—CH$_2$— (L-4-oxopyrrolidinyl) | | p-[(thiomorpholin-4-yl)-C(O)O-]benzyl- | —OH |
| p-CH$_3$-φ- | R$^2$/R$^3$ = cyclic —CH$_2$—C(O)—CH$_2$— (L-4-oxopyrrolidinyl) | | p-[(4-methylpiperazin-1-yl)-C(O)O-]benzyl- | —OH |
| p-F-φ- | R$^2$/R$^3$ = cyclic —CH$_2$—S—C(CH$_3$)$_2$— (L-5,5-dimethylthiazolidin-4-yl) | | p-[(4-(pyrimidin-2-yl)piperazin-1-yl)-C(O)O-]benzyl- | —OH |
| quinolin-8-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OH |
| pyridin-4-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OCH(CH$_3$)$_2$ |
| p-F-φ- | R$^2$/R$^3$ = cyclic —CH$_2$—S—C(CH$_3$)$_2$— (L-5,5-dimethylthiazolidin-4-yl) | | p-[(4-(pyridin-2-yl)piperazin-1-yl)C(O)O-]benzyl- | —OCH(CH$_3$)$_2$ |
| m-F-φ- | R$^2$/R$^3$ = cyclic 3 carbon atoms (L-pyrrolidinyl) | | p-[(CH$_3$)$_2$NC(O)O-]benzyl- | —OH |
| p-F-φ- | R$^2$/R$^3$ = cyclic —CH$_2$—CH$_2$—S— (thiazolidin-2-yl) | | p-[(CH$_3$)$_2$NC(O)O-]benzyl- | —OH |
| p-F-φ- | R$^2$/R$^3$ = cyclic —CH$_2$—CH$_2$—S— (thiazolidin-2-yl) | | p-[(CH$_3$)$_2$NC(O)O-]benzyl- | —OC(CH$_3$)$_3$ |

TABLE 1-continued

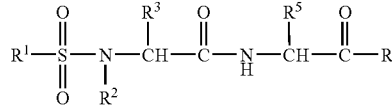

| R¹ | R² | R³ | R⁵ | R⁶ |
|---|---|---|---|---|
| p-CH₃-φ- | R²/R³ = cyclic —CH₂—C(O)—CH₂— (L-4-oxopyrrolidinyl) | | p-[(thiomorpholin-4-yl)C(O)O-]benzyl- | —OH |
| p-NH₂—C(=N)-φ- | R²/R³ = cyclic 3 carbon atoms (L-pyrrolidinyl) | | p-[(thiomorpholin-4-yl)C(O)O-]benzyl- | —OCH₃ |
| p-CH₃-φ- | R²/R³ = cyclic —CH₂—C(O)—CH₂— (L-4-oxopyrrolidinyl) | | p-[(4-methylpiperazin-1-yl)-C(O)O-]benzyl- | —OH |
| p-F-φ- | R²/R³ = cyclic —CH₂—CH₂—S— (thiazolidin-2-yl) | | p-[(4-pyridin-2-yl)piperazin-1-yl)-C(O)O-]benzyl- | —OH |
| p-NO₂-φ- | R²/R³ = cyclic 3 carbon atoms (L-pyrrolidinyl) | | p-[(4-pyridin-2-yl)piperazin-1-yl)-C(O)O-]benzyl- | —OC(CH₃)₃ |
| p-F-φ- | R²/R³ = cyclic —CH₂—CH₂—S— (thiazolidin-2-yl) | | p-[(4-pyridin-2-yl)piperazin-1-yl)-C(O)O-]benzyl- | —OC(CH₃)₃ |
| p-Br-φ- | R²/R³ = cyclic —CH₂—S—C(CH₃)₂— (L-5,5-dimethylthiazolidin-4-yl) | | p-[(4-pyridin-2-yl)piperazin-1-yl)-C(O)O-]benzyl- | —OH |
| p-CH₃-φ- | R²/R³ = cyclic 3 carbon atoms (L-pyrrolidinyl) | | p-[(4-(φC(O)-)piperazin-1-yl)C(O)O-]benzyl- | —OH |
| p-CH₃-φ- | R²/R³ = cyclic 3 carbon atoms (L-pyrrolidinyl) | | p-[(4-(φNHC(S)-)piperazin-1-yl)C(O)O-]benzyl- | —OCH(CH₃)₂ |
| p-F-φ- | R²/R³ = cyclic —CH₂—CH₂—S— (thiazolidin-2-yl) | | p-[(4-CH₃-homopiperazin-1-yl)C(O)O-]benzyl- | —OC(CH₃)₃ |
| p-CH₃-φ- | R²/R³ = cyclic 3 carbon atoms (L-pyrrolidinyl) | | p-[p-CH₃-φ-SO₂N(CH₃)CH₂CH₂N(CH₃)—C(O)O-]benzyl- | —OCH(CH₃)₂ |
| p-CH₃-φ- | R²/R³ = cyclic 3 carbon atoms (L-pyrrolidinyl) | | p-[φNHC(O)O—CH₂CH₂NHC(O)O-]benzyl- | —OCH(CH₃)₂ |
| 3-Cl-4-F-φ- | R²/R³ = cyclic —CH₂CH₂—SO₂—CH₂— (L-1,1-dioxothiomorpholin-3-yl) | | p-[(CH₃)₂NC(O)O-]benzyl- | —OC(CH₃)₃ |
| 1-methylpyrazol-4-yl- | R²/R³ = cyclic —CH₂CH₂—S—CH₂— (L-thiomorpholin-3-yl) | | p-[(CH₃)₂NC(O)O-]benzyl- | —OC(CH₃)₃ |
| p-CH₃-φ- | R²/R³ = cyclic —CH₂CH(—OSO₂CH₃)—CH₂— (L-4-methanesulfoxy-pyrrolidinyl) | | p-[(CH₃)₂NC(O)O-]benzyl- | —OC(CH₃)₃ |
| p-H₂NC(O)-φ- | R²/R³ = cyclic 3 carbon atoms (L-pyrrolidinyl) | | p-[(CH₃)₂NC(O)O-]benzyl- | —OH |
| p-H₂N—C(=N)-φ | R²/R³ = cyclic 3 carbon atoms (L-pyrrolidinyl) | | p-[(CH₃)₂NC(O)O-]benzyl- | —OH |
| p-H₂NC(O)-φ- | R²/R³ = cyclic 3 carbon atoms (L-pyrrolidinyl) | | p-[(thiomorpholin-4-yl)C(O)O-]benzyl- | —OH |
| p-H₂N—C(=N)-φ | R²/R³ = cyclic 3 carbon atoms (L-pyrrolidinyl) | | p-[(thiomorpholin-4-yl)C(O)O-]benzyl- | —OH |
| p-NO₂-φ- | R²/R³ = cyclic 3 carbon atoms (L-pyrrolidinyl) | | p-[(4-(pyridin-2-yl)piperazin-1-yl)-C(O)O-]benzyl- | —OH |
| p-F-φ- | R²/R³ = cyclic —CH₂—S—C(CH₃)₂— (L-5,5-dimethylthiazolidin-4-yl) | | 3-chloro-4-[(4-(pyridin-2-yl)piperazin-1-yl)C(O)O-]-benzyl- | —OCH₂CH₃ |
| p-F-φ- | R²/R³ = cyclic —CH₂—S—C(CH₃)₂— (L-5,5-dimethylthiazolidin-4-yl) | | 3-chloro-4-[(4-(pyridin-2-yl)piperazin-1-yl)C(O)O-]-benzyl- | —OH |

TABLE 1-continued $$R^1-\underset{\underset{O}{\overset{O}{\|}}}{\overset{\overset{O}{\|}}{S}}-\underset{R^2}{\overset{R^3}{\underset{|}{N}}}-CH-\overset{O}{\overset{\|}{C}}-\underset{H}{\overset{}{N}}-\overset{R^5}{\underset{|}{CH}}-\overset{O}{\overset{\|}{C}}-R^6$$

| R¹ | R² | R³ | R⁵ | R⁶ |
|---|---|---|---|---|
| p-F-φ- | R²/R³ = cyclic —CH₂—CH₂—S— (thiazolidin-2-yl) | | p-[(4-CH₃-homopiperazin-1-yl)C(O)O-]-benzyl- | —OH |
| 1-methylpyrazol-4-yl- | R²/R³ = cyclic —CH₂—S—C(CH₃)₂— (L-5,5-dimethylthiazolidin-4-yl) | | 3-chloro-4-[(CH₃)₂NC(O)O-]benzyl- | —OCH(CH₃)₂ |
| 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| p-CH₃-φ- | R²/R³ = cyclic 3 carbon atoms (L-pyrrolidinyl) | | p-[(4-(pyridin-2-yl)piperazin-1-yl)C(O)O-]benzyl- | —OH |
| p-CH₃-φ- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| p-CH₃-φ- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| p-F-φ- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| p-F-φ- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| p-CH₃-φ- | R²/R³ = cyclic —CH₂CH₂N(—SO₂—CH₃)CH₂— (4-methanesulfonyl-piperazin-2-yl) | | p-[(CH₃)₂NC(O)O-]benzyl- | —OH |
| p-CH₃-φ- | R²/R³ = cyclic —CH₂CH(—OSO₂—CH₃)CH₂— (L-4-methanesulfoxy-pyrrolidinyl) | | p-[(CH₃)₂NC(O)O-]benzyl- | —OH |
| 3,4-difluoro-φ- | R²/R³ = cyclic —CH₂—CH₂—S—CH₂— (L-thiomorpholin-3-yl) | | p-[(CH₃)₂NC(O)O-]benzyl- | —OC(CH₃)₃ |
| pyridin-3-yl | R²/R³ = cyclic —CH₂—S—C(CH₃)₂— (L-5,5-dimethylthiazolidin-4-yl) | | p-[(thiomorpholin-4-yl)C(O)O-]benzyl- | —OCH(CH₃)₂ |
| 3,4-difluoro-φ- | R²/R³ = cyclic —CH₂—CH₂—S—CH₂— (L-thiomorpholin-3-yl) | | p-[(CH₃)₂NC(O)O-]benzyl- | —OH |
| p-F-φ- | R²/R³ = cyclic —CH₂CH(OH)CH₂— (L-4-hydroxypyrrolidinyl) | | p-[(CH₃)₂NC(O)O-]benzyl- | —OCH(CH₃)₂ |
| p-Br-φ- | R²/R³ = cyclic —CH₂—S—C(CH₃)₂— (L-5,5-dimethylthiazolidin-4-yl) | | p-[(4-(pyridin-2-yl)piperazin-1-yl)C(O)O-]benzyl- | —OC(CH₃)₃ |
| p-CF₃O-φ- | R²/R³ = cyclic —CH₂—S—C(CH₃)₂— (L-5,5-dimethylthiazolidin-4-yl) | | p-[(CH₃)₂NC(O)O-]benzyl- | —OH |
| p-CF₃O-φ- | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| p-CF₃O-φ- | R²/R³ = cyclic —CH₂—S—C(CH₃)₂— (L-5,5-dimethylthiazolidin-4-yl) | | p-[(4-(pyridin-2-yl)piperazin-1-yl)C(O)O-]benzyl- | —OC(CH₃)₃ |
| p-F-φ- | R²/R³ = cyclic 3 carbon atoms (L-pyrrolidinyl) | | p-[(4-(pyridin-2-yl)piperazin-1-yl)C(O)O-]benzyl- | —OH |
| p-F-φ- | R²/R³ = cyclic —CH₂CH(PH)CH₂— (L-4-hydroxypyrrolidinyl) | | p-[(4-(pyridin-2-yl)piperazin-1-yl)C(O)O-]benzyl- | —OH |
| p-CF₃O-φ- | R²/R³ = cyclic —CH₂—S—C(CH₃)₂— (L-5,5-dimethylthiazolidin-4-yl) | | p-[(4-(pyridin-2-yl)piperazin-1-yl)C(O)O-]benzyl- | —OH |

TABLE 1-continued

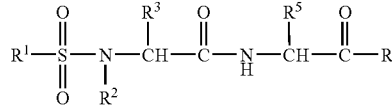

| R$^1$ | R$^2$ | R$^3$ | R$^5$ | R$^6$ |
|---|---|---|---|---|
| 1-methylimidazol-4-yl- | R$^2$/R$^3$ = cyclic 3 carbon atoms (L-pyrrolidinyl) | | 3-chloro-4-[(CH$_3$)$_2$NC(O)O)-]benzyl- | —OH |
| 1-methylimidazol-4-yl- | R$^2$/R$^3$ = cyclic 3 carbon atoms (L-pyrrolidinyl) | | 3-chloro-4-[(CH$_3$)$_2$NC(O)O)-]benzyl- | —OCH(CH$_3$)$_2$ |
| 1-methylimidazol-4-yl- | R$^2$/R$^3$ = cyclic 3 carbon atoms (L-pyrrolidinyl) | | p-[(4-(pyridin-2-yl)piperazin-1-yl)C(O)O-]benzyl- | —OH |
| 1-methylimidazol-4-yl- | R$^2$/R$^3$ = cyclic —CH$_2$—S—C(CH$_3$)$_2$— (L-5,5-dimethylthiazolidin-4-yl) | | p-[(4-(pyridin-2-yl)piperazin-1-yl)C(O)O-]benzyl- | —OH |
| 1-methylpyrazol-4-yl- | R$^2$/R$^3$ = cyclic 3 carbon atoms (L-pyrrolidinyl) | | p-[(4-(pyridin-2-yl)piperazin-1-yl)C(O)O-]benzyl- | —OH |
| 1-methylpyrazol-4-yl- | R$^2$/R$^3$ = cyclic 3 carbon atoms (L-pyrrolidinyl) | | p-[(4-(pyridin-2-yl)piperazin-1-yl)C(O)O-]benzyl- | —OCH(CH$_3$)$_2$ |
| 1-methylpyrazol-4-yl- | R$^2$/R$^3$ = cyclic 3 carbon atoms (L-pyrrolidinyl) | | p-[(4-(pyridin-2-yl)piperazin-1-yl)C(O)O-]benzyl- | —OC(CH$_3$)$_3$ |
| 1-methylpyrazol-4-yl- | R$^2$/R$^3$ = cyclic —CH$_2$—S—C(CH$_3$)$_2$— (L-5,5-dimethylthiazolidin-4-yl) | | p-[(4-(pyridin-2-yl)piperazin-1-yl)C(O)O-]benzyl- | —OC(CH$_3$)$_3$ |
| 1-methylimidazol-4-yl- | R$^2$/R$^3$ = cyclic 3 carbon atoms (L-pyrrolidinyl) | | 3-chloro-4-[(4-(pyridin-2-yl)piperazin-1-yl)C(O)O]benzyl- | —OCH(CH$_3$)$_2$ |
| 1-methylpyrazol-4-yl- | —CH$_2$—S—C(CH$_3$)$_2$— (L-5,5-dimethylthiazolidin-4-yl) | | p-[(CH$_3$)$_2$NC(O)O-]benzyl- | —OCH$_2$CH$_2$Oϕ |
| 1-methylpyrazol-4-yl- | R$^2$/R$^3$ = cyclic —CH$_2$—S—C(CH$_3$)$_2$— (L-5,5-dimethylthiazolidin-4-yl) | | 3-chloro-4-[(4-(pyridin-2-yl)piperazin-1-yl)C(O)O-]-benzyl- | —OH |
| 1-methylpyrazol-4-yl- | R$^2$/R$^3$ = cyclic —CH$_2$—S—C(CH$_3$)$_2$— (L-5,5-dimethylthiazolidin-4-yl) | | 3-chloro-4-[(4-(pyridin-2-yl)piperazin-1-yl)C(O)O-]-benzyl- | —OCH$_2$CH$_3$ |
| 1,5-dimethyl-3-chloropyrazol-4-yl- | R$^2$/R$^3$ = cyclic —CH$_2$—S—C(CH$_3$)$_2$— (L-5,5-dimethylthiazoliodin-4-yl) | | p-[4-[5-CF$_3$-pyridin-2-yl)piperazin-1-C(O)O-]benzyl- | —OH |
| p-F-ϕ- | R$^2$/R$^3$ = cyclic —CH$_2$CH(OH)CH$_2$— (L-4-hydroxypyrrolidinyl) | | p-[(CH$_3$)$_2$NC(O)O-]benzyl- | —OC(CH$_3$)$_3$ |
| pyridin-4-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OH |
| 1-methylpyrazol-4-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OCH$_2$C(CH$_3$)$_3$ |
| 1-methylpyrazol-4-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OCH$_2$O—C(O)C(C(CH$_3$)$_3$ |
| pyridin-3-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OCH$_2$C(CH$_3$)$_3$ |
| 1-methylpyrazol-4-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | 2-CH$_3$O-ϕ-O- |
| 1-methylpyrazol-4-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OCH$_2$cyclopropyl |
| 1-methylpyrazol-4-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OCH$_2$CH$_2$CH$_3$ |
| 1-methylpyrazol-4-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OCH$_2$CH$_2$CH$_2$CH$_3$ |

TABLE 1-continued $$R^1-\underset{\underset{O}{\overset{O}{\|}}}{\overset{O}{\underset{\|}{S}}}-\underset{R^2}{\overset{R^3}{\underset{|}{N}}}-CH-\overset{O}{\overset{\|}{C}}-\underset{H}{\overset{R^5}{\underset{|}{N}}}-CH-\overset{O}{\overset{\|}{C}}-R^6$$

| R¹ | R² | R³ | R⁵ | R⁶ |
|---|---|---|---|---|
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —O—CH₃ |
| pyridin-3-yl- | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| pyridin-3-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂CH₃ |
| pyridin-3-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂cyclopropyl |

In a preferred embodiment of the compounds of Formulae I and IA, the compounds are defined by Formula IB below:

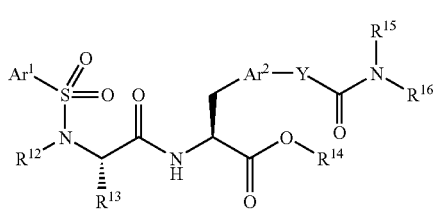

IB wherein:

$Ar^1$ is selected from the group consisting of aryl, substituted aryl, heteroaryl, and substituted heteroaryl;

$Ar^2$ is selected from the group consisting of aryl, substituted aryl, heteroaryl and substituted heteroaryl;

$R^{12}$ is selected from the group consisting of alkyl, substituted alkyl, cycloalkyl, and substituted cycloalkyl or $R^{12}$ and $R^{13}$ together with the nitrogen atom bound to $R^{12}$ and the carbon atom bound to $R^{13}$ form a heterocyclic or substituted heterocyclic group;

$R^{13}$ is selected from the group consisting of hydrogen, alkyl, and substituted alkyl, or $R^{12}$ and $R^{13}$ together with the nitrogen atom bound to $R^{12}$ and the carbon atom bound to $R^{13}$ form a heterocyclic or substituted heterocyclic group;

$R^{14}$ is selected from the group consisting of hydrogen, alkyl, substituted alkyl, cycloalkyl, substituted cycloalkyl, aryl, and substituted aryl;

$R^{15}$ is selected from the group consisting of alkyl, and substituted alkyl, or $R^{15}$ and $R^{16}$ together with the nitrogen atom to which they are bound form a heterocyclic or substituted heterocyclic group;

$R^{16}$ is selected from the group consisting of alkyl and substituted alkyl or $R^{15}$ and $R^{16}$ together with the nitrogen atom to which they are bound form a heterocyclic or substituted heterocyclic group; and Y is selected from the group consisting of —O—, —NR¹⁰⁰—, and —CH₂— wherein $R^{100}$ is hydrogen or alkyl; and pharmaceutically acceptable salts thereof.

Preferably, in the compounds of Formula IB above, $R^{12}$ is alkyl, substituted alkyl, or $R^{12}$ and $R^{13}$ together with the nitrogen atom bound to $R^{12}$ and the carbon atom bound to $R^{13}$ form a heterocyclic or substituted heterocyclic group. Preferably, in the compounds of Formula IB above, $R^{14}$ is hydrogen or alkyl.

Preferably, in the compounds of Formula IB above, $Ar^1$ is selected from the group consisting of phenyl, 4-methylphenyl, 4-t-butylphenyl, 2,4,6-trimethylphenyl, 2-fluorophenyl, 3-fluorophenyl, 4-fluorophenyl, 2,4-difluorophenyl, 3,4-difluorophenyl, 3,5-difluorophenyl, 2-chlorophenyl, 3-chlorophenyl, 4-chlorophenyl, 3,4-dichlorophenyl, 3,5-dichlorophenyl, 3-chloro-4-fluorophenyl, 4-bromophenyl, 2-methoxyphenyl, 3-methoxyphenyl, 4-methoxyphenyl, 3,4-dimethoxyphenyl, 4-t-butoxyphenyl, 4-(3'-dimethylamino-n-propoxy)-phenyl, 2-carboxyphenyl, 2-(methoxycarbonyl)phenyl, 4-(H₂NC(O)—)phenyl, 4-(H₂NC(S)—)phenyl, 4-cyanophenyl, 4-trifluoromethylphenyl, 4-trifluoromethoxyphenyl, 3,5-di-(trifluoromethyl)phenyl, 4-nitrophenyl, 4-aminophenyl, 4-(CH₃C(O)NH—)phenyl, 4-(PhNHC(O)NH—)phenyl, 4-amidinophenyl, 4-methylamidinophenyl, 4-[CH₃SC(=NH)—]phenyl, 4-chloro-3-[H₂NS(O)₂-]phenyl, 1-naphthyl, 2-naphthyl, pyridin-2-yl, pyridin-3-yl, pyridine-4-yl, pyrimidin-2-yl, quinolin-8-yl, 2-(trifluoroacetyl)-1,2,3,4-tetrahydroisoquinolin-7-yl, 2-thienyl, 5-chloro-2-thienyl, 2,5-dichloro-4-thienyl, 1-N-methylimidazol-4-yl, 1-N-methylpyrazol-3-yl, 1-N-methylpyrazol-4-yl, 1-N-butylpyrazol-4-yl, 1-N-methyl-3-methyl-5-chloropyrazol-4-yl, 1-N-methyl-5-methyl-3-chloropyrazol-4-yl, 2-thiazolyl and 5-methyl-1,3,4-thiadiazol-2-yl.

Preferably, in the compounds of Formula IB above, $R^{12}$ and $R^{13}$ together with the nitrogen atom bound to $R^{12}$ and the carbon atom bound to $R^{13}$ form a heterocyclic or substituted heterocyclic of the formula:

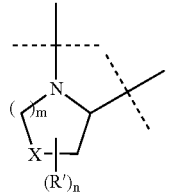

wherein

X is selected from the group consisting of —S—, —SO—, —SO₂, and optionally substituted —CH₂—;

m is an integer of 0 to 12;

n is an integer of 0 to 2; and

R' is selected from the group consisting of alkyl, substituted alkyl, and amino.

Preferably, m is 1, X is —S— or —CH₂—, R' is alkyl or substituted alkyl.

Even more preferably, $R^{12}$ and $R^{13}$ together with the nitrogen atom bound to $R^{12}$ and the carbon atom bound to $R^{13}$ form a heterocyclic or substituted heterocyclic selected from the group consisting of azetidinyl, thiazolidinyl, piperidinyl, piperazinyl, thiomorpholinyl, pyrrolidinyl, 4-hydroxypyrrolidinyl, 4-oxopyrrolidinyl, 4-fluoropyrrolidinyl, 4,4-difluoropyrrolidinyl, 4-(thiomorpholin-4-ylC(O)O—)pyrrolidinyl, 4-[CH₃S(O)₂O—]pyrrolidinyl, 3-phenylpyrrolidinyl, 3-thiophenylpyrrolidinyl, 4-aminopyrrolidinyl, 3-methoxypyrrolidinyl, 4,4-dimethylpyrrolidinyl, 4-N-Cbz-piperazinyl, 4-[CH₃S(O)₂—]piperazinyl, thiazolidin-3-yl, 5,5-dimethylthiazolidin-3-yl, 5,5-dimethylthiazolindin-4-yl, 1,1-dioxothiazolidinyl, 1,1-dioxo-5,5-dimethylthiazolidin-2-yl and 1,1-dioxothiomorpholinyl.

Preferably, in the compounds of Formula IB, $Ar^2$ is selected from the group consisting of phenyl, 2-pyridyl, 3-pyridyl, 4-pyridyl, and 4-pyrid-2-onyl.

Preferably, in Formula IB, Y is —O—, and when Y is —O—, the moiety —OC(O)NR$^{15}$R$^{16}$ is preferably selected from the group consisting of (CH₃)₂NC(O)O—, (piperidin-1-yl)C(O)O—, (4-hydroxypiperidin-1-yl)C(O)O—, (4-formyloxypiperidin-1-yl)C(O)O—, (4-ethoxycarbonylpiperidin-1-yl)C(O)O—, (4-carboxylpiperidin-1-yl)C(O)O—, (3-hydroxymethylpiperidin-1-yl)C(O)O—, (4-hydroxymethylpiperidin-1-yl)C(O)O—, (4-piperidon-1-yl ethylene ketal)C(O)O—, (piperazin-1-yl)-C(O)O—, (1-Boc-piperazin-4-yl)-C(O)O—, (4-methylpiperazin-1-yl)C(O)O—, (4-methylhomopiperazin-1-yl)C(O)O—, (4-(2-hydroxyethyl)piperazin-1-yl)C(O)O—, (4-phenylpiperazin-1-yl)C(O)O—, (4-(pyridin-2-yl)piperazin-1]-yl)C(O)O—, (4-(4-trifluoromethylpyridin-2-yl)piperazin-1-yl)C(O)O—, (4-(pyrimidin-2-yl)piperazin-1-yl)C(O)O—, (4-acetylpiperazin-1-yl)C(O)O—, (4-(phenylC(O)—)piperazin-1-yl)C(O)O—, (4-(pyridin-4'-ylC(O)—)piperazin-1-yl)C(O)O, (4-(phenylNHC(O)—)piperazin-1-yl)C(O)O—, (4-(phenylNHC(S)—)piperazin-1-yl)C(O)O—, (4-methanesulfonylpiperazin-1-yl-C(O)O—, (4-trifluoromethanesulfonylpiperazin-1-yl-C(O)O—, (morpholin-4-yl)C(O)O—, (thiomorpholin-4-yl)C(O)O—, (thiomorpholin-4'-yl sulfone)-C(O)O—, (pyrrolidin-1-yl)C(O)O—, (2-methylpyrrolidin-1-yl)C(O)O—, (2-(methoxycarbonyl)pyrrolidin-1-yl)C(O)O—, (2-(hydroxymethyl)pyrrolidin-1-yl)C(O)O—, (2-(N,N-dimethylamino)ethyl)(CH₃)NC(O)O—, (2-(N-methyl-N-toluene-4-sulfonylamino)ethyl)(CH₃)N—C(O)O—, (2-(morpholin-4-yl)ethyl)(CH₃)NC(O)O—, (2-(hydroxy)ethyl)(CH₃)NC(O)O—, bis(2-(hydroxy)ethyl)NC(O)O—, (2-(formyloxy)ethyl)(CH₃)NC(O)O—, (CH₃OC(O)CH₂)HNC(O)O—, and 2-[(phenylNHC(O)O—)ethyl-]HNC(O)O—.

Preferably, the compound is the compound of Formula M below:

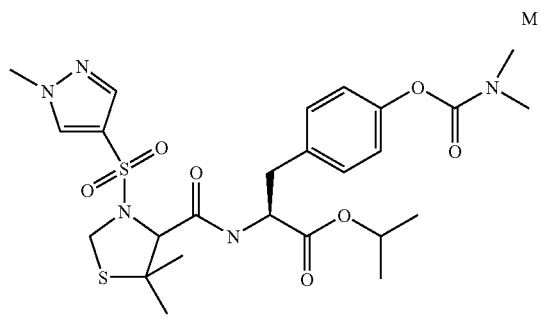

M

In a preferred embodiment, the compounds are defined by Formula IC below

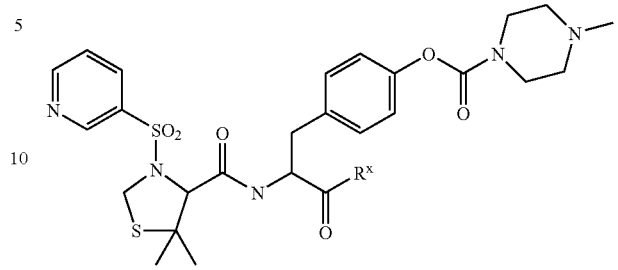

IC wherein $R^x$ is hydroxy or $C_{1-5}$ alkoxy and pharmaceutically acceptable salts thereof. Preferably, the compound is N-[N-(3-pyridinesulfonyl)-L-3,3-dimethyl-4-thiaprolyl]-O-[1-methylpiperazin-4-ylcarbonyl]-L-tyrosine isopropyl ester (the compound of Formula N).

In another aspect, the compounds that can be utilized as combination therapies with methotrexate for the treatment of RA are compounds defined by Formula II below. These compounds have a binding affinity to VLA-4 as expressed by an $IC_{50}$ of about 15 μM or less (measured as described in Example A below):

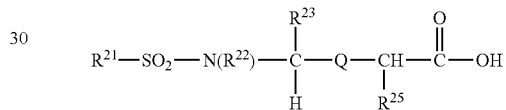

II wherein:

$R^{21}$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^{22}$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and $R^{21}$ and $R^{22}$ together with the nitrogen atom bound to $R^{22}$ and the $SO_2$ group bound to $R^{21}$ can form a heterocyclic or a substituted heterocyclic group;

$R^{23}$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and where $R^{22}$ and $R^{23}$ together with the nitrogen atom bound to $R^{22}$ and the carbon atom bound to $R^{23}$ can form a saturated heterocyclic group or a saturated substituted heterocyclic group with the proviso that when monosubstituted, the substituent on said saturated substituted heterocyclic group is not carboxyl;

Q is —C(X)NR⁷— wherein $R^7$ is selected from the group consisting of hydrogen and alkyl;

X is selected from the group consisting of oxygen and sulfur; and $R^{25}$ is —CH₂Ar²²—R²⁵' where $Ar^{22}$ is aryl or heteroaryl and $R^{25'}$ is selected from the group consisting of aryl, heteroaryl, substituted aryl, substituted heteroaryl, heterocyclic, substituted heterocyclic, aryloxy, substituted aryloxy, aralkoxy, substituted aralkoxy, heteroaryloxy, substituted heteroaryloxy, heterocyclic-O—, substituted heterocyclic-O—, heteroaralkoxy, and substituted heteroaralkoxy;

and pharmaceutically acceptable salts thereof.

In another embodiment, the compounds of this invention can also be provided as prodrugs which-convert (e.g., hydrolyze, metabolize, etc.) in vivo to a compound of Formula II above. In a preferred example of such an embodiment, the carboxylic acid in the compound of Formula II is modified into a group which, in vivo, will convert to the carboxylic acid (including salts thereof). In a particularly preferred embodiment, such prodrugs are represented by compounds of Formula IIA:

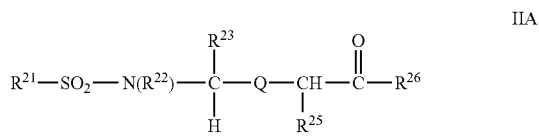

where
$R^{21}$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^{22}$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, and substituted heteroaryl, and $R^{21}$ and $R^{22}$ together with the nitrogen atom bound to $R^{22}$ and the $SO_2$ group bound to $R^{21}$ can form a heterocyclic or a substituted heterocyclic group;

$R^{23}$ is selected from the group consisting of hydrogen, alkyl, substituted alkyl, cycloalkyl, substituted cycloalkyl, aryl, substituted aryl, heteroaryl, substituted heteroaryl, heterocyclic, and substituted heterocyclic, and $R^{22}$ and $R^{23}$ together with the nitrogen atom bound to $R^{22}$ and the carbon atom bound to $R^{23}$ can form a saturated heterocyclic group or a saturated substituted heterocyclic group with the proviso that when monosubstituted, the substituent on said saturated substituted heterocyclic group is not carboxyl;

$R^{25}$ is —$CH_2Ar^{22}$-$R^{25'}$ where $Ar^{22}$ is aryl or heteroaryl and $R^{25'}$ is selected from the group consisting of aryl, heteroaryl, substituted aryl, substituted heteroaryl, heterocyclic, substituted heterocyclic, aryloxy, substituted aryloxy, aralkoxy, substituted aralkoxy, heteroaryloxy, substituted heteroaryloxy, heterocyclic-O—, substituted heterocyclic-O—, heteroaralkoxy, and substituted heteroaralkoxy;

$R^{26}$ is selected from the group consisting of 2,4-dioxo-tetrahydrofuran-3-yl (3,4-enol), amino, alkoxy, substituted alkoxy, cycloalkoxy, substituted cycloalkoxy, —O—(N-succinimidyl), —NH-adamantyl, —O-cholest-5-en-3-β-yl, —NHOY where Y is hydrogen, alkyl, substituted alkyl, aryl, and substituted aryl, —NH(CH$_2$)$_p$COOY where p is an integer of from 1 to 8 and Y is as defined above, —OCH$_2$NR$^{29}$R$^{30}$ where $R^{29}$ is selected from the group consisting of —C(O)-aryl and —C(O)-substituted aryl and $R^{30}$ is selected from the group consisting of hydrogen and —CH$_2$COOR$^{31}$ where $R^{31}$ is alkyl, and —NHSO$_2$Z' where Z' is alkyl, substituted alkyl, cycloalkyl, substituted cycloalkyl, aryl, substituted aryl, heteroaryl, substituted heteroaryl, heterocyclic or substituted heterocyclic;

Q is —C(X)NR$^7$— wherein $R^7$ is selected from the group consisting of hydrogen and alkyl; and X is selected from the group consisting of oxygen and sulfur;

and pharmaceutically acceptable salts thereof.

Further description of the compounds of the above Formulae II and IIA and procedures and reaction conditions for preparing these compounds are described in U.S. Ser. No. 09/127,346 (filed Jul. 31, 1998), Ser. No. 09/688,820 (Continuation, filed Oct. 17, 2000 and issued as U.S. Pat. No. 6,583,139) and Ser. No. 10/382,988 (Continuation, filed Mar. 7, 2003), all of which are herein incorporated by reference in their entirety.

Preferably, in the compounds of Formulae II and IIA above, $R^{21}$ is selected from the group consisting of alkyl, substituted alkyl, aryl, substituted aryl, heterocyclic, substituted heterocylic, heteroaryl and substituted heteroaryl. More preferably $R^{21}$ is selected from the group consisting of aryl, substituted aryl, heteroaryl and substituted heteroaryl.

Even more preferably, in the compounds of Formulae II and IIA above, $R^{21}$ is selected from the group consisting of 4-methylphenyl, 4-chlorophenyl, 1-naphthyl, 2-naphthyl, 4-methoxyphenyl, phenyl, 2,4,6-trimethylphenyl, 2-(methoxycarbonyl)phenyl, 2-carboxyphenyl, 3,5-dichlorophenyl, 4-trifluoromethylphenyl, 3,4-dichlorophenyl, 3,4-dimethoxyphenyl, 4-(CH$_3$C(O)NH—)phenyl, 4-trifluoromethoxyphenyl, 4-cyanophenyl, 3,5-di-(trifluoromethyl)phenyl, 4-t-butylphenyl, 4-t-butoxyphenyl, 4-nitrophenyl, 2-thienyl, 1-N-methyl-3-methyl-5-chloropyrazol-4-yl, 1-N-methylimidazol-4-yl, 4-bromophenyl, 4-amidinophenyl, 4-methylamidinophenyl, 4-[CH$_3$SC(=NH)]phenyl, 5-chloro-2-thienyl, 2,5-dichloro-4-thienyl, 1-N-methyl-4-pyrazolyl, 2-thiazolyl, 5-methyl-1,3,4-thiadiazol-2-yl, 4-[H$_2$NC(S)]phenyl, 4-aminophenyl, 4-fluorophenyl, 2-fluorophenyl, 3-fluorophenyl, 3,5-difluorophenyl, pyridin-3-yl, pyrimidin-2-yl, 4-(3'-dimethylamino-n-propoxy)-phenyl, and 1-methylpyrazol-4-yl.

Preferably, $R^{22}$, in the compounds of Formulae II and IIA above, is hydrogen, methyl, phenyl, benzyl, —(CH$_2$)$_2$-2-thienyl, and —(CH$_2$)$_2$—φ.

In another preferred embodiment, $R^{22}$ and $R^{23}$, in the compounds of Formulae II and IIA above, and $R^{32}$ and $R^{33}$, in the compounds of Formula IIB, together with the nitrogen atom bound to $R^{22}$ or $R^{32}$ and the carbon atom bound to $R^{23}$ or $R^{33}$ form a saturated heterocyclic group or a saturated substituted heterocyclic group with the proviso that when monosubstituted, the substituent on said saturated substituted heterocyclic group is not carboxyl.

Q, in the compounds of Formulae II and IIA above, is preferably —C(O)NH— or —C(S)NH—.

In the compounds of Formulae II and IIA, $R^{25}$ is preferably selected from the group consisting of all possible isomers arising by substitution with the following groups: 4-(2-carboxyphenoxy)benzyl, 4-(benzyloxy)benzyl, 4-[(1-methylpiperidin-4-yl)-O—]benzyl, 4-(imidazolid-2-one-1-yl)benzyl, and 4-(3-formylimidazolid-2-one-1-yl)benzyl.

In the compounds of Formula IIA, $R^{26}$ is preferably 2,4-dioxo-tetrahydrofuran-3-yl (3,4-enol), methoxy, ethoxy, iso-propoxy, n-butoxy, t-butoxy, cyclopentoxy, neo-pentoxy, 2α-iso-propyl-4-β-methylcyclohexoxy, 2-β-isopropyl-4-β-methylcyclohexoxy, —NH$_2$, benzyloxy, —NHCH$_2$COOH, —NHCH$_2$CH$_2$COOH, —NH-adamantyl, —NHCH$_2$CH$_2$COOCH$_2$CH$_3$, —NHSO$_2$-p-CH$_3$—φ, —NHOR$^8$ where $R^8$ is hydrogen, methyl, iso-propyl or benzyl, O-(N-succinimidyl), —O-cholest-5-en-3-β-yl, —OCH$_2$—OC(O)C(CH$_3$)$_3$, —O(CH$_2$)$_z$NHC(O)W where z is 1 or 2 and W is selected from the group consisting of pyrid-3-yl, N-methylpyridyl, and N-methyl-1,4-dihydro-pyrid-3-yl, —NR"C(O)—R' where R' is aryl, heteroaryl or heterocyclic and R" is hydrogen or —CH$_2$C(O)OCH$_2$CH$_3$.

Preferred compounds within the scope of Formulae II and IIA above include by way of example the following:
N-(Toluene-4-sulfonyl)-L-prolyl-4-(α-methylbenzyloxy)-L-phenylalanine N-(Toluene-4-sulfonyl)-L-prolyl-4-(2-carboxyphenoxy)-L-phenylalanine
N-(Toluene-4-sulfonyl)-L-prolyl-O-(benzyl)-L-tyrosine
and pharmaceutically acceptable salts thereof.

Preferred compounds of Formulae II and IIA above include those set forth in Table 2 below.

TABLE 2

$$R^{21}-SO_2-N(R^{22})-\underset{\underset{H}{|}}{\overset{\overset{R^{23}}{|}}{C}}-Q-\underset{\underset{R^{25}}{|}}{CH}-\overset{\overset{O}{\|}}{C}-R^{26}$$

| $R^{21}$ | $R^{22}$ | $R^{23}$ $R^{25'}$ | | $R^{26}$ | $Q = -C(O)NR^7-$ wherein $R^7$ is: |
|---|---|---|---|---|---|
| p-CH$_3$-ψ- | $R^{22}/R^{23}$ = cyclic 3 carbon atoms (L-pyrrolidinyl) | | p-[O-(o-carboxyphenyl)]-benzyl- | —OH | H |
| p-CH$_3$-ψ- | $R^{22}/R^{23}$ = cyclic 3 carbon atoms (L-pyrrolidinyl) | | p-benzyloxybenzyl- | —OH | H |
| p-CH$_3$-ψ- | $R^{22}/R^{23}$ = cyclic 3 carbon atoms (L-pyrrolidinyl) | | p-[(1-methylpiperidin-4-yl)-O-]benzyl- | —OCH$_2$CH$_3$ | H |
| p-CH$_3$-ψ- | $R^{22}/R^{23}$ = cyclic 3 carbon atoms (L-pyrrolidinyl) | | p-[(imidazolid-2-one-1-yl)benzyl- | —OC(CH$_3$)$_3$ | H |
| p-CH$_3$-ψ- | $R^{22}/R^{23}$ = cyclic 3 carbon atoms (L-pyrrolidinyl) | | p-[3-formylimidazolid-2-one-1-yl)benzyl- | —OH | H |
| p-CH$_3$-ψ- | $R^{22}/R^{23}$ = cyclic 3 carbon atoms (L-pyrrolidinyl) | | p-[(imidazolid-2-one-1-yl)benzyl- | —OH | H |
| p-CH$_3$-ψ- | $R^{22}/R^{23}$ = cyclic 3 carbon atoms (L-pyrrolidinyl) | | p-[1-H-2-oxo-3-methyl tetrahydro pyrimidin-1-yl]benzyl- | —Ot-Bu | H |
| p-CH$_3$-ψ- | $R^{22}/R^{23}$ = cyclic 3 carbon atoms (L-pyrrolidinyl) | | p-[1-H-2-oxo-3-methyl tetrahydro pyrimidin-1-yl]benzyl- | —OH | H |
| p-CH$_3$-ψ- | $R^{22}/R^{23}$ = cyclic 3 carbon atoms (L-pyrrolidinyl) | | 4-[2-methoxy phenyl]-benzyl- | —Ot-Bu | H |
| p-CH$_3$-ψ- | $R^{22}/R^{23}$ = cyclic 3 carbon atoms (L-pyrrolidinyl) | | 4-[2-methoxy phenyl]-benzyl- | —OH | H |
| p-CH$_3$-ψ- | $R^{22}/R^{23}$ = cyclic 3 carbon atoms (L-pyrrolidinyl) | | p-[2,4,5-trioxo-3-(3-chlorophenyl)-tetrahydroimidazol-1-yl]-benzyl- | —OBz | H |

In a preferred embodiment of the compounds of Formulae II and IIA, the compounds are defined by Formula IIB below:

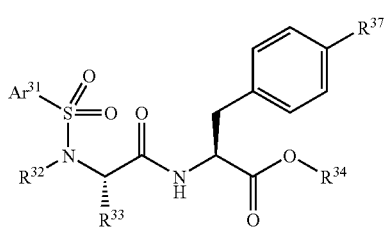

IIB wherein:

Ar$^{31}$ is selected from the group consisting of aryl, substituted aryl, heteroaryl, and substituted heteroaryl;

R$^{32}$ is selected from the group consisting of alkyl, substituted alkyl, cycloalkyl, and substituted cycloalkyl or R$^{32}$ and R$^{33}$ together with the nitrogen atom bound to R$^{32}$ and the carbon atom bound to R$^{33}$ form a heterocyclic or substituted heterocyclic group;

R$^{33}$ is selected from the group consisting of hydrogen, alkyl, and substituted alkyl, or R$^{32}$ and R$^{33}$ together-with the nitrogen atom bound to R$^{32}$ and the carbon atom bound to R$^{33}$ form a heterocyclic or substituted heterocyclic group;

R$^{34}$ is selected from the group consisting of hydrogen, alkyl, substituted alkyl, cycloalkyl, substituted cycloalkyl, aryl, and substituted aryl; and R$^{37}$ is aryl, heteroaryl, substituted aryl, substituted heteroaryl, heterocyclic, substituted heterocyclic, aryloxy, substituted aryloxy, aralkoxy, substituted aralkoxy, heteroaryloxy, substituted heteroaryloxy;

and pharmaceutically acceptable salts thereof.

Preferably, in the compounds of Formula IIB above, R$^{32}$ is alkyl, substituted alkyl, or R$^{32}$ and R$^{33}$ together with the nitrogen atom bound to R$^{32}$ and the carbon atom bound to R$^{33}$ form a heterocyclic or substituted heterocyclic group and R$^{34}$ is hydrogen or alkyl.

Preferably, in the compounds of Formula IIB above, R$^{37}$ is aryl, substituted aryl, heteroaryl, substituted heteroaryl, heterocyclic, or substituted heterocyclic. In a preferred embodiment, R$^{37}$ is substituted aryl wherein the aryl is substituted with one to three substituents independently selected from the group consisting alkyl and alkoxy. In a preferred embodiment, R$^{37}$ is substituted heteroaryl wherein the heteroaryl is substituted with one to three substituents independently selected from the group consisting alkyl, alkoxy, and oxo. In another preferred embodiment $R^{37}$ is substituted aryl or heteroaryl wherein aryl or heteroaryl is 2,6-di-substituted. In yet another preferred embodiment $R^{37}$ is 2,6-di-substituted aryl wherein the substituents are independently selected from the group consisting of alkyl and alkoxy. In yet another preferred embodiment $R^{37}$ is 2,6-di-substituted heteroaryl wherein the substituents are independently selected from the group consisting of alkyl, oxo, and alkoxy. In another preferred embodiment, $R^{37}$ is selected from the group consisting of 2,6-dialkoxyaryl, 2,6-dialkoxyheteroaryl, 2-alkyl-6-alkoxyaryl, 2-alkyl-6-alkoxyheteroaryl, 2-oxo-6-alkoxyheteroaryl, 2-oxo-6-alkylheteroaryl, and optionally substituted imidazolidin-2,4-dion-3-yl.

Preferably in the compounds of Formula IIB above, $Ar^{31}$ is selected from the group consisting of 4-methylphenyl, 4-chlorophenyl, 1-naphthyl, 2-naphthyl, 4-methoxyphenyl, phenyl, 2,4,6-trimethylphenyl, 2-(methoxycarbonyl)phenyl, 2-carboxyphenyl, 3,5-dichlorophenyl, 4-trifluoromethylphenyl, 3,4-dichlorophenyl, 3,4-dimethoxyphenyl, 4-($CH_3C(O)$NH—)phenyl, 4-trifluoromethoxyphenyl, 4-cyanophenyl, 3,5-di-(trifluoromethyl)phenyl, 4-t-butylphenyl, 4-t-butoxyphenyl, 4-nitrophenyl, 2-thienyl, 1-N-methyl-3-methyl-5-chloropyrazol-4-yl, 1-N-methylimidazol-4-yl, 4-bromophenyl, 4-amidinophenyl, 4-methylamidinophenyl, 4-[$CH_3SC$(=NH)]phenyl, 5-chloro-2-thienyl, 2,5-dichloro-4-thienyl, 1-N-methyl-4-pyrazolyl, 2-thiazolyl, 5-methyl-1,3,4-thiadiazol-2-yl, 4-[$H_2NC(S)$]phenyl, 4-aminophenyl, 4-fluorophenyl, 2-fluorophenyl, 3-fluorophenyl, 3,5-difluorophenyl, pyridin-3-yl, pyrimidin-2-yl, 4-(3'-dimethylamino-n-propoxy)-phenyl, and 1-methylpyrazol-4-yl.

When describing the compounds, compositions and methods of this invention, the following terms have the following meanings, unless otherwise indicated.

Compound Preparation for Compounds of Formulae I and II

The compounds of Formulae I and II can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

According to the following compound preparation, $R^1$, $R^2$, $R^3$, $R^5$, $R^6$, and $R^7$ are as defined herein for Formulae I, IA, II, and IIA. In addition, according to the following compound preparation, $R^1$ is equivalent to:
  $Ar^1$ as herein defined for Formula IB,
  $R^{21}$ as herein defined for Formulae II and IIA, and
  $Ar^{21}$ as herein defined for Formula IIB;

$R^2$ is equivalent to:
  $R^{12}$ as herein defined for Formula IB,
  $R^{22}$ as herein defined for Formulae II and IIA, and
  $R^{32}$ as herein defined for Formula IIB;

$R^3$ is equivalent to:
  $R^{13}$ as herein defined for Formula IB,
  $R^{23}$ as herein defined for Formulae II and IIA, and
  $R^{33}$ as herein defined for Formula IIB;

$R^5$ is equivalent to:
  $R^{25}$ as herein defined for Formulae II and IIA; and
$R^6$ is equivalent to:
  OH for Formulae I and II,
  $OR^{14}$ as herein defined for Formula IB,
  $R^{26}$ as herein defined for Formula IIA, and
  $OR^{34}$ as herein defined for Formula IIB.

In a preferred method of synthesis, the compounds of Formulae I, IA, II, and IIA, wherein Q is —C(O)$NR^7$—, and compounds of Formulae IB, IC, and IIB are prepared by first coupling an amino acid of Formula A:

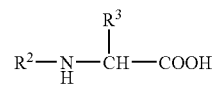

A with a sulfonyl chloride of Formula B:

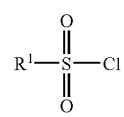

B to provide an N-sulfonyl amino acid of Formula C:

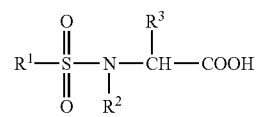

C

This reaction is typically conducted by reacting the amino acid of Formula A with at least one equivalent, preferably about 1.1 to about 2 equivalents, of sulfonyl chloride B in an inert-diluent such as dichloromethane and the like. Generally, the reaction is conducted at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like, as the base. Upon completion of the reaction, the resulting N-sulfonyl amino acid C is recovered by conventional methods including neutralization, extraction, precipitation, chromatography, filtration, and the like.

The amino acids of Formula A employed in the above reaction are either known compounds or compounds that can be prepared from known compounds by conventional synthetic procedures. Examples of suitable amino acids for use in this reaction include, but are not limited to, L-proline, trans-4-hydroxyl-L-proline, cis-4-hydroxyl-L-proline, trans-3-phenyl-L-proline, cis-3-phenyl-L-proline, L-(2-methyl)proline, L-pipecolinic acid, L-azetidine-2-carboxylic acid, L-indoline-2-carboxylic acid, L 1,2,3,4-tetrahydroisoquinoline-3-carboxylic acid, L-thiazolidine-4-carboxylic acid, L-(5,5-dimethyl)thiazolidine-4-carboxylic acid, L-thiamorpholine-3-carboxylic acid, glycine, 2-tert-butylglycine, D,L-phenylglycine, L-alanine, α-methylalanine, N-methyl-L-phenylalanine, L-diphenylalanine, sarcosine, D,L-phenylsarcosine, L-aspartic acid β-tert-butyl ester, L-glutamic acid γ-tert-butyl ester, L-(O-benzyl)serine, 1-aminocyclopropanecarboxylic acid, 1-aminocyclobutanecarboxylic acid, 1-aminocyclopentanecarboxylic acid (cycloleucine) 1-aminocyclohexanecarboxylic acid, L-serine and the like. If desired, the corresponding carboxylic acid esters of the amino acids of Formula A, such as the methyl esters, ethyl esters and the like, can be employed in the above reaction with the sulfonyl chloride B. Subsequent hydrolysis of the ester group to the carboxylic acid using conventional reagents and conditions, i.e., treatment with an alkali metal hydroxide in an inert diluent such as methanol/water, then provides the N-sulfonyl amino acid C.

Similarly, the sulfonyl chlorides of Formula B employed in the above reaction are either known compounds or compounds that can be prepared from known compounds by conventional synthetic procedures. Such compounds are typically prepared from the corresponding sulfonic acid, i.e., from compounds of the formula $R^1$—$SO_3H$, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the sulfonyl chlorides of Formula B can be prepared from the corresponding thiol compound, i.e., from compounds of the formula $R^1$—$SH$, by treating the thiol with chlorine ($Cl_2$) and water under conventional reaction conditions.

Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl amino acids of Formula C.

The intermediate N-sulfonyl amino acids of Formula C can also be prepared by reacting a sulfonamide of Formula D:

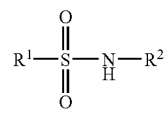

D with a carboxylic acid derivative of the formula $L(R^3)$ $CHCOOR^y$ where L is a leaving group, such as chloro, bromo, iodo, mesylate, tosylate and the like, and $R^y$ is hydrogen or an alkyl group. This reaction is typically conducted by contacting the sulfonamide D with at least one equivalent, preferably 1.1 to 2 equivalents, of the carboxylic acid derivative in the presence of a suitable base, such as triethylamine, in an inert diluent, such as DMF, at a temperature ranging from about 24° C. to about 37° C. for about 0.5 to about 4 hours. This reaction is further described in Zuckermann et al., *J. Am. Chem. Soc.,* 1992, 114, 10646-10647. Preferred carboxylic acid derivatives for use in this reaction are α-chloro and α-bromocarboxylic acid esters such as tert-butyl bromoacetate and the like. When a carboxylic acid ester is employed in this reaction, the ester group is subsequently hydrolyzed using conventional procedures to afford an N-sulfonyl amino acid of Formula C.

The compounds of the present invention are then prepared by coupling the intermediate N-sulfonyl amino acid of Formula C with an amino acid derivative of Formula E:

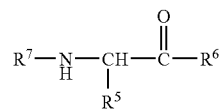

E

This coupling reaction is typically conducted using well-known coupling reagents such as carbodiimides, BOP reagent (benzotriazol-1-yloxy-tris(dimethylamino)phosphonium hexafluorophosphonate) and the like. Suitable carbodiimides include, by way of example, dicyclohexylcarbodiimide (DCC), 1-(3-dimethylamino-propyl)-3-ethylcarbodiimide (EDC) and the like. If desired, polymer supported forms of carbodiimide coupling reagents may also be used including, for example, those described in *Tetrahedron Letters,* 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting the N-sulfonylamino acid C with about 1 to about 2 equivalents of the coupling reagent and at least one equivalent, preferably about 1 to about 1.2 equivalents, of amino acid derivative E in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound of the present invention is recovered by conventional methods including neutralization, extraction, precipitation, chromatography, filtration, and the like.

Alternatively, the N-sulfonyl amino acid C can be converted into an acid halide and the acid halide coupled with amino acid derivative E to provide compounds of the present invention. The acid halide of C can be prepared by contacting C with an inorganic acid halide, such as thionyl chloride, phosphorous trichloride, phosphorous tribromide or phosphorous penta-chloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon-tetrachloride, at temperature in the range of about 0° C. to about 80° C. for about 1 to about 48 hours. A catalyst, such as DMF, may also be used in this reaction.

The acid halide of N-sulfonyl amino acid C is then contacted with at least one equivalent, preferably about 1.1 to about 1.5 equivalents, of amino acid derivative E in an inert diluent, such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, the compound of the present invention is recovered by conventional methods including neutralization, extraction, precipitation, chromatography, filtration, and the like.

Alternatively, the compounds of the present invention can be prepared by first forming a diamino acid derivative of Formula F:

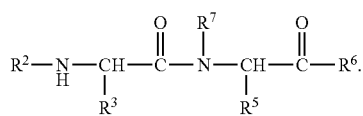

F

The diamino acid derivatives of Formula F can be readily prepared by coupling an amino acid of Formula A with an amino acid derivative of Formula E using conventional amino acid coupling techniques and reagents, such carbodiimides, BOP reagent and the like, as described above. Diamino acid F can then be sulfonated using a sulfonyl chloride of Formula B and using the synthetic procedures described above to provide a compound of the present invention.

The amino acid derivatives of Formula E employed in the above reactions are either known compounds or compounds that can be prepared from known compounds by conventional synthetic procedures. For example, amino acid derivatives of Formula E can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 hours. The resulting C-alkylated malonate is then deacetylated, hydrolyzed and decarboxylated by heating in aqueous hydrochloric acid at reflux for about 6 to about 12 hours to provide the amino acid, typically as the hydrochloride salt.

Examples of amino acid derivatives of Formula E suitable for use in the above reactions include, but are not limited to, L-tyrosine methyl ester, L-3,5-diiodotyrosine methyl ester, L-3-iodotyrosine methyl ester, β-(4-hydroxy-naphth-1-yl)-L-alanine methyl ester, β-(6-hydroxy-naphth-2-yl)-L-alanine methyl ester, and the like. If desired, of course, other esters or amides of the above-described compounds may also be employed.

For ease of synthesis, the compounds of the present invention are typically prepared as an ester, i.e., where $R^6$ is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 10 hours. Alternatively, benzyl esters may be removed by hydrogenolysis using a palladium catalyst, such as palladium on carbon. The resulting carboxylic acids may be coupled, if desired, to amines such as β-alanine ethyl ester, hydroxyamines such as hydroxylamine and N-hydroxysuccinimide, alkoxyamines and substituted alkoxyamines such as O-methylhydroxylamine and O-benzylhydroxylamine, and the like, using conventional coupling reagents and conditions as described above.

As will be apparent to those skilled in the art, other functional groups present on any of the substituents of the compounds of the present invention can be readily modified or derivatized either before or after the above-described coupling reactions using well-known synthetic procedures. For example, a nitro group present on a substituent of a compound of the present invention or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on, e.g., the $R^3$ substituent, can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid. Compounds having a pyridyl group can be readily prepared by using, for example, β-(2-pyridyl)-, β-(3-pyridyl)- or β-(4-pyridyl)-L-alanine derivatives in the above-described coupling reactions.

Additionally, when a substituent of a compound of the present invention or an intermediate thereof contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on such a substituent may be prepared, for example, by reduction of the corresponding nitro compound as described above. Alternatively, such compounds can be prepared by using an amino acid derivative of Formula E derived from lysine, 4-aminophenylalanine and the like in the above-described coupling reactions.

By way of illustration, a compound of the present invention or an intermediate thereof having a substituent containing a primary or secondary amino group can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris(dimethylamino)-phosphonium hexafluorophosphonate) and the like, in an inert diluent, such as dichloromethane, chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxybenzotriazole and the like, is used to facilitate the acylation reaction. Examples of carboxylic acids suitable for use in this reaction include, but are not limited to, N-tert-butyloxycarbonylglycine, N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of the present invention or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about of about −70° C. to about 40° C. for about 1 to about 24 hours. If desired, an acylation catalyst such as 4-(N,N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoromethylbenzoyl chloride, isonicotinoyl chloride, nicotinoyl chloride, picolinoyl chloride, acetic anhydride, succinic anhydride and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of the present invention or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride and the like. Similarly, sulfamoyl chlorides, such as dimethylsulfamoyl chloride, can be used to provide sulfamides (e.g., >N—$SO_2$—N<).

Additionally, a primary and secondary amino group present on a substituent of a compound of the present invention or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate, fluorescein isothiocyanate (isomer L), and the like.

Furthermore, when a compound of the present invention or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of the present invention or an intermediate thereof has a substituent containing a hydroxyl group, the hydroxyl group can be further modified or derivatized either before or after the above coupling reactions to provide, by way of example, ethers, carbamates and the like. Compounds of Formulae I and II having a hydroxyl group on the $R^5$ substituent, for example, can be prepared using an amino acid derivative of Formula E derived from tyrosine and the like in the above-described reactions.

By way of example, a compound of the present invention or an intermediate thereof having a substituent containing a hydroxyl group can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino)ethyl chloride, 3-(N,N-ethylamino)propyl chloride, 3-(N-benzyl-N-methylamino) propyl chloride, N-(2-chloroethyl)morpholine, 2-(hexamethyleneimino)ethyl chloride, 3-(N-methylpiperazine)propyl chloride, 1-(3-chlorophenyl)-4-(3-chloropropyl) piperazine, 2-(4-hydroxy-4-phenylpiperidine) ethyl chloride, N-tert-butyloxycarbonyl-3-piperidinemethyl tosylate and the like.

Alternatively, a hydroxyl group present on a substituent of a compound of the present invention or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of the present invention or an intermediate thereof containing a aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of the present invention or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of the present invention or an intermediate thereof contains a primary or secondary hydroxyl group, such hydroxyl groups can be readily converted into a leaving group and displaced to form, for example, amines, sulfides and fluorides. For example, derivatives of 4-hydroxy-L-proline can be converted into the corresponding 4-amino, 4-thio or 4-fluoro-L-proline derivatives via nucleophilic displacement of the derivatized hydroxyl group. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino ($-NH_2$) compound.

Similarly, a tosylate group can be readily displaced by a thiol to form a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of the present invention or an intermediate thereof having a substituent containing an iodoaryl group, for example, when $R^5$, of Formula I or II, is a (4-iodophenyl)methyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra(triphenylphosphine), in an inert diluent, such as tetrahydrofuran, at a temperature ranging from about 24° C. to about 30° C. until the reaction is complete. This reaction is further described, for example, in Rieke, *J. Org. Chem.* 1991, 56, 1445.

In some cases, the compounds of the present invention or intermediates thereof may contain substituents having one or more sulfur atoms. Such sulfur atoms will be present, for example, when the amino acid of Formula A employed in the above reactions is derived from L-thiazolidine-4-carboxylic acid, L-(5,5-dimethyl)thiazolidine-4-carboxylic acid, L-thiamorpholine-3-carboxylic acid and the like. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, *"Advanced Organic Chemistry"*, 4th Ed., pp. 1202-1202, Wiley Publishers, (1992).

As described above, the compounds of the present invention having an $R^2$ substituent other an hydrogen can be prepared using an N-substituted amino acid of Formula A, such as sarcosine, N-methyl-L-phenylalanine and the like, in the above-described coupling reactions. Alternatively, such compounds can be prepared by N-alkylation of a sulfonamide of Formula I or C (where $R^2$ is hydrogen) using conventional synthetic procedures. Typically, this N-alkylation reaction is conducted by contacting the sulfonamide with at least one equivalent, preferably 1.1 to 2 equivalents, of an alkyl or substituted alkyl halide in the presence of a suitable base, such as potassium carbonate, in an inert diluent, such as acetone, 2-butanone and the like, at a temperature ranging from about 25° C. to about 70° C. for about 2 to about 48 hours. Examples of alkyl or substituted alkyl halides suitable for use in this reaction include, but are not limited to, methyl iodide, and the like.

Additionally, the sulfonamides of Formula I or C wherein $R^2$ is hydrogen and $R^1$ is a 2-alkoxycarbonylaryl group can be intramolecularly cyclized to form 1,2-benzisothiazol-3-one derivatives or analogues thereof. This reaction is typically conducted by treating a sulfonamide, such as N-(2-methoxycarbonylphenylsulfonyl)glycine-L-phenylalanine benzyl ester, with about 1.0 to 1.5 equivalents of a suitable base, such as an alkali metal hydride, in a inert diluent, such as tetrahydrofuran, at a temperature ranging from about 0° C. to about 30° C. for about 2 to about 48 hours to afford the cyclized 1,2-benzisothiazol-3-one derivative.

Lastly, the compounds of Formula I or II where Q is —C(S) $NR^7$— are prepared by using an amino thionoacid derivative in place of amino acid A in the above described synthetic procedures. Such amino thionoacid derivatives can be prepared by the procedures described in Shalaky et al., *J. Org. Chem.*, 61:9045-9048 (1996) and Brain et al., *J. Org. Chem.*, 62:3808-3809 (1997) and references cited therein.

Compounds of Formulae III-IX

In one aspect, the compounds that can be utilized as combination therapies with methotrexate for the treatment of RA are compounds of Formulae IIIa, IIIb, IVa, IVb, Va, Vb, Vc, Vd, Ve, VIa, VIb, VIIa, VIIb, VIIc, VIId, VIIe, VIIIa, VIIIb, IXa, IXb, IXc, IXd, and IXe.

In one aspect, the compounds that can be utilized as combination therapies with methotrexate for the treatment of RA are compounds defined by Formula IIIa and/or IIIb below. These compounds have a binding affinity to VLA-4 as expressed by an $IC_{50}$ of about 15 μM or less (measured as described in Example A below):

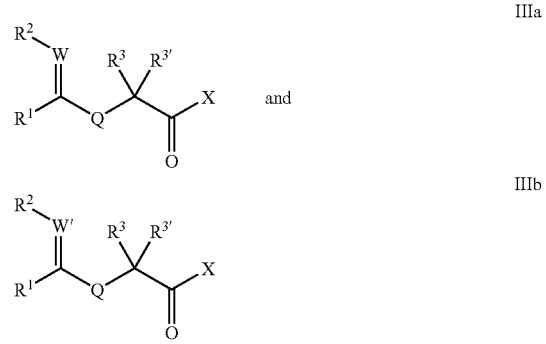

wherein, in Formula IIIa, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in Formula IIIb, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of Formula IIa or IIIb is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$- substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where each R is independently hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, —N[S(O)₂—R']₂ and —N[S(O)₂—NR']₂ where each R' is independently selected from the group consisting of alkyl, substituted alkyl, aryl, substituted aryl, heteroaryl, substituted heteroaryl, heterocyclic and substituted heterocyclic;

R³ and R³' are independently selected from the group consisting of hydrogen, isopropyl, —CH₂Z where Z is selected from the group consisting of hydrogen, hydroxyl, acylamino, alkyl, alkoxy, aryloxy, aryl, aryloxyaryl, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic and substituted heterocyclic, and where R³ and R³' are joined to form a substituent selected from the group consisting of =CHZ where Z is defined above provided that Z is not hydroxyl or thiol, cycloalkyl, substituted cycloalkyl, cycloalkenyl, substituted cycloalkenyl, heterocyclic and substituted heterocyclic;

Q is selected from the group consisting of —O—, —S—, —S(O)—, —S(O)₂, and —NR⁴—;

R⁴ is selected from the group consisting of hydrogen, alkyl, substituted alkyl, alkenyl, substituted alkenyl, cycloalkyl, substituted cycloalkyl, cycloalkenyl, substituted cycloalkenyl, aryl, substituted aryl, heteroaryl, substituted heteroaryl, heterocyclic and substituted heterocyclic or, optionally, R⁴ and R¹ or R⁴ and R², together with the atoms to which they are bound, are joined to form a heteroaryl, a substituted heteroaryl, a heterocyclic or a substituted heterocyclic group;

W is selected from the group consisting of nitrogen and carbon; and

W' is selected from the group consisting of nitrogen, carbon, oxygen, sulfur, S(O), and S(O)₂;

X is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R" where each R" is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic and substituted heterocyclic;

and enantiomers, diastereomers and pharmaceutically acceptable salts thereof;

and further wherein the compound of Formula IIIa and/or IIIb has a binding affinity to VLA-4 as expressed by an IC₅₀ of about 15 μM or less.

Preferably, R³ is —(CH₂)ₓ—Ar—R⁹, where Ar is aryl, substituted aryl, heteroaryl and substituted heteroaryl; R⁹ is selected from the group consisting of acyl, acylamino, acyloxy, aminoacyl, aminocarbonylamino, aminothiocarbonylamino, aminocarbonyloxy, oxythiocarbonylamino, thioamidino, thiocarbonylamino, aminosulfonylamino, aminosulfonyloxy, aminosulfonyl, oxysulfonylamino and oxysulfonyl; and x is an integer from 0 to 4. R³ is preferably alkyl or hydrogen; more preferably, R³' is hydrogen.

More preferably, R³ is a group of the formula:

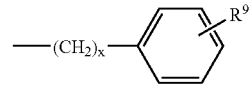

wherein R⁹ and x are as defined herein. Preferably, R⁹ is in the para position of the phenyl ring; and x is an integer of from 1 to 4, more preferably, x is 1.

In a preferred embodiment, R⁹ is selected from —O-Z-NR¹¹R¹¹' and —O-Z-R¹² wherein R¹¹ and R¹¹' are independently selected from the group consisting of hydrogen, alkyl, substituted alkyl, cycloalkyl, substituted cycloalkyl, cycloalkenyl, substituted cycloalkenyl, heterocyclic, substituted heterocyclic, and where R¹¹ and R¹¹' are joined to form a heterocycle or a substituted heterocycle, R¹² is selected from the group consisting of heterocycle and substituted heterocycle, and Z is selected from the group consisting of —C(O)— and —SO₂—. More preferably, R⁹ is —OC(O)NR¹¹R¹¹', wherein R¹¹ and R¹¹' are as defined herein.

Z is preferably —C(O)—. Preferably, Q is —NR⁴—.

In a preferred embodiment, the compounds that can be utilized as combination therapies with methotrexate for the treatment of RA are compounds defined by Formula IVa and/or IVb below.

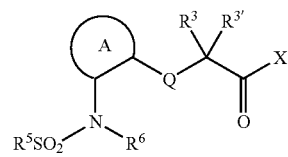

IVa

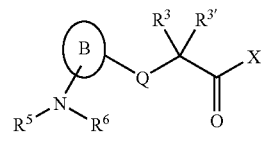

IVb wherein R³, R³' and X are as defined herein;

ring A and ring B independently form a heteroaryl or substituted heteroaryl group having two nitrogen atoms in the heteroaryl ring;

R⁵ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

R⁶ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —SO₂R¹⁰ where R¹⁰ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

or optionally, one of, $R^4$ and ring A, $R^4$ and $R^5$, $R^4$ and $R^6$, or $R^5$ and $R^6$, together with the atoms to which they are bound, can be joined to form a heterocyclic or substituted heterocyclic ring;

and enantiomers, diastereomers and pharmaceutically acceptable salts thereof; and provided that ring B does not form a 6-amino or substituted amino pyrimidin-4-yl group.

Preferably, ring A forms a pyridazine, pyrimidine or pyrazine ring; more preferably, a pyrimidine or pyrazine ring; wherein the pyridazine, pyrimidine or pyrazine ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

Preferably, ring B forms a pyridazine, pyrimidine, pyrazine, 1-oxo-1,2,5-thiadiazole or a 1,1-dioxo-1,2,5-thiadiazole ring; more preferably, a pyrimidine, pyrazine, 1-oxo-1,2,5-thiadiazole or a 1,1-dioxo-1,2,5-thiadiazole ring; wherein the pyridazine, pyrimidine or pyrazine ring is optionally substituted with 1 to 3 substituents selected from the group consisting of alkyl, substituted alkyl, alkoxy, substituted alkoxy, amino, substituted amino; cycloalkyl, substituted cycloalkyl, aryl, substituted aryl, heteroaryl, substituted heteroaryl, heterocyclic, substituted heterocyclic and halogen.

Preferably the compounds that can be utilized as combination therapies with methotrexate for the treatment of RA are compounds defined by Formula IVa.

In another preferred embodiment, the compounds that can be utilized as combination therapies with methotrexate for the treatment of RA are compounds defined by Formula Va, Vb, Vc, Vd, or Ve:

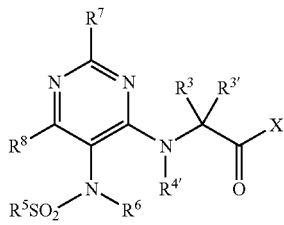

Va

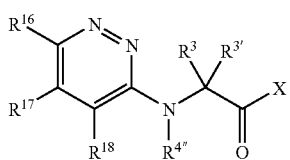

Vb

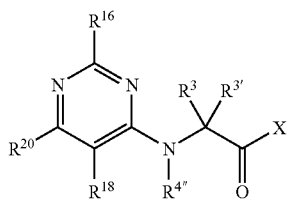

Vc

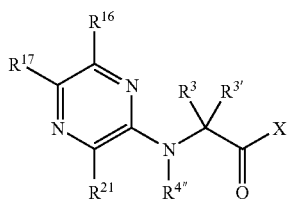

Vd

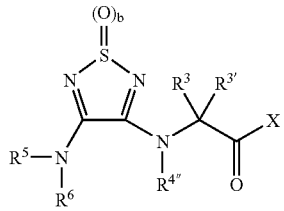

Ve wherein $R^3$, $R^{3'}$ and X are as defined herein;

$R^{4'}$ is selected from the group consisting of hydrogen and alkyl or, optionally, one of, $R^{4'}$ and $R^5$, $R^{4'}$ and $R^6$, $R^5$ and $R^6$, $R^5$ and $R^8$, or $R^6$ and $R^8$, together with the atoms to which they are bound, are joined to form a heterocyclic, a substituted heterocyclic, a heteroaryl or substituted heteroaryl group optionally containing from 1 to 3 additional hetero ring atoms selected from the group consisting of oxygen, nitrogen and sulfur;

$R^{4''}$ is selected from the group consisting of hydrogen and alkyl;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

$R^7$ and $R^8$ are independently selected from the group consisting of hydrogen, alkyl, substituted alkyl, cycloalkyl, substituted cycloalkyl, amino, substituted amino, aryl, substituted aryl, heteroaryl, substituted heteroaryl, heterocyclic, substituted heterocyclic and halogen;

$R^{16}$ and $R^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and $R^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

$R^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

$R^{21}$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic;

b is 1 or 2;

and enantiomers, diastereomers and pharmaceutically acceptable salts thereof.

Preferably, the compounds that can be utilized as combination therapies with methotrexate for the treatment of RA are compounds of Formula Va, Vc, or Vd.

Preferably, in the compounds of Formula Va, Vc, and Vd $R^5$, $R^{18}$, and $R^{21}$ are independently selected from the group consisting of heteroaryl, substituted heteroaryl, heterocyclic, and substituted heterocyclic;

$R^7$ and $R^{16}$ are independently amino or substituted amino;

$R^3$ is a group of the formula:

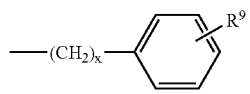

wherein $R^9$ is selected from the group consisting acyl, acylamino, acyloxy, aminoacyl, aminocarbonylamino, aminothiocarbonylamino, aminocarbonyloxy, oxycarbonylamino, oxythiocarbonylamino, thioamidino, thiocarbonylamino, aminosulfonylamino, aminosulfonyloxy, aminosulfonyl, oxysulfonylamino and oxysulfonyl; and x is an integer from 0 to 4; and $R^{3'}$ is hydrogen.

In another embodiment, the compounds that can be utilized as combination therapies with methotrexate for the treatment of RA are compounds defined by Formula VIa and/or VIb:

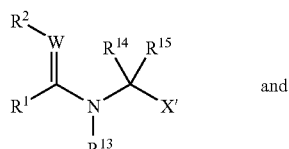

VIa and

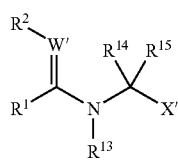

VIb wherein, in Formula VIa, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in Formula VIb, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of Formula VIa or VIb is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)$_2$—R']$_2$ and —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic;

$R^{13}$ is selected from the group consisting of hydrogen, $C_{1-10}$ alkyl, Cy, and Cy-$C_{1-10}$ alkyl, wherein alkyl is optionally substituted with one to four substituents independently selected from $R^a$; and Cy is optionally substituted with one to four substituents independently selected from $R^b$;

$R^{14}$ is selected from the group consisting of hydrogen, $C_{1-10}$ alkyl, $C_{2-10}$ alkenyl, $C_{2-10}$ alkynyl, Cy, Cy-$C_{1-10}$ alkyl, Cy-$C_{2-10}$ alkenyl and Cy-$C_{2-10}$ alkynyl, wherein alkyl, alkenyl, and alkynyl are optionally substituted with one to four substituents selected from phenyl and $R^x$, and Cy is optionally substituted with one to four substituents independently selected from $R^y$;

or $R^{13}$, $R^{14}$ and the atoms to which they are attached together form a mono- or bicyclic ring containing 0-2 additional heteroatoms selected from N, O and S;

$R^{15}$ is selected from the group consisting of $C_{1-10}$ alkyl, $C_{2-10}$ alkenyl, $C_{2-10}$ alkynyl, aryl, aryl-$C_{1-10}$, alkyl, heteroaryl, heteroaryl-$C_{1-10}$ alkyl, wherein alkyl, alkenyl and alkynyl are optionally substituted with one to four substituents selected from RX, and aryl and heteroaryl are optionally substituted with one to four substituents independently selected from $R^y$;

or $R^{14}$, $R^{15}$ and the carbon to which they are attached form a 3-7 membered mono- or bicyclic ring containing 0-2 heteroatoms selected from N, O and S;

$R^a$ is selected from the group consisting of Cy and a group selected from $R^x$, wherein Cy is optionally substituted with one to four substituents independently selected from $R^c$;

$R^b$ is selected from the group consisting of $R^a$, $C_{1-10}$ alkyl, $C_{2-10}$ alkenyl, $C_{2-10}$ alkynyl, aryl $C_{1-10}$alkyl, heteroaryl $C_{1-10}$ alkyl, wherein alkyl, alkenyl, alkynyl, aryl, heteroaryl are optionally substituted with a group independently selected from $R^c$;

R$^c$ is selected from the group consisting of halogen, NO$_2$, C(O)OR$^f$, C$_{1-4}$ alkyl, C$_{1-4}$ alkoxy, aryl, aryl C$_{1-4}$ alkyl, aryloxy, heteroaryl, NR$^f$R$^g$, R$^f$C(O)R$^g$, NR$^f$C(O)NR$^f$R$^g$, and CN;

R$^d$ and R$^e$ are independently selected from hydrogen, C$_{1-10}$ alkyl, C$_{2-10}$ alkenyl, C$_{2-10}$ alkynyl, Cy and Cy C$_{1-10}$alkyl, wherein alkyl, alkenyl, alkynyl and Cy are optionally substituted with one to four substituents independently selected from R$^c$;

or R$^d$ and R$^e$ together with the atoms to which they are attached form a heterocyclic ring of 5 to 7 members containing 0-2 additional heteroatoms independently selected from oxygen, sulfur and nitrogen;

R$^f$ and R$^g$ are independently selected from hydrogen, C$_{1-10}$ alkyl, Cy and Cy-C$_{1-10}$ alkyl wherein Cy is optionally substituted with C$_{1-10}$ alkyl; or R$^f$ and R$^g$ together with the carbon to which they are attached form a ring of 5 to 7 members containing 0-2 heteroatoms independently selected from oxygen, sulfur and nitrogen;

R$^h$ is selected from the group consisting of hydrogen, C$_{1-10}$ alkyl, C$_{2-10}$ alkenyl, C$_{2-10}$ alkynyl, cyano, aryl, aryl C$_{1-10}$ alkyl, heteroaryl, heteroaryl C$_{10}$ alkyl, and —SO$_2$R$^i$; wherein alkyl, alkenyl, and alkynl are optionally substituted with one to four substitutents independently selected from R$^a$; and aryl and heteroaryl are each optionally substituted with one to four substituents independently selected from R$^b$;

R$^i$ is selected from the group consisting of C$_{1-10}$ alkyl, C$_{2-10}$ alkenyl, C$_{2-10}$ alkynyl, and aryl; wherein alkyl, alkenyl, alkynyl and aryl are each optionally substituted with one to four substituents independently selected from R$^c$;

R$^x$ is selected from the group consisting of —OR$^d$, —NO$_2$, halogen, —S(O)$_m$R$^d$, —SR$^d$, —S(O)$_2$OR$^d$, S(O)$_m$NR$^d$R$^e$, —NR$^d$R$^e$, —O(CR$^f$R$^g$)$_n$NR$^d$R$^e$, C(O)R$^d$, —CO$_2$R$^d$, —CO$_2$(CR$^f$R$^g$)$_n$CONR$^d$R$^e$, —OC(O)R$^d$, —CN, —C(O)NR$^d$R$^e$, —NR$^d$C(O)R$^e$, —OC(O)NR$^d$R$^e$, —NR$^d$C(O)OR$^e$—NR$^d$C(O)NR$^d$R$^e$, —CR$^d$(N—OR$^e$), CF$_3$, oxo, NR$^d$C(O)NR$^d$SO$_2$R$^i$, NR$^d$S(O)$_m$R$^e$, —OS(O)$_2$OR$^d$, and —OP(O)(OR$^d$)$_2$;

R$^y$ is selected from the group consisting of R$^x$, C$_{1-10}$ alkyl, C$_{2-10}$ alkenyl, C$_{2-10}$ alkynyl, aryl C$_{1-10}$alkyl, heteroaryl C$_{1-10}$ alkyl, cycloalkyl, heterocyclyl; wherein alkyl, alkenyl, alkynyl and aryl are each optionally substituted with one to four substitutents independently selected from R$^x$;

Cy is cycloalkyl, heterocyclyl, aryl, or heteroaryl;

m is an integer from 1 to 2;

n is an integer from 1 to 10;

W is selected from the group consisting of carbon and nitrogen;

W' is selected from the group consisting of carbon, nitrogen, oxygen, sulfur, S(O) and S(O)$_2$;

X' is selected from the group consisting of —C(O)OR$^d$, —P(O)(OR$^d$)(OR$^e$), —P(O)(R$^d$)(OR$^e$), —S(O)$_m$OR$^d$, C(O)NR$^d$R$^h$, and -5-tetrazolyl;

and enantiomers, diastereomers and pharmaceutically acceptable salts thereof;

and further wherein the compound of Formula VIa and/or VIb has a binding affinity to VLA-4 as expressed by an IC$_{50}$ of about 15 µM or less.

Preferably, R$^1$ and R$^2$, together with the carbon atom and W to which they are bound respectively, are joined to form a heteroaryl or substituted heteroaryl group having two nitrogen atoms in the heteroaryl ring. Optionally, the heteroaryl ring may contain other heteroatoms such as oxygen or sulfur. More preferably, R$^1$ and R$^2$, together with the carbon atom and W to which they are bound respectively, are joined to form a pyridazine, pyrimidine, pyrazine, 1-oxo-1,2,5-thiadiazole or 1,1-dioxo-1,2,5-thiadiazole ring, more preferably, a pyrimidine, pyrazine, 1-oxo-1,2,5-thiadiazole or 1,1-dioxo-1,2,5-thiadiazole ring; wherein the pyridazine, pyrimidine, pyrazine, 1-oxo-1,2,5-thiadiazole or 1,1-dioxo-1,2,5-thiadiazole ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

Preferably, X' is —C(O)OR$^d$.

In another preferred embodiment, the compounds that can be utilized as combination therapies with methotrexate for the treatment of RA are compounds defined by Formula VIIa, VIIb, VIIc, VIId, or VIIe:

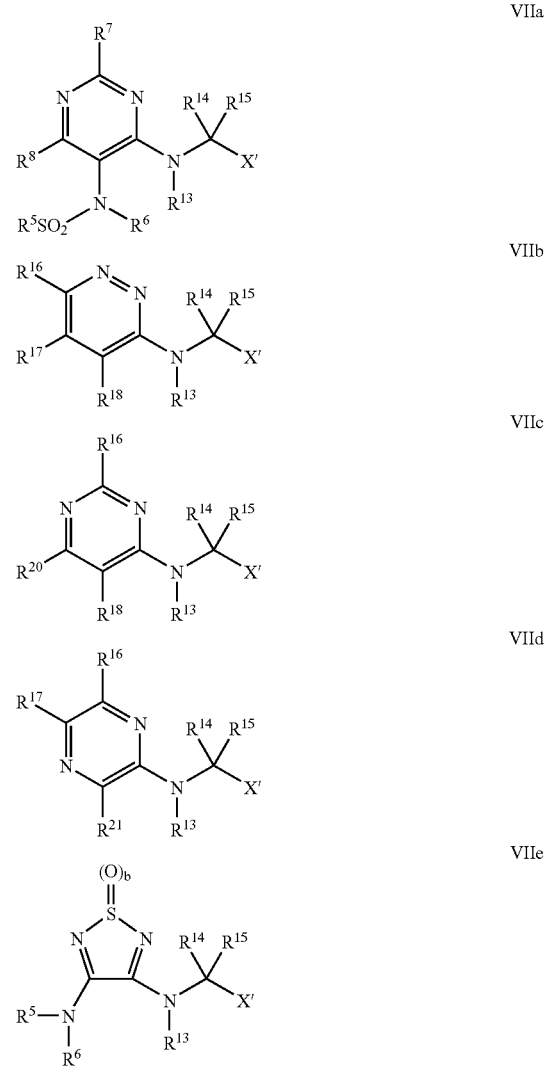

wherein R$^{13}$, R$^{14}$, R$^{15}$ and X' are as defined herein;

R$^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

R$^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —SO$_2$R$^{10}$ where R$^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl; and R$^7$ and R$^8$ are independently selected from the group consisting of hydrogen, alkyl, substituted alkyl, cycloalkyl, substituted cycloalkyl, amino, substituted amino, aryl, substituted aryl, heteroaryl, substituted heteroaryl, heterocyclic, substituted heterocyclic and halogen;

R$^{16}$ and R$^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and R$^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

R$^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

R$^2$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic;

b is 1 or 2;

and enatiomers, diastereomers and pharmaceutically acceptable salts thereof.

Preferably, the compounds that can be utilized as combination therapies with methotrexate for the treatment of RA are compounds of Formula VIIa, VIIc, or VIId.

In another embodiment, the compounds that can be utilized as combination therapies with methotrexate for the treatment of RA are compounds defined by Formula VIIIa and/or VIIIb:

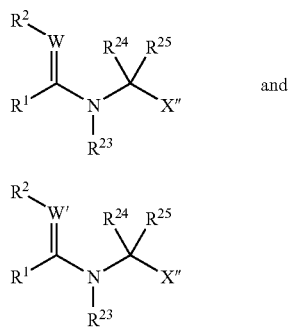

wherein, in Formula VIIIa, R$^1$ and R$^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in Formula VIIb, R$^1$ and R$^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of Formula VIIa or VIIb is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)$_2$—R']$_2$ and —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic;

R$^{23}$ is selected from the group consisting of hydrogen, C$_{1-10}$ alkyl optionally substituted with one to four substituents independently selected from R$^{a'}$ and Cy optionally substituted with one to four substituents independently selected from R$^{b'}$;

R$^{24}$ is selected from the group consisting of Ar$^1$—Ar$^2$—C$_{1-10}$ alkyl, Ar$^1$—Ar$^2$—C$_{2-10}$ alkenyl, Ar$^1$—Ar$^2$—C$_{2-10}$ alkynyl, wherein Ar$^1$ and Ar$^2$ are independently aryl or heteroaryl each of which is optionally substituted with one to four substituents independently selected from R$^{b'}$; alkyl, alkenyl and alkynyl are optionally substituted with one to four substituents independently selected from R$^{a'}$;

R$^{25}$ is selected from the group consisting of hydrogen, C$_{1-10}$ alkyl, C$_{2-10}$ alkenyl, C$_{2-10}$ alkynyl, aryl, aryl C$^{1-10}$alkyl, heteroaryl, and heteroaryl C$_{1-10}$ alkyl, wherein alkyl, alkenyl and alkynyl are optionally substituted with one to four substituents selected from R$^{a'}$, and aryl and heteroaryl are optionally substituted with one to four substituents independently selected from R$^{b'}$;

R$^{a'}$ is selected from the group consisting of Cy, —OR$^{d'}$, —NO$_2$, halogen —S(O)$_m$R$^{d'}$, —SR$^{d'}$, —S(O)$_2$OR$^{d'}$, —S(O)$_m$ NR$^{d'}$R$^{e'}$, —NR$^{d'}$R$^{e'}$, —O(CR$^{f'}$R$^{g'}$)$_n$NR$^{d'}$R$^{e'}$, —C(O)R$^{d'}$, —CO$_2$R$^{d'}$, —CO$_2$(CR$^{f'}$R$^{g'}$)$_n$CONR$^{d'}$R$^{e'}$, —OC(O)R$^{d'}$, —CN, —C(O)NR$^{d'}$R$^{e'}$, —NR$^{d'}$C(O)R$^{e'}$, —OC(O)NR$^{d'}$R$^{e'}$, —NR$^{d'}$C(O)OR$^{e'}$, —NR$^{d'}$C(O)NR$^{d'}$R$^{e'}$, —CR$^{d'}$(N—OR$^{e'}$), CF$_3$, and —OCF$_3$;

wherein Cy is optionally substituted with one to four substituents independently selected from R$^{c'}$;

R$^{b'}$ is selected from the group consisting of R$^{a'}$, C$_{1-10}$ alkyl, C$_{2-10}$ alkenyl, C$_{2-10}$ alkynyl, aryl C$_{1-10}$ alkyl, heteroaryl C$_{1-10}$ alkyl, wherein alkyl, alkenyl, aryl, heteroaryl are optionally substituted with a group independently selected from R$^{c'}$;

R$^{c'}$ is selected from the group consisting of halogen, amino, carboxy, C$_{1-4}$ alkyl, C$_{1-4}$ alkoxy, aryl, aryl C$_{1-4}$alkyl, hydroxy, CF$_3$, and aryloxy;

R$^{d'}$ and R$^{e'}$ are independently selected from hydrogen, C$_{1-10}$ alkyl, C$_{2-10}$ alkenyl, C$_{2-10}$ alkynyl, Cy and Cy C$_{1-10}$alkyl, wherein alkyl, alkenyl, alkynyl and Cy are optionally substituted with one to four substituents independently selected from R$^{c'}$; or R$^{d'}$ and R$^{e'}$ together with the atoms to which they are attached form a heterocyclic ring of 5 to 7 members containing 0-2 additional heteroatoms independently selected from oxygen, sulfur and nitrogen;

R$^{f'}$ and R$^{g'}$ are independently selected from hydrogen, C$_{1-10}$ alkyl, Cy and Cy-C$_{1-10}$ alkyl; or R$^{f'}$ and R$^{g'}$ together with the carbon to which they are attached form a ring of 5 to 7 members containing 0-2 heteroatoms independently selected from oxygen, sulfur and nitrogen;

R$^{h'}$ is selected from the group consisting of hydrogen, C$_{1-10}$ alkyl, C$_{2-10}$ alkenyl, C$_{2-10}$ alkynyl, cyano, aryl, aryl C$_{1-10}$ alkyl, heteroaryl, heteroaryl C$_{10}$ alkyl, or —SO$_2$R$^{i'}$;

wherein alkyl, alkenyl, and alkynyl are optionally substituted with one to four substitutents independently selected from R$^{a'}$; and aryl and heteroaryl are each optionally substituted with one to four substituents independently selected from R$^{b'}$;

R$^{i'}$ is selected from the group consisting of C$_{1-10}$ alkyl, C$_{2-10}$ alkenyl, C$_{2-10}$ alkynyl, and aryl;

wherein alkyl, alkenyl, alkynyl and aryl are each optionally substituted with one to four substituents independently selected from R$^{c'}$;

Cy is cycloalkyl, heterocyclyl, aryl, or heteroaryl;

X" is selected from the group consisting of —C(O)OR$^{d'}$, —P(O)(OR$^{d'}$)(OR$^{e'}$), —P(O)(R$^{d'}$)(OR$^{e'}$), —S(O)$_m$OR$^{d'}$, —C(O)NR$^{d'}$R$^{h'}$, and -5-tetrazolyl;

m is an integer from 1 to 2;

n is an integer from 1 to 10;

and enantiomers, diastereomers and pharmaceutically acceptable salts thereof;

and further wherein the compound of Formula VIIIa and/or VIIb has a binding affinity to VLA-4 as expressed by an IC$_{50}$ of about 15 µM or less.

Preferably, R$^1$ and R$^2$, together with the carbon atom and W to which they are bound respectively, are joined to form a heteroaryl or substituted heteroaryl group having two nitrogen atoms in the heteroaryl ring. Optionally, the heteroaryl ring may contain other heteroatoms such as oxygen or sulfur. More preferably, R$^1$ and R$^2$, together with the carbon atom and W to which they are bound respectively, are joined to form a pyridazine, pyrimidine, pyrazine, 1-oxo-1,2,5-thiadiazole or 1,1-dioxo-1,2,5-thiadiazole ring; more preferably, a pyrimidine, pyrazine, 1-oxo-1,2,5-thiadiazole or 1,1-dioxo-1,2,5-thiadiazole ring; wherein the pyridazine, pyrimidine, pyrazine, 1-oxo-1,2,5-thiadiazole or 1,1-dioxo-1,2,5-thiadiazole ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

Preferably, X" is —C(O)OR$^{d'}$.

Preferably, R$^{24}$ is —CH$_2$—Ar$^2$—Ar$^1$ and R$^{25}$ is hydrogen.

In another preferred embodiment, the compounds that can be utilized as combination therapies with methotrexate for the treatment of RA are compounds defined by Formula IXa, IXb, IXc, IXd, or IXe:

IXa

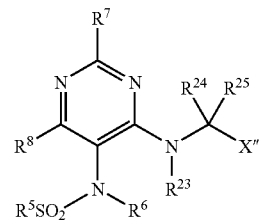

IXb

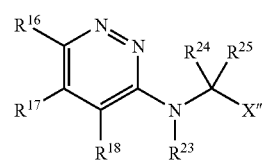

IXc

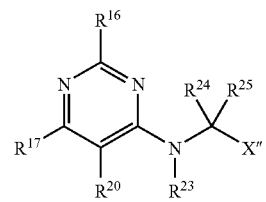

IXd

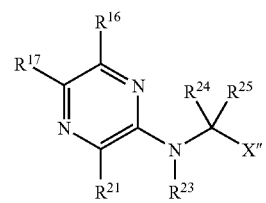

IXe

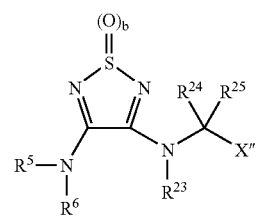

wherein R$^{23}$, R$^{24}$, R$^{25}$ and X" are as defined herein;

R$^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

R$^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —SO$_2$R$^{10}$ where R$^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl; and $R^7$ and $R^8$ are independently selected from the group consisting of hydrogen, alkyl, substituted alkyl, cycloalkyl, substituted cycloalkyl, amino, substituted amino, aryl, substituted aryl, heteroaryl, substituted heteroaryl, heterocyclic, substituted heterocyclic and halogen;

$R^{16}$ and $R^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and $R^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

$R^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

$R^{21}$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic;

b is 1 or 2;

and enantiomers, diastereomers and pharmaceutically acceptable salts thereof.

Preferably, the compounds that can be utilized as combination therapies with methotrexate for the treatment of RA are compounds of Formula IX a, IXc, or IXd.

In the above compounds, when X is other than —OH or pharmaceutical salts thereof, X is preferably a substituent which will convert (e.g., hydrolyze, metabolize, etc.) in vivo to a compound where X is —OH or a salt thereof. Accordingly, suitable X groups are any art recognized pharmaceutically acceptable groups which will hydrolyze or otherwise convert in vivo to a hydroxyl group or a salt thereof including, by way of example, esters (X is alkoxy, substituted alkoxy, cycloalkoxy, substituted cycloalkoxy, alkenoxy, substituted alkenoxy, cycloalkenoxy, substituted cycloalkenoxy, aryloxy, substituted aryloxy, heteroaryloxy, substituted heteroaryloxy, heterocyclooxy, substituted heterocyclooxy, and the like).

Unless otherwise defined, $R^3$ and $R^{15}$ in the above compounds are preferably selected from all possible isomers arising by substitution with the following groups:

4-methylbenzyl,
4-hydroxybenzyl,
4-methoxybenzyl,
4-t-butoxybenzyl,
4-benzyloxybenzyl,
4-[(φ—CH(CH$_3$) 0-]benzyl,
4-[(φ—CH(COOH)O—]benzyl,
4-[BocNHCH$_2$C(O)NH—]benzyl,
4-chlorobenzyl,
4-[NH$_2$CH$_2$C(O)NH—]benzyl,
4-carboxybenzyl,
4-[CbzNHCH$_2$CH$_2$NH—]benzyl,
3-hydroxy-4-((φ-OC(O)NH—)benzyl,
4-[HOOCCH$_2$CH$_2$C(O)NH—]benzyl, benzyl,
4-[2'-carboxylphenoxy-]benzyl,
4-[(φ-C(O)NH—]benzyl,
3-carboxybenzyl,
4-iodobenzyl,
4-hydroxy-3,5-diiodobenzyl,
4-hydroxy-3-iodobenzyl,
4-[2'-carboxyphenyl-]benzyl,
φ—CH$_2$CH$_2$—,
4-nitrobenzyl,
2-carboxybenzyl,
4-[dibenzylamino]-benzyl,
4-[(1'-cyclopropylpiperidin-4'-yl)C(O)NH—]benzyl,
4-[—NHC(O)CH$_2$NHBoc]benzyl,
4-carboxybenzyl,
4-hydroxy-3-nitrobenzyl,
4-[—NHC(O)CH(CH$_3$)NHBoc]benzyl,
4-[—NHC(O)CH(CH$_2$φ)NHBoc]benzyl,
isobutyl,
methyl,
4-[CH$_3$C(O)NH—]benzyl,
—CH$_2$-(3-indolyl),
n-butyl,
t-butyl-OC(O)CH$_2$—,
t-butyl-OC(O)CH$_2$CH$_2$—,
H$_2$NC(O)CH$_2$—,
H$_2$NC(O)CH$_2$CH$_2$—,
BocNH—(CH$_2$)$_4$—,
t-butyl-OC(O)—(CH$_2$)$_2$—,
HOOCCH$_2$—,
HOOC(CH$_2$)$_2$—,
H$_2$N(CH$_2$)$_4$—,
isopropyl,
(1-naphthyl)-CH$_2$—,
(2-naphthyl)-CH$_2$—,
(2-thiophenyl)-CH$_2$—,
(φ-CH$_2$—OC(O)NH—(CH$_2$)$_4$—,
cyclohexyl-CH$_2$—,
benzyloxy-CH$_2$—,
HOCH$_2$—,
5-(3-N-benzyl)imidazolyl-CH$_2$—,
2-pyridyl-CH$_2$—,
3-pyridyl-CH$_2$—,
4-pyridyl-CH$_2$—,
5-(3-N-methyl)imidazolyl-CH$_2$—,
N-benzylpiperid-4-yl-CH$_2$—,
N-Boc-piperidin-4-yl-CH$_2$—,
N-(phenyl-carbonyl)piperidin-4-yl-CH$_2$—,
H$_3$CSCH$_2$CH$_2$—,
1-N-benzylimidazol-4-yl-CH$_2$—,
iso-propyl-C(O)NH—(CH$_2$)$_4$—,
iso-butyl-C(O)NH—(CH$_2$)$_4$—,
phenyl-C(O)NH—(CH$_2$)$_4$—,
benzyl-C(O)NH—(CH$_2$)$_4$—,
allyl-C(O)NH—(CH$_2$)$_4$—,
4-(3-N-methylimidazolyl)-CH$_2$—,
4-imidazolyl,
4-[(CH$_3$)$_2$NCH$_2$CH$_2$CH$_2$—O—]benzyl,
4-[(benzyl)$_2$N-]-benzyl,
4-aminobenzyl,
allyloxy-C(O)NH(CH$_2$)$_4$—,
allyloxy-C(O)NH(CH$_2$)$_3$—,
allyloxy-C(O)NH(CH$_2$)$_2$—,
NH$_2$C(O)CH$_2$—,
φ-CH=,
2-pyridyl-C(O)NH—(CH$_2$)$_4$—,
4-methyl pyrid-3-yl-C(O)NH—(CH$_2$)$_4$—,
3-methylthien-2-yl-C(O)NH—(CH$_2$)$_4$—,
2-pyrrolyl-C(O)NH—(CH$_2$)$_4$—,
2-furanyl-C(O)NH—(CH$_2$)$_4$—,
4-methylphenyl-SO$_2$—N(CH$_3$)CH$_2$C(O)NH(CH$_2$)$_4$—,
4-[cyclopentylacetylenyl]-benzyl, 4-[—NHC(O)—(N-Boc)-pyrrolidin-2-yl)]-benzyl-,
1-N-methylimidazol-4-yl-CH$_2$—,
1-N-methylimidazol-5-yl-CH$_2$—,
imidazol-5-yl-CH$_2$—,
6-methylpyrid-3-yl-C(O)NH—(CH$_2$)$_4$—,
4-[2'-carboxymethylphenyl]-benzyl,
4-[—NHC(O)NHCH$_2$CH$_2$CH$_2$-φ]-benzyl,
4-[—NHC(O)NHCH$_2$CH$_2$-φ]-benzyl,
—CH$_2$C(O)NH(CH$_2$)$_4$φ,
4-[(φ(CH$_2$)$_4$O—]-benzyl,
4-[—C≡C-φ-4'φ]-benzyl,
4-[—C≡C-CH$_2$—O—S(O)$_2$-4'-CH$_3$-φ]-benzyl,
4-[—C≡C—CH$_2$NHC(O)NH$_2$]-benzyl,
4-[—C≡C—CH$_2$—O-4'-COOCH$_2$CH$_3$-φ]-benzyl,
4-[—C≡C—CH(NH$_2$)-cyclohexyl]-benzyl,
—(CH$_2$)$_4$NHC(O)CH$_2$-3-indolyl,
—(CH$_2$)$_4$NHC(O)CH$_2$CH$_2$-3-indolyl,
—(CH$_2$)$_4$NHC(O)-3-(5-methoxyindolyl),
—(CH$_2$)$_4$NHC(O)-3-(1-methylindolyl),
—(CH$_2$)$_4$NHC(O)-4-(—SO$_2$(CH$_3$)-φ,
—(CH$_2$)$_4$NHC(O)-4-(C(O)CH$_3$)-phenyl,
—(CH$_2$)$_4$NHC(O)-4-fluorophenyl,
—(CH$_2$)$_4$NHC(O)CH$_2$O-4-fluorophenyl,
4-[—C≡C—(2-pyridyl)]benzyl,
4-[—C≡C—CH$_2$—O-phenyl]benzyl,
4-[—C≡C—CH$_2$OCH$_3$]benzyl,
4-[—C≡C-(3-hydroxyphenyl)]benzyl,
4-[—C≡C—CH$_2$—O-4'-(—C(O)OC$_2$H$_5$)phenyl]benzyl,
4-[—C≡C—CH$_2$CH(C(O)OCH$_3$)$_2$]benzyl,
4-[—C≡C—CH$_2$NH-(4,5-dihydro-4-oxo-5-phenyl-oxazol-2-yl),
3-aminobenzyl,
4-[—C≡C—CH$_2$CH(NHC(O)CH$_3$)C(O)OH]-benzyl,
—CH$_2$C(O)NHCH(CH$_3$)φ,
—CH$_2$C(O)NHCH$_2$-(4-dimethylamino)-φ,
—CH$_2$C(O)NHCH$_2$-4-nitrophenyl,
—CH$_2$CH$_2$C(O)N(CH$_3$)CH$_2$-φ,
—CH$_2$CH$_2$C(O)NHCH$_2$CH$_2$—(N-methyl)-2-pyrrolyl,
—CH$_2$CH$_2$C(O)NHCH$_2$CH$_2$CH$_2$CH$_3$,
—CH$_2$CH$_2$C(O)NHCH$_2$CH$_2$-3-indolyl,
—CH$_2$C(O)N(CH$_3$)CH$_2$phenyl,
—CH$_2$C(O)NH(CH$_2$)$_2$—(N-methyl)-2-pyrrolyl,
—CH$_2$C(O)NHCH$_2$CH$_2$CH$_2$CH$_3$,
—CH$_2$C(O)NHCH$_2$CH$_2$-3-indolyl,
—(CH$_2$)$_2$C(O)NHCH(CH$_3$)φ,
—(CH$_2$)$_2$C(O)NHCH$_2$-4-dimethylaminophenyl,
—(CH$_2$)$_2$C(O)NHCH$_2$-4nitrophenyl,
—CH$_2$C(O)NH-4-[—NHC(O)CH$_3$-phenyl],
—CH$_2$C(O)NH-4-pyridyl,
—CH$_2$C(O)NH-4-[dimethylaminophenyl],
—CH$_2$C(O)NH-3-methoxyphenyl,
—CH$_2$CH$_2$C(O)NH-4-chlorophenyl,
—CH$_2$CH$_2$C(O)NH-2-pyridyl,
—CH$_2$CH$_2$C(O)NH-4-methoxyphenyl,
—CH$_2$CH$_2$C(O)NH-3-pyridyl,
4-[(CH$_3$)$_2$NCH$_2$CH$_2$O—]benzyl,
—(CH$_2$)$_3$NHC(NH)NH—SO$_2$-4-methylphenyl,
4-[(CH$_3$)$_2$NCH$_2$CH$_2$O—]benzyl,
—(CH$_2$)$_4$NHC(O)NHCH$_2$CH$_3$,
—(CH$_2$)$_4$NHC(O)NH-phenyl,
—(CH$_2$)$_4$NHC(O)NH-4-methoxyphenyl,
4-[4'-pyridyl-C(O)NH—]benzyl,
4-[3'-pyridyl-C(O)NH—]benzyl,
4-[—NHC(O)NH-3'-methylphenyl]benzyl,
4-[—NHC(O)CH$_2$NHC(O)NH-3'-methylphenyl]benzyl,
4-[—NHC(O)-(2',3'-dihydroindol-2-yl)]benzyl,
4-[—NHC(O)-(2',3'-dihydro-N-Boc-indol-2-yl)]benzyl,
p-[—OCH$_2$CH$_2$-1'-(4'-pyrimidinyl)-piperazinyl]benzyl,
4-[—OCH$_2$CH$_2$-(1'-piperidinyl)benzyl,
4-[—OCH$_2$CH$_2$-(1'-pyrrolidinyl)]benzyl,
4-[—OCH$_2$CH$_2$-(1'-piperidinyl)]benzyl-,
—CH$_2$-3-(1,2,4-triazolyl),
4-[—OCH$_2$CH$_2$CH$_2$-4-(3'-chlorophenyl)-piperazin-1-yl]benzyl,
4-[—OCH$_2$CH$_2$N(φ)CH$_2$CH$_3$]benzyl,
4-[—OCH$_2$-3'-(N-Boc)-piperidinyl]benzyl,
4-[di-n-pentylamino]benzyl,
4-[n-pentylamino]benzyl,
4-[di-iso-propylamino-CH$_2$CH$_2$O—]benzyl,
4-[—OCH$_2$CH$_2$—(N-morpholinyl)]benzyl,
4-[—O—(3'-(N-Boc)-piperidinyl]benzyl,
4-[—OCH$_2$CH(NHBoc)CH$_2$cyclohexyl]benzyl,
p-[OCH$_2$CH$_2$—(N-piperidinyl]benzyl,
4-[—OCH$_2$CH$_2$CH$_2$-(4-m-chlorophenyl)-piperazin-1-yl]benzyl,
4-[—OCH$_2$CH$_2$—(N-homopiperidinyl)]benzyl,
4-[—NHC(O)-3'-(N-Boc)-piperidinyl]benzyl,
4-[—OCH$_2$CH$_2$N(benzyl)$_2$]benzyl,
—CH$_2$-2-thiazolyl,
3-hydroxybenzyl,
4-[—OCH$_2$CH$_2$N(CH$_3$)$_2$]benzyl,
4-[—NHC(S)NHCH$_2$CH$_2$—(N-morpholino)]benzyl,
4-[—OCH$_2$CH$_2$N(C$_2$H$_5$)$_2$]benzyl,
4-[—OCH$_2$CH$_2$CH$_2$N(C$_2$H$_5$)$_2$]benzyl,
4-[CH$_3$(CH$_2$)$_4$NH—]benzyl,
4-[N-n-butyl,N-n-pentylamino-]benzyl,
4-[—NHC(O)-4'-piperidinyl]benzyl,
4-[—NHC(O)CH(NHBoc)(CH$_2$)$_4$NHCbz]benzyl,
4-[—NHC(O)—(1',2',3',4'-tetrahydro-N-Boc-isoquinolin-1'-yl]benzyl,
p-[—OCH$_2$CH$_2$CH$_2$-1'-(4'—methyl)-piperazinyl]benzyl,
—(CH$_2$)$_4$NH-Boc,
3-[—OCH$_2$CH$_2$CH$_2$N(CH$_3$)$_2$]benzyl,
4-[—OCH$_2$CH$_2$CH$_2$N(CH$_3$)$_2$]benzyl,
3-[—OCH$_2$CH$_2$-(1'-pyrrolidinyl)]benzyl,
4-[—OCH$_2$CH$_2$CH$_2$N(CH$_3$)benzyl]benzyl,
4-[—NHC(S)NHCH$_2$CH$_2$CH$_2$—(N-morpholino)]benzyl,
4-[—OCH$_2$CH$_2$—(N-morpholino)]benzyl,
4-[—NHCH$_2$-(4'-chlorophenyl)]benzyl,
4-[—NHC(O)NH-(4'-cyanophenyl)]benzyl,
4-[—OCH$_2$COOH]benzyl,
4-[—OCH$_2$COO-t-butyl]benzyl,
4-[—NHC(O)-5'-fluoroindol-2'-yl]benzyl,
4-[—NHC(S)NH(CH$_2$)$_2$-1-piperidinyl]benzyl,
4-[—N(SO$_2$CH$_3$)(CH$_2$)$_3$—N(CH$_3$)$_2$]benzyl,
4-[—NHC(O)CH$_2$CH(C(O)OCH$_2$φ)-NHCbz]benzyl,
4-[—NHS(O)$_2$CF$_3$]benzyl,
3-[—O—(N-methylpiperidin-4'-yl]benzyl,
4-[—C(=NH)NH$_2$]benzyl,
4-[—NHSO$_2$—CH$_2$Cl]benzyl,
4-[—NHC(O)-(1',2',3',4'-tetrahydroisoquinolin-2'-yl]benzyl,
4-[—NHC(S)NH(CH$_2$)$_3$—N-morpholino]benzyl,
4-[—NHC(O)CH(CH$_2$CH$_2$CH$_2$CH$_2$NH$_2$)NHBoc]benzyl,
4-[—C(O)NH$_2$]benzyl,
4-[—NHC(O)NH-3'-methoxyphenyl]benzyl,
4-[—OCH$_2$CH$_2$-indol-3'-yl]benzyl,
4-[—OCH$_2$C(O)NH-benzyl]benzyl,
4-[—OCH$_2$C(O)O-benzyl]benzyl,
4-[—OCH$_2$C(O)OH]benzyl,
4-[—OCH$_2$-2'-(4',5'-dihydro)imidazolyl]benzyl,
—CH$_2$C(O)NHCH$_2$-(4-dimethylamino)phenyl,
—CH$_2$C(O)NHCH$_2$-(4-dimethylamino)phenyl, 4-[—NHC(O)-L-2'-pyrrolidinyl-N—SO$_2$-4'-methylphenyl]benzyl,
4-[—NHC(O)NHCH$_2$CH$_2$CH$_3$]benzyl,
4-aminobenzyl]benzyl,
4-[—OCH$_2$CH$_2$-1-(4-hydroxy-4-(3-methoxypyrrol-2-yl)-piperazinyl]benzyl,
4-[—O—(N-methylpiperidin-4'-yl)]benzyl,
3-methoxybenzyl,
4-[—NHC(O)-piperidin-3'-yl]benzyl,
4-[—NHC(O)-pyridin-2'-yl]benzyl,
4-[—NHCH$_2$-(4'-chlorophenyl)]benzyl,
4-[—NHC(O)—(N-(4'-CH$_3$—φ—SO$_2$)-L-pyrrolidin-2'-yl)]benzyl,
4-[—NHC(O)NHCH$_2$CH$_2$—φ]benzyl,
4-[—OCH$_2$C(O)NH$_2$]benzyl,
4-[—OCH$_2$C(O)NH-t-butyl]benzyl,
4-[—OCH$_2$CH$_2$-1-(4-hydroxy-4-phenyl)-piperidinyl]benzyl,
4-[—NHSO$_2$—CH=CH$_2$]benzyl,
4-[—NHSO$_2$—CH$_2$CH$_2$Cl]benzyl,
—CH$_2$C(O)NHCH$_2$CH$_2$N(CH$_3$)$_2$,
4-[(1'-Cbz-piperidin-4'-yl)C(O)NH—]benzyl,
4-[(1'-Boc-piperidin-4'-yl)C(O)NH—]benzyl,
4-[(2'-bromophenyl)C(O)NH—]benzyl,
4-[—NHC(O)-pyridin-4'-yl]benzyl,
4-[(4'-(CH$_3$)$_2$NC(O)O—)phenyl)-C(O)NH—]benzyl,
4-[—NHC(O)-1'-methylpiperidin-4'-yl-]benzyl,
4-(dimethylamino)benzyl,
4-[—NHC(O)-(1'-N-Boc)-piperidin-2'-yl]benzyl,
3-[—NHC(O)-pyridin-4'-yl]benzyl,
4-[(tert-butyl-O(O)CCH$_2$—O-benzyl)-NH—]benzyl,
[BocNHCH$_2$C(O)NH—]butyl,
4-benzylbenzyl,
2-hydroxyethyl,
4-[(Et)$_2$NCH$_2$CH$_2$CH$_2$NHC(S)NH—]benzyl,
4-[(1'-Boc-4'-hydroxypyrrolidin-2'-yl)C(O)NH—]benzyl,
4-[(φCH$_2$CH$_2$CH$_2$NHC(S)NH—]benzyl,
4-[(perhydroindolin-2'-yl)C(O)NH—]benzyl,
2-[4-hydroxy-4-(3-methoxythien-2-yl)piperidin-1-yl]ethyl,
4-[(1'-Boc-perhydroindolin-2'-yl)-C(O)NH—]benzyl,
4-[N-3-methylbutyl-N-trifluoromethanesulfonyl)amino]benzyl,
4-[N-vinylsulfonyl)amino]benzyl,
4-[2-(2-azabicyclo[3.2.2]octan-2-yl)ethyl-O—]benzyl,
4-[4'-hydroxypyrrolidin-2'-yl)C(O)NH—]benzyl,
4-(φNHC(S)NH)benzyl
4-(EtNHC(S)NH)benzyl,
4-(φCH$_2$NHC(S)NH)benzyl,
3-[(1'-Boc-piperidin-2'-yl)C(O)NH—]benzyl,
3-[piperidin-2'-yl-C(O)NH—]benzyl,
4-[(3'-Boc-thiazolidin-4'-yl)C(O)NH—]benzyl,
4-(pyridin-3'-yl-NHC(S)NH)benzyl,
4-(CH$_3$—NHC(S)NH)benzyl,
4-(H$_2$NCH$_2$CH$_2$CH$_2$C(O)NH)benzyl,
4-(BocHNCH$_2$CH$_2$CH$_2$C(O)NH)benzyl,
4-(pyridin-4'-yl-CH$_2$NH)benzyl,
4-[(N,N-di(4-N,N-dimethylamino)benzyl)amino]benzyl,
4-[(1-Cbz-piperidin-4-yl)C(O)NH—]butyl,
4-[(φCH$_2$OCH$_2$(BocHN)CHC(O)NH]benzyl,
4-[(piperidin-4'-yl)C(O)NH—]benzyl,
4-[(pyrrolidin-2'-yl)C(O)NH—]benzyl,
4-(pyridin-3'-yl-C(O)NH)butyl,
4-(pyridin-4'-yl-C(O)NH)benzyl,
4-(pyridin-4'-yl-C(O)NH)butyl,
4-(pyridin-3'-yl-C(O)NH)benzyl,
4-[CH$_3$NHCH$_2$CH$_2$CH$_2$C(O)NH—]benzyl,
4-[CH$_3$N(Boc)CH$_2$CH$_2$CH$_2$C(O)NH—]benzyl, 4-(aminomethyl)benzyl,
4-[(φCH$_2$OCH$_2$(H$_2$N)CHC(O)NH]benzyl,
4-[(1',4'-di(Boc)piperazin-2'-yl)-C(O)NH—]benzyl,
4-[(piperazin-2'-yl)-C(O)NH—]benzyl,
4-[(N-toluenesulfonylpyrrolidin-2'-yl)C(O)NH—]butyl,
4-[—NHC(O)-4'-piperidinyl]butyl,
4-[—NHC(O)-1'-N-Boc-piperidin-2'-yl]benzyl,
4-[—NHC(O)-piperidin-2'-yl]benzyl,
4-[(1'-N-Boc-2',3'-dihydroindolin-2'-yl)-C(O)NH]benzyl,
4-(pyridin-3'-yl-CH$_2$NH)benzyl,
4-[(piperidin-1'-yl)C(O)CH$_2$—O—]benzyl,
4-[(CH$_3$)$_2$CH)$_2$NC(O)CH$_2$—O—]benzyl,
4-[HO(O)C(Cbz-NH)CHCH$_2$CH$_2$—C(O)NH—]benzyl,
4-[(φCH$_2$O(O)C(Cbz-NH)CHCH$_2$CH$_2$—C(O)NH—]benzyl,
4-[—NHC(O)-2'-methoxyphenyl]benzyl,
4-[(pyrazin-2'-yl)C(O)NH—]benzyl,
4-[HO(O)C(NH$_2$)CHCH$_2$CH$_2$—C(O)NH—]benzyl,
4-(2'-formyl-1',2',3',4'-tetrahydroisoquinolin-3'-yl-CH$_2$NH—)benzyl,
N-Cbz-NHCH$_2$—,
4-[(4'-methylpiperazin-1-yl)C(O)O—]benzyl,
4-[CH$_3$(N-Boc)NCH$_2$C(O)NH—]benzyl,
4-[—NHC(O)-(1',2',3',4'-tetrahydro-N-Boc-isoquinolin-3'-yl]-benzyl,
4-[CH$_3$NHCH$_2$C(O)NH—]benzyl,
(CH$_3$)$_2$NC(O)CH$_2$—,
4-(N-methylacetamido)benzyl,
4-(1',2',3',4'-tetrahydroisoquinolin-3'-yl-CH$_2$NH—)benzyl,
4-[(CH$_3$)$_2$NHCH$_2$C(O)NH—]benzyl,
(1-toluenesulfonylimidizol-4-yl)methyl,
4-[(1'-Boc-piperidin-4'-yl)C(O)NH—]benzyl,
4-trifluoromethylbenzyl,
4-[(2'-bromophenyl)C(O)NH—]benzyl,
4-[(CH$_3$)$_2$NC(O)NH—]benzyl,
4-[CH$_3$OC(O)NH—]benzyl,
4-[(CH$_3$)$_2$NC(O)O—]benzyl,
4-[(CH$_3$)$_2$NC(O)N(CH$_3$)—]benzyl,
4-[CH$_3$OC(O)N(CH$_3$)—]benzyl,
4-(N-methyltrifluoroacetamido)benzyl,
4-[(1'-methoxycarbonylpiperidin-4'-yl)C(O)NH—]benzyl,
4-[(4'-phenylpiperidin-4'-yl)C(O)NH—]benzyl,
4-[(4'-phenyl-1'-Boc-piperidin-4'-yl)-C(O)NH—]benzyl,
4-[(piperidin-4'-yl)C(O)O—]benzyl,
4-[(1'-methylpiperidin-4'-yl)-O—]benzyl,
4-[(1'-methylpiperidin-4'-yl)C(O)O—]benzyl,
4-[(4'-methylpiperazin-1'-yl)C(O)NH—]benzyl,
3-[(CH$_3$)$_2$NC(O)O—]benzyl,
4-[(4'-phenyl-1'-Boc-piperidin-4'-yl)-C(O)O—]benzyl,
4-(N-toluenesulfonylamino)benzyl,
4-[(CH$_3$)$_3$CC(O)NH—]benzyl,
4-[(morpholin-4'-yl)C(O)NH—]benzyl,
4-[(CH$_3$CH$_2$)$_2$NC(O)NH—]benzyl,
4-[—C(O)NH-(4'-piperidinyl)]benzyl,
4-[(2'-trifluoromethylphenyl)C(O)NH—]benzyl,
4-[(2'-methylphenyl)C(O)NH—]benzyl,
4-[(CH$_3$)$_2$NS(O)$_2$O—]benzyl,
4-[(pyrrolidin-2'-yl)C(O)NH—]benzyl,
4-[—NHC(O)-piperidin-1'-yl]benzyl,
4-[(thiomorpholin-4'-yl)C(O)NH—]benzyl,
4-[(thiomorpholin-4'-yl sulfone)-C(O)NH—]benzyl,
4-[(morpholin-4'-yl)C(O)O—]benzyl,
3-nitro-4-(CH$_3$OC(O)CH$_2$O—)benzyl,
(2-benzoxazolinon-6-yl)methyl-,
(2H-1,4-benzoxazin-3 (4H)-one-7-yl)methyl-, 4-[(CH$_3$)$_2$NS(O)$_2$NH—]benzyl,
4-[(CH$_3$)$_2$NS(O)$_2$N(CH$_3$)—]benzyl,
4-[(thiomorpholin-4'-yl)C(O)O—]benzyl,
4-[(thiomorpholin-4'-yl sulfone)-C(O)O—]benzyl,
4-[(piperidin-1'-yl)C(O)O—]benzyl,
4-[(pyrrolidin-1'-yl)C(O)O—]benzyl,
4-[(4'-methylpiperazin-1'-yl)C(O)O—]benzyl,
4-[(2'-methylpyrrolidin-1-yl)-,
(pyridin-4-yl)methyl-,
4-[(piperazin-4'-yl)-C(O)O—]benzyl,
4-[(1'-Boc-piperazin-4'-yl)-C(O)O—]benzyl,
4-[(4'-acetylpiperazin-1'-yl)C(O)O—]benzyl,
p-[(4'-methanesulfonylpiperazin-1'-yl)-benzyl,
3-nitro-4-[(morpholin-4'-yl)-C(O)O—]benzyl,
4-{[(CH$_3$)$_2$NC(S)]$_2$N-}benzyl,
N-Boc-2-aminoethyl-,
4-[(1, 1-dioxothiomorpholin-4-yl)-C(O)O—]benzyl,
4-[(CH$_3$)$_2$NS(O)$_2$-]benzyl,
4-(imidazolid-2'-one-1'-yl)benzyl,
4-[(piperidin-1'-yl)C(O)O—]benzyl,
1-N-benzyl-imidazol-4-yl-CH$_2$—,
3,4-dioxyethylenebenzyl (i.e., 3,4-ethylenedioxybenzyl),
3,4-dioxymethylenebenzyl (i.e., 3,4-methylenedioxybenzyl),
4-[—N(SO$_2$)(CH$_3$)CH$_2$CH$_2$CH$_2$N(CH$_3$)$_2$]benzyl,
4-(3'-formylimidazolid-2'-one-1'-yl)benzyl,
4-[NHC(O)CH(CH$_2$CH$_2$CH$_2$CH$_2$NH$_2$)NHBoc]benzyl,
[2'-[4"-hydroxy-4"'-(3'''-methoxythien-2'''-yl)piperidin-2"-yl]ethoxy]benzyl, and
p-[(CH$_3$)$_2$NCH$_2$CH$_2$N(CH$_3$)C(O)O—]benzyl.

Preferably, $R^5$ in the above compounds is selected from the group consisting of alkyl, substituted alkyl, aryl, substituted aryl, heterocyclic, substituted heterocylic, heteroaryl and substituted heteroaryl. Even more preferably $R^5$ is selected from the group consisting of 4-methylphenyl, methyl, benzyl, n-butyl, n-hexyl, 4-chlorophenyl, 1-naphthyl, 2-naphthyl, 4-methoxyphenyl, phenyl, 2,4,6-trimethylphenyl, 2-(methoxycarbonyl)phenyl, 2-carboxyphenyl, 3,5-dichlorophenyl, 4-trifluoromethylphenyl, 3,4-dichlorophenyl, 3,4-dimethoxyphenyl, 4-(CH$_3$C(O)NH—)phenyl, 4-trifluoromethoxyphenyl, 4-cyanophenyl, isopropyl, 3,5-di-(trifluoromethyl)phenyl, 4-t-butylphenyl, 4-t-butoxyphenyl, 4-nitrophenyl, 2-thienyl, 1-N-methyl-3-methyl-5-chloropyrazol-4-yl, phenethyl, 1-N-methylimidazol-4-yl, 4-bromophenyl, 4-amidinophenyl, 4-methylamidinophenyl, 4-[CH$_3$SC(=NH)]phenyl, 5chloro-2-thienyl, 2,5-dichloro-4-thienyl, 1-N-methyl-4-pyrazolyl, 2-thiazolyl, 5-methyl-1,3,4-thiadiazol-2-yl, 4-[H$_2$NC(S)]phenyl, 4-aminophenyl, 4-fluorophenyl, 2-fluorophenyl, 3-fluorophenyl, 3,5-difluorophenyl, pyridin-3-yl, pyrimidin-2-yl, 4-(3'-dimethylamino-n-propoxy)-phenyl, and 1-methylpyrazol-4-yl.

Preferably, $R^{13}$ in the above compounds is selected from hydrogen or $C_{1-6}$ alkyl; more preferably, hydrogen or $C_{1-3}$ alkyl; and still more preferably, hydrogen or methyl.

In a preferred embodiment, $R^{14}$ in the above compounds is preferably hydrogen and $R^{15}$ is preferably $C_{1-10}$ alkyl or Cy-$C_{1-10}$ alkyl, wherein alkyl is optionally substituted with one to four substituents selected from phenyl and $R^x$, and Cy is optionally substituted with one to four substituents independently selected from-$R^y$, or $R^{14}$ and $R^{15}$ and the carbon to which they are attached together from a 3-7 membered mono- or bicyclic carbon only ring. For the purpose of $R^{15}$, Cy is preferably aryl, more preferably phenyl. In a preferred embodiment, $R^{15}$ is phenyl-$C_{1-3}$ alkyl, wherein phenyl is optionally substituted with one or two groups selected from $R^y$. Additional preferred embodiments for $R^{14}$ and $R^{15}$ are disclosed in International Patent Application Publication No. WO 98/53814, which application is incorporated herein by reference in its entirety.

In a preferred embodiment of the above compounds, $R^{16}$ is substituted amino; $R^{17}$ and/or $R^{20}$ are hydrogen; and $R^{18}$ and/or $R^{21}$ are alkyl, substituted alkyl, aryl or substituted aryl.

In a preferred embodiment, $R^{23}$ in the above compounds is hydrogen. Preferably, $R^{24}$ in the above compounds is $Ar^1$—$Ar^2$—$C_{1-10}$ alkyl wherein $Ar^1$ and $Ar^2$ are optionally substituted with from 1 to 4 groups independently selected from $R^b$ and $R^{25}$ is hydrogen. More preferably, $R^{24}$ is $Ar^1$—$Ar^2$—$C_{1-3}$ alkyl wherein $Ar^1$ and $Ar^2$ are optionally substituted with from 1 to 4 groups independently selected from $R^b$; still more preferably, $R^{24}$ is —CH$_2$—$Ar^2$—$Ar^1$ and $R^{25}$ is hydrogen. Additional preferred embodiments are disclosed in International Patent Application Publication No. WO 98/53817, which application is incorporated herein by reference in its entirety.

Preferably, $R^3$ and $R^{3'}$, or $R^{14}$ and $R^{15}$, or $R^{24}$ and $R^{25}$ are derived from L-amino acids or other similarly configured starting materials. Alternatively, racemic mixtures can be used.

Preferably, x in the above compounds is an integer from 1 to 4.

Preferred compounds include those set forth in Tables 3-6 below:

TABLE 3

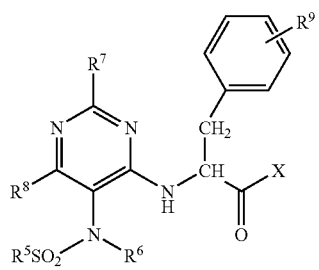

| $R^5$ | $R^6$ | $R^7$ | $R^8$ | $R^9$ | X |
|---|---|---|---|---|---|
| 4-CH$_3$-Ph- | H— | H— | H— | 4-(CH$_3$)$_2$NC(O)O— | —OC(CH$_3$)$_3$ |
| 4-CH$_3$-Ph- | H— | H— | H— | 4-(CH$_3$)$_2$NC(O)O— | —OH |
| 4-CH$_3$-Ph- | CH$_3$— | H— | H— | 4-(CH$_3$)$_2$NC(O)O— | —OC(CH$_3$)$_3$ |
| 4-CH$_3$-Ph- | CH$_3$— | H— | H— | 4-(CH$_3$)$_2$NC(O)O— | —OH |
| 4-HC$_3$-Ph- | 4-CH$_3$-Ph- | H— | H— | 4-(CH$_3$)$_2$NC(O)O— | —OH |

TABLE 3-continued

| R⁵ | R⁶ | R⁷ | R⁸ | R⁹ | X |
|---|---|---|---|---|---|
| 1-CH₃-pyrazol-4-yl- | CH₃— | H— | H— | 4-(CH₃)₂NC(O)O— | —OH |
| 4-CH₃-Ph- | CH₃— | H— | H— | 4-(CH₃)₂NC(O)O— | —OCH(CH₃)₂ |
| 3-pyridyl- | CH₃— | H— | H— | 4-(CH₃)₂NC(O)O— | —OC(CH₃)₃ |
| 1-(n-C₄H₉)-pyrazol-4-yl- | CH₃— | H— | H— | 4-(CH₃)₂NC(O)O— | —OC(CH₃)₃ |
| 4-CH₃-Ph- | CH₃— | H— | H— | H— | —OH |
| 1-(n-C₄H₉)-pyrazol-4-yl- | CH₃— | H— | H— | 4-(CH₃)₂NC(O)O— | —OH |
| 3-pyridyl | CH₃— | H— | H— | 4-(CH₃)₂NC(O)O— | —OH |
| 4-CH₃-Ph- | CH₃— | (CH₃)₂N— | H— | H— | —OH |
| 1-CH₃-pyrazol-4-yl- | CH₃— | H— | H— | 4-(CH₃)₂NC(O)O— | —OCH(CH₃)₂ |
| 3-pyridyl- | CH₃— | H— | H— | 4-(1-CH₃-piperazin-4-yl)C(O)O— | —OCH(CH₃)₂ |
| 3-pyridyl- | CH₃— | H— | H— | 4-(1-CH₃-piperazin-4-yl)C(O)O— | —OC(CH₃)₃ |
| 3-pyridyl- | CH₃— | H— | H— | 4-(1-CH₃-piperazin-4-yl)-C(O)O— | —OH |

Ph = phenyl

TABLE 4

| R¹⁶' | R²⁰' | R¹⁸' | R¹⁹ | X |
|---|---|---|---|---|
| Cl— | H— | NO₂— | 4-(CH₃)₂NC(O)O— | —OH |
| H— | H— | PhCH₂O— | H— | —OH |
| H— | H— | PhCH₂O— | 4-(CH₃)₂NC(O)O— | —OH |
| H— | H— | Ph- | 4-(CH₃)₂NC(O)O— | —OH |
| H— | H— | 3-NO₂-Ph- | 4-(CH₃)₂NC(O)O— | —OH |
| H— | H— | 3-pyrridyl- | 4-(CH₃)₂NC(O)O— | —OH |
| H— | H— | 2-PhCH₂CH₂— | 4-(CH₃)₂NC(O)O— | —OH |
| H— | H— | 2-CH₃-Ph- | 4-(CH₃)₂NC(O)O— | —OH |
| H— | H— | (CH₃)₂NC(O)—(CH₂)₂— | 4-(CH₃)₂NC(O)O— | —OH |
| H— | Ph- | H— | 4-(CH₃)₂NC(O)O— | —OH |
| H— | 2-CF₃-Ph- | H— | 4-(CH₃)₂NC(O)O— | —OH |
| H— | 2-HOCH₂Ph- | H— | 4-(CH₃)₂NC(O)O— | —OH |
| HN— | H— | CF₃CH₂— | 4-(CH₃)₂NC(O)O— | —OH |
| H— | H— | PhCH₂— | 4-(CH₃)₂NC(O)O— | —OH |
| H— | H— | 2-HC-Ph- | 4-(CH₃)₂NC(O)O— | —OCH(CH₃)₂ |
| H— | H— | 2-PhCH₂CH₂— | 4-(CH₃)₂NC(O)O— | —OCH(CH₃)₂ |
| H— | H— | 2-PhCH₂CH₂— | H— | —OCH(CH₃)₂ |
| ccyclohexyl-(CH₃)N— | H— | H— | 4-(CH₃)₂NC(O)O— | —OH |

TABLE 4-continued

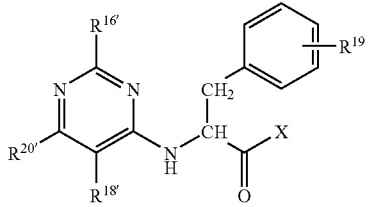

| R16' | R20' | R18' | R19 | X |
|---|---|---|---|---|
| H— | H— | CH3CH2CH2— | 4-(CH3)2NC(O)O— | —OH |
| H— | H— | 2-HC3O-Ph- | 4-(CH3)2NC(O)O— | —OH |
| H— | H— | 2-F-Ph-- | 4-(CH3)2NC(O)O— | —OH |
| (CH3)2CH—(CH3)N— | H— | 2-HC3-Ph- | 4-(CH3)2NC(O)O— | —OH |
| (CH3)2CH—NH— | H— | 2-CH3-Ph- | 4-(CH3)2NC(O)O— | —OH |
| (CH3)2CHCH2—(CH3)N— | H— | 2-CH3-Ph- | 4-(CH3)2NC(O)O— | —OH |
| CH3CH2CH2—(CH3)N— | H— | 2-CH3—Ph— | 4-(CH3)2NC(O)O— | —OH |
| (CH3)2N— | H— | 2-CH3-Ph- | 4-(CH3)2NC(O)O— | —OH |
| cyclohexyl-(CH3)N— | H— | 3-pyridyl | 4-(CH3)2NC(O)O— | —OH |
| H— | H— | 2-PhCF2CH2— | 4-(CH3)2NC(O)O— | —OH |
| H— | Cl— | 2-PhCF2CH2— | 4-(CH3)2NC(O)O— | —OH |
| (HOCH2CH2)2N— | H— | H— | 4-(CH3)2NC(O)O— | —OH |
| (HOCH2CH2)2N— | H— | 2-CH3-Ph- | 4-(CH3)2NC(O)O— | —OH |
| Ph(CH3)N— | H— | 2-CH3-Ph- | 4-(CH3)2NC(O)O— | —OH |
| (CH3)2CHO— | H— | 2-CH3-Ph- | 4-(CH3)2NC(O)O— | —OH |
| (CH3)2CHCH2—CH2(CH3)N— | H— | 2-CH3-Ph- | 4-(CH3)2NC(O)O— | —OH |
| CH3NH— | H— | 2-CH3-Ph- | 4-(CH3)2NC(O)O— | —OH |
| 2-CH3-Ph- | H— | 2-CH3-Ph- | 4-(CH3)2NC(O)O— | —OH |
| HOCH2CH2—(CH3)N— | H— | 2-HC3-Ph- | 4-(CH3)2NC(O)O— | —OH |
| cyclohexyl-NH— | H— | 2-CH3-Ph- | 4-(CH3)2NC(O)O— | —OH |
| 1-CH3-piperidin-4-yl-(CH3)N— | H— | 2-CH3-Ph- | 4-(CH3)2NC(O)O— | —OH |
| (CH3)2CH—(CH3CH2—)N— | H— | 2-CH3-Ph- | 4-(CH3)2NC(O)O— | —OH |
| H— | H— | 2,4,6-tri-CH3-Ph- | 4-(CH3)2NC(O)O— | —OH |
| H— | H— | (CH3)2CH— | 4-(CH3)2NC(O)O— | —OH |
| CH3(CH2)3—(CH3)N— | H— | 2-HC3-Ph- | 4-(CH3)NC(O)O— | —OH |
| CH3CH2CH2—(CH3CH2—)N— | H— | 2-CH3-Ph- | 4-(CH3)2NC(O)O— | —OH |
| (CH3CH2)2N— | H— | 2-CH3-Ph- | 4-(CH3)2NC(O)O— | —OH |
| CH3CH2—(CH3)N— | H— | 2-CH3-Ph- | 4-(CH3)2NC(O)O— | —OH |
| H— | H— | cyclohexyl- | 4-(CH3)2NC(O)O— | —OH |
| (furan-2-yl)CH2—(CH3)N— | H— | 2-CH3-Ph- | 4-(CH3)2NC(O)O— | —OH |
| 4-Cl-Ph-(CH3)N— | H— | 2-HC3-Ph- | 4-(CH3)2NC(O)O— | —OH |
| H— | H— | thien-3-yl- | 4-(CH3)2NC(O)O— | —OH |
| H— | H— | thien-22-yl- | 4-(CH3)2NC(O)O— | —OH |
| HOCH2CH2—(CH3)N— | H— | 2-F-Ph- | 4-(CH3)2NC(O)O— | —OH |
| H— | H— | piperidin-1-yl- | 4-(CH3)2NC(O)O— | —OH |
| H— | H— | (CH3CH2CH2)2—CH— | 4-(CH3)2NC(O)O— | —OH |
| cyclobutyl- | H— | 2-HC3-Ph- | 4-(CH3)2NC(O)O— | —OH |
| H— | H— | 2-HOCH2-Ph- | 4-(CH3)2NC(O)O— | —OH |
| H— | H— | 2,6-di-F-Ph- | 4-(CH3)2NC(O)O— | —OH |
| H— | H— | 2,4-di-CH3O—pyrimidin-5-yl | 4-(CH3)2NC(O)O— | —OH |
| cyclohexyl-(CH3)N— | H— | 2-CH3-Ph- | 4-(CH3)2NC(O)O— | —OH |
| H— | H— | 2-CF3-Ph- | 4-(CH3)2NC(O)O— | —OH |
| cyclohexyl-(CH3)2N— | H— | 2-CH3O-Ph- | 2,6-di-CH3O-Ph- | —OH |
| (CH3)2CH—(CH3)N— | H— | 2-F-Ph | 2,6-di-CH3O-Ph- | —OH |
| (CH3)2CH—(CH3)N— | H— | 2-F-Ph- | 2-CH3O-Ph- | —OH |
| cyclohexyl-(CH3)N— | H— | 2,6-di-F-Ph- | 2,6-di-F-Ph- | —OH |

TABLE 4-continued

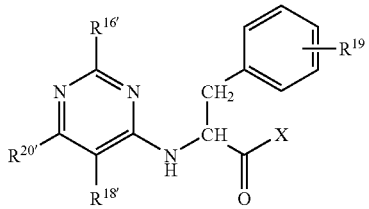

| $R^{16'}$ | $R^{20'}$ | $R^{18'}$ | $R^{19}$ | X |
|---|---|---|---|---|
| cyclohexyl-$(CH_3)N$— | H— | 2-HOCH$_2$-Ph- | 2,6-di-CH$_2$O-Ph- | —OH |
| $(HOCH_2CH_2)_2N$— | H— | 2,4,6-tri-CH$_3$-Ph- | 2,6-di-CH$_3$O-Ph- | —OH |
| cyclohexyl-$(CH_3)N$— | H— | 2-CF$_3$-Ph- | 2-NC-Ph- | —OH |
| cyclohexyl-$(CH_3)N$— | H— | thien-3-yl | 2,6-di-CH$_3$O-Ph- | —OH |
| cyclohexyl-$(CH_3)N$— | H— | thien-2-yl- | 4-CF$_3$-Ph- | —OH |
| cyclohexyl-$(CH_3)N$— | H— | 3-pyridyl- | 2,6-di-CH$_3$O-Ph- | —OH |
| cyclohexyl-$(CH_3)N$— | H— | 2-NO$_2$-Ph- | 2,6-di-CH$_3$O-Ph- | —OH |
| cyclohexyl-$(CH_3)N$— | H— | 2,6-di-Cl-Ph- | 2,6-di-CH$_3$O-Ph- | —OH |
| cyclohexyl-$(CH_3)N$— | H— | 4-pyridyl- | 3-HOCH$_2$-Ph- | —OH |
| $(CH_3)_2CH$—$(CH_3CH_2$—$)N$— | H— | 2,6-di-CH$_3$O-Ph- | 2,6-di-CH$_3$O-Ph- | —OH |
| cyclohexyl-$(CH_3)N$— | H— | 2,6-di-Cl-Ph- | 2,6-di-CH$_3$O-Ph- | —OH |
| $CH_3CH_2$—$(CH_3)N$— | H— | 2,4,6-tri-CH$_3$-Ph- | 2-NC-Ph- | —OH |
| $(CH_3)_2CH$—$(CH_3)N$— | H— | 2,4,6-tri-CH$_3$-Ph- | 3-pyridyl- | —OH |
| $(HOCH_2CH_2)_2N$— | H— | 2,4,6-tri-CH$_3$-Ph- | 2-NC-Ph- | —OH |
| 1-CH$_3$-piperidin-4-yl-$(CH_3)N$— | H— | 2-NC-Ph- | 2,6-di-F-Ph- | —OH |
| $(CH_3)_2CH$—$(CH_3CH_2$—$)N$— | H— | 2,4,6-tri-CH$_3$-Ph- | 2-CH$_3$-Ph- | —OH |
| 4-Cl-Ph-$(CH_3)N$— | H— | 2,4,6-tri-CH$_3$-Ph- | 2,6-di-CH$_3$O-Ph- | —OH |
| H— | H— | PhCH$_2$CH$_2$—$(CH_3)N$— | 4-$(CH_3)_2NC(O)O$— | —OH |
| H— | H— | $CH_3(CH_2)_5$—$(CH_3)N$— | 4-$(CH_3)_2NC(O)O$— | —OH |
| H— | H— | $(CH_3)_2CH$—$(CH_3)N$— | 4-$(CH_3)_2NC(O)O$— | —OH |
| H— | H— | $(CH_3)_3C$—$(CH_3)N$— | 4-$(CH_3)_2NC(O)O$— | —OH |
| H— | H— | $(CH_3)_2CH$—$(CH_3CH_2$—$)N$— | 4-$(CH_3)_2NC(O)O$— | —OH |
| H— | H— | 4-pyridyl-CH$_2$CH$_2$—$(CH_3)N$— | 4-$(CH_3)_2NC(O)O$— | —OH |
| H— | H— | PhCH$_2$CH$_2$—$(CH_3)N$— | 22,6-di-CH$_3$O-Ph- | —OH |
| H— | H— | $CH_3(CH_2)_5$—$(CH_3)N$— | 2,6-di-CH$_3$O-Ph- | —OH |
| H— | H— | $(CH_3)_2CH$—$(CH_3)N$— | 2,6-di-CH$_3$O-Ph- | —OH |
| H— | H— | $(CH_3)_3C$—$(CH_3)N$— | 2,6-di-CH$_3$O-Ph- | —OH |
| H— | H— | $(CH_3)_2CH$—$(CH_3CH_2$—$)N$— | 2,6-di-CH$_3$O-Ph- | —OH |
| H— | H— | 4-pyridyl-CH$_2$CH$_2$—$(CH_3)N$— | 2,6-di-CH$_3$O-Ph- | —OH |
| cyclohexyl-$(CH_3)N$— | H— | $CH_3CH_2$— | 4-$(CH_3)_2NC(O)O$— | —OH |
| H— | H— | $CF_3CH_2$— | 2,6-di-CH$_3$O-Ph- | —OH |
| cyclohexyl-$(CH_3)N$— | H— | 2-CH$_3$-Ph- | 2,6-di-CH$_3$O-Ph- | —OH |
| H— | H— | 2-F-Ph- | 2,6-di-CH$_3$O-Ph- | —OH |
| $CH_3CH_2CH_2$—$(CH_3)N$— | H— | 2-CH$_3$-Ph- | 2,6-di-CH$_3$O-Ph- | —OH |

Ph = phenyl

TABLE 5

| R⁵ | R⁶ | R⁷' | R⁸' | R⁹' | X |
|---|---|---|---|---|---|
| 4-CH₃-Ph- | CH₃— | H— | H— | 4-(CH₃)₂NC(O)O— | —OH |
| 4-CH₃-Ph- | CH₃— | H— | H— | 4-(CH₃)₂NC(O)O— | —OCH(CH₃)₂ |

Ph = phenyl

TABLE 6

| R⁵ | R⁶ | b | R⁹' | X |
|---|---|---|---|---|
| CH₃(CH₂)₅— | CH₃(CH₂)₅— | 2 | 4-HO— | —OH |
| CH₃(CH₂)₅— | CH₃(CH₂)₅— | 2 | 4-(CH₃)₂NC(O)O— | —OH |
| CH₃— | CH₃— | 1 | 4-(CH₃)₂NC(O)O— | —OCH(CH₃)₃ |
| 3-CH₃-PhNH—C(O)NH(CH₂)₂— | H— | 2 | 4-(CH₃)₂NC(O)O— | —OH |
| CH₃(CH₂)₅— | CH₃(CH₂)₅— | 2 | 4-(1-CH₃-piperazin-4-yl)C(O)O— | —OH |

Ph = phenyl

Accordingly, the following are preferred compounds of Formulae III-IX:

N-(2-chloro-5-nitropyrimidin-4-yl)-L-4-(N,N-dimethylcarbamyloxy)phenylalanine,

N-[5-(N-4-toluenesulfonylamino)pyrimidin-4-yl]-L-4-(N,N-dimethylcarbamyloxy)phenylalanine tert-butyl ester, N-[5-(N-4-toluenesulfonylamino)pyrimidin-4-yl]-L-4-(N,N-dimethylcarbamyloxy)phenylalanine, N-[5-(N-methyl-N-4-toluenesulfonylamino)pyrimidin-4-yl]-L-4-(N,N-dimethylcarbamyloxy)phenylalanine tert-butyl ester, N-[5-(N-methyl-N-4-toluenesulfonylamino)pyrimidin-4-yl]-L-4-(N,N-dimethylcarbamyloxy)phenylalanine, N-[5-(N,N-di-4-toluenesulfonylamino)pyrimidin-4-yl]-L-4-(N,N-dimethylcarbamyloxy)phenylalanine, N-[5-[N-(1-N'-methylpyrazol-4-ylsulfonyl)-N-methylamino]pyrimidin-4-yl]-L-4-(N,N-dimethylcarbamyloxy)phenylalanine, N-[5-(N-methyl-N-4-toluenesulfonylamino)pyrimidin-4-yl]-L-4-(N,N-dimethylcarbamyloxy)phenylalanine isopropyl ester, N-[5-(N-methyl-N-3-pyridylsulfonylamino)pyrimidin-4-yl]-L-4-(N,N-dimethylcarbamyloxy)phenylalanine tert-butyl ester, N-(5-(N-methyl-N-(1-butylpyrazol-4-yl)sulfonylamino)pyrimidin-4-yl)-L-4-(N,N-dimethylcarbamyloxy)phenylalanine, N-(5-(2,4-dimethoxypyrimidin-5-yl)pyrimidin-4-yl)-L-4-(N,N-dimethylcarbamyloxy)phenylalanine, N-(5-(2,6-difluorophenyl)pyrimidin-4-yl)-L-4-(N,N-dimethylcarbamyloxy)phenylalanine, N-(5-(2-hydroxymethylphenyl)pyrimidin-4-yl)-L-4-(N,N-dimethylcarbamyloxy)phenylalanine, N-(2-(N-cyclohexylamino)-5-(2-tolyl)pyrimidin-4-yl)-L-4-(N,N-dimethylcarbamyloxy)phenylalanine, N-(2-(N-methyl-N-(1-methylpiperidin-4-yl)amino)-5-(2-tolyl)pyrimidin-4-yl)-L-4-(N,N-dimethylcarbamyloxy)phenylalanine, N-(2-(N-ethyl-N-isopropylamino)-5-(2-tolyl)pyrimidin-4-yl)-L-4-(N,N-dimethylcarbamyloxy)phenylalanine, N-(5-(2,4-6-trimethylphenyl)pyrimidin-4-yl)-L-4-(N,N-dimethylcarbamyloxy)phenylalanine, N-(5-isopropylpyrimidin-4-yl)-L-4-(N,N-dimethylcarbamyloxy)phenylalanine, N-(2-(N-methyl-N-butylamino)-5-(2-tolyl)pyrimidin-4-yl)-L-4-(N,N-dimethylcarbamyloxy)phenylalanine, N-(2-(N-ethyl-N-propylamino)-5-(2-tolyl)pyrimidin-4-yl)-L-4-(N,N-dimethylcarbamyloxy)phenylalanine, N-(2-(N,N-diethylamino)-5-(2-tolyl)pyrimidin-4-yl)-L-4-(N,N-dimethylcarbamyloxy)phenylalanine, N-(2-(N-methyl-N-ethylamino)-5-(2-tolyl)pyrimidin-4-yl)-L-4-(N,N-dimethylcarbamyloxy)phenylalanine, N-(5-benzyloxypyrimidin-4-yl)-L-phenylalanine, N-(5-benzyloxypyrimidin-4-yl)-L-4-(N,N-dimethylcarbamyloxy)phenylalanine, N-(5-(N-methyl-N-4-toluenesulfonylamino)pyrimidin-4-yl)-L-phenylalanine, N-(5-(N-methyl-N-3-pyridinesulfonylamino)pyrimidin-4-yl)-L-4-(N,N-dimethylcarbamyloxy)phenylalanine, N-(5-phenylpyrimidin-4-yl)-L-4-(N,N-dimethylcarbamyloxy)phenylalanine, N-(3-(N-methyl-N-4-toluenesulfonylamino)pyrazin-2-yl)-L-4-(N,N-dimethylcarbamyloxy)phenylalanine, N-(5-(2,2,2-trifluoroethyl)pyrimidin-4-yl)-L-4-(N,N-dimethylcarbamyloxy)phenylalanine,
N-(5-(N-methyl-N-3-pyridinesulfonylamino)pyrimidin-4-yl)-L-4-(4-methylpiperazin-1-ylcarbonyloxy)phenylalanine isopropyl ester,
N-(5-benzylpyrimidin-4-yl)-L-4-(N,N-dimethylcarbamyloxy)phenylalanine,
N-(5-(N-methyl-N-3-pyridinesulfonylamino)pyrimidin-4-yl)-L-4-(4-methylpiperazin-1-ylcarbonyloxy)phenylalanine tert-butyl ester,
N-(5-(2-trifluoromethylphenyl)pyrimidin-4-yl)-L-4-(N,N-dimethylcarbamyloxy)phenylalanine,
N-(5-(2-N,N-dimethylcarbamylethyl)pyrimidin-4-yl)-L-4-(N,N-dimethylcarbamyloxy)phenylalanine,
N-(5-(N-methyl-N-3-(1-methylpyrazole)sulfonylamino)pyrimidin-4-yl)-L-4-(N,N-dimethylcarbamyloxy)phenylalanine isopropyl ester,
N-(6-phenylpyrimidin-4-yl)-L-4-(N,N-dimethylcarbamyloxy)phenylalanine,
N-(6-(2-trifluoromethylphenyl)pyrimidin-4-yl)-L-4-(N,N-dimethylcarbamyloxy)phenylalanine,
N-(6-(2-hydroxymethylphenyl)pyrimidin-4-yl)-L-4-(N,N-dimethylcarbamyloxy)phenylalanine,
N-(5-cyclohexylpyrimidin-4-yl)-L-4-(N,N-dimethylcarbamyloxy)phenylalanine,
N-(2-(N-methyl-N-2-furanmethylamino)-5-(2-tolyl)pyrimidin-4-yl)-L-4-(N,N-dimethylcarbamyloxy)phenylalanine,
N-(2-(N-methyl-N-4-chlorophenylamino)-5-(2-tolyl)pyrimidin-4-yl)-L-4-(N,N-dimethylcarbamyloxy)phenylalanine,
N-(5-(3-thienyl)pyrimidin-4-yl)-L-4-(N,N-dimethylcarbamyloxy)phenylalanine,
N-(5-(2-thienyl)pyrimidin-4-yl)-L-4-(N,N-dimethylcarbamyloxy)phenylalanine,
N-(2-(N-methyl-N-2-hydroxyethylamino)-5-(2-fluorophenyl)pyrimidin-4-yl)-L-4-(N,N-dimethylcarbamyloxy)phenylalanine,
N-(5-(piperidin-1-yl)pyrimidin-4-yl)-L-4-(N,N-dimethylcarbamyloxy)phenylalanine,
N-(5-(1-propylbutyl)pyrimidin-4-y)-L-4-(N,N-dimethylcarbamyloxy)phenylalanine,
N-(2-(N-methyl-N-cyclobutylamino)-5-(2-tolyl)pyrimidin-4-yl)-L-4-(N,N-dimethylcarbamyloxy)phenylalanine,
N-(2-(N,N-bis-(2-hydroxyethyl)amino)pyrimidin-4-yl)-L-4-(N,N-dimethylcarbamyloxy)phenylalanine,
N-(2-(N,N-bis-(2-hydroxyethyl)amino)-5-(2-tolyl)pyrimidin-4-yl)-L-4-(N,N-dimethylcarbamyloxy)phenylalanine,
N-(2-(N-methyl-N-phenylamino)-5-(2-tolyl)pyrimidin-4-yl)-L-4-(N,N-dimethylcarbamyloxy)phenylalanine,
N-(2-(isopropoxy)-5-(2-tolyl)pyrimidin-4-yl)-L-4-(N,N-dimethylcarbamyloxy)phenylalanine,
N-(2-(N-methyl-N-3-methylbutylamino)-5-(2-tolyl)pyrimidin-4-yl)-L-4-(N,N-dimethylcarbamyloxy)phenylalanine,
N-(2-(N-methylamino)-5-(2-tolyl)pyrimidin-4-yl)-L-4-(N,N-dimethylcarbamyloxy)phenylalanine,
N-(2-(2-tolyl)-5-(2-tolyl)pyrimidin-4-yl)-L-4-(N,N-dimethylcarbamyloxy)phenylalanine,
N-(2-(N-methyl-N-2-hydroxyethylamino)-5-(2-tolyl)pyrimidin-4-yl)-L-4-(N,N-dimethylcarbamyloxy)phenylalanine,
N-(2-(N-methyl-N-2-methylpropylamino)-5-(2-tolyl)pyrimidin-4-yl)-L-4-(N,N-dimethylcarbamyloxy)phenylalanine,
N-(2-(N-methyl-N-propylamino)-5-(2-tolyl)pyrimidin-4-yl)-L-4-(N,N-dimethylcarbamyloxy)phenylalanine,
N-(2-(N,N-dimethylamino)-5-(2-tolyl)pyrimidin-4-yl)-L-4-(N,N-dimethylcarbamyloxy)phenylalanine,
N-(2-(N-methyl-N-cyclohexylamino)-5-(3-pyridyl)pyrimidin-4-yl)-L-4-(N,N-dimethylcarbamyloxy)phenylalanine,
N-(5-(2-phenyl-2,2-difluoroethyl)pyrimidin-4-yl)-L-4-(N,N-dimethylcarbamyloxy)phenylalanine,
N-(5-(2-phenyl-2,2-difluoroethyl)-6-chloropyrimidin-4-yl)-L-4-(N,N-dimethylcarbamyloxy)phenylalanine,
N-(5-(2-phenylethyl)pyrimidin-4-yl)-L-4-(N,N-dimethylcarbamyloxy)phenylalanine,
N-(2-(N-methyl-N-cyclohexylamino)pyrimidin-4-yl)-L-4-(N,N-dimethylcarbamyloxy)phenylalanine,
N-(5-propylpyrimidin-4-yl)-L-4-(N,N-dimethylcarbamyloxy)phenylalanine,
N-(5-(2-methoxyphenyl)pyrimidin-4-yl)-L-4-(N,N-dimethylcarbamyloxy)phenylalanine,
N-(5-(2-fluorophenyl)pyrimidin-4-yl)-L-4-(N,N-dimethylcarbamyloxy)phenylalanine,
N-(2-(N-Methyl-N-isopropylamino)-5-(2-tolyl)pyrimidin-4-yl)-L-4-(N,N-dimethylcarbamyloxy)phenylalanine,
N-(2-(N-isopropylamino)-5-(2-tolyl)pyrimidin-4-yl)-L-4-(N,N-dimethylcarbamyloxy)phenylalanine,
N-(5-(2-phenylethyl)pyrimidin-4-yl)-L-4-(N,N-dimethylcarbamyloxy)phenylalanine isopropyl ester,
N-(3-(N-methyl-N-4-toluenesulfonylamino)pyrazin-2-yl)-L-phenylalanine isopropyl ester,
N-(5-(2-phenylethyl)pyrimidin-4-yl)-L-phenylalanine isopropyl ester,
N-(5-(N-methyl-N-3-pyridinesulfonylamino)pyrimidin-4-yl)-L-4-(4-methylpiperazin-1-ylcarbonyloxy)phenylalanine,
N-(2-(N-methyl-N-cyclohexylamino)-5-(2-tolyl)pyrimidin-4-yl)-L-4-(N,N-dimethylcarbamyloxy)phenylalanine,
N-(2-(N-methyl-N-cyclohexylamino)-5-ethylpyrimidin-4-yl)-L-4-(N,N-dimethylcarbamyloxy)phenylalanine,
N-(5-(2-tolyl)pyrimidin-4-yl)-L-4-(N,N-dimethylcarbamyloxy)phenylalanine isopropyl ester,
N-(5-(3-nitrophenyl)pyrimidin-4-yl)-L-4-(N,N-dimethylcarbamyloxy)phenylalanine,
N-(5-(3-pyridyl)pyrimidin-4-yl)-L-4-(N,N-dimethylcarbamyloxy)phenylalanine,
N-(5-(2-phenylethyl)pyrimidin-4-yl)-L-4-(N,N-dimethylcarbamyloxy)phenylalanine,
N-(2-N,N-dimethylamino-5-(N-methyl-N-4-toluenesulfonylamino)pyrimidin-4-yl)-L-phenylalanine,
N-(5-(2-tolyl)pyrimidin-4-yl)-L-4-(N,N-dimethylcarbamyloxy)phenylalanine,
N-(2-(N-methyl-N-cyclohexylamino)-5-(2-methoxyphenyl)pyrimidin-4-yl)-L-4-(2,6-dimethoxyphenyl)phenylalanine,
N-(2-(N-methyl-N-isopropylamino)-5-(2-fluorophenyl)pyrimidin-4-yl)-L-4-(2,6-dimethoxyphenyl)phenylalanine,
N-(2-(N-methyl-N-isopropylamino)-5-(2-fluorophenyl)pyrimidin-4-yl)-L-4-(2-methoxyphenyl)phenylalanine,
N-(2-(N-methyl-N-cyclohexylamino)-5-(2,6-difluorophenyl)pyrimidin-4-yl)-L-4-(2,6-difluorophenyl)phenylalanine,
N-(2-(N-methyl-N-cyclohexylamino)-5-(2-hydroxymethylphenyl)pyrimidin-4-yl)-L-4-(2,6-dimethoxyphenyl)phenylalanine, N-(2-(N,N-bis-(2-hydroxyethyl)amino)-5-(2,4,6-trimethylphenyl)pyrimidin-4-yl)-L-4-(2,6-dimethoxyphenyl)phenylalanine,
N-(2-(N-methyl-N-cyclohexylamino)-5-(2-trifluoromethylphenyl)pyrimidin-4-yl)-L-4-(2-cyanophenyl)phenylalanine,
N-(2-(N-methyl-N-cyclohexylamino)-5-(3-thienyl)pyrimidin-4-yl)-L-4-(2,6-dimethoxyphenyl)phenylalanine,
N-(2-(N-methyl-N-cyclohexylamino)-5-(2-thienyl)pyrimidin-4-yl)-L-4-(4-trifluoromethylphenyl)phenylalanine,
N-(2-(N-methyl-N-cyclohexylamino)-5-(3-pyridyl)pyrimidin-4-yl)-L-4-(2,6-dimethoxyphenyl)phenylalanine,
N-(2-(N-methyl-N-cyclohexylamino)-5-(3-nitrophenyl)pyrimidin-4-yl)-L-4-(2,6-dimethoxyphenyl)phenylalanine,
N-(2-(N-methyl-N-cyclohexylamino)-5-(2,6-dichlorophenyl)pyrimidin-4-yl)-L-4-(2,6-dimethoxyphenyl)phenylalanine,
N-(2-(N-methyl-N-cyclohexylamino)-5-(4-pyridyl)pyrimidin-4-yl)-L-4-(3-hydroxymethylphenyl)phenylalanine,
N-(2-(N-ethyl-N-isopropylamino)-5-(2,6-dimethoxyphenyl)pyrimidin-4-yl)-L-4-(2,6-dimethoxyphenyl)phenylalanine,
N-(2-(N-methyl-N-cyclohexylamino)-5-(2,3-dichlorophenyl)pyrimidin-4-yl)-L-4-(2,6-dimethoxyphenyl)phenylalanine,
N-(2-(N-methyl-N-ethylamino)-5-(2,4,6-trimethylphenyl)pyrimidin-4-yl)-L-4-(2-cyanophenyl)phenylalanine,
N-(2-(N-methyl-N-isopropylamino)-5-(2,4,6-trimethylphenyl)pyrimidin-4-yl)-L-4-(3-pyridyl)phenylalanine,
N-(2-(N,N-bis-(2-hydroxyethyl)amino)-5-(2,4,6-trimethylphenyl)pyrimidin-4-yl)-L-4-(2-cyanophenyl)phenylalanine,
N-(2-(N-methyl-N-(1-methylpiperidin-4-yl)amino)-5-(2-cyanophenyl)pyrimidin-4-yl)-L-4-(2,6-difluorophenyl)phenylalanine,
N-(2-(N-ethyl-N-isopropylamino)-5-(2,4,6-trimethylphenyl)pyrimidin-4-yl)-L-4-(o-tolyl)phenylalanine,
N-(2-(N-methyl-N-4-chlorophenylamino)-5-(2,4,6-trimethylphenyl)pyrimidin-4-yl)-L-4-(2,6-dimethoxyphenyl)phenylalanine,
N-(5-(N-methyl-N-2-(phenyl)ethylamino)pyrimidin-4-yl)-L-4-(N,N-dimethylcarbamyloxy)phenylalanine,
N-(5-(N-methyl-N-hexylamino)pyrimidin-4-yl)-L-4-(N,N-dimethylcarbamyloxy)phenylalanine,
N-(5-(N-methyl-N-isopropylamino)pyrimidin-4-yl)-L-4-(N,N-dimethylcarbamyloxy)phenylalanine,
N-(5-(N-methyl-N-tert-butylamino)pyrimidin-4-yl)-L-4-(N,N-dimethylcarbamyloxy)phenylalanine,
N-(5-(N-ethyl-N-isopropylamino)pyrimidin-4-yl)-L-4-(N,N-dimethylcarbamyloxy)phenylalanine,
N-(5-(N-methyl-N-2-(4-pyridyl)ethyl-pyrimidin-4-yl)-L-4-(N,N-dimethylcarbamyloxy)phenylalanine,
N-(5-(N-methyl-N-2-(phenyl)ethylamino)pyrimidin-4-yl)-L-4-(4-(2,6-dimethoxyphenyl)phenylalanine,
N-(5-(N-methyl-N-hexylamino)pyrimidin-4-yl)-L-4-(2,6-dimethoxyphenyl)phenylalanine,
N-(5-(N-methyl-N-isopropylamino)pyrimidin-4-yl)-L-4-(2,6-dimethoxyphenyl)phenylalanine,
N-(5-(N-methyl-N-tert-butylamino)pyrimidin-4-yl)-L-4-(2,6-dimethoxyphenyl)phenylalanine,
N-(5-(N-ethyl-N-isopropylamino)pyrimidin-4-yl)-L-4-(2,6-dimethoxyphenyl)phenylalanine,
N-(5-(N-methyl-N-2-(4-pyridyl)ethyl-pyrimidin-4-yl)-L-4-(2,6-dimethoxyphenyl)phenylalanine,
N-(2-(N-methyl-N-cyclohexylamino)-5-ethylpyrimidin-4-yl)-L-4-(N,N-dimethylcarbamyloxy)phenylalanine,
N-(4-(N,N-di-n-hexylamino)-1,1-dioxo-1,2,5-thiadiazol-3-yl)-L-tyrosine,
N-(4-(N,N-di-n-hexylamino)-1,1-dioxo-1,2,5-thiadiazol-3-yl)-L-4-(N,N-dimethylcarbamyloxy)phenylalanine,
N-(4-(N,N-dimethylamino)-1-oxo-1,2,5-thiadiazol-3-yl)-L-4-(N,N-dimethylcarbamyloxy)phenylalanine tert-butyl ester,
N-[4-(2-(3-methylphenylaminocarbonylamino)eth-1-ylamino)-1,1-dioxo-1,2,5-thiadiazol-3-yl]-L-4-(N,N-dimethylcarbamyloxy)phenylalanine
N-(4-(N,N-di-n-hexylamino)-1,1-dioxo-1,2,5-thiadiazol-3-yl)-L-4-(4-methylpiperazin-1-ylcarbonyloxy)phenylalanine,
N-(5-(2,2,2-trifluoroethyl)pyrimidin-4-yl)-L-4-(2,6-dimethoxyphenyl)phenylalanine,
N-(2-(N-cyclohexyl-N-methyl)-5-(2-tolyl)pyrimidin-4-yl)-L-4-(2,6-dimethoxyphenyl)phenylalanine,
N-(5-(2-fluorophenyl)pyrimidin-4-yl)-L-4-(2,6-dimethoxyphenyl)phenylalanine,
N-(2-(N-methyl-N-propyl)-5-(2-tolyl)pyrimidin-4-yl)-L-4-(2,6-dimethoxyphenyl)phenylalanine,
N-(3-chloropyrazin-2-yl)-L-4-[1-(tert-butoxycarbonyl)piperidin-4-ylcarbonylamino]phenylalanine ethyl ester,
and pharmaceutically acceptable salts thereof.

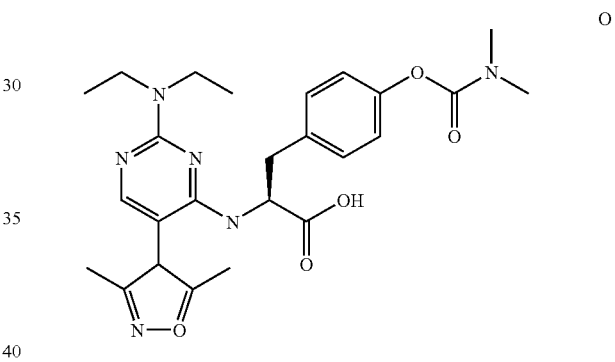

Further description of the compounds of the above Formulae III-IX procedures and reaction conditions for preparing these compounds are described in U.S. Ser. No. 09/489,377 (filed Jan. 21, 2000, and issued as U.S. Pat. No. 6,492,372), herein incorporated by reference in its entirety.

Further description of these type of compounds is described in U.S. Patent Publication 20030139402, a divisional application of U.S. Ser. No. 09/489,377, herein incorporated by reference in its entirety.

Compound Preparation for Compounds of Formulae III-IX

The compounds of Formulae III-IX can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of Formulae III-IX will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In a preferred method of synthesis, the compounds of Formulae III-IX are prepared by coupling an amino acid derivative of the formula:

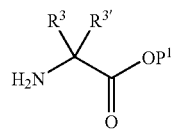

where $R^3$ and $R^{3'}$ are as defined herein and $P^1$ is a carboxylic acid protecting group (such as an alkyl group, i.e., methyl, ethyl and the like), with a suitably functionalized heteroaryl or heterocyclic intermediate. For example, such coupling reactions may be performed by displacing a leaving group, such as chloro, bromo, iodo, tosyl and the like, from the heteroaryl or heterocyclic intermediate with the amino group of the amino acid derivative; or by reductive alkylation of the amino group of amino acid derivative with a carbonyl-functionalized intermediate. Such coupling reactions are well-known to those skilled in the art.

By way of illustration, the synthesis of a representative compound of Formula III is shown in Scheme 1.

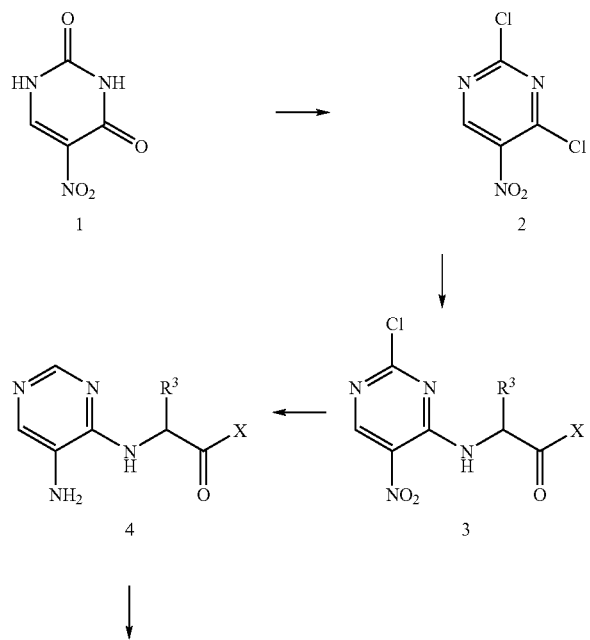

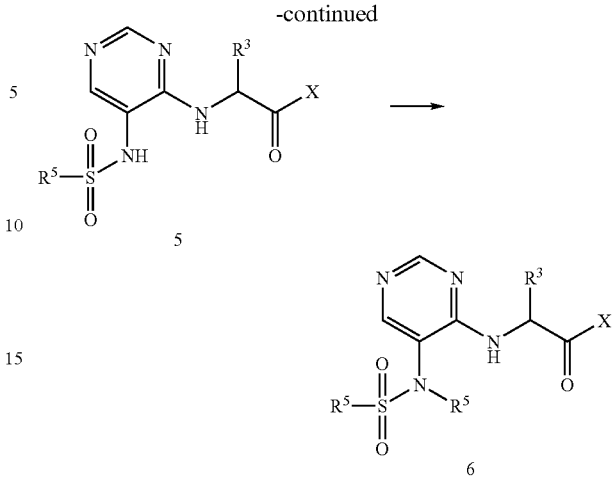

As shown in Scheme 1, 5-nitrouracil, 1, (commercially available from Aldrich Chemical Company, Milwaukee, Wis. USA) is treated with phosphorus oxychloride and N,N-dimethylaniline according to the procedure described in Whittaker, *J. Chem. Soc.* 1951, 1565 to give 1,3-dichloro-4-nitropyrimidine, 2.

1,3-Dichloro-4-nitropyrimidine, 2, is then reacted with about one molar equivalent of an amino acid derivative of the formula $H_2N$—$CH(R^3)C(O)X$ where $R^3$ and X are as defined herein or X is —$OP^1$ where $P^1$ is a carboxylic acid protecting group, in the presence of a trialkylamine, such as diisopropylethylamine (DIEA). Typically, this reaction is conducted in an inert diluent, such as dichloromethane, at a temperature ranging from about 0° C. to about 10° C. for about 5 min. to about 6 hours to afford intermediate 3.

The nitro group of intermediate 3 is then reduced using a conventional reducing agent, such as hydrogen and a palladium on carbon catalyst. When hydrogen and palladium on carbon are employed as the reducing agent, the chloro group of intermediate 3 is also removed. This reaction is typically conducted by contacting 3 with a Degussa-type palladium on carbon catalyst (typically 20%) and excess sodium bicarbonate in an inert diluent, such as methanol, under hydrogen (typically about 55 psi) for about 12 to 36 hours at ambient temperature to afford amino intermediate 4.

Amino intermediate 4 is then reacted with a sulfonyl chloride of the formula $R^5$—$S(O)_2$—Cl, where $R^5$ is as defined herein, to provide sulfonamide intermediate 5. This reaction is typically conducted by reacting the amino intermediate 4 with at least one equivalent, preferably about 1.1 to about 2 equivalents, of the sulfonyl chloride in an inert diluent such as dichloromethane and the like. Generally, the reaction is conducted at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like, as the base. Upon completion of the reaction, the resulting sulfonamide 5 is recovered by conventional methods including neutralization, extraction, precipitation, chromatography, filtration, and the like.

Other heteroaryl intermediates may also be employed in the above described reactions including, but not limited to, 2-chloro-3-nitropyrazine (*J. Med. Chem.* 1984, 27, 1634); 4-chloro-5-nitroimidazole (*J. Chem. Soc.* 1930, 268); and the like.

The amino acid derivatives employed in the above reactions are either known compounds or compounds that can be prepared from known compounds by conventional synthetic procedures. For example, amino acid derivatives can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 hours. The resulting C-alkylated malonate is then deacetylated, hydrolyzed and decarboxylated by heating in aqueous hydrochloric acid at reflux for about 6 to about 12 hours to provide the amino acid, typically as the hydrochloride salt.

Examples of amino acid derivatives suitable for use in the above reactions include, but are not limited to, L-alanine methyl ester, L-isoleucine methyl ester, L-leucine methyl ester, L-valine methyl ester, β-tert-butyl-L-aspartic acid methyl ester, L-asparagine tert-butyl ester, ε-Boc-L-lysine methyl ester, ε-Cbz-L-lysine methyl ester, γ-tert-butyl-L-glutamic acid methyl ester, L-glutamine tert-butyl ester, L-(N-methyl)histidine methyl-ester, L-(N-benzyl)histidine methyl ester, L-methionine methyl ester, L-(O-benzyl)serine methyl ester, L-tryptophan methyl ester, L-phenylalanine methyl ester, L-phenylalanine isopropyl ester, L-phenylalanine benzyl ester, L-phenylalaninamide, N-methyl-L-phenylalanine benzyl ester, 3-carboxy-D,L-phenylalanine methyl ester, 4-carboxy-D,L-phenylalanine methyl ester, L-4-chlorophenylalanine methyl ester, L-4-(3-dimethylaminopropyloxy)-phenylalanine methyl ester, L-4-iodophenylalanine methyl ester, L-3,4-methylenedioxyphenylalanine methyl ester, L-3,4-ethylenedioxyphenylalanine methyl ester, L-4-nitrophenylalanine methyl ester, L-tyrosine methyl ester, D,L-homophenylalanine methyl ester, L-(O-methyl)tyrosine methyl ester, L-(O-tert-butyl)tyrosine methyl ester, L-(O-benzyl)tyrosine methyl ester, L-3,5-diiodotyrosine methyl ester, L-3-iodotyrosine methyl ester, β-(1-naphthyl)-L-alanine methyl ester, β-(2-naphthyl)-L-alanine methyl ester, β-(2-thienyl)-L-alanine methyl ester, β-cyclohexyl-L-alanine methyl ester, β-(2-pyridyl)-L-alanine methyl ester, β-(3-pyridyl)-L-alanine methyl ester, β-(4-pyridyl)-L-alanine methyl ester, β-(2-thiazolyl)-D,L-alanine methyl ester, β-(1,2,4-triazol-3-yl)-D,L-alanine methyl ester, and the like. If desired, of course, other esters or amides of the above-described compounds may also be employed.

Additionally, α-hydroxy and α-thio carboxylic acids may also be employed in the above-described reactions. Such compounds are well-known in the art and are either commercially available or may be prepared from commercially available starting materials using conventional reagents and reaction conditions.

The sulfonyl chlorides employed in the above reaction are also either known compounds or compounds that can be prepared from known compounds by conventional synthetic procedures. Such compounds are typically prepared from the corresponding sulfonic acid, i.e., from compounds of the formula $R^5$—$SO_3H$ where $R^5$ is as defined above, using phosphorous trichloride and phosphorous pentachloride. This reaction is generally conducted-by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the sulfonyl chloride can be prepared from the corresponding thiol compound, i.e., from compounds of the formula $R^5$—SH where $R^5$ is as defined herein, by treating the thiol with chlorine ($Cl_2$) and water under conventional reaction conditions.

Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the sulfonamide intermediate 5.

If desired, sulfonamide intermediate 5 can be alkylated at the sulfonamide nitrogen atom to provide compound 6. For example, 5 can be contacted with excess diazomethane (generated, for example, using 1-methyl-3-nitro-1-nitrosoguanidine and sodium hydroxide) to afford 6 where $R^6$ is methyl. Other conventional alkylation procedures and reagents may also be employed to prepare various compounds of this invention.

In another preferred embodiment, compounds of Formulae III-IX may be prepared by displacement of a leaving group as shown in Scheme 2:

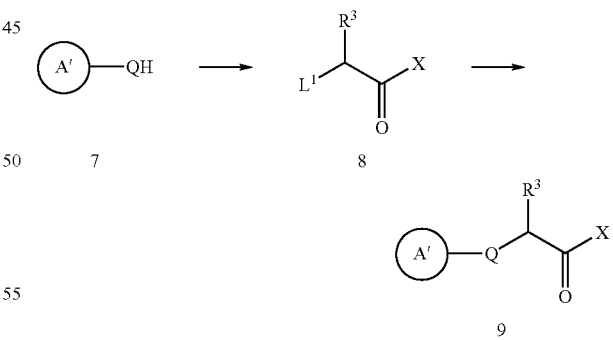

where $R^3$, (and X are as defined herein; A' is heteroaryl, substituted heteroaryl, heterocyclic or substituted heterocyclic containing two nitrogen atoms in the heteroaryl or heterocyclic ring; and $L^1$ is a leaving group, such as chloro, bromo, iodo, sulfonate ester and the like.

Typically, this reaction is conducted by combining approximately stoichiometric equivalents of 7 and 8 in a suitable inert diluent such as water, dimethylsulfoxide (DMSO) and the like, with an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. This reaction is further described in U.S. Pat. No. 3,598,859, which is incorporated herein by reference in its entirety. Upon reaction completion, the product 9 is recovered by conventional methods including precipitation, chromatography, filtration and the like.

In still another alternative embodiment, compounds of Formulae III-IX in which Q is NR$^4$ can be prepared by reductive amination of a suitable 2-oxocarboxylic acid ester, 10, such as a pyruvate ester, as shown in Scheme 3:

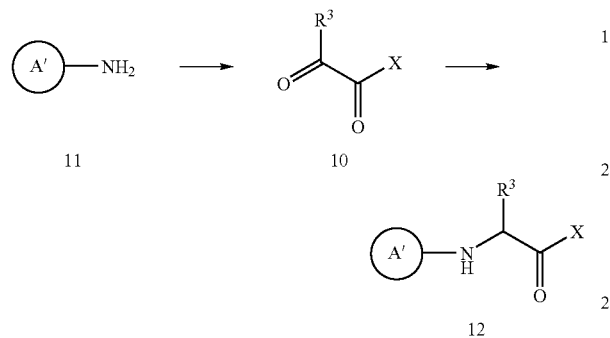

where A', R$^3$ and X are as defined herein.

Generally, this reaction is conducted by combining equamolar amounts of 10 and 11 in an inert diluent such as methanol, ethanol and the like under conditions which provide for imine formation (not shown). The imine formed is then reduced under conventional conditions by a suitable reducing agent such as sodium cyanoborohydride, H$_2$/palladium on carbon and the like to form the product 12. In a particularly preferred embodiment, the reducing agent is H$_2$/palladium on carbon which is incorporated into the initial reaction medium thereby permitting imine reduction in situ in a one pot procedure to provide 12. The reaction is preferably conducted at from about 20° C. to about 80° C. at a pressure of from 1 to 40 atmospheres until reaction completion which typically occurs within 1 to about 24 hours. Upon reaction completion, the product 12 is recovered by conventional methods including chromatography, filtration and the like.

Alternatively, certain compounds of Formulae III-IX can be prepared via a rhodium-catalyzed insertion reaction as shown in Scheme 4:

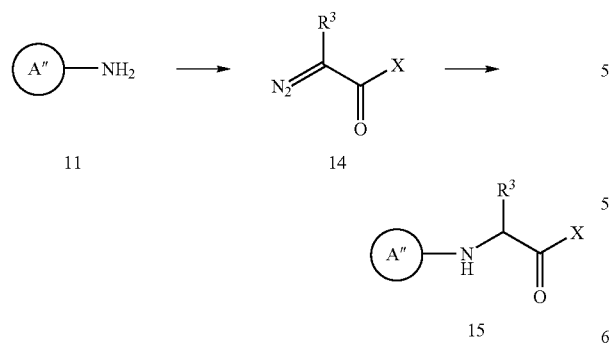

where A" is heteroaryl or substituted heteroaryl containing two nitrogen atoms in the heteroaryl ring, and R$^3$ and X (preferably alkoxy) are as defined herein. Typically, this reaction is conducted using rhodium acetate dimer, Rh$_2$(OAc)$_4$, in an inert diluent such as toluene at a temperature ranging from about 25° C. to about 80° C. for about 1 to 12 hours to afford 15. This reaction is described further in B. R. Henke et. al., *J. Med. Chem.* 1998, 41, 5020-5036 and references cited therein.

Similarly, certain compounds of Formulae III-IX can be prepared by the copper-catalyzed coupling reaction shown in Scheme 5:

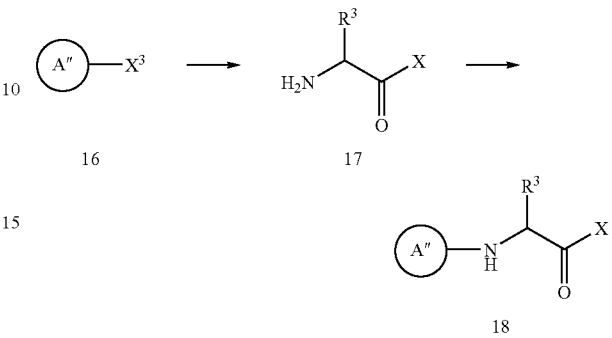

where A" is as defined herein, X$^3$ is halogen, such as chloro, bromo or iodo (preferably iodo), and R$^3$ and X (preferably alkoxy) are as defined herein. Typically, this reaction is conducted using copper iodide (CuI) and potassium carbonate in an inert diluent such as N,N-dimethyl acetamide (DMA) at a temperature ranging from about 60° C. to about 120° C. for about 12 to 36 hours to afford 15. This reaction is described further in D. Ma et. al., *J. Am. Chem. Soc.* 1998, 120, 12459-12467 and references cited therein.

For ease of synthesis, the compounds of Formulae III-IX are typically prepared as an ester, i.e., where X is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 12 hours. Alternatively, benzyl esters may be removed by hydrogenolysis using a palladium catalyst, such as palladium on carbon, and tert-butyl esters can be removed using formic acid to afford the corresponding carboxylic acid.

As will be apparent to those skilled in the art, other functional groups present on any of the substituents of the compounds of Formulae III-IX can be readily modified or derivatized either before or after the above-described synthetic reactions using well-known synthetic procedures. For example, a nitro group present on a substituent of a compound of Formulae III-IX or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on the R$^3$ and/or R$^{3'}$ substituent can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid.

Additionally, when the $R^3$ and/or $R^{3'}$ substituent of a compound of Formulae III-IX or an intermediate thereof contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on the $R^3$ and/or $R^{3'}$ substituent may be prepared, for example, by reduction of the corresponding nitro compound as described above.

By way of illustration, a compound of Formulae III-IX or an intermediate thereof having a substituent containing a primary or secondary amino group, such as where $R^3$ is a (4-aminophenyl)methyl group, can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris (dimethylamino)phosphonium hexafluorophosphonate) and the like, in an inert diluent, such as dichloromethane, chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxy-benzotriazole and the like, is used to facilitate the acylation reaction. Examples of carboxylic acids suitable for use in this reaction include, but are not limited to, N-tert-butyloxycarbonylglycine, N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of Formulae III-IX or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about −70° C. to about 40° C. for about 1 to about 24 hours. If desired, an acylation catalyst such as 4-(N,N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoro-methylbenzoyl chloride, isonicotinoyl chloride, nicotinoyl chloride, picolinoyl chloride, acetic anhydride, succinic anhydride, and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of Formulae III-IX or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride, and the like. Similarly, sulfamoyl chlorides, such as dimethylsulfamoyl chloride, can be used to provide sulfamides (e.g., >N—SO$_2$—N<).

Additionally, a primary and secondary amino group present on a substituent of a compound of Formulae III-IX or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate, fluorescein isothiocyanate (isomer I) and the like.

Furthermore, when a compound of Formulae III-IX or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of Formulae III-IX or an intermediate thereof has a substituent containing a hydroxyl group, the hydroxyl group can be further modified or derivatized either before or after the above coupling reactions to provide, by way of example, ethers, carbamates and the like. Compounds having a hydroxyl group on the $R^3$ substituent, for example, can be prepared using an amino acid derivative derived from tyrosine and the like in the above-described reactions.

By way of example, a compound of Formulae III-IX or an intermediate thereof having a substituent containing a hydroxyl group, such as where $R^3$ is a (4-hydroxyphenyl) methyl group, can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino)ethyl chloride, 3-(N,N-ethylamino)propyl chloride, 3-(N-benzyl-N-methylamino) propyl chloride, N-(2-chloroethyl)morpholine, 2-(hexamethyleneimino)ethyl chloride, 3-(N-methylpiperazine)propyl chloride, 1-(3-chlorophenyl)-4-(3-chloropropyl) piperazine, 2-(4-hydroxy-4-phenylpiperidine)ethyl chloride, N-tert-butyloxycarbonyl-3-piperidinemethyl tosylate, and the like.

Alternatively, a hydroxyl group present on a substituent of a compound of Formulae III-IX or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of Formulae III-IX or an intermediate thereof containing an aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of Formulae III-IX or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of Formulae III-IX or an intermediate thereof contains a primary or secondary hydroxyl group, such hydroxyl groups can be readily converted into a leaving group and displaced to form, for example, amines, sulfides and fluorides. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino (—NH$_2$) compound.

Similarly, a tosylate group can be readily displaced by a thiol to form a sulfide. This reaction is typically conducted by contacting the tosylate with at least one equivalent of a thiol, such as thiophenol; in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of Formulae III-IX or an intermediate thereof having a substituent containing an iodoaryl group, for example, when $R^3$ is a (4-iodophenyl)methyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra(triphenylphosphine), in an inert diluent, such as tetrahydrofuran, at a temperature ranging from about 24° C. to about 30° C. until reaction completion. This reaction is further described, for example, in Rieke, *J. Org. Chem.* 1991, 56, 1445. Additional methods for preparing biaryl derivatives are disclosed in International Publication Number WO 98/53817, published Dec. 3, 1998, the disclosure of which is incorporated herein by reference in its entirety.

In some cases, the compounds of Formulae III-IX or intermediates thereof may contain substituents having one or more sulfur atoms. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, "Advanced Organic Chemistry," 4th Ed.; pp. 1201-1202, Wiley Publisher, 1992.

Other procedures and reaction conditions for preparing the compounds of this invention are described in the examples set forth below. Additionally, other procedures for preparing compounds useful in certain aspects of this invention are disclosed in U.S. Ser. No. 09/489,378, filed on Jan. 21, 2000, entitled "Compounds Which Inhibit Leucocyte Adhesion Mediated by VLA-4," now issued as U.S. Pat. No. 6,479,492, the disclosure of which is incorporated herein by reference in its entirety.

Compounds of Formulae X-XV

In one aspect, the compounds that can be utilized as combination therapies with methotrexate for the treatment of RA are compounds of Formulae X, XI, XII, XIII, XIV, and XV.

In one aspect, the compounds that can be utilized as combination therapies with methotrexate for the treatment of RA are compounds defined by Formula X below. These compounds have a binding affinity to VLA-4 as expressed by an $IC_{50}$ of about 15 μM or less (measured as described in Example A below):

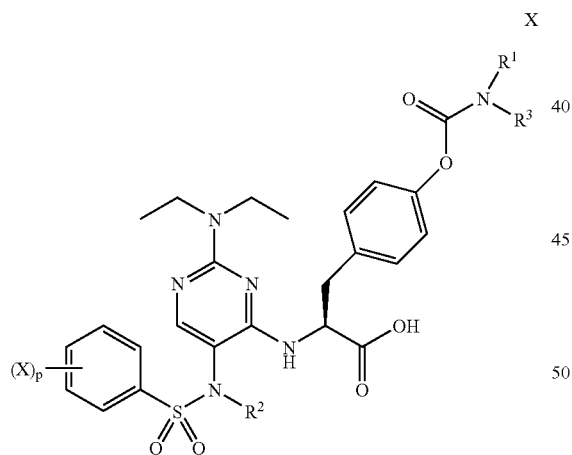

X wherein each X is independently fluoro, chloro or bromo;
p is an integer from 0 to 3;
$R^1$ and $R^3$ together with the nitrogen atom to which they are bound form an azetidinyl, pyrrolidinyl, pyrrolyl, 2,5-dihydopyrrol-1-yl, piperidinyl, or 1,2,3,6-tetrahydropyridin-1-yl;
$R^2$ is selected from the group consisting of lower alkyl, lower alkenyl, and lower alkylenecycloalkyl;
and pharmaceutically acceptable salts thereof.

In a preferred embodiment, $R^1$ and $R^3$ together with the nitrogen atom to which they are bound form an azetidinyl, pyrrolidinyl, or piperidinyl group.

In one aspect, the compounds that can be utilized as combination therapies with methotrexate for the treatment of RA are compounds defined by Formula XI below. These compounds have a binding affinity to VLA-4 as expressed by an $IC_{50}$ of about 15 μM or less (measured as described in Example A below):

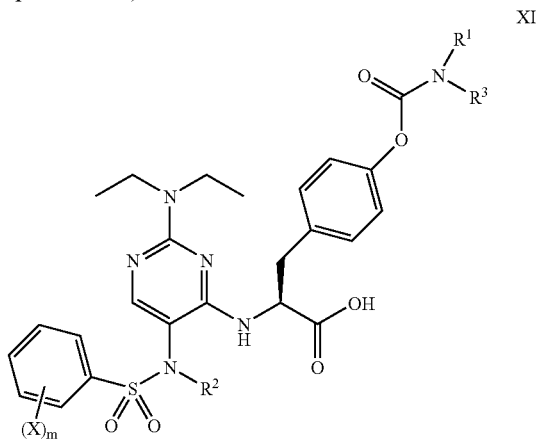

XI wherein each X is independently selected from the group consisting of fluoro and chloro;
m is an integer equal to 1 or 2;
$R^2$ is selected from the group consisting of lower alkyl, lower alkenyl, and lower alkylenecycloalkyl;
$R^1$ and $R^3$ together with the nitrogen atom to which they are bound form an azetidinyl, pyrrolidinyl, or piperidinyl group;
and pharmaceutically acceptable salts thereof.

In one aspect, the compounds that can be utilized as combination therapies with methotrexate for the treatment of RA are compounds defined by Formula XII below. These compounds have a binding affinity to VLA-4 as expressed by an $IC_{50}$ of about 15 μM or less (measured as described in Example A below):

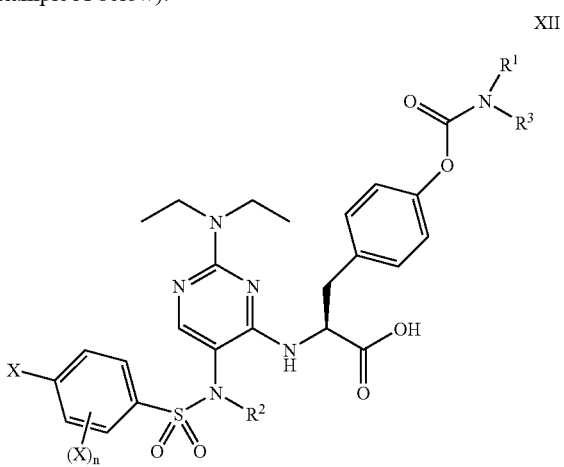

XII wherein each X is independently fluoro or chloro;
n is zero or one;
$R^2$ is —$CH_2$—R' where R' is selected from the group consisting of hydrogen, methyl or —CH=$CH_2$;
$R^1$ and $R^3$ together with the nitrogen atom to which they are bound form an azetidinyl, pyrrolidinyl, or piperidinyl group;
and pharmaceutically acceptable salts thereof.

In one aspect, the compounds that can be utilized as combination therapies with methotrexate for the treatment of RA are compounds defined by Formula XIII below. These compounds have a binding affinity to VLA-4 as expressed by an $IC_{50}$ of about 15 μM or less (measured as described in Example A below):

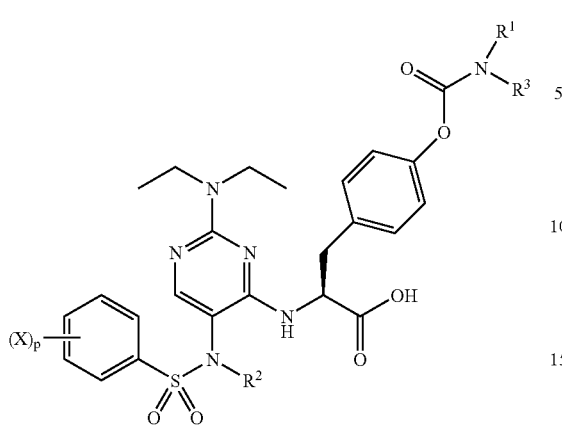

XIII wherein each X is independently fluoro, chloro or bromo;
p is an integer from 0 to 3;
$R^1$ and $R^3$ together with the nitrogen atom to which they are bound form an azetidinyl, pyrrolidinyl, pyrrolyl, 2,5-dihydopyrrol-1-yl, piperidinyl, or 1,2,3,6-tetrahydropyridin-1-yl;
$R^2$ is lower alkynyl;
and pharmaceutically acceptable salts thereof.

In a preferred embodiment, $R^1$ and $R^3$ together with the nitrogen atom to which they are bound form an azetidinyl, pyrrolidinyl, or piperidinyl group and $R^2$ is propargyl.

In one aspect, the compounds that can be utilized as combination therapies with methotrexate for the treatment of RA are compounds defined by Formula XIV below. These compounds have a binding affinity to VLA-4 as expressed by an $IC_{50}$ of about 15 μM or less (measured as described in Example A below):

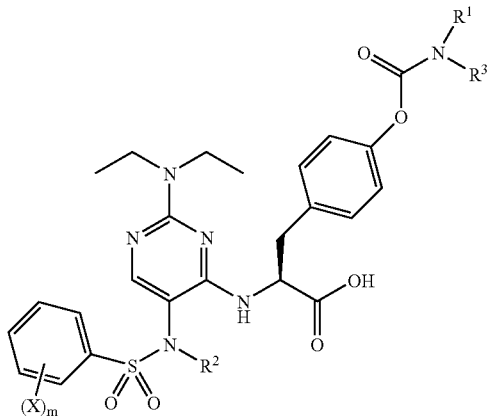

XIV wherein each X is independently selected from the group consisting of fluoro and chloro;
m is an integer equal to 1 or 2;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

In one aspect, the compounds that can be utilized as combination therapies with methotrexate for the treatment of RA are compounds defined by Formula XV below. These compounds have a binding affinity to VLA-4 as expressed by an $IC_{50}$ of about 15 μM or less (measured as described in Example A below):

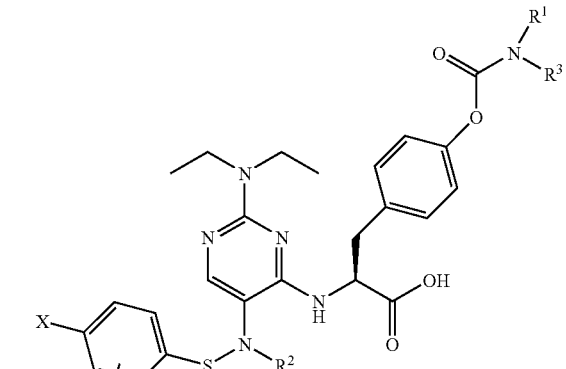

XV wherein each X is independently fluoro or chloro;
n is zero or one;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

N-[2-N',N'-diethylamino-5-aminosulfonylphenylpyrimidin-4-yl]-p-carbomyloxy-phenylalanine compounds within the scope of this invention include those set forth in Table 7 as follows:

TABLE 7

| $R^1$ and $R^3$ | $R^2$ | (X) | Example No. |
|---|---|---|---|
| pyrrolidinyl | ethyl | 4-chlorophenyl | 505 |
| pyrrolidinyl | ethyl | 4-fluorophenyl | 506 |
| pyrrolidinyl | methyl | 4-fluorophenyl | 507 |
| pyrrolidinyl | methyl | 4-chlorophenyl | 508 |
| piperidinyl | methyl | 4-fluorophenyl | 509 |
| piperidinyl | ethyl | 4-fluorophenyl | 510 |
| azetidinyl | ethyl | 4-fluorophenyl | 511 |
| azetidinyl | methyl | 4-fluorophenyl | 512 |
| azetidinyl | methyl | 4-chlorophenyl | 513 |
| azetidinyl | ethyl | 4-chlorophenyl | 514 |
| pyrrolidinyl | methyl | 2,4-difluorophenyl | 515 |
| pyrrolidinyl | ethyl | 2,4-difluorophenyl | 516 |
| azetidinyl | methyl | 2,4-difluorophenyl | 517 |
| azetidinyl | ethyl | 2,4-difluorophenyl | 518 |
| pyrrolidinyl | propargyl | 4-fluorophenyl | 519 |
| pyrrolidinyl | propargyl | 2,4-difluorophenyl | 520 |
| azetidinyl | propargyl | 2,4-difluorophenyl | 521 |
| azetidinyl | propargyl | 4-fluorophenyl | 522 |
| pyrrolidinyl | propargyl | 4-chlorophenyl | 523 |

Specific compounds within the scope of this invention include the following compounds. As used below, these compounds are named based on phenylalanine derivatives but, alternatively, these compounds could have been named based on N-[2-N',N'-diethylamino-5-aminosulfonylphenyl-pyrimidin-4-yl]-p-carbomyloxyphenylalanine derivatives or 2-{2-diethylamino-5-[(benzenesulfonyl)methylamino]-pyrimidin-4-ylamino}-p-carbamoyloxy-phenyl)propionic acid derivatives.

N-(2-[N',N'-diethylamino]-5-[N''-(4-chlorophenylsulfonyl)-N''-ethylamino]pyrimidin-4-yl)-4'-(pyrrolidin-1-ylcarbonyloxy)-L-phenylalanine;

N-(2-[N',N'-diethylamino]-5-[N''-(4-fluorophenylsulfonyl)-N''-ethylamino]pyrimidin-4-yl)-4'-(pyrrolidin-1-ylcarbonyloxy)-L-phenylalanine;

N-(2-[N',N'-diethylamino]-5-[N''-(4-fluorophenylsulfonyl)-N''-methylamino]pyrimidin-4-yl)-4'-(pyrrolidin-1-ylcarbonyloxy)-L-phenylalanine;

N-(2-[N',N'-diethylamino]-5-[N''-(4-chlorophenylsulfonyl)-N''-methylamino]pyrimidin-4-yl)-4'-(pyrrolidin-1-ylcarbonyloxy)-L-phenylalanine;

N-(2-[N',N'-diethylamino]-5-[N''-(4-fluorophenylsulfonyl)-N''-methylamino]pyrimidin-4-yl)-4'-(piperidin-1-ylcarbonyloxy)-L-phenylalanine;

N-(2-[N',N'-diethylamino]-5-[N''-(4-fluorophenylsulfonyl)-N''-ethylamino]pyrimidin-4-yl)-4'-(piperidin-1-ylcarbonyloxy)-L-phenylalanine;

N-(2-[N',N'-diethylamino]-5-[N''-(4-fluorophenylsulfonyl)-N''-ethylamino]pyrimidin-4-yl)-4'-(azetidin-1-ylcarbonyloxy)-L-phenylalanine;

N-(2-[N',N'-diethylamino]-5-[N''-(4-fluorophenylsulfonyl)-N''-methylamino]pyrimidin-4-yl)-4'-(azetidin-1-ylcarbonyloxy)-L-phenylalanine;

N-(2-[N',N'-diethylamino]-5-[N''-(4-chlorophenylsulfonyl)-N''-methylamino]pyrimidin-4-yl)-4'-(azetidin-1-ylcarbonyloxy)-L-phenylalanine;

N-(2-[N',N'-diethylamino]-5-[N''-(4-chlorophenylsulfonyl)-N''-ethylamino]pyrimidin-4-yl)-4'-(azetidin-1-ylcarbonyloxy)-L-phenylalanine;

N-(2-[N',N'-diethylamino]-5-[N''-(2,4-difluorophenylsulfonyl)-N''-methylamino]pyrimidin-4-yl)-4'-(pyrrolidin-1-ylcarbonyloxy)-L-phenylalanine;

N-(2-[N',N'-diethylamino]-5-[N''-(2,4-difluorophenylsulfonyl)-N''-ethylamino]pyrimidin-4-yl)-4'-(pyrrolidin-1-ylcarbonyloxy)-L-phenylalanine;

N-(2-[N',N'-diethylamino]-5-[N''-(2,4-difluorophenylsulfonyl)-N''-methylamino]pyrimidin-4-yl)-4'-(azetidin-1-ylcarbonyloxy)-L-phenylalanine;

N-(2-[N',N'-diethylamino]-5-[N''-(2,4-difluorophenylsulfonyl)-N''-ethylamino]pyrimidin-4-yl)-4'-(azetidin-1-ylcarbonyloxy)-L-phenylalanine;

N-(2-[N',N'-diethylamino]-5-[N''-(4-fluorophenylsulfonyl)-N''-propargylamino]pyrimidin-4-yl)-4'-(pyrrolidin-1-ylcarbonyloxy)-L-phenylalanine;

N-(2-[N',N'-diethylamino]-5-[N''-(2,4-difluorophenylsulfonyl)-N''-propargylamino]pyrimidin-4-yl)-4'-(pyrrolidin-1-ylcarbonyloxy)-L-phenylalanine;

N-(2-[N',N'-diethylamino]-5-[N''-(2,4-difluorophenylsulfonyl)-N''-propargylamino]pyrimidin-4-yl)-4'-(azetidin-1-ylcarbonyloxy)-L-phenylalanine;

N-(2-[N',N'-diethylamino]-5-[N''-(4-fluorophenylsulfonyl)-N''-propargylamino]pyrimidin-4-yl)-4'-(azetidin-1-ylcarbonyloxy)-L-phenylalanine;

N-(2-[N',N'-diethylamino]-5-[N''-(4-chlorophenylsulfonyl)-N''-propargylamino]pyrimidin-4-yl)-4'-(pyrrolidin-1-ylcarbonyloxy)-L-phenylalanine; and pharmaceutically acceptable salts thereof.

Preferably, the compound is the compound of Formula P below:

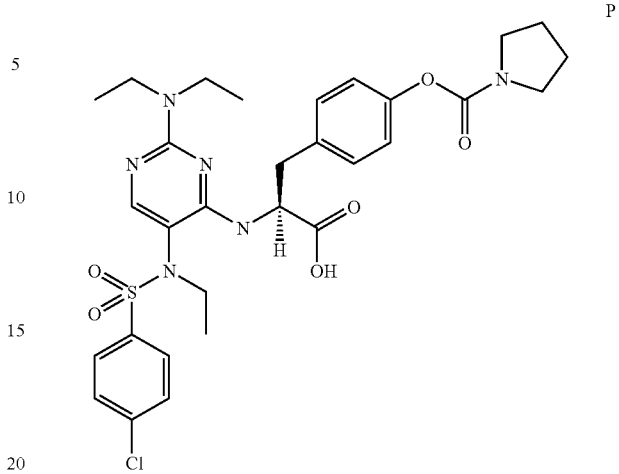

P

In another embodiment, preferably the compound is the compound of Formula Q below:

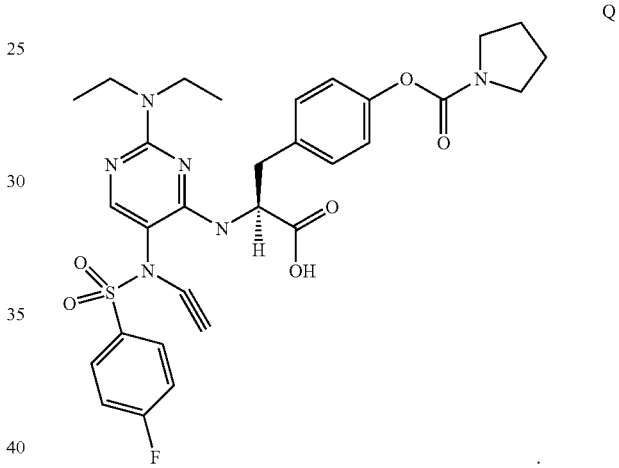

Q

Compound Preparation of Compounds of Formulae X-XV

The compounds of Formulae X-XV can be prepared from readily available starting materials using the methods and procedures set forth in the examples below. These methods and procedures outline specific reaction protocols for preparing N-[2-N',N'-diethylamino-5-aminosulfonylphenyl-yrimidin-4-yl]-p-carbomyloxy-phenylalanine compounds. Compounds within the scope not exemplified in these examples and methods are readily prepared by appropriate substitution of starting materials which are either commercially available or well known in the art.

Other procedures and reaction conditions for preparing the compounds of this invention are described in the examples set forth below. Additionally, other procedures for preparing compounds useful in certain aspects of this invention are disclosed in U.S. Pat. No. 6,492,372, issued Dec. 10, 2002; the disclosure of which is incorporated herein by reference in its entirety.

Compounds of Formulae XVI-XXI

In one aspect, the compounds that can be utilized as combination therapies with methotrexate for the treatment of RA are compounds of Formulae XVI, XVII, XVIII, XIX, XX, and XXI.

In one aspect, the compounds that can be utilized as combination therapies with methotrexate for the treatment of RA are compounds defined by Formula XVI below. These compounds have a binding affinity to VLA-4 as expressed by an IC$_{50}$ of about 15 μM or less (measured as described in Example A below):

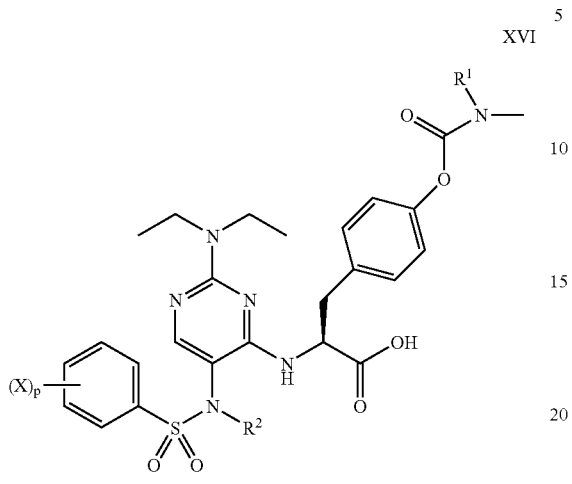

XVI wherein each X is independently fluoro, chloro or bromo;
p is 0 or an integer from 1-3;
R$^1$ is selected from the group consisting of methyl and ethyl;
R$^2$ is selected from the group consisting of lower alkyl, lower alkenyl, and lower alkylenecycloalkyl;
and pharmaceutically acceptable salts thereof.

In one aspect, the compounds that can be utilized as combination therapies with methotrexate for the treatment of RA are compounds defined by Formula XVII below. These compounds have a binding affinity to VLA-4 as expressed by an IC$_{50}$ of about 15 μM or less (measured as described in Example A below):

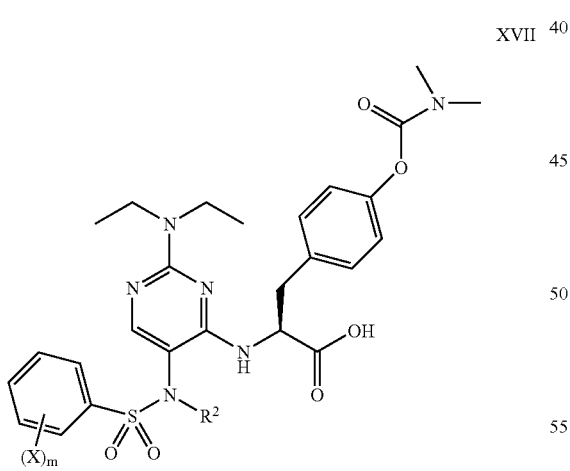

XVII wherein each X is independently selected from the group consisting of fluoro and chloro,
m is an integer equal to 1 or 2;
R$^2$ is selected from the group consisting of lower alkyl, lower alkenyl, and lower alkylenecycloalkyl;
and pharmaceutically acceptable salts thereof.

In one aspect, the compounds that can be utilized as combination therapies with methotrexate for the treatment of RA are compounds defined by Formula XVIII below. These compounds have a binding affinity to VLA-4 as expressed by an IC$_{50}$ of about 15 μM or less (measured as described in Example A below):

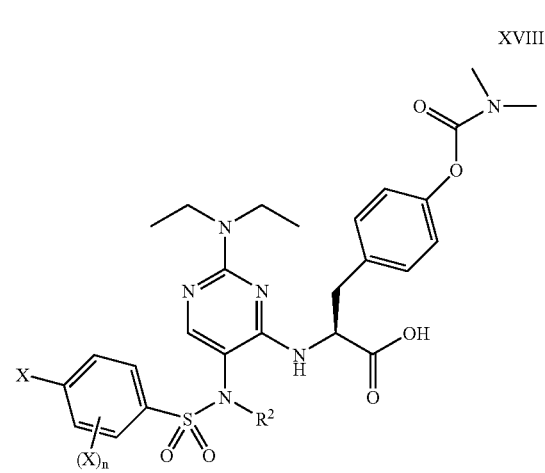

XVIII wherein each X is independently fluoro or chloro;
n is zero or one;
R$^2$ is —CH$_2$—R' where R' is selected from the group consisting of hydrogen, methyl or —CH=CH$_2$;
and pharmaceutically acceptable salts thereof.

In one aspect, the compounds that can be utilized as combination therapies with methotrexate for the treatment of RA are compounds defined by Formula XIX below. These compounds have a binding affinity to VLA-4 as expressed by an IC$_{50}$ of about 15 μM or less (measured as described in Example A below):

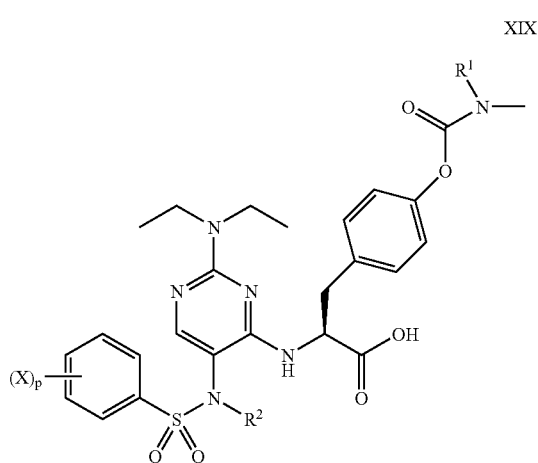

XIX wherein each X is independently fluoro, chloro or bromo;
p is 0 or an integer from 1-3;
R$^1$ is selected from the group consisting of methyl and ethyl;
R$^2$ is lower alkynyl;
and pharmaceutically acceptable salts thereof.

In one aspect, the compounds that can be utilized as combination therapies with methotrexate for the treatment of RA are compounds defined by Formula XX below. These compounds have a binding affinity to VLA-4 as expressed by an IC$_{50}$ of about 15 µM or less (measured as described in Example A below):

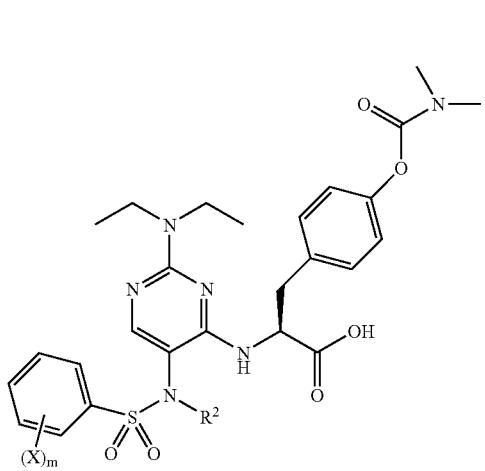

wherein each X is independently selected from the group consisting of fluoro and chloro, m is an integer equal to 1 or 2;

R$^2$ is lower alkynyl;

and pharmaceutically acceptable salts thereof.

In one aspect, the compounds that can be utilized as combination therapies with methotrexate for the treatment of RA are compounds defined by Formula XXI below. These compounds have a binding affinity to VLA-4 as expressed by an IC$_{50}$ of about 15 µM or less (measured as described in Example A below):

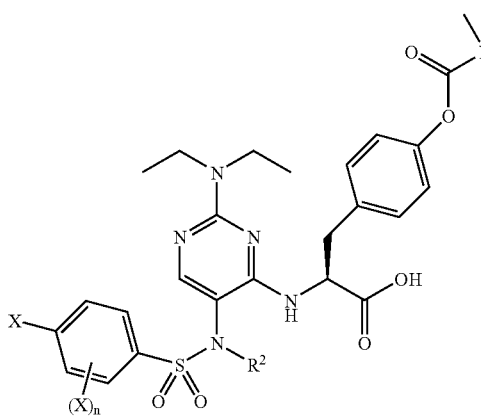

wherein each X is independently fluoro or chloro;

n is zero or one;

R$^2$ is lower alkynyl;

and pharmaceutically acceptable salts thereof.

R$^2$ is preferably propargyl in any of one of Formula XIX, XX or XXI.

N-[2-N', N'-diethylamino-5-aminosulfonylphenylpyrimidin-4-yl]-p-carbomyloxyphenylalanine compounds within the scope of this invention include those set forth in Table 8 as follows:

TABLE 8

| Example No. | | R$^2$ |
|---|---|---|
| 524 | 4-fluorophenyl | methyl |
| 525 | 4-chlorophenyl | methyl |
| 526 | 3,4-difluorophenyl | methyl |
| 527 | 3,4-dichlorophenyl | methyl |
| 528 | phenyl | methyl |
| 529 | 2-fluorophenyl | methyl |
| 530 | 3-fluorophenyl | methyl |
| 531 | 4-fluorophenyl | isopropyl |
| 532 | 4-fluorophenyl | ethyl |
| 533 | 3,4-difluorophenyl | isopropyl |
| 534 | 4-chlorophenyl | isopropyl |
| 535 | 3,4-difluorophenyl | ethyl |
| 536 | 4-chlorophenyl | ethyl |
| 537 | 4-fluorophenyl | cyclopropylmethyl |
| 538 | 3,5-difluorophenyl | methyl |
| 539 | 3,5-difluorophenyl | ethyl |
| 540 | 2,4-difluorophenyl | methyl |
| 541 | 2,4-difluorophenyl | ethyl |
| 542 | 3,5-dichlorophenyl | methyl |
| 543 | 3,5-dichlorophenyl | ethyl |
| 544 | 4-fluorophenyl | n-propyl |
| 545 | 4-fluorophenyl | allyl |
| 546 | 4-fluorophenyl | isobutyl |
| 547 | 4-fluorophenyl | n-butyl |
| 548 | 2,6-difluorophenyl | Methyl |
| 549 | 2,3-difluorophenyl | methyl |
| 550 | 4-fluorophenyl | propargyl |
| 551 | 2,4-difluorophenyl | propargyl |
| 552 | 4-fluorophenyl | 2-trisfluoroethyl |

Specific compounds within the scope of this invention include the following. As used below, these compounds are named based on propionic acid derivatives but, alternatively, these compounds could have been named based on N-[2-N', N'-diethylamino-5-aminosulfonylphenyl pyrimidin-4-yl]-p-carbomyloxy-phenylalanine derivatives.

2-{2-diethylamino-5-[(4-chlorobenzenesulfonyl)methylamino]-pyrimidin-4-ylamino}-3-(4-dimethylcarbamoyloxyphenyl)propionic acid;

2-{2-diethylamino-5-[(4-fluorobenzenesulfonyl)methylamino]-pyrimidin-4-ylamino}-3-(4-dimethylcarbamoyloxyphenyl)propionic acid;

2-{2-diethylamino-5-[(3,4-difluorobenzenesulfonyl)methylamino]-pyrimidin-4-ylamino}-3-(4-dimethylcarbamoyloxyphenyl)propionic acid;

2-{2-diethylamino-5-[(3,4-dichlorobenzenesulfonyl)methylamino]-pyrimidin-4-ylamino}-3-(4-dimethylcarbamoyloxyphenyl)propionic acid;
2-{2-diethylamino-5-[(benzenesulfonyl)methylamino]-pyrimidin-4-ylamino}-3-(4-dimethylcarbamoyloxyphenyl) propionic acid;
2-{2-diethylamino-5-[(2-fluorobenzenesulfonyl)methylamino]-pyrimidin-4-ylamino}-3-(4-dimethylcarbamoyloxyphenyl)propionic acid;
2-{2-diethylamino-5-[(3-fluorobenzenesulfonyl)methylamino]-pyrimidin-4-ylamino}-3-(4-dimethylcarbamoyloxyphenyl)propionic acid;
2-{2-diethylamino-5-[(4-fluorobenzenesulfonyl)isopropylamino]-pyrimidin-4-ylamino}-3-(4-dimethylcarbamoyloxyphenyl)propionic acid;
2-{2-diethylamino-5-[(4-fluorobenzenesulfonyl)ethylamino]-pyrimidin-4-ylamino}-3-(4-dimethylcarbamoyloxyphenyl)propionic acid;
2-{2-diethylamino-5-[(3,4-difluorobenzenesulfonyl)isopropylamino]-pyrimidin-4-ylamino}-3-(4-dimethylcarbamoyloxyphenyl)propionic acid;
2-{2-diethylamino-5-[(4-chlorobenzenesulfonyl)isopropylamino]-pyrimidin-4-ylamino}-3-(4-dimethylcarbamoyloxyphenyl)propionic acid;
2-{2-diethylamino-5-[(3,4-difluorobenzenesulfonyl)ethylamino]-pyrimidin-4-ylamino}-3-(4-dimethylcarbamoyloxyphenyl)propionic acid;
2-{2-diethylamino-5-[(4-chlorobenzenesulfonyl)ethylamino]-pyrimidin-4-ylamino}-3-(4-dimethylcarbamoyloxyphenyl)propionic acid;
2-{2-diethylamino-5-[(4-fluorobenzenesulfonyl)cylclopropylmethyl-amino]pyrimidin-4-ylamino}-3-(4-dimethylcarbamoyloxyphenyl)propionic acid;
2-{2-diethylamino-5-[(3,5-difluorobenzenesulfonyl)methylamino]-pyrimidin-4-ylamino}-3-(4-dimethylcarbamoyloxyphenyl)propionic acid;
2-{2-diethylamino-5-[(3,5-difluorobenzenesulfonyl)ethylamino]-pyrimidin-4-ylamino}-3-(4-dimethylcarbamoyloxyphenyl)propionic acid;
2-{2-diethylamino-5-[(2,4-difluorobenzenesulfonyl)methylamino]-pyrimidin-4-ylamino}-3-(4-dimethylcarbamoyloxyphenyl)propionic acid;
2-{2-diethylamino-5-[(2,4-difluorobenzenesulfonyl)ethylamino]-pyrimidin-4-ylamino}-3-(4-dimethylcarbamoyloxyphenyl)propionic acid;
2-{2-diethylamino-5-[(3,5-dichlorobenzenesulfonyl)methylamino]-pyrimidin-4-ylamino}-3-(4-dimethylcarbamoyloxyphenyl)propionic acid;
2-{2-diethylamino-5-[(3,5-dichlorobenzenesulfonyl)ethylamino]-pyrimidin-4-ylamino}-3-(4-dimethylcarbamoyloxyphenyl)propionic acid;
2-{2-diethylamino-5-[(4-fluorobenzenesulfonyl)-n-propylamino]-pyrimidin-4-ylamino}-3-(4-dimethylcarbamoyloxyphenyl)propionic acid;
2-{2-diethylamino-5-[(4-fluorobenzenesulfonyl)allylamino]-pyrimidin-4-ylamino}-3-(4-dimethylcarbamoyloxyphenyl)propionic acid;
2-{2-diethylamino-5-[(4-fluorobenzenesulfonyl)isobotylamino]-pyrimidin-4-ylamino}-3-(4-dimethylcarbamoyloxyphenyl)propionic acid;
2-{2-diethylamino-5-[(4-fluorobenzenesulfonyl)-n-butylamino]-pyrimidin-4-ylamino}-3-(4-dimethylcarbamoyloxyphenyl)propionic acid;
2-{2-diethylamino-5-[(2,6-difluorobenzenesulfonyl)methylamino]-pyrimidin-4-ylamino}-3-(4-dimethylcarbamoyloxyphenyl)propionic acid;
2-{2-diethylamino-5-[(2,3-difluorobenzenesulfonyl)ethylamino]-pyrimidin-4-ylamino}-3-(4-dimethylcarbamoyloxyphenyl)propionic acid;
2-{2-Diethylamino-5-[(4-fluorobenzenesulfonyl)propargylamino] pyrimidin-4-ylamino}-3-(4-dimethylcarbamoyloxyphenyl)propionic acid;
2-{2-Diethylamino-5-[(2,4-difluorobenzenesulfonyl)propargylamino] pyrimidin-4-ylamino}-3-(4-dimethylcarbamoyloxyphenyl)propionic acid;
2-{2-Diethylamino-5-[(4-fluorobenzenesulfonyl)-(2-trisfluoroethyl)-amino]pyrimidin-4-ylamino}-3-(4-dimethylcarbamoyloxyphenyl)propionic acid;

and pharmaceutically acceptable salts thereof.

Compound Preparation for Compounds of Formulae XVI-XXI

The compounds of Formulae XVI-XXI can be prepared from readily available starting materials using the methods and procedures set forth in the examples below. These methods and procedures outline specific reaction protocols for preparing N-[2-N',N'-diethylamino-S-aminosulfonylphenyl-yrimidin-4-yl]-p-carbomyloxy-phenylalanine compounds. Compounds within the scope not exemplified in these examples and methods are readily prepared by appropriate substitution of starting materials which are either commercially available or well known in the art.

Other procedures and reaction conditions for preparing the compounds of this invention are described in the examples set forth below. Additionally, other procedures for preparing compounds useful in certain aspects of this invention are disclosed in U.S. Pat. No. 6,492,372 the disclosure of which is incorporated herein by reference in its entirety.

Pharmaceutical Formulations of the Compounds

In general, the compounds of the subject invention will be administered in a therapeutically effective amount by any of the accepted modes of administration for these compounds. The compounds can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compounds can be administered continuously by infusion or by bolus injection. Preferably, the compounds are administered by parenteral routes. More preferably, the compounds are administered by intravenous routes. Such compositions are prepared in a manner well known in the pharmaceutical art.

The actual amount of the compound of the subject invention, i.e., the active ingredient, will depend on a number of factors, such as the severity of the disease, i.e., the condition or disease to be treated, age and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. The effective blood level of the compounds of the subject invention is preferably greater than or equal to 10 ng/ml.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described supra. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The active compound is effective over a wide dosage range and is generally administered in a pharmaceutically or therapeutically effective amount. The therapeutic dosage of the compounds of the present invention will vary according to, for example, the particular use for which the treatment is made, the manner of administration of the compound, the health and condition of the patient, and the judgment of the prescribing physician. For example, for intravenous ad-ministration, the dose will typically be in the range of about 0.5 mg to about 100 mg per kilogram body weight, preferably about 3 mg to about 50 mg per kilogram body weight. Effective doses can be extrapolated from dose-response curves derived from in vitro or animal model test systems. Typically, the clinician will administer the compound until a dosage is reached that achieves the desired effect.

According to one aspect of the invention, the compounds are administered in combination with methotrexate, to treat, ameliorate, or palliate the symptoms of rheumatoid arthritis. When administered in combination, the compounds may be administered in the same formulation as the methotrexate, or in a separate formulation. The compounds may be administered prior to, following, or concurrently with the methotrexate such that the benefitsd of the combination therapy are achieved. The calculation of appropriate dosages will be well within the purvue of the skilled artisan. Standard doses of methotrexate for the treatment of rheumatoid arthritis range from 2 mg to 20 mg per dose per week. Dosages of the compounds are as set forth above. The methotrexate dosage may be administered as a single dose or as a divided dose. Once a response has been achieved, the dosage may be reduced if possible to the lowest effective dose. The maximum recommended dose is 20 mg/week. Preferably, methotrexate is administered orally or via injection.

When employed as pharmaceuticals, the compounds of the subject invention are usually administered in the form of pharmaceutical compositions. This invention also includes pharmaceutical compositions, which contain as the active ingredient, one or more of the compounds of the subject invention above, associated with one or more pharmaceutically acceptable carriers or excipients. The excipient employed is typically one suitable for administration to human subjects or other mammals. In making the compositions of this-invention, the active ingredient is usually mixed with an excipient, diluted by an excipient or, enclosed within a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active compound in the pharmaceutical composition and unit dosage form thereof may be varied or adjusted widely depending upon the particular application, the manner or introduction, the potency of the particular compound, and the desired concentration. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. The concentration of therapeutically active compound may vary from about 1 mg/ml to 250 g/ml.

Preferably, the compound can be formulated for parenteral administration in a suitable inert carrier, such as a sterile physiological saline solution. For example, the concentration of compound in the carrier solution is typically between about 1-100 mg/ml. The dose administered will be determined by route of administration. Preferred routes of administration include parenteral or intravenous administration. A therapeutically effective dose is a dose effective to produce a significant steroid tapering. Preferably, the amount is sufficient to produce a statistically significant amount of steroid tapering in a subject.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the present invention as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer: alendronate (where the moles of buffer are taken as the combined moles of the buffer ingredients, e.g., sodium citrate and citric acid) of formulation to maintain a pH in-the range of 4 to 8 and generally, a 1:1 to 10:1 mole ratio of buffer (combined) to drug present is used.

A useful buffer in the invention is sodium citrate/citric acid in the range of 5 to 50 mg per ml. sodium citrate to 1 to 15 mg per ml. citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide, a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic-effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The compounds of this invention can be administered in a sustained release form. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly(vinyl alcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e., injectable microspheres composed of lactic acid-glycolic acid copolymer and leuprolide acetate), and poly-D-(−)-3-hydroxybutyric acid (EP 133,988).

The compounds of this invention can be administered in a sustained release form, for example a depot injection, implant preparation, or osmotic pump, which can be formulated in such a manner as to permit a sustained release of the active ingredient. Implants for sustained release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated-by the host. The implant is placed in proximity to the site of protein deposits (e.g., the site of formation of amyloid deposits associated with neurodegenerative disorders), so that the local concentration of active agent is increased at that site relative to the rest of the body.

The following formulation examples illustrate pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/capsule) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/capsule) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules, which after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides | to 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water | to 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Hard gelatin tablets, each containing 15 mg of active ingredient are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
| --- | --- |
| Active Ingredient | 250.0 mg |
| Isotonic saline | 1000 ml |

Therapeutic compound compositions generally are placed into a container having a sterile access port, for example, an intravenous solution bag or vial having a stopper pierceable by a hypodermic injection needle or similar sharp instrument.

FORMULATION EXAMPLE 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

An aerosol formulation may be prepared as follows:

A solution of the candidate compound in 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
| --- | --- | --- |
| Sodium Bicarbonate | 0.5 g | 0.5% |
| Saline | q.s. ad 100.0 mL | q.s. ad 100% |

Procedure:

1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

B. Preparation of 30.0 mg/mL Candidate Compound: 10.0 mL

| Ingredient | Gram/10.0 mL | Final Concentration |
| --- | --- | --- |
| Candidate Compound | 0.300 g | 30.0 mg/mL |
| 0.5% Sodium Bicarbonate/Saline Stock Solution | q.s. ad 10.0 mL | q.s ad 100% |

Procedure:

1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix thoroughly.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

According to one aspect of the invention, the compound may be administered alone with methotrexate, as a combination of compounds and with methotrexate, or in combination with anti-alpha-4-antibodies and methotrexate. The compounds of the present invention may also be administered in combination with an immunosuppressant, wherein the immunosuppressant is typically used to treat the condition or disease for which the compound of the present invention is being administered. The immunosuppressant may b,e, but is not limited to, azathioprine, 6-mercaptopurine, or mycophenolate.

When administered in combination, the small compounds may be administered in the same formulation as these other compounds or compositions, or in a separate formulation. When administered in combinations, the compounds may be administered prior to, following, or concurrently with the other compounds and methotrexate.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

Polymer Conjugates

Compounds of the present invention may be formulated and administered as polymer conjugates, preferably PEG derivatives. Polymer conjugates may exhibit benefits over non-conjugated polymers, such as improved solubility and stability.

As such, single polymer molecules may be employed for conjugation with the compounds of the present invention, although it is also contemplated that more than one polymer molecule can be attached as well. The conjugated compounds of the present invention may find utility in both in vivo as well as non-in vivo applications. Additionally, it will be recognized that the conjugating polymer may utilize any other groups, moieties, or other conjugated species, as appropriate to the end use application. By-way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render it reactive and enable it to cross-link to a drug molecule and to enhance various properties or characteristics of the overall conjugated material. Accordingly, the polymer may contain any functionality, repeating groups, linkages, or other constitutent structures which do not preclude the efficacy of the conjugated the compounds of the present invention composition for its intended purpose.

Illustrative polymers that may usefully be employed to achieve these desirable characteristics are described supra, as well as in PCT WO 01/54690 (to Zheng et al.) incorporated by reference herein in its entirety. The polymer may be coupled to the compounds of the present invention (preferably via a linker moiety) to form stable bonds that are not significantly cleavable by human enzymes. Generally, for a bond to be not "significantly" cleavable requires that no more than about 20% of the bonds connecting the polymer and the compounds of the present invention to which the polymer is linked, are cleaved within a 24 hour period, as measured by standard techniques in the art including, but not limited to, high pressure liquid chromatography (HPLC).

The compounds of the present inventions are conjugated most preferably via a terminal reactive group on the polymer although conjugations can also be branched from non-terminal reactive groups. The polymer with the reactive group(s) is designated herein as "activated polymer". The reactive group selectively reacts with reactive groups on the compounds of the present invention. The activated polymer(s) is reacted so that attachment may occur at any available functional group on compounds of the present invention. Amino, carbon, free carboxylic groups, suitably activated carbonyl groups, hydroxyl, guanidyl, oxidized carbohydrate moieties, amino, carbon and mercapto groups of the compounds of the present invention (if available) can be used as attachment sites.

Generally, about 1.0 to about 10 moles of activated polymer per mole of the compounds of the present invention, depending on concentration, is employed. The final amount is a balance between maximizing the extent of the reaction while minimizing non-specific modifications of the product and, at the same time, defining chemistries that will maintain optimum activity, while at the same time optimizing the half-life of the compounds of the present invention. Preferably, at least about 50% of the biological activity of the compounds of the present invention is retained, and most preferably 100% is retained.

The reactions may take place by any suitable art-recognized method used for reacting biologically active materials with inert polymers. Generally, the process involves preparing an activated polymer and thereafter reacting the compounds of the present invention with the activated polymer to produce a soluble compound suitable for formulation. This modification reaction can be performed by several methods, which may involve one or more steps. The polymeric substances included herein are preferably water-soluble at room temperature. A non-limiting list of such polymers includes polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In the preferred practice of the present invention, polyalkylene glycol residues of $C_1$-$C_4$ alkyl polyalkylene glycols, preferably polyethylene glycol (PEG), or poly(oxy)alkylene glycol residues of such glycols are advantageously incorporated in the polymer systems of interest. Thus, the polymer to which the compounds of the present invention are attached may be a homopolymer of polyethylene glycol (PEG) or is a polyoxyethylated polyol, provided in all cases that the polymer is soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained.

Examples of polyoxyethylated polyols include, but are not limited to, polyoxyethylated glycerol, polyoxyethylated sorbitol, polyoxyethylated glucose, or the like. The glycerol backbone of polyoxyethylated glycerol is the same backbone occurring naturally in, for example, animals and humans in mono-, di-, and triglycerides. Therefore, this branching would not necessarily be seen as a foreign agent in the body.

Those of ordinary skill in the art will recognize that the foregoing list is merely illustrative and that all polymer materials having the qualities described herein are contemplated. The polymer need not have any particular molecular weight, but it is preferred that the molecular weight be between about 300 and 100,000, more preferably between 10,000 and 40,000. In particular, sizes of 20,000 or more are most effective at preventing loss of the product due to filtration in the kidneys.

Polyethylene glycol (PEG) and related polyalkylene oxides (PAOs) are known in the art as being useful adjuncts for the preparation of drugs. See for example, PCT WO 93/24476. PEG has also been conjugated to proteins, peptides and enzymes to increase aqueous solubility and circulating life in vivo as well as reduce antigenicity. See, for example, U.S. Pat. Nos. 5,298,643 and 5,321,095, both to Greenwald et al. PCT WO 93/24476 discloses using an ester linkage to covalently bind an organic molecule to water-soluble polyethylene glycols. Thus, the compounds of the invention are preferably administered as polyethylene glycol (PEG) derivatives. Further description of polyethylene glycol derivatives of the compounds of the present invention and reaction conditions for preparing these derivatives are described in U.S. Ser. No. 60/538,573, entitled "Polyethylene Glycol Conjugates of Dipeptides," filed Jan. 23, 2004, herein incorporated by reference in its entirety.

As such, the compounds or conjugates of this invention may contain one or more polyethylene glycol (PEG) substituents covalently attached thereto. Such conjugates demonstrate improved serum half-life, as compared to compounds lacking polyethylene glycol substituents. Without being limited to any theory, the improved serum half-life is believed to be associated with the covalent conjugation of at least one polyethylene glycol entity onto the structure of the compound.

The term "PEG" refers to polymers comprising multiple oxyalkylene units. Such polymers are optionally monocapped with a substituent preferably selected from alkyl, aryl, substituted alkyl, and substituted aryl. Inclusive of such polymers are those diamino capped polyoxyalkylene polymers which are known in the art as Jeffamines®. Still further, such polymers can optionally contain one or more non-oxyalkylene units such as the commercially available poly[di(ethylene glycol)adipates, poly[di(ethylene glycol)phthalate diols, and the like.

By PEG derivative is meant a polyethylene glycol polymer in which one or both of the terminal hydroxyl groups found in polyethylene glycol itself has been modified. Examples of suitable modifications include replacing one or both hydroxyl group(s) with alternative functional groups, which may be protected or unprotected, with low molecular weight ligands, or with another macromolecule or polymer. Modification of the terminal hydroxyl groups in the polyethylene glycol may be achieved by reacting the polyethylene glycol with compounds comprising complementary reactive functional groups, including functional groups which are able to undergo a reaction with the hydroxyl groups in polyethylene glycol. The PEG derivatives of the compounds of this invention may contain one or more polyethylene glycol (PEG) substituents covalently attached thereto by a linking group.

"Linking group" or "linker" refers to a group or groups that covalently links a non-PEG substituted compound of the present invention with one or more PEG groups. Each linker may be chiral or achiral, linear, branched or cyclic and may be homogenous or heterogeneous in its atom content (e.g., linkers containing only carbon atoms or linkers containing carbon atoms as well as one or more heteroatoms present on the linker.

The PEG group or groups are covalently attached to the linker using conventional chemical techniques providing for covalent linkage of the PEG group to the linker. The linker, in turn, may be covalently attached to the otherwise, non-PEG substituted compounds of the present invention. Reaction chemistries resulting in such linkages are well known in the art. Such reaction chemistries involve the use of complementary functional groups on the linker, the non-PEG substituted compound of the present invention and the PEG groups. Preferably, the complementary functional groups on the linker are selected relative to the functional groups available on the PEG group for bonding or which can be introduced onto the PEG group for bonding. Again, such complementary functional groups are well known in the art.

Such polymers have a number average molecular weight of from about 100 to 100,000; preferably from about 1,000 to 50,000; more preferably from about 10,000 to about 40,000.

The polymer conjugates of the invention may provide enhanced in vivo retention as compared to the non-conjugated compounds. The improved retention of the conjugate within the body results in lower required dosages of the drug, which in turn results in fewer side effects and reduced likelihood of toxicity. In addition, the drug formulation comprising these polymer conjugates may be administered less frequently to the patient while achieving a similar or improved therapeutic effect. The conjugates of this invention have improved inhibition, in vivo, of adhesion of leukocytes to endothelial cells mediated by VLA-4 by competitive binding to VLA-4. Preferably, the compounds of this invention can be used in I.V. formulations.

The therapeutic dosage of the polymer conjugates of the present invention will vary according to, for example, the particular use-for which the treatment is made, the manner of administration of the compound, the health and condition of the patient, and the judgment of the prescribing physician. For example, for intravenous administration, the dose will typically be in the range of about 20 µg to about 2000 µg per kilogram body weight, preferably about 20 µg to about 500 µg, more preferably about 100 µg to about 300 µg per kilogram body weight. Suitable dosage ranges for intranasal administration are generally about 0.1 pg to 1 mg per kilogram body weight. Effective doses can be extrapolated from dose-response curves derived from in vitro or animal model test systems.

When formulated and administered as polymer conjugates, the compounds or conjugates of this invention are characterized as containing one or more polyethylene glycol substituents covalently attached thereto. Without being limited to any theory, the improved serum half-life is believed to be associated with covalent conjugation of at least one polyethylene glycol entity onto the structure of the compound.

Accordingly, the compounds of the present invention may be PEG derivatives of formula XXII below:

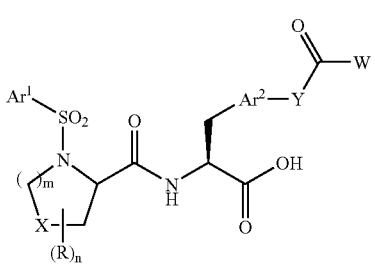

XXII wherein

R is selected from the group consisting of a PEG moiety, amino, substituted amino, alkyl and substituted alkyl wherein each amino, substituted amino, alkyl and substituted alkyl is optionally substituted with a PEG moiety wherein, in each case, the PEG moiety optionally comprises a linker which covalently links the PEG moiety;

$Ar^1$ is selected from the group consisting of aryl, substituted aryl, heteroaryl and substituted heteroaryl wherein each of aryl, substituted aryl, heteroaryl and substituted heteroaryl is optionally substituted with a PEG moiety wherein the PEG moiety optionally comprises a linker which covalently links the PEG moiety to $Ar^1$;

$Ar^2$ is selected from the group consisting of aryl, substituted aryl, heteroaryl and substituted heteroaryl wherein each of aryl, substituted aryl, heteroaryl and substituted heteroaryl is optionally substituted with a PEG moiety wherein the PEG moiety optionally comprises a linker which covalently links the PEG moiety to $Ar^2$;

X is selected from the group consisting of —S—, —SO—, —SO$_2$ and optionally substituted —CH$_2$—;

Y is selected from the group consisting of —O— and —NR$^1$— wherein R$^1$ is selected from the group consisting of hydrogen and alkyl;

W is selected from the group consisting of a PEG moiety which optionally comprises a linker and —NR$^2$R$^3$ wherein R$^2$ and R$^3$ are independently selected from the group consisting of alkyl, substituted alkyl, and where R$^2$ and R$^3$, together with the nitrogen atom bound thereto, form a heterocyclic ring or a substituted heterocyclic ring wherein each of alkyl, substituted alkyl, heterocyclic and substituted heterocyclic is optionally substituted with a PEG moiety which further optionally comprises a linker;

m is an integer equal to 0, 1 or 2;

n is an integer equal to 0 to 2; and pharmaceutically acceptable salts thereof;

provided that at least one of R, $Ar^1$, $Ar^2$, W and —NR$^2$R$^3$ contains a PEG moiety;

further provided that when R is a PEG moiety, n is one and X is not —S—, —SO—, or —SO$_2$—;

and still further provided that the compound of formula XXII has a molecular weight of no more than 100,000.

Preferably the PEG derivates of formula XXII are the of the L isomer as shown below:

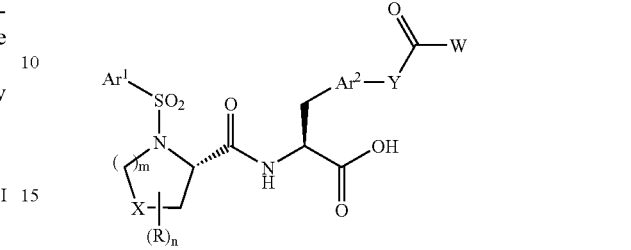

XXIIa

In another aspect, the compounds of the present invention may be PEG derivatives of formula XXIII below:

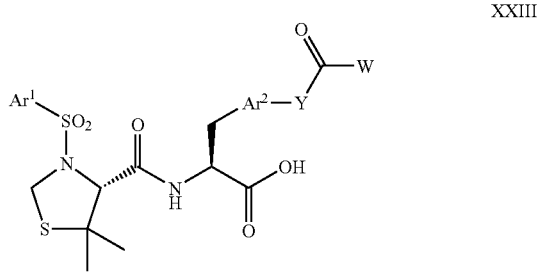

XXIII wherein $Ar^1$, $Ar^2$, Y and W are as defined above; and pharmaceutically acceptable salts thereof;

provided that at least one of $Ar^1$, $Ar^2$, W and —NR$^2$R$^3$ contains a PEG moiety which optionally comprises a linker;

and further provided that the compound of formula XXIII has a molecular weight of no more than 100,000.

In another aspect, the compounds of the present invention may be PEG derivatives of formula XXIV below:

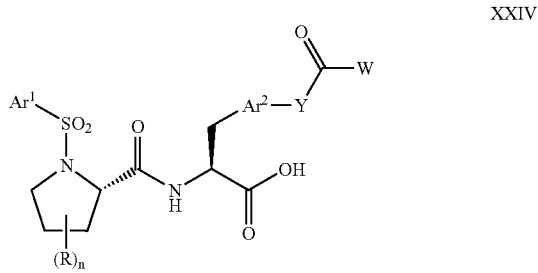

XXIV wherein

R, $Ar^1$, $Ar^2$, Y, W and n are as defined above; and pharmaceutically acceptable salts thereof;

provided that at least one of R, $Ar^1$, $Ar^2$, W and —NR$^2$R$^3$ contains a PEG moiety which optionally comprises a linker;

and further provided that the compound of formula XXVI has a molecular weight of no more than 100,000.

In another aspect, the compounds of the present invention may be PEG derivatives of formula XXV below:

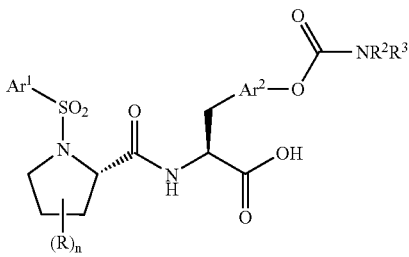

XXV wherein
R, $R^2$, $R^3$, $Ar^1$, $Ar^2$ and n are as defined above; and
pharmaceutically acceptable salts thereof;
provided that at least one of R, $Ar^1$, $Ar^2$, and $—NR^2R^3$ contains a PEG moiety which optionally comprises a linker;
and further provided that the compound of formula XXV has a molecular weight of no more than 100,000.

In another of its aspects, the compound of this invention is directed to a PEG derivative of formula XXVI below:

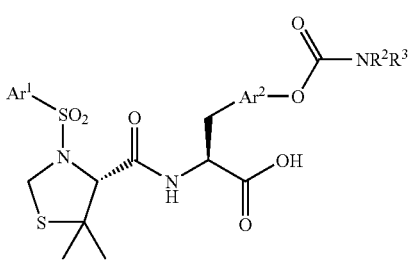

XXVI wherein
$R^2$, $R^3$, $Ar^1$, and $Ar^2$ are as defined above; and
pharmaceutically acceptable salts thereof;
provided that at least one of $Ar^1$, $Ar^2$ and $—NR^2R^3$ contains a PEG moiety which optionally comprises a linker;
and further provided that the compound of formula XXVI has a molecular weight of no more than 100,000.

In another aspect, the compounds of this invention can be PEG derivatives of formula XXVII:

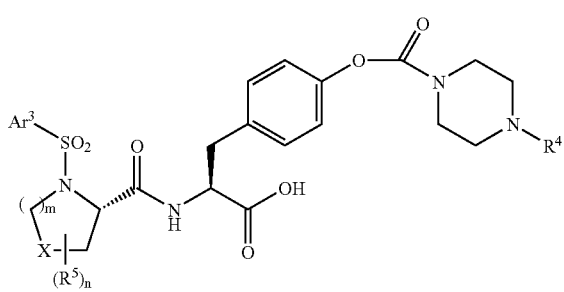

XXVII wherein
$R^4$ is a PEG moiety which optionally comprises a linker;
$R^5$ is selected from the group consisting of alkyl and substituted alkyl;
$Ar^3$ is selected from the group consisting of aryl, substituted aryl, heteroaryl and substituted heteroaryl;
X is selected from the group consisting of —S—, —SO—, and —$SO_2$— or optionally substituted —$CH_2$—;
m is an integer equal to 0, 1 or 2;
n is an integer equal to 0 to 2; and
pharmaceutically acceptable salts thereof;
provided that the compound of formula XXVII has a molecular weight of no more than 100,000.

In another aspect, the compound of the invention can be a PEG derivative of formula XXVIII:

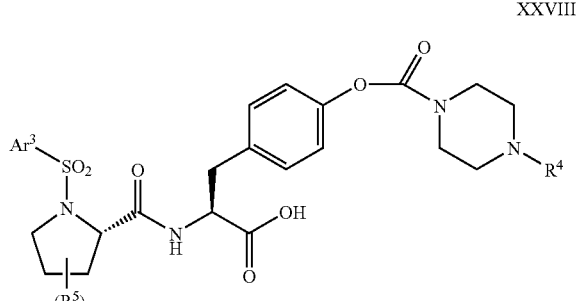

XXVIII wherein
$R^4$ is a PEG moiety which optionally comprises a linker;
$R^5$ is selected from the group consisting of alkyl and substituted alkyl;
$Ar^3$ is selected from the group consisting of aryl, substituted aryl, heteroaryl and substituted heteroaryl;
n is an integer equal to 0 to 2; and
pharmaceutically acceptable salts thereof;
provided that the compound of formula XXVIII has a molecular weight of no more than 100,000.

In another aspect, the compound of the invention can be a PEG derivative of formula XXIX.

XXIX wherein
$R^4$ is a PEG moiety which optionally comprises a linker;
$Ar^3$ is selected from the group consisting of aryl, substituted aryl, heteroaryl and substituted heteroaryl;
pharmaceutically acceptable salts thereof;
provided that the compound of formula XXIX has a molecular weight of no more than 100,000.

Preferably, when $Ar^1$ does not contain a PEG moiety, $Ar^1$ in formulas XXII-XXVI and $Ar^3$ in formulas XXVII-XXIX is selected from the group consisting of:
phenyl,
4-methylphenyl,
4-t-butylphenyl,
2,4,6-trimethylphenyl,
2-fluorophenyl, 3-fluorophenyl,
4-fluorophenyl,
2,4-difluorophenyl,
3,4-difluorophenyl,
3,5-difluorophenyl,
2-chlorophenyl,
3-chlorophenyl,
4-chlorophenyl,
3,4-dichlorophenyl,
3,5-dichlorophenyl,
3-chloro-4-fluorophenyl,
4-bromophenyl,
2-methoxyphenyl,
3-methoxyphenyl,
4-methoxyphenyl,
3,4-dimethoxyphenyl,
4-t-butoxyphenyl,
4-(3'-dimethylamino-n-propoxy)-phenyl,
2-carboxyphenyl,
2-(methoxycarbonyl)phenyl,
4-($H_2NC(O)$—)phenyl,
4-($H_2NC(S)$—)phenyl,
4-cyanophenyl,
4-trifluoromethylphenyl,
4-trifluoromethoxyphenyl,
3,5-di-(trifluoromethyl)phenyl,
4-nitrophenyl,
4-aminophenyl,
4-($CH_3C(O)NH$—)phenyl,
4-(PhNHC(O)NH—)phenyl,
4-amidinophenyl,
4-methyl amidinophenyl,
4-[$CH_3SC(=NH)$—]phenyl,
4-chloro-3-[$H_2NS(O)_2$-]phenyl,
1-naphthyl,
2-naphthyl,
pyridin-2-yl,
pyridin-3-yl,
pyridine-4-yl,
pyrimidin-2-yl,
quinolin-8-yl,
2-(trifluoroacetyl)-1,2,3,4-tetrahydroisoquinolin-7-yl,
2-thienyl,
5-chloro-2-thienyl,
2,5-dichloro-4-thienyl,
1-N-methylimidazol-4-yl,
1-N-methylpyrazol-3-yl,
1-N-methylpyrazol-4-yl,
1-N-butylpyrazol-4-yl,
1-N-methyl-3-methyl-5-chloropyrazol-4-yl,
1-N-methyl-5-methyl-3-chloropyrazol-4-yl,
2-thiazolyl, and 5-methyl-1,3,4-thiadiazol-2-yl.

When $Ar^1$ contains a PEG group, $Ar^1$ is preferably of the formula:

—$Ar^1$-Z-$(CH_2CHR^7O)_pR^8$ wherein
$Ar^1$ is selected from the group consisting of aryl, substituted aryl, heteroaryl, and substituted heteroaryl,
Z is selected from the group consisting of a covalent bond, a linking group of from 1 to 40 atoms, —O—, and —$NR^9$—, where $R^9$ is selected from the group consisting of hydrogen and alkyl,
$R^7$ is selected from the group consisting of hydrogen and methyl;
$R^8$ is selected from the group consisting of hydrogen, alkyl, substituted alkyl, aryl, substituted aryl, and —$CH_2CHR^7NR^{10}R^{11}$ where $R^7$ is as defined above and $R^{10}$ and $R^{11}$ are independently selected from the group consisting of hydrogen and alkyl; and p is an integer such that the molecular weight of the PEG moiety ranges from 100 to 100,000.

Preferably, when R does not contain a PEG moiety, the substituent of the formula:

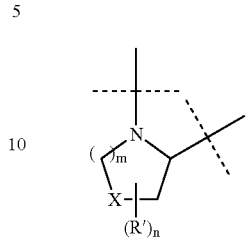

where X, m and n are as defined above, and R' is alkyl or substituted alkyl is preferably selected from the group consisting of:
azetidinyl, thiazolidinyl, piperidinyl, piperazinyl, thiomorpholinyl, pyrrolidinyl, 4-hydroxypyrrolidinyl, 4-oxopyrrolidinyl, 4-fluoropyrrolidinyl, 4,4-difluoropyrrolidinyl, 4-(thiomorpholin-4-ylC(O)O—)pyrrolidinyl, 4-[$CH_3S(O)_2$O—]pyrrolidinyl, 3-phenylpyrrolidinyl, 3-thiophenylpyrrolidinyl, 4-aminopyrrolidinyl, 3-methoxypyrrolidinyl, 4,4-dimethylpyrrolidinyl, 4-N-Cbz-piperazinyl, 4-[$CH_3S(O)_2$-]piperazinyl, 5,5-dimethylthiazolindin-4-yl, 1,1-dioxothiazolidinyl, 1,1-dioxo-5,5-dimethylthiazolidin-2-yl and 1,1-dioxothiomorpholinyl.

When the substituent of the formula:

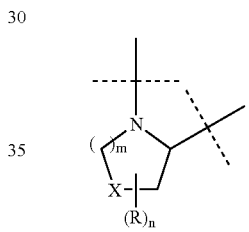

contains a PEG moiety, then preferably the substituent is of the formula:

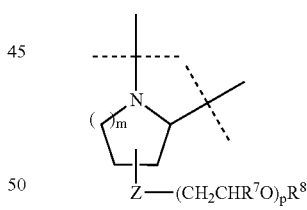

wherein
m is an integer equal to zero, one or two;
Z is selected from the group consisting of a covalent bond, a linking group of from 1 to 40 atoms, —O—, and —$NR^9$—, where $R^9$ is selected from the group consisting of hydrogen and alkyl,
$R^7$ is selected from the group consisting of hydrogen and methyl;
$R^8$ is selected from the group consisting of hydrogen, alkyl, substituted alkyl, aryl, substituted aryl, and —$CH_2CHR^7NR^{10}R^{11}$ where $R^7$ is as defined above and $R^{10}$ and $R^{11}$ are independently selected from the group consisting of hydrogen and alkyl; and p is an integer such that the molecular weight of the PEG moiety ranges from 100 to 100,000.

Preferably, when Ar² does not contain a PEG moiety, Ar² in formulas I-V is preferably selected from the group consisting of phenyl, 2-pyridyl, 3-pyridyl, 4-pyridyl, and 4-pyrid-2-onyl.

When Ar² contains a PEG moiety, Ar² in formulas XXII-XXVI is preferably represented by the formula:

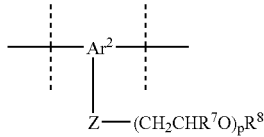

where Ar² is selected from the group consisting of aryl, substituted aryl, heteroaryl and substituted heteroaryl;

Z is selected from the group consisting of a covalent bond, a linking group of from 1 to 40 atoms, —O—, and —NR⁹—, where R⁹ is selected from the group consisting of hydrogen and alkyl, R⁷ is selected from the group consisting of hydrogen and methyl;

R⁸ is selected from the group consisting of hydrogen, alkyl, substituted alkyl, aryl, substituted aryl, and —CH₂CHR⁷NR¹⁰R¹¹ where R⁷ is as defined above and R¹⁰ and R¹¹ are independently selected from the group consisting of hydrogen and alkyl; and p is an integer such that the molecular weight of the PEG moiety ranges from 100 to 100,000.

Preferably, in formulas XXII-XXIV, —YC(O)W is —OC(O)NR²R³. When R² and R³ do not contain a PEG moiety, —OC(O)NR²R³ in formulas XXII-XXVI is preferably selected from the group:

(CH₃)₂NC(O)O—,
(piperidin-1-yl)C(O)O—,
(4-hydroxypiperidin-1-yl)C(O)O—,
(4-formyloxypiperidin-1-yl)C(O)O—,
(4-ethoxycarbonylpiperidin-1-yl)C(O)O—,
(4-carboxylpiperidin-1-yl)C(O)O—,
(3-hydroxymethylpiperidin-1-yl)C(O)O—,
(4-hydroxymethylpiperidin-1-yl)C(O)O—,
(4-piperidon-1-yl ethylene ketal)C(O)O—,
(piperazin-1-yl)-C(O)O—,
(1-Boc-piperazin-4-yl)-C(O)O—,
(4-methylpiperazin-1-yl)C(O)O—,
(4-methylhomopiperazin-1-yl)C(O)O—,
(4-(2-hydroxyethyl)piperazin-1-yl)C(O)O—,
(4-phenylpiperazin-1-yl)C(O)O—,
(4-(pyridin-2-yl)piperazin-1]-yl)C(O)O—,
(4-(4-trifluoromethylpyridin-2-yl)piperazin-1-yl)C(O)O—,
(4-(pyrimidin-2-yl)piperazin-1-yl)C(O)O—,
(4-acetylpiperazin-1-yl)C(O)O—,
(4-(phenylC(O)—)piperazin-1-yl)C(O)O—,
(4-(pyridin-4'-ylC(O)—)piperazin-1-yl)C(O)O,
(4-(phenylNHC(O)—)piperazin-1-yl)C(O)O—,
(4-(phenylNHC(S)—)piperazin-1-yl)C(O)O—,
(4-methanesulfonylpiperazin-1-yl-C(O)O—,
(4-trifluoromethanesulfonylpiperazin-1-yl-C(O)O—,
(morpholin-4-yl)C(O)O—,
(thiomorpholin-4-yl)C(O)O—,
(thiomorpholin-4'-yl sulfone)-C(O)O—,
(pyrrolidin-1-yl)C(O)O—,
(2-methylpyrrolidin-1-yl)C(O)O—,
(2-(methoxycarbonyl)pyrrolidin-1-yl)C(O)O—,
(2-(hydroxymethyl)pyrrolidin-1-yl)C(O)O—,
(2-(N,N-dimethylamino)ethyl)(CH₃)NC(O)O—,
(2-(N-methyl-N-toluene-4-sulfonylamino)ethyl)(CH₃)N—C(O)O—,
(2-(morpholin-4-yl)ethyl)(CH₃)NC(O)O—,
(2-(hydroxy)ethyl)(CH₃)NC(O)O—,
bis(2-(hydroxy)ethyl)NC(O)O—,
(2-(formyloxy)ethyl)(CH₃)NC(O)O—,
(CH₃OC(O)CH₂)HNC(O)O—, and
2-[(phenylNHC(O)O—)ethyl-]HNC(O)O—.

When R² and/or R³ comprise a PEG moiety, the PEG moiety is preferably represented by the formula:

-Z'—(CH₂CHR⁷O)ₚR⁸

Z' is selected from the group consisting of a covalent bond and a linking group of from 1 to 40 atoms;

R⁷ is selected from the group consisting of hydrogen and methyl;

R⁸ is selected from the group consisting of hydrogen, alkyl, substituted alkyl, aryl, substituted aryl, and —CH₂CHR⁷NR¹⁰R¹¹ where R⁷ is as defined above and R¹⁰ and R¹¹ are independently selected from the group consisting of hydrogen and alkyl; and p is an integer such that the molecular weight of the PEG moiety ranges from 100 to 100,000.

Preferred —YC(O)W substituents comprising a PEG moiety include the following:

—OC(O)NH(CH₂CH₂O)ₚCH₂CH₂NH₂;
—OC(O)NH(CH₂CH(CH₃)O)ₚCH₂CH(CH₃)NH₂;
—NHC(O)O(CH₂CH₂O)ₚH;
—NHC(O)O(CH₂CH(CH₃)O)ₚH;
—NHC(O)O(CH₂CH₂O)ₚCH₃;
—NHC(O)O(CH₂CH(CH₃)O)ₚCH₃;
—NHC(O)O(CH₂CH₂O)ₚ-φ;
—NHC(O)O(CH₂CH(CH₃)O)ₚ-φ;
—NHC(O)NH(CH₂CH₂O)ₚCH₂CH₂NH₂;
—NHC(O)NH(CH₂CH(CH₃)O)ₚCH₂CH(CH₃)NH₂;
—OC(O)NH-(1,4)-φ-O—(CH₂CH₂O)ₚH;
—OC(O)NH-(1,4)-φ-O—(CH₂CH(CH₃)O)ₚH;
—OC(O)NH-(1,4)-φ-O—(CH₂CH₂O)ₚCH₃;
—OC(O)NH-(1,4)-φ-O—(CH₂CH(CH₃)O)ₚCH₃;
—OC(O)NH(CH₂CH(CH₃)O)ₚCH₂CH(CH₃)OCH₃;
—NHC(O)NH(CH₂CH₂O)ₚCH₃;
—NHC(O)NH(CH₂CH(CH₃)O)ₚCH₃;

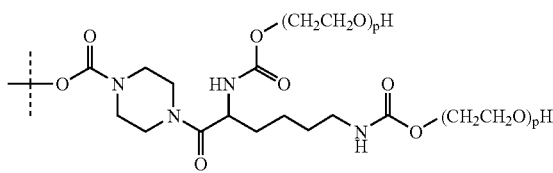

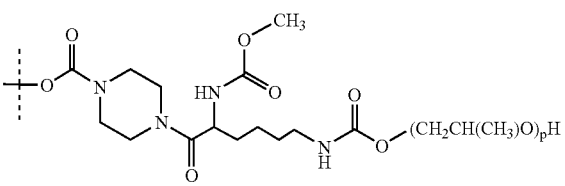

189
190
-continued
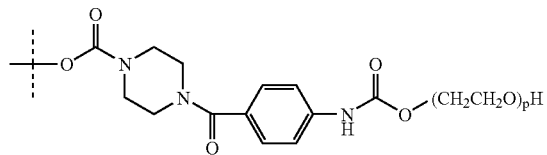
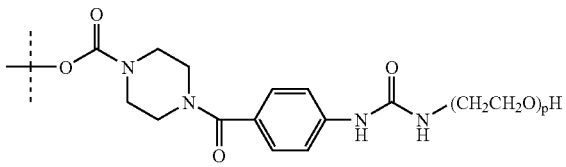
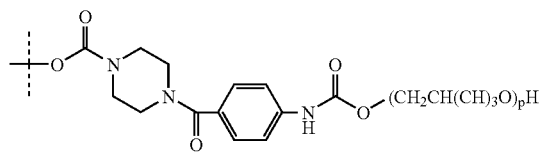
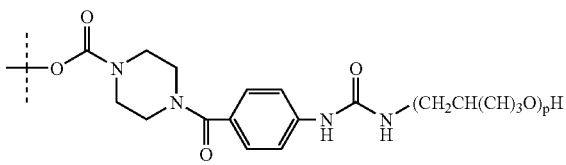
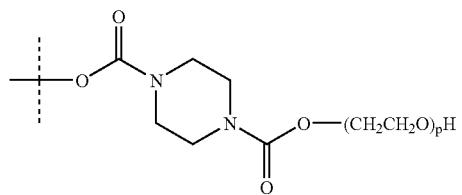
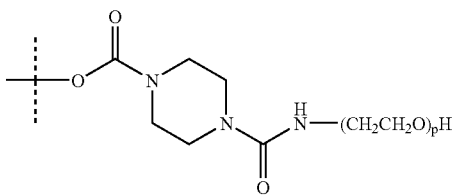
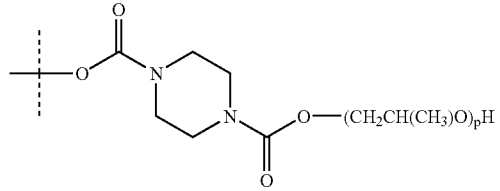
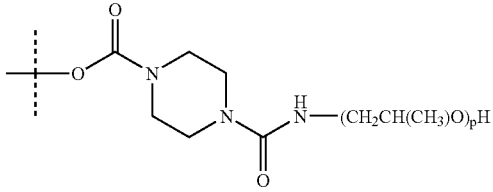
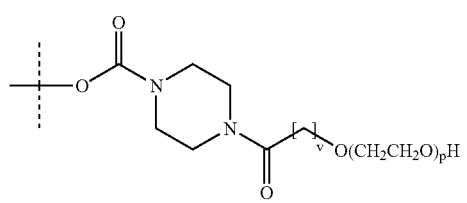
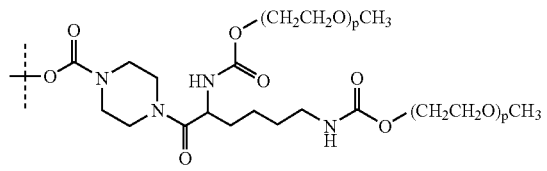
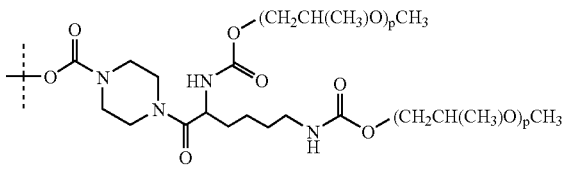
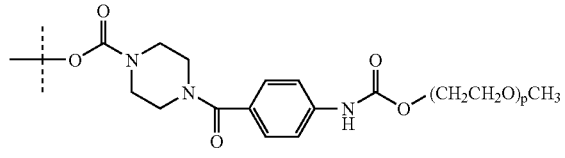
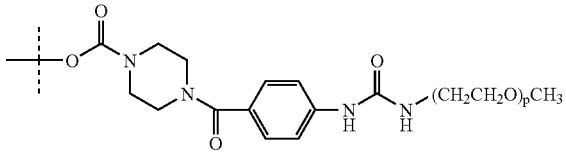
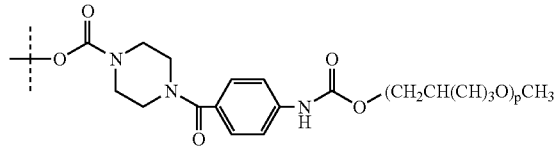
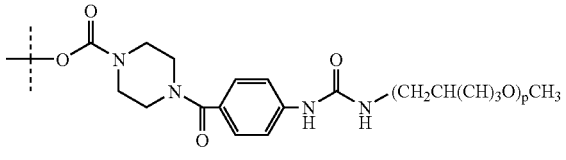
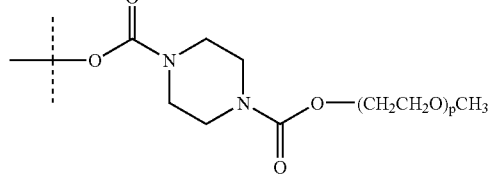
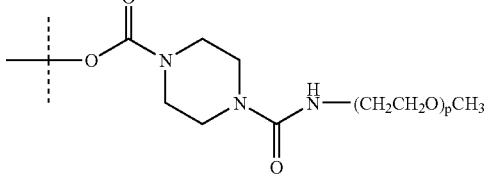

-continued
| 191 | 192 |
|---|---|
| 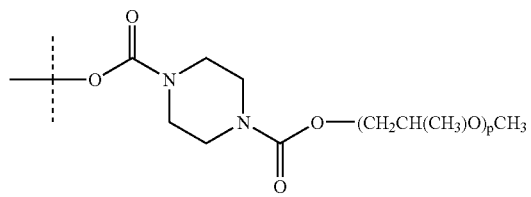 | 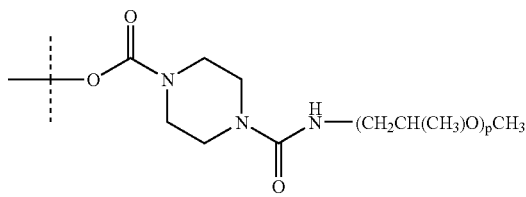 |
| 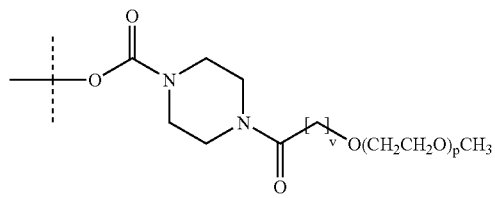 | 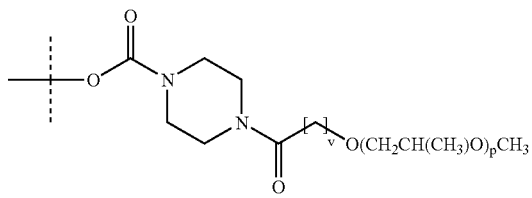 |
| 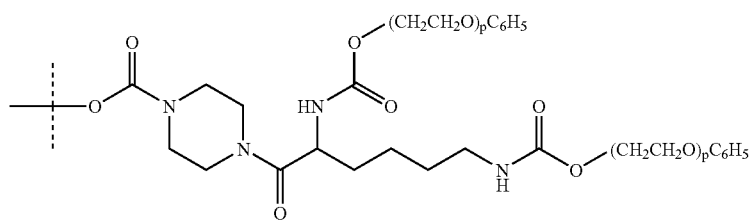 | |
| 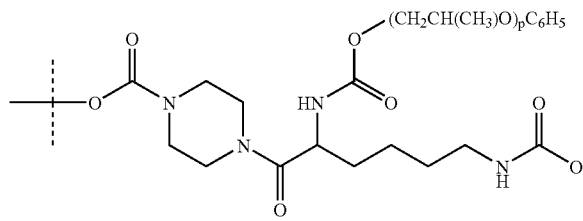 | |
| 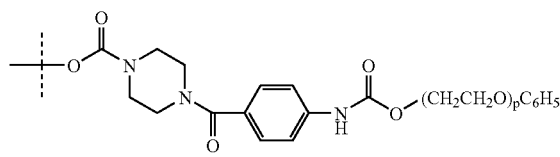 | 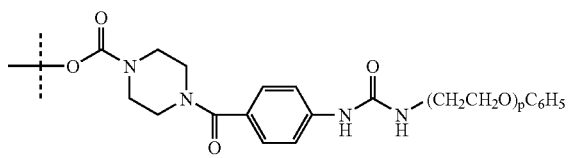 |
| 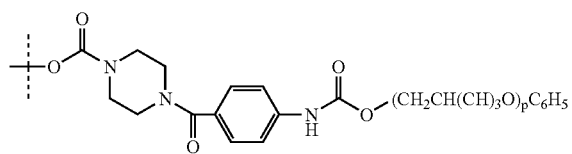 | 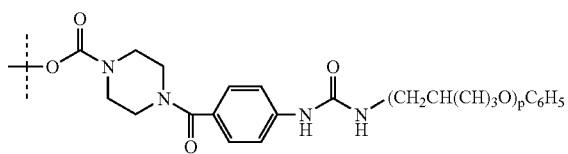 |
| 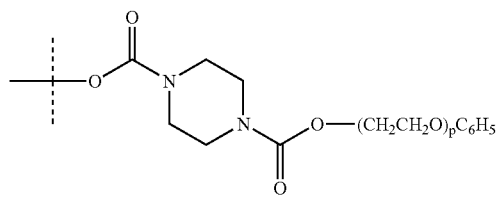 | 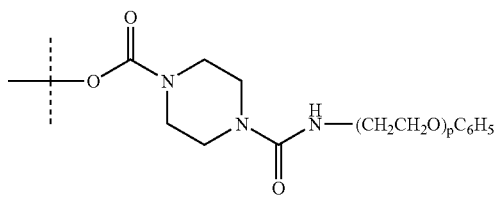 |
| 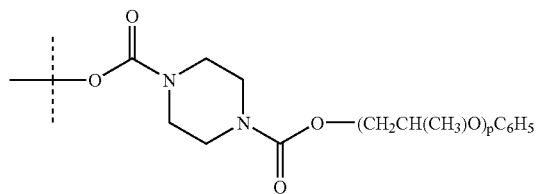 | 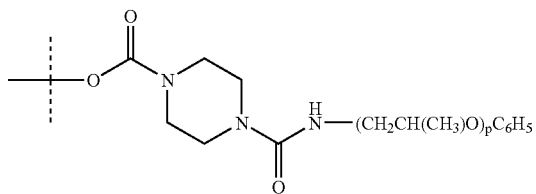 |

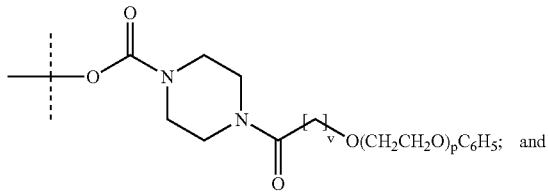 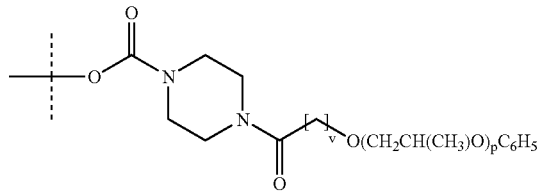
where ɸ or $C_6H_5$ is phenyl and p is an integer such that the molecular weight of the PEG moiety ranges from about 100 to 100,000 and v is 1 to 5.
Preferred PEG derivatives of this invention include those set forth below:
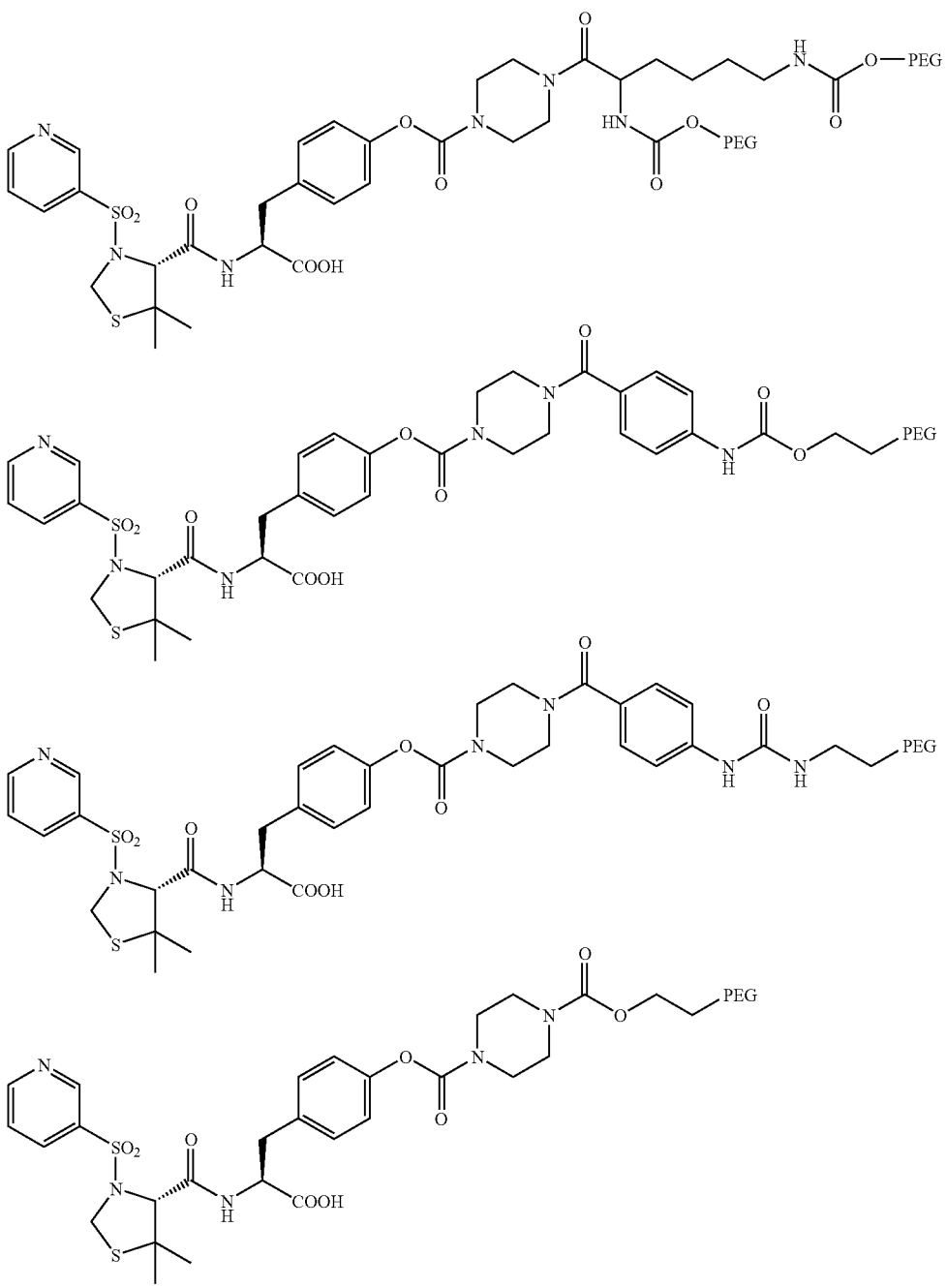

-continued
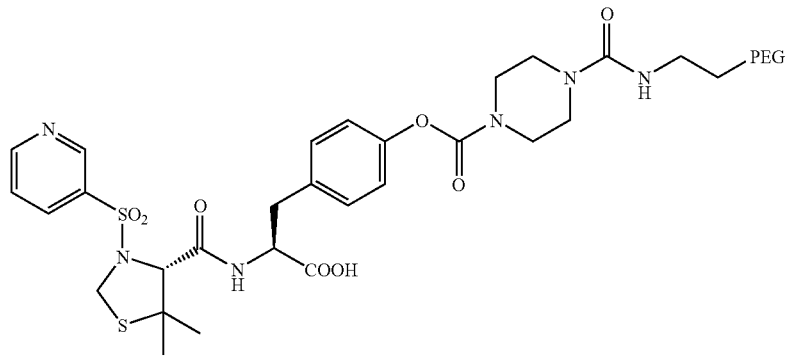
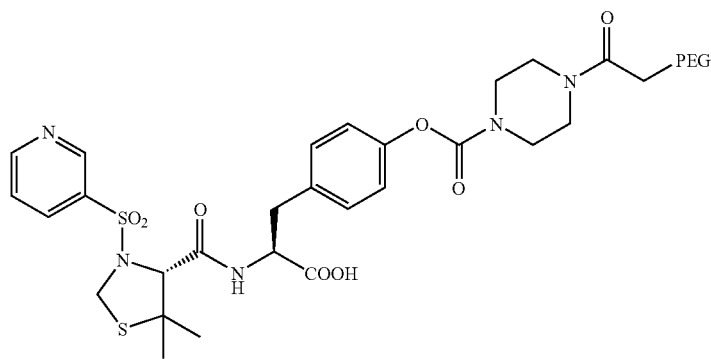
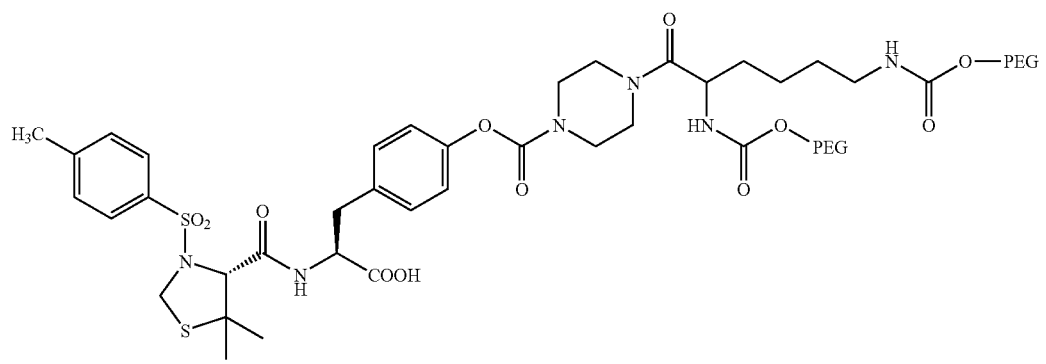
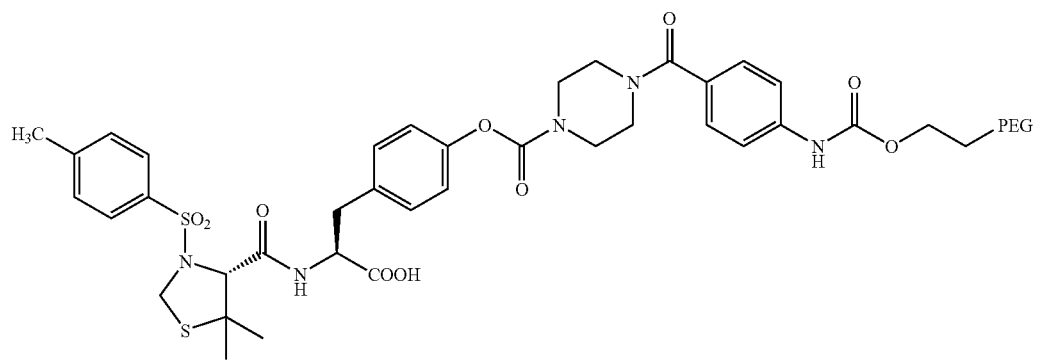

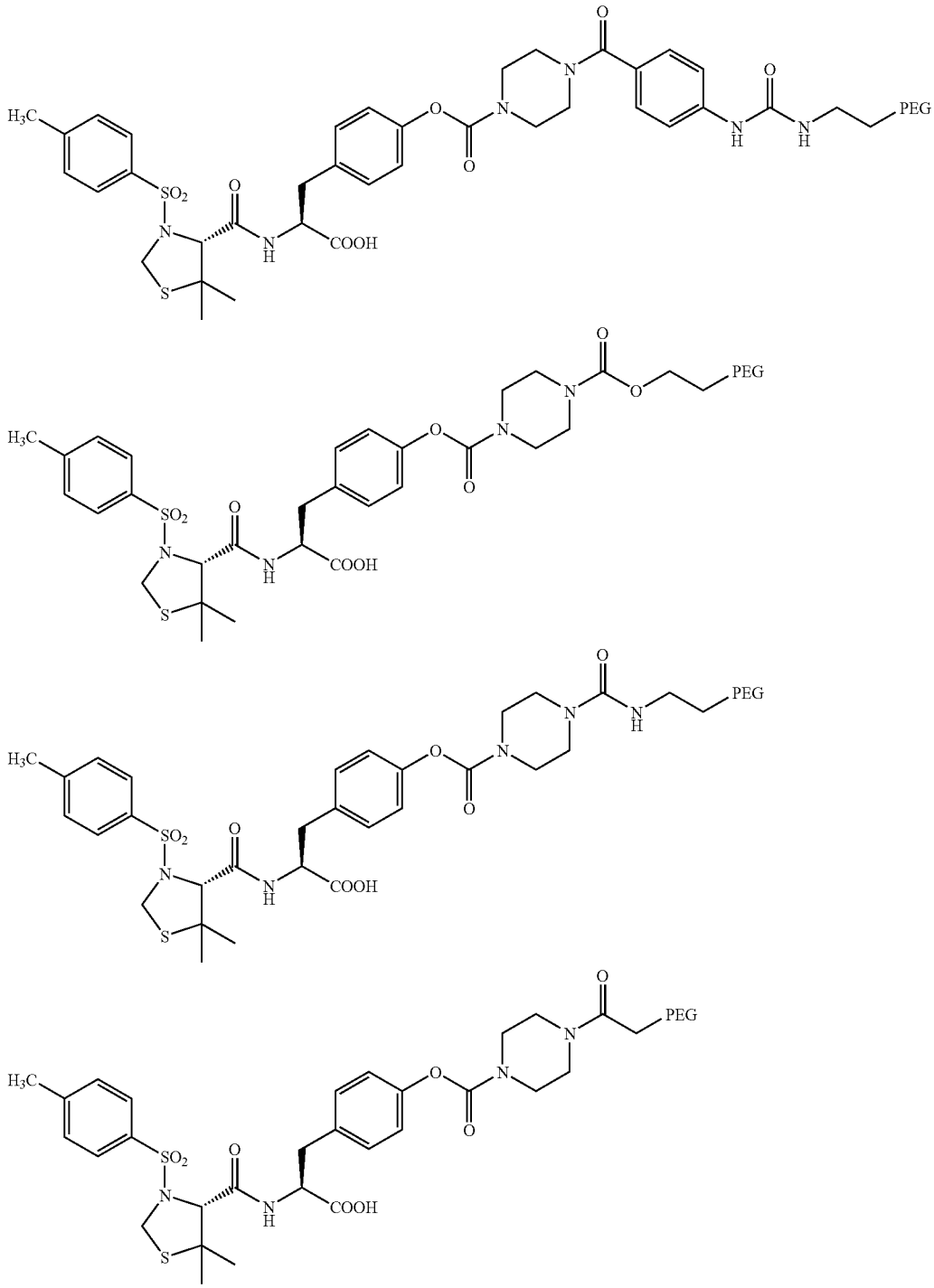

where, in each case, PEG is a methyl capped polyoxyethylene group having a molecular weight (Mw) of approximately 20,000.

"Linking group" or "linker" of from 1 to 40 atoms is a di- to hexavalent group or groups that covalently links a non-PEG substituted compound of formula I (i.e., none of $Ar^1$, $Ar^2$, R or —Y—C(O)—W— contain a PEG group) with 1 to 5 PEG groups. Each linker may be chiral or achiral, linear, branched or cyclic and may be homogenous or heterogeneous in its atom content (e.g., linkers containing only carbon atoms or linkers containing carbon atoms as well as one or more heteroatoms present on the linker in the form of alcohols, ketones, aldehydes, carboxyl groups, amines, amides, carbamates, ureas, thiols, ethers, etc., or residues thereof) Preferably, the linker contains 1 to 25 carbon atoms and 0 to 15 heteroatoms selected from oxygen, $NR^{22}$, sulfur, —S(O)— and —S(O)$_2$—, where $R^{22}$ is as defined above.

The PEG group or groups are covalently attached to the linker using conventional chemical techniques providing for covalent linkage of the PEG group to the linker. The linker, in turn, is covalently attached to the otherwise, non-PEG substituted compound of formula I. Reaction chemistries resulting in such linkages are well known in the art Such reaction chemistries involve the use of complementary functional groups on the linker, the non-PEG substituted compound of formula XXII and the PEG groups. Preferably, the complementary functional groups on the linker are selected relative to the functional groups available on the PEG group for bonding or which can be introduced onto the PEG group for bonding. Again, such complementary functional groups are well known in the art. For example, reaction between a carboxylic acid of either the linker or the PEG group and a primary or secondary amine of the PEG group or the linker in the presence of suitable, well-known activating agents results in formation of an amide bond covalently linking the PEG group to the linker; reaction between an amine group of either the linker or the PEG group and a sulfonyl halide of the PEG group or the linker results in formation of a sulfonamide bond covalently linking the PEG group to the linker; and reaction between an alcohol or phenol group of either the linker or the PEG group and an alkyl or aryl halide of the PEG group or the linker results in formation of an ether bond covalently linking the PEG group to the linker.

Table 9 below illustrates numerous complementary reactive groups and the resulting bonds formed by reaction therebetween.

TABLE 9

Representative Complementary Binding Chemistries

| First Reactive Group | Second Reactive Group | Linkage |
|---|---|---|
| Hydroxyl | Isocyanate | urethane |
| Amine | Epoxide | β-hydroxyamine |
| sulfonyl halid | Amine | sulfonamide |
| Carboxyl | Amine | amide |
| Hydroxyl | alkyl/aryl halide | ether |

Preferred linkers include, by way of example, the following —O—, —NR$^{22}$—, —NR C(O)O—, —OC(O)NR$^{22}$—, —NR$^{22}$C(O)—, —C(O)NR$^{22}$—, —NR$^{22}$C(O)NR$^{22}$—, -alkylene-NR$^{22}$C(O)O—, -alkylene-NR$^{22}$C(O)NR$^{22}$—, -alkylene-OC(O)NR$^{22}$—, -alkylene-NR$^{22}$—, -alkylene-O—, -alkylene-NR$^{22}$C(O)—, -alkylene-C(O)NR$^{22}$—, —NR$^3$C(O)O-alkylene-, —NR$^{22}$C(O)NR$^{22}$-alkylene-, —OC(O)NR$^{22}$-alkylene, —NR$^{22}$-alkylene-, —O-alkylene-, —NR$^{22}$C(O)-alkylene-, —C(O)NR$^{22}$-alkylene-, -alkylene-NR$^{22}$C(O)O-alkylene-, -alkylene-NR$^3$C(O)NR$^{22}$-alkylene-, -alkylene-OC(O)NR$^{22}$-alkylene-, -alkylene-NR$^{22}$-alkylene-, alkylene-O-alkylene-, -alkylene-NR$^{22}$C(O)-alkylene-, —C(O)NR$^{22}$-alkylene-, and

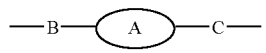

where

is selected from the group consisting of aryl, substituted aryl, cycloalkyl, substituted cycloalkyl, heteroaryl, substituted heteroaryl, heterocyclic and substituted heterocyclic, and B and C are independently selected from the group consisting of a bond, —O—, CO, —NR$^{22}$—, —NR$^{22}$C(O)O—, —OC(O)NR$^{22}$—, —NR$^{22}$C(O)—, —C(O)NR$^{22}$—, —NR$^{22}$C(O)NR$^{22}$—, -alkylene-NR$^{22}$C(O)O—, -alkylene-NR$^{22}$C(O)NR$^{22}$—, -alkylene-OC(O)NR$^{22}$—, -alkylene-NR$^{22}$—, -alkylene-O—, -alkylene-NR$^{22}$C(O)—, alkylene-C(O)NR$^{22}$—, —NR$^{22}$C(O)O-alkylene-, —NR$^{22}$C(O)NR$^{22}$-alkylene-, —OC(O)NR$^{22}$-alkylene-, —NR$^{22}$-alkylene-, —O-alkylene-, —NR$^{22}$C(O)-alkylene-, —C(O)NR$^{22}$-alkylene-, -alkylene-NR$^{22}$C(O)O-alkylene-, -alkylene-NR$^{22}$C(O)NR$^{22}$-alkylene-, -alkylene-OC(O)NR$^{22}$-alkylene-, -alkylene-NR$^{22}$-alkylene-, alkylene-O-alkylene-, -alkylene-NR$^{22}$C(O)-alkylene-, and —C(O)NR$^{22}$-alkylene-, where R$^{22}$ is as defined above.

"PEG" or "PEG moiety" refers to polymers comprising multiple oxyalkylene units. Such polymers are optionally mono-capped with a substituent preferably selected from alkyl, aryl, substituted alkyl, and substituted aryl. Inclusive of such polymers are those diamino capped polyoxyalkylene polymers which are known in the art as Jeffamines®. Still further, such polymers can optionally contain one or more non-oxyalkylene units such as the commercially available poly[di(ethylene glycol)adipates, poly[di(ethylene glycol)phthalate diols, and the like. Also included are block copolymers of oxyalkylene, polyethylene glycol, polypropylene glycol, and polyoxyethylenated polyol units.

Such polymers have a number average molecular weight of from about 100 to 100,000; preferably from about 1,000 to 50,000; more preferably from about 10,000 to about 40,000. In a particularly preferred embodiment, the molecular weight of the total amount of PEG arising from single or multiple PEG moieties bound in the molecule does not exceed 100,000; more preferably 50,000 and even more preferably 40,000.

In a preferred embodiment, the -[linking group]$_u$-PEG group where u is zero or one can be represented by the formula:

-Z'—[(CH$_2$CHR$^7$O)$_p$R$^8$]$_t$ where Z' is selected from the group consisting of a covalent bond, a linking group of from 1 to 40 atoms, —O—, —S—, —NR$^{22}$—, —C(O)O—, —C(O)NR$^{22}$—, and —C(O)— where R$^{22}$ is selected from the group consisting of hydrogen and alkyl, R$^7$ is selected from the group consisting of hydrogen and methyl;

R$^8$ is selected from the group consisting of hydrogen, alkyl, substituted alkyl, aryl, substituted aryl, —CH$_2$CHR$^7$SR$^7$ and —CH$_2$CHR$^7$NR$^{10}$R$^{11}$ where R$^7$ is as defined above and R$^{10}$ and R$^{11}$ are independently selected from the group consisting of hydrogen and alkyl;

p is an integer such that the molecular weight of the PEG moiety ranges from 100 to 100,000; and t is an integer from 1 to 5 provided that t is one less than the valency of the linking group and is one when there is no linking group.

When Z' is linking group, multiple PEG groups can be present. For example, if the linking group is trivalent, then 2 PEG groups can be attached and the remaining valency is employed to link to the molecule of formula XXII. Preferably the number of PEG groups is 1 or 2. In any event, when multiple PEG groups are present, the total aggregate molecular weight of the PEG groups does not exceed 100,000.

PEG Derivative Preparation

The compounds of this invention can be prepared from readily available starting materials using the following-general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The compounds of this invention are preferably characterized by containing one or more PEG moieties at one of several sites of a compound of formula XXIIa:

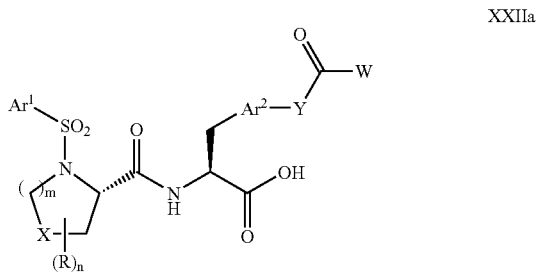

XXIIa

Specifically, the PEG moiety can be incorporated into the $Ar^1$ substituent, the R substituent, the $Ar^2$ substituent and/or in the —YC(O)W substituent wherein the PEG moiety is either directly attached or is attached via a linker. The synthetic protocol for insertion of a PEG moiety at each of these positions is similar and entails reaction of a functional group on the PEG moiety or the linking group covalently bound to the PEG moiety with a complementary functional group on the non-PEG substituted compounds of formula XXIIa.

Initially, non-PEG substituted compounds of formula XXIIa are well known in the art and are exemplified in a number of issued patents including, without limitation, U.S. Pat. Nos. 6,489,300 and 6,436,904 both of which are incorporated herein by reference in their entirety. Non-PEG variants of compounds of formula Ia include those having complementary functional groups or groups derivatizable to complementary functional groups on one or more of the $Ar^1$, R, $Ar^2$ and —YC(O)W moieties. For illustrative purposes, compounds having a complementary functional group (—OH) on the $Ar^2$ moiety (e.g., tyrosine) are recited below as a suitable starting point for addition of a PEG group to the molecule either directly or through a linker.

Such compounds can be prepared by first coupling a heterocyclic amino acid, 1, with an appropriate aryl sulfonyl chloride as illustrated in Scheme 1 below:

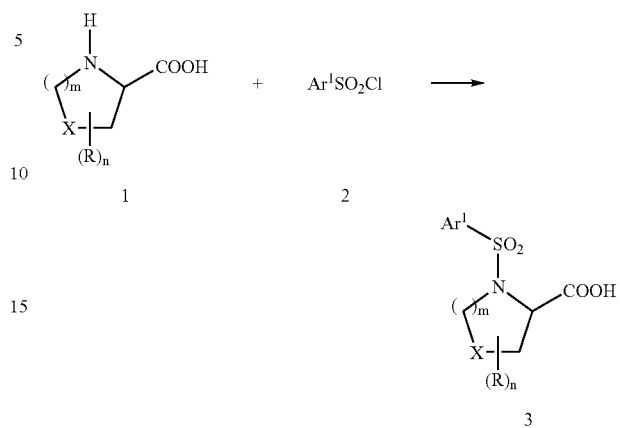

Scheme 1 where R, $Ar^1$, X, m and n are as defined above.

Specifically, in Scheme 1 above, heterocyclic amino acid, 1, is combined with a stoichiometric equivalent or excess amount (preferably from about 1.1 to about 2 equivalents) of arylsulfonyl halide, 2, in a suitable inert diluent such as dichloromethane and the like. Generally, the reaction is conducted at a temperature ranging from about −70° C. to about 40° C. until the reaction is substantially complete, which typically occurs within 1 to 24 hours. Preferably, the reaction is conducted in the presence of a suitable base to scavenge the acid generated during the reaction. Suitable bases include, by way of example, tertiary amines, such as triethylamine, diisopropylethylamine, N-methyl-morpholine and the like. Alternatively, the reaction can be conducted under Schotten-Baumann-type conditions using an aqueous alkali solution such as an aqueous solution of sodium hydroxide, an aqueous phosphate solution buffered to pH 7.4, and the like. The resulting product, 3, can be recovered by conventional methods, such as chromatography, filtration, evaporation, crystallization, and the like or, alternatively, used in the next step without purification and/or isolation.

Heterocyclic amino acids, 1, employed in the above reaction are either known compounds or compounds that can be prepared from known compounds by conventional synthetic procedures. Examples of suitable amino acids for use in this reaction include, but are not limited to, L-proline, trans-4-hydroxyl-L-proline, cis-4-hydroxyl-L-proline, trans-3-phenyl-L-proline, cis-3-phenyl-L-proline, L-(2-methyl)proline, L-pipecolinic acid, L-azetidine-2-carboxylic acid, L-thiazolidine-4-carboxylic acid, L-(5,5-dimethyl)thiazolidine-4-carboxylic acid, L-thiamorpholine-3-carboxylic acid. If desired, the corresponding carboxylic acid esters of the amino acids, 1, such as the methyl esters, ethyl esters, t-butyl esters, and the like, can be employed in the above reaction with the arylsulfonyl chloride. Subsequent hydrolysis of the ester group to the carboxylic acid using conventional reagents and conditions, i.e., treatment with an alkali metal hydroxide in an inert diluent such as methanol/water, then provides the N-sulfonyl amino acid, 3.

Similarly, the arylsulfonyl chlorides, 2, employed in the above reaction are either known compounds or compounds that can be prepared from known compounds by conventional synthetic procedures. Such compounds are typically prepared from the corresponding sulfonic acid, i.e., from compounds of the formula $Ar^1 SO_3H$ where $Ar^1$ is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the arylsulfonyl chlorides, 2, can be prepared from the corresponding thiol compound, i.e., from compounds of the $Ar^1$—SH where $Ar^1$ is as defined herein, by treating the thiol with chlorine ($Cl_2$) and water under conventional reaction conditions.

Alternatively, arylsulfonyl chlorides, 2, employed in the above reaction may be prepared by chlorosulfonylation of substituted benzene or heterocycloalkyl group using Cl—$SO_3$H.

Examples of arylsulfonyl chlorides suitable for use in this invention include, but are not limited to, benzenesulfonyl chloride, 1-naphthalenesulfonyl chloride, 2-naphthalenesulfonyl chloride, p-toluenesulfonyl chloride, o-toluenesulfonyl chloride, 4-acetamidobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamido-benzenesulfonyl chloride, 4-nitrobenzenesulfonyl chloride, 4-trifluoromethyl-benzenesulfonyl chloride, 4-trifluoromethoxybenzenesulfonyl chloride, 2,4,6-trimethylbenzenesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl amino acid, 3.

The N-arylsulfonyl amino acid, 3, is then coupled to commercially available tyrosine esters as shown in Scheme 2 below:

Scheme 2

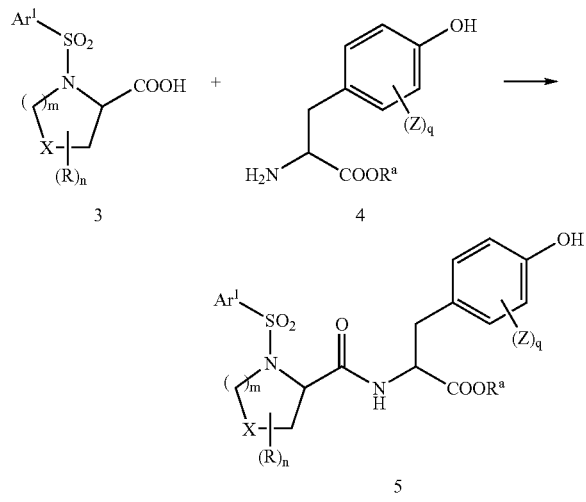

where R, $Ar^1$, X, m and n are as defined above, $R^a$ is hydrogen or alkyl but preferably is an alkyl group such as t-butyl, Z represents optional substitution on the aryl ring and q is zero, one or two.

This coupling reaction is typically conducted using well-known coupling reagents such as carbodiimides, BOP reagent (benzotriazol-1-yloxy-tris(dimethylamino)-phosphonium hexafluorophosphonate) and the like. Suitable carbodiimides include, by way of example, dicyclohexylcarbodiimide (DCC), 1-(3-dimethylaminopropyl)-3-ethylcarbodiimide (EDC) and the like. If desired, polymer supported forms of carbodiimide coupling reagents may also be used including, for example, those described in Tetrahedron Letters, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting the N-sulfonylamino acid, 3, with about 1 to about 2 equivalents of the coupling reagent and at least one equivalent, preferably about 1 to about 1.2 equivalents, of tyrosine derivative, 4, in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound 5 is recovered by conventional methods including neutralization, evaporation, extraction, precipitation, chromatography, filtration, and the like.

Alternatively, the N-sulfonyl amino acid, 3, can be converted into an acid halide which is then coupled with compound, 4, to provide compound 5. The acid halide can be prepared by contacting compound 3 with an inorganic acid halide, such as thionyl chloride, phosphorous trichloride, phosphorous tribromide or phosphorous pentachloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as DMF, may also be used in this reaction.

The acid halide of N-sulfonyl amino acid, 3, is then contacted with at least one equivalent, preferably about 1.1 to about 1.5 equivalents, of the tyrosine derivative, 4, in an inert diluent, such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, compound 5 is recovered by conventional methods including neutralization, evaporation, extraction, precipitation, chromatography, filtration, and the like.

Aternatively, compound 5 can be prepared by first forming a diamino acid derivative and then coupling the diamino acid to the arylsulfonyl halide, 2, as shown in scheme 3 below:

Scheme 3

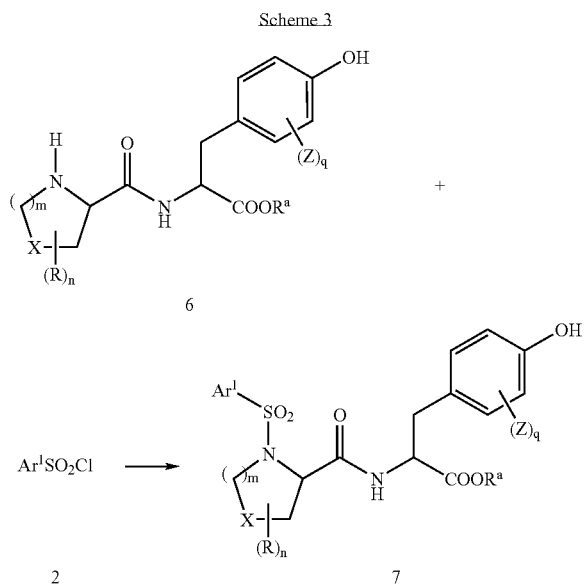

where R, $R^a$, $Ar^1$, X, Z, m, n and q are as defined above.

The diamino acid, 6, can be readily prepared by coupling amino acid, 1, with amino acid, 4, using conventional amino acid coupling techniques and reagents, such carbodiimides, BOP reagent and the like, as described above. Diamino acid, 6, can then be sulfonated using sulfonyl chloride, 2, and using the synthetic procedures described above to provide compound 7.

The tyrosine derivatives, 4, employed in the above reactions are either known compounds or compounds that can be prepared from known compounds by conventional synthetic procedures. For example, tyrosine derivatives, 4, suitable for use in the above reactions include, but are not limited to, L-tyrosine methyl ester, L-tyrosine t-butyl-ester, L-3,5-diiodotyrosine methyl ester, L-3-iodotyrosine methyl ester, β-(4-hydroxy-naphth-1-yl)-L-alanine methyl ester, β-(6-hydroxy-naphth-2-yl)-L-alanine methyl ester, and the like. If desired, of course, other esters or amides of the above-described compounds may also be employed.

The N-arylsulfonyl-heterocyclic amino acid-tyrosine derivative, 7, can be used as a starting point to prepare PEG derivatives at the $Ar^2$ group by coupling reactions shown in Schemes 4-14 below which coupling reactions are illustrative only in demonstrating how PEG moieties can be introduced. In some cases, the PEG moiety can be directly introduced onto the phenoxy group and, in other cases, the PEG moiety can be introduced by linkage through a linker moiety.

Specifically, Scheme 4 illustrates the following:

Scheme 4

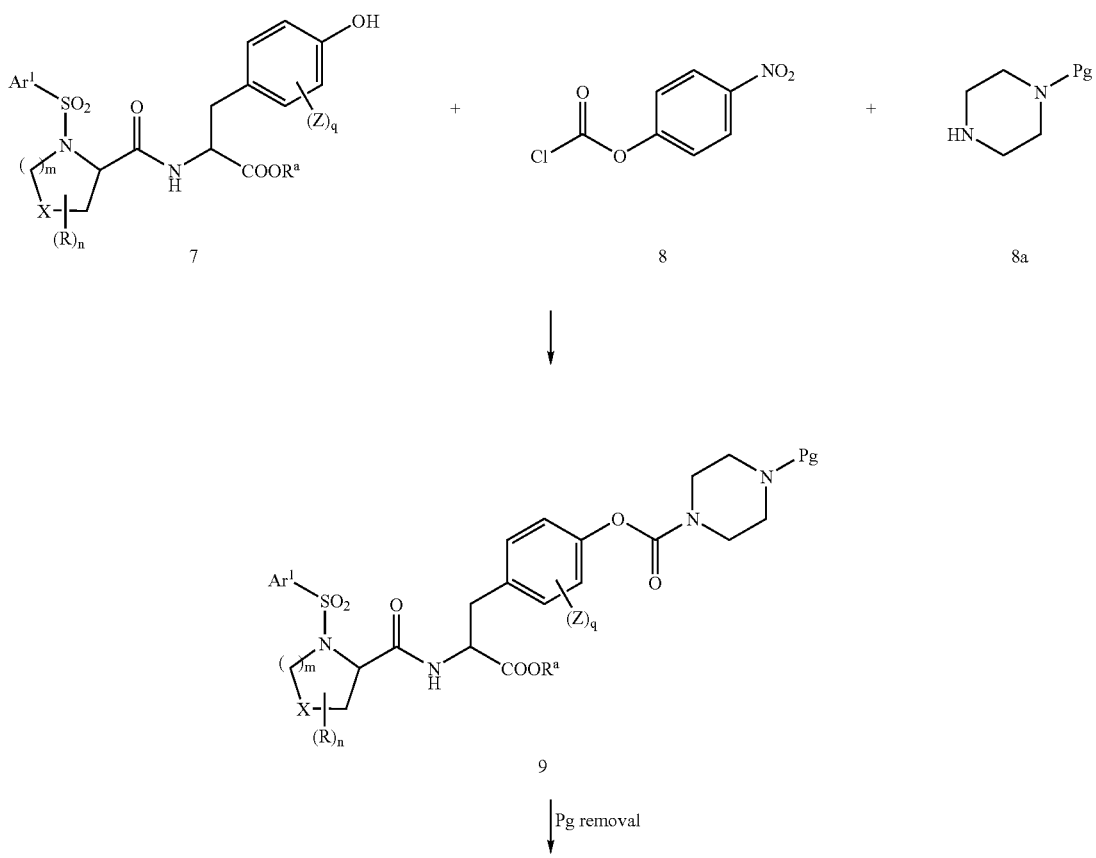

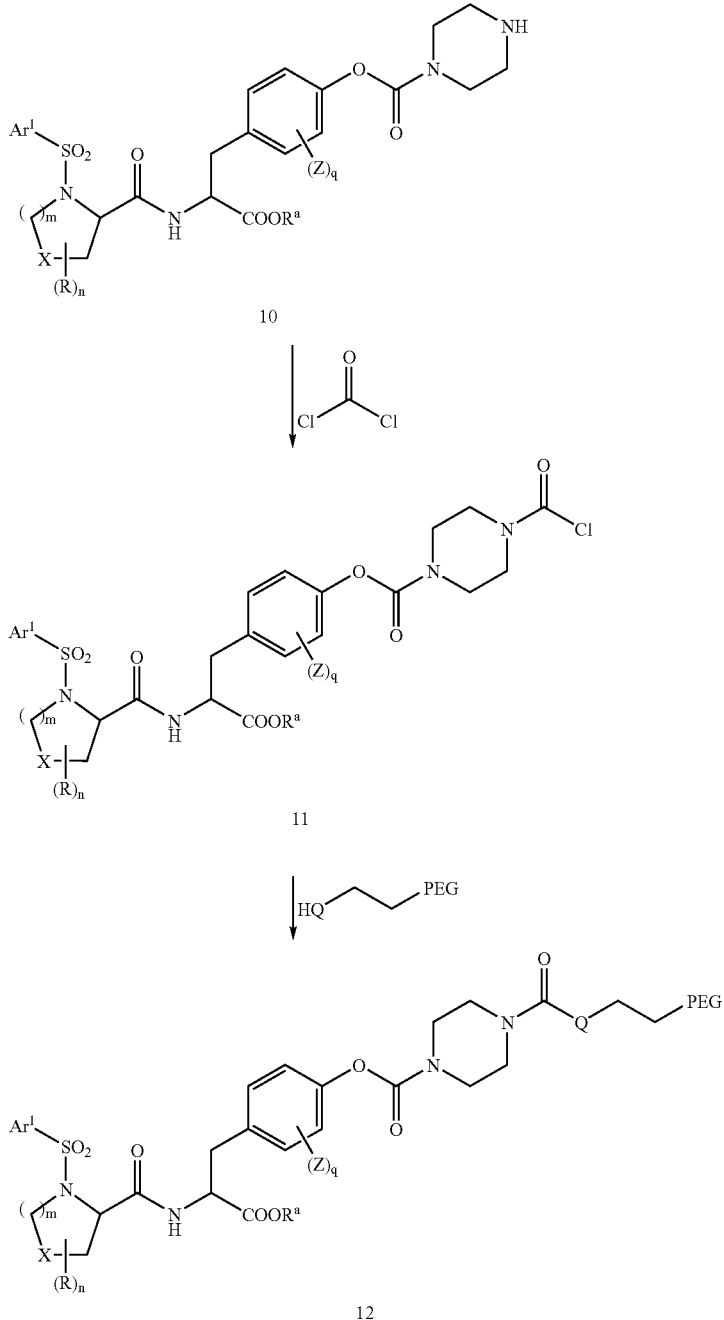

wherein $Ar^1$, R, $R^a$, m, n, q, X, and Z are as defined above whereas Q is oxygen, sulfur and NH, Pg is an amine protecting group such as CBZ, Boc, etc, which is preferably orthogonally removeable as compared to the $R^a$ carboxyl protecting group and PEG is preferably a methyl capped poly(oxyethylene) group having a molecular weight of from 100 to 100,000.

In Scheme 4, the PEG moiety is covalently attached to the N-piperazinylcarbonyltyrosine moiety ($R^2/R^3$ are joined together with the nitrogen atom attached thereto to form a piperazine ring) via a linker entity which constitutes the group:

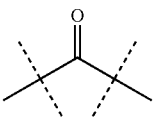

Specifically, in Scheme 4, compound 7, prepared as above, is combined with at least an equivalent and preferably an excess of 4-nitrophenyl chloroformate, 8, in a suitable solvent such as methylene chloride, chloroform and the like and preferably under an inert atmosphere. The reaction is preferably conducted at a temperature of from about −40° to about 0° C. in the presence of a suitable base to scavenge the acid generated. Suitable bases include, by way of example, triethylamine, diisopropylethylamine, and the like. After formation of the intermediate mixed carbonate (not shown), at least an approximately equimolar amount of N-Pg piperazine, 8a, is added to the reaction solution. This reaction is allowed to continue at room temperature for about 1 to 24 hours. Upon completion of the reaction, the compound 9 is recovered by conventional methods including neutralization, evaporation, extraction, precipitation, chromatography, filtration, and the like, or, alternatively, is used in the next reaction without purification and/or isolation.

Conventional removal of the protecting group provides for the free piperazine derivative, 10. Removal is accomplished in accordance with the blocking group employed. For example, a trifluoromethylcarbonyl protecting group is readily removed via an aqueous solution of potassium carbonate. Further, suitable protecting groups for various functional groups as well as suitable conditions for protecting and deprotecting particular functional groups are well known in the art. See, for example, T. W. Greene and G. M. Wuts, *Protecting Groups in Organic Chemistry*, Second Edition, Wiley, New York, 1991, and references cited therein.

The free piperazine derivative, 10, is then converted to the corresponding carbamyl chloride, 11 by reaction in a biphasic reaction mixture of phosgene in toluene (Fluka), dichloromethane and aqueous bicarbonate solution. Subsequent reaction of the carbamyl chloride, 11, with a mono-capped PEG compound such as commercially available $CH_3(OCH_2CH_2)_pOH$ provides for PEG derivative 12. The reaction is conducted in a suitable solvent such as methylene chloride, chloroform, etc. typically in the presence of a catalytic amount of DMAP and a base to scavenge the acid generated during reaction. The reaction is continued until substantially complete which typically occurs within 4 to 24 hours.

When $R^a$ is alkyl, subsequent hydrolysis of the ester derivative provides for the free carboxyl group or a salt thereof.

A specific example of this reaction scheme up to formation of the piperazine derivative 10 is illustrated in Scheme 5 below:

Scheme 5

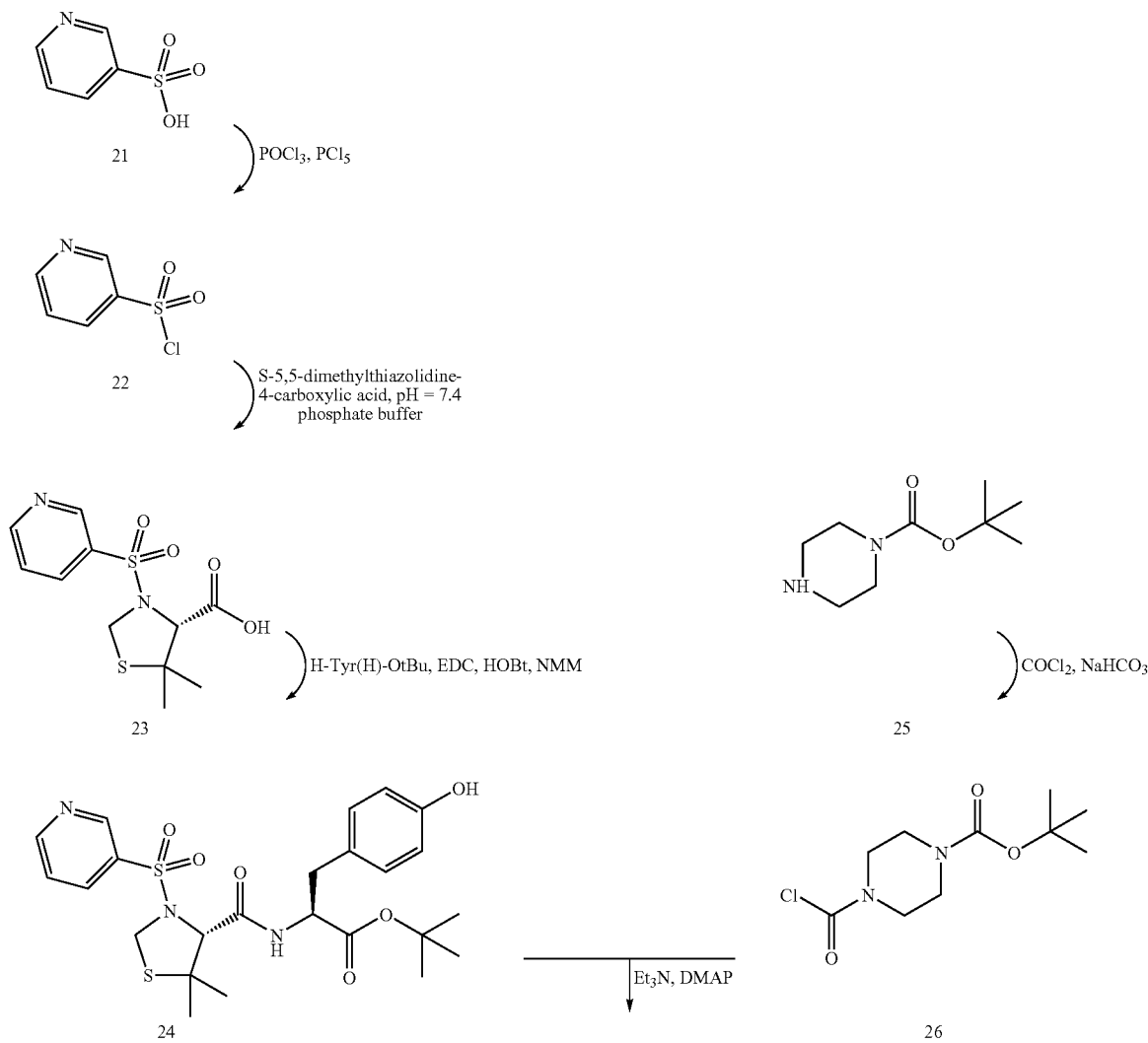

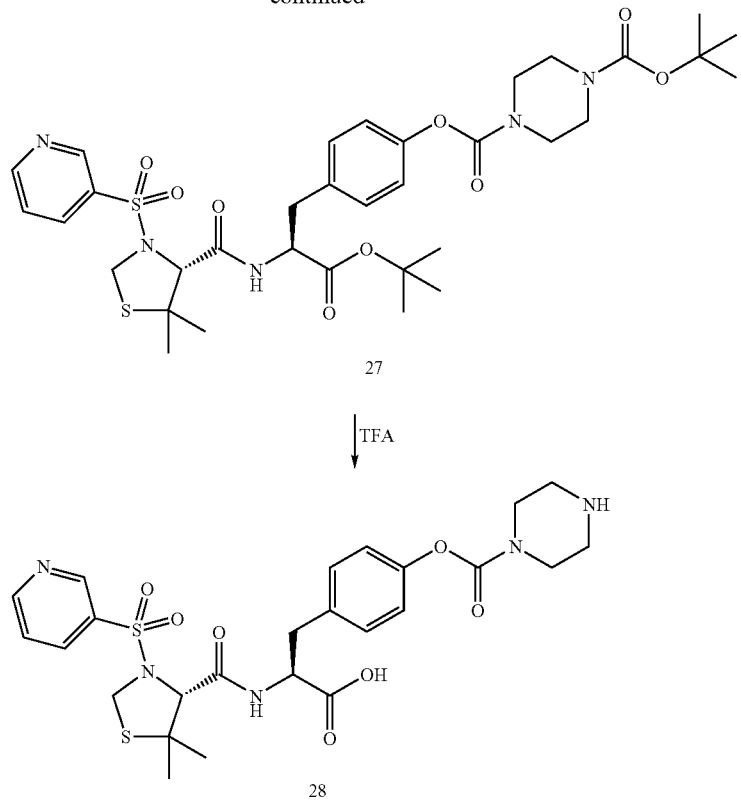

Specifically, commercially available 3-pyridinesulfonic acid, 21, is converted under conventional conditions to the corresponding sulfonyl chloride, 22, by contact with $POCl_3/PCl_5$ using conditions well known in the art. Coupling of sulfonyl chloride, 22, with commercially available S-5,5-dimethylthiazolidine-4-carboxylic acid, 23, is accomplished under conventional conditions preferably in the presence of a phosphate buffer (pH 7.4) using an excess of sulfonyl chloride. The reaction is preferably conducted at a temperature of from about −10 to 20° C. until the reaction is substantially complete, which typically occurs within 0.5 to 5 hours. The resulting product, 24, can be recovered by conventional methods, such as chromatography, filtration, evaporation, crystallization, and the like or, alternatively, used in the next step without purification and/or isolation.

The N-pyridyl sulfonyl-5,5-dimethylthiazolidine-4-carboxylic acid compound, 23, is next coupled to t-butyl tyrosine using conventional amino acid coupling conditions. Specifically, this coupling reaction is conducted using well known coupling reagents such as 1-(3-dimethylaminopropyl)-3-ethylcarbodiimide (EDC), 1-hydroxy-benzotriazole (HOBt) and N-methylmorpholine to facilitate the coupling reaction.

This coupling-reaction is typically conducted by contacting the N-sulfonylamino acid, 23, with about 1 to about 2 equivalents of the coupling reagent and at least one equivalent, preferably about 1 to about 1.2 equivalents, of tyrosine t-butyl ester in an inert diluent, such as dichloromethane, chloroform, acetonitrile, tetrahydrofuran, N,N-dimethylformamide and the like. Generally, this reaction is conducted at a temperature ranging from about 0° C. to about 22° C. for about 12 to about 24 hours. Upon completion of the reaction, the compound 24 is recovered by conventional methods including neutralization, evaporation, extraction, precipitation, chromatography, filtration, and the like or, alternatively, is employed in the next step without purification and/or isolation.

Separately, mono-N-Boc-piperazine, 25, is converted to the corresponding carbamyl chloride, 26, by reaction with phosgene in the manner described above. Upon completion of the reaction, the compound 26 is recovered by conventional methods including neutralization, evaporation, extraction, precipitation, chromatography, filtration, and the like or, alternatively, is employed in the next step without purification and/or isolation.

Coupling of compound 24 with compound 26 to provide for compound 27 proceeds under conventional conditions in an inert diluent such as dichloromethane, with a catalytic amount of DMAP and preferably in the presence of a base to scavenge the acid generate. The reaction is run at a temperature of about −20 to about 22° C. for about 2 to about 24 hours. Upon completion of the reaction, compound 27 is recovered by conventional methods including neutralization, evaporation, extraction, precipitation, chromatography, filtration, and the like or, alternatively, is employed in the next step without purification and/or isolation.

Removal of both the amino Boc protecting group and the t-butyl ester proceeds in the presence of trifluoroacetic acid to provide for compound 28 which can be recovered by conventional methods including neutralization, evaporation, extraction, precipitation, chromatography, filtration, and the like.

Scheme 6 below illustrates the preparation of a piperazine compound orthogonally protected on one of the amine groups relative to the carboxyl protecting group found on the pheny lalanine compound such that after coupling, the piperazine protecting group can be removed differentially from that of the carboxyl protecting group. Such orthogonal protection is necessary if subsequent reactions on the resulting compound require a carboxyl protecting group to avoid undesired side reactions.
Scheme 6
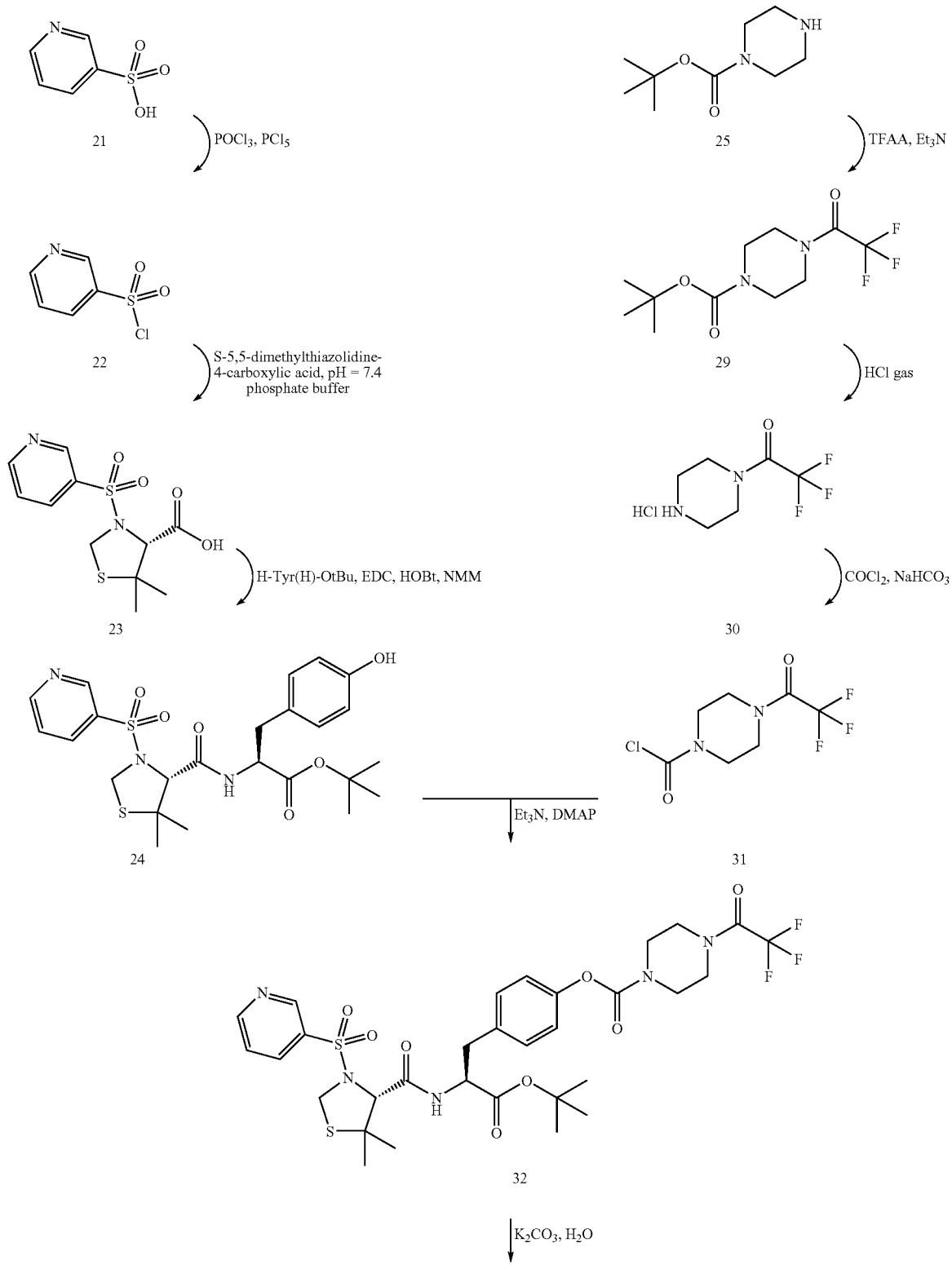

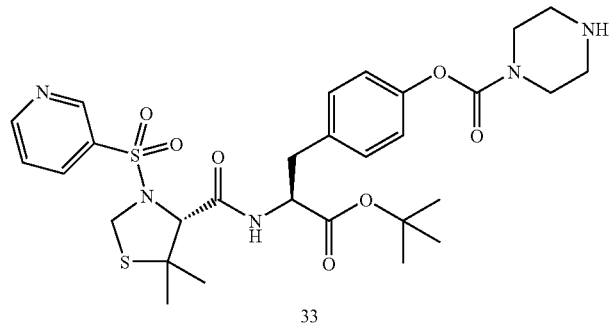

33

Specifically, in Scheme 6, compound 24 is prepared in the manner described above. N-t-Boc-piperazine, 25, is conventionally converted to N-t-Boc-N'-trifluoromethyl-carbonylpiperazine, 29, by contact with an excess of trifluoroacetic anhydride in the presence of a suitable amine such as triethylamine to scavenge the acid generated during reaction in a suitable solvent such as dichloromethane. Generally, this reaction is conducted at a temperature ranging from about −20° C. to about 22° C. for about 1 to about 24 hours. Upon completion of the reaction, compound 29 can be recovered by conventional methods including neutralization, evaporation, extraction, precipitation, chromatography, filtration, and the like or, alternatively and preferably, is employed in the next step without purification and/or isolation.

In turn, removal of the t-Boc protecting group on the N-t-Boc-N'-trifluoromethylcarbonylpiperazine, 29, proceeds under conventional conditions using gaseous HCl bubbled through an inert solvent such as methylene chloride, EtOAc, EtO₂, and the like under ambient conditions to provide for the hydrochloride salt of N'-trifluoromethylcarbonylpiperazine, 30. Generally, this reaction is conducted at a temperature ranging from about −20° C. to about 22° C. for about 0.5 to about 4 hours. Upon completion of the reaction, compound 30 can be recovered by conventional methods including neutralization, evaporation, extraction, precipitation, chromatography, filtration, and the like or, alternatively and preferably, is employed in the next step without purification and/or isolation.

Conversion of N'-trifluoromethylcarbonylpiperazine, 30, to the N-carbamyl chloride derivative, 31, conventionally proceeds by contact with phosgene in the manner described above. Upon completion of the reaction, compound 31 can be recovered by conventional methods including neutralization, evaporation, extraction, precipitation, chromatography, filtration, and the like or, alternatively and preferably, is employed in the next step without purification and/or isolation.

Compounds 31 and 24 are coupled under conditions similar to those described above to provide for compound 32 which is orthogonally protected at the amino moiety of the piperazine group as well as the carboxyl moiety of the phenylalanine group. Selective removal of the trifluoromethylcarbonyl amino protecting group proceeds under conventional conditions using an aqueous solution of potassium carbonate to provide for compound 33.

Scheme 7 below illustrates a first route for derivatization of compound 28 to provide for PEG substitution. In this scheme, the amino moiety of the piperazine group is employed as a complementary functional group to the activated carboxyl group of the lysine derivative to form a covalent amide bond thereby introducing two PEG moieties into the compound through a linker of the formula

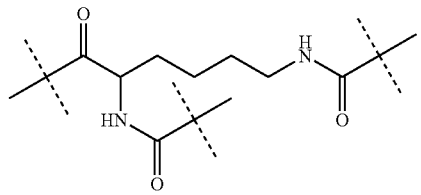

which linker comprises 8 carbon atoms and 5 heteroatoms.

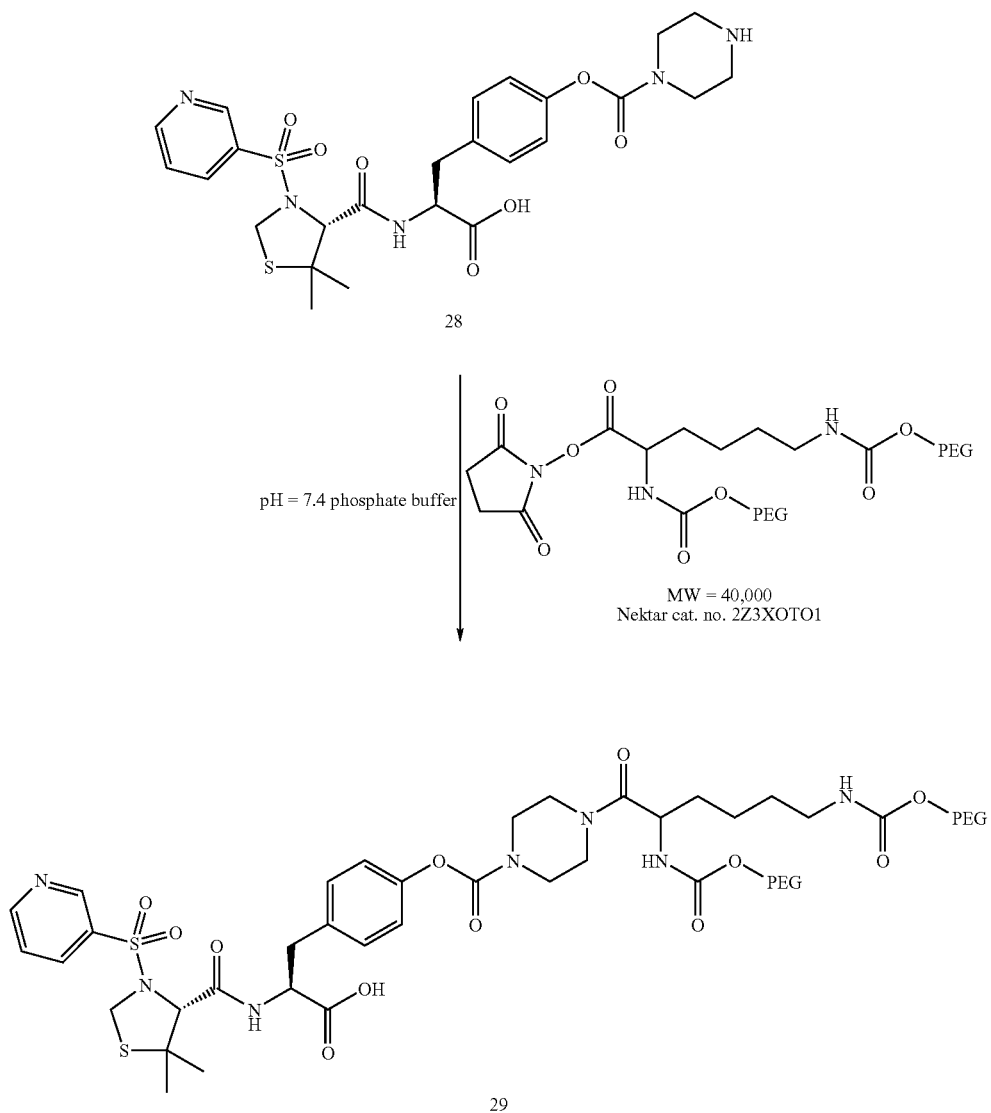

Specifically, in Scheme 7, conjugation of an excess of compound 28 (1.1 to 10 eq) with commercially available N-hydroxysuccinimidyl ester of a di-PEG substituted lysine derivative, in the presence of phosphate buffered aqueous solution provides for compound 29 which is recovered by dialysis. The commercially available N-hydroxy-succinimidyl ester of a di-PEG substituted lysine derivative has a weight average molecular weight of about 40,000 which means that each PEG moiety has a number average molecular weight of about 20,000. The reaction is run at a temperature of about 0 to about 22° C.

Scheme 8 illustrates a second route for derivatization to provide for PEG substitution. In this scheme, the amino moiety of the piperazine group is employed as a complementary functional group to an in situ formed activated carboxyl group of a commercially available carboxyl-PEG compound which under conventional reactive conditions forms a covalent amide bond thereby introducing a single PEG moiety into the compound. In this embodiment, the carboxyl-PEG compound is represented by the formula $HOOC(CH_2)_v(OCH_2CH_2)_pOCH_3$ where p and v are as defined above and the resulting linker to the PEG group is represented by $—C(O)(CH_2)_v—$. Carboxylated PEG compounds can be made by oxidation of the hydroxy terminated PEG compounds using conventional methods and reagents.

Scheme 8

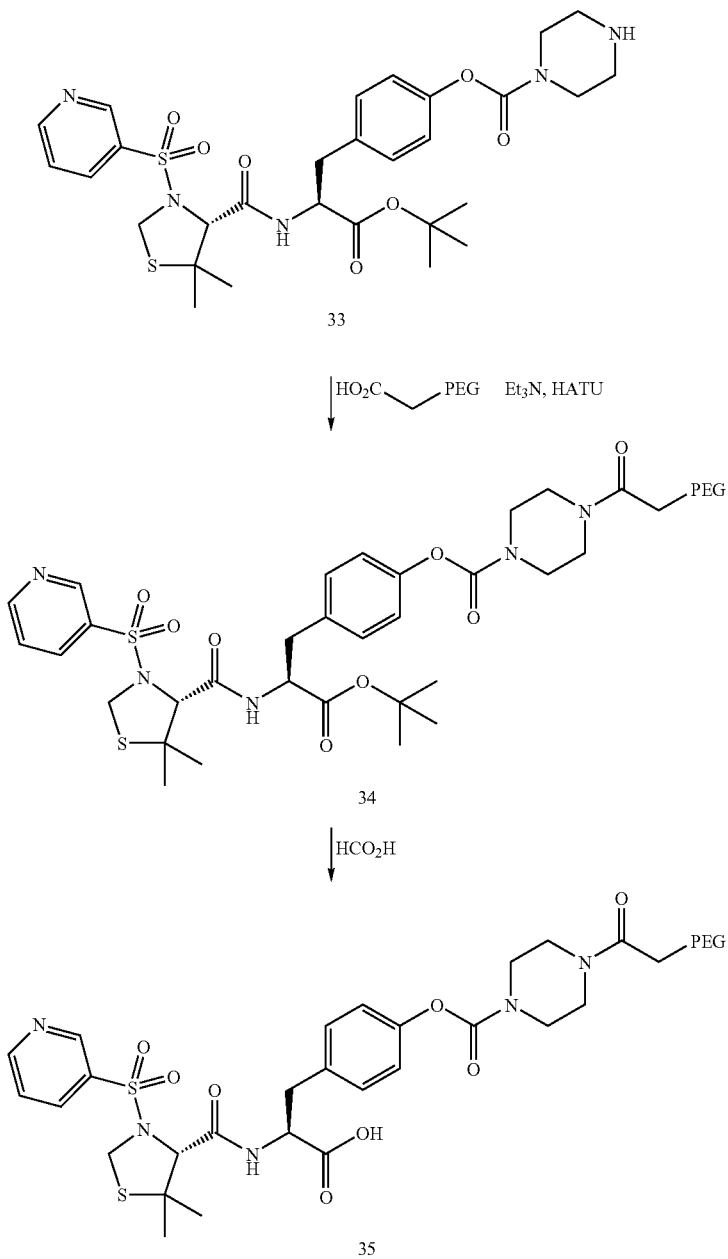

Specifically, in Scheme 8, an excess (1.1 to 10 equiv) of compound 33, prepared as in Scheme 7, is added to at least an equivalent of a commercially available carboxyl-PEG compound which is convertd in situ to an activated ester (not shown) by contact with at least an equivalent and preferably an excess of HATU [O-(7-azabenzotriazol-1-yl)-1,1,3,3,-tetramethyluronium hexafluorophosphate] in the presence of a suitable amine such as triethylamine. Coupling of the carboxyl-PEG compound to compound 33 preferably proceeds at a temperature of from about 0 to about 22° C. for about 2 to about 24 hours. Upon completion of the reaction, the compound 34 is recovered by conventional methods including neutralization, evaporation, extraction, precipitation, chromatography, filtration, and the like or, alternatively, is employed in the next step without purification and/or isolation.

Conventional removal of the t-butyl carboxyl protecting group with an excess of formic acid provides for a mono-PEG compound of formula XXII of this invention.

Scheme 9 illustrates a third route for derivatization to provide for PEG substitution. In this scheme, the amino moiety of the piperazine group is employed as a complementary functional group to an in situ formed chloroformate of a commercially available mono-hydroxy-PEG compound which under conventional reactive conditions forms a covalent carbamate bond thereby introducing a single PEG moiety into the compound. In this embodiment, the mono-hydroxy- PEG compound is represented by the formula HOCH$_2$CH$_2$(OCH$_2$CH$_2$)$_p$OCH$_3$ where p is as defined above and the resulting linker is represented by —C(O)—.
Specifically, in Scheme 9, the hydroxyl group of a commercially available mono-s hydroxy PEG, 36, is converted to the corresponding chloroformate, 37 by reaction with phos-
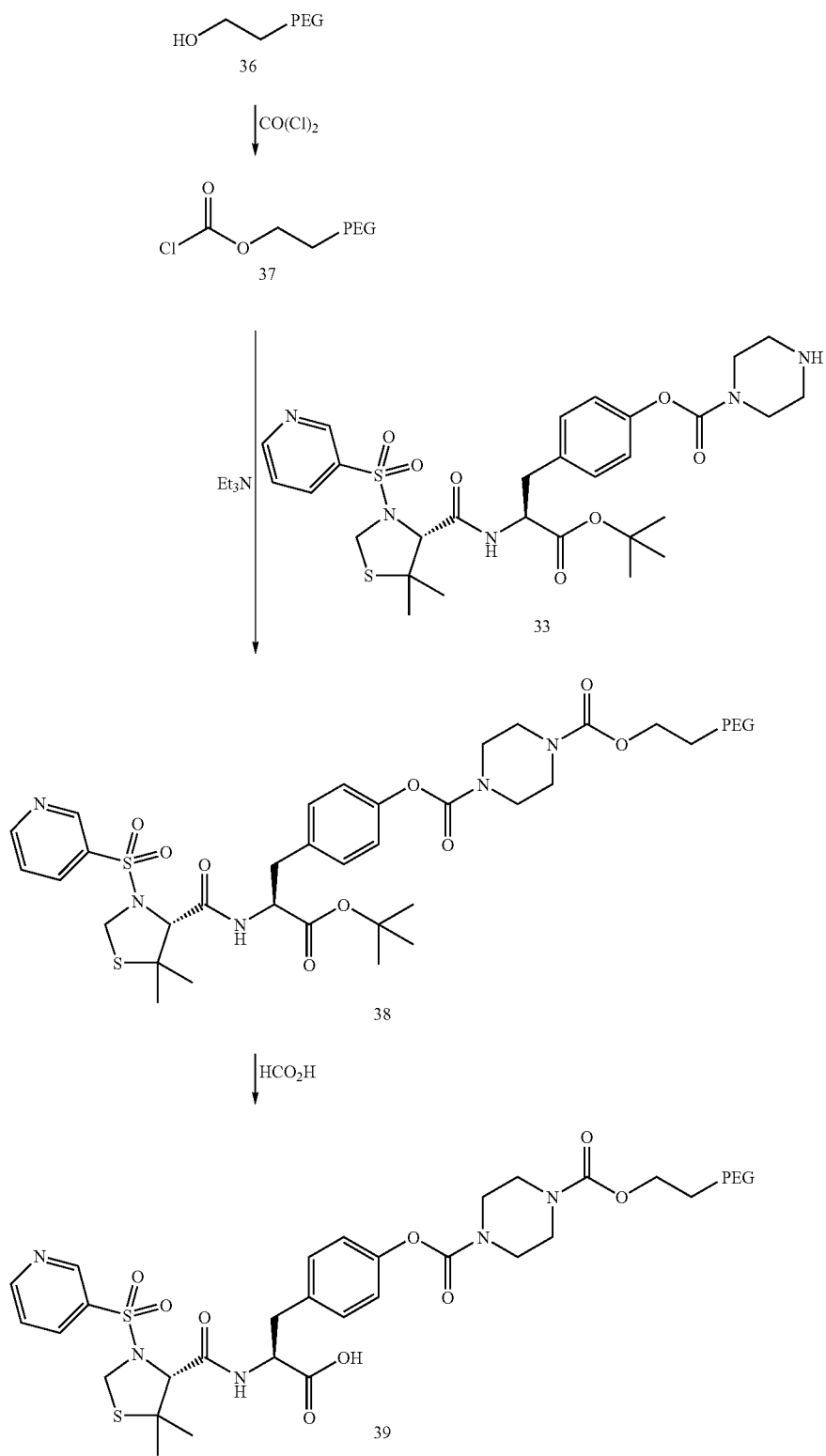

gene in toluene (Fluka), in dichloromethane. The product is isolated by evaporation and is employed in the next step without further purification.

A slight excess (1.1 to 10 eq) of chloroformate 37 is contacted with compound 33 prepared as above, in the presence of a suitable base such as triethylamine to scavenge the acid generated. Coupling of the chloroformate-PEG compound to compound 33 preferably proceeds at a temperature of from about 0 to about 22° C. for about 2 to about 4 hours. Upon completion of the reaction, the compound 38 is recovered by conventional methods including neutralization, evaporation, extraction, precipitation, chromatography, filtration, and the like or, alternatively, is employed in the next step without purification and/or isolation.

Conventional removal of the t-butyl carboxyl protecting group with an excess of formic acid provides for a mono-PEG compound, 39, of formula XXII of this invention.

Scheme 10 illustrates the synthesis of two intermediates useful for subsequent PEG substitution. In this scheme, the amino moiety of the piperazine group is employed as a complementary functional group which is derivatized for subsequent PEG substitution.

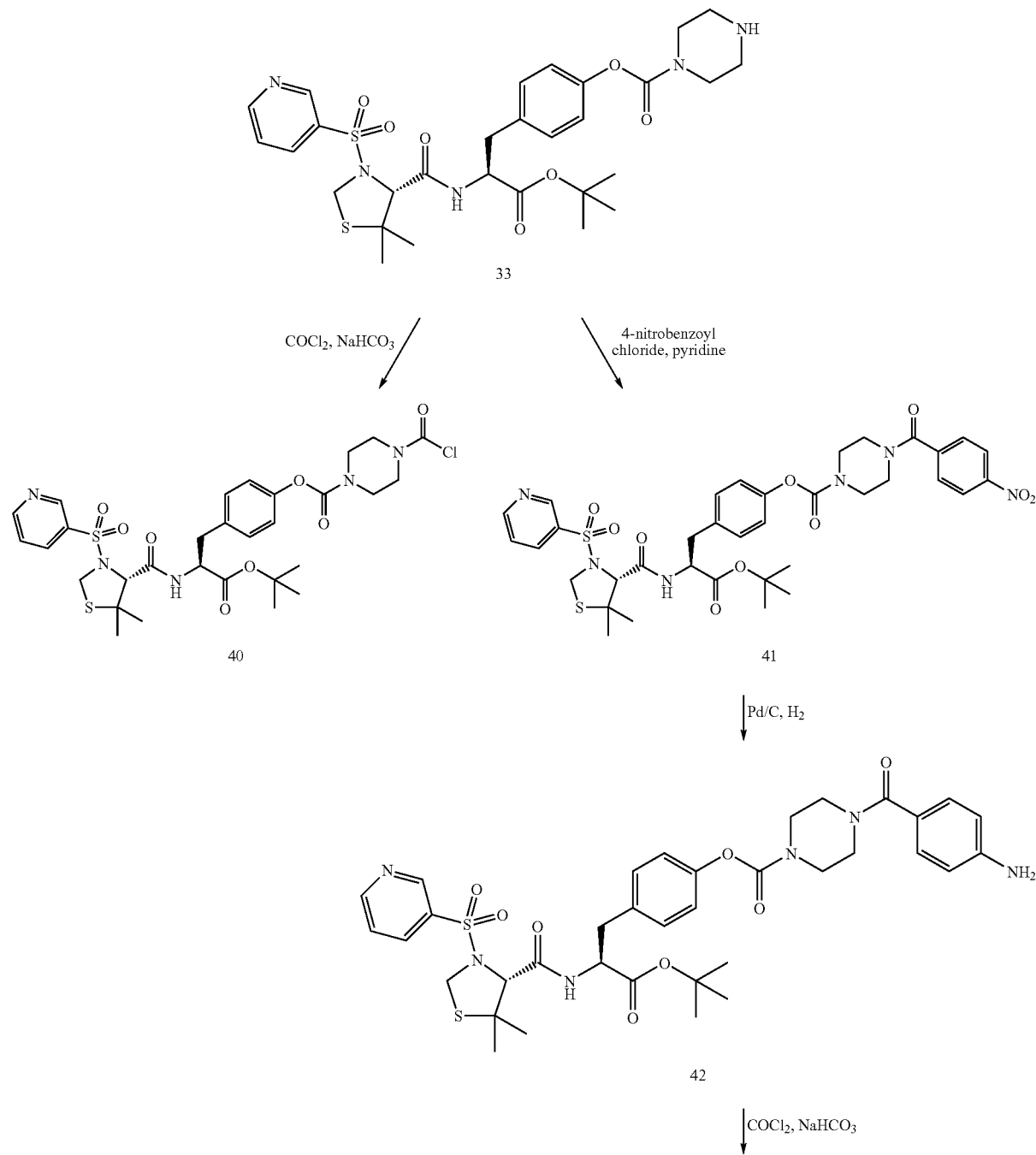

-continued

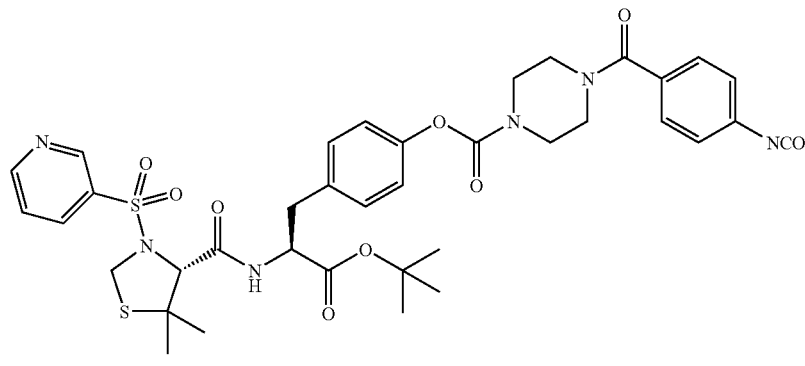

43

Specifically, in Scheme 10, conversion of amino moiety of the piperazine group to the corresponding N-carbamyl chloride derivative, 40, proceeds by contact with an excess of phosgene in the presence of a suitable base such as sodium bicarbonate to scavenge the acid generated during reaction. Upon completion of the reaction, compound 40 can be recovered by conventional methods including neutralization, evaporation, extraction, precipitation, chromatography, filtration, and the like or, alternatively and preferably, is employed in the next step (illustrated in Scheme 11) without purification and/or isolation.

Alternatively, the amino moiety of the piperazine group of compound 33 can be converted to the corresponding amide, compound 41, by reaction with at least an equivalent and preferably an excess of 4-nitrobenzoyl chloride in the presence of a base such as pyridine (which can also act as a solvent) to scavenge the acid generated during reaction. The reaction preferably proceeds at a temperature of from about 0 to about 22° C. for about 1 to about 24 hours. Upon completion of the reaction, compound 41 is recovered by conventional methods including neutralization, evaporation, extraction, precipitation, chromatography, filtration, and the like or, alternatively, is employed in the next step without purification and/or isolation.

Subsequent reduction of the para-nitro substituent of the phenyl group provides for the amine substituent in compound 42. Reduction is conventionally conducted using palladium/carbon under a hydrogen atmosphere typically at elevated pressures in a suitable diluent such as methanol. The reaction proceeds until substantial completion which typically occurs within about 24 to about 72 hours. During the reaction, additional catalyst is added as required to affect reaction completion. Upon completion of the reaction, the compound 42 is recovered by conventional methods including neutralization, evaporation, extraction, precipitation, chromatography, filtration, and the like or, alternatively, is employed in the next step without purification and/or isolation.

Conversion of the para-amino substituent of the phenyl group of compound 42 to the corresponding isocyanate, 43, occurs by reaction with an excess of phosgene in the presence of a suitable base such as sodium bicarbonate which scavenges the acid generated. The reaction proceeds until substantial completion which typically occurs within about 0.5 to about 5 hours at about 0° C. to about 22° C. Upon completion of the reaction, the compound 43 is recovered by conventional methods including neutralization, evaporation, extraction, precipitation, chromatography, filtration, and the like or, alternatively, is employed in the next step without purification and/or isolation.

Scheme 11 illustrates a fourth route for derivatization to provide for PEG substitution. In this scheme, the carbamyl chloride moiety of the piperazine group of compound 40 is employed as a complementary functional group to form a carbamate or urea bond with a commercially available mono-hydroxy- or mono-amino-PEG compound which under conventional reactive conditions. In this embodiment, the PEG compound is represented by the formula $HQCH_2CH_2(OCH_2CH_2)_pOCH_3$ where p and Q are as defined above and the resulting linker is represented by —C(O)—.

Scheme 11

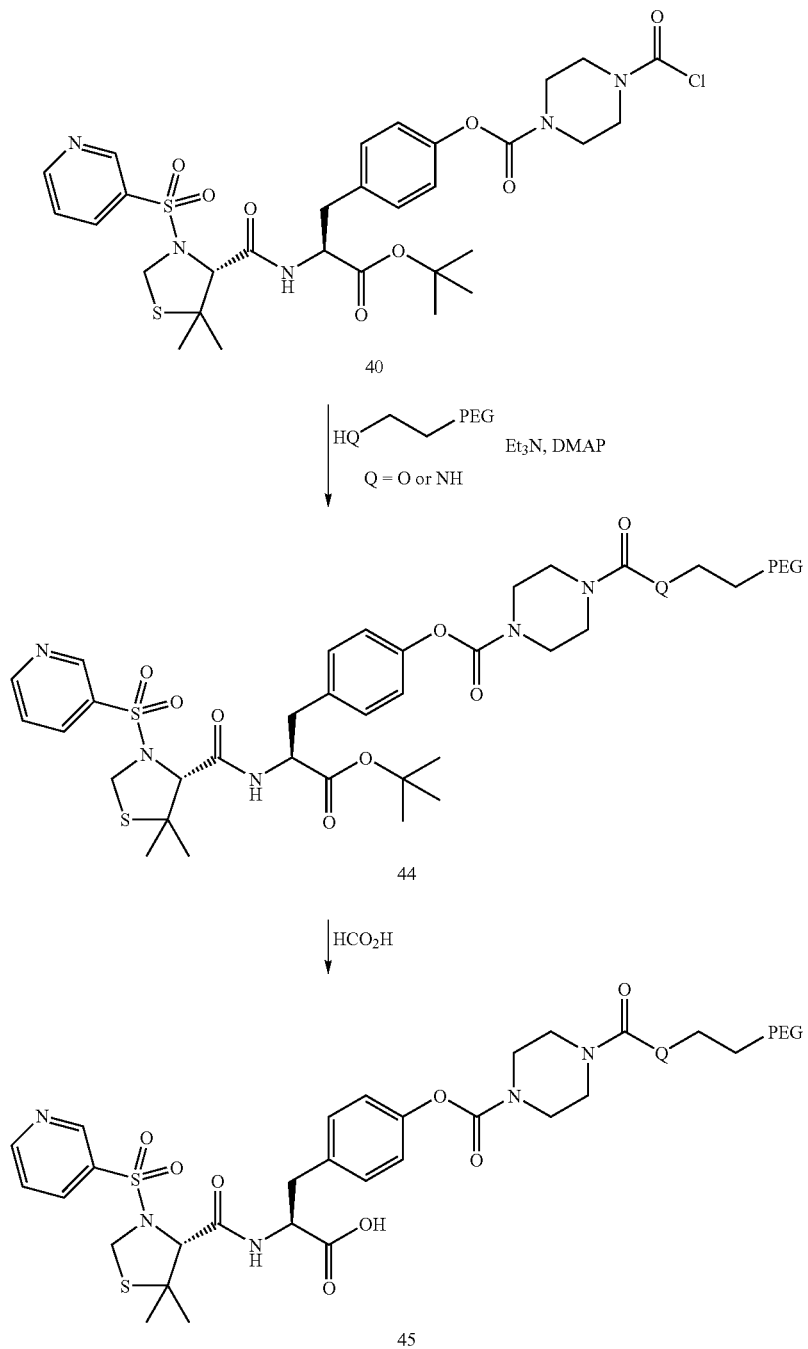

Specifically, in Scheme 11, an excess (1.1 to 10 eq) of carbamyl chloride, 40, is contacted in an inert solvent such as dichloromethane with a suitable mono-hydroxy- or mono-amino-PEG compound preferably in the presence of a suitable base such as triethylamine and/or catalytic amounts of 4-N,N-dimethylaminopyridine (DMAP). The reaction proceeds until substantial completion which typically occurs within about 4 to about 48 hours. Upon completion of the reaction, the compound 44 is recovered by conventional methods including neutralization, evaporation, extraction, precipitation, chromatography, filtration, and the like or, alternatively, is employed in the next step without purification and/or isolation.

When Q is a hydroxyl group, the resulting product contains a carbamate functionality covalently linking the PEG group to the VLA-4 antagonist through a linker represented by —C(O)—. When Q is an amino group, the resulting product contains a urea functionality covalently linking the PEG group to the VLA-4 antagonist through a linker represented by —C(O)—.

Conventional removal of the t-butyl carboxyl protecting group with an excess of formic acid provides for a mono-PEG compound, 45, of formula XXIIa of this invention.

Scheme 12 illustrates a fifth route for derivatization to provide for PEG substitution. In this scheme, the isocyanate moiety of the phenyl group of compound 43 is employed as a complementary functional group to form a carbamate or urea bond with a commercially available mono-hydroxy- or mono-amino-PEG compound which under conventional reactive conditions. In this embodiment, the PEG compound is represented by the formula $HQCH_2CH_2(OCH_2CH_2)_p OCH_3$ where p and Q are as defined above and the resulting linker is represented by:

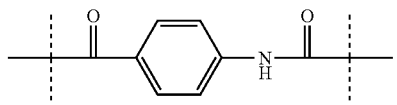

where the linker comprises 8 carbon atoms and 3 heteroatoms.

Scheme 12

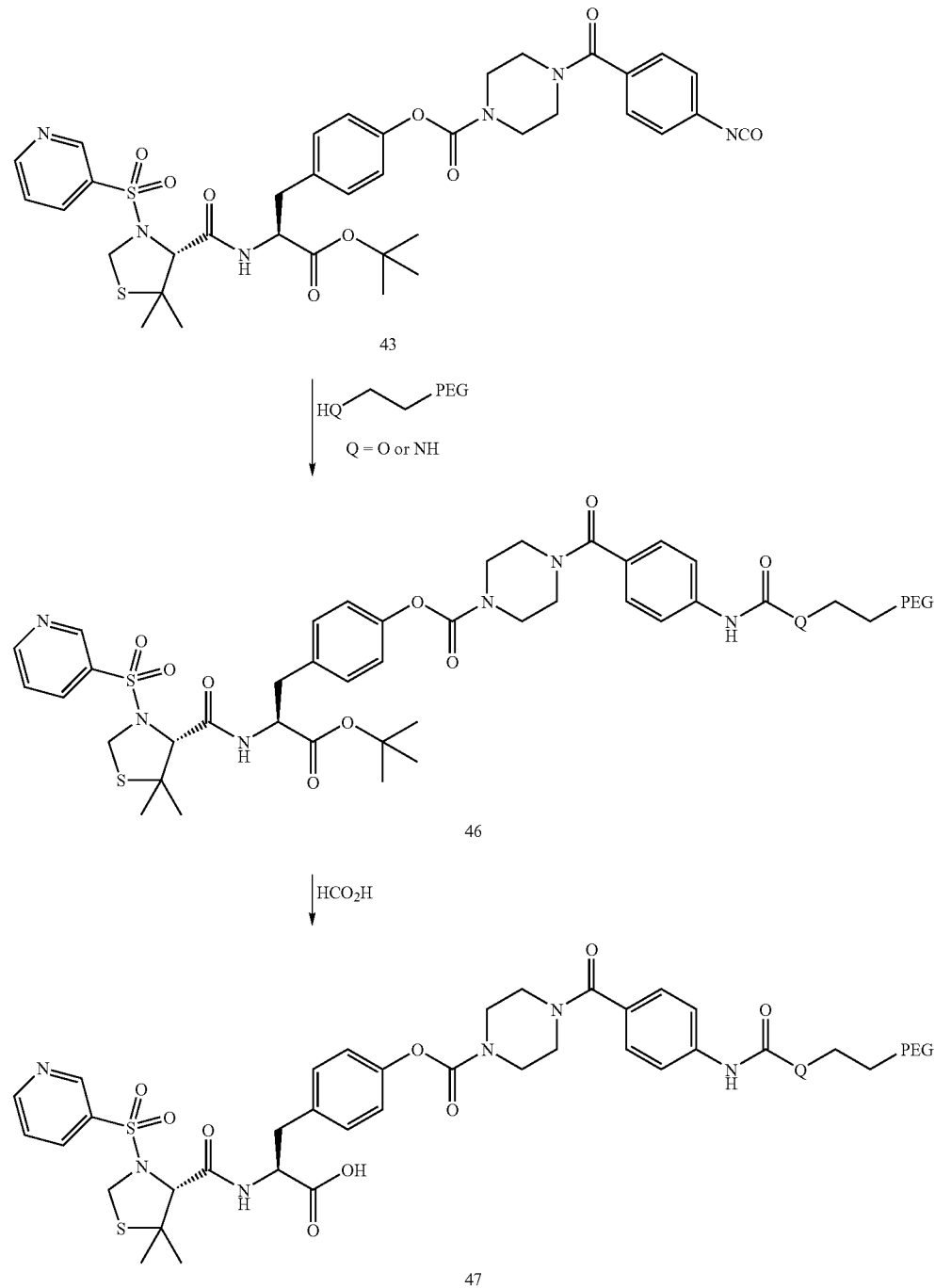

Specifically, in Scheme 12, an excess (1.1 to 10 eq) isocyanate, 43, is contacted with a suitable mono-hydroxy- or mono-amino-PEG compound in a suitable inert diluent such as dichloromethane or toluene. The reaction is preferably maintained at a temperature of from about 0° to about 105° C. until substantial completion which typically occurs within about 1 to about 24 hours. Upon completion of the reaction, compound 46 is recovered by conventional methods including neutralization, evaporation, extraction, precipitation, chromatography, filtration, and the like or, alternatively, is employed in the next step without purification and/or isolation.

When Q is a hydroxyl group, the resulting product contains a carbamate functionality covalently linking the PEG group to the VLA-4 antagonist through a —C(O)— linking group. When Q is an amino group, the resulting product contains a urea functionality covalently linking the PEG group to the VLA-4 antagonist through a —C(O)— linking group.

Conventional removal of the t-butyl carboxyl protecting group with an excess of formic acid provides for a mono-PEG compound, 47, of formula XXII of this invention.

In the Schemes above, amine moieties located on other portions of the molecule can be employed in the manner described above to covalently link a PEG group to the molecule. For example, amines located on $Ar^1$, on the heterocyclic amino acid or on $Ar^2$ can be similarly derivatized to provide for PEG substitution. The amine moieties can be included in these substituents during synthesis and appropriately protected as necessary. Alternatively, amine precursors can be employed. For example, as shown in Scheme 10, reduction of a nitro group provides for the corresponding amine. Similarly, reduction of a cyano group provides for a $H_2NCH_2$— group. Nitro and cyano substituted $Ar^1$ groups are provided in U.S. Pat. No. 6,489,300 as is an amino substituted $Ar^1$ group.

Further, the amino substitution can be incorporated into the heterocyclic amino acid functionality and then derivatized to include a PEG moiety found in formula XXII as R. For example, the heterocyclic amino acid functionality can be 2-carboxylpiperazine depicted in U.S. Pat. No. 6,489,300. Alternatively, commercially available 3- or 4-hydroxyproline can be oxidized to the corresponding ketone and then reductively aminated with ammonia in the presence of sodium cyanoborohydride to form the corresponding amine moiety. Still further, 4-cyanoproline can be reduced to provide for a substituted alkyl group of the formula —$CH_2NH_2$ which can be derivatized through the amine.

Still further, the amine moiety can be incorporated into the $Ar^2$ functionality. Preferably, the amine moiety is present as an amine precursor such as a nitro or cyano group bound to $Ar^2$.

In the schemes above, the reactions of the amine with a complementary functional group can be reversed such that the carboxyl or hydroxyl group is on the VLA-4 antagonist of formula XXIIa (without any PEG substituents) and the amine group could be part of the PEG moiety. In such cases, the amine group, preferably terminating the PEG moiety, can be converted to an isocyanate, using phosgene and $Et_3N$, and reacted with the hydroxyl group to form a carbamate as illustrated in Scheme 13 below:

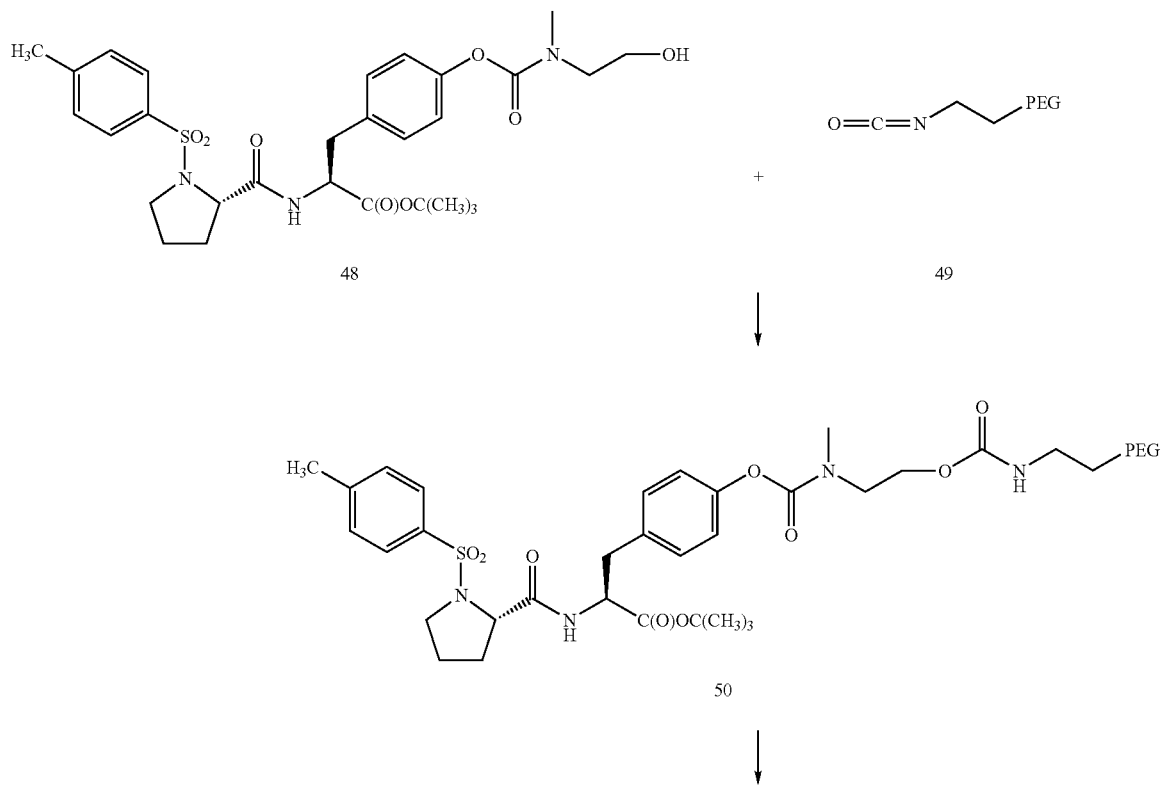

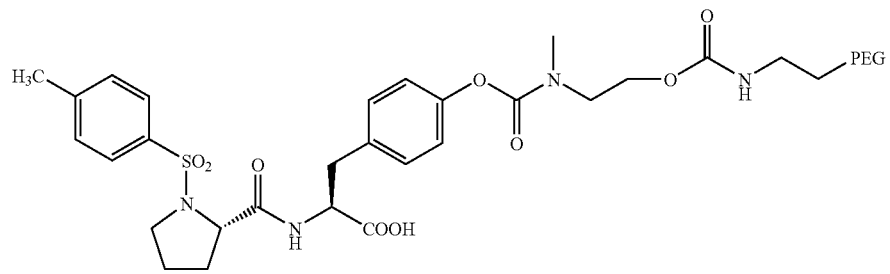

51

Specifically, compound 48 described in U.S. Pat. No. 6,489,300 is contacted with at least an equivalent and preferably an excess of 49 in the manner described above to provide-for the corresponding carbamate, 50. Deprotection, as described above, then provides for compound 51.

Alternatively, in Scheme 13, the hydroxyl functionality can be reacted with phosgene to provide for the chlorocarbonyloxy derivative which reacts with an amine group of a monoamine compound to provide for the carbamate.

Carboxyl functionality, for example on the $Ar^1$ moiety, can be converted to the corresponding amide by reaction with a mono-amino-PEG compound in the manner described above in Scheme 8.

Scheme 14

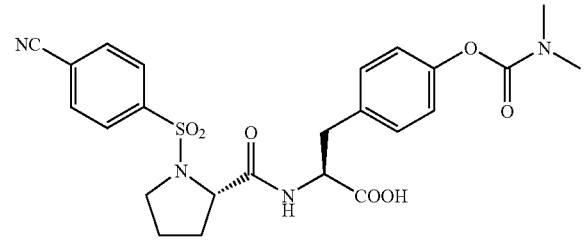

52

↓ tBuOH, H$_2$SO$_4$, MgSO$_4$

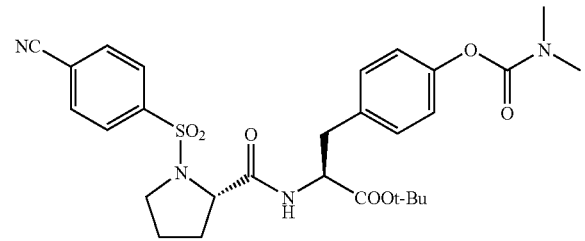

53

↓ H$_2$, Pd/C

-continued

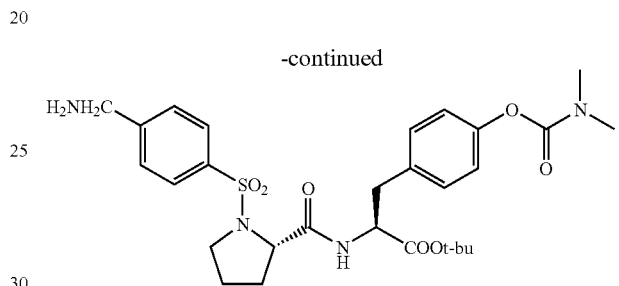

54

↓ 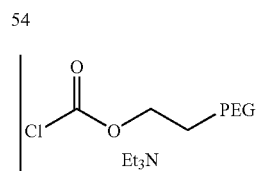
Et$_3$N

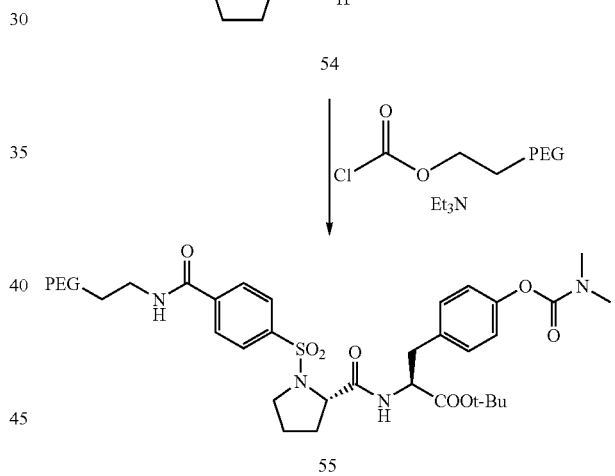

55

↓ H$_2$CO$_2$H

56

Specifically, in Scheme 14, known compound 52, described in U.S. Pat. No. 6,489,300, is t-butyl protected under convention conditions to provide the cyano compound 53, which is hydrogenated under conditions to provide the aminomethyl compound 54. The aminomethyl group is reacted with Et$_3$N and a PEG chloroformate, as illustrated previously in Scheme 9, to provide the carbamate-linked conjugate t-butyl ester 55. Treatment of the t-butyl ester with HCO₂H provides the conjugate carboxylic acid 56.

Suitable PEG compounds are commercially available or can be prepared by art recognized procedures. For example, mono-capped linear PEGs with one terminal amine are available in varying molecular weights (e.g., 2 kilodaltons (kDa), 5 kDa, 10 kDa and 20 kDa from Nektar, San Carlos, Calif.). Preferred mono-capped PEGs having one terminal amine group can be represented by the formula $H_2NCH_2CH_2(OCH_2CH_2)_pOCH_3$.

Mono-capped linear PEGs with one terminal alcohol are available in varying molecular weights (e.g., 2 kilodaltons (kDa), 5 kDa, 10 kDa and 20 kDa from Nektar, San Carlos, Calif.). Preferred mono-capped linear PEGs having one terminal alcohol can be represented by the formula $HOCH_2CH_2(OCH_2CH_2)_pOCH_3$.

Diamino-capped linear PEGs having an amino group at both termini are commercially available and are sometimes referred to as "Jeffamines" (tradename of Huntsman). Preferred diamino-capped linear PEGs having an amino group at both termini can be represented by the formula: $H_2NCH_2CH_2(OCH_2CH_2)_pNH_2$.

Scheme 15 below illustrates an alternative synthesis of 3-aminopyrrolidinyl derivatives useful as starting materials in this invention for subsequent PEG substitution at the amino group.

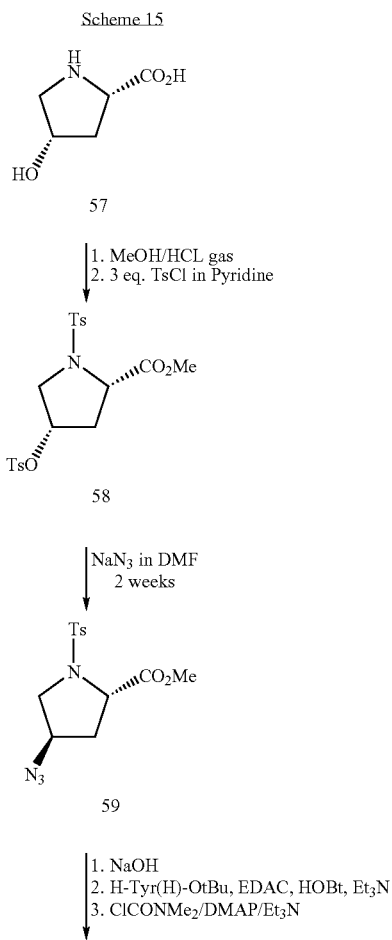

Scheme 15

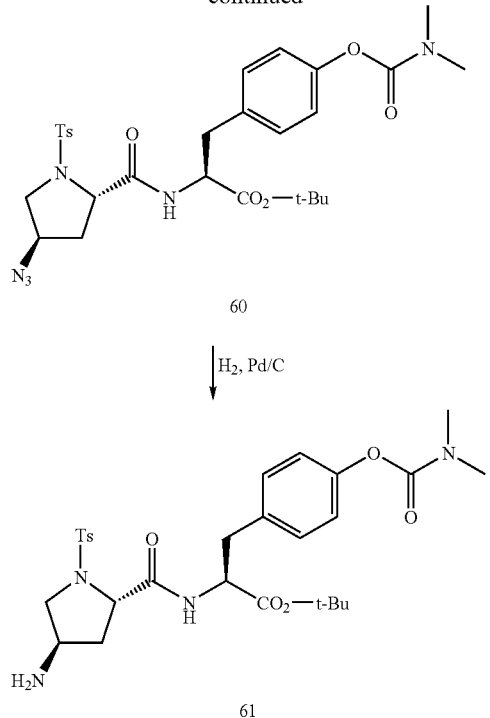

Using conventional methods, commercially available cis-4-hydroxy L-proline, 57, is treated with methanolic hydrogen chloride for several hours at reflux, followed by evaporation, and the so generated methyl ester hydrochloride is treated with excess tosyl chloride in pyridine for two days at room temperature, giving the product, 58. Compound 58 is isolated by neutralizing the pyridine using weak aqueous acid and extracting the product with an organic solvent such as EtOAc. The product 58 may be purified by crystallization, flash chromatography, or more preferably be used in subsequent steps without purification.

Reaction of 58 with a saturated solution of excess sodium azide in DMF at room temperature for 15 days affords compound 59. Compound 59 is isolated by dilution of the reaction mixture with water, followed by extraction with an organic solvent such as EtOAc. The product 59 may be purified by crystallization, flash chromatography, or more preferably be used in subsequent steps without purification.

Compound 59 is treated with sodium hydroxide, in a mixture of water and methanol, thus hydrolyzing the methyl ester and generating a carboxylic acid, which is isolated by acidification and extraction with an organic solvent such as EtOAc. The carboxylic acid is treated with L-tyrosine t-butyl ester [H-Tyr(H)-OtBu], EDAC, HOBt, and Et3N in DMF, generating a dipeptide, which is isolated by dilution with water and extraction with an organic solvent such as EtOAc. The dipeptide is treated with ClCONMe2, Et3N, and DMAP in DCM at reflux for 24 hours, generating the carbamate, 60 which is isolated by dilution with EtOAc, sequential washing with weak aqueous acid and base, and then evaporation. Compound 60 is rigorously purified by flash chromatography.

Finally, compound 61 is prepared by shaking of a solution of 60 in methanol, with a Pd/C catalyst under an atmosphere of hydrogen. The product, 61, is isolated by removal of the catalyst by filtration and evaporation.

Still further, the synthesis of varying mono-capped mono-hydroxy PEGs are described in detail by Campbell, U.S. Pat. No. 4,604,103 which is incorporated herein by reference in its entirety. If a mono-capped mono-amino PEG is preferred, the mono-capped mono-hydroxy PEGs can readily be converted to the corresponding chloride by conventional methods and subsequently converted to an amine by contact with an excess of ammonia.

The PEGs of this invention comprise, for example, the following:

| | |
|---|---|
| HO(alkylene-O)$_p$H | dihydroxy-PEG |
| HO(alkylene-O)$_p$R$^b$ | mono-capped mono-hydroxy PEG |
| H$_2$N(alkylene-O)$_p$R$^b$ | mono-capped mono-amino PEG |
| H$_2$N(alkylene-O)$_p$CH$_2$CH$_2$NH$_2$ | Jeffamines | where p and alkylene are as defined herein and R$^b$ is preferably selected from the group consisting of alkyl, substituted alkyl, aryl and substituted aryl.

The PEG derivatives described herein can be used in the pharmaceuticals formulations described above. Preferably, the formulations are administered orally or parenterally to a subject in need thereof.

Antibodies & Immunoglobulins

In one specific embodiment, the agents of the invention are immunoglobulins that selectively bind to an alpha-4 integrin or a dimer comprising alpha-4 integrin, such as alpha-4 beta-1 or alpha-4 beta-7. The immunoglobulins are preferably antibodies or fragments thereof that bind to an alpha-4 integrin or dimer thereof. Also contemplated herein are immunoglobulin molecules that bind to VCAM-1 in a manner such that they inhibit VCAM-1 interaction with VLA-4. By antibodies is meant to include complete immunoglobulins such as IgG1 or IgM, or inhibitors derived from antibodies, such as Antegren™. Preferably, the immunoglobulins recognize epitopes on VLA-4 and by recognizing and binding to these epitopes, the immunoglobulines inhibit VLA-4 from interacting with VCAM-1.

When the agent of the invention is an antibody, a monoclonal antibody is the preferred antibody. In contrast to polyclonal antibody preparations, which typically include different antibodies directed against different epitopes, each monoclonal antibody is directed against a single epitope on the antigen. A second advantage of monoclonal antibodies is that they are synthesized by means that are uncontaminated by other immunoglobulins, e.g., by phage display or isolation from a hybridoma. Although the present invention intends to encompass both polyclonal and monoclonal antibodies as agents of the invention, monoclonal antibodies are preferred as they are highly specific, and the invention is thus discussed primarily in terms of monoclonal antibodies.

"Native antibodies and immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V$_H$) followed by a number of constant domains. Each light chain has a variable domain at one end (V$_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., 1985, *J. Mol. Biol.*, 186: 651-63; Novotny et al., 1985, *Proc. Natl. Acad. Sci. USA*, 82: 4592-6).

In addition, other antibodies can be identified using techniques available in the art. For example, monoclonal antibodies of the present invention can be produced using phage display technology. Antibody fragments, which selectively bind to an alpha-4 integrin or a dimer comprising an alpha-4 integrin, are then isolated. Exemplary preferred methods for producing such antibodies via phage display are disclosed in U.S. Pat. Nos. 6,225,447; 6,180,336; 6,172,197; 6,140,471; 5,969,108; 5,885,793; 5,872,215; 5,871,907; 5,858,657; 5,837,242; 5,733,743 and 5,565,332.

A "variant" antibody, refers herein to an immunoglobulin molecule that differs in amino acid sequence from a "parent" antibody amino acid sequence by virtue of addition, deletion and/or substitution of one or more amino acid residue(s) in the parent antibody sequence. The parent antibody or immunoglobulin can be a polyclonal antibody, monoclonal antibody, humanized antibody, Primatized® antibody or any antibody fragment. In the preferred embodiment, the variant-comprises one or more amino acid substitution(s) in one or more hypervariable region(s) of the parent antibody. For example, the variant may comprise at least one, e.g., from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. No N-terminal, C-terminal, or internal extensions, deletions, or insertions into the antibody sequence shall be construed as affecting sequence identity or homology. The variant retains the ability to bind the receptor and preferably has properties that are superior to those of the parent antibody. For example, the variant may have a stronger binding affinity, enhanced ability to activate the receptor, etc. To analyze such properties, one should compare a Fab form of the variant to a Fab form of the parent antibody or a full-length form of the variant to a full-length form of the parent antibody. The variant antibody of particular interest herein is one which displays at least about 10 fold, preferably at least about 20 fold, and most preferably at least about 50 fold, enhancement in biological activity when compared to the parent antibody. The "parent" antibody herein is one that is encoded by an amino acid sequence used for the preparation of the variant. Preferably, the parent antibody has a human framework region and has human antibody constant region(s). For example, the parent antibody may be a humanized or human antibody. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody-in-situ within recombinant cells since at least one component of the antibody's natural environment will not be present. Ordinarily, however, isolated antibodies will be prepared by at least one purification step.

Monoclonal Antibodies. Monoclonal antibodies can also be produced using the conventional hybridoma methods. These methods have been widely applied to produce hybrid cell lines that secrete high levels of monoclonal antibodies against many specific antigens, and can also be used to produce monoclonal antibodies of the present invention. For example, mice (e.g., Balb/c mice) can be immunized with an antigenic alpha-4 epitope by intraperitoneal injection. After sufficient time has passed to allow for an immune response, the mice are sacrificed and the spleen cells obtained and fused with myeloma cells, using techniques well known in the art. The resulting fused cells, hybridomas, are then grown in a selective medium, and the surviving cells grown in such medium using limiting dilution conditions. After cloning and recloning, hybridomas can be isolated that secrete antibodies (for example, of the IgG or IgM class or IgG1 subclass) that selectively bind to the target, alpha-4 or a dimer comprising an alpha-4 integrin. To produce agents specific for human use, the isolated monoclonal can then be used to produce chimeric and humanized antibodies. Antibodies can also be prepared that are anti-peptide antibodies. Such anti-peptide antibodies would be prepared against peptides of alpha-4 integrin.

Chimeric, Primatized® and humanized antibodies can be produced from non-human antibodies, and can have the same or similar binding affinity as the antibody from which they are produced. Techniques developed for the production of chimeric antibodies (Morrison et al., 1984 *Proc. Natl. Acad. Sci.* 81: 6851; Neuberger et al., 1984 *Nature* 312: 604; Takeda et al., 1985 *Nature* 314: 452) by splicing the genes from a mouse antibody molecule of appropriate antigen specificity together with genes from, for example, a human antibody molecule of appropriate biological activity can be used; such antibodies are within the scope of this invention. For example, a nucleic acid encoding a variable (V) region of a mouse monoclonal antibody can be joined to a nucleic acid encoding a human constant (C) region, e.g., IgG1 or IgG4. The resulting antibody is thus a species hybrid, generally with the antigen binding domain from the non-human antibody and the C or effector domain from a human antibody.

Humanized antibodies are antibodies with variable regions that are primarily from a human antibody (the acceptor antibody), but which have complementarity determining regions substantially from a non-human antibody (the donor antibody). See, e.g., Queen et al., 1989 *Proc. Natl. Acad. Sci. USA* 86: 10029-33; WO 90/07861; and U.S. Pat. Nos. 6,054,297; 5,693,761; 5,585,089; 5,530,101 and 5,224,539. The constant region or regions of these antibodies are generally also from a human antibody. The human variable domains are typically chosen from human antibodies having sequences displaying a high homology with the desired non-human variable region binding domains. The heavy and light chain variable residues can be derived from the same antibody, or a different human antibody. In addition, the sequences can be chosen as a consensus of several human antibodies, such as described in WO 92/22653.

Specific amino acids within the human variable region are selected for substitution based on the predicted conformation and antigen binding properties. This can be determined using techniques such as computer modeling, prediction of the behavior and binding properties of amino acids at certain locations within the variable region, and observation of effects of substitution. For example, when an amino acid differs between a non-human variable region and a human variable region, the human variable region can be altered to reflect the amino acid composition of the non-human variable region.

In a specific embodiment, the antibodies used in the chronic dosage regime of the present invention are humanized antibodies as disclosed in U.S. Pat. No. 5,840,299, which is incorporated herein by reference.

In another embodiment, transgenic mice containing human antibody genes can be immunized with an antigenic alpha-4 structure and hybridoma technology can be used to generate human antibodies that selectively bind to alpha-4.

Chimeric, human and/or humanized antibodies can be produced by recombinant expression, e.g., expression in human hybridomas (Cole et al., *Monoclonal Antibodies and Cancer Therapy*, Alan R. Liss, p. 77 (1985)), in myeloma cells or in Chinese Hamster Ovary (CHO) cells. Alternatively, antibody-coding sequences can be incorporated into vectors suitable for introducing into the genome of animal thereby producing a transgenic animal. One example would be to produce such antibodies in the milk of a transgenic animal such as a bovine. See, e.g., U.S. Pat. Nos. 5,849,992 and 5,304,489. Suitable transgenes include trangenes having a promoter and/or enhancer from a mammary gland specific gene, for example casein or β-lactoglobulin.

Natalizumab And Related Humanized Antibodies

The invention provides for a method of using humanized immunoglobulins that specifically bind to a VLA-4 ligand either alone or in combination to diagnose and/or treat rheumatoid arthritis. One preferred antibody for use in such methods of treatment and in medicaments includes that described in U.S. Pat. No. 5,840,299 assigned to Elan Pharmaceuticals, which is herein incorporated in its entirety. Another aspect contemplates the use of fragments of these antibodies as assessed in vivo.

The humanized antibodies comprise a humanized light chain and a humanized heavy chain. In one aspect, the humanized light chain can comprise three complementarity determining regions (i.e., CDR1, CDR2 and CDR3) having amino acid sequences from the corresponding complementarity determining regions of a mouse 21-6 immunoglobulin light chain, and a variable region framework from a human kappa light chain variable region framework sequence except in at least one position selected from a first group consisting of positions L45, L49, L58 and L69, wherein the amino acid position is occupied by the same amino acid present in the equivalent position of the mouse 21.6 immunoglobulin light chain variable region framework.

The humanized heavy chain comprises three complementarity determining regions (i.e., CDR1, CDR2 and CDR3) having amino acid sequences from the corresponding complementarity determining regions of a mouse 21-6 immunoglobulin heavy chain, and a variable region framework from a human heavy chain variable region framework sequence except in at least one position selected from a group consisting of H27, H28, H29, H30, H44, H71, wherein the amino acid position is occupied by the same amino acid present in the equivalent position of the mouse 21-6 immunoglobulin heavy chain variable region framework. The immunoglobulins specifically bind to VLA-4 with an affinity having a lower limit of about $10^7$ M$^{-1}$ and an upper limit of about five times the affinity of the mouse 21-6 immunoglobulin.

Usually, the humanized light and heavy chain variable region frameworks are from RE1 and 21/28'CL variable region framework sequences respectively. When the humanized light chain variable region framework is from RE1, at least two framework amino acids are replaced. One amino acid is from the first group of positions described supra. The other amino acids are from a third-group-consisting of positions L104, L105 and L107. This position is occupied by the same amino acid present in the equivalent position of a kappa light chain from a human immunoglobulin other than RE1.

Some humanized immunoglobulins have a mature light chain variable region sequence designated La or Lb, or a mature heavy chain variable region sequence designated Ha, Hb or Hc (FIG. 13). Preferred humanized immunoglobulins include those having a La light chain and an Ha, Hb or Hc heavy chain.

The humanized immunoglobulins have variable framework regions substantially from a human immunoglobulin (termed an acceptor immunoglobulin) and complementarity determining regions substantially from a mouse immunoglobulin termed mu MAb 21.6 (referred to as the donor immunoglobulin). The constant region(s), if present, are also substantially from a human immunoglobulin. The humanized antibodies exhibit a specific binding affinity for VLA-4 of at least $10^7$, $10^8$, or $10^{10}$ M$^{-1}$. Usually the upper limit of binding affinity of the humanized antibodies for VLA-4 is within a factor of three or five of that of mu MAb 21.6 (about $10^9$ M$^{-1}$). Often the lower limit of binding affinity is also within a factor of three or five of that of mu MAb 21.6.

Humanized antibodies can be produced as exemplified, for example, with the mouse MAb 21.6 monoclonal antibody. The starting material for production of humanized antibodies is mu MAb 21.6. The isolation and properties of this antibody are described in U.S. Pat. No. 6,033,655 (assigned to Elan Pharmaceuticals, Inc.), which is herein incorporated by reference in its entirety. Briefly, mu MAb 21.6 is specific for the $\alpha_4$ subunit of VLA-4 and has been shown to inhibit human lymphocyte binding to tissue cultures of rat brain cells stimulated with tumor necrosis factor. From N-terminal to C-terminal, both light and heavy chains comprise the domains FR1, CDR1, FR2, CDR2, FR3, CDR3 and FR4. The assignment of amino acids to each domain is in accordance with the numbering convention of Kabat.

The next step involved selecting human antibodies to supply framework residues. The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., *Protein Engineering* 4: 773 (1991); Kolbinger et al., *Protein Engineering* 6: 971 (1993).

Suitable human antibody sequences are identified by computer comparisons of the amino acid sequences of the mouse variable regions with the sequences of known human antibodies. The comparison is performed separately for heavy and light chains but the principles are similar for each. This comparison reveals that the mu 21.6 light chain shows greatest sequence identity to human light chains of subtype kappa 1; the mu 21.6 heavy chain shows greatest sequence identity to human heavy chains of subtype one, as defined by Kabat, supra. Thus, light and heavy human framework regions are usually derived from human antibodies of these subtypes, or from consensus sequences of such subtypes. The preferred light and heavy chain human variable regions showing greatest sequence identity to the corresponding regions from mu MAb 21.6 are from antibodies RE1 and 21/28'CL respectively.

Computer modeling can then be used to further enhance the humanized antibody's ability to bind to its cognate antigen. The unnatural juxtaposition of murine CDR regions with human variable framework region can result in unnatural conformational restraints, which, unless corrected by substitution of certain amino acid residues, lead to loss of binding affinity. The selection of amino acid residues for substitution is determined, in part, by computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. For example, for the light chain of mu MAb 21.6, the starting point for modeling the framework regions, CDR1 and CDR2 regions, was the human light chain RE1. For the CDR3 region, the starting point was the CDR3 region from the light chain of a different human antibody HyHEL-5. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

As-noted supra, the humanized antibodies of the invention comprise variable framework regions substantially from a human immunoglobulin and complementarity determining regions substantially from a mouse immunoglobulin termed mu MAb 21.6. Having identified the complementarity determining regions (CDRs) of mu MAb 21.6 and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a HAMA response in humans. Amino acids are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

When an amino acid differs between a mu MAb 21.6 variable framework region and an equivalent human variable framework region, the human framework amino acid should usually be substituted by the equivalent mouse amino acid if it is reasonably expected that the amino acid:

(1) non-covalently binds antigen directly (e.g., amino acids at positions L49, L69 of mu MAb 21.6),
(2) is adjacent to a CDR region, is part of a CDR region under the alternative definition proposed by Chothia et al., supra, or otherwise interacts with a CDR region (e.g., is within about 3 Å of a CDR region) (e.g., amino acids at positions L45, L58, H27, H28, H29, H30 and H71 of mu MAb 21.6), or
(3) participates in the $V_L$-$V_H$ interface (e.g., amino acids at position H44 of mu MAb 21.6).

Other candidates for substitution are acceptor human framework amino acids that are unusual for a human immunoglobulin at that position (e.g., amino acids at positions L104, L105 and L107 of mu MAb 21.6). These amino acids can be substituted with amino acids from the equivalent position of more typical human immunoglobulins. Alternatively, amino acids from equivalent positions in the mouse MAb 21.6 can be introduced into the human framework regions when such amino acids are typical of human immunoglobulin at the equivalent positions.

In general, substitution of all or most of the amino acids fulfilling the above criteria is desirable. Occasionally, however, there is some ambiguity about whether a particular amino acid meets the above criteria, and alternative variant immunoglobulins are produced, one of which has that particular substitution, the other of which does not. The humanized antibodies will usually contain a substitution of a human light chain framework residue with a corresponding mu MAb 21.6 residue in at least 1, 2 or 3, and more usually 4, of the following positions: L45, L49, L58 and L69. The humanized antibodies also usually contain a substitution of a human heavy chain framework residue in at least 1, 2, 3, 4, or 5, and sometimes 6, of the following positions: H27, H28, H29, H30, H44 and H71. Optionally, H36 may also be substituted. In preferred embodiments when the human light chain acceptor immunoglobulin is RE1, the light chain also contains substitutions in at least 1 or 2, and more usually 3, of the following positions: L104, L105 and L107. These positions are substituted with the amino acid from the equivalent position of a human immunoglobulin having a more typical amino acid residues. Appropriate amino acids to substitute are shown in FIGS. 13 and 14.

Usually the CDR regions in humanized antibodies are substantially identical, and more usually, identical to the corresponding CDR regions in the mu MAb 21.6 antibody. Occasionally, however, it is desirable to change one of the residues in a CDR region. For example, Example 4 identifies an amino acid similarity between the mu MAb 21.6 CDR3 and the VCAM-1 ligand. This observation suggests that the binding affinity of humanized antibodies might be improved by redesigning the heavy chain CDR3 region to resemble VCAM-1 even more closely. Accordingly, one or more amino acids from the CDR3 domain can be substituted with amino acids from the VCAM-1 binding domain. Although not usually desirable, it is sometimes possible to make one or more conservative amino acid substitutions of CDR residues without appreciably affecting the binding affinity of the resulting humanized immunoglobulin.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. However, in general, such substitutions are undesirable.

Production of Variable Regions.

Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion variants of target polypeptide DNA. See Adelman et al., *DNA* 2: 183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Selection of Constant Region.

The variable segments of humanized antibodies produced as described supra are typically linked to at least a portion of an immunoglobulin constant region (Fc), typically that of a human immunoglobulin. Human constant region DNA sequences can be isolated in accordance with well-known procedures from a variety of human cells, but preferably immortalized B-cells (see Kabat et al., supra, and WO 87/02671) (each of which is incorporated by reference in its entirety). Ordinarily, the antibody will contain both light chain and heavy chain constant regions. The heavy chain constant region usually includes CH1, hinge, CH2, CH3, and CH4 regions.

The humanized antibodies include antibodies having all types of constant regions, including IgM, IgG, IgD, IgA and IgE, and any isotype, including IgG1, IgG2, IgG3 and IgG4. When it is desired that the humanized antibody exhibit cytotoxic activity, the constant domain is usually a complement-fixing constant domain and the class is typically IgG, When such cytotoxic activity is not desirable, the constant domain may be of the $IgG_2$ class. The humanized antibody may comprise sequences from more than one class or isotype.

Other Anti-VLA-4 Antibodies

Other anti-VLA-4 antibodies include but are not limited to HP1/2, HP-2/1, HP2/4, L25, and P4C2. These antibodies may also be administered in an effective amount to diagnose and/or treat imflammatory bowel conditions as one skilled in the art as discussed herein and as generally known in the art would readily appreciate.

Frequently, monoclonal antibodies created in mice are later humanized to avoid the human anti-mouse antibody (HAMA) immune response in a human subject injected with a mouse antibody. This occurs by CDR grafting or reshaping. Thus, typically the antibodies are first mouse monoclonal antibodies that through CDR grafting or reshaping become humanized, as discussed above for the 21.6 antibody.

Specifically, the humanized antibodies have specificity for VLA-4 and have the ability to diagnose and/or treat imflammatory bowel conditions. These antibodies are derived from sources (e.g., mouse typically) that at least one or more of the complementarity determining regions (CDRs) of the variable domains are derived from a donor non-human anti-VLA-4 antibody, and in which there may or may not have been minimal alteration of the acceptor antibody heavy and/or light variable framework region in order to retain donor antibody binding specificity. Preferably, the antigen binding regions of the CDR-grafted heavy chain variable domain comprise the CDRs corresponding to positions 31-35 (CDR1), 50-65 (CDR2) and 95-102 (CDR3). In a preferred embodiment, the heavy chain further includes non-human residues at framework positions 27-30 (Kabat numbering). The heavy chain can further include non-human residues at framework position 75 (Kabat numbering). The heavy chain can further include non-human residues at framework position(s) 77-79 or 66-67 and 69-71 or 84-85 or 38 and 40 or 24 (Kabat numbering). Preferably, the antigen binding regions of the CDR-grafted light chain variable domain comprise CDRs corresponding to positions 24-34 (CDR1), 50-56 (CDR2) and 89-97 (CDR3). In a preferred embodiment, the light chain further includes non-human residues at framework-positions 60- and 67 (Kabat numbering). These residue designations are numbered according to the Kabat numbering (Kabat et al., 5$^{th}$ ed. 4 vol. SEQUENCES OF PROTEINS OF IMMUNOLOGICAL INTEREST, U.S. Department of Health Human Services, NIH, USA (1991)).

Synthesis and Humanization of Mouse Antibody HP1/2. HP1/2 is another antibody that is directed against VLA-4. The method of preparing a humanized version of this antibody for use in human subjects is described herein and is further described in U.S. Pat. No. 6,602,503 assigned to Biogen, Inc., and hereby incorporated by reference in its entirety. The sequences of the humanized antibodies are provided as follows. The HP1/2 V$_H$ DNA sequence and its translated amino acid sequence are:

```
5'-gtc   aaa ctg cag cag tct ggg gca gag ctt gtg aag cca ggg gcc tca
48
     N-Val  Lys Leu Gln Gln Ser Gly Ala Glu Leu Val Lys Pro Gly Ala Ser
     1                   5                   10                  15 gtc   aag ttg ttc tgc aca gct tct ggc ttc aac att aaa gac acc tat
96
     Val   Lys Leu Phe Cys Thr Ala Ser Gly Phe Asn Ile Lys Asp Thr Tyr
                           20                  25                  30 atg   cac tgg gtg aag cag agg cct caa cag ggc ctg gag tgg att gga
144
     Met   His Trp Val Lys Gln Arg Pro Gln Gln Gly Leu Glu Trp Ile Gly
                           35                  40                  45 agg   att gat cct gcg agt ggc gat act aaa tat gac ccg aag ttc cag
192
     Arg   Ile Asp Pro Ala Ser Gly Asp Thr Lys Tyr Asp Pro Lys Phe Gln
                           50                  55                  60 gtc   aag gcc act att aca gcg gac acg tcc tcc aac aca gcc tgg ctg
240
     Val   Lys Ala Thr Ile Thr Ala Asp Thr Ser Ser Asn Thr Ala Trp Leu
           65                  70                  75                  80 cag   ctc agc agc ctg aca tct gag gac act gcc gtc tac tac tgt gca
288
     Gln   Leu Ser Ser Leu Thr Ser Glu Asp Thr Ala Val Tyr Tyr Cys Ala
                           85                  90                  95 gac   gga atg tgg gta tca acg gga tat gct ctg gac ttc tgg ggc caa
336
     Asp   Gly Met Trp Val Ser Thr Gly Tyr Ala Leu Asp Phe Trp Gly Gln
                           100                 105                 110 ggg   acc acg gtc acc gtc tcc tca-3'
```

-continued

```
360
    Gly     Thr Thr Val Thr Val Ser Ser-C
            115             120
```

A comparison between HP1/2 V$_H$ the two sequences and a consensus sequence of family IIC revealed that the only unusual residues are at amino acid positions 80, 98 and 121 (i.e., 79, 94 and 121 in Kabat numbering). Although Tyr-80 is invariant in subgroup IIC other sequenced murine V$_H$ regions have other aromatic amino acids at this position, although none have Trp. The majority of human and murine V$_H$S have an arginine residue at Kabat position 94. The presence of Asp-94 in HP1/2 V$_H$ is extremely rare; there is only one reported example of a negatively charged residue at this position. Proline at Kab at position 113 is also unusual but is unlikely to be important in the conformation of the CDRs because of its distance from them. The amino acids making up CDR1 have been found in three other sequenced murine V$_H$ regions. However, CDR2 and CDR3 are unique to HP1/2 and are not found in any other reported murine V$_H$.

The HP1/2 V$_K$ DNA sequence and its translated amino acid sequence are as follows:

```
        5'-agt   att gtg atg acc cag act ccc aaa ttc ctg ctt gtt tca gca gga
    48
        N-Ser   Ile Val Met Thr Gln Thr Pro Lys Phe Leu Leu Val Ser Ala Gly
                1           5               10              15 gac     agg gtt acc ata acc tgc aag gcc agt cag agt gtg act aat gat
    96
        Asp     Arg Val Thr Ile Thr Cys Lys Ala Ser Gln Ser Val Thr Asn Asp
                        20              25              30 gta     gct tgg tac caa cag aag cca ggg cag tct cct aaa ctg ctg ata
    144
        Val     Ala Trp Tyr Gln Gln Lys Pro Gly Gln Ser Pro Lys Leu Leu Ile
                        35              40              45 tat     tat gca tcc aat cgc tac act gga gtc cct gat cgc ttc act ggc
    192
        Tyr     Tyr Ala Ser Asn Arg Tyr Thr Gly Val Pro Asp Arg Phe Thr Gly
                50              55              60 agt     gga tat ggg acg gat ttc act ttc acc atc agc act gtg cag gct
    240
        Ser     Gly Tyr Gly Thr Asp Phe Thr Phe Thr Ile Ser Thr Val Gln Ala
                65                      70              75              80 gaa     gac ctg gca gtt tat ttc tgt cag cag gat tat agc tct ccg tac
    288
        Glu     Asp Leu Ala Val Tyr Phe Cys Gln Gln Asp Tyr Ser Ser Pro Tyr
                                85              90              95 acg     ttc gga ggg ggg acc aag ctg gag atc-3'
    318
        Thr     Phe Gly Gly Gly Thr Lys Leu Glu Ile-C
                        100             105
```

HP1/2 $V_K$ is a member of Kabat family V (Kabat et al., 5$^{th}$ ed., 4 vol., SEQUENCES OF PROTEINS OF IMMUNOLOGICAL INTEREST, U.S. Department of Health Human Services (1991)) and has no unusual residues. The amino acids of CDR1 and CDR3 are unique. The amino acids making up CDR2 have been reported in one other murine $V_K$.

Design of a CDR-grafted Anti-VLA-4 Antibody. To design a CDR-grafted anti-VLA-4 antibody, it was necessary to determine which residues of murine HP1/2 comprise the CDRs of the light and heavy chains. Three regions of hypervariability amid the less variable framework sequences are found on both light and heavy chains (Wu and Kabat, J. Exp. Med. 132: 211-250 (1970); Kabat et al., (1991)). In most cases these hypervariable regions correspond to, but may extend beyond, the CDR. CDRs of murine HP1/2 were elucidated in accordance with Kabat et al., (1991) by alignment with other $V_H$ and $V_K$ sequences. The CDRs of murine HP1/2 $V_H$ were identified and correspond to the residues identified in the humanized $V_H$ sequences as follows:

| | |
|---|---|
| CDR1 | $AA_{31}$-$AA_{35}$ |
| CDR2 | $AA_{50}$-$AA_{66}$ |
| CDR3 | $AA_{99}$-$AA_{110}$ |

These correspond to $AA_{31}$-$AA_{35}$, $AA_{50}$-$AA_{65}$, and $AA_{95}$-$AA_{102}$, respectively, in Kabat numbering. The CDRs of murine HP1/2 $V_K$ were identified and correspond to the residues identified in the humanized $V_K$ sequences as follows:

| | |
|---|---|
| CDR1 | $AA_{24}$-$AA_{34}$ |
| CDR2 | $AA_{50}$-$AA_{56}$ |
| CDR3 | $AA_{89}$-$AA_{97}$ |

These correspond to the same numbered amino acids in Kabat numbering. Thus, only the boundaries of the $V_K$, but not $V_H$, CDRs corresponded to the Kabat CDR residues. The human frameworks chosen to accept the HP1/2 (donor) CDRs were NEWM and RE1 for the heavy and light chains, respectively. The NEWM and the RE1 sequences have been published in Kabat et al., (1991).

The DNA and corresponding amino acid sequence of the humanized heavy chain variable region of the humanized HP1/2 antibody is:

```
        5'-atg   gac tgg acc tgg agg gtc ttc tgc ttg ctg gct gta gca cca ggt
    48

N-Met    Asp Trp Thr Trp Arg Val Phe Cys Leu Leu Ala Val Ala Pro Gly
        1                     5                  10                  15 gcc      cac tcc cag gtc caa ctg cag gag tcc ggt gct gaa gtt gtt aaa
    96

Ala      His Ser Gln Val Gln Leu Gln Glu Ser Gly Ala Glu Val Val Lys
                              20                  25                  30 ccg      ggt tcc tcc gtt aaa ctg tcc tgc aaa gct tcc ggt ttc aac atc
    144

Pro      Gly Ser Ser Val Lys Leu Ser Cys Lys Ala Ser Gly Phe Asn Ile
                              35                  40                  45 aaa      gac acc tac atg cac tgg gtt aaa cag cgt ccg ggt cag ggt ctg
    192

Lys      Asp Thr Tyr Met His Trp Val Lys Gln Arg Pro Gly Gln Gly Leu
                              50                  55                  60 gaa      tgg atc ggt cgt atc gac ccg gct tcc ggt gac acc aaa tac gac
    240

Glu      Trp Ile Gly Arg Ile Asp Pro Ala Ser Gly Asp Thr Lys Tyr Asp
        65                            70                  75                  80 ccg      aaa ttc cag gtt aaa gct acc atc acc gct gac gaa tcc acc tcc
    288

Pro      Lys Phe Gln Val Lys Ala Thr Ile Thr Ala Asp Glu Ser Thr Ser
                              85                  90                  95 acc      gct tac ctg gaa ctg tcc tcc ctg cgt tcc gaa gac acc gct gtt
```

```
336
     Thr      Ala Tyr Leu Glu Leu Ser Ser Leu Arg Ser Glu Asp Thr Ala Val
                          100           105           110 tac      tac tgc gct gac ggt atg tgg gtt tcc acc ggt tac gct ctg gac
384
     Tyr      Tyr Cys Ala Asp Gly Met Trp Val Ser Thr Gly Tyr Ala Leu Asp
                          115           120           125 ttc      tgg ggt cag ggt acc acg gtc acc gtc tcc tca ggt gag tcc-3'
429
     Phe      Trp Gly Gln Gly Thr Thr Val Thr Val Ser Ser Gly Glu Ser-C
                          130           135           140
```

The DNA and corresponding amino acid sequence of the humanized light chain variable region of the humanized HP1/2 antibody:

```
     5'-atg   ggt tgg tcc tgc atc atc ctg ttc ctg gtt gct acc gct acc ggt
48
     N-Met    Gly Trp Ser Cys Ile Ile Leu Phe Leu Val Ala Thr Ala Thr Gly
              1              5             10            15 gtt      cac tcc atc gtt atg acc cag tcc ccg gac tcc ctg gct gtt tcc
96
     Val      His Ser Ile Val Met Thr Gln Ser Pro Asp Ser Leu Ala Val Ser
                           20            25            30 ctg      ggt gaa cgt gtt acc atc aac tgc aaa gct tcc cag tcc gtt acc
144
     Leu      Gly Glu Arg Val Thr Ile Asn Cys Lys Ala Ser Gln Ser Val Thr
                           35            40            45 aac      gac gtt gct tgg tac cag cag aaa ccg ggt cag tcc ccg aaa ctg
192
     Asn      Asp Val Ala Trp Tyr Gln Gln Lys Pro Gly Gln Ser Pro Lys Leu
                           50            55            60 ctg      atc tac tac gct tcc aac cgt tac acc ggt gtt ccg gac cgt ttc
240
     Leu      Ile Tyr Tyr Ala Ser Asn Arg Tyr Thr Gly Val Pro Asp Arg Phe
              65                 70            75            80 tcc      ggt tcc ggt tac ggt acc gac ttc acc ttc acc atc tcc tcc gtt
288
     Ser      Gly Ser Gly Tyr Gly Thr Asp Phe Thr Phe Thr Ile Ser Ser Val
                           85            90            95 cag      gct gaa gac gtt gct gtt tac tac tgc cag cag gac tac tcc tcc
```

-continued

```
336
    Gln     Ala Glu Asp Val Ala Val Tyr Tyr Cys Gln Gln Asp Tyr Ser Ser
                    100             105             110
    ccg     tac acc ttc ggt ggt ggt acc aaa ctg gag atc taa ggatcctc-3'
383
    Pro     Tyr Thr Phe Gly Gly Gly Thr Lys Leu Glu Ile-C
                    115             120
```

In addition to the above humanized HP1/2 antibody light and heavy chains, other acceptor heavy and light chains regions can also be utilized for insertion of the donor HP1/2 regions. All the following constructs contain Ser-75 (Kabat numbering). The STAW construct further contains Gln to Thr at position 77, Phe to Ala at position 78, and Ser to Trp at position 79 (Kabat numbering). The $V_H$ DNA sequence and its translated amino acid sequence are set forth below:

```
        5'-atg  gac tgg acc tgg agg gtc ttc tgc ttg ctg gct gta gca cca ggt
    48
        N-Met   Asp Trp Thr Trp Arg Val Phe Cys Leu Leu Ala Val Ala Pro Gly
        1                   5               10              15
        gcc     cac tcc cag gtc caa ctg cag gag agc ggt cca ggt ctt gtg aga
    96
        Ala     His Ser Gln Val Gln Leu Gln Glu Ser Gly Pro Gly Leu Val Arg
                        20              25              30
        cct     agc cag acc ctg agc ctg acc tgc acc gtg tct ggc ttc aac att
    144
        Pro     Ser Gln Thr Leu Ser Leu Thr Cys Thr Val Ser Gly Phe Asn Ile
                        35              40              45
        aaa     gac acc tat atg cac tgg gtg aga cag cca cct gga cga ggt ctt
    192
        Lys     Asp Thr Tyr Met His Trp Val Arg Gln Pro Pro Gly Arg Gly Leu
                        50              55              60
        gag     tgg att gga agg att gat cct gcg agt ggc gat act aaa tat gac
    240
        Glu     Trp Ile Gly Arg Ile Asp Pro Ala Ser Gly Asp Thr Lys Tyr Asp
        65                      70              75              80
        ccg     aag ttc cag gtc aga gtg aca atg ctg gta gac acc agc agc aac
    288
        Pro     Lys Phe Gln Val Arg Val Thr Met Leu Val Asp Thr Ser Ser Asn
                        85              90              95
        aca     gcc tgg ctg aga ctc agc agc gtg aca gcc gcc gac acc gcg gtc
    336
        Thr     Ala Trp Leu Arg Leu Ser Ser Val Thr Ala Ala Asp Thr Ala Val
                        100             105             110
        tat     tat tgt gca gac gga atg tgg gta tca acg gga tat gct ctg gac
```

-continued

```
384
    Tyr      Tyr Cys Ala Asp Gly Met Trp Val Ser Thr Gly Tyr Ala Leu Asp
                     115             120             125 ttc      tgg ggc caa ggg acc acg gtc acc gtc tcc tca ggt gag tcc-3'
429
    Phe      Trp Gly Gln Gly Thr Thr Val Thr Val Ser Ser Gly Glu Ser-C
                     130             135             140
```

The KAITAS construct contains the additional changes of Arg to Lys (position 66), Val to Ala (position 67), Met to Ile (position 69), Leu to Thr (position 70) and Val to Ala (position 71) (Kabat numbering. The KAITAS $V_H$ DNA sequence and its translated amino acid sequence are set forth below:

```
    5'-atg   gac tgg acc tgg agg gtc ttc tgc ttg ctg gct gta gca cca ggt
48
    N-Met    Asp Trp Thr Trp Arg Val Phe Cys Leu Leu Ala Val Ala Pro Gly
    1                5               10              15 gcc      cac tcc cag gtc caa ctg cag gag agc ggt cca ggt ctt gtg aga
96
    Ala      His Ser Gln Val Gln Leu Gln Glu Ser Gly Pro Gly Leu Val Arg
                     20              25              30 cct      agc cag acc ctg agc ctg acc tgc acc gtg tct ggc ttc aac att
144
    Pro      Ser Gln Thr Leu Ser Leu Thr Cys Thr Val Ser Gly Phe Asn Ile
                     35              40              45 aaa      gac acc tat atg cac tgg gtg aga cag cca cct gga cga ggt ctt
192
    Lys      Asp Thr Tyr Met His Trp Val Arg Gln Pro Pro Gly Arg Gly Leu
                     50              55              60 gag      tgg att gga agg att gat cct gcg agt ggc gat act aaa tat gac
240
    Glu      Trp Ile Gly Arg Ile Asp Pro Ala Ser Gly Asp Thr Lys Tyr Asp
    65               70              75              80 ccg      aag ttc cag gtc aaa gcg aca att acg gca gac acc agc agc aac
288
    Pro      Lys Phe Gln Val Lys Ala Thr Ile Thr Ala Asp Thr Ser Ser Asn
                     85              90              95 cag      ttc agc ctg aga ctc agc agc gtg aca gcc gcc gac acc gcg gtc
336
    Gln      Phe Ser Leu Arg Leu Ser Ser Val Thr Ala Ala Asp Thr Ala Val
                     100             105             110
```

-continued

```
   tat    tat tgt gca gac gga atg tgg gta tca acg gga tat gct ctg gac
384
   Tyr    Tyr Cys Ala Asp Gly Met Trp Val Ser Thr Gly Tyr Ala Leu Asp
                 115              120              125 ttc    tgg ggc caa ggg acc acg gtc acc gtc tcc tca ggt gag tcc-3'
429
   Phe    Trp Gly Gln Gly Thr Thr Val Thr Val Ser Ser Gly Glu Ser-C
                 130              135              140
```

The SSE construct comprises the additional changes of Ala to Ser (position 84) and Ala to Glu (position 85) (Kabat numbering). The SSE $V_H$ DNA sequence and its translated amino acid sequence are set forth below:

```
         5'-cag  gtc caa ctg cag gag agc ggt cca ggt ctt gtg aga cct agc cag
      48
         N-Gln   Val Gln Leu Gln Glu Ser Gly Pro Gly Leu Val Arg Pro Ser Gln
         1                 5              10              15 acc     ctg agc ctg acc tgc acc gtg tct ggc ttc aac att aaa gac acc
      96
         Thr     Leu Ser Leu Thr Cys Thr Val Ser Gly Phe Asn Ile Lys Asp Thr
                              20              25              30 tat     atg cac tgg gtg aga cag cca cct gga cga ggt ctt gag tgg att
     144
         Tyr     Met His Trp Val Arg Gln Pro Pro Gly Arg Gly Leu Glu Trp Ile
                              35              40              45 gga     agg att gat cct gcg agt ggc gat act aaa tat gac ccg aag ttc
     192
         Gly     Arg Ile Asp Pro Ala Ser Gly Asp Thr Lys Tyr Asp Pro Lys Phe
                              50              55              60 cag     gtc aga gtg aca atg ctg gta gac acc agc agc aac cag ttc agc
     240
         Gln     Val Arg Val Thr Met Leu Val Asp Thr Ser Ser Asn Gln Phe Ser
         65                    70              75              80 ctg     aga ctc agc agc gtg aca tct gag gac acc gcg gtc tat tat tgt
     288
         Leu     Arg Leu Ser Ser Val Thr Ser Glu Asp Thr Ala Val Tyr Tyr Cys
                              85              90              95 gca     gac gga atg tgg gta tca acg gga tat gct ctg gac ttc tgg ggc
     336
         Ala     Asp Gly Met Trp Val Ser Thr Gly Tyr Ala Leu Asp Phe Trp Gly
                              100             105             110 caa     ggg acc acg gtc acc gtc tcc tca ggt gag tcc-3'
```

```
                 372
                     Gln    Gly Thr Thr Val Thr Val Ser Ser Gly Glu Ser-C
                                  115                 120
```

The KRS construct comprises the additional changes of Arg to Lys (position 38) and Pro to Arg (position 40) (Kabat numbering). The KRS V$_H$ DNA sequence and its translated amino acid sequence are set forth below:

```
              5'-atg  gac tgg acc tgg agg gtc ttc tgc ttg ctg gct gta gca cca ggt
          48
              N-Met  Asp Trp Thr Trp Arg Val Phe Cys Leu Leu Ala Val Ala Pro Gly
                1                  5                 10                 15 gcc    cac tcc cag gtc caa ctg cag gag agc ggt cca ggt ctt gtg aga
          96
              Ala    His Ser Gln Val Gln Leu Gln Glu Ser Gly Pro Gly Leu Val Arg
                                 20                 25                 30 cct    agc cag acc ctg agc ctg acc tgc acc gtg tct ggc ttc aac att
         144
              Pro    Ser Gln Thr Leu Ser Leu Thr Cys Thr Val Ser Gly Phe Asn Ile
                                 35                 40                 45 aaa    gac acc tat atg cac tgg gtg aaa cag cga cct gga cga ggt ctt
         192
              Lys    Asp Thr Tyr Met His Trp Val Lys Gln Arg Pro Gly Arg Gly Leu
                                 50                 55                 60 gag    tgg att gga agg att gat cct gcg agt ggc gat act aaa tat gac
         240
              Glu    Trp Ile Gly Arg Ile Asp Pro Ala Ser Gly Asp Thr Lys Tyr Asp
                65                 70                 75                 80 ccg    aag ttc cag gtc aga gtg aca atg ctg gta gac acc agc agc aac
         288
              Pro    Lys Phe Gln Val Arg Val Thr Met Leu Val Asp Thr Ser Ser Asn
                                 85                 90                 95 cag    ttc agc ctg aga ctc agc agc gtg aca gcc gcc gac acc gcg gtc
         336
              Gln    Phe Ser Leu Arg Leu Ser Ser Val Thr Ala Ala Asp Thr Ala Val
                                100                105                110 tat    tat tgt gca gac gga atg tgg gta tca acg gga tat gct ctg gac
         384
              Tyr    Tyr Cys Ala Asp Gly Met Trp Val Ser Thr Gly Tyr Ala Leu Asp
                                115                120                125 ttc    tgg ggc caa ggg acc acg gtc acc gtc tcc tca ggt gag tcc-3'
```

```
429
    Phe     Trp Gly Gln Gly Thr Thr Val Thr Val Ser Ser Gly Glu Ser-C
                130            135           140
```

The AS construct comprises the change Val to Ala at position 24 (Kabat numbering). The AS $V_H$ DNA sequence and its translated amino acid sequence are:

```
     5'-atg  gac tgg acc tgg agg gtc ttc tgc ttg ctg gct gta gca cca ggt
48
     N-Met   Asp Trp Thr Trp Arg Val Phe Cys Leu Leu Ala Val Ala Pro Gly
       1              5              10             15 gcc     cac tcc cag gtc caa ctg cag gag agc ggt cca ggt ctt gtg aga
96
     Ala     His Ser Gln Val Gln Leu Gln Glu Ser Gly Pro Gly Leu Val Arg
                     20             25             30 cct     agc cag acc ctg agc ctg acc tgc acc gcg tct ggc ttc aac att
144
     Pro     Ser Gln Thr Leu Ser Leu Thr Cys Thr Ala Ser Gly Phe Asn Ile
                     35             40             45 aaa     gac acc tat atg cac tgg gtg aga cag cca cct gga cga ggt ctt
192
     Lys     Asp Thr Tyr Met His Trp Val Arg Gln Pro Pro Gly Arg Gly Leu
                     50             55             60 gag     tgg att gga agg att gat cct gcg agt ggc gat act aaa tat gac
240
     Glu     Trp Ile Gly Arg Ile Asp Pro Ala Ser Gly Asp Thr Lys Tyr Asp
             65             70             75             80 ccg     aag ttc cag gtc aga gtg aca atg ctg gta gac acc agc agc aac
288
     Pro     Lys Phe Gln Val Arg Val Thr Met Leu Val Asp Thr Ser Ser Asn
                            85             90             95 cag     ttc agc ctg aga ctc agc agc gtg aca gcc gcc gac acc gcg gtc
336
     Gln     Phe Ser Leu Arg Leu Ser Ser Val Thr Ala Ala Asp Thr Ala Val
                     100            105            110 tat     tat tgt gca gac gga atg tgg gta tca acg gga tat gct ctg gac
384
     Tyr     Tyr Cys Ala Asp Gly Met Trp Val Ser Thr Gly Tyr Ala Leu Asp
                     115            120            125 ttc     tgg ggc caa ggg acc acg gtc acc gtc tcc tca ggt gag tcc-3'
```

```
                    -continued
429
    Phe    Trp Gly Gln Gly Thr Thr Val Thr Val Ser Ser Gly Glu Ser-C
              130             135            140
```

The humanized light chain generally requires few, if any, modifications. However, in the preparation of humanized anti-VLA-4 antibodies, several empirical changes did improve the immunological activity of the antibody towards its ligand. For example, the humanized heavy chain with the Ser mutation with the murine light chain was about 2.5 fold lower potency than murine HP1/2. The same humanized heavy chain with a humanized light chain was about 4-fold lower potency.

A humanized $V_K$ construct (VK1) comprises a Ser to Asp substitution at position 60, and a Ser for a Tyr at position 67. The DNA sequence and its translated amino acid sequence are set forth below:

```
        5'-atg   ggt tgg tcc tgc atc atc ctg ttc ctg gtt gct acc gct acc ggt
    48
        N-Met    Gly Trp Ser Cys Ile Ile Leu Phe Leu Val Ala Thr Ala Thr Gly
        1                 5              10             15 gtt      cac tcc gac atc cag ctg acc cag agc cca agc agc ctg agc gcc
    96
        Val      His Ser Asp Ile Gln Leu Thr Gln Ser Pro Ser Ser Leu Ser Ala
                              20            25             30 agc      gtg ggt gac aga gtg acc atc acc tgt aag gcc agt cag agt gtg
   144
        Ser      Val Gly Asp Arg Val Thr Ile Thr Cys Lys Ala Ser Gln Ser Val
                              35            40             45 act      aat gat gta gct tgg tac cag cag aag cca ggt aag gct cca aag
   192
        Thr      Asn Asp Val Ala Trp Tyr Gln Gln Lys Pro Gly Lys Ala Pro Lys
                              50            55             60 ctg      ctg atc tac tat gca tcc aat cgc tac act ggt gtg cca agc aga
   240
        Leu      Leu Ile Tyr Tyr Ala Ser Asn Arg Tyr Thr Gly Val Pro Ser Arg
             65                70             75            80 ttc      agc ggt agc ggt agc ggt acc gac ttc acc ttc acc atc agc agc
   288
        Phe      Ser Gly Ser Gly Ser Gly Thr Asp Phe Thr Phe Thr Ile Ser Ser
                              85            90             95 ctc      cag cca gag gac atc gcc acc tac tac tgc cag cag gat tat agc
   336
        Leu      Gln Pro Glu Asp Ile Ala Thr Tyr Tyr Cys Gln Gln Asp Tyr Ser
                             100           105            110 tct      ccg tac acg ttc ggc caa ggg acc aag gtg gaa atc aaa cgt aag     tg-3'
```

-continued

```
386
   Ser     Pro Tyr Thr Phe Gly Gln Gly Thr Lys Val Glu Ile Lys Arg Lys-C
                   115             120             125
```

Another $V_K$ construct (i.e., VK2) has the DQMDY sequences of the original RE 1 framework restored. The DNA and corresponding amino acid sequence are provided below:

```
   5'-atg ggt tgg tcc tgc atc atc ctg ttc ctg gtt gct acc gct acc ggt
48
   N-Met Gly Trp Ser Cys Ile Ile Leu Phe Leu Val Ala Thr Ala Thr Gly
       1               5                   10                  15 gtc cac tcc gac atc cag atg acc cag agc cca agc agc ctg agc gcc
96
   Val His Ser Asp Ile Gln Met Thr Gln Ser Pro Ser Ser Leu Ser Ala
                   20                  25                  30 agc gtg ggt gac aga gtg acc atc acc tgt aag gcc agt cag agt gtg
144
   Ser Val Gly Asp Arg Val Thr Ile Thr Cys Lys Ala Ser Gln Ser Val
                   35              40                  45 act aat gat gta gct tgg tac cag cag aag cca ggt aag gct cca aag
192
   Thr Asn Asp Val Ala Trp Tyr Gln Gln Lys Pro Gly Lys Ala Pro Lys
           50                  55                  60 ctg ctg atc tac tat gca tcc aat cgc tac act ggt gtg cca gat aga
240
   Leu Leu Ile Tyr Tyr Ala Ser Asn Arg Tyr Thr Gly Val Pro Asp Arg
       65                  70                  75              80 ttc agc ggt agc ggt tat ggt acc gac ttc acc ttc acc atc agc agc
288
   Phe Ser Gly Ser Gly Tyr Gly Thr Asp Phe Thr Phe Thr Ile Ser Ser
                       85                  90                  95 ctc cag cca gag gac atc gcc acc tac tac tgc cag cag gat tat agc
336
   Leu Gln Pro Glu Asp Ile Ala Thr Tyr Tyr Cys Gln Gln Asp Tyr Ser
                   100                 105                 110 tct ccg tac acg ttc ggc caa ggg acc aag gtg gaa atc aaa cgt aag tg-3'
386
   Ser Pro Tyr Thr Phe Gly Gln Gly Thr Lys Val Glu Ile Lys Arg Lys-C
                   115             120             125
```

A third $V_K$ construct is VK3 has SVM versus DQM in the amino terminus and two other residue changes. The DNA and corresponding amino acid sequence are:

```
5'-atg ggt tgg tcc tgc atc atc ctg ttc ctg gtt gct acc gct acc ggt
48
   N-Met Gly Trp Ser Cys Ile Ile Leu Phe Leu Val Ala Thr Ala Thr Gly
     1               5                  10                  15 gtc cac tcc gac atc cag atg acc cag agc cca agc agc ctg agc gcc
96
     Val His Ser Asp Ile Gln Met Thr Gln Ser Pro Ser Ser Leu Ser Ala
                    20                  25                  30 agc gtg ggt gac aga gtg acc atc acc tgt aag gcc agt cag agt gtg
144
     Ser Val Gly Asp Arg Val Thr Ile Thr Cys Lys Ala Ser Gln Ser Val
                35                  40                  45 act aat gat gta gct tgg tac cag cag aag cca ggt aag gct cca aag
192
     Thr Asn Asp Val Ala Trp Tyr Gln Gln Lys Pro Gly Lys Ala Pro Lys
         50                  55                  60 ctg ctg atc tac tat gca tcc aat cgc tac act ggt gtg cca gat aga
240
     Leu Leu Ile Tyr Tyr Ala Ser Asn Arg Tyr Thr Gly Val Pro Asp Arg
      65                  70                  75                  80 ttc agc ggt agc ggt tat ggt acc gac ttc acc ttc acc atc agc agc
288
     Phe Ser Gly Ser Gly Tyr Gly Thr Asp Phe Thr Phe Thr Ile Ser Ser
                    85                  90                  95 ctc cag cca gag gac atc gcc acc tac tac tgc cag cag gat tat agc
336
     Leu Gln Pro Glu Asp Ile Ala Thr Tyr Tyr Cys Gln Gln Asp Tyr Ser
                   100                 105                 110 tct ccg tac acg ttc ggc caa ggg acc aag gtg gaa atc aaa cgt aag tg-3'
386
     Ser Pro Tyr Thr Phe Gly Gln Gly Thr Lys Val Glu Ile Lys Arg Lys-C
               115                 120                 125
```

Details regarding how each of these light and heavy chain sequences were prepared are provided in U.S. Pat. No. 6,602,503, which is hereby incorporated by reference in its entirety for all puposes. Various combinations of the above light and heavy chains can be prepared based on computer modeling as known in the art.

Additional antibodies that recognize and bind to $\alpha_4$ integrin are known in the art. These include but are not limited to GG5/3 (Keszthelyi et al., *Neurology* 47(4): 1053-1059 (1996)), FW3-218-1 (ATCC No.: HB-261; an IgG2b antibody against sheep α4 integrin), and R1-2 (ATCC No.: HB-227; IgG2b antibody developed in *Rattus norvegicus*).

Whether the antibodies are developed in mouse or other animals, each of the sequences can be genetically engineered such that they are humanized based on what is known in the art and with the aid of computer modeling. The anti-α4 integrin humanized antibodies can then be assessed for their ability-to diagnose and/or treat imflammatory bowel conditions on the in vitro and in vivo assays disclosed herein.

Antibody Fragments. Also contemplated for use in treating rheumatoid arthritis are antibody fragments of antibodies that bind to anti-alpha4 or VCAM-1 such that they inhibit VLA-4 and VCAM-1 interaction. Antibody fragments include Fab, F(ab')$_2$, scFv and Fv fragments which can be used in the compositions disclosed herein.

The term "Fab fragment" as used herein refers to a partial antibody molecule containing a single antigen-binding region, which consists of a portion of both the heavy and light chains of the molecule.

The term "F(ab')$_2$ fragment" as used herein refers to a partial antibody molecule containing both antigen binding regions, and which consists of the light chains and a portion of the heavy chains of the molecule.

The term "Fv fragment" as used herein refers to the portion of the antibody molecule involved in antigen recognition and binding.

The term "scFv" as used herein refers to single chain Fv (scFv) fragments. These scFv fragments are recombinant antibody derivatives that consist only of the variable domains of antibody heavy and light chains connected by a flexible linker. scFv antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see Pluckthun in *The Pharmacology of Monoclonal Antibodies*, vol. 113, 269-315 (Rosenburg and Moore eds., Springer-Verlag, New York 1994).

Also included in antibody fragments are diabodies. The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., 1993 *Proc. Natl. Acad. Sci. USA* 90: 6444-8.

Antibody fragments also include linear antibodies. The expression "linear antibodies" when used throughout this application refers to the antibodies described in, e.g., Zapata et al., 1995 *Protein Eng.* 8(10): 1057-62. Briefly, these antibodies comprise a pair of tandem Fd segments ($V_H$-$C_H$1-$V_H$-$C_H$1), which form a pair of antigen binding regions. Linear antibodies can be bispecific or monospecific.

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

Antibody Purification. When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10: 163-7 (1992) describe a procedure for isolating antibodies, which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. In instances when the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells is preferably subjected to at least one purification step prior to LPHIC. Examples of suitable purification steps include hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., 1983 *J. Immunol. Meth.* 62: 1-13). Protein G is recommended for all mouse isotypes and for human γ3 (Guss et al., 1986 *EMBO J.* 5: 1567-75). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H$3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin-(such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminant(s) is subjected to LPHIC. Often, the antibody composition to be purified will be present in a buffer from the previous purification step. However, it may be necessary to add a buffer to the antibody composition prior to the LPHIC step. Many buffers are available and can be selected by routine experimentation. The pH of the mixture comprising the antibody to be purified and at least one contaminant in a loading buffer is adjusted to a pH of about 2.5-4.5 using either an acid or base, depending on the starting pH. Preferably, the loading buffer has a low salt concentration (i.e., less than about 0.25 M salt).

The mixture is loaded on the HIC column. HIC columns normally comprise a base matrix (e.g., cross-linked agarose or synthetic copolymer material) to which hydrophobic ligands (e.g., alkyl or aryl groups) are coupled. A preferred HIC column comprises an agarose resin substituted with phenyl groups (e.g., a Phenyl SEPHAROSE™ column). Many HIC columns are available commercially. Examples include, but are not limited to, Phenyl SEPHAROSE 6 FAST FLOW™ column with low or high substitution (Pharmacia LKB Biotechnology, AB, Sweden); Phenyl SEPHAROSE™ High Performance column (Pharmacia LKB Biotechnology, AB, Sweden); Octyl SEPHAROSE™ High Performance column (Pharmacia LKB Biotechnology, AB, Sweden); FRACTOGEL™ EMD Propyl or FRACTOGEL™ EMD Phenyl columns (E. Merck, Germany); MACRO—PREP™ Methyl or MACRO-PREP™ t-Butyl Supports (Bio-Rad, California); WP HI-Propyl ($C_3$)™ column (J. T. Baker, New Jersey); and TOYOPEARL™ ether, phenyl or butyl columns (TosoHaas, PA).

The antibody is eluted from the column using an elution buffer, which is normally the same as the loading buffer. The elution buffer can be selected using routine experimentation. The pH of the elution buffer is between about 2.5-4.5 and has a low salt concentration (i.e., less than about 0.25 M salt). It has been discovered that it is not necessary to use a salt gradient to elute the antibody of interest; the desired product is recovered in the flow through fraction, which does not bind significantly to the column.

The LPHIC step provides a way to remove a correctly folded and disulfide bonded antibody from unwanted contaminants (e.g., incorrectly associated light and heavy fragments). In particular, the method provides a means to substantially remove an impurity characterized herein as a correctly folded antibody fragment whose light- and -heavy chains fail to associate through disulfide bonding.

Diagnostic or therapeutic formulations of the purified protein can be made by providing the antibody composition in the form of a physiologically acceptable carrier, examples of which are provided below.

To remove contaminants (e.g., unfolded antibody and incorrectly associated light and heavy fragments) from the HIC column so that it can be re-used, a composition including urea (e.g., 6.0 M urea, 1% MES buffer pH 6.0, 4 mM ammonium sulfate) can be flowed through the column. Other methods are known in the art.

Immunoglobulin Formulations. Antibodies and immunoglobulins having the desired therapeutic effect may be administered in a physiologically acceptable carrier to a subject. The antibodies may be administered in a variety of ways including but not limited to parenteral administration, including subcutaneous, subdural, intravenous, intramuscular, intrathecal, intraperitoneal, intracerebral, intraarterial, or intralesional routes of administration, localized (e.g., surgical application or surgical suppository), and pulmonary (e.g., aerosols, inhalation, or powder).

Depending upon the manner of introduction, the immunoglobulins may be formulated in a variety of ways. The concentration of therapeutically active immunoglobulin in the formulation (i.e., a formulation sufficient to inhibit rheumatoid arthritis) may vary from about 1 mg/ml to 1 g/ml. Preferably, the immunoglobulin composition, when administered to a subject in need thereof, reaches a blood level of immunoglobulin in the subject of about 10 ng/ml or more.

Preferably, the immunoglobulin is formulated for parenteral administration in a suitable inert carrier, such as a sterile physiological saline solution. For example, the concentration of immunoglobulin in the carrier solution is typically between about 1-100 mg/ml. The dose administered will be determined by route of administration. Preferred routes of administration include parenteral or intravenous administration.

According to one aspect of the invention, the immunoglobulins are administered in combination with methotrexate, to treat, ameliorate, or palliate the symptoms of rheumatoid arthritis. When administered in combination, the immunoglobulins may be administered in the same formulation as the methotrexate, or in a separate formulation. The compounds may be administered prior to, following, or concurrently with the methotrexate such that the benefitsd of the combination therapy are achieved. The calculation of appropriate dosages will be well within the purvue of the skilled artisan. Standard doses of methotrexate for the treatment of rheumatoid arthritis range from 2 mg to 20 mg per dose per week. Dosages of the compounds are as set forth above. The methotrexate dosage may be administered as a single dose or as a divided dose. Once a response has been achieved, the dosage may be reduced if possible to the lowest effective dose. The maximum recommended dose is 20 mg/week. Preferably, methotrexate is administered orally or via injection.

According to an important feature of the invention, an immunoglobulin that recognizes and binds to VLA-4 may be administered alone, or in combination with an anti-inflammatory agent, which is typically used to treat rheumatoid arthritis. Administration of anti-inflammatory agents can occur prior to, concurrent with or after administration with the immunoglobulin.

A therapeutically effective amount of an anti-alpha-4 integrin antibody or immunoglobulin, e.g., Antegren™ (also known as natalizumab), can be estimated by comparison with established effective doses for known antibodies, taken together with data obtained for Antegren™ in both in vivo and in vitro models. As is known in the art, adjustments in the dose may be necessary due to immunoglobulin degeneration or metabolism, systemic versus localized delivery, as well as the age, body weight, general health, sex, diet, time of administration, drug interactions and the severity of the condition of the subject to whom the immunoglobulin is administered. Such adjustments may be made and appropriate doses determined by one of skill in the art through routine experimentation.

Therapeutic formulations of the immunoglobulin are prepared for storage by mixing the immunoglobulin having the desired degree of purity with optional physiologically acceptable carriers, excipients, or stabilizers (*Remington's Pharmaceutical Sciences*, $16^{th}$ ed., A. Osol, Ed., 1980 and more recent editions), in the form of lyophilized cake or aqueous solutions. Acceptable immunoglobulin carriers, excipients or stabilizers are nontoxic, nontherapeutic and/or nonimmunogenic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG). Specific examples of carrier molecules include but are not limited to glycosaminoglycans (e.g., heparin sulfate), hyaluronic acid, keratan-sulfate, chondroitin 4-sulfate, chondroitin 6-sulfate, heparan sulfate and dermatin sulfate, perlecan and pentopolysulfate.

Pharmaceutical compositions comprising immunoglobulins can also include if desired, pharmaceutically acceptable, non-toxic carriers or diluents, which are vehicles commonly used to formulated pharmaceutical compositions for animal or human administration. The diluent is selected so as not to affect the biological activity of the combination. Examples include but are not limited to distilled water, physiological phosphate-buffered saline, Ringer's solutions, dextrose solution, and Hank's solution.

The agents of the invention can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol. The formulations may also contain conventional additives, such as solubilizers, isotonic agents, suspending agents, emulsifying agents, stabilizers and preservatives.

The immunoglobulins may also be utilized in aerosol formulation to be administered via inhalation or pulmonary delivery. The agents of the present invention can be formulated into pressurized acceptable propellants such as dichlorodifluoromethane, propane, nitrogen and the like.

The immunoglobulin also may be entrapped in microcapsules prepared, for example, by coacervation techniques or by interfacial polymerization (e.g., hydroxymethylcellulose or gelatin-microcapsules and poly-methylmethacylate microcapsules), in colloidal drug delivery systems (e.g., liposomes, albumin microspheres, microemulsions, nano-particles and nanocapsules), or in macroemulsions. Such techniques are disclosed in *Remington's Pharmaceutical Sciences*, supra.

The immunglobulin to be used for in vivo administration must be sterile. This is readily accomplished by filtration through sterile filtration membranes, prior to or following lyophilization and reconstitution. The immunglobulin ordinarily will be stored in lyophilized form or in solution.

Therapeutic immunglobulin compositions generally are placed into a container having a sterile access port, for example, an intravenous solution bag or vial having a stopper pierceable by a hypodermic injection needle or similar sharp instrument.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly(vinylalcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e., injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for immunglobulin stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, developing specific polymer matrix compositions, and the like.

Sustained-release immunglobulin compositions also include liposomally entrapped immunglobulin. Liposomes containing the immunglobulin are prepared by methods known per se. See, e.g., Epstein et al., *Proc. Natl. Acad. Sci. USA* 82: 3688-92 (1985); Hwang et al., *Proc. Natl. Acad. Sci. USA* 77: 4030-4 (1980); U.S. Pat. Nos. 4,485,045; 4,544,545; 6,139,869; and 6,027,726. Ordinarily, the liposomes are of the small (about 200 to about 800 Angstroms), unilamellar type in which the lipid content is greater than about 30 mole percent (mol. %) cholesterol; the selected proportion being adjusted for the optimal immunglobulin therapy.

The immunoglobulins of this invention can be administered in a sustained release form, for example a depot injection, implant preparation, or osmotic pump, which can be formulated in such a manner as to permit a sustained release of the active ingredient. Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of protein deposits (e.g., the site of formation of amyloid deposits associated with neurodegenerative disorders), so that the local concentration of active agent is increased at that site relative to the rest of the body.

In addition, immunoglobulins which prevent RA may be provided by administering a polynucleotide encoding a whole or partial antibody (e.g., a single chain Fv) to a subject. The polynucleotide is administered to a subject in an appropriate vehicle to allow the expression of the immunoglobulin in the subject in a therapeutically effective amount.

Certain agents of the invention, including antibodies and peptides, are sometimes administered in combination with an adjuvant. A variety of adjuvants can be used in combination with an anti alpha-4 agent to elicit an immune response. Preferred adjuvants augment the intrinsic response to an agent without causing conformational changes in the agent that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, NY, 1995); U.S. Pat. No. 5,057,540), (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., 1997 *N. Engl. J. Med.* 336: 86-91). Another adjuvant is CpG (WO 98/40100). Alternatively, an agent can be coupled to an adjuvant. However, such coupling should not substantially change the conformation of the desired alpha-4 epitope so as to affect the nature of the host immune response. Adjuvants can be administered as a component of a therapeutic composition with an active agent or can be administered separately, before, concurrently with, or after administration of the therapeutic agent.

A preferred class of adjuvants for administration is aluminum salts (alum), such as aluminum hydroxide, aluminum phosphate, aluminum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™, or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi Immunochem, Hamilton, Mont.) containing 2% squalene, 0.2% Tween 80, and one or more bacterial cell wall components from the group consisting of monophosphoryl lipid A, trehalose dimycolate (TDM), and cell wall skeleton (CWS), preferably MPL+ CWS (Detox™). Another class of preferred adjuvants is saponin adjuvants, such as Stimulon™ (QS-21; Aquila, Framingham, Mass.) or particles generated therefrom such as ISCOMs (immunostimulating complexes) and ISCOMATRIX. Other adjuvants include Incomplete Freund's Adjuvant (IFA), cytokines, such as interleukins (e.g., IL-1, IL-2, and IL-12), macrophage colony stimulating factor (M-CSF), and tumor necrosis factor (TNF). Such adjuvants are generally available from commercial sources.

An adjuvant can be administered with an agent as a single composition, or can be administered before, concurrent with or after administration of the agent. The agent and an adjuvant can be packaged and supplied in the same vial or can be packaged in separate vials and mixed before use. The agent and adjuvant are typically packaged with a label indicating the intended therapeutic application. If the agent and adjuvant are packaged separately, the packaging typically includes instructions for mixing before use. The choice of an adjuvant and/or carrier depends on such factors as the stability of the formulation containing the adjuvant, the route of administration, the dosing schedule, and the efficacy of the adjuvant for the species being vaccinated. In humans, a preferred pharmaceutically acceptable adjuvant is one that has been approved for human administration by pertinent regulatory bodies. Examples of such preferred adjuvants for humans include alum, MPL and QS-21. Optionally, two or more different adjuvants can be used simultaneously. Preferred combinations include alum with MPL, alum with QS-21, MPL with QS-21, and alum, QS-21 and MPL together. Also, Incomplete Freund's adjuvant can be used (Chang et al., *Advanced Drug Delivery Reviews* 32, 173-186 (1998)), optionally in combination with any of alum, QS-21, and MPL and all combinations thereof.

Antegren™. Antegren™ is a humanized monoclonal antibody that has therapeutic potential in that it prevents migration of inflammatory cells from blood vessels to sites of inflammation. Antegren™ binds to cell surface receptors known as alpha-4-beta-1 (VLA-4) and alpha-4-beta7 integrins. These receptors help white blood cells, particularly T lymphocytes and eosinophils, move from the inside of blood vessels out into surrounding tissues of the body at sites of inflammation, where these cells then participate in the inflammatory process. Antegren™ blocks these receptors, thus preventing the cells from contributing to the inflammatory response.

The typical method of administering Antegren™ is intravenous. Intravenous administration requires the final formulation to be isotonic. For example, a formulation of Antegren™, 5 mg/mL in 50 mM L-histidine, 150 mM NaCl, pH 6.0 was initially chosen. During a Phase II study, protein precipitation of the antibody was observed during the dilution and introduction of Antegren™ into the clinical dosing apparatus. Polysorbate 80 was introduced into the formulation to resolve the observed protein precipitation.

The two factors that have been shown to accelerate the precipitation of the Antegren™ antibody are the presence of trace levels of silicone oil and denaturation at the air-liquid interface. The silicone oil was introduced into the product upon use of standard lubricated polypropylene syringes equipped with siliconized rubber stoppers. The introduction of the silicone oil is sufficient to cause discernible antibody precipitation upon gentle agitation and room temperature storage. The aggregation and subsequent precipitation caused by denaturation at the air-liquid interface has become more discernable problematic with the drug being shipped to more clinical sites. Both causes of protein precipitation have been resolved by the addition of polysorbate 80 at a concentration of 0.02% (w/v).

The addition of polysorbate 80 to the formulation also overcomes the problem of precipitating or aggregating antibody when preparing formulations with higher protein content. Initial work focused on agitation-induced aggregation at high protein concentrations, including 50 mg/mL. By subjecting the material to agitation using a vortex-type mixer, aggregated species were detected by size exclusion-high performance liquid chromatography (SEC-HPLC). This model identified polysorbate 80 as an effective inhibitor of aggregation, while sucrose and other buffering components had little beneficial effect.

The effectiveness of the addition of 0.02% (w/v) polysorbate 80 in preventing agitation-induced precipitation at a protein concentration of 5 mg/mL was assessed following addition of 10 μL of a 10% polysorbate 80 solution to vials of Antegren™ (Lot No. AN100226-0003). The vials were shaken on their sides along with several vials of Antegren™ in Formulation #1 at 150 rotations per minute in a horizontal plane. Within 3 hours of this treatment at room temperature, the vials of Formulation #1 were laden with particles and appeared turbid while the vials with 0.02% (w/v) polysorbate 80 remained clear and free of particles.

The observed aggregation is presumed to be caused by the air-surface interface, as vials completely filled with Antegren™ in the absence of polysorbate 80 were shaken for extended periods of time without additional particle formation being induced.

An evaluation of the ability of 0.02% (w/v) polysorbate 80 to inhibit the protein precipitation facilitated by trace levels of silicone was conducted. A vial of Antegren™ (Lot No. AN100226-0003) was adjusted to 0.02% (w/v) polysorbate 80 and drawn into a commercially available, lubricated 60 mL polypropylene syringe. The material was allowed to stand for several hours at room temperature. Visual inspection confirmed that no precipitation was occurring. The material was then filtered through a 0.2 μm filter into a 5-mL vial and inspected and found to be substantially free of particles after several days, while vials treated in the same manner in the absence of polysorbate 80 (Formulation #1) were laden with particles.

Further descriptions of Antegren™ and procedures for preparing this humanized monoclonal antibody are also described in U.S. Pat. No. 5,840,299, which is herein incorporated by reference in its entirety.

Further descriptions of formulations for Antegren™ and procedures for preparing such forumulations of this humanized monoclonal antibody are also described in U.S. provisional Application Ser. No. 60/445,181, which is herein incorporated by reference in its entirety.

Agents and Small Molecule Alpha-4 Integrin Antogonist Compounds that Selectively Bind to Alpha-4 Integrins Various types of agents with the ability to bind to and inhibit alpha-4 integrin can be used in the practice of the invention. Many such agents have been identified and characterized, and specific agents are described below. Given the teachings disclosed herein, it is well within the skill of one in the art to identify other agents that will be able to inhibit the alpha-4-comprising integrin dimers in a manner that biologically mimics or is similar to the specifically described agents, and the present invention is intended to include the chronic administration of such agents. As it is also contemplated to include combinations of agents, discussion of agents other than small compounds are also provided.

Drug Combinations. The anti-alpha-4 integrin agents (e.g., anti-alpha-4 integrin antibodies and methotrexate and small compound alpha-4 integrin antagonists and methotrexate) can be combined with other compounds or compositions used to treat, ameliorate or palliate symptoms associated with RA.

Dosage forms of the agents to be used in combination with the compounds and compositions disclosed herein would vary depending on the subject and drug combination being utilized.

The benefit of such combination therapies is that it may lessen the class-specific and agent-specific side effects currently encountered with some of the drugs. Combinations of drugs that can lessen the quantity of a particular drug administered may reduce adverse side effects experienced by a patient.

When administered in combination, the small compound alpha-4-integrin antagonists may be administered in the same formulation as these other compounds or compositions, or in a separate formulation. When administered in combination, the anti-alpha-4-antibodies are generally administered in a separate formulation than the other compounds and compositions. When administered in combinations, the anti-alpha-4 agents may be administered prior to, following, or concurrently with the other compounds and compositions used to treat, ameliorate, or palliate symptoms.

Chronic Administration Dosage Regimes

The chronic treatment regime of the present invention provides anti-alpha-4 agent at a level that will maintain sufficient receptor saturation to treat rheumatoid arthritis in a patient in need of such. The methods of the invention entails administration once per every two weeks or once a month to once every two months, with repeated dosings taking place over a period of at least six months, and more preferably for a year or longer. The methods of the invention involve obtaining and maintaining a receptor saturation level in a human patient of a dimer comprising alpha-4 integrin (e.g., VLA-4) in a range of from about 65% to 100%, more preferably between 75%, to 100%, and even more preferably between 80-100%. These receptor saturation levels are maintained at these levels chronically (e.g., over a period of 6 months or so) to allow for continued suppression of pathological inflammation.

In a specific embodiment, the anti-alpha-4 agent is an antibody, preferably a humanized or human antibody, and the dosing is on a monthly basis. In another specific embodiment, the anti-alpha-4 agent is a compound of Formula I-XXIX as provided above. Levels of receptor saturation can be monitored to determine the efficacy of the dosing regime, and physiological markers measured to confirm the success of the dosage regime. As a confirmation, serum levels of the antibody can be monitored to identify clearance of the antibody and to determine the potential effect of half-life on the efficacy of the treatment.

The amount of agent administered in a dosage unit may depend on whether adjuvant is also administered, with higher dosages generally being required in the presence of adjuvant. For immunization with an agent of the invention, the dosage ranges from about 0.0001 to 100 mg/kg, and more usually 0.01 to 5 mg/kg, of the host body weight. For example dosages can be 1 mg/kg body weight or 10 mg/kg body weight. Dosage and frequency vary depending on the half-life of the agent in the patient. The dosage and frequency of administration can vary depending on whether the treatment is prophylactic or therapeutic. For an antibody administration, each dosing injection is generally between 2.0 to 8.0 mg/kg dosage. For a compound administration, each dosing injection is generally between 1.0 to 10.0 mg/kg dosage. In accordance with the teachings provided herein, effective dosages can be monitored by obtaining a fluid sample from a patient. For this, generally a blood serum or cerebrospinal fluid sample it taken and integrin receptor saturation is determined using methods well known in the art. Ideally, a sample is taken prior to initial dosing; subsequent samples are taken and measured prior to and/or after each immunization.

When adjuvant is being administered, the dosage level is increased in accordance with the particular adjuvant and the level of immunogenicity of the anti-alpha-4 agent. Doses for individual agents, selected in accordance with the present invention, are determined according to standard dosing methods, taken in conjunction with the teachings provided herein.

As an alternative to chronic administration comprised of repeated individual dosings, an anti-alpha-4 agent can be administered as a sustained release formulation, provided the dosage is such that the levels of receptor saturation remain sufficient to suppress inflammation. For example, controlled release systems can be used to chronically administer an anti-alpha-4 agent within the scope of this invention. Discussions of appropriate controlled release dosage forms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems. Physical systems include, but not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., non-erodible, erodible, environmental agent ingression, and degradable), and materials physically dispersed in non-porous, polymeric, or elastomeric matrices (e.g., non-erodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

The methods of the invention can be used to treat a patient that is affected with a disorder involving or arising from pathological inflammation, or to prophylactically treat a patient at risk for a particular disorder. The dosage regimes necessary for prophylactic versus therapeutic treatment can vary, and will need to be designed for the specific use and disorder treated.

In some methods, two or more agents (e.g., monoclonal antibodies with different binding specificities) are administered simultaneously, in which case the dosage of each agent administered falls within the ranges indicated. Intervals can also be irregular as indicated by measuring receptor saturation levels or by following other indicia of the disease process.

Those of skill will readily appreciate that dose levels can vary as a function of the specific agent, the severity of the symptoms and the susceptibility of the subject to side effects. Some of the specific agents are more potent than others. Preferred dosages for a given agent are readily determinable by those of skill in the art by a variety of means. A preferred means is to measure the physiological potency of a given agent.

In prophylactic applications, pharmaceutical compositions are chronically administered to a patient susceptible to, or otherwise at risk of, a particular disease in an amount sufficient to eliminate or reduce the risk or delay the outset of the disease. Such an amount is defined to be a prophylactically effective dose.

The anti alpha-4 agents of the invention can be used with effective amounts of other therapeutic agents against acute and chronic inflammation. Such agents include other antagonists of adhesion molecules (e.g., other integrins, selecting, and immunoglobulin (Ig) superfamily members (see Springer, Nature (1990) 346:425-433; Osborn (1990) Cell 62:3; Hynes (1992) Cell 9:11)). Integrins are heterodimeric transmembrane glycoproteins consisting of an a chain (120-180 kDa) and a P chain (90-110 kDa), generally having short cytoplasmic domains. For example, three important integrins, LFA-1, Mac-1 and P150,95, have different alpha subunits, designated CD11a, CD11b and CD11c, and a common beta subunit designated CD18. LFA-1($\alpha_L\beta_2$) is expressed on lymphocytes, granulocyte and monocytes, and binds predominantly to an Ig-family member counter-receptor termed ICAM-1 and related ligands. ICAM-1 is expressed on many cells, including leukocytes and endothelial cells, and is up-regulated on vascular endothelium by cytokines such as TNF and IL-1. Mac-1 ($\alpha_M\beta_2$) is distributed on neutrophils and monocytes, and also binds to ICAM-1. The third $\beta_2$ integrin, P150,95 ($\alpha_x\beta_2$), is also found on neutrophils and monocytes. The selectins consist of L-selectin, E-selectin and P-selectin.

Other antiinflammatory agents that can be used in combination with the anti alpha-4 agents include antibodies and other antagonists of cytokines, such as interleukins IL-1 through IL-13, tumor necrosis factors $\alpha$ and $\beta$ (TNF-$\alpha$ and TNF-$\beta$), interferons $\alpha$, $\beta$ and $\gamma$, tumor growth factor Beta (TGF-$\beta$), colony stimulating factor (CSF) and granulocyte monocyte colony stimulating factor (GM-CSF). Other anti-inflammatory agents include antibodies and other antagonists of chemokines such as MCP-1, MIP-1$\alpha$, MIP-1$\beta$, RANTES, exotaxin and IL-8. Other anti-inflammatory agents include NSAIDS, steroids and other small molecule inhibitors of inflammation. Formulations, routes of administration and effective concentrations of agents for combined therapies are as described above for the humanized antibodies against alpha-4 integrin.

Treatment Regimes

The invention further relates to regimes for the treatment of rheumatoid arthritis. These regimes may include administering to a subject about 2 mg to about 20 mg of methotrexateate as well as an antibody to alpha-4 integrin or an immunologically active antigen binding fragment thereof. Alternatively, the regimen may include administering to a subject about 2 mg to about 20 mg of methotrexateate as well as a small molecule alpha-4 integrin antagonist. Preferably, the subject is a mammal. More preferably, the mammal is human. Preferably, the antibody to alpha-4 integrin or immunologically active antigen binding fragment is administered in an amount of about 0.01 mg/kg of body weight to about 50 mg/kg of body weight. Preferably, the small molecule alpha-4 integrin antagonist is administered in an amount of about 2 mg to about 20 mg of methotrexate and about 0.01 mg/kg of body weight to about 100 mg/kg of body weight of a compound.

The regimen may be administered at any time of day or week, and in any order, such that a therapeutically effective does is achieved. The antibodies, fragments or compounds may be administered prior to, following, or concurrently with the methotrexate such that the benefitsd of the combination therapy are achieved. The amount of methotrexate administered per week should not exceed 20 mg.

EXAMPLES

The following examples are put forth so as to provide those of ordinary skill in the art with a complete disclosure and description of how to make and use the present invention, and is not intended to limit the scope of what the inventors regard as their invention nor is it intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Synthesis of Compounds

Synthesis of Compounds of Formulae I and II

In the examples below, if an abbreviation is not defined above, it has its generally accepted meaning. Further, all temperatures are in degrees Celsius (unless otherwise indicated). The following Methods were used to prepare the compounds set forth below as indicated.

Method 1

N-Tosylation Procedure

N-Tosylation of the appropriate amino acid was conducted via the method of Cupps, Boutin and Rapoport *J. Org. Chem.* 1985, 50, 3912.

Method 2

Methyl Ester Preparation Procedure

Amino acid methyl esters were prepared using the method of Brenner and Huber *Helv. Chim. Acta* 1953, 36, 1109.

Method 3

BOP Coupling Procedure

The desired dipeptide ester was prepared by the reaction of a suitable N-protected amino acid (1 equivalent) with the appropriate amino acid ester or amino acid ester hydrochloride (1 equivalent), benzotriazol-1-yloxy-tris(dimethylamino)phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method 4

Hydrogenation Procedure I

Hydrogenation was performed using 10% palladium on carbon (10% by weight) in methanol at 30 psi overnight. The mixture was filtered through a pad of Celite and the filtrate concentrated to yield the desired amino compound.

Method 5

Hydrolysis Procedure I

To a chilled (0° C.) THF/$H_2O$ solution (2:1, 5-10 mL) of the appropriate ester was added LiOH (or NaOH) (0.95 equivalents). The temperature was maintained at 0° C. and the reaction was complete in 1-3 hours. The reaction mixture was extracted with ethyl acetate and the aqueous phase was lyophilized resulting in the desired carboxylate salt.

Method 6

Ester Hydrolysis Procedure II

To a chilled (0° C.) THF/$H_2O$ solution (2:1, 5-10 mL) of the appropriate ester was added LiOH (1.1 equivalents). The temperature was maintained at 0° C. and the reaction was complete in 1-3 hours. The reaction mixture was concentrated and the residue was taken up into $H_2O$ and the pH adjusted to 2-3 with aqueous HCl. The product was extracted with ethyl acetate and the combined organic phase was washed with brine, dried over $MgSO_4$, filtered and concentrated to yield the desired acid.

Method 7

Ester Hydrolysis Procedure III

The appropriate ester was dissolved in dioxane/$H_2O$ (1:1) and 0.9 equivalents of 0.5 N NaOH was added. The reaction was stirred for 3-16 hours and than concentrated. The resulting residue was dissolved in $H_2O$ and extracted with ethyl acetate. The aqueous phase was lyophilized to yield the desired carboxylate sodium salt.

Method 8

Sulfonylation Procedure I

To the appropriately protected aminophenylalanine analog (11.2 mmol), dissolved in methylene chloride (25 ml) and cooled to −78° C. was added the desired sulfonyl chloride (12 mmol) followed by dropwise addition of pyridine (2 mL). The solution was allowed to warm to room temperature and was stirred for 48 hr. The reaction solution was transferred to a 250 mL separatory funnel with methylene chloride (100 mL) and extracted with 1N HCl (50 mL×3), brine (50 mL), and water (100 mL). The organic phase was dried ($MgSO_4$) and the solvent concentrated to yield the desired product.

Method 9

Reductive Amination Procedure

Reductive amination of Tos-Pro-p-NH2-Phe with the appropriate aldehyde was conducted using acetic acid, sodium triacetoxyborohydride, methylene chloride and the combined mixture was stirred at room temperature overnight. The crude product was purified by flash chromatography.

Method 10

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in $Et_2O$ and reconcentrated. This procedure was repeated and the resulting solid was placed under high vacuum overnight.

Method 11 tert-Butyl Ester Hydrolysis Procedure I

The tert-butyl ester was dissolved in $CH_2Cl_2$ and treated with TFA. The reaction was complete in 1-3 hr at which time the reaction mixture was concentrated and the residue dissolved in $H_2O$ and lyophilized to yield the desired acid.

Method 12

EDC Coupling Procedure I

To a $CH_2Cl_2$ solution (5-20 mL) of N-(toluene-4-sulfonyl)-L-proline (1 equivalent), the appropriate amino acid ester hydrochloride (1 equivalent), N-methylmorpholine (1.1-2.2 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was poured into $H_2O$ and the organic phase was washed with sat. $NaHCO_3$, brine, dried ($MgSO_4$ or $Na_2SO_4$), filtered and concentrated. The crude product was purified by column chromatography.

Method 13

EDC Coupling Procedure II

To a DMF solution (5-20 mL) of the appropriate N-protected amino acid (1 equivalent), the appropriated amino acid ester hydrochloride (1 equivalent), $Et_3N$ (1.1 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was partitioned between EtOAc and $H_2O$ and the organic phase washed with 0.2 N citric acid, $H_2O$, sat. $NaHCO_3$, brine, dried ($MgSO_4$ or $Na_2SO_4$), filtered and concentrated. The crude product was purified by column chromatography or preparative TLC.

Method 14

Sulfonylation Procedure II

The appropriate sulfonyl chloride was dissolved in $CH_2Cl_2$ and placed in an ice bath. L-Pro-L-Phe-OMe.HCl (1 equivalent) and $Et_3N$ (1.1 equivalent) was added and the reaction allowed to warm to room temperature and stirred overnight under an atmosphere of nitrogen. The reaction mixture was concentrated and the residue partitioned between EtOAc and H₂O and the organic phase washed with sat. NaHCO₃, brine, dried (MgSO₄ or Na₂SO₄), filtered and concentrated. The crude product was purified by column chromatography or preparative TLC.

Method 15

Sulfonylation Procedure III

To a solution of L-Pro-L-4-(3-dimethylaminopropyloxy)-Phe-OMe [prepared using the procedure described in Method 10] (1 equivalent) in CH₂Cl₂ was added Et₃N (5 equivalents) followed by the appropriate sulfonyl chloride (1.1 equivalent). The reaction was allowed to warm to room temperature and stirred overnite under an atmosphere of nitrogen. The mixture was concentrated, dissolved in EtOAc, washed with sat. NaHCO₃ and 0.2 N citric acid. The aqueous phase was made basic with solid NaHCO₃ and the product extracted with EtOAc. The organic phase was washed with brine, dried (MgSO₄ or Na₂SO₄), filtered and concentrated. The crude methyl ester was purified by preparative TLC. The corresponding acid was prepared using the procedure described in Method 7.

Method 16

Hydrogenation Procedure II

To a methanol (10-15 mL) solution of the azlactone was added NaOAc (1 equivalent) and 10% Pd/C. This mixture was placed on the hydrogenator at 40 psi H₂. After 8-16 hours, the reaction mixture was filtered through a pad of Celite and the filtrate concentrated to yield the dehydrodipeptide methyl ester. The ester was dissolved in dioxane/H₂O (5-10 mL), to which was added 0.5 N NaOH (1.05 equivalents). After stirring for 1-3 hours, the reaction mix was concentrated and the residue was redissolved in H₂O and washed with EtOAc. The aqueous phase was made acidic with 0.2 N HCl and the product was extracted with EtOAc. The combined organic phase was washed with brine (1×5 mL), dried (MgSO₄ or Na₂SO₄), filtered and concentrated to yield the acid as approximately a 1:1 mixture of diastereomers.

Method 17 tert-Butyl Ester Hydrolysis Procedure II

The tert-butyl ester was dissolved in CH₂Cl₂ (5 mL) and treated with TFA (5 mL). The reaction was complete in 1-3 hours at which time the reaction mixture was concentrated and the residue dissolved in H₂O and concentrated. The residue was redissolved in H₂O and lyophilized to yield the desired product.

Example 1

Synthesis of N-(Toluene-4-sulfonyl)-L-prolyl-L-4-(4-methylpiperazin-1-ylcarbonyloxy)phenylalanine Ethyl Ester The title compound was prepared following the procedure outlined for the preparation of Example 4 and substitution of appropriate starting materials.

NMR data was as follows:

$^1$H NMR ((CD₃)₂SO): δ=8.33 (d, 1H), 7.70 (d, 2H), 7.41 (d, 2H), 7.24 (d, 2H), 7.00 (d, 2H), 4.52-4.44 (m, 1H), 4.09-4.00 (m, 3H), 3.53 (bs, 2H), 3.38-3.31 (m, 3H), 3.11-3.01 (m, 3H), 2.39 (s, 3H), 2.32 (bs, 4H), 2.19 (s, 3H), 1.61-1.50 (m, 3H), 1.43-1.38 (m, 1H), 1.13 (t, 3H).

$^{13}$C NMR ((CD₃)₂SO): δ=171.1, 171.1, 153.9, 149.8, 143.6, 134.1, 133.9, 130.0, 129.8, 127.4, 121.5, 61.2, 60.7, 54.2, 54.1, 53.3, 49.0, 45.7, 44.0, 43.4, 35.8, 30.5, 23.8, 21.0, 14.0.

Example 2

Synthesis of N-(Toluene-4-sulfonyl)-L-prolyl-L-4-(N,N-dimethylcarbamyloxy)phenylalanine Ethyl Ester Into a reaction vial were combined 7.00 g (15.2 mmol, 1.0 eq) Ts-Pro-Tyr(H)—OEt and 1.86 g (15.2 mmol, 1.0 eq) DMAP. Methylene chloride (50 mL), triethylamine (2.12 mL-1.54 g, 15.2 mmol, 1.0 eq), and dimethylcarbamyl, chloride (1.68 mL-1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The workup of the reaction solution was as follows: add 50 mL EtOAc and 50 mL hexanes to the reaction mixture, and wash-with 3×50 mL 0.5 mL hexanes-to the reaction mixture, and wash with 3×50 mL 0.5 M citric acid, 2×50 mL water, 2×50 mL 10% K₂CO₃, and 1×50 mL sat. NaCl. Dry with MgSO₄. Filter. Evaporate to obtain 8.00 g (99%) of the title compound as a clear oil, which solidifies upon standing. Recrystallize from 5:3:2 heptane/EtOAc/CH₂Cl₂.

NMR data was as follows:

$^1$H NMR ((CD₃)₂SO): δ=8.32 (d, 1H), 7.70 (d, 2H), 7.41 (d, 2H), 7.23 (d, 2H), 7.00 (d, 2H), 4.52-4.44 (m, 1H), 4.09-4.02 (m, 3H), 3.37-3.31 (m, 1H), 3.11-2.96 (m, 3H), 3.00 (s, 3H), 2.87 (s, 3H), 2.39 (s, 3H), 1.61-1.50 (m, 3H), 1.43-1.38 (m, 1H), 1.13 (t, 3H).

$^{13}$C NMR ((CD₃)₂SO): δ=171.1, 171.1, 154.0, 150.0, 143.6, 133.9, 133.9, 130.0, 129.8, 127.4, 121.5, 61.2, 60.6, 53.3, 49.0, 36.3, 36.1, 35.8, 30.5, 23.8, 21.0, 14.0.

Example 3

Synthesis of N-(Toluene-4-sulfonyl)-L-prolyl-L-4-(4-methylpiperazin-1-ylcarbonyloxy)phenylalanine Isopropyl Ester The title compound was prepared following the procedure outlined for the preparation of Example 4 and substitution of appropriate starting materials.

NMR data was as follows:

$^1$H NMR (CDCl₃): δ=7.72 (d, 2H), 7.36 (d, 1H), 7.33 (d, 2H), 7.16 (d, 2H), 7.03 (d, 2H), 5.07 (Sept., 1H), 4.78 (dt, 1H), 4.08-4.05 (m, 1H), 3.67 (bs, 2H), 3.57 (bs, 2H), 3.41-3.35 (m, 1H), 3.24 (dd, 1H), 3.15-3.07 (m, 1H), 3.04 (dd, 1H), 3.46-2.43 (m, 7H), 2.34 (s, 3H), 2.05-2.02 (m, 1H).

$^{13}$C NMR (CDCl₃): δ=170.9, 170.4, 153.6, 150.5, 144.3, 133.2, 133.1, 130.2, 130.0, 127.9, 121.7, 69.5, 62.2, 54.7, 53.4, 49.6, 46.1, 44.3, 43.7, 37.2, 29.7, 24.1, 21.6, 21.6, 21.4.

Example 4

Synthesis of N-(Toluene-4-sulfonyl)-L-prolyl-L-4-(4-methylpiperazin-1-ylcarbonyloxy)phenylalanine tert-Butyl Ester Combine 41.2 g (84.34 mmol, 1.0 eq) Ts-Pro-Tyr(H)-OtBu and 17.0 g (84.34 mmol, 1.0 eq) 4-nitrophenyl chloroformate. Add 700 mL CH₂Cl₂. Cap with a septum. Attach a N₂ line. Immerse the flask in a 4:1 water/EtOH+dry ice slurry, and stir to cool to −15° C. Add 29.38 mL (21.33 g, 210.81 mmol, 2.5 eq) Et₃N over five minutes with stirring. Stir at −10 to −15° C. for 1 h. Add 9.35 mL (8.45 g, 84.34 mmol, 1.0 eq) N-methyl piperazine over 3 minutes with stirring. Stir overnight while warming to room temperature. Dilute with 700 mL hexanes. Wash repeatedly with 10% $K_2CO_3$, until no yellow color (4-nitrophenol) is seen in the aqueous layer. Wash with sat. NaCl. Dry over anhydrous $MgSO_4$. Filter. Evaporate. Dissolve in 500 mL EtOH, and evaporate, to remove $Et_3N$. Repeat once. Dissolve in 400 mL EtOH, and add 600 mL water with stirring, to precipitate a solid or oil. If an oil, stir vigorously to solidify. Isolate the solid by filtration. Repeat dissolution, precipitation, and filtration, once. Rinse with water to remove traces of yellow color. High vacuum to constant mass yields the title compound as a white solid.

NMR data was as follows:

$^1$H NMR ($CDCl_3$): δ=7.72 (d, 2H), 7.33 (d, 3H), 7.17 (d, 2H), 7.02 (d, 2H), 4.71 (q, 1H), 4.09-4.06 (m, 1H), 3.67 (bs, 2H), 3.57 (bs, 2H), 3.41-3.34 (m, 1H), 3.22 (dd, 1H), 3.16-3.09 (m, 1H), 3.03 (dd, 1H), 2.46-2.43 (m, 7H), 2.34 (s, 3H), 2.05-2.02 (m, 1H), 1.57-1.43 (m, 3H), 1.47 (s, 9H).

$^{13}$C NMR ($CDCl_3$): δ=171.8, 169.9, 153.6, 150.4, 144.3, 133.4, 133.1, 130.3, 130.0, 127.9, 121.6, 82.6, 62.3, 54.5, 53.8, 49.6, 46.1, 44.3, 43.7, 37.3, 29.7, 27.8, 24.1, 21.4.

Example 5

Synthesis of N-(Toluene-4-sulfonyl)-L-prolyl-L-4-(4-methylpiperazin-1-ylcarbonyloxy)phenylalanine The title compound was prepared from the product of Example 1 using the procedure described in Method 7.

NMR data was as follows:

$^1$H NMR ($CD_3OD$): δ=7.74 (d, 2H), 7.42 (d, 2H), 7.26 (d, 2H), 7.04 (d, 2H), 4.58-4.54 (m, 1H), 4.16-4.12 (m, 1H), 3.70 (bs, 2H) 3.53 (bs, 2H), 3.43-3.31 (m, 1H), 3.26-3.13 (m, 7H), 2.82'(s, 3H), 2.43 (s, 3H), 1.98-1.94 (m, 1H), 1.76-1.51 (m, 3H).

$^{13}$C NMR ($CD_3OD$): δ=175.7, 173.6, 154.8, 151.6, 146.1, 136.3, 134.8, 131.9, 131.3, 129.1, 122.7, 63.6, 55.9, 53.9, 50.7, 43.5, 37.6, 31.3, 25.5, 21.5.

Example 6

Synthesis of N-Toluene-4-sulfonyl)-L-prolyl-L-4-(N,N-dimethylcarbamyloxy)phenylalanine n-Butyl Ester The title compound was prepared following the procedure outlined for the preparation of Example 2 and substitution of appropriate starting materials.

NMR data was as follows:

$^1$H NMR ($CD_3$)$_2$SO: δ=8.31 (d, 1H), 7.70 (d, 2H), 7.41 (d, 2H), 7.23 (d, 2H), 6.99 (d, 2H), 4.53-4.46 (m, 1H), 4.10-4.01 (m, 1H), 3.63-3.30 (m, 1H), 3.10-2.96 (m, 3H), 3.00 (s, 3H), 2.88 (s, 3H), 2.39 (s, 3H), 1.59-1.30 (m, 6H), 1.33-1.20 (m, 2H), 0.85 (t, 3H).

$^{13}$C NMR ($CD_3$)$_2$SO: δ=171.4, 171.3, 154.2, 150.2, 143.7, 134.0, 130.1, 130.0, 127.6, 121.7, 64.3, 61.2, 59.2, 53.4, 49.0, 36.2, 36.0, 35.8, 30.0, 23.8, 21.0, 18.5, 13.5.

Example 7

Synthesis of N-(Toluene-4-sulfonyl)-L-prolyl-L-4-(N,N-dimethylcarbamyloxy)phenylalanine Cyclopentyl Ester The title compound was prepared following the procedure outlined for the preparation of Example 2 and substitution of appropriate starting materials.

NMR data was as follows:

$^1$H NMR ($CD_3$)$_2$SO: δ=8.27 (d, 1H), 7.70 (d, 2H), 7.41 (d, 2H), 7.22 (d, 2H), 6.99 (d, 2H), 5.04 (bs, 1H), 4.48-4.40 (m, 1H), 4.08-4.05 (m, 1H), 3.34-3.30 (m, 1H), 3.09-2.95 (m, 3H), 3.00 (s, 3H), 2.88 (s, 3H), 2.39 (s, 3H), 1.76-1.74 (m, 2H), 1.57-1.40 (m, 10H).

$^{13}$C NMR ($CD_3$)$_2$SO: δ=171.3, 171.0, 154.2, 150.2, 432.7, 134.1, 130.1, 130.0, 127.6, 121.6, 77.4, 61.2, 53.4, 49.0, 36.2, 36.1, 35.7, 32.0, 30.5, 23.8, 23.2, 21.0.

Example 8

Synthesis of N-(Toluene-4-sulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^1$H NMR ($CD_3$)$_2$SO: δ=8.18 (d, 1H), 7.71 (d, 2H), 7.41 (d, 2H), 7.23 (d, 2H), 6.99 (d, 2H), 4.42-4.38 (m, 1H), 4.10-4.07 (m, 1H), 3.37-3.30 (m, 1H), 3.09-2.95 (m, 3H), 3.00 (s, 3H), 2.88 (s, 3H), 2.39 (s, 3H), 1.58-1.50 (m, 3H), 1.40-1.30 (m, 1H), 1.36 (s, 9H).

$^{13}$C NMR ($CD_3$)$_2$SO: δ=171.1, 170.3, 154.2, 150.2, 143.8, 134.2, 134.1, 130.2, 130.0, 127.6, 121.6, 81.0, 61.3, 53.8, 49.0, 36.3, 36.0, 35.9, 30.5, 27.5, 23.8, 21.0.

Example 9

Synthesis of N-(Toluene-4-sulfonyl)-L-prolyl-L-4-(N,N-dimethylcarbamyloxy)phenylalanine The title compound was prepared from the product of Example 2 using the procedure described in Method 7.

NMR data was as follows:

$^1$H NMR ($CD_3$)$_2$SO: δ=8.13 (d, 1H), 7.70 (d, 2H), 7.41 (d, 2H), 7.23 (d, 2H), 6.99 (d, 2H), 4.51-4.44 (m, 1H), 4.11-4.09 (m, 1H), 3.40-3.34 (m, 2H), 3.11-2.94 (m, 3H), 3.00 (s, 3H), 2.87 (s, 3H), 2.39 (s, 3H), 1.59-1.36 (m, 4H).

$^{13}$CNMR($CD_3$)$_2$SO: δ=172.7, 171.2, 153.6, 150.2, 143.8, 134.3, 134.0, 130.2, 130.0, 127.6, 121.6, 61.3, 53.2, 49.0, 36.3, 36.1, 35.9, 30.4, 23.8, 21.0.

Example 10

Synthesis of N-(Toluene-4-sulfonyl)-L-prolyl-L-3-(N,N-dimethylcarbamyloxy)phenylalanine Ethyl Ester The title compound was prepared following the procedure outlined for the preparation of Example 2 and substitution of appropriate starting materials.

NMR data was as follows:

$^1$H NMR ($CDCl_3$): δ=7.74 (m, 2H), 7.70-7.36 (m, 4H), 7.24-7.14 (m, 3H), 6.93-4.90 (m, 1H), 4.78-4.27 (m, 3H), 4.05-3.55 (m, 0.5H), 3.48-3.43 (m, 0.5H), 3.37-3.30 (m, 3H), 3.02-3.08 (bs, 3H), 2.99 (bs, 3H), 2.45 (s, 1.5H), 2.43 (s, 1.5H), 2.12 (m, 1H), 198, 1.80 (m, 0.5M), 1.62-1.44 (m, 2.5H), 1.29 (t, 1.5H), 1.24 (t, 1.5H).

$^{13}$C NMR ($CDCl_3$): δ=171.1, 171.0, 170.9, 154.9, 154.8, 151.8, 151.6, 144.4, 144.3, 137.6, 137.1, 133.1, 132.9, 130.0, 129.9, 129.5, 129.2, 127.9, 127.9, 126.5, 126.1, 122.9, 122.7, 120.7, 120.5.

Example 11

Synthesis of N-(Toluene-4-sulfonyl)-L-(5,5-dimethyl)thiaprolyl-L-4-(N,N-dimethylcarbamyloxy) phenylalanine Isopropyl Ester The title compound was prepared following the procedure outlined for the preparation of Example 2 and substitution of appropriate starting materials.

NMR data was as follows:
$^1$H NMR (CDCl$_3$): δ=7.76 (d, 2H), 7.35 (d, 2H), 7.22 (d, 2H), 7.01 (m, 3H), 5.05 (m, 1H), 4.85 (m, 1H), 4.57 (d, 1H), 4.38 (d, 1H), 3.86 (s, 1H), 3.19-3.00 (m, 2H), 3.09 (s, 3H), 3.01 (s, 3H), 2.45 (s, 3H), 1.24 (t, 6H), 1.16 (s, 3H), 1.09 (s, 3H).
$^{13}$CNMR(CDCl$_3$): δ=170.3, 168.4, 154.9, 150.6, 144.8, 132.9, 132.8, 130.3, 130.0, 128.2, 121.7, 73.4, 69.5, 54.5, 53.2, 50.4, 37.7, 36.5, 36.3, 29.0, 23.8, 21.5, 21.4.

Example 12

Synthesis of N-(Toluene-4-sulfonyl)-L-(5,5-dimethyl)thiaprolyl-L-4-(N,N-dimethylcarbamyloxy) phenylalanine tert-Butyl Ester The title compound was prepared following the procedure outlined for the preparation of Example 2 and substitution of appropriate starting materials.

NMR data was as follows:
$^1$H NMR (CDCl$_3$): δ=7.75 (d, 2H), 7.34 (d, 2H), 7.23 (d, 2H), 7.05-6.98 (m, 3H), 4.76 (m, 1H), 4.56 (d, 1H), 4.40 (d, 1H), 3.85 (s, 1H), 3.09-3.00 (m, 8H), 2.44 (s, 3H), 1.43 (s, 3H), 1.16 (s, 3H), 1.09 (s, 3H). $^{13}$C NMR (CDCl$_3$): δ=169.8, 168.3, 154.9, 150.6, 144.8, 133.2, 132.9, 130.4, 130.0, 128.2, 121.6, 82.6, 73.4, 54.6, 53.8, 50.4, 37.8, 36.5, 36.3, 29.0, 27.7, 23.8, 21.5.

Example 13

Synthesis of N-(Toluene-4-sulfonyl)-L-(5,5-dimethyl)thiaprolyl-L-4-(N,N-dimethylcarbamyloxy) phenylalanine The title compound was prepared from the product of Example 11 using the procedure described in Method 7.

NMR data was as follows:
$^1$H NMR (CDCl$_3$): δ=7.76 (d, 2H), 7.35 (d, 2H), 7.25 (d, 2H), 7.14 (d, 1H), 7.02 (d, 2H), 5.17 (br s, 1H), 4.89 (m, 1H), 4.56 (d, 1H), 4.40 (d, 1H), 3.90 (s, 1H), 3.30-3.00 (m, 8H), 2.43 (s, 3H), 1.09 (s, 6H).
$^{13}$C NMR (CDCl$_3$): δ=172.7, 169.3, 155.2, 150.6, 144.9, 133.1, 132.7, 130.5, 130.1, 128.1, 121.9, 73.3, 54.5, 53.3, 50.5, 36.9, 36.6, 36.4, 29.0, 23.7, 21.5.

Example 14

Synthesis of N-(Toluene-4-sulfonyl)-L-[(1,1-dioxo)thiamorpholin-3-carbonyl]-L-4-(N,N-dimethylcarbamyloxy)phenylalanine tert-Butyl Ester L-Thiamorpholine-5-carboxylic acid was prepared by the method of Larsson and Carlson (*Acta Chemica Scan.* 1994, 48, 517-525). N-(Toluene-4-sulfonyl)-L-thiamorpholine-5-carboxylic acid was prepared using the procedure described in Method 1 and was then coupled to t-butyl tyrosine in DMF in the presence of BOP and NMM, to give after aqueous workup and flash chromatography N-(Toluene-4-sulfonyl)-L-[thiamorpholin-3-carbonyl]-L-4-phenylalanine tert-butyl ester.

Formation of the 4-(N,N-dimethylcarbamyloxy) group was per Example 2 above and oxidation of the thiamorpholino group to the 1,1-dioxo-thiamorpholino group was per Larsson and Carlson (*Acta Chemica Scan.* 1994, 48, 522).

NMR data was as follows:
$^1$H NMR (CDCl$_3$): δ=7.68 (d, 2H), 7.37 (d, 2H), 7.08 (m, 4H), 6.73 (d, 1H), 5.11 (m, 1H), 4.62 (m, 1H), 4.23 (m, 1H), 4.00 (m, 1H), 3.82 (m, 1H), 3.14 (s, 3H), 3.03 (s, 3H), 2.80 (m, 5H), 2.44 (s, 3H), 1.48 (s, 9H).
$^{13}$C NMR (CDCl$_3$): δ=171.3, 169.9, 164.4, 145.6, 135.4, 132.6, 130.8, 130.4, 127.3, 121.9, 83.0, 56.1, 53.8, 49.4, 48.7, 44.5, 42.0, 36.9, 36.6, 36.4, 27.8, 21.5.

Example 15

Synthesis of N-(Toluene-4-sulfonyl)-L-[(1,1-dioxo)thiamorpholin-3-carbonyl]-L-4-(N,N-dimethylcarbamyloxy)phenylalanine The title compound was prepared from-the product of Example 14 using the procedure described in Method 11.

NMR data was as follows:
$^1$H NMR (CD$_3$OD): δ=7.77 (d, 2H), 7.40 (d, 2H), 7.22 (d, 2H), 7.00 (d, 2H), 5.19 (m, 1H), 4.65 (m, 1H), 4.30 (m, 1H), 3.95 (m, 1H), 3.61 (m, 1H), 3.20 (m, 5H), 3.09 (s, 3H), 2.97 (s, 3H), 2.43 (s, 3H).
$^{13}$CNMR(CD$_3$OD): δ=174.1, 168.0, 157.0, 152.0, 146.4, 137.7, 135.3, 131.7, 131.6, 128.8, 123.0, 57.1, 54.8, 51.1, 50.9, 48.0, 47.7, 43.2, 37.4, 36.8, 36.7, 21.5.

Example 16

Synthesis of N-(Toluene-4-sulfonyl)-L-(5,5-dimethyl)thiaprolyl-L-4-(4-methylpiperazin-1-ylcarbonyloxy)phenylalanine tert-Butyl Ester The title compound was prepared following the procedure outlined for the preparation of Example 4 and substitution of appropriate starting materials.

NMR data was as follows:
$^1$H NMR (CDCl$_3$): δ=7.74 (d, 2H), 7.33 (d, 2H), 7.25 (d, 2H), 7.20-7.00 (m, 3H), 4.74 (m, 1H), 4.55 (d, 1H), 4.38 (d, 1H), 3.83 (s, 1H), 3.66 (br m, 2H), 3.57 (br m, 2H), 3.08-3.05 (m, 2H), 2.45-2.42 (m, 7H), 2.33 (s, 3H), 1.42 (s, 9H), 1.15 (s, 3H), 1.08 (s, 3H).
$^{13}$C NMR (CDCl$_3$): δ=169.7, 168.2, 153.6, 150.3, 144.7, 133.3, 132.7, 130.4, 129.9, 128.1, 121.5, 82.6, 73.4, 54.5, 53.7, 50.4, 46.0, 44.2, 43.6, 37.7, 28.9, 27.7, 23.8, 21.4.

Example 17

Synthesis of N-(Toluene-4-sulfonyl)-L-(5,5-dimethyl)thiaprolyl-L-4-(4-methylpiperazin-1-ylcarbonyloxy)phenylalanine The title compound was prepared from the product Example 16 using the procedure described in Method 11.

NMR data was as follows:
$^1$H NMR (CDCl$_3$): δ=8.31 (d, 1H), 7.72 (d, 2H), 7.42-7.35 (m, 4H), 7.08 (d, 2H), 4.90-4.68 (m, 1H), 4.64-4.61 (m, 1H), 4.47-4.44 (m, 1H), 4.01 (s, 1H), 3.36-3.32 (br m, 4H), 3.27-3.25 (m, 1H), 3.22-3.10 (m, 1H), 2.94 (s, 3H), 2.43 (s, 3H), 1.14 (s, 3H), 1.07 (s, 3H).

Example 18

Synthesis of N-(Toluene-4-sulfonyl)sarcosyl-L-4-(N,N-dimethylcarbamyloxy)phenylalanine Isopropyl Ester The title compound was prepared following the procedure outlined for the preparation of Example 2 and substitution of appropriate starting materials.

NMR data was as follows:

$^1$H NMR (CDCl$_3$): δ=7.66 (d, 2H), 7.34 (d, 2H), 7.18 (d, 2H), 7.07 (d, 2H), 6.98 (d, 1H), 5.03 (m, 1H), 4.81 (m, 1H), 3.69 (d, 1H), 3.49 (d, 1H), 3.08 (m, 2H), 3.04 (s, 3H), 2.99 (s, 3H), 2.63 (s, 3H), 2.43 (s, 3H).

$^{13}$C NMR (CDCl$_3$): δ=167.4, 154.9, 150.8, 144.4, 132.6, 130.2, 130.1, 127.7, 122.0, 110.9, 69.5, 57.3, 53.9, 53.0, 37.1, 36.6, 21.6, 21.4.

Example 19

Synthesis of N-(Toluene-4-sulfonyl)sarcosyl-L-4-(N,N-dimethylcarbamyloxy)phenylalanine tert-Butyl Ester The title compound was prepared following the procedure for the preparation of Example 2 and substitution of appropriate starting materials.

NMR data was as follows:

$^1$H NMR (CDCl$_3$): δ=7.67 (d, 2H), 7.34 (d, 2H), 7.19 (d, 2H), 7.03 (d, 2H), 6.98 (d, 1H), 4.76 (m, 1H), 3.67 (q, 1H), 3.06 (m, 2H), 3.16 (s, 3H), 2.99 (s, 3H), 2.64 (s, 3H), 2.43 (s, 3H), 1.42 (s, 9H).

$^{13}$C NMR (CDCl$_3$): δ=170.0, 137.2, 154.9, 150.7, 144.3, 133.2, 132.9, 130.3, 130.0, 127.7, 121.9, 82.6, 83.9, 53.3, 37.2, 36.6, 36.4, 27.9, 21.4.

Example 20

Synthesis of N-(Toluene-4-sulfonyl)sarcosyl-L-4-(N,N-dimethylcarbamyloxy)phenylalanine The title compound was prepared from the product of Example 18 using the procedure described in Method 7.

NMR data was-as follows:

$^1$H NMR (CDCl$_3$): δ=7.41 (d, 2H), 7.10 (d, 2H), 6.98 (d, 2H), 6.75 (d, 2H), 4.42 (m, 1H), 3.43 (m, 2H), 3.04 (m, 2H), 2.80 (s, 3H), 2.69 (s, 3H), 2.33 (s, 3H), 2.14 (s, 3H).

$^{13}$C NMR (CDCl$_3$): δ=174.2, 170.2, 156.9, 151.9, 145.6, 135.5, 135.2, 131.4, 131.1, 128.9, 123.0, 54.6, 54.0, 37.4, 36.8, 36.7, 21.4.

Example 21

Synthesis of N-(Toluene-4-sulfonyl)-L-prolyl-L-4-(N,N-dimethylaminosulfonyloxy)phenylalanine tert-Butyl Ester Substituting dimethysulfamoyl chloride for dimethylcarbamyl chloride, and following the method for the preparation of Example 2, gave the title compound.

NMR data was as follows:

$^1$H NMR (CDCl$_3$): δ=7.72 (d, 2H), 7.34 (d, 2H), 7.21 (s, 4H), 4.69 (m, 1H), 4.04 (m, 1H), 3.4 (m, 1H), 3.24 (m, 3H), 2.96 (s, 6H), 2.42 (s, 3H), 2.02 (m, 1H), 1.45 (m, 13H).

$^{13}$CNMR(CDCl$_3$): δ=166.3, 165.3, 144.8, 140.0, 130.9, 126.4, 125.6, 123.5, 117.3, 95.5, 78.3, 57.8, 49.2, 45.2, 34.2, 32.9, 25.0, 23.4, 19.7, 17.1.

Example 22

Synthesis of N-(Toluene-4-sulfonyl)-L-prolyl-L-4-(N,N-dimethylaminosulfonyloxy)phenylalanine The title compound was prepared from the product of Example 21 using the procedure described in method 11.

NMR data was as follows:

$^1$H NMR (CD$_3$OD): δ=7.73 (d, 2H), 7.41 (d, 2H), 7.38 (d, 2H), 7.22 (d, 2H), 4.69 (m, 1H), 4.11 (m, 1H), 3.41 (m, 2H), 3.19 (m, 2H), 2.94 (s, 6H), 2.41 (s, 3A), 1.78 (m, 1H), 1.61 (m, 3H).

$^{13}$C NMR (CD$_3$OD): δ=174.3, 174.0, 150.8, 145.9, 137.3, 135.1, 132.1, 131.2, 129.1, 123.1, 63.3, 54.6, 50.6, 39.1, 37.5, 31.6, 25.3, 21.5.

Example 23

Synthesis of N-(Toluene-4-sulfonyl)-sarcosyl-L-(4-morpholinecarbamyloxy) phenylalanine t-butyl ester Substituting sacrosine for L-proline in the preparation of Ts-Pro-Tyr(H)—O-t-butyl ester and substitution of 4-morpholinecarbonyl chloride for dimethylcarbamyl chloride, and following the method for the preparation of Example 2, gave the title compound as a white solid.

NMR data was as follows:

$^1$H NMR (CDCl$_3$): δ 7.61 (d, 2H), 7.28 (d, 2H), 7.16 (d, 2H), 7.02 (d, 2H), 4.69 (m, 1H), 3.67 (m, 8H), 3.58 (m, 1H), 3.48 (m, 1H), 3.06 (m, 2H), 2.59 (s, 3H), 2.36 (s, 3H), 1.26 (s, 9H).

$^{13}$CNMR (CDCl$_3$): δ 169.7, 167.1, 153.5, 150.1, 144.1, 133.1, 133.0, 133.0, 130.1, 129.8, 127.4, 121.6, 82.6, 66.3, 53.6, 53.1, 44.5, 43.7, 36.9, 36.4, 27.6, 21.2.

Example 24

Synthesis of N-(Toluene-4-sulfonyl)sarcosyl-L-4-(isonipecotoyloxy)phenylalanine

The title compound was prepared from the product of Example 23 using the procedure described in Method 11.

NMR data was as follows:

$^1$H NMR (CD$_3$OD): δ=7.30 (d, 2H), 7.02 (d, 2H), 6.88 (d, 2H), 6.67 (d, 2H), 4.33 (m, 1H), 3.32 (m, 3H), 3.25 (m, 2H), 3.12 (m, 3H), 2.89 (m, 1H), 2.70 (m, 3H), 2.22 (s, 3H), 2.03 (s, 3H).

$^{13}$C NMR (CD$_3$OD): δ=174.2, 170.3, 155.6, 151.7, 145.6, 135.8, 135.2, 131.5, 131.1, 128.9, 123.0, 67.5, 54.6, 54.0, 37.4, 36.8, 21.5.

Example 25

Synthesis of N-(Toluene-4-sulfonyl)-L-[(1,1-dioxo)thiamorpholin-3-carbonyl]-L-4-(morpholin-4-ylcarbonyloxy)phenylalanine tert-Butyl Ester Substitution of 4-morpholinecarbonyl chloride for dimethylcarbamyl chloride, and following the methods for the preparation of Example 2 and 14, gave the title compound as a white solid.

—NMR-data was as follows:

$^1$H NMR (CDCl$_3$): δ=7.76 (d, 1H), 7.68 (d, 1H), 7.37 (m, 2H), 7.14 (m, 2H), 7.05 (m, 1H), 6.97 (d, 1H), 6.80 (d, 0.5H), 6.57 (d, 0515H), 5.09 (m, 0.5H), 4.91 (m, 0.5H), 4.75 (m, 0.5H), 4.62 (m, 0.5H), 4.25 (m, 0.5H), 4.09 (m, 2H), 3.79 (m, 4H), 3.65 (m, 4H), 2.91 (s, 3H), 2.44 (s, 3H), 1.69 (s, 4H), 1.44 (s, 5H).

$^{13}$C NMR (CDCl$_3$): δ=170.0, 169.8, 164.8, 164.4, 153.7, 150.4, 145.6, 145.4, 135.4, 135.3, 132.9, 130.8, 130.7, 130.5, 130.4, 127.5, 127.2, 122.1, 121.8, 83.01, 82.8, 66.4, 56.1, 56.1, 53.7, 53.6, 49.5, 49.3, 48.6, 44.7, 43.9, 42.0, 41.6, 36.9, 36.3, 27.8, 21.5.

Example 26

Synthesis of N-(Toluene-4-sulfonyl)-L-[(1,1-dioxo) thiamorpholin-3-carbonyl]-L-4-(morpholin-4-ylcarbonyloxy)phenylalanine The title compound was prepared from the product of Example 25 using the procedure described in Method 11.

NMR data was as follows:

$^1$H NMR (CD$_3$OD): δ=7.67 (m, 2H), 7.32 (m, 2H), 7.08 (m, 2H), 6.93 (m, 2H), 5.09 (m, 1H), 4.54 (m, 1H), 4.19 (m, 0.5H), 4.02 (m, 0.5H), 3.81 (m, 0.5H), 3.66 (m, 8H), 2.99 (m, 7H), 2.32 (s, 3H).

$^{13}$C NMR (CD$_3$OD): δ=174.0, 168.0, 155.7, 151.9, 151.8, 146.6, 146.4, 137.5, 135.5, 135.3, 131.7, 131.6, 131.6, 128.8, 123.3, 122.9, 67.6, 57.3, 57.1, 54.8, 51.1, 50.9, 50.6, 46.0, 45.3, 45.2, 43.0, 37.4, 37.0, 21.5.

Example 27

Synthesis of N-(4-Fluorobenzenesulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^{13}$C NMR (CDCl$_3$): δ 7.87-7.83 (m, 2H), 7.26-7.13 (m, 5H), 4.74-4.69 (m, 1H), 4.05 (m, 1H), 3.36 (m, 1H), 3.24-3.17 (m, 1H), 3.11-3.01 (m, 4H), 2.97 (s, 3H), 2.05-2.02 (m, 1H), 1.60-1.47 (m, 3H), 1.46 (s, 9H).

$^{13}$C NMR (CDCl$_3$): δ 170.6, 170.0, 165.7, 154.9, 150.6, 133.2, 132.4, 130.7, 130.2, 121.7, 116.7, 82.7, 62.3, 53.7, 49.6, 37.2, 36.6, 36.4, 29.9, 27.9, 24.2.

Example 28

Synthesis of N-(Toluene-4-sulfonyl)sarcosyl-L-4-(4-methylpiperazin-1-ylcarbonyloxy)phenylalanine tert-Butyl Ester The title compound was prepared following the procedure outlined for the preparation of Example 4 and substitution of appropriate starting materials.

NMR data was as follows:

$^1$H NMR (CDCl$_3$): δ=8.17 (d, 1H), 7.59 (d, 2H), 7.26 (d, 2H), 7.13 (d, 2H), 7.00 (d, 2H), 4.66 (m, 1H), 3.60 (m, 6H), 3.04 (m, 2H), 2.56 (s, 3H), 2.40 (m, 7H), 2.34 (s, 3H), 1.41 (s, 9H).

$^{13}$C NMR (CDCl$_3$): δ=169.7, 167.0, 153.4, 150.2, 144.0, 133.0, 132.9, 130.1, 129.8, 127.4, 121.6, 82.2, 54.3, 53.5, 53.1, 45.8, 44.2, 43.5, 36.9, 27.6, 21.2.

Example 29

Synthesis of N-(Toluene-4-sulfonyl)-L-(1,1-dioxo-5,5-dimethyl)-thiaprolyl-L-4-(N,N-dimethylcarbamyloxy)phenylalanine tert-Butyl Ester The product of Example 12 was oxidized by the method of Larsson and Carlson (*Acta Chemica Scan.* 1994, 48, 517-525), yielding the title compound as a white solid.

NMR data was as follows:

$^1$H NMR (CDCl$_3$): δ=7.73 (d, 2H), 7.36 (d, 2H), 7.21 (d, 2H), 7.06-6.95 (m, 3H), 4.79 (m, 1H), 4.38 (dd, 2H), 4.10 (s, 1H), 3.18-2.95 (m, 8H), 2.43 (s, 3H), 1.45 (s, 9H), 1.33 (s, 3H), 1.08 (s, 3H).

$^{13}$C NMR (CDCl$_3$): δ=169.8, 166.2, 154.9, 120.7, 145.8, 133.0, 131.9, 130.2, 128.5, 121.9, 82.9, 68.0, 60.9, 59.3, 53.9, 37.5, 36.6, 36.3, 27.7, 21.6, 19.3, 18.5.

Example 30

Synthesis of

N-(1-Methylimidazolyi-4-sulfonyl)-L-prolyl-L-4-(N,N-dimethylcarbamyloxy)phenylalanine The title compound was prepared from the product of Example 106 using the procedure described in Method 11.

NMR data was as follows:

$^1$H NMR (CDCl$_3$): δ=8.07 (d, 1H), 7.75 (s, 1H), 7.71 (s, 1H), 7.25 (d, 2H), 7.01 (d, 2H), 4.71-4.66 (m, 1H), 4.28-4.24 (m, 1H), 3.77 (s, 3H), 3.42-3.05 (m, 3H), 3.09 (s, 3H), 2.96 (s, 3H), 1.84-1.69 (m, 2H), 1.61-1.54 (m, 2H).

$^{13}$C NMR (CDCl$_3$): δ=174.4, 174.1, 156.9, 151.9, 141.8, 137.7, 135.6, 131.6, 127.6, 122.9, 63.7, 54.7, 50.8, 37.4, 36.8, 36.7, 34.3, 31.6, 25.4.

Preparative Example A

Synthesis of 2-(Saccharin-2-yl)propionoyl-L-4-(N,N-dimethylcarbamyloxy)phenylalanine tert-Butyl Ester N-(Benzisothiazolone)-L-alanyl-L-tyrosine t-butyl ester was prepared by first combining sodium hydride (washed free of mineral oil) in THF chilled to 0° C., and a solution of N-(2-methoxycarbonyl)sulfonyl-L-alanine-L-tyrosine t-butyl ester in THF which was added dropwise. The reaction was stirred at 0° C. for one hour and then at room temperature for two hours. The reaction mixture was extracted with EtOAc and 0.2 N HCl, the combined EtOAc layers were washed successively with 0.2 N HCl, sat. NaHCO$_3$, and sat. NaCl. The organic layer was dried over MgSO$_4$, filtered and concentrated. The residue was filtered by silica gel chromatography to afford N-(benzisothiazolone)-L-alanyl-L-tyrosine t-butyl ester.

The title compound was then prepared following the procedure described in Example 2.

NMR data was as follows:

$^1$H NMR (DMSO-d$_6$, 400 MHz) (1:1 mixture of diastereomers) δ=8.15 (m, 2H); 8.5 (m, 3H); 7.20 (m, 2H); 6.95 (m, 2H); 4.75 (m, 1H); 4.30 (m, 1H); 3.05 (s, 3H); 2.95 (m, 2H); 2.90 (s, 3H); 1.75 and 1.65 (two d, 3H); 1.30 and 1.35 (two s, 9H).

Example 31

Synthesis of N-(Toluene-4-sulfonyl)-L-(1,1-dioxo-5,5-dimethyl)-thiaprolyl-L-4-(N,N-dimethylcarbamyloxy)phenylalanine The title compound was prepared from the product of Example 29 using the procedure described in Method 11.

NMR data was as follows:

$^1$H NMR (CDCl$_3$): δ=7.75 (m, 3H), 7.29 (m, 4H), 7.08 (d, 2H), 4.95 (m, 1H), 4.46-4.20 (m, 3H), 3.17 (s, 3H), 3.30-3.10 (m, 2H), 3.02 (s, 3H), 2.43 (s, 3H), 1.15 (s, 3H), 0.88 (s, 3H).

$^{13}$C NMR (CDCl$_3$): δ=127.2, 167.5, 155.8, 150.3, 145.4, 133.6, 132.6, 130.8, 130.2, 128.3, 121.9, 67.9, 65.8, 60.8, 53.9, 36.8, 36.6, 35.8, 21.6, 18.8, 15.0.

Example 32

Synthesis of N-(4-Fluorobenzenesulfonyl)-L-prolyl-L-4-(N,N-dimethylcarbamyloxy)phenylalanine The title compound was prepared from the product of Example 27 using the procedure described in Method 11.

NMR data was as follows:

$^1$H NMR (CDCl$_3$): δ=7.88-7.84 (m, 2H), 7.54 (d, 1H), 7.26-7.18 (m, 4H), 7.01 (d, 2H), 6.92 (s, 3H), 4.88-4.83 (m, 1H), 4.14-4.11 (m, 1H), 3.39-3.29 (m, 2H), 3.13 (m, 2H), 3.00 (s, 3H), 2.99 (s, 3H), 1.92-1.89 (m, 1H), 1.59-1.43 (m, 3H).

$^{13}$C NMR (CDCl$_3$): δ=173.1, 172.4, 165.6, 155.5, 150.4, 133.2, 131.9, 130.6, 130.3, 121.8, 116.6, 61.9, 53.1, 49.6, 36.6, 36.3, 30.2, 23.9.

Example 33

Synthesis of N-(Toluene-4-sulfonyl)-D-prolyl-L-4-(4-methylpiperazin-1-yl)phenylalanine t-butyl Ester The title compound was prepared following the procedure outlined for the preparation of Example 4 and substitution of appropriate starting materials.

NMR data was as follows:

$^1$H NMR (CDCl$_3$): δ=7.72 (d, 2H), 7.33 (d, 3H), 7.17 (d, 2H), 7.02 (d, 2H), 4.71 (q, 1H), 4.09-4.06 (m, 1H), 3.67 (bs, 2H), 3.57 (bs, 2H), 3.41-3.34 (m, 1H), 3.22 (dd, 1H), 3.16-3.09 (m, 1H), 3.03 (dd, 1H), 2.46-2.43 (m, 7H), 2.05-2.02 (m, 1H), 1.57-1.43 (m, 3H), 1.47 (s, 9H).

$^{13}$C NMR (CDCl$_3$): δ=170.8, 169.9, 153.6, 150.4, 144.3, 133.4, 133.1, 130.3, 130.0, 127.9, 121.6, 82.6, 62.3, 54.5, 53.8, 49.6, 46.1, 44.3, 43.7, 37.3, 29.7, 27.8, 24.1, 21.4.

Example 34

Synthesis of N-(Toluene-4-sulfonyl)-N-methyl-L-alanyl-L-4-(4-methylpiperazin-1-ylcarbonyloxy)phenylalanine t-butyl ester The title compound was prepared following the procedure outlined for the preparation of Example 4 and substitution of appropriate starting materials.

NMR data was as follows:

$^1$H NMR (CDCl$_3$): δ=7.68 (d, 2H), 7.31 (d, 2H), 7.17 (d, 2H), 7.04 (d, 2H), 6.86 (d, 1H), 4.65 (m, 1H), 4.47 (q, 1H), 3.71-3.53 (m, 4H), 3.24-2.92 (m, 2H), 2.50-2.40 (m, 10H), 2.35 (s, 3H), 1.45 (s, 9H), 0.92 (d, 3H).

$^{13}$CNMR (CDCl$_3$): δ=170.1, 169.9, 153.6, 150.4, 143.9, 135.6, 133.3, 130.2, 129.9, 127.2, 121.8, 82.4, 55.4, 54.6, 53.6, 46.0, 44.2, 43.7, 37.2, 29.6, 27.8, 21.4, 11.5.

Example 35

Synthesis of N-(4-Nitrobenzenesulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^1$H NMR (CDCl$_3$): δ=8.38-8.34 (m, 2H), 8.05-8.00 (m, 2H), 7.16-2.12 (m, 2H), 7.03-6.94 (m, 3H), 4.74-4.68 (m, 1H), 4.15-4.14 (m, 1H), 3.41-3.32 (m, 1H), 3,23-3.14 (m, 2H), 3.08 (s, 3H), 3.03 (m, 1H), 2.98 (s, 3H), 2.05 (m, 1H), 1.66-1.48 (m, 3H), 1.47 (s, 9H).

$^{13}$C NMR (CDCl$_3$): δ=170.0, 169.9, 154.8, 150.6, 150.4, 142.4, 132.9, 130.2, 129.0, 124.5, 121.6, 82.7, 62.2, 53.4, 49.4, 37.0, 36.5, 36.2, 30.1, 27.7, 24.1.

Example 36

Synthesis of N-(Toluene-4-sulfonyl)-L-[(1,1-dioxo)-thiamorpholin-3-carbonyl]-L-4-(N,N-dimethylaminosulfonyloxy)phenylalanine tert-Butyl Ester The title compound was prepared using the procedure described for the preparation of Example 21 and substitution of appropriate starting materials.

NMR data was as follows:

$^1$H NMR (CDCl$_3$): δ=7.73 (d, 1H), 7.67 (d, 1H), 7.35 (m, 2H), 7.27 (m, 2H), 6.88 (d, 1H), 6.66 (d, 1H), 5.08 (m, 0.5H), 4.97 (m, 0.5H), 4.71 (m, 0.5H), 4.61 (m, 0.5H), 4.25 (m, 0.5H), 4.03 (m, 1H), 3.21-3.04 (m, 4H), 2.89 (s, 3H), 2.83 (s, 3H), 2.78 (m, 3H), 2.42 (s, 3H), 1.44 (s, 4.5H), 1.38 (s, 4.5H).

$^{13}$C NMR (CDCl$_3$): δ=169.8, 169.6, 164.9, 164.5, 149.3, 149.1, 145.6, 145.4, 135.4, 135.0, 134.6, 130.9, 130.6, 130.5, 127.4, 127.2, 122.0, 121.8, 83.0, 83.0, 56.0, 53.7, 49.2, 49.1, 48.5, 41.9, 41.4, 38.6, 36.8, 36.2, 27.7, 21.5.

Example 37

Synthesis of N-(Toluene-4-sulfonyl)sarcosyl-L-4-(thiomorpholin-4-ylcarbonyloxy)phenylalanine tert-Butyl Ester Substituting thiomorpholine for N-methylpiperazine, and following the method for the preparation of Example 4, gave the title compound.

NMR data was as follows:

$^1$H NMR (CDCl$_3$): δ=7.65 (d, 2H), 7.33 (d, 2H), 7.20 (d, 2H), 7.04 (d, 2H), 4.76 (m, 1H), 3.89 (m, 4H), 3.68 (d, 1H), 3.48 (d, 1H), 3.10 (m, 2H), 2.66 (m, 7H), 2.41 (s, 3H), 1.43 (s, 9H).

$^{13}$C NMR (CDCl$_3$): δ=169.9, 167.2, 153.5, 150.3, 144.3, 133.1, 130.3, 130.0, 127.6, 121.8, 82.5, 53.8, 53.3, 47.0, 36.4, 37.2, 36.6, 27.8, 27.3, 27.0, 21.4.

Example 38

Synthesis of N-(Toluene-4-sulfonyl)-L-N-methylalanyl-L-4-(4-methylpiperazin-1-ylcarbonyloxy)phenylalanine The title compound was prepared from the product of Example 34 using the procedure described in Method 11.

NMR data was as follows:

$^1$H NMR (CDCl$_3$): δ=7.65 (d, 2H), 7.34 (d, 2H), 7.27 (d, 2H), 7.09 (d, 2H), 4.64-4.50 (m, 2H), 4.48-4.23 (m, 2H), 3.60-2.96 (m, 8H), 2.92 (s, 3H), 2.55 (s, 3H), 2.40 (s, 3H), 0.93 (d, 3H).

$^{13}$C NMR (CDCl$_3$): δ=174.3, 173.1, 154.9, 151.6, 145.5, 137.0, 136.1, 131.6, 131.2, 128.5, 123.1, 56.4, 54.8, 54.0, 43.8, 37.3, 30.2, 21.5, 13.2.

Example 39

Synthesis of N-(Toluene-4-sulfonyl)-L-prolyl-L-4-(1,1-dioxothiomorpholin-4-ylcarbonyloxy)phenylalanine The title compound was prepared from the product of Example 81 using the procedure described in Method 11.

NMR data was as follows:

$^1$H NMR (CD$_3$OD): δ=8.03 (m, 1H), 7.73 (d, 2H), 7.41 (d, 2H), 7.28 (d, 2H), 7.08 (d, 2H), 4.70-4.65 (m, 1H), 4.12-4.00 (m, 5H), 3.38-3.36 (m, 1H), 3.31-3.06 (m, 7H), 2.43 (s, 3H), 1.77-1.48 (m, 5H).

$^{13}$C NMR (CD$_3$OD): δ=168.4, 159.1, 130.0, 129.1, 125.6, 125.1, 123.0, 116.9, 57.2, 48.8, 46.3, 44.5, 31.5, 25.6, 19.3, 15.4.

Example 40

Synthesis of N-(Toluene-4-sulfonyl)-L-prolyl-t-4-(thiomorpholin-4-ylcarbonyloxy)phenylalanine The title compound was prepared from the product of Example 82 using the procedure described in Method 11.

NMR data was as follows:

$^1$H NMR (CD$_3$OD): δ=7.73 (d, 2H), 7.41 (d, 2H), 7.27 (d, 2H), 7.04 (d, 2H), 4.68-4.65 (m, 1H), 4.10-4.07 (m, 1H), 3.90 (t, 2H), 3.77 (t, 2H), 3.38-3.11 (m, 4H), 2.66 (m, 4H), 2.43 (s, 3H), 1.80-1.48 (m, 5H).

$^{13}$C NMR (CD$_3$OD): δ=168.4, 168.2, 149.4, 145.7, 139.8, 129.7, 129.0, 125.6, 125.1, 123.1, 116.9, 57.2, 48.8, 44.6, 42.1, 36.0, 31.4, 25.7, 22.1, 21.8, 19.3, 15.4.

Example 41

Synthesis of N-(Toluene-4-sulfonyl)-L-prolyl-L-4-(isonipecotoyloxy)phenylalanine The title compound was prepared from the product of Example 80 using the procedure described in Method 11.

NMR data was as follows:

$^1$H NMR (CD$_3$OD): δ=8.08 (m, 1H), 7.73 (d, 2H), 7.41 (d, 2H), 7.27 (d, 2H), 7.03 (d, 2H), 4.71 (m, 1H), 4.11-4.08 (m, 1H), 3.61 (t, 2H), 3.47-3.38 (m, 3H), 3.31-3.11 (m, 4H), 2.43 (s, 3H), 1.77-1.47 (m, 10H).

$^{13}$C NMR (CD$_3$OD): δ=168.3, 168.1, 158.8, 149.6, 145.9, 139.8, 129.5, 129.0, 125.6, 125.1, 123.1, 116.9, 57.2, 48.6, 44.6, 40.6, 40.1, 36.0, 31.4, 25.7, 20.9, 20.6, 19.3.

Example 42

Synthesis of N-(Toluene-4-sulfonyl)-L-prolyl-L-4-(pyrrolidin-1-ylcarbonyloxy)phenylalanine The title compound was prepared from the product of Example 83 using the procedure described in Method 11.

NMR data was as follows:

$^1$H NMR (CD$_3$OD): δ=8.08 (m, 1H), 7.73 (d, 2H), 7.41 (d, 2H), 7.04 (d, 2H), 7.27 (d, 2H), 4.72-4.68 (m, 1H), 4.11-4.08 (m, 1H), 3.57-3.53 (t, 2H), 3.43-3.28 (m, 3H), 3.25-3.06 (m, 4H), 2.43 (s, 3H), 1.99-1:80 (m, 4H), 1.78-1.49 (m, 5H).

$^{13}$CNMR(CD$_3$OD): δ=168.2, 158.3, 149.2, 145.8, 139.8, 129.4, 129.1, 125.6, 125.1, 123.1, 116.9, 57.2, 48.7, 44.5, 41.5, 31.4, 25.7, 20.6, 19.8, 19.3, 15.4.

Example 43

Synthesis of N-(Toluene-4-sulfonyl)-L-prolyl-L-4-(morpholin-4-ylcarbonyloxy)phenylalanine The title compound was prepared from the product of Example 108 using the procedure described in Method 11.

NMR data was as follows:

$^1$H NMR (CD$_3$OD): δ=7.73 (d, 2H), 7.41 (d, 2H), 7.27 (d, 2H), 7.04 (d, 2H), 4.95-4.93 (m, 1H), 4.10-4.07 (m, 1H), 3.71-3.65 (m, 6H), 3.50 (t, 2H), 3.40-3.10 (m, 4H), 2.43 (s, 3H), 1.78-1.48 (m, 4H).

$^{13}$C NMR (CD$_3$OD): δ=168.4, 168.2, 149.6, 145.7, 139.8, 129.1, 125.6, 125.1, 123.1, 116.8, 61.5, 57.2, 44.5, 36.0, 31.4, 25.6, 19.3, 15.4.

Example 44

Synthesis of N-(Toluene-4-sulfonyl)-L-prolyl-L-4-(4-methylpiperazin-1-ylcarbonyloxy)phenylalanine Neopentyl Ester Titanium isopropoxide (0.3 equivalents) was added to Tos-Pro-Tyr ethyl ester (1 equivalent) and an excess of neopentyl alcohol. The mixture was heated to reflux under an argon atmosphere overnight. Excess neopentyl alcohol was removed under reduced pressure and the residue purified by flash column chromatography (silica, hexane: EtOAc 2:1) to give the neopentyl ester a white solid (0.9 g, 85%). The title compound was prepared following the procedure described in Example 4.

NMR data was as follows:

$^1$H NMR (DMSO-d$_6$, 400 MHz) δ=8.29 (d, 1H, J=7.91 Hz); 7.68 (d, 2H, J=8.45 Hz); 7.40 (d, 2H, J=8.34 Hz); 7.24 (d, 2H, J=8.57 Hz); 7.00 (d, 2H, J=8.57 Hz); 4.56 (m, 1H); 4.07 (m, 1H); 3.73 (s, 2H); 3.55 (br s, 2H); 3.40 (m, 3H); 3.10 (m, 3H); 2.40 (s, 3H); 2.35 (br s, 4H); 2.20 (s, 3H); 1.55 (m, 3H); 1.37 (m, 1H); 0.85 (s, 9H).

Example 45

Synthesis of N-(Toluene-4-sulfonyl)-L-prolyl-L-4-(N,N-dimethylcarbamyloxy)phenylalanine Neopentyl Ester Titanium isopropoxide (0.3 equivalents) was added to Tos-Pro-Tyr ethyl ester (1 equivalent) and an excess of neopentyl alcohol. The mixture was heated to reflux under an argon atmosphere overnight. Excess neopentyl alcohol was removed under reduced pressure and the residue purified by flash column chromatography (silica, hexane: EtOAc 2:1) to give the neopentyl ester a white solid (0.9 g, 85%). The title compound was prepared following the procedure described in Example 2.

NMR data was as follows:

$^1$H NMR (DMSO-d$_6$, 400 MHz) δ=8.28 (d, 1H, J=8.13 Hz); 7.68 (d, 2H, J=8.4 Hz); 7.40 (d, 2H, J=7.9 Hz); 7.23 (d, 2H, J=8.56 Hz); 6.99 (d, 2H, J=8.35 Hz); 4.57 (m, 3H); 2.40 (s, 3H); 1.55 (m, 3H); 1.38 (m, 1H); 0.85 (s, 9H).

Example 46

Synthesis of 2-(Saccharin-2-yl)propionoyl-L-4-(4-methylpiperazin-1-ylcarbonyloxy)phenylalanine tert-Butyl Ester The title compound was prepared following the procedure described in Preparative Example A and Example 4.

NMR data was as follows:
¹H NMR (DMSO-d₆, 400 MHz) (1:1 mixture of diastereomers) δ=8.31 (m, 1H); 8.26 (m, 1H); 8.03 (m, 3H); 7.20 (m, 2H); 7.00 (m, 2H); 4.73 (m, 1H); 4.30 (m, 1H); 3.58 (br s, 2H); 3.40 (br s, 2H); 3.02 (m, 1H); 2.95 (m, 1H); 2.35 (br s, 4H); 2.20 (s, 3H); 2.75 and 2.65 (two d, 3H); 1.35 and 1.32 (two s, 9H).

Example 47

Synthesis of 2-(Saccharin-2-yl)propionoyl-L-4-(N,N-dimethylcarbamyloxy)phenylalanine The title compound was prepared from the product of Preparative Example A using the procedure described in Method 11.
NMR data was as follows:
¹H NMR (DMSO-d₆, 400 MHz) (1:1 mixture of diastereomers) δ=12.75 (br s, 1H); 8.28 (m, 2H); 8.05 (m, 3H); 7.20 (m, 2H); 7.00 and 9.95 (two d, 2H); 4.75 (m, 1H); 4.40 (m, 1H); 3.10 (m, H); 3.05 (s, 3H); 2.95 (m, 1H); 2.90 (s, 3H); 2.75 and 2.60 (two d, 3H).

Example 48

Synthesis of N-(Toluene-4-sulfonyl)-L-N-methylalanyl-L-4-(N,N-dimethylcarbamyloxy)phenylalanine tert-Butyl Ester The title compound was prepared following the procedure for the synthesis of Example 2 with the substitution of appropriate starting materials.
NMR data was as follows:
¹H NMR (CDCl₃): δ=7.68 (d, 2H), 7.31 (d, 2H), 7.17 (d, 2H), 7.04 (d, 2H), 6.87 (d, 2H), 4.67 (m, 1H), 4.48 (q, 1H), 3.09 (s, 3H), 3.00 (s, 3H), 3.14-2.92 (m, 2H), 2.46 (s, 3H), 2.43 (s, 3H), 1.45 (s, 9H), 0.92 (d, 3H).
¹³C NMR (CDCl₃): δ=170.2, 169.9, 154.9, 150.6, 143.9, 135.6, 133.2, 130.2, 130.0, 127.3, 121.9, 82.5, 55.5, 53.7, 37.2, 36.6, 36.4, 29.7, 27.8, 21.4, 11.5.

Example 49

Synthesis of N-(Toluene-4-sulfonyl)-L-(thiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (*Acta Chemica Scan.* 1994, 48, 517-525). N-(Toluene-4-sulfonyl)-L-thiamorpholine-3-carboxylic acid was prepared using the procedure described in Method 1. The title compound was prepared following the procedure for the synthesis of Example 2 with substitution of appropriate starting materials.
NMR data was as follows:
¹H NMR (CDCl₃): δ=7.69 (d, 2H), 7.31 (d, 2H), 7.16 (d, 2H), 6.98 (d, 2H), 6.86 (d, 1H), 4.71 (m, 1H), 4.62 (m, 1H), 3.94 (m, 1H), 3.31 (m, 1H), 3.09 (m, 4H), 2.98 (s, 3H), 2.67 (m, 1H), 2.50 (m, 1H), 2.40 (s, 3H), 2.31 (m, 1H), 2.10 (m, 1H), 1.49 (s, 9H).
¹³C NMR (CDCl₃): δ=169.9, 167.4, 154.8, 150.6, 144.2, 136.8, 132.8, 130.4, 130.2, 127.3, 121.8, 82.6, 55.2, 54.0, 43.3, 36.5, 36.3, 27.8, 25.2, 24.6, 21.4.

Example 50

Synthesis of N-(Toluene-4-sulfonyl)sarcosyl-L-4-(1,1-dioxothiomorpholin-4-ylcarbonyloxy)phenylalanine The title compound was prepared from the product of Example 121 using the procedure described in Method 11.
NMR data was as follows:
¹H NMR (CD₃OD): δ=7.67 (d, 2H), 7.40 (d, 2H), 7.27 (d, 2H), 7.09 (d, 2H), 4.61 (m, 1H), 4.12 (m, 2H), 3.99 (m, 2H), 3.60 (m, 2H), 3.23 (m, 8H), 2.58 (s, 3H), 2.42 (s, 3H).
¹³C NMR (CD₃OD): δ=174.2, 170.3, 155.0, 151.6, 145.6, 136.1, 135.2, 131.5, 131.1, 128.9, 123.0, 54.6, 54.0, 52.4, 52.2, 44.4, 44.0, 37.4, 36.8, 21.4.

Example 51

Synthesis of N-(Toluene-4-sulfonyl)-L-(1,1-dioxothiamorpholin-3-carbonyl)-L-4-(N,N-dimethylcarbamyloxy)phenylalanine tert-Butyl Ester The title compound was prepared from the product of Example 49 following the procedure described by Larsson and Carlson (*Acta Chemica Scan.* 1994, 48, 522).
NMR data was as follows:
¹H NMR (CDCl₃): δ=7.76 (d, 2H), 7.37 (d, 2H), 7.08 (d, 2H), 6.98 (d, 2H), 6.56 (d, 1H), 4.95 (m, 1H), 4.62 (m, 1H), 3.99 (m, 2H), 3.25 (m, 1H), 3.07 (s, 3H), 2.97 (m, 8H), 2.44 (s, 3H), 1.48 (s, 9H).
¹³C NMR (CDCl₃): δ=170.0, 164.8, 154.9, 150.7, 145.4, 135.3, 132.6, 130.7, 130.3, 127.5, 122.3, 82.8, 56.1, 53.6, 49.5, 48.6, 41.6, 36.6, 36.4, 27.9, 21.6.

Example 52

Synthesis of N-(Toluene-4-sulfonyl)-L-(1,1-dioxothiamorpholin-3-carbonyl)-L-4-(morpholin-4-ylcarbonyloxy)phenylalanine tert-Butyl Ester The title compound was prepared following the procedure described for the preparation of Example 71.
NMR data was as follows:
¹H NMR (CDCl₃): δ=7.75 (d, 2H), 7.36 (d, 2H), 7.12 (d, 2H), 6.98 (d, 2H), 6.58 (d, 1H), 4.93 (m, 1H), 4.63 (m, 1H), 4.09 (m, 2H), 3-0.72 (m, 4H), 3.63 (m, 2H), 3.51 (m, 2H), 3.24 (m, 1H), 2.96 (m, 4H), 2.43 (s, 3H), 1.46 (s, 9H).
¹³C NMR (CDCl₃): δ=170.0, 164.8, 153.7, 150.4, 145.4, 135.2, 132.9, 130.7, 130.4, 127.5, 122.1, 82.9, 66.4, 56.1, 53.6, 49.4, 48.5, 44.7, 43.9, 41.6, 36.3, 27.8, 21.6.

Example 53

Synthesis of N-(Toluene-4-sulfonyl)-L-N-methylalanyl-L-4-(N,N-dimethylcarbamyloxy)phenylalanine The title compound was prepared from the product of Example 48 using the procedure described in Method 11.
NMR data was as follows:
¹H NMR (CDCl₃): δ=7.68 (d, 2H), 7.31 (d, 2H), 7.20 (d, 2H), 7.11-7.04 (m, 3H), 6.35 (br s, 1H), 4.81 (m, 1H), 4.52 (q, 1H), 3.35-2.98 (m, 2H), 3.09 (s, 3H), 3.00 (s, 3H), 2.45 (s, 3H), 2.43 (s, 3H), 0.91 (d, 3H).
¹³C NMR (CDCl₃): δ=173.7, 170.8, 155.2, 150.6, 144.0, 135.4, 133.2, 130.2, 130.0, 127.3, 122.1, 55.5, 53.2, 36.6, 36.5, 36.4, 29.8, 21.4, 11.6.

Example 54

Synthesis of N-(4-Fluorobenzenesulfonyl)-L-(thiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (*Acta Chemica Scan.* 1994, 48, 517-525). N-(Toluene-4-sulfonyl)-L-thiamorpholine-3-carboxylic acid was prepared using the procedure described in Method 1.

The title compound was then prepared following the procedure for the synthesis of Example 2.

NMR data was as follows:
$^1$H NMR (CDCl$_3$): δ=7.87-7.82 (m, 2H), 7.20 (t, 2H), 7.16 (d, 2H), 7.00 (d, 2H), 6.76 (d, 1H), 4.74 (t, 1H), 4.65 (q, 1H), 3.92 (d, 1H), 3.32 (dd, 1H), 3.17-3.00 (m, 2H), 3.09 (s, 3H), 2.99 (s, 3H), 2.76-2.66 (m, 1H), 2.62 (dd, 1H), 2.46 (dt, 1H), 2.22 (d, 1H), 1.49 (s, 9H).
$^{13}$C NMR (CDCl$_3$)δ=170.0, 167.2, 165.5, 154.8, 150.7, 135.8, 132.7, 130.5, 130.1, 121.9, 116.9, 82.8, 55.3, 53.9, 43.4, 36.6, 36.4, 36.3, 27.9, 25.8, 25.0.

Example 55

Synthesis of N-(4-Fluorobenzenesulfonyl)-L-(1,1-dioxothiamorpholin-3-carbonyl)-L-4-(N,N-dimethylcarbamyloxy)phenylalanine tert-Butyl Ester The title compound was prepared from the product of Example 54 following the procedure described by Larsson and Carlson (*Acta Chemica Scan.* 1994, 48, 522).

NMR-data was as follows:
$^1$H NMR (CDCl$_3$): δ=7.92-7.88 (m, 2H), 7.24 (t, 2H), 7.09 (d, 2H), 6.97 (d, 2H), 6.41 (d, 1H), 4.96 (d, 1H), 4.62 (d, 1H), 4.03 (d, 1H), 3.26 (dd, 1H), 3.13-2.92 (m, 6H), 3.09 (s, 3H), 2.97 (s, 3H), 1.49 (s, 9H).
$^{13}$C NMR (CDCl$_3$): δ=170.1, 165.9, 164.5, 154.9, 150.7, 134.0, 132.4, 130.5, 130.4, 122.2, 117.3, 83.0, 56.1, 53.4, 50.0, 49.1, 41.7, 36.6, 36.3, 36.1, 27.9.

Example 56

Synthesis of N-(Pyridine-3-sulfonyl)-L-prolyl-L-4-(N,N-dimethylcarbamyloxy)phenylalanine tert-Butyl Ester N-Benzyl-L-proline was coupled to L-tyrosine t-butyl ester using the procedure described in Method 12. N-Benzyl-L-prolyl-L-(N,N-dimethylcarbamyloxy)phenyl-alanine t-butyl ester was prepared following the procedure described for the preparation of Example 2. L-Prolyl-L-(4-N,N-dimethylcarbamyloxy)phenylalanine t-butyl ester was prepared from the product of the previous reaction using the procedure described in Method 4. The title compound was prepared using the procedure described for the preparation of 3-pyridine sulfonyl chloride (see Crowell et al., *J. Med. Chem.*, 1989, 32, 2436-2442) and the product of the last reaction.

NMR data was as follows:
$^1$H NMR (CDCl$_3$): δ=9.95 (d, 1H), 8.83 (dd, 1H), 8.14-8.10 (m, 1H), 7.51-7.47 (m, 1H), 7.16-7.13 (m, 3H), 7.02-6.99 (m, 2H), 4.72-4.69 (m, 1H), 4.09-4.06 (m, 1H), 3.41-3.39 (m, 1H), 3.23-3.17 (m, 1H), 3.13-2.98 (m, 1H), 3.07 (s, 3H), 2.97 (s, 3H), 2.04 (m, 1H), 1.59-1.47 (m, 3H), 1.45 (s, 9H).
$^{13}$C NMR (CDCl$_3$): δ=170.1, 169.9, 154.8, 153.9, 150.5, 148.4, 135.5, 133.0, 130.1, 123.9, 121.6, 82.6, 52.2, 53.6, 49.5, 37.1, 36.5, 36.3, 29.9, 27.8, 24.0.

Preparative Example B

Synthesis of N-(Pyrimidine-2-sulfonyl)-L-prolyl-L-4-(N,N-dimethylcarbamyloxy)phenylalanine tert-Butyl Ester The title compound was prepared by substituting 2-pyrimidine sulfonyl chloride (see Skulnick et al., *J. Med. Chem.*, 1997, 40, 1149-1164) and following the method for the preparation of Example 56.

NMR data was as follows:
$^1$H NMR (CDCl$_3$): δ=8.28 (d, 2H), 7.39 (d, 1H), 7.02 (d, 2H), 6.88 (d, 2H), 6.54 (m, 1H), 4.76-4.69 (m, 1H), 4.57-4.55 (m, 1H), 3.64 (m, 1H), 3.55-3.52 (m, 1H), 3.09-3.03 (m, 1H), 3.08 (s, 3H), 2.99-2.95 (m, 1H), 2.98 (s, 3H), 2.32 (m, 1H), 2.01-1.97 (m, 3H), 1.37 (s, 9H).
$^{13}$C NMR (CDCl$_3$): δ=172.1, 170.4, 160.6, 157.7, 154.8, 150.3, 133.0, 130.1, 121.3, 110.5, 82.0, 60.7, 53.3, 47.5, 37.1, 36.5, 36.3, 28.9, 27.7, 24.1.

Example 57

Synthesis of N-(4-Nitrobenzenesulfonyl)-L-prolyl-L-4-(N,N-dimethylcarbamyloxy)phenylalanine The title compound was prepared from the product of Example 35 using the procedure described in method 11.

NMR data was as follows:
$^1$H NMR (CDCl$_3$): δ=8.36 (d, 2H), 8.02 (d, 2H), 7.42 (d, 1H), 7.20 (d, 2H), 7.01 (d, 2H), 4.86 (m, 1H), 4.18-4.15 (m, 1H), 3.46-3.43 (m, 1H), 3.32-3.26 (m, 1H), 3.19-3.11 (m, 2H), 3.09 (s, 3H), 3.01 (s, 3H), 1.91 (m, 1H), 1.65-1.54 (m, 3H).
$^{13}$C NMR (CDCl$_3$): δ=172.9, 171.7, 155.5, 150.4, 150.4, 142.1, 133.2, 130.5, 129.1, 124.6, 121.8, 61.9, 52.9, 49.6, 36.6, 36.3, 36.3, 30.6, 24.1.

Example 58

Synthesis of N-(4-Cyanobenzenesulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:
$^1$H NMR (CDCl$_3$): δ=7.94 (d, 2H), 7.82 (d, 2H), 7.13 (d, 2H), 7.05-6.99 (m, 3H), 4.71-4.66 (m, 1H), 4.12-4.09 (m, 1H), 3.36-3.35 (m, 1H), 3.22-3.11 (m, 2H), 3.07 (s, 3H), 3.06-3.01 (m, 1H), 2.97 (s, 3H), 2.05 (m, 1H), 1.63-1.37 (m, 3H), 1.46 (s, 9H).
$^{13}$C NMR (CDCl$_3$): δ=170.1, 169.9, 154.8, 150.6, 140.8, 133.1, 132.9, 130.2, 128.4, 121.7, 117.1, 116.9, 82.7, 62.2, 53.4, 49.4, 37.0, 36.5, 36.3, 30.1, 27.8, 24.1.

Example 59

Synthesis of N-(Toluene-4-sulfonyl)-L-(1,1-dioxothiamorpholin-3-carbonyl)-L-4-(N,N-dimethylaminosulfonyloxy)phenylalanine The title compound was prepared from the product of Example 36 using the procedure described in Method 11.

NMR data was as follows:
$^1$H NMR (CD$_3$OD): δ=7.79 (m, 2H), 7.44 (m, 2H), 7.27 (m, 2H), 7.17 (m, 2H), 5.21 (m, 1H), 4.64 (m, 1H), 4.14 (m, 1H), 3.61 (m, 2H), 3.24 (m, 2H), 3.08 (m, 2H), 2.89 (s, 6H), 2.80 (m, 2H), 2.43 (s, 3H).
$^{13}$C NMR (CD$_3$OD): δ=173.9, 168.1, 168.0, 150.8, 150.8, 146.7, 146.5, 137.6, 137.5, 137.1, 136.9, 132.2, 132.1, 131.7, 131.6, 128.8, 123.3, 123.1, 57.3, 54.8, 51.0, 50.8, 50.5, 47.9, 47.8, 43.2, 43.0, 39.0, 39.0, 37.4, 37.0, 21.5.

Example 60

Synthesis of N-(Toluene-4-sulfonyl)-L-(1,1-dioxothiamorpholin-3-carbonyl)-L-4-(N,N-dimethylcarbamyloxy)phenylalanine The title compound was prepared from the product of Example 51 using the procedure described in Method 11.
NMR data was as follows:
$^1$H NMR (CDCl$_3$): δ=7.79 (d, 2H), 7.43 (d, 2H), 7.20 (d, 2H), 7.00 (d, 2H), 5.21 (m, 1H), 4.65 (m, 1H), 4.12 (m, 1H), 3.75 (m, 1H), 3.29 (m, 3H), 3.08 (s, 3H), 3.00 (m, 1H), 3.00 (m, 1H), 2.97 (s, 3H), 2.80 (m, 3H), 2.44 (s, 3H).
$^{13}$C NMR (CDCl$_3$): δ=165.1, 159.0, 147.9, 143.1, 137.6, 128.6, 126.1, 122.7, 122.6, 119.8, 114.3, 48.3, 45.8, 41.6, 34.0, 28.0, 27.8, 27.7, 12.5.

Example 61

Synthesis of N-(Toluene-4-sulfonyl)-L-(1,1-dioxo)thiaprolyl-L-4-(N,N-dimethylcarbamyloxy)phenylalanine tert-Butyl Ester The title compound was prepared from N-(toluene-4-sulfonyl)-L-thiaprolyl-L-4-(N,N-dimethylcarbamyloxy)phenylalanine tert-butyl ester, prepared as per the examples herein, following the procedure described by Larsson and Carlson (*Acta Chemica Scan.* 1994, 48, 522).
NMR data was as follows:
$^1$H NMR (CDCl$_3$): δ=7.77 (d, 2H), 7.38 (d, 2H), 7.18 (m, 3H), 7.09 (d, 2H), 4.83-4.57 (m, 3H), 3.77-3.60 (m, 2H), 3.36-3.23 (m, 1H), 3.15-3.00 (m, 7H), 2.85-2.73 (m, 1H), 2.46 (s, 3H), 1.50 (s, 9H).

Example 62

Synthesis of N-(4-Fluorobenzenesulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.
NMR data was as follows:
$^1$H NMR (CDCl$_3$): δ=7.96 (d, 2H), 7.80 (d, 2H), 7.26-7.13 (m, 3H), 7.01 (d, 2H), 4.72-4.70 (m, 1H), 4.11-4.08 (m, 1H), 3.40-3.37 (m, 1H), 3.25-3.10 (m, 2H), 3.07 (s, 3H), 3.04-3.02 (m, 1H), 2.98 (s, 3H), 2.06 (m, 1H), 2.06-2.04 (m, 1H), 1.61-1.52 (m, 3H), 1.46 (s, 9H).
$^{13}$C NMR (CDCl$_3$): δ=170.3, 169.9, 154.9, 150.6, 139.9, 134.9, 133.1, 130.2, 128.4, 126.5, 121.7, 82.7, 62.3, 5.35, 49.6, 37.2, 36.6, 36.3, 30.0, 27.8 24.1.

Example 63

Synthesis of N-(1-Methylpyrazolyl-4-sulfonyl)-L-prolyl-L-4-(N,N-dimethylcarbamyloxy)phenylalanine The title compound was prepared from the product of Example 117 using the procedure described in Method 11.
NMR data was as follows:
$^1$H NMR (CDCl$_3$): δ=8.84 (br s, 1H), 7.93 (s, 1H), 7.79 (s, 1H), 7.68-7.65 (m, 1H), 7.18 (d, 2H), 6.99 (d, 2H), 4.88-4.81 (m, 1H), 4.08-4.06 (m, 1H), 3.92 (s, 3H), 3.45-3.40 (m, 1H), 3.34-3.27 (m, 1H), 3.11-3.01 (m, 5H), 2.97 (s, 3H), 1.82 (m, 1H), 1.66-1.57 (m, 2H), 1.45 (m, 1H).
$^{13}$C NMR (CDCl$_3$): δ=173.1, 172.9, 159.1, 158.6, 150.4, 138.8, 133.4, 133.2, 130.3, 121.9, 117.3, 62.0, 53.1, 49.7, 39.4, 36.6, 36.5, 36.4, 30.4, 23.9.

Example 64

Synthesis of N-(Toluene-4-sulfonyl)-L-(1,1-dioxo)thiaprolyl-L-4-(N,N-dimethylcarbamyloxy)phenylalanine The title compound was prepared from the product of Example 61 using the procedure described in Method 11.
NMR data was as follows:
$^1$H NMR (CDCl$_3$): δ=8.34 (d, 1H), 7.70 (d, 2H), 7.33 (d, 2H), 7.14 (d, 2H), 7.01 (d, 2H), 5.07 (m, 1H), 4.93 (m, 1H), 4.43 (d, 1H), 4.01 (d, 1H), 3.68 (m, 1H), 3.37 (m, 1H), 3.17 (s, 3H), 3.14 (m, 1H), 3.09 (s, 3H), 2.54 (m, 1H), 2.43 (s, 3H).
$^{13}$C NMR (CDCl$_3$): δ=171.5, 166.4, 156.4, 150.5, 145.5, 134.2, 134.1, 131.4, 130.3, 128.1, 121.8, 64.3, 59.2, 53.7, 50.5, 36.9, 36.5, 35.8, 21.6.

Example 65

Synthesis of N-(4-Fluorobenzenesulfonyl)-L-thiaprolyl-L-4-(N,N-dimethylcarbamyloxy)phenylalanine The title compound was prepared from the product of Example 84 using the procedure described in Method 11.
NMR data was as follows:
$^1$H NMR (CDCl$_3$): δ=7.83 (m, 2H), 7.73 (d, 1H), 7.16 (m, 4H), 6.99 (d, 2H), 5.57 (br s, 1H), 4.87 (m, 1H), 4.76 (m, 1H), 4.53 (d, 1H), 4.10 (d, 1H), 3.34 (m, 1H), 3.22 (d, 2H), 3.12 (s, 3H), 3.04 (s, 3H), 2.43 (m, 1H).
$^{13}$C NMR (CDCl$_3$): δ=172.1, 168.7, 155.7, 150.5, 133.6, 133.1, 130.8, 130.7, 121.7, 116.9, 116.6, 65.3, 53.3, 51.3, 36.8, 36.4, 36.1, 33.4.

Example 66

Synthesis of N-(4-Fluorobenzenesulfonyl)-L-(5,5-dimethyl)-thiaprolyl-L-4-(N,N-dimethylcarbamyloxy)phenylalanine tert-Butyl Ester The title compound was prepared following the procedure described for the preparation of Example 2 with the substitution of appropriate starting materials.
NMR data was as follows:
$^1$H NMR (CDCl$_3$): δ=7.91 (m, 2H), 7.26 (m, 4H), 7.02 (d, 2H), 6.96 (d, 1H), 4.75 (m, 1H), 4.55 (d, 1H), 4.42 (d, 1H), 3.86 (s, 1H), 3.08 (s, 3H), 3.05 (m, 2H), 3.00 (s, 3H), 1.43 (s, 9H), 1.17 (s, 3H), 1.16 (s, 3H).
$^{13}$C NMR (CDCl$_3$): δ=169.9, 168.1, 167.6, 164.2, 154.9, 150.6, 133.1, 132.2, 131.0, 130.9, 130.4, 121.7, 116.9, 116.6, 82.7, 73.5, 54.7, 53.7, 50.5, 37.8, 36.6, 36.4, 29.1, 27.8, 23.8.

Example 67

Synthesis of N-(4-Fluorobenzenesulfonyl)-L-(1,1-dioxothiamorpholin-3-carbonyl)-L-4-(1,1-dioxothiomorpholin-4-ylcarbonyloxy)phenylalanine tert-Butyl Ester The title compound was prepared following the procedure described for the preparation of Example 68.

NMR data was as follows:

$^1$H NMR (CDCl$_3$): δ=7.91-7.87 (m, 2H), 7.27-7.25 (m, 2H), 7.15 (d, 2H), 6.51 (d, 1H), 4.93-4.90 (m, 1H), 4.64-4.58 (m, 1H), 4.14-3.99 (m, 7H), 3.28-2.90 (m, 10H), 1.47 (s, 9H).

$^{13}$C NMR (CDCl$_3$): δ=170.1, 167.6, 164.5, 153.1, 149.8, 133.9, 133.4, 130.7, 130.5, 121.7, 117.4, 117.1, 83.1, 56.1, 53.4, 51.6, 49.9, 48.9, 43.1, 41.6, 36.2, 27.8.

Example 68

Synthesis of N-(Toluene-4-sulfonyl)-L-(1,1-di-oxothiamorpholin-3-carbonyl)-L-4-(1,1-dioxothio-morpholin-4-ylcarbonyloxy)phenylalanine tert-Butyl Ester Substituting thiomorpholine for N-methylpiperazine, and following the method for the preparation of Example 4 and oxidation of the sulfur group in the thiomorpholino ring per by Larsson and Carlson (*Acta Chemica Scan.* 1994, 48, 522) gave the title compound as a white solid.

NMR data was as follows:

$^1$H NMR (CDCl$_3$): δ=7.75 (d, 2H), 7.35 (d, 2H), 7.17 (d, 2H), 6.99 (d, 2H), 6.65 (d, 1H), 4.92-4.90 (m, 1H), 4.63-4.60 (m, 1H), 4.15-3.95 (m, 7H), 3.30-3.23 (m, 1H), 3.14 (t, 4H), 3.07-2.80 (m, 6H), 2.45 (s, 3H), 1.48 (s, 9H).

$^{13}$C NMR (CDCl$_3$): δ=169.9, 164.8, 153.1, 149.8, 145.5, 135.1, 133.6, 130.7, 127.5, 121.8, 82.9, 60.3, 56.1, 53.7, 51.8, 49.3, 48.4, 43.1, 42.7, 41.5, 36.3, 27.8, 21.5.

Example 69

Synthesis of N-(4-Fluorobenzenesulfonyl)-L-prolyl-L-4-(thiomorpholin-4-ylcarbonyloxy)phenylalanine tert-Butyl Ester The title compound was prepared following the procedure described in Example 37 and substitution of appropriate starting materials.

NMR data was as follows:

$^1$H NMR (CDCl$_3$): δ=7.88-7.83 (m, 2H), 7.26-7.15 (m, 5H), 7.01 (d, 2H), 4.74-4.67 (m, 1H), 4.08-4.05 (m, 1H), 3.91-3.80 (m, 4H), 3.41-3.35 (m, 1H), 3.24-3.00 (m, 3H), 2.70-2.65 (t, 4H), 2.06-2.04 (m, 1H). 1.60-1.46 (m, 12H).

$^{13}$C NMR (CDCl$_3$): δ=170.5, 169.8, 153.4, 150.2, 133.5, 130.7, 130.5, 130.3, 121.6, 116.8, 116.5, 82.6, 62.2, 53.6, 49.6, 47.0, 46.4, 37.2, 29.8, 27.8, 27.3, 27.0, 24.1.

Example 70

Synthesis of N-(4-Fluorobenzenesulfonyl)-L-(5,5-dimethyl)-thiaprolyl-L-4-(N,N-dimethylcarbamy-loxy)phenylalanine The title compound was prepared from the product of Example 66 using the procedure described in Method 11.

NMR data was as follows:

$^1$H NMR (CDCl$_3$): δ=7.90 (m, 2H), 7.30-7.14 (m, 5H), 7.02 (d, 2H), 5.83 (br s, 1H), 4.90 (m, 1H), 4.57 (d, 1H), 4.40 (d, 1H), 3.96 (s, 1H), 3.09 (s, 3H), 3.28-3.02 (m, 2H), 3.00 (s, 3H), 1.13 (s, 6H).

$^{13}$C NMR (CDCl$_3$): δ=173.2, 169.2, 164.2, 163.9, 155.3, 150.6, 133.1, 132.0, 131.0, 130.9, 130.6, 122.0, 117.0, 116.7, 73.3, 54.6, 53.3, 50.5, 37.0, 36.7, 36.4, 29.0, 23.7.

Example 71

Synthesis of N-(4-Fluorobenzenesulfonyl)-L-(1,1-dioxothiamorpholin-3-carbonyl)-L-4-(morpholin-4-ylcarbonyloxy)phenylalanine tert-Butyl Ester Substituting 4-morpholinecarbamyl chloride for dimethylcarbamyl chloride, and following the methods for the preparation of Example 2, gave the title compound as a white solid.

NMR data was as follows:

$^1$H NMR (CDCl$_3$): δ=7.91-7.87 (m, 2H), 7.26-7.20 (m, 2H), 7.11 (d, 2H), 6.98 (d, 2H), 6.43 (d, 1H), 4.95-4.92 (m, 1H), 4.62-4.60 (m, 1H), 4.05-4.00 (m, 2H), 3.74 (t, 4H), 3.66-3.52 (m, 4H), 3.30-2.92 (m, 6H), 1.48 (s, 9H).

$^{13}$C NMR (CDCl$_3$): δ=170.1, 164.5, 150.4, 134.6, 132.7, 130.5, 122.0, 117.4, 117.1, 83.1, 66.5, 56.1, 53.4, 49.9, 49.0, 44.7, 44.0, 41.6, 36.2, 27.8.

Example 72

Synthesis of N-(4-Trifluoromethoxybenzenesulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:

$^1$H NMR (CDCl$_3$): δ=7.89 (d, 2H), 7.35 (d, 2H), 7.25-7.13 (m, 3H), 7.01 (d, 2H), 4.70 (m, 1H), 4.09-4.06 (m, 1H), 3.39-3.36 (m, 1H), 3.24-3.01 (m, 5H), 2.98 (s, 3H), 2.05 (m, 1H), 1.62-1.47 (m, 3H), 1.46 (s, 9H).

$^{13}$CNMR(CDCl$_3$): δ=170.4, 169.9, 154.9, 152.7, 150.6, 134.6, 113.2, 130.2, 130.1, 121.7, 120.2, 82.7, 62.2, 53.6, 49.6, 37.2, 36.6, 36.3, 29.9, 27.8, 24.1.

Example 73

Synthesis of N-(Toluene-4-sulfonyl)-L-(1,1-di-oxothiamorpholin-3-carbonyl)-L-4-(N,N-dimethylcarbamyloxy)phenylalanine Isopropyl Ester Following the method for the preparation of Example 2 and oxidation of the sulfur group in the thiomorpholino ring per by Larsson and Carlson (*Acta Chemica Scan.* 1994, 48, 522) gave the title compound.

NMR data was as follows:

$^1$H NMR (CDCl$_3$): δ=7.70 (d, 2H), 7.31 (d, 2H), 7.04 (d, 2H), 6.93 (d, 2H), 6.59 (d, 1H), 5.01 (m, 2H), 4.65 (m, 1H), 4.01 (d, 1H), 3.90 (d, 1H), 3.25 (m, 1H), 3.00 (s, 3H), 2.82 (m, 8H), 2.37 (s, 3H), 1.22 (s, 3H), 1.20 (s, 3H).

$^{13}$C NMR (CDCl$_3$): δ=170.3, 165.0, 154.6, 150.5, 145.1, 135.2, 132.3, 130.4, 130.0, 127.2, 122.1, 69.5, 55.9, 53.1, 49.1, 48.5, 41.4, 36.3, 36.1, 35.9, 21.4.

Example 74

Synthesis of N-(4-Fluorobenzenesulfonyl)-L-(1,1-dioxo-5,5-dimethyl)thiaprolyl-L-4-(N,N-dimethylcarbamyloxy)phenylalanine tert-Butyl Ester The title compound was prepared from the product of Example 66 following the procedure described by. Larsson and Carlson (*Acta Chemica Scan.* 1994, 48, 522).

NMR data was as follows:
¹H NMR (CDCl₃): δ=7.88 (m, 2H), 7.24 (m, 4H), 7.05 (d, 2H), 6.95 (d, 1H), 4.80 (m, 1H), 4.40 (m, 2H), 4.10 (s, 1H), 3.17-3.03 (m, 2H), 3.10 (s, 3H), 3.01 (s, 3H), 1.47 (s, 9H), 1.36 (s, 3H), 1.11 (s, 3H).
¹³C NMR (CDCl₃): δ=169.8, 168.6, 166.0, 154.5, 150.8, 139.7, 133.0, 131.5, 131.4, 130.3, 122.0, 117.1, 116.8, 83.0, 68.0, 60.9, 59.3, 53.8, 37.4, 36.6, 36.4, 27.8, 18.9, 18.8.

Example 75

Synthesis of N-(Toluene-4-sulfonyl)-L-(1,1-dioxo-5,5-dimethyl)thiaprolyl-L-4-(N,N-dimethylcarbamyloxy)phenylalanine Isopropyl Ester The title compound was prepared from the product of Example 11 following the procedure described by Larsson and Carlson (*Acta Chemica Scan.* 1994, 48, 522).
NMR data was as follows:
¹H NMR (CDCl₃): δ=7.75 (d, 2H), 7.38 (d, 2H), 7.21 (d, 2H), 7.03 (m, 3H), 5.08 (m, 1H), 4.89 (m, 1H), 4.38 (m, 2H), 4.10 (s, 1H), 3.22-3.04 (m, 2H), 3.10 (s, 3H), 3.00 (s, 3H), 2.43 (s, 3H), 1.26 (m, 9H), 1.09 (s, 3H).
¹³CNMR(CDCl₃): δ=170.3, 166.3, 150.8, 145.9, 132.8, 131.9, 130.3, 128.6, 122.0, 69.8, 68.0, 60.9, 59.4, 53.4, 37.4, 36.6, 36.4, 21.6, 21.5, 19.2, 18.6.

Example 76

Synthesis of N-(4-Fluorobenzenesulfonyl)-L-(5,5-dimethyl)thiaprolyl-L-4-(N,N-dimethylcarbamyloxy)phenylalanine The title compound was prepared from the product of Example 74 using the procedure described in Method 11.
NMR data was as follows:
¹³C NMR (CDCl₃): δ=171.7, 167.9, 137.3, 164.5, 155.9, 150.4, 133.6, 131.8, 131.3, 131.2, 130.8, 121.9, 117.1, 116.8, 67.8, 60.9, 59.9, 53.8, 36.8, 36.6, 36.0, 19.1, 19.0.

Example 77

Synthesis of N-(Pyrimidine-2-sulfonyl)-L-prolyl-L-4-(N,N-dimethylcarbamyloxy)phenylalanine The title compound was prepared from the product of Preparative Example B using the procedure described in Method 11.
NMR data was as follows:
¹H NMR (CDCl₃): δ=8.45 (br m, 2H), 8.22 (br s, 1H), 7.55 (d, 1H), 7.11 (d, 2H), 6.95 (d, 2H), 6.81 (m, 1H), 4.80-4.74 (m, 2H), 3.70 (m, 1H), 3.55 (m, 1H), 3.20-3.08 (m, 4H), 2.98 (s, 3H), 2.89-2.76 (m, 1H), 2.13-1.96 (m, 3H), 1.60 (m, 1H).
¹³C NMR (CDCl₃): δ=190.0, 173.6, 171.0, 155.2, 153.9, 150.6, 133.2, 130.1, 121.9, 110.3, 62.0, 55.1, 48.2, 36.6, 36.6, 36.3, 30.2, 23.4.

Example 78

Synthesis of N-(Toluene-4-sulfonyl)-L-(1,1-dioxothiamorpholin-3-carbonyl)-L-4-(4-methylpiperazin-1-ylcarbonyloxy)phenylalanine tert-Butyl Ester Following the method for the preparation of Example 4 and oxidation of the sulfur group in the thiamorpholino ring per Larsson and Carlson (*Acta Chemica Scan.* 1994, 48, 522) gave the title compound.

NMR data was as follows:
¹H NMR (CDCl₃): δ=7.76 (d, 2H), 7.37 (d, 2H), 7.12 (d, 2H), 6.96 (d, 2H), 6.57 (d, 1H), 4.95 (m, 1H), 4.62 (m, 1H), 4.03 (m, 2H), 3.67 (m, 4H), 3.25 (m, 1H), 2,89 (m, 4H), 2.45 (m, 6H), 2.35 (s, 3H), 1.48 (s; 9H).
¹³C NMR (CDCl₃): δ=170.0, 164.8, 153.7, 150.5, 145.4, 135.3, 132.8, 130.7, 130.4, 127.5, 122.2, 82.9, 56.2, 54.6, 54.5, 53.6, 49.5, 48.6, 46.0, 44.2, 43.7, 41.6, 36.3, 27.9, 21.6.

Example 79

Synthesis of N-(4-Fluorobenzenesulfonyl)-L-(1,1-dioxo)thiaprolyl-L-4-(N,N-dimethylcarbamyloxy)phenylalanine The title compound was prepared from the product of Example 85 using the procedure described in Method 11.
NMR data was as follows:
¹H NMR (CDCl₃): δ=4.98, (m, 1H), 4.90 (m, 1H), 4.44 (d. 1H), 4.03 (d, 1H), 3.67 (m, 1H), 3.37(m, 1H), 3.25-3.02 (m, 1H), 3.20 (s, 3H), 3.11 (s, 3H), 2.68 (m, 1H).
¹³C NMR (CDCl₃): δ=171.7, 167.9, 166.3, 164.4, 157.0, 156.4, 150.5, 139.6, 134.0, 133.1, 131.3, 131.1, 130.9, 121.9, 117.2, 116.9, 64.1, 58.8, 53.7, 50.6, 36.9, 36.5, 35.6.

Example 80

Synthesis of N-(Toluene-4-sulfonyl)-L-prolyl-L-4-(isonipecotoyloxy)phenylalanine tert-Butyl Ester Substituting piperazine for N-methylpiperazine, and following the methods for the preparation of Example 4, gave the title compound as a white solid.
NMR data was as follows:
¹H NMR (CDCl₃): δ=7.70 (d, 2H), 7.32-7.26 (m, 2H), 7.14 (d, 2H), 7.01 (d, 2H), 4.72-4.68 (m, 1H), 4.07-4.05 (m, 1H), 3.60-3.49 (m, 4H), 3.37-3.31 (m, 1H), 3.22-2.98 (m, 3H), 2.42 (s, 3H), 2.02 (m, 2H), 1.61-1.55 (m, 6H), 1.50-1.45 (m, 13H).
¹³C NMR (CDCl₃): δ=177.3, 170.7, 169.8, 150.6, 144.3, 133.1, 130.1, 129.9, 127.9, 121.6, 110.8, 82.5, 62.2, 57.2, 53.7, 49.5, 44.9, 37.2, 29.7, 27.8, 25.7, 24.1, 21.4.

Example 81

Synthesis of N-(Toluene-4-sulfonyl)-L-prolyl-L-4-(1,1-dioxothiomorpholin-4-ylcarbonyloxy)phenylalanine tert-Butyl Ester The product of Example 82 was oxidized by the method of Larsson and Carlson (*Acta Chemica Scan.* 1994, 48, 517-525), yielding the title compound as a white solid.
NMR data was as follows:
¹H NMR (CDCl₃): δ=7.69 (d, 2H), 7.33-7.29 (m, 3H), 7.20 (d, 2H), 7.00 (d, 2H), 4.71-4.66 (m, 1H), 4.13-4.04 (m, 5H), 3.37-3.32 (m, 1H), 3.21-3.00 (m, 7H), 2.41 (s, 3H), 2.05-2.01 (m, 1H), 1.52-1.44 (m, 12H).
¹³C NMR (CDCl₃): δ=170.7, 169.7, 149.8, 144.3, 134.4, 133.3, 130,6, 130.0, 127.9, 121.4, 82.7, 62.4, 54.0, 52.1, 49.7, 43.2, 37.6, 29.7, 28.1, 24.4, 21.7.

Example 82

Synthesis of

-N-(Toluene-4-sulfonyl)-L-prolyl-L-4-(thiomorpholin-4-ylcarbonyloxy)phenylalanine tert-Butyl Ester Substituting thiomorpholine for N-methylpiperazine, and following the methods for the preparation of Example 4, gave the title compound as a white solid.

NMR data was as follows:

$^1$H NMR (CDCl$_3$): δ=7.70 (d, 2H), 7.31-7.26 (m, 2H), 7.16 (d, 2H), 7.00 (d, 2H), 4.72-4.66 (m, 1H), 4.07-4.04 (m, 1H), 3.89-3.79 (m, 4H), 3.37-3.32 (m, 1H), 3.22-2.99 (m, 3H), 2.67 (t, 4H), 2.42 (s, 3H), 2.02 (m, 2H), 1.50-1.45 (m, 12H).

$^{13}$CNMR(CDCl$_3$): δ=177.2, 170.7, 169.8, 153.5, 150.2, 144.3, 133.6, 132.9, 130.3, 129.9, 127.9, 121.5, 82.5, 62.4, 53.7, 49.5, 47.0, 46.4, 37.2, 29.6, 27.8, 27.3, 24.1, 21.4.

Example 83

Synthesis of N-(Toluene-4-sulfonyl)-L-prolyl-L-4-(pyrrolidin-1-ylcarbonyloxy)phenylalanine tert-Butyl Ester Substituting pyrrolidinecarbonyl chloride for dimethylcarbamyl chloride, and following the methods for the preparation of Example 2, gave the title compound as a white solid.

NMR data was as follows:

$^1$H NMR (CDCl$_3$): δ=7.71 (d, 2H), 7.32 (d, 2H), 7.15 (d, 2H), 7.04 (d, 2H), 4.73-4.67 (m, 1H), 4.07-4.04 (m, 1H), 3.53 (t, 2H), 3.45 (t, 2H), 3.36-3.32 (m, 1H), 3.24-2.98 (m, 3H), 2.42 (s, 3H), 2.03-1.88 (m, 5H), 1.75 (s, 1H), 1.52 (1.24 (m, 12H).

$^{13}$C NMR (CDCl$_3$): δ=170.7, 169.8, 153.1, 150.4, 144.3, 133.1, 130.1, 129.9, 127.9, 121.6, 110.8, 99.8, 82.5, 62.2, 53.7, 49.5, 46.3, 37.2, 29.7, 27.8, 25.6, 24.8, 24.0, 21.4.

Example 84

Synthesis of N-(4-Fluorobenzenesulfonyl)-L-thiaprolyl-L-4-(N,N-dimethylcarbamyloxy)phenylalanine tert-Butyl Ester The title compound was prepared following the procedures described for the preparation of Example 2 and substitution of appropriate starting materials.

NMR data was as follows:

$^1$H NMR (CDCl$_3$): δ=7.87 (m, 2H), 7.28-7.13 (m, 5H), 7.02 (d, 2H), 4.70-4.60 (m, 2H), 4.58 (d, 1H), 4.06 (d, 1H), 3.38-3.01 (m, 3H), 3.09 (s, 3H), 3.00 (s, 3H), 2.58 (m, 1H), 1.47 (s, 9H).

$^{13}$C NMR (CDCl$_3$): δ=169.7, 167.8, 154.9, 150.7, 132.7, 130.9, 130.7, 130.4, 121.8, 117.1, 116.8, 82.9, 65.1, 53.9, 51.4, 36.8, 36.6, 36.4, 33.1, 27.9.

Example 85

Synthesis of N-(4-Fluorobenzenesulfonyl)-L-(1,1-dioxo)thiaprolyl-L-4-(N,N-dimethylcarbamyloxy)phenylalanine tert-Butyl Ester The title compound was prepared from the product of Example 84 following the procedure oxidation procedure of Larsson and Carlson (*Acta Chemica Scan.* 1994, 48, 517-525).

NMR data was as follows:

$^1$H NMR (CDCl$_3$): δ=7.90 (m, 2H), 7.30-7.04 (m, 7H), 4.83-4.58 (m, 3H), 3.66 (m, 2H), 3.32-3.24 (m, 1H), 3.09-2.85 (m, 2H), 3.10 (s, 3H), 3.01 (s, 3H), 1.50 (s, 9H).

$^{13}$C NMR (CDCl$_3$): δ=173.1, 169.8, 168.0, 165.6, 154.9, 150.9, 132.6, 131.1, 131.0, 130.3, 122.3, 117.3, 117.0, 83.2, 62.8, 57.8, 53.9, 49.0, 36.8, 36.6, 36.4, 27.9.

Example 86

Synthesis of N-(2,5-Dichlorothiophene-3-sulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:

$^1$H NMR (CDCl$_3$): δ=7.14 (d, 2H), 7.09 (s, 1H), 7.07 (d, 1H), 7.01 (d, 2H), 4.73-4.66 (m, 1H), 4.32-4.28 (m, 1H), 3.42-3.17 (m, 3H), 3.08 (s, 3H), 3.06-3.01 (m, 1H), 2.98 (s, 3H), 2.17-2.04 (m, 1H), 1.84-1.60 (m, 2H), 1.60-1.46 (m, 1H), 1.45 (s, 9H).

$^{13}$C NMR (CDCl$_3$): δ=170.2, 169.9, 154.9, 150.6, 133.4, 133.1, 131.2, 130.2, 127.9, 127.0, 121.7, 82.7, 62.2, 53.6, 49.3, 37.2, 36.6, 36.4, 30.1, 27.8, 24.2.

Example 87

Synthesis of N-(4-Acetamidobenzenesulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:

$^1$H NMR (CDCl$_3$): δ=8.58 (s, 1H), 7.70-7.67 (m, 4H), 7.32 (d, 1H), 7.14 (d, 2H), 7.01 (d, 2H), 4.68 (m, 1H), 3.99 (m, 1H), 3.37-3.34 (m, 1H), 3.23-3.16 (m, 1H), 3.11-3.01 (m, 1H), 3.08 (s, 3H), 2.98 (s, 3H), 2.13 (s, 3H), 1.97-1.94 (m, 1H), 1.55-1.47 (m, 3H), 1.44 (s, 9H).

$^{13}$C NMR (CDCl$_3$): δ=171.1, 169.9, 169.4, 155.0, 150.6, 143.3, 133.3, 130.2, 130.0, 128.9, 121.7, 119.4, 82.7, 62.2, 53.8, 49.6, 37.2, 36.6, 36.4, 29.9, 27.8, 24.4, 24.1.

Example 88

Synthesis of N-(4-tert-Butylbenzenesulfonyl)-L-(1,1-dioxothiamorpholin-3-carbonyl)-L-4-(N,N-dimethylcarbamyloxy)phenylalanine tert-Butyl Ester The title compound was prepared following the procedure outlined for the preparation of Example 73 and substitution of appropriate starting materials.

NMR data was as follows:

$^1$H NMR (CDCl$_3$): δ=7.81 (d, 2H), 7.59 (d, 2H), 7.07 (d, 2H), 6.97 (d, 2H), 6.46 (d, 1H), 4.95 (m, 1H), 4.62 (m, 1H), 4.06 (m, 2H), 3.23 (m, 1H), 3.07 (m, 4H), 2.97 (m, 4H), 2.81 (m, 4H), 1.55 (s, 9H), 1.37 (s, 9H).

$^{13}$C NMR (CDCl$_3$): δ=170.0, 164.9, 158.2, 154.8, 150.6, 135.0, 132.6, 130.2, 127.4, 126.9, 122.2, 82.7, 56.1, 53.5, 49.7, 48.8, 41.5, 36.5, 36.3, 36.1, 35.2, 30.8, 27.8.

Example 89

Synthesis of N-(Pyridine-3-sulfonyl)-L-prolyl-L-4-(N,N-dimethylcarbamyloxy)phenylalanine The title compound-was prepared from-the product of Example 56 using the procedure described in Method 11.

NMR data was as follows:
¹H NMR (CD₃OD): δ=8.95 (s, 1H), 8.83 (d, 1H), 8.28-8.24 (m, 1H), 7.73-7.69 (m, 1H), 7.30 (d, 2H), 7.05 (d, 2H), 4.68-4.63 (m, 1H), 4.29-4.25 (m, 1H), 3.47-3.41 (m, 1H), 3.38-3.22 (m, 2H), 3.09 (s, 3H), 3.06-3.02 (m, 1H), 2.96 (s, 3H), 1.92-1.66 (m, 4H).
¹³C NMR (CD₃OD): δ=174.2, 173.9, 160.6, 160.0, 156.9, 152.9, 152.0, 147.9, 139.1, 136.9, 135.7, 131.6, 126.5, 123.1, 63.1, 54.8, 50.4, 37.5, 36.8, 36.7, 32.2, 25.5.

Example 90

Synthesis of N-(2-Fluorobenzenesulfonyl)-L-(1,1-dioxothiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (*Acta Chemica Scan.* 1994, 48, 517-525). N-(2-fluorobenzene-4-sulfonyl)-L-thiamorpholine-3-carboxylic acid was prepared using the procedure described in Method 1. The title compound was prepared according to the procedures set forth above using suitable starting materials.
NMR data was as follows:
¹H NMR (CDCl₃): δ=7.92 (m, 1H), 7.69 (m, 1H), 7.34 (m, 2H), 7.16 (m, 2H), 6.99 (m, 2H), 6.60 (d, 1H), 5.01 (m, 1H), 4.64 (m, 1H), 4.03 (m, 2H), 3.29 (m, 1H), 3.06 (m, 6H), 2.90 (m, 7H), 1.49 (d, 9H).
¹³C NMR (CDCl₃): δ=169.9, 164.8, 160.3, 156.9, 154.9, 150.7, 136.6, 136.4, 132.7, 131.0, 130.3, 128.8, 126.4, 126.2, 125.1, 122.2, 118.1, 117.8, 82.7, 56.3, 56.7, 50.2, 49.5, 41.8, 36.5, 36.3, 27.8.

Example 91

Synthesis of N-(3-Fluorobenzenesulfonyl)-L-(1,1-dioxothiamorpholin-3-carbonyl)-L-4-(N,N-dimethylcarbamyloxy)phenylalanine tert-Butyl Ester L-Thiamorpholine-5-carboxylic acid was prepared by the method of Larsson and Carlson (*Acta Chemica Scan.* 1994, 48, 517-525). N-(3-fluorobenzene-4-sulfonyl)-L-thiamorpholine-5-carboxylic acid was prepared using the procedure described in Method 1. The title compound was prepared according to the procedures set forth above using suitable starting materials.
NMR data was as follows:
¹H NMR (CDCl₃): δ=7.66 (m, 1H), 7.58 (m, 2H), 7.34 (m, 1H), 7.07 (d, 1H), 6.92 (d, 1H), 6.42 (d, 1H), 5.00 (m, 1H), 4.58 (m, 1H), 4.02 (m, 2H), 3.22 (m, 1H), 3.05 (s, 3H), 2.98 (m, 6H), 1.45 (s, 9H).
¹³C NMR (CDCl₃): δ=170.0, 164.5, 164.4, 161.0, 154.9, 150.6, 140.3, 140.2, 132.5, 131.9, 131.8, 130.2, 123.2, 123.1, 122.2, 121.4, 121.2, 115.0, 114.7, 82.9, 56.1, 53.4, 49.9, 49.1, 41.7, 36.5, 36.3, 36.0, 27.8.

Example 92

Synthesis of N-(2,4-Difluorobenzenesulfonyl)-L-(1,1-dioxothiamorpholin-3-carbonyl)-L-4-(N,N-dimethylcarbamyloxy)phenylalanine tert-Butyl Ester L-Thiamorpholine-5-carboxylic acid was prepared by the method of Larsson and Carlson (*Acta Chemica Scan.* 1994, 48, 517-525). N-(2,4-difluorobenzene-4-sulfonyl)-L-thiamorpholine-5-carboxylic acid was prepared using the procedure described in Method 1. The title compound was prepared according to the procedures set forth above using suitable starting materials.

NMR data was as follows:
¹H NMR (CDCl₃): δ=7.93 (m, 1H), 7.15 (m, 2H), 7.04 (m, 4H), 6.53 (d, 1H), 4.97 (m, 1H), 4.64 (m, 1H), 4.05 (m, 2H), 3.21 (m, 3H), 3.17 (s, 3H), 2.97 (m, 5H), 1.43 (s, 9H).
¹³C NMR (CDCl₃): δ=170.0, 164.6, 154.9, 150.7, 132.6, 132.6, 130.3, 122.6, 122.1, 112.6, 112.3, 107.0, 106.7, 106.3, 82.8, 56.3, 53.5, 50.5, 49.8, 42.0, 36.5, 36.3, 27.8.

Example 93

Synthesis of N-(4-Acetamidobenzenesulfonyl)-L-prolyl-L-4-(N,N-dimethylcarbamyloxy)phenylalanine The title compound was prepared from the product of Example 87 using the procedure described in Method 11.
NMR data was as follows:
¹H NMR (CD₃OD): δ=8.05 (d, 1H), 7.78 (m, 4H), 7.26 (d, 2H); 7.02 (d, 2H), 4.94 (m, 1H), 4.72-4.67 (m, 1H), 4.13-4.09 (m, 1H), 3.40-3.36 (m, 1H), 3.30-3.05 (m, 3H), 3.08 (s, 3H), 2.97 (s, 3H), 2.15 (s, 3H), 1.81-1.51 (m, 4H).
¹³C NMR (CD₃OD): δ=174.3, 174.2, 172.3, 156.9, 152.0, 144.9, 135.5, 132.4, 131.6, 130.2, 122.9, 120.7, 63.2, 54.7, 50.6, 37.5, 36.8, 36.7, 31.7, 25.4, 24.0.

Example 94

Synthesis of N-(4-Trifluoromethoxybenzenesulfonyl)-L-prolyl-L-4-(N,N-dimethylcarbamyloxy)phenylalanine The title compound was prepared from the product of Example 72 using the procedure described in Method 11.
NMR data was as follows:
¹H NMR (CD₃OD): δ=7.93 (d, 2H), 7.48 (d, 2H), 7.28 (d, 2H), 7.03 (d, 2H), 4.72-4.68 (m, 1H), 4.17-4.13 (m, 1H), 3.45-3.42 (m, 1H), 3.28-3.11 (m, 2H), 3.14-3.07 (m, 1H), 3.09 (s, 3H), 2.97 (s, 3H), 1.85-1.69 (m, 3H), 1.59 (m, 1H).
¹³C NMR (CD₃OD): δ=174.2, 174.1, 157.0, 153.9, 152.0, 137.3, 135.6, 131.7, 131.5, 123.0, 122.5, 121.8, 63.1, 54.7, 50.6, 37.4, 36.8, 36.6, 31.9, 25.4.

Example 95

Synthesis of N-(4-Fluorobenzenesulfonyl)-L-(5,5-dimethyl)thiaprolyl-L-4-(N,N-dimethylcarbamyloxy)phenylalanine tert-Butyl Ester The title compound was prepared using the procedure described in Example 2 and substitution of appropriate starting materials.
NMR data was as follows:
¹H NMR (CDCl₃): δ=7.90 (m, 2H), 7.22 (m, 4H), 7.00 (m, 3H), 5.08 (m, 1H), 4.84 (m, 1H), 4.56 (d, 1H), 4.42 (d, 1H), 3.88 (s, 1H), 3.15-2.99 (m, 2H), 3.09 (s, 3H), 3.00 (s, 3H), 1.26-1.16 (m, 12H).
¹³C NMR (CDCl₃): δ=170.4, 168.2, 167.5, 164.1, 154.9, 150.7, 132.8, 132.2, 132.1, 131.0, 130.8, 130.3, 121.8, 116.9, 116.6, 73.5, 69.6, 54.6, 53.2, 50.5, 37.6, 36.6, 36.3, 29.1, 23.8, 21.6, 21.5.

Example 96

Synthesis of N-(4-Cyanobenzenesulfonyl)-L-prolyl-L-4-(N,N-dimethylcarbamyloxy)phenylalanine The title compound was prepared from the product of Example 58 using the procedure described in Method 11.
NMR data was as follows:
¹H NMR (CD₃OD): δ=8.14 (d, 1H), 7.94-7.89 (m, 4H), 7.29 (d, 2H), 7.03 (d, 2H), 4.70-4.66 (m, 1H), 4;21-4.17 (m, 1H), 3.47-3.40 (m, 1H), 3.31-3.21 (m, 2H), 3.11-3.04 (m, 1H), 3.09 (s, 3H), 2.97 (s, 3H), 1.87-1.72 (m, 3H), 1.70-1.61 (m, 1H).

$^{13}$C NMR (CD$_3$OD): δ=174.2, 173.9, 157.0, 152.0, 142.9, 135.7, 134.5, 131.7, 129.7, 123.0, 118.6, 111.8, 63.0, 54.7, 50.5, 37.4, 36.8, 36.7, 32.0, 25.4.

Example 97

Synthesis of N-(Toluene-4-sulfonyl)-L-(3,3-dimethyl)prolyl-L-4-(N,N-dimethylcarbamyloxy)phenylalanine tert-Butyl Ester The title compound was prepared using the procedure described for the preparation of Example 98.
NMR data was as follows:
$^1$H NMR (CDCl$_3$): δ=7.76 (d, 1H), 7.75 (d, 1H), 7.35 (d, 1H), 7.34 (d, 1H), 7.33 (d, 1H), 7.20 (d, 1H), 7.10 (d, 1H), 7.03 (d, 1H), 6.91 (d, 0.5H), 6.08 (d, 0.5H), 4.86 (ddd, 0.5H), 4.77 (q, 0.5H), 3.61-3.47 (m, 2H), 3.27-3.02 (m, 3H), 3.09 (s, 3H), 3.00 (s, 3H), 2.45 (s, 1.5H), 2.43 (s, 1.5H), 1.75-1.68 (m, 0.5H), 1.61-1.51 (m, 0.5H), 1.45 (s, 4.5H), 1.40 (s, 4.5H), 1.48-1.25 (m, 3H); 0.95 (s, 1.5H), 0.80 (s, 1.5H); 0.61 (s, 1.5H).
$^{13}$C NMR (CDCl$_3$): δ=170.4, 170.1, 170.0, 169.6, 155.0, 154.9, 150.7, 150.6, 144.3, 144.2, 133.4, 133.1, 132.8, 132.6, 130.7, 130.2, 129.9, 129.8, 128.0, 121.8, 121.7, 82.6, 82.2, 71.5, 71.2, 53.6, 52.7, 47.3, 47.2, 42.7, 42.5, 38.2, 38.1, 37.7, 37.5, 36.6, 36.3, 27.8, 27.8, 27.2, 23.4, 23.2, 21.5.

Example 98

Synthesis of N-(Toluene-4-sulfonyl)-L-(3,3-dimethyl)prolyl-L-4-(N,N-dimethylcarbamyloxy)phenylalanine Isopropyl Ester 3,3-Dimethyl proline (see Sharma and Lubell, *J. Org. Chem.* 1996, 61, 202-209) was N-tosylated using the procedure described in Method 1. The title compound was then prepared following the procedure described for the preparation of Example 2.
NMR data was as follows:
$^1$H NMR (CDCl$_3$): δ=7.76 (d, 1H), 7.74 (d, 1H), 7.36 (d, 1H), 7.33 (d, 2H), 7.19 (d, 1H), 7.10 (d, 1H), 7.03 (d, 1H), 6.91 (d, 0.5H), 6.89 (d, 0.5H), 5:06 (sept., 0.5H), 4.96 (sept., 0.5H), 4.98-4.83 (m, 1H), 3.59-3.48 (m, 2H), 3.31-3.03 (m, 3H), 3.09 (s, 3H), 3.00 (s, 3H), 2.45 (s, 1.5H), 2.43 (s, 1.5H), 1.75-1.66 (m, 0.5), 1.62-1.52 (m, 0.5H), 1.34-1.22 (m, 3H), 1.27 (s, 1.5H), 1.25 (s, 1.5H), 1.22 (s, 1.5H), 1.20 (s, 1.5H), 0.95 (s, 1.5H), 0.78 (s, 1.5H), 0.60 (s, 1.5H), 0.57 (s, 1.5H).
$^{13}$C NMR (CDCl$_3$): δ=170.8, 170.6, 170.0, 169.7, 154.9, 150.8, 150.6, 144.4, 144.2, 133.2, 132.5, 132.5, 130.7, 130.2, 129.9, 129.8, 128.0, 122.0, 121.8, 71.5, 17.2, 69.5, 69.3, 53.0, 52.2, 47.3, 47.2, 42.8, 42.5, 38.2, 38.1, 37.6, 37.2, 36.6, 36.3, 27.1, 23.4, 23.2, 21.6, 21.6, 21.5, 21.5.

Other compounds prepared by the methods described above include those set forth in Examples 99-137. In addition, Examples 101, 109, 111, 117, 132 and 137 are exemplified as follows:

Example 101

Synthesis of N-(Toluene-4-sulfonyl)-L-prolyl-4-(N,N-dimethylcarbamyloxy)-L-phenylalanine Isopropyl Ester The title compound was prepared following the procedure outlined for the preparation of Example 2.
NMR data was as follows:
$^1$H NMR (CD$_3$)$_2$SO: δ=8.28 (d, 1H), 7.70 (d, 2H), 7.41 (d, 2H), 7.23 (d, 2H), 6.99 (d, 2H), 4.86 (sept, 1H), 4.47 (m, 1H), 4.40 (m, 1H), 4.10 (m, 1H), 4.07 (m, 1H), 3.38 (m, 1H), 3.30 (m, 1H), 3.09 (m, 3H), 2.95 (s, 3H), 3.00 (s, 3H), 2.88 (s, 3H), 2.39 (s, 3H), 1.63 (m, 3H), 1.51 (m, 3H), 1.44 (m, 1H), 1.39 (m, 1H), 1.16 (d, 3H), 1.11 (d, 3H).

$^{13}$C NMR (CD$_3$)$_2$SO: δ=171.3, 170.8, 154.2, 150.2, 143.7, 134.1, 130.2, 130, 127.6, 121.6, 68.2, 61.2, 53.5, 49, 36.3, 36.1, 35.7, 30.5, 23.8, 21.4, 21.4, 21.

Example 109

Synthesis of N-(Benzylsulfonyl)-L-(5,5-dimethyl)thiaprolyl-L-(4-N,N-dimethylcarbamyloxy)phenylalanine The title compound was prepared from the product of Example 111 using the procedure described in Method 11.
Physical data was as follows:
MS (FAB) (M+H)$^+$550.
Calcd. for: C$_{25}$H$_{31}$N$_3$O$_7$S$_2$; C, 54.62; H, 5.68; N 7.64.
Found: C 54.51; H 5.60; N 7.63.

Example 111

Synthesis of N-(Benzylsulfonyl)-L-(5,5-dimethyl)thiaprolyl-L-(4-N,N-dimethylcarbamyloxy)phenylalanine tert-Butyl Ester The title compound was prepared following the procedure outlined for the preparation of Example 2 and by substituting the appropriate starting materials.
Physical data was as follows:
MS [M+H]$^+$ 550.
Calcd. for: C$_{29}$H$_{39}$N$_3$O$_7$S$_2$; C, 57.52; H, 6.45; N, 6.94.
Found: C, 57.32; H, 6.52; N, 6.81.

Example 117

Synthesis of N-(Methyl-pyrazole-4-sulfonyl)-L-prolyl-L-(4-N,N-dimethylcarbamyloxy)phenyalanine tert-Butyl Ester Substituting N-methyl-pyrazole sulfonyl chloride (see Dickson, U.S. Pat. No. 3,665,009 (May 23, 1972) and following the method for the preparation of Example 56, gave the title compound.
NMR data was as follows:
$^1$H NMR (CDCl$_3$): δ=7.83 (s, 1H), 7.76 (s, 1H), 7.26 (m, 1H), 7.15 (m, 2H), 7.00 (m, 2H), 4.69 (m, 1H), 3.95 (m, 1H), 3.93 (s, 3H), 3.38 (m, 1H), 3.23-3.11 (m, 1H), 3.10-2.99 (m, 4H), 2.99 (s, 3H), 2.05 (m, 1H), 1.66-1.46 (m, 3H), 1.44 (s, 9H).
$^{13}$CNMR(CDCl$_3$): δ 170.7, 169.9, 154.9, 150.6, 138.9, 133.2, 132.5, 130.2, 121.7, 117.9, 82.6, 62.4, 53.7, 49.7, 39.6, 37.7, 36.6, 36.4, 29.9, 27.9, 24.2.

Example 132

Synthesis of N-(4-Fluorobenzenesulfonyl)-L-prolyl-L-4-(1,1-dioxothiomorpholin-4-ylcarbonyloxy)-phenylalanine tert-Butyl Ester Substituting thiamorpholine for N-methylpiperazine, and following the method for the preparation of Example 4 and 14, gave the title compound.
NMR data was as follows:
$^1$H NMR (CDCl$_3$): δ=7.87-7.82 (m, 2H), 7.28-7.17 (m, 5H), 7.01 (d, 2H), 4.71-4.69 (m, 1H), 4.14-4.05 (m, 5H), 3.39-3.36 (m, 1H), 3.23-3.01 (m, 7H), 2.05-2.03 (m, 1H), 1.58-1.44 (m, 12H).
$^{13}$C NMR (CDCl$_3$): δ=170.4, 169.8, 153.0, 149.7, 134.2, 130.6, 130.5, 121.3, 116.8, 116.5, 82.6, 62.1, 53.6, 51.8, 49.5, 43.1, 42.7, 37.2, 29.7, 27.8, 24.2.

Example 137

Synthesis of N-(Methyl-pyrazole-4-sulfonyl)-L-prolyl-L-(4-N,N-dimethylcarbamyloxy)-phenylalanine Isopropyl Ester The title compound was prepared following the procedure described for the preparation of Example 117.

NMR data was as follows:

¹H NMR (CDCl₃): δ 7.83 (s, 1H), 7.76 (s, 1H), 7.27 (d, 1H), 7.13 (d, 2H), 7.01 (d, 2H), 5.06-5.02 (m, 1H), 4.80-4.73 (m, 1H), 3.97-3.94(m, 1H), 3.93 (s, 3H), 3.44-3.37 m, 1H), 3.25-3.19 (m, 1H), 3.09-3.00 (m, 5H), 2.97 (s, 3H), 2.06-2.02 (m, 1H), 1.66-1.48 (m, 3H), 1.23 (d, 6H).

¹³C NMR (CDCl₃): δ 170.8, 170.5, 154.9, 150.6, 138.9, 132.9, 32.5, 130.2, 121.7, 117.8, 69.5, 62.3, 53.2, 49.7, 39.6, 37.1, 36.6, 36.3, 29.9, 24.1, 21.6, 21.5.

TABLE 10

$$R^1-\underset{\underset{O}{\|}}{\overset{\overset{O}{\|}}{S}}-\underset{R^2}{N}-\underset{R^3}{CH}-\overset{\overset{O}{\|}}{C}-\underset{H}{N}-\underset{R^5}{CH}-\overset{\overset{O}{\|}}{C}-R^6$$

| R¹ | R² | R³ | R⁵ | R⁶ | Ex. No. |
|---|---|---|---|---|---|
| p-CH₃-ψ- | R²/R³ = cyclic 3 carbon atoms (L-pyrrolidinyl) | | p-[(4-methylpiperazin-1-yl)C(O)O—]benzyl- | —O-n-butyl | 99 |
| p-CH₃-ψ- | R²/R³ = cyclic 3 carbon atoms (L-pyrrolidinyl) | | p-[(4-methylpiperazin-1-yl)C(O)O—]benzyl- | —O-cyclopentyl | 100 |
| p-CH₃-ψ- | R²/R³ = cyclic 3 carbon atoms (L-pyrrolidinyl) | | p-[(CH₃)₂NC(O)O—]benzyl- | —OCH(CH₃)₂ | 101 |
| p-CH₃-ψ- | R²/R³ = cyclic 3 carbon atoms (L-pyrrolidinyl) | | p-[(piperidin-4-yl)C(O)O—]benzyl- | —OCH₂CH₃ | 102 |
| ψ-CH₂— | R²/R³ = cyclic 3 carbon atoms (L-pyrrolidinyl) | | p-[(1-methylpiperidin-4-yl)C(O)O—]benzyl- | —OCH₂CH₃ | 103 |
| ψ-CH₂— | R²/R³ = cyclic 3 carbon atoms (L-pyrrolidinyl) | | p-[(4-methylpiperazin-1-yl)C(O)O—]beenzyl- | —OH | 104 |
| p-CH₃-ψ- | R²/R³ = cyclic 3 carbon atoms (L-pyrrolidinyl) | | p-[(1-Boc-4-phenylpiperidin-4-yl)-C(O)O—]benzyl- | —OCH₂CH₃ | 105 |
| 1-methylimidazol-4-yl | R²/R³ = cyclic 3 c arbon atoms (L-pyrrolidinyl) | | p-[(CH₃)₂NC(O)O—]benzyl- | —OC(CH₃)₃ | 106 |
| p-NH₂-ψ- | R²/R³ = cyclic 3 carbon atoms (L-pyrrolidinyl) | | p-[(CH₃)₂NC(O)O—]benzyl- | —OC(CH₃)₃ | 107 |
| p-CH₃-ψ- | R²/R³ = cyclic 3 carbon atoms (L-pyrrolidinyl) | | p-[(morpholin-4-yl)C(O)O—]benzyl- | —OC(CH₃)₃ | 108 |
| ψ-CH₂— | R²/R³ = cyclic —CH₂—S—C(CH₃)₂— (L-5,5-dimethylthiazolidin-4-yl) | | p-[(CH₃)₂NC(O)O—]benzyl- | —OH | 109 |
| p-CH₃-ψ- | R²/R³ = cyclic —CH₂CH₂—NH—CH₂— (L-piperazinyl) | | p-[(CH₃)₂NC(O)O—]benzyl- | —OH | 110 |
| ψ-CH₂— | R²/R³ = cyclic —CH₂—S—C(CH₃)₂— (L-5,5-dimeethylthiazolidin-4-yl) | | p-[(CH₃)₂NC(O)O—]ben zyl- | —OC(CH₃)₃ | 111 |
| p-CH₃-ψ- | R²/R³ = cyclic 3 carbon atoms (L-pyrrolidinyl) | | p-[(CH₃)₂NC(O)O—]benzyl- | —NH-adamantyl | 112 |
| p-CH₃-ψ- | R²/R³ = cyclic 3 carbon atoms (L-pyrrolidinyl) | | p-[(CH₃)₂NC(O)O—]benzyl- | —NHCH₂C(O)OH | 113 |
| p-HC₃-ψ- | R²/R³ = cyclic 3 carbon atoms (L-pyrrolidinyl) | | p-[(CH₃)₂NS(O)₂O—]benzyl- | —OCH₃ | 114 |
| p-CH₃-ψ- | R²/R³ = cyclic —CH₂CH₂—NH—CH₂— (L-piperazinyl) | | p-[(CH₃)₂NC(O)O—]benzyl- | —OC(CH₃)₃ | 115 |
| p-CH₃-ψ- | R²/R³ = cyclic —CH₂CH₂—(Cbz)NHCH₂— [L-4-N-(Cbz)-piperazinyl] | | p-[(CH₃)₂NC(O)O—]benzyl- | —OC(CH₃)₃ | 116 |
| 1-methylpyrazol-4-yl | R²/R³ = cyclic 3 carbon atoms (L-pyrrolidinyl) | | p-[(CH₃)₂NC(O)O—]benzyl- | —OC(CH₃)₃ | 117 |

TABLE 10-continued

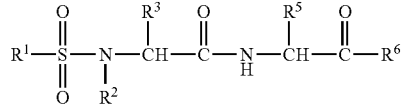

| R¹ | R² | R³ | R⁵ | R⁶ | Ex. No. |
|---|---|---|---|---|---|
| 3-pyridyl | R²/R³ = cyclic 3 carbon atoms (L-pyrrolidinyl) | | p-[(CH₃)₂NC(O)O—]benzyl- | —OH | 118 |
| p-CH₃-ψ | R²/R³ = cyclic 3 carbon atoms (L-pyrrolidinyl) | | p-[(1-Boc-piperazin-4-yl)C(O)O—]benzyl- | —OCH₂CH₃ | 119 |
| p-CH₃-ψ | R²/R³ = cyclic 3 carbon atoms (L-pyrrolidinyl) | | p-[(morpholin-4-yl)C(O)O—]benzyl- | —OCH₂CH₃ | 120 |
| p-CH₃-ψ | —CH₃ | H | p-[(thiomorpholin-4-yl sulfone)-C(O)O—]benzyl- | —OC(CH₃)₃ | 121 |
| p-CH₃-ψ | —CH₃ | H | p-[(thiomorpholin-4-yl)C(O)O—]benzyl- | —OH | 122 |
| p-CH₃-ψ | R²/R³ = cyclic 3 carbon atoms (L-pyrrolidinyl) | | p-[(CH₃)₂NC(O)O—]benzyl- | 2,4-dioxo-tetrahydrofuran-3-yl (3,4-enol) | 123 |
| p-CH₃-ψ | R²/R³ = cyclic 3 carbon atoms (L-pyrrolidinyl) | | p-[(piperazin-4-yl)C(O)O—]benzyl- | —OH | 124 |
| p-CH₃-ψ | R²/R³ = cyclic 3 carbon atoms (L-pyrrolidinyl) | | p-[(1-Boc-piperazin-4-yl)C(O)O—]benzyl- | —OC(CH₃)₃ | 125 |
| p-CH₃-ψ | R²/R³ = cyclic 3 carbon atoms (L-pyrrolidinyl) | | p-[(piperazin-4-yl)C(O)O—]benzyl- | —OCH₂CH₃ | 126 |
| p-CH₃-ψ | R²/R³ = cyclic 3 carbon atoms (L-pyrrolidinyl) | | p-[(4-acetylpiperazin-1-yl)C(O)O—]benzyl- | —OCH₂CH₃ | 127 |
| p-CH₃-ψ | R²/R³ = cyclic 3 carbon atoms (L-pyrrolidinyl) | | p-[(4-methanesulfonylpiperazin-1-yl)-C(O)O—]benzyl- | —OCH₃CH₃ | 128 |
| p-CH₃-ψ | R²/R³ = cyclic 3 carbon atoms (L-pyrrolidinyl) | | 3-nitro-4-[(morpholin-4-yl)-C(O)O—]benzyl- | / —OH | 129 |
| p-CH₃-ψ | R²/R³ = cyclic 3 carbon atoms (L-pyrrolidinyl) | | p-[(1-Boc-piperazin-4-yl)C(O)O—]benzyl- | —OH | 130 |
| p-CH₃-ψ | —CH₃ | —C(CH₃)₃ | p-[(4-methylpiperazin-1-yl)C(O)O—]benzyl- | —OC(CH₃)₃ | 131 |
| p-F-ψ | R²/R³ = cyclic 3 carbon atoms (L-pyrrolidinyl) | | p-[(1,1-dioxothiomorpholin-4-yl)-C(O)O—]benzyl- | —OC(CH₃)₃ | 132 |
| p-F-ψ | R²/R³ = cyclic 3 carbon atoms (L-pyrrolidinyl) | | p-[(morpholin-4-yl)C(O)O—]benzyl- | —OC(CH₃)₃ | 133 |
| p-CH₃-ψ | R²/R³ = cyclic —CH₂—CH₂—SO₂—CH₂— (L-1,1-dioxothiomorpholin-3-yl) | | p-[(morpholin-4-yl)C(O)O—]benzyl- | —OH | 134 |
| 1-methylpyrazol-4-yl | R²/R³ = cyclic 3 carbon atoms (L-pyrrolidinyl) | | p-[(4-methylpiperazin-1-yl)C(O)O—]benzyl- | —OC(CH₃)₃ | 135 |
| morpholin-4-yl | R²/R³ = cyclic 3 carbon atoms (L-pyrrolidinyl) | | p-[(CH₃)₂NC(O)O—]benzyl- | —OC(CH₃)₃ | 136 |
| 1-methylpyrazol-4-yl | R²/R³ = cyclic 3 carbon atoms (L-pyrrolidinyl) | | p-[(CH₃)₂NC(O)O—]benzyl- | —OCH(CH₃)₂ | 137 |

Additional compounds prepared by the methods described above include the following:

Example 138

Synthesis of N-(1-Methylpyrazole-4-sulfonyl)-L-(5,5-dimethyl)thiaprolyl-L-4-(N,N-dimethylcarbamyloxy)phenylalanine tert-Butyl Ester The N-methylpyrazole sulfonyl chloride was prepared by adding N-methylpyrazole to chilled (0° C.) chlorosulfonic acid. The reaction mixture was allowed to warm to room temperature and then heated to 100° C. overnight under a stream of N₂. The reaction mixture was then cooled to room temperature and chilled to 0° C. To this solution was added thionyl chloride (2.5 eq.) and the reaction was stirred at room temperature for 30 min., then warmed to 70° C. for two hours. The reaction was cooled to room temperature and then chilled in an ice bath. Water and ice were slowly added to the reaction mixture to precipitate a white solid which was collected by filtration. The desired sulfonyl chloride was washed with cold water and hexane.

The title compound was then prepared following the procedure outlined for the preparation of Example 2 by substitution of the appropriate starting materials, mp: 169-170° C.

Example 139

Synthesis of N-(1-Methylpyrazole-4-sulfonyl)-L-(5,5-dimethyl)thiaprolyl-L-4-(N,N-dimethylcarbamyloxy)phenylalanine The title compound was prepared from the product of Example 138 using the procedure described in Method 11.
NMR data was as follows:
$^1$H NMR (CDCl$_3$): 8=7.94 (s, 1H); 7.79 (s, 1H); 7.25 (d, 2H, J=8.8 Hz); 7.0 (d, 2H, J=8.8 Hz); 5.15 (br s, 1H); 4.80 (m, 1H); 4.54 (d, 1H, J=9.HHz); 4.39 (d, 1H, J=9.3 Hz); 3.93 (s, 3H); 3.88 (s, 1H); 3.23-3.02 (m, 2H0; 3.07 (s, 3H); 2.98 (s, 3H); 1.27 (s, 3H); 1.14 (s, 3H).
$^{13}$C NMR (CDCl$_3$): 173.86, 169.05, 155.23, 150.47, 139.21, 133.59, 133.15, 130.53, 121.84, 117.57, 73, 58, 54, 71, 53.75, 50.42, 39.60, 37.18, 36.60, 36.36, 35.11, 28.97, 23.95.

Example 140

Synthesis of N-(Toluene-4-sulfonyl)-L-prolyl-L-4-(N-(1,4-dioxa-8-aza-spiro[4.5]decan-8-yl)carbonyloxy)phenylalanine Ethyl Ester The title compound was prepared following the procedure outlined for Example 4 by substitution of the appropriate starting materials.
Physical data was as follows:
MS (+ESI): 630 [M+H]$^+$.
Anal. Calcd. for $C_{31}H_{39}N_3O_9S.0.2\ CH_2Cl_2$: C, 57.94; H, 6.14; N, 6.50.
Found: C, 57.73; H, 5.90; N, 6.47.

Example 141

Synthesis of N-(Toluene-4-sulfonyl)-L-prolyl-L-4-(N-(1,4-dioxa-8-aza-spiro[4.5]decan-8-yl)carbonyloxy)phenylalanine The product of Example 140 was hydrolyzed using the procedure described in Method 5 but-employing methanol as the solvent and running the reaction at 25° C. for 24 h. The solvent was then evaporated, the residue taken up in H$_2$O, washed with methylene chloride and lyophilized to afford the title compound.
Physical data was as follows:
MS (+ESI): 619 [M+H]$^+$.
Anal. Calcd. for $C_{29}H_{35}N_3O_9SLi.1.5H_2O$: C, 53.37; H, 6.02; N, 6.44.
Found: C, 53.40; H, 5.58; N, 6.48.

Example 142

Synthesis of N-(Toluene-4-sulfonyl)-L-prolyl-L-4-(4'-acetylpiperazin-1-ylcarbonyloxy)phenylalanine The product of Example 127 was hydrolyzed using the procedure described in Method 5 but employing methanol as the solvent and running the reaction at 25° C. for 24 h. The solvent was then evaporated, the residue taken up in H$_2$O, washed with methylene chloride and lyophilized to afford the title compound.

Physical data was as follows:
MS (+ESI): 587 [M+H]$^+$.
Anal. Calcd; for $C_{28}H_{33}N_4O_8SLi.3H_2O$: C, 52.01; H, 6.08; N, 8.66.
Found: C, 52.03; H, 5.36; N, 8.04.

Example 143

Synthesis of N-(Toluene-4-sulfonyl)-L-prolyl-L-4-(4'-methanesulfonylpiperazin-1-ylcarbonyloxy)phenylalanine The product of Example 128 was hydrolyzed using the procedure described in Example 142.
Physical data was as follows:
MS (+ESI): 623 [M+H]$^+$.
Anal. Calcd. for $C_{27}H_{33}N_4O_9S_2Li.2\ H_2O$: C, 48.79; H, 5.61; N, 8.43.
Found: C, 48.66; H, 5.14; N, 8.04.

Example 144

Synthesis of N-(Toluene-4-sulfonyl)-L-prolyl-L-4-(4'-phenylpiperazin-1-ylcarbonyloxy)phenylalanine The ethyl ester of the title compound was prepared following the procedure outlined for Example 4 by substitution of the appropriate starting materials. The ethyl ester was then hydrolyzed using the procedure described in Example 142.
Physical data was as follows:
MS (−ESI): 619 [M−H]$^−$.
Anal. Calcd. for $C_{32}H_{36}N_4O_7SLi.2H_2O$: C, 58.00; H, 5.93; N, 8.45.
Found: C, 57.65; H, 5.49; N, 8.13.

Example 145

Synthesis of N-(Toluene-4-sulfonyl)-L-prolyl-L-4-(piperazin-1-ylcarbonyloxy)phenylalanine tert-Butyl Ester The product of Example 125 (0.7 g, 1 mmol) was dissolved in methylene chloride (9 mL). The solution was cooled to 0° C. and trifluoroacetic acid (1.0 mL) was added and the resulting clear solution was stirred for 4 h. The reaction solution was then diluted with additional methylene chloride (50 mL), washed with saturated sodium bicarbonate solution (3×50 mL), dried (K$_2$CO$_3$) and the solvent stripped off to give a white solid (0.465 g). Flash chromotography (9:1 CH$_2$Cl$_2$: EtOH) of this material gave a clear oil which was washed several times with hexane to give a white solid (0.289 g, 48%).
Physical data was as follows:
MS (+ESI): 601.7 [M+1]$^+$.
Anal. Calcd. for $C_{30}H_{40}N_4O_7S.0.25\ CH_2Cl_2$: C, 58.42; H, 6.56; N, 9.01.
Found: C, 58.79; H, 6.51; N, 8.74.

Example 146

Synthesis of 2-(Saccharin-2-yl)propionyl-L-4-(4'-methylpiperazin-1-ylcarbonyloxy)phenylalanine The title compound was prepared from the product of Example 46 using the procedure described in Method 11, mp=117-122° C. (with foaming).

Physical data was as-follows:
Anal. Calcd. for $C_{25}H_{28}N_4O_8S.1.5H_2O$: C, 52.53; H, 5.47; N, 9.80.
Found: C, 52.26; H, 5.36; N, 9.23.

Example 147

Synthesis of N-(Toluene-4-sulfonyl)-L-prolyl-L-4-(4'-methanesulfonyl piperazin-1-ylcarbonyloxy)phenylalanine tert-Butyl Ester The title compound was prepared following the procedure outlined for Example 128 by substitution of the appropriate starting materials.
Physical data was as follows:
MS (+ESI): 696 $[M+NH_4]^+$.
Anal. Calcd. for $C_{31}H_{42}N_4O_9S_2.0.5\ CH_2Cl_2$: C, 51.62; H, 6.00; N, 7.76.
Found: C, 51.55; H, 6.21; N, 7.60.

Example 148

Synthesis of N-(Toluene-4-sulfonyl)-L-prolyl-L-4-(N,N-dimethylcarbamyloxy)phenylalanine (N'-tert-butoxycarbonyl-2-amino-2-methylpropyl) Ester $(BOC)_2O$ (96 mg, 0.44 mmol) was added to a solution of the product from Example 9 (200 mg, 0.4 mmol.), N-Boc-2-amino-2-methyl-1-propanol (965 mg, 0.5 mmol) and a catalytic amount of DMAP in THF (92 mL) containing pyridine (50 µl). The mixture was stirred at room temperature under argon for 48 h. The mixture was poured into 1N HCl and extracted with ethyl acetate. The organic phase was washed (1N HCl), dried ($MgSO_4$) and the solvent was removed under reduced pressure. The residue was purified by flash chromatography (EtOAc:hexanes 2:1) to give the desired compound as an amorphous white foam (150 mg., 55%).
Physical data was as follows:
MS: $[M+H]^+$ at 675.
MS (+ESI): $[M+NH_4]^+$ at 692 (100%).

Example 149

Synthesis of N-(Toluene-4-sulfonyl)-L-prolyl-L-4-(N,N-dimethylcarbamyloxy)phenylalanine 2-(Morpholin-4-yl)ethyl Ester The title compound was prepared following the procedure outlined for Example 148 by substituting 2-morpholinoethanol for N-Boc-2-amino-2-methyl-1-propanol.
Physical data was as follows:
Anal. Calcd. for $C_{30}H_{40}N_4O_8S.0.5H_2O$: C, 57.58; H, 6.60; N, 8.95.
Found: C, 57.26; H, 6.29; N, 8.82.

Example 150

Synthesis of N-(Toluene-4-sulfonyl)-L-prolyl-L-4-(4'-acetylpiperazin-1-ylcarbonyloxy)phenylalanine tert-Butyl Ester The title compound was prepared following the procedure outlined for Example 127 by substitution of the appropriate starting materials.
Physical data was as follows:
MS (+ESI): 660.4 $[M+NH_4]^+$.
Anal. Calcd. for $C_{32}N_{42}N_4O_8S.0.15\ CH_2Cl_2$: C, 58.91; H, 6.50; N, 8.55.
Found: C, 58.64; H, 6.36; N, 8.40.

Example 151

Synthesis of N-(Toluene-4-sulfonyl)-L-prolyl-L-4-(4'-hydroxypiperidin-1-ylcarbonyloxy)phenylalanine tert-Butyl Ester The title compound was prepared following the procedure outlined for Example 4 by substituting 4-piperidinol for N-methyl piperazine.
Physical data was as follows:
Anal. Calcd. for $C_{31}H_{41}N_3O_8S.0.6H_2O.0.22$ EtOAc: C, 59.28; H, 6.86; N, 6.51
Found: C, 58.92; H, 6.37; N, 6.47.

Example 152

Synthesis of N-(Toluene-4-sulfonyl)-L-prolyl-L-4-(N-(2'-(morpholin-4'-yl)ethyl)carbamyloxy)phenylalanine tert-Butyl Ester The title compound was prepared following the procedure outlined for Example 4 by substituting 4-(2-aminoethyl)morpholine for N-methyl piperazine.
Physical data was as follows:
Anal. Calcd. for $C_{32}H_{44}N_4O_8S.0.25H_2O$: C, 59.20; H, 6.91; N, 8.63
Found: C, 59.01; H, 6.54; N, 8.38.

Example 153

Synthesis of N-(Toluene-4-sulfonyl)-L-prolyl-L-4-(N-(1,4-dioxa-8-aza-spiro [4.5] decan-8-yl)carbonyloxy)phenylalanine tert-Butyl Ester The title compound was prepared following the procedure outlined for Example 4 by substitution of the appropriate starting materials.
Physical data was as follows:
MS (−ESI): 656 $[M-H]^-$.
Anal. Calcd. for $C_{33}H_{43}N_3O_9S.0.1\ CH_2Cl_2$: C, 59.67; H, 6.54; N, 6.31.
Found: C, 59.83; H, 6.63; N, 6.66.

Example 154

Synthesis of N-(Toluene-4-sulfonyl)-L-prolyl-L-4-(N-(2'-hydroxyethyl)-N-methylcarbamyloxy)phenylalanine tert-Butyl Ester The title compound was prepared folllowing the procedure outlined for Example 4 by substituting 2-(methylamino)ethanol for N-methyl piperazine.
Physical data was as follows:
Anal. Calcd. for $C_{29}H_{39}N_3O_8S.0.5H_2O$: C, 58.18; H, 6.73; N, 7.02.
Found: C, 57.95; H, 6.5; N, 6.9.

Example 155

Synthesis of N-(Toluene-4-sulfonyl)-L-prolyl-L-4-(4'-formyloxypiperidin-1-ylcarbonyloxy)phenylalanine The title compound was prepared by treating the product of Example 151 with formic acid overnight with stirring. The title compound was obtained as a white foam (130 mg., 94%), following removal of excess formic acid.

NMR data was as follows:

$^1$H NMR (DMSO-d$_6$, 400 MHZ) δ 12.8 (s, 1H); 8.23 (s, 1H); 8.09 (d, 1H); 7.69 (d, 2H), 7.4 (d, 2H); 7.23 (d, 2H), 7.02 (d, 2H); 5.00 (m, 1H); 4.45 (m, 1H); 4.10 (m, 1H); 3.6-3.8 (br, 2H); 3.4 (br s, 1H); 3.25 (m, 2H); 3.10 (m, 2H); 2.95 (m, 1H); 2.35 (s, 3H); 1.95 (m, 2H); 1.56-1.75 (m, 5H); 1.4 (m, 1H).

IR(KBr, cm$^{-1}$) 3400, 2950, 1720, 1680, 1510, 1430, 1325, 1250, 1150, 1010, 650, 75, 540.

MS ((+)ESI, m/z (%)) 605 (100 [M+NH, 1$^+$).

Anal. Calcd. for C$_{28}$H$_{33}$N$_3$O$_9$S.0.66H$_2$O: C, 56.09; H, 5.77; N, 7.01.

Found: C, 56.14; H, 5.83; N, 6.78.

Example 156

Synthesis of N-(Toluene-4-sulfonyl)-L-prolyl-L-4-(4'-hydroxypiperidin-1-ylcarbonyloxy)phenylalanine Isopropyl Ester The title compound was prepared following the procedure outlined for Example 4 by substitution of the appropriate starting materials, mp. 64-67° C. (with foaming).

Physical data was as follows:

Anal. Calcd. for C$_{30}$H$_{39}$N$_3$O$_8$S.0.75H$_2$O.0.1 EtOAc: C, 58.51; H, 6.67; N, 6.73.

Found: C, 58.55; H, 6.09; N, 6.78.

Example 157

Synthesis of N-(Toluene-4-sulfonyl)-L-prolyl-L-4-(4'-(2-hydroxyethyl)piperazin-1-ylcarbonyloxy)phenylalanine tert-Butyl Ester The carbonate was prepared by treatment of Tos-Pro-Tyr-t-butyl ester with 4-nitrophenyl chloroformate, followed by addition of N-(2-hydroxylethyl)piperazine (triethylamine, methylene chloride, chilled to 0° C., then stirred at room temperature overnight). The crude product was purified by flash chromatography (silica, 95:5 EtOAc:EtOH) to afford a white solid, mp. 158-160° C. (0.387 g, 58%).

NMR data was as follows:

$^1$H NMR (DMSO-d$_6$, 400 MHZ) δ 8.15 (d, 1H, J=7.90 Hz); 7.70(d, 2H, J=6.59 Hz); 7.40 (d, 2H, J=7.90 Hz); 7.23(d, 2H, J=8.56 Hz); 7.00 (d, 2H, J=8.56 Hz); 4.42 (m, 1H); 4.38 (m, 1H); 4.08 (m, 1H); 3.51 (m, 4H); 3.34 (m, 3H); 3.09 (m, 1H); 2.99 (m, 2H); 2.43 (m, 6H); 2.39 (s, 3H); 1.59 (m, 3H); 1.39 (m, 1H); 1.35 (s, 9H).

IR (KBr, cm$^{-1}$) 3505, 3400, 2990, 2930, 2890, 1730, 1700, 1670, 1510, 1430, 1350, 1220, 1200, 1160, 670, 590, 545.

MS ((-)ESI, m/z (%)) 643 (98 [M-NH$_4$]).

Anal. Calcd. for C$_{32}$H$_{44}$N$_4$O$_8$S: C, 59.61; H, 6.88; N, 8.69.

Found: C, 59.06; H, 6.95; N, 8.43.

Example 158

Synthesis of N-(Toluene-4-sulfonyl)-L-prolyl-L-4-(N-(2'-formyloxyethyl)-N-methylcarbamyloxy)phenylalanine The title compound was prepared by treating the product of Example 154 with formic acid overnight with stirring. The title compound was obtained as a white foam (110 mg., 77%), following removal of excess formic acid.

NMR data was as follows:

$^1$H NMR (DMSO-d$_6$, 400 MHz) δ 12.8 (s, 1H); 8.25 (d, 1H); 8.08 (d, 1H); 7.69 (d, 2H), 7.40 (d, 2H); 7.22 (d, 2H), 6.98 (dd, 2H); 4.47 (m, 1H); 4.35 (m, 1H); 4.27 (m, 1H); 4.10 (m, 1H); 3.65 (m, 1H); 3.55 (m, 1H); 2.85-3.15 (overlapping m, 7H); 2.40 (s, 3H); 1.55 (m, 3H); 1.40 (m, 1H).

IR (KBr, cm$^{-1}$) 3420, 2910, 1725, 1510, 1400, 1340, 1270, 1150, 675, 590, 550.

MS ((+)ESI, m/z (%)) 579 (100 [M+NH, 1$^+$).

Anal. Calcd. for C$_{26}$H$_{31}$N$_3$O$_9$S.0.66H$_2$O: C, 54.45; H, 5.68; N, 7.33

Found: C, 54.41; H, 5.60; N, 7.24.

Example 159

Synthesis of N-(Toluene-4-sulfonyl)-L-prolyl-L-4-(N-(2'-hydroxyethyl)-N-methylcarbamyloxy)phenylalanine Isopropyl Ester The title compound was prepared following the procedure outlined for Example 4 by substitution of the appropriate starting materials, mp. 49-52° C.

Physical data was as follows:

Anal Calcd. for C$_{28}$H$_{37}$N$_3$O$_8$S.0.5H$_2$O: C, 57.52; H, 6.55; N, 7.19.

Found: C, 57.56; H, 6.38; N, 7.14.

Example 160

Synthesis of N-(Toluene-4-sulfonyl)-L-prolyl-4-(N-(methoxycarbonylmethyl)carbamyloxy)phenylalanine tert-Butyl Ester The carbonate was prepared by treatment of Tos-Pro-Tyr-t-butyl ester with 4-nitrophenyl chloroformate, followed by addition of glycine methyl ester (triethylamine, methylenechloride, chilled to 0°, then stirred at room temperature overnight). The crude product was purified by flash chromatography (silica, 3:2 EtOAc:hexane) to afford a white foam (0.640 g, 35%).

NMR data was as follows:

$^1$H NMR (DMSO-d$_6$, 400 MHz) δ 8.15 (d, 1H, J=8.12 Hz); 8.12 (d, 2H, J=6.15 Hz); 7.73 (d, 2H, J=8.34 Hz); 7.40 (d, 2H, J=7.90 Hz); 7.24 (d, 2H, J=8.56 Hz); 6.98 (d, 2H, J=8.34 Hz); 4.25 (m, 1H); 4.07 (m, 1H); 3.83 (d, 2H, J=6.15 Hz); 3.64 (s, 3H); 3.32 (m, 1H); 3.02 (m, 3H); 2.39 (s, 3H); 1.56 (m, 3H); 1.41 (m, 1H); 1.35 (s, 9H).

IR (KBr, CM$^{-1}$) 3400, 2990, 1745, 1680, 1500, 1370, 1350, 1200, 1160, 670, 600.

MS ((+)ESI, m/z (%)) 621 (100[M+NH$_4$]$^+$).

Anal. Calcd. for C$_{29}$H$_{37}$N$_3$O$_9$S: c, 57.70; H, 6.18; N, 6.96.

Found: C, 57.63; H, 6.11; N, 6.74.

Example 161

Synthesis of N-(1-Methylpyrazole-4-sulfonyl)-L-(5,5-dimethyl) thiaprolyl-L-4-(N,N-dimethylcarbamyloxy)phenylalanine Isopropyl Ester The title compound was prepared following the procedure outlined for Example 138 by substitution of the appropriate starting materials.

NMR data was as follows:

$^1$H NMR (CDCl$_3$): δ 7.91 (s, 1H), 7.81 (s, 1H), 7.21 (d, 2H, J=8.2 Hz), 7.03 (m, 3H); 5.03 (m, 1H), 4.84 (m, 1H), 4.55 (d, 1H), 4.42 (d, 1H), 3.96 (s, 3H), 3.83 (s, 1H), 3.18-3.01 (m, 2H), 3.10 (s, 3H), 3.01 (s, 3H), 1.28 (s, 3H), 1.24 (m, 6H), 1.17 (s, 3H).

$^{13}$C NMR (CDCl$_3$): δ 170.43, 166.31, 154.92, 150.68, 132.91, 132.88, 130.34, 121.78, 117.69, 73.76, 69.61, 54, 79, 53.2, 50.52, 39.61, 37.62, 36.58, 36.35, 28.96, 24.02, 21.57, 21.49.

Example 162

Synthesis of N-(Toluene-4-sulfonyl)-L-prolyl-L-4-(4'-methoxypiperidin-1-ylcarbonyloxy)phenylalanine Isopropyl Ester The title compound was prepared following the procedure outlined for Example 156 by substitution of the appropriate starting materials.

NMR data was as follows:

$^1$H NMR (DSMO-d$_6$, 400 MHz) δ 8.10 (d, 1H); 7.72 (d, 2H); 7.41 (d, 2H); 7.24 (d, 2H); 7.02 (d, 2H); 4.92 (m, 1H); 4.45 (m, 1H); 4.10 (m, 1H); 3.8 (br s, 1H); 3.65 (br s, 1H); 3.40 (M, 2H); 3.25 (s, 3H); 2.95-3.15 (overlapping m, 5H); 2.40 (s, 3H); 1.85 (br, 2H); 1.4-1.6 (m, 6H); 1.18 (d, 3H); 1.12 (d, 3H).

IR (KBr, cm$^{-1}$) 3400, 2950, 1720, 1520, 1425, 1340, 1210, 1160, 1100, 625, 590, 540.

MS ((+) ESI, m/z (%)) 633 [M+NH]$^+$).

Example 163

Synthesis of N-(Toluene-4-sulfonyl)-L-prolyl-L-4-(4'-methoxypiperidin-1-ylcarbonyloxy)phenylalanine The title compound was prepared from the product of Example 162 using the procedure described in Method 5.

NMR data was as follows:

$^1$H NMR (DMSO-d$_6$, 400 MHz) δ 12.8 (s, 1H); 8.10 (d, 1H); 7.72 (d, 2H); 7.41 (d, 2H); 7.24 (d, 2H); 7.02 (d, 2H); 4.45 (m, 1H); 4.10 (m, 1H); 3.8 (br s, 1H); 3.65 (br s, 1H); 3.40 (m, 2H); 3.25 (s, 3H); 2.95-3.15 (overlapping m, 5H); 2.40 (s, 3H); 1.85 (br, 2H); 1.4-1.6 (m, 6H).

IR (KBr, cm$^{-1}$) 3400, 2950, 1720, 1520, 1425, 1340, 1210, 1160, 1100, 625, 590, 540.

MS ((−)ESI, m/z (%)) 572 (100 [M−H]$^-$).

Anal. Calcd. for C$_{28}$H$_{35}$N$_3$O$_8$S.0.33EtOAc.1H$_2$O: C, 56.73; H, 6.44; N, 6.77. Found: C, 56.96; H, 6.01; N, 6.76.

Example 164

Synthesis of N-(Toluene-4-sulfonyl)-L-4-oxoprolyl-L-4-(N,N-dimethylcarbamyloxy)phenylalanine tert-Butyl Ester Dichloromethane (7 mL) was cooled to −60° C. (chloroform/dry ice bath). Oxalyl chloride (0.15 mL) was added. The product from Example 165 (870 mg) and dry DMSO (0.26 mL) were dissolved in dichloromethane (8 mL) and added slowly to the above solution. The reaction was stirred at −60° C. for 30 minutes under dry conditions. Triethylamine (1.05 mL) was added. After 5 minutes, the dry ice bath was removed. The reaction was stirred at room temperature for 1 hour. The solvent was evaporated in vacuo. Ethyl acetate (30 mL) was added to the residue. The mixture was washed with citric acid solution (5%, 2×30 mL) and saturated NaHCO$_3$ solution (2×30 mL); and finally with brine. The solution was dried over MgSo$_4$. The solvent was evaporated in vacuo, and the residue was flushed on a silica gel column to give 440 mg of the desired product, mp: 78-80° C.

Example 165

Synthesis of N-(Toluene-4-sulfonyl)-L-trans-4-hydroxyprolyl-L-4-(N,N-dimethylcarbamyloxy)phenylalanine tert-Butyl Ester N-(Toluene-4-sulfonyl)-L-trans-4-hydroxyprolyl-L-4-(hydroxy)phenylalanine tert-butyl ester (1.60 g) and dimethylcarbamyl chloride (0.30 mL) were dissolved in DMF at 0° C. in an ice bath. Potassium carbonate powder (2.03 g) was added to the solution. The ice bath was removed after 5 minutes. The reaction was stirred at room temperature for 6 hours. The solid was filtered. Ethyl acetate (40 mL) was added to the solution. The solution was washed with citric acid solution (5%, 40 mL) 2 times, and saturated NaHCO$_3$ solution (40 mL) 1 time. The solution was then washed with brine and dried with MgSO$_4$. The solvent was evaporated in vacuo to give 1.07 g of the title compound, mp: 170-172° C.

Example 166

Synthesis of N-(3-Fluorobenzenesulfonyl)-L-prolyl-L-4-(N,N-dimethylcarbamyloxy)phenylalanine tert-Butyl Ester N-(3-Fluorobenzenesulfonyl)-L-prolyl-L-4-(hydroxy)phenylalanine tert-butyl ester (700 mg) and dimethylcarbamyl chloride (0.2 mL) were dissolved in DMF (15 mL) at 0° C. in an ice bath. Potassium carbonate powder (1.375 g) was added to the solution. The ice bath was removed after 5 minutes. The reaction was stirred at room temperature for 6 hours. The solid was filtered. Ethyl acetate (20 mL) was added to the solution. The solution was washed with citric acid solution (5%, 30 mL, 2×), and saturated NaHCO$_3$ solution. The solution was then washed with brine and dried with MgSO$_4$. The solvent was evaporated in vacuo to give 890 mg of the title compound, mp: 107-109° C.

Example 167

Synthesis of N-(Morpholino-sulfonyl)-L-prolyl-L-(4-N,N-dimethylcarbamyloxy)phenylalanine tert-Butyl Ester N-(Morpholino-sulfonyl)-L-proline was prepared using the procedure described by Cheeseright et al., *J. Chem. Soc. Perkin Trans.* 1 1994, 12, 1595-1600. The title compound was prepared following the procedure described for the preparation of Example 2.

NMR data was as follows:

$^1$H NMR (CDCl$_3$): δ 7.13 (d, 2H), 7.03 (d, 2H), 6.92 (d, 1H), 4.71 (q, 1H), 4.25 (t, 1H), 3.67 (t, 4H), 3.39 (dt, 1H), 3.28-3.19 (m, 1H), 3.23 (t, 4H), 3.18 (dd, 1H), 3.08 (dd, 1H), 3.09 (s, 3H), 3.00 (s, 3H), 2.16-2.08 (m, 2H), 1.98-1.86 (m, 1H), 1.78-1.66 (m, 1H), 1.45 (s, 9H).

$^{13}$C NMR (CDCl$_3$): δ 171.2, 170.4, 154.8, 150.7, 132.9, 130.3, 121.7, 82.7, 66.3, 62.6, 53.3, 49.6, 46.2, 37.0, 36.6, 36.3, 30.5, 27.8, 24.7.

Example 168

Synthesis of N-(Morpholino-sulfonyl)-L-prolyl-L-(4-N,N-dimethylcarbamyloxy)phenylalanine The title compound was prepared from the product of Example 167 using the procedure described in Method 11.

NMR data was as follows:

$^1$H NMR (CD$_3$OD): δ 8.04 (d, 1H), 7.25 (d, 2H), 7.01 (d, 2H), 4.71-4.64 (m, 1H), 4.22 (dd, 1H), 3.62-3.50 (m, 4H), 3.43-3.31 (m, 2H), 3.24 (dd, 1H), 3.11 (t, 4H), 3.09 (s, 3H), 3.03 (dd, 1H), 2.97 (s, 3H), 2.22-2.11 (m, 1H), 1.98-1.80 (m, 3H).

$^{13}$C NMR(CD$_3$OD): δ 174.65, 174.58, 174.00, 156.60, 151.70, 135.30, 131.20, 122.70, 67.10, 63.10, 54.59, 54.50, 50.6, 47.10, 37.10, 36.50, 36.40, 32.0, 25.60.

Example 169

Synthesis of N-(1-Methylpyrazole-4-sulfonyl)-L-(1,1-dioxothiamorpholin-3-carbonyl)-L-4-(N,N-dimethylcarbamyloxy)phenylalanine tert-Butyl Ester The title compound was prepared following the procedures described for the preparation of Examples 14 and 117.

NMR data was as follows:

$^1$H NMR (CDCl$_3$): δ 7.93 (s, 1H), 7.80 (s, 1H), 7.12 (d, 2H), 6.98 (d, 2H), 6.44 (d, 1H0HH), 4.95 (m, 1H), 4.66 (m, 1H), 4.04 (m, 2H), 3.98 (s, 3H), 3.19 (m, 2H), 3.06 (m, 6H), 2.98 (m, 4H), 1.42 (m, 9H).

$^{13}$C NMR (CDCl$_3$): δ 170.58, 164.75, 154.91, 150.75, 139.33, 132.73, 132.43, 130.43, 122.18, 119.66, 83.07, 56.02, 53.23, 50.03, 49.03, 41.49, 39.63, 36.56, 36.31, 36.16, 27.87.

Example 170

Synthesis of N-(2-Fluorobenzenesulfonyl)-L-(1,1-dioxothiamorpholin-3-carbonyl)-L-4-(N,N-dimethylcarbamyloxy)phenylalanine The title compound was prepared from the product of Example 90 using the procedure described in Method 11.

NMR data was as follows:

$^1$H NMR (CD$_3$OD): δ 7.90 (m, 1H), 7.72 (m, 1H), 7.56 (d, 1H), 7.37 (m, 2H), 7.20 (d, 2H), 7.07 (d, 2H); 5;18 (m, 1H), 4.59 (m, 1H), 4.26 (m, 1H), 3.76 (m, 2H), 3.36 (m, 1H), 3.21 (m, 2H), 3.08 (m, 6H), 2.96 (s, 3H).

$^{13}$C NMR (CD$_3$OD): δ 173.85, 168.04, 162.06, 158.69, 156.92, 152.06, 137.69, 135.05, 131.83, 131.59, 129.77, 128.44, 128.26, 126.21, 123.17, 119.04, 118.75, 57.04, 54.99, 52.08, 51.66, 43.36, 37.24, 36.83, 36.66.

Example 171

Synthesis of N-(2,4-Difluorobenzenesulfonyl)-L-(1,1-dioxothiamorpholin-3-carbonyl)-L-4-(N,N-dimethylcarbamyloxy)phenylalanine The title compound was prepared from the product of Example 92 using the procedure described in Method 11.

NMR data was as follows:

$^1$H NMR (CD$_3$OD): δ 8.88 (m, 1/2H), 8.14 (m, 1/2H), 7.90 (m, 1H), 7.64 (m, 1H), 7.20 (m, 2H), 7.10 (m, 1H), 7.03 (m, 2H), 5.16 (m, 1H), 4.63 (m, 1H), 4.28 (m, 1H), 3.75 (m, 2H), 3.41 (m, 1H), 3.15 (m, 5H), 3.02 (m, 4H).

$^{13}$C NMR (CD$_3$OD): δ 173.91, 168.04, 156.93, 152.05, 135.15, 133.81, 133.67, 131.60, 123.13, 113.48, 113.18, 107.38, 107.02, 57.02, 55.02, 52.29, 51.84, 43.45, 37.34, 36.83, 36.66.

Example 172

Synthesis of N-(Toluene-4-sulfonyl)-L-(thiamorpholin-3-carbonyl)-L-4-(N,N-dimethylcarbamyloxy)phenylalanine The title compound was prepared from the product of Example 49 using the procedure described in Method 11.

NMR data was as follows:

$^1$H NMR (CDCl$_3$): δ 7.67 (d, 2H), 7.32 (d, 2H), 7.21 (d, 2H), 7.10 (d, 1H), 7.00 (d, 2H), 5.40 (bs, >1H), 4.85 (m, 2H), 3.95 (m, 1H), 3.41 (m, 1H), 3.07 (m, 6H), 2.98 (m, 4H), 2.62 (m, 1H), 2.41 (m, 5H), 2.13 (m, 1H).

$^{13}$C NMR (CDC$_3$): δ173.40, 168.49, 155.26, 144.44, 136.88, 132.95, 130.51, 130.30, 127.28, 122.08, 55.34, 53.45, 43.43, 36.62, 36.38, 35.85, 25.25, 24.54, 21.43.

Example 173

Synthesis of N-(Pyridine-3-sulfonyl)-L-(5,5-dimethyl-thiaprolyl-L-4-(N,N-dimethylcarbamyloxy)phenylalanine Isopropyl Ester The title compound was prepared following the procedure outlined for the preparation of Example 56 by substitution of the appropriate starting materials.

NMR data was as follows:

$^1$H NMR (CDCl$_3$): δ 9.13 (m, 1H), 8.90 (m, 1H), 8.19 (m, 1H), 7.56 (m, 1H), 7.23 (d, 2H), 7.04 (d, 2H), 6.93 (d, 1H), 5.07 (m, 1H), 4.85 (m, 1H), 4.62 (d, 1H), 4.48 (d, 1H), 3.92 (s, 1H), 3.20-3.05 (m, 2H), 3.12 (s, 3H), 3.03 (s, 3H), 1.32-1.16 (m, 12H).

$^{13}$CNMR(CDCl$_3$): δ 170.30, 167.75, 154.19, 150.67, 148.59, 135.72, 132.94, 132.72, 130.27, 123.91, 121.78, 73.62, 69.64, 54.69, 53.12, 50.48, 37.50, 36.53, 36.29, 29.05, 23.73, 21.54, 21.46.

Example 174

Synthesis of N-(3-Fluorobenzenesulfonyl)-L-(1,1-dioxothiamorpholin-3-carbonyl)-L-4-(N,N-dimethylcarbamyloxy)phenylalanine The title compound was prepared from the product of Example 91 using the procedure described in Method 11.

NMR data was as follows:

$^1$H NMR (CD$_3$OD): δ 7.68 (m, 3H), 7.44 (m, 1H), 7.20 (m, 2H), 7.01 (m, 2H), 5.21 (m, 1H), 4.60 (m, 1H), 4.20 (m, 1H), 3.75 (m, 1H), 3.43 (m, 1H), 3.21 (m, 3H), 3.02 (m, 4H), 2.96 (m, 4H).

$^{13}$C NMR (CD$_3$OD): δ 173.98, 167.98, 165.89, 162.56, 156.94, 152.06, 142.70, 142.61, 135.11, 133.30, 133.19, 131.57, 124.71, 123.25, 122.21, 121.93, 116.05, 115.71, 57.27, 54.87, 54.79, 51.29, 51.06, 43.24, 37.11, 36.83.

Example 175

Synthesis of N-(1-Methylpyrazole-4-sulfonyl)-L-(1,1-dioxothiamorpholin-3-carbonyl)-L-4-(N,N-dimethylcarbamyloxy)phenylalanine The title compound was prepared from the product of Example 169 using the procedure described in Method 11.

NMR data was as follows:

$^1$H NMR (CD$_3$OD): δ 8.11 (s, 1H), 7.83 (s, 1H), 7.36 (d, 1H), 7.24 (d, 2H), 7.02 (d, 2H), 5.16 (m, 1H), 4.69 (m, 1H), 4.19 (m, 1H), 3.90 (s, 3H), 3.81 (m, 2H), 3.33 (m, 3H), 3.10 (s, 3H), 3.02 (m, 4H).

$^{13}$C NMR (CD$_3$OD): δ 174.07, 168.11, 156.93, 152.08, 140.12, 135.05, 134.90, 131.67, 123.28, 121.82, 57.33, 54.77, 50.83, 50.64, 42.94, 39.80, 37.02, 36.84, 36.76.

Example 176

Synthesis of N-(4-tert-Butylbenzenesulfonyl)-L-(1,1-dioxothiamorpholin-3-carbonyl)-L-4-(N,N-dimethylcarbamyloxy)phenylalanine The title compound was prepared from the product of Example 88 using the procedure described in Method 11.

NMR data was as follows:

$^1$H NMR (CD$_3$OD): δ 7.70 (d, 2H), 7.53 (d, 2H), 7.04 (d, 2H), 6.87 (d, 2H), 5.09 (m, 1H), 4.48 (m, 1H), 3.99 (m, 1H), 3.60 (m, 1H), 2.90 (m, 5H), 2.80 (m, 5H), 1.15 (s, 9H).

$^{13}$C NMR (CD$_3$OD): δ 173.95, 168.09, 159.33, 156.88, 152.09, 137.52, 135.03, 131.54, 128.68, 128.15, 123.32, 57.27, 54.81, 50.75, 43.04, 36.97, 36.82, 36.65, 36.16, 31.35.

Example 177

Synthesis of N-(Toluene-4-sulfonyl)-(3,3-dimethyl)prolyl-L-4-(N,N-dimethylcarbamyloxy)phenylalanine The title compound was prepared from the product of Example 97 using the procedure described in Method 11.

NMR data was as follows:

$^1$H NMR (CDCl$_3$): δ 7.77 (d, 1H), 7.75 (d, 1H), 7.42-7.33 (m, 3.5H), 7.27 (d, 1H), 7.19 (d, 0.5H), 7.10 (d, 1H), 7.03 (d, 1H), 5.07-5.00 (m, 0.5H), 4.94-4.87 (m, 0.5), 3.67 (d, 1H), 3.58-3.52 (m, 1H), 3.35-3.25 (m, 1H), 3.19-3.08 (m, 2H), 3.11 (s, 3H), 3.02 (s, 3H), 2.45 (s, 1.5H), 2.43 (s, 1.5H), 1.70-1.57 (m, 1H), 1.34-1.27 (m, 1H), 0.94 (s, 1.5H), 0.75 (s, 1.5H), 0.54 (s, 6H).

$^{13}$C NMR(CDCl$_3$): δ 174.6, 174.4, 171.8, 171.4, 155.7, 150.5, 150.4, 144.5, 144.4, 133.5, 132.6, 130.9, 130.6, 130.0, 129.9, 128.0, 127.9, 122.2, 122.0, 71.2, 70.9, 53.3, 52.2, 47.3, 47.1, 43.0, 42.7, 38.1, 37.9, 36.6, 36.4, 27.0, 26.8, 23.3, 23.0.

Example 178

Synthesis of N-(2,5-Dichlorothiophene-3-sulfonyl)-L-prolyl-L-4-(N,N-dimethylcarbamyloxy)phenylalanine The title compound was prepared from the product of Example 86 using the procedure described in Method 11.

NMR data was as follows:

$^1$H NMR (CD$_3$OD): δ 8.10 (d, 1H), 7.25 (d, 2H), 7.20 (s, 1H), 7.0 (d, 2H), 4.65 (m, 1H), 4.35 (m, 1H), 3.55-3.35 (m, 2H), 3.30-3.20 (m, 2H), 3.15-3.00 (m, 4H), 2.95 (s, 3H), 2.05-1.80 (m, 2H), 1.80-1.65 (m, 2H).

$^{13}$C NMR (CD$_3$OD): δ 174.2, 173.9, 156.9, 151.9, 135.9, 135.5, 132.3, 131.6, 128.9, 128.6, 122.9, 63.1, 54.8, 54.7, 50.3, 37.4, 36.8, 36.7, 32.1, 25.5.

Example 179

Synthesis of N-(4-Methoxybenzenesulfonyl)-L-prolyl-L4-(N,N-dimethylcarbamyloxy)phenylalanine The title compound was prepared from the product of Example 180 using the procedure described in Method 7.

NMR data was as follows:

$^1$H NMR (CD$_3$OD): δ 7.78 (d, 2H), 7.27 (d, 2H), 7.09 (d, 2H), 7.02 (d, 2H), 4.71-4.67 (m, 1H), 4.10-4.06 (m, 1H), 3.88 (s, 3H), 3.41-3.31 (m, 1H), 3.28-3.07 (m, 6H), 2.97 (s, 3H), 1.81-1.50 (m, 4H).

$^{13}$C NMR (CD$_3$OD): δ 168.3, 168.2, 159.2, 150.9, 145.9, 129.5, 125.6, 125.3, 123.5, 116.9, 109.6, 57.2, 50.2, 48.7, 44.6, 31.4, 30.8, 30.6, 25.7, 19.3.

Example 180

Synthesis of N-(4-Methoxybenzenesulfonyl)-L-prolyl-L4-(N,N-dimethylcarbamyloxy)phenylalanine Isopropyl Ester The title compound was prepared using the procedure described in Example 2 by substitution of the appropriate starting materials.

NMR data was as follows:

$^1$H NMR (CDCl$_3$): δ 7.76 (d, 2H), 7.34 (d, 1H), 7.14 (d, 2H), 7.03-6.97 (m, 4H), 5.08-5.04 (m, 1H), 4.77 (m, 1H), 4.05-4.03 (m, 1H), 3.86 (s, 3H), 3.37-3.34 (m, 1H), 3.26-3.19 (m, 1H), 3.10-3.01 (m, 4H), 2.98 (s, 3H), 2.02 (m, 1H), 1.56-1.46 (m, 3H), 1.25 (d, 6H).

$^{13}$C NMR (CDCl$_3$): δ 170.8, 170.3, 163.4, 154.8, 150.5, 132.9, 130.1, 129.9, 127.6, 121.6, 114.3, 69.4, 62.1, 55.4, 53.2, 49.5, 37.1, 36.5, 36.2, 29.7, 24.0, 21.5, 21.4.

Example 181

Synthesis of N-(Toluene-4-sulfonyl)-L-(1-oxo-thiomorpholin-3-carbonyl)thiaprolyl-L-4-(N,N-dimethylcarbamyloxy)phenylalanine The title compound was prepared from the product of Example 182 using the procedure described in Method 11.

NMR data was as follows:

$^1$H NMR (CD$_3$OD): δ 7.90 (m, 1H), 7.78 (m, 2H), 7.40 (m, 2H), 7.26 (m, 2H), 7.03 (m, 2H), 5.14 (m, 1H), 4.64 (m, 2H), 3.81 (m, 1H), 3.71 (m, 2H), 3.19 (m, 1H), 3.14 (m, 3H), 3.02 (m, 4H), 2.84 (m, 1H), 2.60 (m, 1H), 2.42 (m, 4H), 2.21 (m, 1H).

$^{13}$C NMR (CD$_3$OD): δ 174.22, 173.93, 169.59, 156.88, 152.08, 152.05, 146.44, 146.26, 137.75, 137.63, 135.61, 134.96, 131.79, 131.64, 131.55, 131.39, 128.75, 128.66, 123.35, 123.06, 57.03, 54.88, 54.66, 51.64, 42.69, 42.51, 40.34, 37.12, 36.83, 36.66, 32.76, 21.51.

Example 182

Synthesis of N-(Toluene-4-sulfonyl)-L-(1-oxo-thiomorpholin-3-carbonyl)-L-4-(N,N-dimethylcarbamyloxy)phenylalanine tert-Butyl Ester The title compound was prepared following the procedure described for the preparation of Example 49. The oxidation of the thiomorpholine group to the 1-oxo-thiomorpholine group was per Larsson and Carlson (*Acta Chemica Scan.* 1994, 48, 517-525).

NMR data was as follows:

$^1$H NMR (CDCl$_3$): δ 7.72 (m, 2H), 7.69 (m, 2H), 7.31 (m, 2H), 7.11 (m, 2H), 7.07 (m, 2H), 6.96 (m, 2H), 4.79 (m, 1H), 4.54 (m, 1H), 3.80 (m, 4H), 3.04 (4H), 2.92 (m, 3H), 2.64 (m, 1H), 2.43 (m, 4H), 1.44 (s, 3H), 1.36 (s, 6H).

$^{13}$C NMR (CDCl$_3$): δ 169.8, 166.5, 166.3, 154.6, 150.5, 150.4, 144.9, 144.4, 135.7, 135.3, 132.8, 130.5, 130.1, 29.9, 127.4, 126.9, 122.1, 121.4, 82.6, 82.2, 55.6, 53.9, 53.1, 50.6, 48.1, 47.8, 41.7, 40.5, 38.3, 36.4, 36.1, 31.1, 27.5, 21.2.

Example 183

Synthesis of N-(3,4-Difluorobenzenesulfonyl)-L-prolyl-4-(N,N-dimethylcarbamyloxy)phenylalanine Isopropyl Ester The title compound was prepared following the procedure described for the preparation of Example 2 by substitution of the appropriate starting materials.

NMR data was as follows:

$^1$H NMR (CDCl$_3$): δ 7.72-7.60 (m, 2H), 7.87-7.37 (m, 1H), 7.13-7.11 (m, 3H), 7.01 (d, 2H), 5.08-5.04 (m, 1H), 4.81-4.74 (m, 1H), 4.09-4.06 (m, 1H), 3.39-3.35 (m, 1H), 3.26-3.19 (m, 1H), 3.12-2.97 (m, 8H), 2.06-2.03 (m, 1H), 1.66-1.57 (m, 3H), 1.26 (d, 6H).

$^{13}$C NMR (CDCl$_3$): δ 170.50, 170.40, 154.90, 153.60, 150.70, 150.30, 133.30, 132.90, 130.10, 125.00, 121.80, 121.80, 118.50, 112.80, 69.60, 62.20, 53.20, 49.60, 37.10, 36.60, 36.30, 30.10, 24.20, 21.59, 21.56.

Example 184

Synthesis of N-(3,4-Difluorobenzenesulfonyl)-L-prolyl-4-(N,N-dimethylcarbamyloxy)phenylalanine The title compound was prepared from the product of Example 183 using the procedure described in Method 7.

NMR data was as follows:

$^1$H NMR (CD$_3$OD): δ 8.10 (d, 1H), 7.84-7.77 (m, 1H), 7.69-7.65 (m, 1H), 7.53-7.45 (m, 1H), 7.28 (d, 2H), 7.02 (d, 2H), 4.72-4.68 (m, 1H), 4.19-4.16 (m, 1H), 3.43-3.39 (m, 1H), 3.31-3.21 (m, 2H), 3.13-3.05 (m, 4H), 2.97 (s, 3H), 1.86-1.61 (m, 4H).

$^{13}$C NMR (CD$_3$OD): δ 174.2, 174.1, 164.7, 156.9, 154.9, 152.0, 151.6, 135.8, 135.6, 131.6, 129.7, 122.9, 119.7, 118.8, 63.1, 54.7, 50.5, 37.4, 36.8, 36.6, 31.9, 25.5.

Example 185

Synthesis of N-(3,4-Difluorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.

NMR data was as follows:

$^1$H NMR (CDCl$_3$): δ 7.71 (m, 2H), 7.33 (m, 1H), 7.07 (d, 2H), 6.91 (d, 2H), 6.36 (d, 1H), 4.95 (m, 1H), 4.61 (m, 1H), 4.03 (m, 2H), 3.16 (m, 2H), 3.13 (m, 4H), 3.07 (m, 1H), 2.93 (s, 9H), 1.43 (s, 9H).

$^{13}$C NMR (CDCl$_3$): δ 170.07, 169.45, 164.42, 155.06, 155.44, 154.81, 152.21, 152.17, 150.58, 148.81, 148.64, 134.90, 134.85, 132.41, 130.29, 124.82, 124.71, 124.66, 121.97, 119.07, 118.76, 117.52, 117.23, 82.92, 55.98, 53.20, 50.10, 49.40, 41.76, 36.41, 36.16, 35.99, 27.64.

Example 186

Synthesis of N-(3,4-Difluorobenzenesulfonyl)-L-(1,1-dioxothiamorpholin-3-carbonyl)-L-4-(N,N-dimethylcarbamyloxy)phenylalanine The title compound was prepared from the product of Example 185 using the procedure described in Method 11.

NMR data was as follows:

$^1$H NMR (CD$_3$OD): δ 6.22 (m, 1H), 6.03 (m, 1H), 5.84 (m, 1H), 5.58 (m, 2H), 5.38 (m, 2H), 3.33 (m, 1H), 3.01 (m, 1H), 2.57 (m, 1H), 2.14 (m, 1H), 1.91 (m, 1H), 1.66 (m, 3H), 1.44 (s, 3H), 1.35 (m, 3H), 1.32 (s, 3H).

$^{13}$C NMR (CD$_3$OD): δ 173.97, 167.89, 156.94, 153.53, 152.07, 150.00, 137.48, 135.17, 131.63, 126.54, 126.43, 123.20, 120.21, 119.96, 118.84, 118.57, 57.25, 54.82, 51.29, 49.86, 43.29, 37.21, 36.85, 36.67.

Example 187

Synthesis of N-(Toluene-4-sulfonyl)-L-(5,5-dimethyl)thiaprolyl-L-(thiomorpholin-4-ylcarbonyloxy)phenylalanine tert-Butyl Ester The title compound was prepared using the procedure described in Example 82 by substitution of the appropriate starting materials.

NMR data was as follows:

$^1$H NMR (CDCl$_3$): δ 7.64 (d, 2H), 7.33 (d, 2H), 7.25 (d, 2H), 7.08-6.97 (m, 3H), 4.76 (m, 1H), 4.57 (d, 1H), 4.38 (d, 1H), 3.83 (s, 1H), 3.95-3.78 (m, 4H), 3.09 (m, 2H), 2.69 (m, 4H), 2.43 (s, 3H), 1.44 (s, 9H), 1.16 (s, 3H), 1.08 (s, 3H).

$^{13}$C NMR (CDCl$_3$): δ 169.78, 168.36, 153.53, 150.28, 144.84, 133.53, 132.76, 130.51, 130.03, 128.19, 121.58, 82.69, 73.42, 54.56, 53.78, 50.46, 47.05, 46.40, 37.80, 29.06, 27.76, 27.37, 27.04, 23.86, 21.52.

Example 188

Synthesis of N-(Toluene-4-sulfonyl)-L-(5,5-dimethyl)thiaprolyl-L-(thiomorpholin-4-ylcarbonyloxy)phenylalanine The title compound was prepared from the product of Example 187 using the procedures described in Method 11.

NMR data was as follows:

$^1$H NMR (CDCl$_3$): δ 7.77 (d, 2H), 7.37 (d, 2H), 7.28 (d, 2H), 7.22 (d, 1H), 7.03 (d, 2H), 5.35 (brs, 1H), 4.91 (m, 1H), 4.60 (d, 1H), 4.39 (d, 1H), 3.91 (s, 1H), 3.96-3.28 (m, 4H), 3.30-3.07 (m, 2H), 2.67 (m, 4H), 2.45 (s, 3H), 1.10 (s, 3H), 1.08 (s, 3H).

$^{13}$C NMR (CDCl$_3$): δ 173.09, 169.45, 153.81, 150.28, 145.02, 133.42, 132.61, 130.60, 130.12, 128.13, 121.86, 73.28, 54.51, 53.31, 50.48, 47.08, 46.47, 36.97, 28.97, 27.35, 27.03, 23.70, 21.52.

Example 189

Synthesis of N-(1-Methylpyrazole-4-sulfonyl)-L-(5,5-dimethyl)thiaprolyl-L-4-(N,N-dimethylcarbamyloxy)phenylalanine Ethyl Ester The title compound was prepared following the procedure described for the preparation of Example 117 by substitution of the appropriate starting materials.

NMR data was as follows:

$^1$H NMR (CDCl$_3$): δ 7.89 (s, 1H), 7.81 (s, 1H), 7.19 (d, 2H), 7.00 (m, 3H), 4.87 (m, 1H), 4.54 (d, 1H), 4.42 (d, 1H), 4.18 (q, 2H), 3.95 (s, 3H), 3.81 (s, 1H), 3.11 (m, 2H), 3.08 (s, 3H), 2.99 (s, 3H), 1.30 (s, 3H), 1.25 (t, 3H), 1.16 (s, 3H).

$^{13}$C NMR (CDCl$_3$): δ 170.98, 168.34, 154.91, 150.71, 139.62, 132.88, 130.28, 121.85, 117.71, 73.77, 61.66, 54.80, 53.16, 50.53, 39.64, 37.63, 36.60, 36.36, 28.98, 24.00, 13.92.

Example 190

Synthesis of N-(Pyridine-3-sulfonyl)-L-(5,5-dimethyl)thiaprolyl-L-4-(N,N-dimethylcarbamyloxy)phenylalanine The title compound was prepared from the product of Example 191 using the procedure described in Method 11.

NMR data was as follows:

$^1$H NMR (CDCl$_3$): δ 9.09 (s, 1H), 8.82 (m, 1H), 8.20 (m, 1H), 7.56 (m, 1H), 7.23 (d, 2H), 7.07 (d, 1H), 5.58 (brs, 1H), 4.83 (m, 1 h), 4.56 (m, 2H), 4.07 (s, 1H), 3.14 (m, 2H), 3.07 (s, 3H), 2.99 (s, 3H), 1.26 (s, 3H), 1.18 (s, 3H).

$^{13}$C NMR (CDCl$_3$): δ 173.04, 168.29, 155.16, 153.39, 150.60, 147.96, 136.43, 133.91, 133.06, 130.66, 130.50, 124.65, 122.14, 121.91, 73.43, 54.58, 53.21, 50.38, 37.18, 36.64, 36.38, 29.25, 23.64.

Example 191

Synthesis of N-(Pyridine-3-sulfonyl)-L-(5,5-dimethyl)thiaprolyl-L-4-(N,N-dimethylcarbamyloxy)phenylalanine tert-Butyl Ester The title compound was prepared following the procedure described for the preparation of Example 56 and substitution of appropriate starting materials.

Physical data was as follows:

MS: [M+H]$^+$593

Anal. Calcd. for C$_{27}$H$_{36}$N$_4$O$_7$S$_2$.0.5H$_2$O: C, 53.88; H, 6.07; N, 9.27.

Found: C, 53.98; H, 6.07; N, 9.27.

Example 192

Synthesis of N-(Pyridine-2-sulfonyl)-L-prolyl-L-4-(N,N-dimethylcarbamyloxy)phenylalanine Isopropyl Ester Substituting 2-pyridinesulfonyl chloride (see Corey et al., *J. Org. Chem.* 1989, 54, 389-393) and following the method for the preparation of Example 56, gave the title compound.

NMR data was as follows:

$^1$H NMR (CDCl$_3$): δ 8.59 (d, 1H), 8.00-7.89 (m, 2H), 7.78 (d, 1H), 7.53-7.49 (m, 1H), 7.16 (d, 2H), 7.01 (d, 2H), 5.05-4.99 (m, 1H), 4.85-4.78 (m, 1H), 4.60-4.57 (m, 1H), 3.44-3.35 (m, 2H), 3.25-3.19 (m, 1H), 3.07 (s, 3H), 3.06-3.01 (m, 1H), 2.97 (s, 3H), 2.19-2.13 (m, 1H), 1.88-1.71 (m, 2H), 1.55 (m, 1H), 1.22-1.19 (m, 6H). 3C NMR (CDCl$_3$): δ 170.90, 170.30, 156.20, 154.80, 150.50, 150.00, 138.00, 133.10, 130.10, 127.00, 123.40, 121.60, 69.20, 62.80, 53.30, 49.60, 37.20, 36.40, 36.20, 29.80, 24.30, 21.42, 21.40.

Example 193

Synthesis of N-(Pyridine-2-sulfonyl)-L-prolyl-L-4-(N,N-dimethylcarbamyloxy)phenylalanine The title compound was prepared from the product of Example 192 using the procedure described in Method 7.

NMR data was as follows:

$^1$H NMR (CD$_3$OD): δ 8.67 (d, 1H), 8.27 (d, 1H), 8.07-8.02 (m, 1H), 7.96-7.91 (m, 1H), 7.65-7.61 (m, 1H), 7.27 (d, 2H), 7.01 (d, 2H), 4.72-4.69 (m, 1H), 4.58-4.54 (m, 1H), 3.44-3.37 (m, 2H), 3.28-3.24 (m, 1H), 3.13-3.05 (m, 4H), 2.96 (s, 3H), 1.94-1.89 (m, 2H), 1.70-1.63 (m, 2H).

$^{13}$CNMR(CD$_3$OD): 6174.5, 174.4, 174.2, 157.7, 156.9, 151.9, 139.9, 135.6, 131.6, 128.8, 124.7, 122.9, 64.1, 54.8, 54.7, 50.9, 37.5, 36.8, 36.7, 31.9, 25.6.

Example 194

Synthesis of N-(Pyridine-2-sulfonyl)-L-(5,5-dimethyl)thiaprolyl-L4-(N,N-dimethylcarbamyloxy)phenylalanine Isopropyl Ester The title compound was prepared following the procedure described for the preparation of Example 192 by substitution of the appropriate starting materials.

NMR data was as follows:

$^1$H NMR (CDCl$_3$): δ 8.64-8.62 (m, 1H), 7.98-7.92 (m, 2H), 7.56-7.51 (m, 1H), 7.28-7.21 (m, 3H), 7.01 (d, 2H), 5.01-4.97 (m, 1H), 4.88-4.85 (m, 2H), 4.80 (d, 1H), 4.63 (d, 1H), 4.19 (s, 1H), 3.11-3.07 (m, 5H), 2.98 (s, 3H), 1.28 (s, 3H), 1.26-1.18 (m, 9H).

$^{13}$C NMR (CDCl$_3$): δ 170.3, 168.4, 155.5, 154.9, 150.7, 150.4, 138.2, 133.0, 130.4, 127.5, 123.5, 121.8, 73.5, 69.5, 54.7, 53.3, 51.0, 37.6, 36.6, 36.4, 29.3, 23.9, 21.52, 21.50.

Example 195

Synthesis of N-(Pyridine-2-sulfonyl)-L-(5,5-dimethyl)thiaprolyl-L-4-(N,N-dimethylcarbamyloxy)phenylalanine The title compound was prepared from the product of Example 194 using the procedure described in Method 7.

NMR data was as follows:

$^1$H NMR (CD$_3$OD): δ 8.70-8.69 (m, 1H), 8.07-8.01 (m, 1H), 7.92-7.89 (m, 1H), 7.67-7.63 (m, 1H), 4.77-4.67 (m, 3H), 4.30 (s, 1H), 3.23-3.06 (m, 5H), 2.97 (s, 3H), 1.27-1.18 (m, 6H).

$^{13}$C NMR (CD$_3$OD): δ 174.1, 171.2, 157.0, 151.9, 151.6, 139.9, 135.7, 131.8, 131.7, 129.0, 124.6, 122.9, 74.3, 61.6, 55.7, 54.9, 51.9, 37.6, 36.8, 36.7, 30.1, 24.9.

Example 196

Synthesis of N-(Toluene-4-sulfonyl)-L-(thiamorpholin-3-carbonyl)-L-4-(N,N-dimethylcarbamyloxy)phenylalanine Isopropyl Ester The title compound was prepared following the procedure described for the preparation of Example 49 by substitution of the appropriate starting materials.

NMR data was as follows:

$^1$H NMR (CDCl$_3$): δ 7.67 (d, 2H), 7.30 (d, 2H), 7.12 (d, 2H), 6.97 (d, 2H), 6.86 (d, 1H), 5.05 (m, 1H), 4.70 (m, 2H), 3.90 (m, 1H), 3.31 (m, 1H), 3.06 (m, 4H), 2.97 (s, 3H), 2.68 (m, 1H), 2.50 (m, 1H), 2.44 (s, 3H), 2.29 (m, 1H), 2.13 (m, 1H), 1.24 (s, 3H), 1.22 (s, 3H).

$^{13}$C NMR (CDCl$_3$): δ 170.35, 167.55, 155.00, 150.61, 144.20, 136.80, 132.51, 130.24, 130.14, 127.20, 121.82, 69.48, 55.14, 53.55, 43.26, 36.43, 36.16, 25.21, 24.56, 21.48, 21.31.

Example 197

Synthesis of N-(3-Fluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.68 (d, 1H), 7.61-7.52 (m, 2H), 7.36 (dt, 1H), 7.21 (d, 2H), 7.02 (d, 2H), 6.94 (d, 1H), 5.05 (sept, 1H), 4.85 (q, 1H), 4.59 (d, 1H), 4.41 (d, 1H), 3.88 (s, 1H), 3.17-3.03 (m, 2H), 3.09 (s, 3H), 3.00 (s, 3H), 1.25 (d, 3H), 1.23 (d, 3H), 1.16 (s, 3H), 1.12 (s, 3H).

$^{13}$C NMR (CDCl$_3$): δ 170.3, 168.1, 162.6, 154.9, 150.7, 137.9, 132.8, 131.3, 130.4, 123.9, 121.8, 121.0, 115.4, 73.5, 69.6, 54.5, 53.2, 50.5, 37.6, 36.6, 36.3, 29.0, 23.7, 21.6, 21.5.

Example 198

Synthesis of N-(2-Fluorobenzenesulfonyl)-L-(5,5-dimethyl)thiaprolyl-L4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.92-7.87 (m, 1H), 7.67-7.59 (m, 1H), 7.33-7.24 (m, 2H), 7.21 (d, 2H), 7.03 (d, 2H), 6.93 (d, 1H), 5.03 (Sept, 1H), 4.83 (q, 1H), 4.67 (d, 1H), 4.63 (d, 1H), 4.03 (s, 1H), 3.16-3.03 (m, 2H), 3.09 (s, 3H), 3.00 (s, 3H), 1.31 (s, 3H), 1.24 (d, 3H), 1.22 (d, 3H), 1.19 (s, 3H).

$^{13}$C NMR (CDCl$_3$): δ 170.3, 168.1, 159.2, 154.9, 150.7, 136.0, 132.9, 132.0, 130.3, 124.6, 121.8, 117.6, 73.3, 69.6, 54.8, 53.2, 50.3, 37.6, 36.6, 36.3, 29.1, 23.9, 21.6, 21.5.

Example 199

Synthesis of N-(3,4-Difluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.77-7.71 (m, 1H), 7.70-7.65 (m, 1H), 7.40-7.31 (m, 1H), 7.20 (d, 2H), 7.02 (d, 2H), 6.87 (d, 1H), 5.05 (Sept, 1H), 4.88-4.82 (m, 1H), 4.55 (d, 1H), 4.44 (d, 1H), 3.91 (s, 1H), 3.17-3.03 (m, 2H), 3.09 (s, 3H), 3.00 (s, 3H), 1.25 (d, 3H), 1.23 (d, 3H), 1.23 (s, 3H), 1.18 (s, 3H).

$^{13}$C NMR (CDCl$_3$): δ 170.4, 167.9, 154.9, 150.7, 133.1, 132.7, 130.4, 124.4, 121.8, 118.5, 118.0, 73.6, 69.7, 54.6, 53.1, 50.5, 37.6, 36.6, 36.3, 29.2, 23.7, 21.6, 21.5.

Example 200

Synthesis of N-(3,5-Difluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation-of Example 2 by substitution of the-appropriate starting-material.

NMR data was as follows:

$^1$H NMR (CDCl$_3$): δ 7.77-7.71 (m, 1H), 7.70-7.65 (m, 1H), 7.40-7.31 (m, 1H), 7.20 (d, 2H), 7.02 (d, 2H), 6.87 (d, 1H), 5.05 (Sept, 1H), 4.88-4.82 (m, 1H), 4.55 (d, 1H), 4.44 (d, 1H), 3.91 (s, 1H), 3.17-3.03 (m, 2H), 3.09 (s, 3H), 3.00 (s, 3H), 1.25 (d, 3H), 1.23 (d, 3H), 1.23 (s, 3H), 1.18 (s, 3H).

$^{13}$C NMR (CDCl$_3$): δ 170.4, 167.9, 154.9, 150.7, 133.1, 132.7, 130.4, 124.4, 121.8, 118.5, 118.0, 73.6, 69.7, 54.6, 53.1, 50.5, 37.6, 36.6, 36.3, 29.2, 23.7, 21.6, 21.5.

Example 201

Synthesis of N-(2,4-Difluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.94-7.86 (m, 1H), 7.20 (d, 2H), 7.03 (d, 2H), 7.02-6.95 (m, 2H), 6.88 (d, 1H), 5.03 (Sept, 1H), 4.82 (q, 1H), 4.67 (d, 1H), 4.61 (d, 1H), 4.01 (s, 1H), 3.16-3.03 (m, 2H), 3.09 (s, 3H), 3.00 (s, 3H), 1.36 (s, 3H), 1.23 (d, 3H), 1.21 (d, 3H), 1.20 (s, 3H).

$^{13}$C NMR (CDCl$_3$): δ 170.3, 167.9, 154.9, 150.7, 133.7, 132.8, 130.3, 121.8, 112.1, 106.1, 73.4, 69.6, 54.9, 53.2, 50.4, 37.6, 36.6, 36.3, 29.1, 23.9, 21.6, 21.5.

Example 202

Synthesis of N-(4-Chlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.82 (d, 2H), 7.53 (d, 2H), 7.21 (d, 2H), 7.02 (d, 2H), 6.93 (d, 1H), 5.05 (Sept, 1H), 4.89-4.82 (m, 1H), 4.55 (d, 1H), 4.41 (d, 1H), 3.87 (s, 1H), 3.17-3.03 (m, 2H), 3.09 (s, 3H), 3.00 (s, 3H), 1.25 (d, 3H), 1.23 (d, 3H), 1.16 (s, 6H).

$^{13}$C NMR (CDCl$_3$): δ 170.3, 168.1, 154.9, 150.7, 140.4, 134.5, 132.8, 130.4, 129.7, 129.5, 121.8, 73.5, 69.6, 54.6, 53.1, 50.5, 37.6, 36.6, 36.3, 29.1, 23.8, 21.6, 21.0.

Example 203

Synthesis of N-(3-Chlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.88 (t, 1H), 7.78-7.75 (m, 1H), 7.64-7.61 (m, 1H), 7.51 (t, 1H), 7.21 (d, 2H), 7.02 (d, 2H), 6.92 (d, 1H), 5.05 (sept, 1H), 4.89-4.82 (m, 1H), 4.58 (d, 1H), 4.40 (d, 1H), 3.88 (s, 1H), 3.18-3.03 (m, 2H), 3.09 (s, 3H), 3.00 (s, 3H), 1.25 (d, 3H), 1.23 (d, 3H), 1.16 (s, 3H), 1.14 (s, 3H).

$^{13}$C NMR (CDCl$_3$): δ 170.3, 168.0, 154.9, 150.7, 137.7, 135.7, 133.9, 132.8, 130.7, 130.3, 127.9, 126.2, 121.8, 73.6, 69.96, 54.5, 53.2, 50.5, 37.6, 36.6, 36.3, 29.1, 23.7, 21.6, 21.5.

Example 204

Synthesis of N-(2-Chlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 8.08 (dd, 1H), 7.54-7.52 (m, 2H), 7.45-7.39 (m, 1H), 7.19 (d, 2H), 7.02 (d, 2H), 6.79 (d, 1H), 5.00 (sept, 1H), 4.78 (d, 1H), 4.75-4.68 (m, 1H), 4.69 (d, 1H), 4.19 (s, 1H), 3.09 (s, 3H), 3.06 (d, 2H), 3.00 (s, 3H), 1.38 (s, 3H), 1.23 (s, 3H), 1.23 (d, 3H), 1.19 (d, 3H).

$^{13}$C NMR (CDCl$_3$): δ 170.3, 168.1, 154.9, 150.7, 135.6, 134.4, 132.8, 132.7, 132.4, 130.3, 127.3, 121.8, 73.3, 69.5, 54.7, 53.3, 50.4, 37.6, 36.6, 36.3, 29.6, 23.7, 21.6, 21.5.

Example 205

Synthesis of N-(3,4-Dichlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR(CDCl$_3$): δ 7.97 (d, 1H), 7.70 (dd, 1H), 7.63 (d, 1H), 7.20 (d, 2H), 7.02 (d, 2H), 6.86 (d, 1H), 5.05 (sept, 1H), 4.89-4.82 (m, 1H), 4.55 (d, 1H), 4.43 (d, 1H), 3.92 (s, 1H), 3.17-3.03 (m, 2H), 3.09 (s, 3H), 3.00 (s, 3H), 1.26 (d, 3H), 1.22 (d, 3H), 1.23 (s, 3H), 1.18 (s, 3H).

$^{13}$C NMR (CDCl$_3$): δ 170.3, 167.9, 154.9, 150.7, 138.7, 136.1, 134.2, 132.7, 131.4, 130.3, 129.8, 127.1, 121.8, 73.6, 69.7, 54.6, 53.1, 50.5, 37.5, 36.6, 36.3, 29.2, 23.7, 21.6, 21.5.

Example 206

Synthesis of N-(3,5-Dichlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.76 (d, 2H), 7.62 (t, 1H), 7.20 (d, 2H), 7.03 (d, 2H), 6.85 (d, 1H), 5.05 (sept, 1H), 4.89-4.82 (m, 1H), 4.57 (d, 1H), 4.42 (d, 1H), 3.92 (s, 1H), 3.18-3.04 (m, 2H), 3.09 (s, 3H), 3.00 (s, 3H), 1.25 (d, 3H), 1.23 (d, 3H), 1.27 (s, 3H), 1.18 (s, 3H).

$^{13}$C NMR (CDCl$_3$): δ 170.3, 167.8, 154.9, 150.7, 139.1, 136.5, 133.7, 132.7, 130.3, 126.2, 121.8, 73.7, 69.7, 54.6, 53.1, 50.5, 37.5, 36.6, 36.3, 29.2, 23.7, 21.6, 21.5.

Example 207

Synthesis of N-(3-Chlorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.

NMR data was as follows:

$^1$H NMR (CDCl$_3$): δ 7.85 (m, 1H), 7.76 (m, 1H), 7.63 (m, 1H), 7.53 (m, 1H), 7.06 (d, 2H), 6.96 (d, 2H), 6.37 (m, 1H), 5.01 (m, 1H), 4.62 (m, 1H), 4.01 (m, 2H), 3.26 (m, 1H), 3.06 (s, 3H), 2.96 (m, 7H), 1.49 (s, 9H).

$^{13}$C NMR (CDCl$_3$): δ 170.0, 164.5, 154.9, 150.6, 140.0, 136.1, 134.2, 132.5, 131.3, 130.2, 127.4, 125.5, 122.2, 82.8, 56.0, 53.3, 49.9, 49.2, 41.7, 36.5, 36.3, 36.0, 27.8.

Example 208

Synthesis of N-(3,4-Dichlorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.

NMR data was as follows:

$^1$H NMR (CDCl$_3$): δ 7.91 (m, 1H), 7.66 (m, 2H), 7.06 (d, 2H), 6.94 (d, 2H), 6.33 (m, 1H), 4.98 (m, 1H), 4.60 (m, 1H), 3.49 (m, 3H), 3.12 (m, 2H), 3.04 (s, 3H), 3.00 (m, 2H), 2.94 (s, 3H), 1.44 (s, 9H).

$^{13}$C NMR (CDCl$_3$): δ 170.0, 164.3, 154.8, 150.6, 138.8, 137.9, 134.3, 132.4 132.0, 130.3, 129.2, 126.4, 122.1, 83.0, 55.5, 53.1, 50.2, 49.5, 41.8, 36.5, 36.2, 36.0, 27.7.

Example 209

Synthesis of N-(4-Methoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:

$^1$H NMR (CDCl$_3$): δ 7.81 (d, 2H), 7.22 (d, 2H), 7.06-6.99 (m, 5H), 5.04 (sept, 1H), 4.89-4.82 (m, 1H), 4.56(d, 1H), 4.39 (d), 3.88 (s, 3H), 3.83 (s, 1H), 3.17-3.03 (m, 2H), 3.09 (s, 3H), 3.00 (s, 3H), 1.25 (d, 3H), 1.22 (d, 3H), 1.15 (s, 3H), 1.12 (s, 3H).

$^{13}$C NMR (CDCl$_3$): δ 170.3, 168.5, 163.8, 154.9, 150.7, 132.9, 130.4, 130.3, 127.4, 121.7, 114.5, 73.5, 69.5, 55.6, 54.6, 53.2, 50.5, 37.7, 36.6, 36.3, 29.1, 23.9, 21.6, 21.5.

Example 210

Synthesis of N-(3-Methoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:

$^1$H NMR (CDCl$_3$): δ 7.47-7.45 (m, 2H), 7.37-7.36 (m, 1H), 7.21 (d, 2H), 7.19-7.15 (m, 1H), 7.04-6.98 (m, 3H), 5.04 (sept, 1H), 4.88-4.82 (m, 1H), 4.58 (d, 1H), 4.40 (d, 1H), 3.89 (s, 1H), 3.87 (s, 3H), 3.17-3.03 (m, 2H), 3.09 (s, 3H), 3.00 (s, 3H), 1.25 (d, 3H), 1.23 (d, 3H), 1.15 (s, 3H), 1.08 (s, 3H).

$^{13}$C NMR (CDCl$_3$): δ 170.3, 168.3, 160.2, 154.9, 150.7, 136.9, 132.9, 130.5, 130.4, 121.7, 120.2, 120.0, 112.6, 73.4, 69.6, 55.7, 54.5, 53.2, 50.4, 37.7, 36.6, 36.3, 29.1, 23.7, 21.6, 21.5.

Example 211

Synthesis of N-(2-Methoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.
NMR data was as follows:
$^1$H NMR (CDCl$_3$): δ 7.92 (dd, 1H), 7.54 (dd, 1H), 7.21 (d, 2H), 7.07-7.00 (m, 4H), 6.96 (d, 1H), 5.01 (sept, 1H), 4.83-4.76 (m, 1H), 4.73 (d, 1H), 4.61 (d, 1H), 4.17 (s, 1H), 3.93 (s, 3H), 3.14-3.03 (m, 2H), 3.09 (s, 3H), 3.00 (s, 3H), 1.36 (s, 3H), 1.22 (d, 3H), 1.21 (s, 3H), 1.19 (d, 3H).
$^{13}$C NMR (CDCl$_3$): δ 170.3, 168.7, 157.7, 154.9, 150.6, 135.4, 133.0, 132.5, 130.3, 125.2, 121.7, 120.5, 112.6, 73.3, 69.5, 56.0, 54.8, 53.3, 50.4, 37.7, 36.6, 36.3, 29.2, 24.1, 21.6, 21.5.

Example 212

Synthesis of N-(3,4-Dimethoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.
NMR data was as follows:
$^1$H NMR (CDCl$_3$): δ 7.50 (dd, 1H), 7.31 (d, 1H), 7.21 (d, 2H), 7.05-7.01 (m, 3H), 6.97 (d, 1H), 5.04 (sept, 1H), 4.89-4.82 (m, 1H), 4.56 (d, 1H), 4.40 (d, 1H), 3.95 (s, 3H), 3.94 (s, 3H), 3.89 (s, 1H), 3.17-3.03 (m, 2H), 3.09 (s, 3H), 3.00 (s, 3H), 1.25 (d, 3H), 1.22 (d, 3H), 1.16 (s, 3H), 1.14 (s, 3H).
$^{13}$C NMR (CDCl$_3$): δ 170.3, 168.5, 154.9, 153.5, 150.7, 149.4, 132.9, 130.4, 127.6, 122.3, 121.7, 110.6, 110.3, 73.5, 69.6, 56.3, 56.1, 54.6, 53.2, 50.5, 37.7, 36.6, 36.3, 29.2, 23.8, 21.6, 21.5.

Example 213

Synthesis of N-(2,4-Difluorobenzenesulfonyl)-L-(thiamorpholin-3-carbonyl)-L-4-(N,N-dimethylcarbamyloxy)phenylalanine Isopropyl Ester The title compound was prepared following the procedure described for the preparation of Example 49 by substitution of the appropriate starting material.
NMR data was as follows:
$^1$H NMR (CDCl$_3$): δ 7.89 (m, 1H), 7.16 (m, 2H), 6.97 (m, 4H), 6.77 (d, 1H), 4.72 (m, 1H), 4.60 (m, 1H), 3.92 (m, 1H), 3.29 (m, 1H), 3.09 (m, 5H), 2.93 (s, 3H), 2.70 (m, 2H), 2.55 (m, 1H), 2.10 (m, 1H), 1.42 (s, 9H).
$^{13}$C NMR (CDCl$_3$): δ 170.0, 168.0, 167.7, 137.1, 164.4, 164.3, 161.1, 160.9, 157.7, 157.5, 154.8, 150.5, 132.7, 132.6, 132.4, 130.4, 124.0, 123.8, 121.7, 112.2, 111.9, 106.5, 106.1, 105.8, 82.6, 55.4, 53.9, 43.5, 36.4, 36.2, 27.7, 26.8, 25.5.

Example 214

Synthesis of N-(3,4-Dichlorobenzenesulfonyl)-L-(1,1-dioxothiamorpholin-3-carbonyl)-L-4-(N,N-dimethylcarbamyloxy)phenylalanine The title compound was prepared from the product of Example 208 using the procedure described in Method 11.
NMR data was as follows:
$^1$H NMR (CD$_3$OD): δ 8.04 (m, 1H), 7.68 (m, 2H), 7.52 (m, 1H), 7.21 (d, 2H), 7.02 (d, 2H), 5.22 (m, 1H), 4.63 (m, 1H), 4.22 (m, 1H), 3.71 (m, 1H), 3.57 (m, 1H), 3.30 (m, 3H), 3.08 (s, 3H), 3.02 (m, 3H), 2.97 (s, 3H).
$^{13}$C NMR (CD$_3$OD): δ 174.0, 168.0, 156.9, 152.1, 140.7, 139.3, 135.2, 133.2, 131.6, 130.7, 128.3, 123.2, 57.2, 54.9, 54.6, 51.7, 51.4, 43.3, 37.3, 36.9, 36.7.

Example 215

Synthesis of N-(3-Chlorobenzenesulfonyl)-L-(1,1-dioxothiamorpholin-3-carbonyl)-L-4-(N,N-dimethylcarbamyloxy)phenylalanine The title compound was prepared from the product of Example 207 using the procedure described in Method 11.
NMR data was as follows:
$^1$H NMR (CD$_3$OD): δ 7.94 (m, 1H), 7.77 (m, 2H), 7.58 (m, 1H), 7.46 (d, 1H), 7.19 (d, 2H), 7.07 (d, 2H), 5.23 (m, 1H), 4.63 (m, 1H), 4.20 (m, 1H), 3.71 (m, 1H), 3.43 (m, 1H), 3.26 (m, 4H), 3.17 (s, 3H), 2.95 (m, 5H).
$^{13}$C NMR (CD$_3$OD): δ 168.0, 152.1, 142.5, 136.8, 135.0, 132.7, 131.6, 128.6, 127.1, 123.3, 57.2, 54.9, 51.4, 51.2, 43.2, 37.2, 36.8, 36.7.

Example 216

Synthesis of N-(3-Chloro-4-fluorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.
NMR data was as follows:
$^1$H NMR (CD$_3$OD): δ 7.93 (d), 7.90 (m), 7.29 (s), 7.27 (d), 7.04 (d), 4.60 (m), 4.46 (d), 3.90-3.40 (m), 3.10 (s), 2.98 (s), 1.43 (s).
$^{13}$C NMR (CD$_3$OD): δ 171.5, 166.5, 156.9, 151.9, 135.2, 131.3, 129.9, 127.9, 127.8, 123.1, 117.8, 117.5, 101.4, 83.7, 57.9, 56.0, 42.9, 37.3, 36.9, 36.7, 28.1.

Example 217

Synthesis of N-(1-Methylpyrazole-4-sulfonyl)-L-(thiamorpholin-3-carbonyl)-L-4-(N,N-dimethylcarbamyloxy)phenylalanine tert-Butyl Ester The title compound was prepared following the procedures described for the preparation of Examples 49 and 117.
NMR data was as follows:
$^1$H NMR (CDCl$_3$): δ 7.77 (s), 7.63 (s), 7.08 (d), 6.93 (d), 6.76 (d), 6.71 (d), 5.50 (d), 5.22 (s), 4.82 (t), 4.61 (q), 3.83 (s), 3.25 (dt), 3.04 (m), 2.90 (s), 2.05 (dd), 1.34 (s).
$^{13}$C NMR (CDCl$_3$): δ 169.3, 166.8, 154.7, 150.4, 138.4, 132.4, 132.2, 130.2, 121.4, 118.3, 105.4, 82.5, 55.2, 53.6, 53.3, 39.5, 38.3, 36.6, 36.3, 36.1, 27.6, 23.5.

Example 218

Synthesis of N-(3,4-Difluorobenzenesulfonyl)-L-(thiamorpholin-3-carbonyl)-L-4-(N,N-dimethylcarbamyloxy)phenylalanine tert-Butyl Ester The title compound was prepared following the procedure described for the preparation of Example 49 by substitution of the appropriate starting materials.

NMR data was as follows:

$^1$H NMR (CD$_3$OD): δ 7.88 (m, 1H), 7.70 (m, 1H), 7.57 (m, 1H), 7.23 (d, 2H), 7.03 (d, 2H), 6.83 (d, 1H), 5.63 (dd, 1H), 5.07 (t, 1H), 4.58 (m, 1H), 3.22-3.00 (m, 3H), 3.09 (s, 3H), 2.98 (s, 3H), 2.07 (dd, 1H), 1.44 (s, 9H).

$^{13}$C NMR (CD$_3$OD): δ 171.3, 169.3, 156.9, 152.0, 135.0, 131.6, 126.5, 122.9, 120.2, 119.9, 119.4, 118.7, 118.4, 106.4, 83.6, 56.5, 55.6, 37.1, 36.8, 36.6, 28.1, 25.2.

Example 219

Synthesis of N-(Toluene-4-sulfonyl)-L-(5,5-dimethyl)thioprolyl-L-(thiomorpholin-4-ylcarbonyloxy)phenylalanine Isopropyl Ester The title compound was prepared using the procedure described in Example 82 by substitution of the appropriate starting materials.

NMR data was as follows:

$^1$H NMR (CDCl$_3$): δ 9.09 (s, 1H), 8.88 (m, 1H), 8.16 (m, 1H), 7.50 (m, 1H), 7.22 (d, 2H), 7.01 (d, 2H), 6.91 (d, 1H), 5.05 (m, 1H), 4.85 (m, 1H), 4.60 (d, 1H), 4.46 (d, 1H), 3.89 (s, 1H), 3.93-3.83 (m, 4H), 3.11 (m, 2H), 2.69 (m, 4H), 1.29-1.16 (m, 12H).

$^{13}$C NMR(CDCl$_3$): δ 170.3, 167.8, 154.3, 153.5, 150.4, 148.7, 135.8, 133.1, 132.9, 130.4, 124.0, 121.8, 73.7, 69.7, 54.7, 53.2, 50.5, 47.1, 46.4, 37.6, 29.1, 27.4, 27.0, 23.8, 21.6, 21.5.

Example 220

Synthesis of N-(3,4-Difluorobenzenesulfonyl)-L-(thiamorpholin-3-carbonyl)-L-4-(N,N-dimethylcarbamyloxy)phenylalanine The title compound was prepared from the product of Example 218 using the procedure described in Method 11.

NMR data was as follows:

$^1$H NMR (CDCl$_3$): δ 7.89 (s, 1H), 7.57-7.46 (m, 2H), 7.35 (d, 1H), 7.32-7.22 (m, 1H), 7.09 (d, 2H), 6.91 (d, 2H), 6.64 (d, 1H), 5.50 (d, 1H), 4.89 (s, 1H), 4.88-4.79 (m, 1H), 3.17-3.02 (m, 3H), 3.02 (s, 3H), 2.93 (s, 3H), 1.75 (dd, 1H).

$^{13}$C NMR (CDCl$_3$): δ 173.6, 167.7, 155.5, 152.0, 151.8, 150.1, 148.4, 132.8, 130.4, 124.6, 121.5, 118.7, 118.5, 117.5, 117.3, 117.1, 106.9, 54.9, 53.0, 36.4, 36.2, 36.0, 23.4.

Example 221

Synthesis of N-(2,5-Dichlorothiophene-3-sulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:

$^1$H NMR (CDCl$_3$): δ 7.18 (d, 2H), 7.11 (s, 1H), 7.00 (d, 2H), 6.87 (d, 1H), 5.03-4.99 (m, 1H), 4.84-4.81 (m, 1H), 4.65-4.56 (m, 2H), 4.07 (s, 1H), 3.10-3.01 (m, 5H), 2.98 (s, 3H), 1.37 (s, 3H), 1.22 (s, 3H), 1.21 (s, 3H), 1.18 (s, 3H).

$^{13}$C NMR (CDCl$_3$): δ 170.3, 167.7, 154.9, 150.7, 132.9, 132.8, 131.9, 130.3, 128.0, 127.0, 121.8, 73.4, 69.6, 54.8, 53.2, 50.5, 37.5, 36.6, 36.3, 29.1, 23.8, 21.6, 21.5.

Example 222

Synthesis of N-(1-Methylpyrazole-4-sulfonyl)-L-(5,5-dimethyl)thiaprolyl-L-4-(thiomorpholin-4-ylcarbonyloxy)phenylalanine Isopropyl Ester The title compound was prepared using the procedure described in Example 82 by substitution of the appropriate starting materials.

NMR data was as follows:

$^1$H NMR (CDCl$_3$): δ 7.89 (s, 1H), 7.80 (s, 1H), 7.21 (d, 2H), 7.01 (m, 3H), 5.03 (m, 1H), 4.83 (m, 1H), 4.54 (d, 1H), 4.40 (d, 1H), 3.95 (s, 3H), 3.86 (m, 4H), 3.80 (s, 1H), 3.09 (m, 2H), 2.68 (m, 4H), 1.28 (s, 3H), 1.22 (m, 6H), 1.16 (s, 3H).

$^{13}$C NMR (CDCl$_3$): δ 170.4, 168.3, 153.5, 150.4, 139.3, 133.3, 132.9, 130.4, 121.7, 117.6, 73.8, 69.7, 54.8, 53.2, 50.5, 47.1, 46.4 39.6, 37.6, 29.0, 27.4, 27.1, 24.6, 21.6, 21.5.

Example 223

Synthesis of N-(8-Quinolinesulfonyl)-L-prolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:

$^1$H NMR (CDCl$_3$): δ 9.01-8.99 (m, 1H), 8.56-8.53 (m, 1H), 8.27-8.23 (m, 1H), 8.07-8.04 (m, 1H), 7.66-7.61 (m, 2H), 7.55-7.51 (m, 1H), 7.17 (d, 2H), 7.01 (d, 2H), 5.27-5.23 (m, 1H), 5.07-4.98 (m, 1H), 4.84-4.76 (m, 1H), 3.34-3.20 (m, 3H), 3.06-2.98 (m, 4H), 2.97 (s, 3H), 2.15-2.09 (m, 1H), 1.64-1.51 (m, 3H), 1.23 (d, 6H).

$^{13}$CNMR(CDCl$_3$): δ 172.0, 170.5, 154.9, 151.5, 150.6, 143.9, 136.8, 135.6, 134.9, 134.1, 133.3, 130.2, 129.2, 125.6, 122.3, 121.7, 69.3, 62.8, 53.5, 48.7, 37.3, 36.5, 36.3, 29.7, 24.3, 21.6, 21.6.

Example 224

Synthesis of N-(8-Quinolinesulfonyl)-L-prolyl-L-4-(N,N-dimethylcarbamyloxy)phenylalanine The title compound was prepared from the product of Example 223 using the procedure described in Method 7.

NMR data was as follows:

$^1$H NMR (CD$_3$OD): δ 9.03-9.01 (m, 1H), 8.49-8.42 (m, 2H), 8.23-8.20 (m, 1H), 8.09-8.07 (m, 1H), 7.73-7.61 (m, 2H), 7.25 (d, 2H), 7.00 (d, 2H), 5.30-5.27 (m, 1H), 4.73-4.69 (m, 1H), 3.38-3.21 (m, 3H), 3.09-3.02 (m, 4H), 2.95 (s, 3H), 1.86 (m, 1H), 1.78-1.73 (m, 1H), 1.58-1.50 (m, 2H).

$^{13}$C NMR (CD$_3$OD): δ 175.3, 174.2, 164.7, 156.9, 152.9, 145.2, 138.5, 136.9, 135.8, 135.6, 131.6, 130.9, 126.9, 123.8, 122.9, 63.9, 54.7, 50.0, 37.5, 36.8, 36.7, 31.6, 25.5.

Example 225

Synthesis of N-(8-Quinolinesulfonyl)-L-(5,5-dimethyl)thiaprolyl-L-4-(N,N-dimethylcarbamyloxy)phenylalanine Isoproplyl Ester The title compound was prepared following the procedure described for the preparation of Example 2 by substitution of the appropriate starting materials.

NMR data was as follows:

$^1$H NMR (CDCl$_3$): δ 9.05-9.03 (m, 1H), 8.53-8.49 (m, 1H), 8.26-8.22 (m, 1H), 8.08-8.05 (m, 1H), 7.65-7.60 (m, 1H), 7.56-7.52 (m, 1H), 7.19 (d, 2H), 7.06 (d, 1H), 7.00 (d, 2H), 5.17 (d, 1H), 4.94 (m, 1H), 7.74-4.78 (m, 2H), 4.66 (s, 1H), 3.08-2.99 (m, 8H), 1.20-1.16 (m, 12H).

$^{13}$C NMR (CDCl$_3$): δ 170.2, 168.9, 154.9, 151.5, 150.6, 144.2, 136.7, 134.4, 134.4, 133.1, 130.3, 129.2, 125.5, 122.3, 121.7, 73.2, 69.3, 54.8, 53.3, 50.6, 37.6, 36.6, 36.3, 29.2, 24.1, 21.5, 21.4.

Example 226

Synthesis of N-(8-Quinolinesulfonyl)-L-(5,5-dimethyl)thiaprolyl-L4-(N,N-dimethylcarbamyloxy)phenylalanine The title compound was prepared from the product of Example 225 using the procedure described in Method 7.

NMR data was as follows:

$^1$H NMR (CD$_3$OD): δ 9.06-9.04 (m, 1H), 8.45-8.39 (m, 2H), 8.23-8.14 (m, 1H), 7.72-7.61 (m, 2H), 7.32 (d, 2H), 7.03 (d, 2H), 5.12 (d, 1H), 4.87 (d, 1H), 4.69-4.64 (m, 2H), 3.28-3.02 (m, 5H), 2.98 (s, 2H), 1.18 (s, 3H), 1.08 (s, 3H).

$^{13}$C NMR (CD$_3$OD): δ 174.1, 171.8, 157.1, 152.9, 152.0, 145.5, 138.4, 137.3, 135.8, 135.6, 135.1, 131.8, 130.9, 126.8, 123.8, 122.9, 73.7, 55.9, 54.8, 51.7, 37.6, 36.8, 36.7, 30.2, 25.0.

Example 227

Synthesis of N-(3-Sulfonamido-4-chloro-benzenesulfonyl)-L-prolyl-L-4-(N,N-dimethylcarbamyloxy)phenylalanine Isopropyl Ester The title compound was prepared following the procedure described for the preparation of Example 2 and substitution of appropriate starting materials.

NMR data was as follows:

$^1$H NMR (CDCl$_3$): δ 8.45 (d, 1H), 7.91 (d, 1H), 7.67 (d, 1H), 7.13 (d, 2H), 7.06 (d, 1H), 7.01 (d, 2H), 5.90 (brs, 2H), 5.06-5.02 (m, 1H), 4.79-4.72 (m, 1H), 4.14-4.10 (m, 1H), 3.42-3.39 (m, 1H), 3.25-3.14 (m, 2H), 3.07 (s, 3H), 3.04-2.97 (m, 1H), 2.96 (s, 3H), 1.98-1.96 (m, 1H), 1.72-1.62 (m, 3H), 1.28-1.25 (m, 6H).

$^{13}$C NMR (CDCl$_3$): δ 170.8, 170.7, 155.1, 150.6, 141.4, 136.9, 136.1, 132.9, 132.8, 131.9, 130.3, 128.7, 121.9, 69.8, 62.1, 53.3, 49.6, 36.9, 36.6, 36.4, 30.4, 24.3, 21.6, 21.6.

Example 228

Synthesis of N-(Toluene-4-sulfonyl)-L-(1-oxothiomorpholin-3-carbonyl)-L-4-(N,N-dimethylcarbamyloxy)phenylalanine Isopropyl Ester The title compound was prepared following the procedure described for the preparation of Example 182 and substitution of appropriate starting materials.

NMR data was as follows:

$^1$H NMR (CDCl$_3$): δ 7.77 (d, 2H), 7.72 (d, 2H), 7.33 (m, 2H), 7.20 (m, 2H), 7.12 (d, 2H), 7.01 (m, 2H), 5.10 (m, 1H), 5.01 (m, 1H), 4.84 (m, 1H), 4.75 (m, 1H), 3.80 (m, 3H), 3.05 (m, 4H), 2.96 (m, 3H), 2.74 (m, 1H), 2.42 (m, 4H), 1.30-1.20 (m, 6H).

$^{13}$C NMR (CDCl$_3$): δ 170.6, 170.4, 166.8, 166.7, 154.9, 150.7, 150.6, 145.1, 144.8, 135.8, 135.5, 132.7, 130.6, 130.4, 130.3, 130.0, 127.7, 127.1, 122.4, 121.8, 69.8, 69.4, 55.8, 53.7, 52.9, 50.8, 48.2, 47.9, 42.0, 41.2, 38.4, 36.6, 36.5, 36.3, 31.2, 21.5, 21.5.

Example 229

Synthesis of N-(2,4-Difluorobenzenesulfonyl)-L-(1-oxothiomorpholin-3-carbonyl)-L-4-(N,N-dimethylcarbamyloxy)phenylalanine tert-Butyl Ester The title compound was prepared following the procedure described for the preparation of Example 182 and substitution of appropriate starting materials.

NMR data was as follows:

$^1$H NMR (CDCl$_3$): δ 7.91 (m, 1H), 7.30 (m, 2H), 6.97 (m, 4H), 4.71 (m, 1H), 4.55 (m, 1H), 3.90 (m, 2H), 3.77 (m, 1H), 3.11 (m, 4H), 2.85 (m, 3H), 2.80 (m, 1H), 2.60 (m, 2H), 1.46 (s, 9H), 1.39 (s, 9H).

$^{13}$C NMR (CDCl$_3$): δ 170.0, 168.0, 167.9, 166.4, 166.2, 164.6, 164.4, 162.7, 161.4, 161.2, 157.9, 157.8, 154.8, 150.6, 150.4, 132.8, 132.5, 132.4, 130.9, 130.4, 130.1, 123.3, 123.1, 122.2, 121.6, 121.1, 122.6, 122.2, 111.9, 106.6, 106.3, 105.9, 82.8, 82.3, 55.8, 54.1, 53.2, 51.6, 49.2, 48.7, 43.1, 42.3, 38.7, 36.5, 36.2, 31.8, 27.7.

Example 230

Synthesis of N-(1-Methylpyrazole-4-sulfonyl)-L-(5,5-dimethyl)thiaprolyl-L-4-(N,N-dimethylcarbamyloxy)phenylalanine 2,2-Dimethylpropyl Ester The product from Example 161 (1 g., 0.72 mmol) was dissolved in neopentyl alcohol (5 mL). Titanium (IV) isopropoxide (260 mg., 0.9 mmol) was added and the mixture heated at 100° C. under an inert atmosphere for 48 h. Excess neopentyl alcohol was removed under reduced pressure and the residue purified by flash column chromatography (silica, 1% MeOH in CHCl$_3$) to give the title compound as a white solid (1.02 g, 97%).

Physical data was as follows:

MS (+) ESI [M+H]$^+$610; [M+NH4]$^+$627 (100%).

Anal. Calcd. For C$_{29}$H$_{39}$N$_5$O$_7$S: C, 53.18; H, 6.45; N, 11.49. Found: C, 53.46; H, 6.38; N, 11.06.

Example 231

Synthesis of N-(Pyridine-3-sulfonyl)-L-(5,5-dimethyl)thiaprolyl-L-4-(N,N-dimethylcarbamyloxy)phenylalanine 2,2-Dimethylpropyl Ester The product from Example 173 was subjected to the transesterification procedure described for the preparation of Example 230. The compound was purfied by flash column chromatography (silica, 1% MeOH in CHCl$_3$) followed by recrystallization from ethyl acetate to give the title compound as a white solid (720 mg, 47%).

Physical data was as follows:

Anal. Calcd. For C$_{28}$H$_{38}$N$_4$O$_7$S$_2$: C, 55.43; H, 6.31; N, 9.23. Found: C, 55.37; H, 6.32; N, 9.22.

Example 232

Synthesis of N-(1-Methylpyrazole-4-sulfonyl)-L-(5,5-dimethyl)thiaprolyl-L-4-(N,N-dimethylcarbamyloxy)phenylalanine Cyclopropylmethyl Ester The product from Example 161 was subjected to the transesterification procedure described for the preparation of Example 230. The title compound was obtained as a white solid following flash column chromatography (silica, 1% MeOH in CHCl$_3$) (860 mg, 70%).

Physical data was as follows:

Anal. Calcd. For C$_{26}$H$_{35}$N$_5$O$_7$S$_2$: C, 52.6; H, 5.94; N, 11.8. Found: C, 52.49; H, 5.93; N, 11.62.

Example 233

Synthesis of N-(1-Methylpyrazole-4-sulfonyl)-L-(5,5-dimethyl)thiaprolyl-L-4-(N,N-dimethylcarbamyloxy)phenylalanine Methyl Ester The title compound was prepared following the procedure described for the preparation of Example 161 and substitution of appropriate starting materials.

Physical data was as follows:

MS (+) ESI [M+H]$^+$554; [M+NH$_4$]$^+$571 (100%).

Anal. Calcd. For C$_{23}$H$_{31}$N$_5$O$_7$S$_2$.0.2 EtOAc: C, 50.04; H, 5.75; N, 12.26. Found: C, 50.12; H, 5.69; N, 12.19.

Example 234

Synthesis of N-(Pyridine-3-sulfonyl)-L-(5,5-dimethyl)thiaprolyl-L-4-(N,N-dimethylcarbamyloxy) phenylalanine Ethyl Ester The product from Example 173 was subjected to the trans-esterification procedure described for the preparation of Example 230. The compound was purified by flash column chromatography (silica, 2% MeOH in CHCl$_3$), followed by recrystallization from ethyl acetate to give the title compound as a white solid (1.2 g, 61%).
Physical data was as follows:
Anal. Calcd. For $C_{25}H_{32}N_4O_7S_2$: C, 53.18; H, 5.71; N, 9.92. Found: C, 53.14; H, 5.72; N, 9.57.

Example 235

Synthesis of N-(Pyridine-3-sulfonyl)-L-(5,5-dimethyl)thiaprolyl-L-4-(N,N-dimethylcarbamyloxy) phenylalanine Cyclopropylmethyl Ester The product from Example 173 was subjected to the trans-esterification procedure described for the preparation of Example 230. The compound was isolated as a white solid following flash column chromatography (silica, 2% MeOH in CHCl$_3$) and recrystallization from EtOAc/hexanes (1 g, 65%).
Physical data was as follows:
Anal. Calcd. For $C_{27}H_{34}N_4O_4S_2$: C, 54.9; H, 5.8; N, 9.48. Found: C, 54.77; H, 5.65; N, 9.46.

Example 236

Synthesis of N-(1-Methylpyrazole-4-sulfonyl)-L-(5,5-dimethyl)thiaprolyl-L-4-(N,N-dimethylcarbamyloxy)phenylalanine 2-Methoxyphenyl Ester To a solution of the compound from Example 139 (1.79 g, 3.31 mmol), 2-methoxy-phenol (0.45 g, 3.64 mmol) and BOP (1.61 g, 3.64 mmol) in methylene chloride (25 mL) at 0° C. was added triethylamine (0.7 mL, 4.97 mmol). The reaction mixture was then slowly warmed to 25° C. where it was stirred, under nitrogen, for 24 h. The reaction was quenched by addition of 100 mL saturated brine and extracted with EtOAc. The organic extract was washed sequentially with 2N HCl (3 times), saturated sodium bicarbonate (3×) and saturated brine (2×), dried over MgSO$_4$, and evaporated to 2.1 g of crude product. Flash chromatography (eluant: 96-4 methylene chloride:EtOAc) afforded 1.85 g of a white solid which upon trituration with hexane gave 1.68 g (79%) of white crystals, mp 72-75° C.
Physical data was as follows:
Anal. Calcd. For $C_{29}H_{35}N_5O_8S_2$: C, 59.94; H, 5.46; N, 10.85.
Found: C, 53.45; H, 5.62; N, 10.31.

Example 237

Synthesis of N-(1-Methylpyrazole-4-sulfonyl)-L-(5,5-dimethyl)thiaprolyl-L-4-(N,N-dimethylcarbamyloxy)phenylalanine n-Butyl Ester A solution of the compound of Example 139 (2 g) in n-butanol (50 mL) was saturated upon ice-cooling with HCl gas. The mixture was stirred at ambient temperature for 36 h, evaporated in vacuo to almost dryness, then partitioned between 5% NaHCO$_3$ and chloroform. The organic layer was dried and evaporated in vacuo to furnish 900 mg of the title compound.
Physical data was as follows:
MS: [(+)ESI], [M+H]$^+$596.

Example 238

Synthesis of N-(1-Methylpyrazole-4-sulfonyl)-L-(5,5-dimethyl)thiaprolyl-L-4-(N,N-dimethylcarbamyloxy)phenylalanine n-Propyl Ester A solution of N-(1-methylpyrazole-4-sulfonyl)-L-(5,5-dimethyl)thiaprolyl-L-4-(N,N-dimethylcarbamyloxy)phenylalanine (2 g) in n-propanol (50 mL) was saturated upon ice-cooling with HCl gas. The mixture was stirred at ambient temperature for 36 hours, evaporated in vacuo to almost dryness, then partioned between 5% NaHCO$_3$ and chloroform. The organic layer was dried and evaporated in vacuo to provide 1500 mg of the title compound.
Physical data was as follows:
MS: [(+)ESI], [M+H]$^+$582.

Example 239

Synthesis of N-(1-Methylpyrazole-4-sulfonyl)-L-(5,5-dimethyl)thiaprolyl-L-4-(N,N-dimethylcarbamyloxy)phenylalanine 2,2-Dimethylpropionyloxymethyl Ester Potassium iodide (324 mg) was added at once to a mixture of the compound of Example 139 (1.08 g), chloromethylpivalate (294 mg) and powdered K$_2$CO$_3$ (222 mg) in DMF (5 mL). The reaction mixture was stirred at ambient temperature overnight, partitioned between water (12 mL) and ethyl acetate (60 mL). The separated organic layer was washed with ice cold 0.1 N sodium thiosulfate, water and brine, then dried over MgSO$_4$, filtered and evaporated in vacuo to yield 750 mg of the title compound.
Physical data was as follows:
MS: [(+)ESI], [M+H]$^+$654.

Example 240

Synthesis of N-(Toluene-4-sulfonyl)-L-prolyl-L-4-(4-phenylpiperazin-1-ylcarbonyloxy)phenylalanine tert-Butyl Ester The title compound was prepared following the procedure outlined for Example 4 by substitution of the appropriate-starting materials. A white solid was obtained, mp. 60-65° C.
Physical data was as follows:
MS (+ESI) 694.3 [M+NH$_4$]$^+$.
Anal. Calcd. for $C_{36}H_{44}N_4O_7S\cdot0.5C_4H_8O_2$: C, 63, 31; H, 6.71; N, 7.77.
Found: C, 63.12; H, 6.58; N, 7.69.

Example 241

Synthesis of N-(Toluene-4-sulfonyl)-L-prolyl-L-4-(4'-(ethoxycarbonyl)piperidin-1-ylcarbonyloxy)phenylalanine tert-Butyl Ester The carbamate was prepared by treatment of Tos-Pro-Tyr-t-butyl ester with 4-nitrophenylchloroformate, followed by addition of ethylisonipecotate (triethylamine, methylene chloride, chilled to 0° C., then stirred at room temperature overnight). The crude product was purified by flash chromatography (silica, 95:5 EtoAc:Et$_3$N) to afford a white solid. (0.78 g, 39%).

NMR data was as follows:

$^1$H NMR (DMSO-d$_6$, 400 MHz): δ 8.15 (d, 1H, J=7.68 Hz); 7.70 (d, 2H, J=8.34 Hz); 7.40 (d, 2H, J=7.90 Hz); 7.22 (d, 2H, J=8.56 Hz); 7.00 (d, 2H, J=8.56 Hz); 4.37 (m, 1H), 4.07 (q, 2H, J=7.14, 14.08 Hz); 4.03 (m, 2H); 3.90 (m, 1H); 3.34 (m, 1H); 3.09 (m, 2H); 3.00 (m, 3H); 2.59 (m, 1H); 2.39 (s, 3H); 1.87 (m, 2H); 1.58 (m, 5H); 1.41 (m, 1H); 1.35 (s, 9H); 1.18 (t, 3H, 7.14 Hz).

IR (KBr, cm$^{-1}$): 3410, 2990, 2950, 1725, 1680, 1510, 1430, 1355, 1220, 1200, 1170, 1000, 675, 595.

MS ((+)ESI, m/z (%)) 689 (100[M+NH$_4$]$^+$); 691 (37[M+NH$_4$]$^+$).

Anal. Calcd. for C$_{34}$H$_{45}$N$_3$O$_9$S: C, 60.79; H, 6.75; N, 6.25. Found: C, 60.59; H, 6.67; N, 6.22.

Example 242

Synthesis of N-(Toluene-4-sulfonyl)-L-prolyl-L-4-(N-(4'-(2'-aminoethyl)morpholino)carbamyloxy) phenylalanine The title compound was prepared from the product of Example 152 using the procedure described in Method 11.

NMR data was as follows:

$^1$H NMR (DMSO-d$_6$, 400 MHz): δ 12.75 (s, 1H); 8.08 (d, 1H); 7.68 (d, 2H); 7.60 (t, 1H); 7.39 (d, 2H); 7.21 (d, 2H); 6.97 (d, 2H); 4.46 (m, 1H); 4.08 (m, 1H); 3.56 (m, 4H); 3.26 (m, 3H); 3.09 (m, 2H); 2.94 (m, 1H); 2.49 (s, 6H); 2.48 (s, 3H); 1.5 (m, 3H); 1.38 (m, 1H).

IR (KBr, cm$^{-1}$) 3400, 2975, 1725, 1650, 1500, 1350, 1150, 650, 575, 550.

MS ((−)ESI, m/z (%)) 587 (100[M−H]$^+$).

Anal. Calcd. for C$_{28}$H$_{36}$N$_4$O$_8$S.HCOOH.0.5H$_2$O: C, 54.11; H, 6.11; N, 8.70. Found: C, 53.96; H, 6.02; N, 8.68.

Example 243

Synthesis of N-(Toluene-4-sulfonyl)-L-prolyl-L-4-[4-(carboxy)piperidin-1-ylcarbonyloxy]phenylalanine The title compound was prepared from the product of Example 241 using the procedures described in Methods 6 and 11.

NMR data was as follows:

$^1$H NMR (DMSO-d$_6$, 400 MHz): δ 12.50 (bs, 2H); 8.08 (d, 1H, J=7.90 Hz); 7.69 (d, 2H, J=8.34 Hz); 7.39 (d, 2H, J=7.90 Hz); 7.22 (D, 2H, J=8.56 Hz); 6.99 (d, 2H, J=8.56 Hz); 4.46 (m, 1H); 4.09 (m, 1H); 4.00 (m, 1H); 3.90 (m, 1H); 3.30 (m, 1H); 3.09 (m, 3H); 2.95 (m, 2H); 2.49 (m, 1H); 2.38 (s, 3H); 1.86 (m, 2H); 1.36-1.61 (m, 6H).

IR (KBr, cm$^{-1}$) 3400, 2960, 1720, 1535, 1430, 1350, 1200, 1160, 670, 590, 550.

MS ((+)ESI, m/z (%)) 605 (100[M+NH$_4$]$^+$).

Anal. Calcd. for C$_{28}$H$_{33}$N$_3$O$_9$S H$_2$O: C, 55.53; H, 5.65; N, 6.94. Found: C, 55.23; H, 5.82; N, 6.59.

Example 244

Synthesis of N-(Toluene-4-sulfonyl)-L-prolyl-L-4-(N,N-bis-(2-hydroxyethyl)carbamyloxy)phenylalanine Isopropyl Ester The carbamate was prepared by treatment of Tos-Pro-Tyr-iPr ester with 4-nitrophenyl chloroformate, followed-by addition of diethanol amine (triethylamine, methylene chloride, chilled to 0° C., stirred at room temperature overnight). The crude product was purified by flash chromatography (silica, 98:2 EtOAc:EtOH) to afford a white foam. (0.180 g, 28%).

NMR data was as follows:

$^1$H NMR (DMSO-d$_6$, 400 MHz): δ 8.26 (d, 1H, J=7.90 Hz); 7.69 (d, 2H, J=8.12 Hz); 7.40 (d, 2H, J=8.12 Hz); 7.23 (D, 2H, J=8.56 Hz); 6.99 (d, 2H, J=8.56 Hz); 4.87 (m, 1H); 4.83 (t, 1H, J=5.49 Hz); 4.76 (t, 1H, J=5.49 Hz); 4.42 (m, 1H); 4.08 (m, 1H); 3.58 (m, 2H); 3.51 (m, 2H); 3.44 (m, 2H); 3.34 (m, 3H); 2.99-3.09 (m, 3H); 2.39 (s, 3H); 1.59 (m, 3H); 1.41 (m, 1H); 1.16 (d, 3H, J=6.15 Hz); 1.12 (d, 3H, J=6.15 Hz).

IR(KBr, cm$^{-1}$) 3420, 2940, 1725, 1535, 1670, 1520, 1460, 1410, 1350, 1220, 1160, 1110, 670, 600, 550.

MS ((+)ESI, m/z (%)) 606 (15[M+H]$^+$); 623 (100[M+NH$_2$]+).

Anal. Calcd. for C$_{29}$H$_{39}$N$_3$O$_9$S H$_2$O: C, 56.66; H, 6.56; N, 6.84.

Found: C, 56.66; H, 6.41; N, 6.72.

Example 245

Synthesis of N-(Toluene-4-sulfonyl)-L-prolyl-L-4-[3-(hydroxymethyl)piperidin-1-ylcarbonyloxy]phenylalanine Isopropyl Ester The carbamate was prepared by treatment of Tos-Pro-Tyr-iPr ester with 4-nitrophenyl chloroformate, followed by addition of 3-piperidine methanol (triethylamine, methylene chloride, chilled to 0° C., stirred at room temperature overnight. The crude product was purified by flash chromatography (silica, 3:2 EtOAc:Hex) to afford a white foam (0.519 g, 67%).

NMR data was as follows:

$^1$H NMR (DMSO-d$_6$, 400 MHz): δ 8.26 (d, 1H, J=7.90 Hz); 7.69 (d, 2H, J=8.12 Hz); 7.40 (d, 2H, J=8.12 Hz); 7.22 (d, 2H, J=8.56 Hz); 6.98 (d, 2H, J=8.34 Hz); 4.85 (M, 1H); 4.57 (bs, 1H); 4.42 (m, 1H); 3.99-4.09 (m, 3H); 3.85 (m, 1H); 3.31 (m, 1H); 3.22 (m, 1H); 2.91-3.10 (m, 4H); 2.80 (m, 1H); 2.55 (m, 1H); 2.39 (s, 3H); 1.51-1.72 (m, 6H); 1.42 (m, 2H); 1.16 (d, 3H, J=6.15 Hz); 1.11 (d, 3H), J=6.15 Hz).

IR (KBr, cm$^{-1}$) 3400, 2990, 2940, 2880, 1725, 1520, 1430, 1350, 1220, 1165, 1100, 660, 600, 550.

MS ((−)ESI, m/z (%)) 614 (30[M−H]).

Anal. Calcd. for C$_{31}$H$_{41}$N$_3$O$_8$S: C, 60.47; H, 6.71; N, 6.82. Found: C, 59.83; H, 6.61; N, 6.59.

Example 246

Synthesis of N-(Toluene-4-sulfonyl)-L-prolyl-L-4-(4-trifluoromethanesulfonylpiperazin-1-ylcarbonyloxy)phenylalanine tert-Butyl Ester The title compound was prepared following the procedure outlined for Example 128 and substitution of appropriate starting materials.

Physical data was as follows:

MS (+ESI):733 [M+H]$^+$.

Anal. Calcd. for C$_{31}$H$_{39}$F$_3$N$_4$O$_9$S$_2$.0.10 C$_4$H$_8$O$_2$: C, 50.20; H, 5.40; N, 7.55.

Found: C, 50.25; H, 5.46; N, 7.07.

Example 247

Synthesis of N-(4-(N-Phenylurea)benzenesulfonyl)-L-prolyl-L-4-(N,N-dimethylcarbamyloxy)phenylalanine tert-Butyl Ester A mixture of Example 107 (250 mg, 0.51 mmol), phenyl isocyanate (62 mg, 0.56 mmol) and triethylamine (76-L, 0.56 mmol) was heated to reflux under argon. Reflux was continued overnight. Solvent was removed under reduced pressure and the residue purified by flash chromatography. (silica, hexanes: EtOAc 1:1 then EtOAc) to give the title compound as an off-white foam (160 mg, 46%), mp 112-115° C.

Physical data was as follows:

MS (+ESI) [M+NH$_4$]$^+$697 (100%).

Example 248

Synthesis of N-(2-Trifluoroacetyl-1,2,3,4-tetrahydroisoquinolin-7-sulfonyl)-L-prolyl-L-4-(N,N-dimethylcarbamyloxy)phenylalanine Isopropyl Ester The title compound was prepared following the procedure described for the preparation of Example 2 and substitution of appropriate starting materials.

NMR data was as follows:

$^1$H NMR (CDCl$_3$): δ 7.70-7.66 (m, 2H), 7.35-7.30 (m, 1H), 7.27-7.21 (m, 1H), 7.14-7.10 (m, 2H), 7.01 (d, 2H), 5.09-4.95 (m, 1H), 4.89-4.75 (m, 2H), 4.14-4.07 (m, 1H), 3.93-3.85 (m, 2H), 3.35-3.20 (m, 2H), 3.13-2.97 (m, 9H), 2.05-2.01 (m, 1H), 1.63 (1.50 (m, 3H), 1.20 (d, 6H).

$^{13}$C NMR (CDCl$_3$): δ 170.7, 170.6, 170.5, 156.3, 155.8, 154.9, 150.6, 140.1, 139.2, 135.1, 135.1, 13.2, 133.0, 133.0, 132.9, 130.2, 130.1, 129.9, 126.9, 126.4, 126.3, 125.8, 121.7, 118.3, 114.5, 69.6, 62.1, 62.0, 53.2, 49.6, 46.6, 46.5, 45.1, 42.7, 40.9, 37.1, 36.6, 36.3, 30.1, 30.0, 29.2, 27.8, 24.2, 24.2, 21.6, 21.6.

Example 249

Synthesis of N-(1-Methylpyrazole-3-sulfonyl)-L-(5,5-dimethyl)thiaprolyl-L-4-(N,N-dimethylcarbamyloxy)phenylalanine Isopropyl Ester Substituting N-methylpyrazole-3-sulfonyl chloride (See European Patent Application, 095925) and following the method for the preparation of Example 56, gave the title compound.

NMR data was as follows:

$^1$H NMR (CDCl$_3$): δ 7.45 (d, 1H), 7.21 (d, 2H), 7.09 (d, 1H), 7.01 (d, 2H), 6.71 (d, 1H), 5.03-4.98 (m, 1H), 4.87-4.84 (m, 1H), 4.60-4.59 (m, 2H), 4.05 (s, 1H), 3.97 (s, 3H), 3.12-3.01 (m, 5H), 2.98 (s, 3H), 1.22-1.15 (m, 12H).

$^{13}$C NMR (CDCl$_3$): δ 170.3, 168.3, 154.9, 150.7, 146.7, 133.0, 131.9, 130.3, 121.7, 108.9, 73.5, 69.5, 54.7, 53.3, 50.7, 39.9, 37.7, 36.6, 36.3, 28.8, 24.1, 21.5, 21.5.

Example 250

Synthesis of N-(1-Methylpyrazole-3-sulfonyl)-L-(5,5-dimethyl)thiaprolyl-L-4-(N,N-dimethylcarbamyloxy)phenylalanine The title compound-was prepared from the product of Example 249 using the procedure described in Method 7.

NMR data was as follows:

$^1$H NMR (CD$_3$OD): δ 8.25 (d, 1H), 7.76 (d, 1H), 7.32 (d, 2H), 7.01 (d, 2H), 6.70 (d, 1H), 4.74-4.71 (m, 1H), 4.68 (d, 1H), 4.56 (d, 1H), 4.12 (s, 1H), 3.97 (s, 3H), 3.24-3.07 (m, 5H), 2.97 (s, 3H), 1.14 (s, 3H), 1.13 (s, 3H).

$^{13}$C NMR (CD$_3$OD): δ 174.1, 171.4, 157.0, 151.9, 148.2, 135.7, 134.2, 131.8, 122.9, 109.6, 74.4, 55.6, 55.0, 51.5, 40.0, 37.6, 36.8, 36.7, 29.6, 24.8.

Example 251

Synthesis of N-(Pyridine-4-sulfonyl)-L-(5,5-dimethyl)thiaprolyl-L-4-(N,N-dimethylcarbamyloxy)phenylalanine Isopropyl Ester The title compound was prepared following the procedure outlined for the preparation of Example 56, where 4-pyridinesulfonyl chloride N-oxide was used in place of 3-pyridinesulfonyl chloride (see Marsais and coworkers, J. Org. Chem. 1987, 52, 1133-1136). Deoxygenation of the N-oxide was accomplished using the procedure of Aoyagi and coworkers, Synthesis 1997, 891.

NMR data was as follows:

$^1$H NMR (CDCl$_3$): δ 8.89-8.87 (m, 2H), 7.72-7.70 (m, 2H), 7.19 (d, 2H), 7.01 (d, 2H), 6.79 (d, 1H), 5.05-5.01 (m, 1H), 4.85-4.82 (m, 1H), 4.58 (d, 1H), 4.45 (d, 1H), 3.91 (s, 1H), 3.11-3.02 (m, 5H), 2.99 (s, 3H), 1.28-1.16 (m, 12H).

$^{13}$C NMR (CDCl$_3$): δ 170.3, 167.7, 154.9, 151.5, 150.7, 144.2, 132.7, 130.3, 121.8, 120.9, 73.6, 69.7, 54.6, 53.1, 50.4, 37.5, 36.6, 36.3, 29.1, 23.6, 21.6, 21.5.

Example 252

Synthesis of N-(Pyridine-4-sulfonyl)-L-(5,5-dimethyl)thiaprolyl-L-4-(N,N-dimethylcarbamyloxy)phenylalanine The title compound was prepared from the product of Example 251 using the procedure described in Method 7.

NMR data was as follows:

$^1$H NMR (CD$_3$OD): δ 8.78 (d, 2H), 7.42 (d, 1H), 7.69 (d, 2H), 7.35 (d, 2H), 7.06 (d, 2H), 4.69-4.61 (m, 3H), 4.16 (s, 1H), 3.25-3.19 (m, 1H), 3.13-3.05 (m, 4H), 2.97 (s, 3H), 1.25 (s, 6H).

$^{13}$C NMR (CD$_3$OD): δ174.1, 170.5, 157.0, 152.2, 152.0, 147.2, 135.8, 131.85, 123.1, 122.7, 73.9, 55.6, 54.9, 54.4, 37.5, 36.8, 36.7, 30.1, 24.8.

Example 253

Synthesis of N-(Toluene-4-sulfonyl)-L-(5,5-dimethyl)thiaprolyl-L-4-(N-methyl-N-(2-dimethylaminoethyl)carbamyloxy)phenylalanine tert-Butyl Ester A solution of the starting acid (500 mg), (2S)-2-amino-3-{4-[(2-dimethylaminoethyl)-methylcarbamoyloxy]phenyl}propionic acid tert-butyl ester (730 mg), HOBt (235 mg), and 4-methylmorpholine (0.87 mL) in DMF (10 mL) was stirred in ice bath at 0° C. 1-[3-(Dimethylamino)propyl]-3-ethylcarbodiimide hydrochloride (360 mg) was added to the solution. The ice bath was removed after 10 minutes. The reaction was stirred at room temperature for 3 hours. Ethyl acetate (20 mg) was added. The solution was washed with saturated NaHCO$_3$ solution (30 mL) 2 times, then washed with brine. The solution was dried with MgSO$_4$. The solvent was evaporated in vacuo, and the residue flash chromatographed on silica gel to give 385 mg of the title compound.

Physical data was as follows:

MS: [(+)ESI], [M+H]$^+$663.

Example 254

Synthesis of N-(Toluene-4-sulfonyl)-L-prolyl-L-4-(N-methyl-N-(2-dimethylaminoethyl)carbamyloxy)phenylalanine tert-Butyl Ester The title compound was prepared following the procedure described for the preparation of Example 253 and substitution of appropriate starting materials.
Physical data was as follows:
MS: [(+)ESI], [M+H]$^+$617.

Example 255

Synthesis of N-(Toluene-4-sulfonyl)-L-(5,5-dimethyl)thiapropyl-L-4-(N-methyl-N-(2-dimethylaminoethyl)carbamyloxy)phenylalanine The title compound was prepared from the product of Example 253 using the procedure described in Method 11.
Physical data was as follows:
MS: [(+)ESI], [M+H]$^+$607.

Example 256

Synthesis of N-(Toluene-4-sulfonyl)-L-prolyl-L-4-(N-methyl-N-(2-dimethylaminoethyl)carbamyloxy)phenylalanine The title compound was prepared from the product of Example 254 using the procedure described in Method 11.
Physical data was as follows:
MS: [(+)ESI], [M+H]$^+$561.

Example 257

Synthesis of N-(4-Fluorobenzenesulfonyl)-L-(5,5-dimethyl)thiaprolyl-L-3-chloro-4-(4-methylpiperazin-1-ylcarbonyloxy)phenylalanine tert-Butyl Ester The title compound was prepared following the procedure described for the preparation of Example 4 and substitution of appropriate starting materials, mp: 64-67° C.
Physical data was as follows:
MS: [M+H]$^+$699.
Anal. Calcd. for $C_{31}H_{40}ClFN_4O_7S_2 \cdot H_2O$: C, 51.90; H, 5.9; N, 7.8.
Found: C, 51.53; H, 5.50; N, 7.62.

Example 259

Synthesis of N-(4-Fluorobenzenesulfonyl)-L-(5,5-dimethyl)thiaprolyl-L-3-chloro-4-(N,N-dimethycarbamyloxy)phenylalanine The title compound was prepared for the product of Example 258 using the procedure described in Method 11.
Physical data was-as follows:
MS: [M+1] 603.
Anal. Calcd. for $C_{24}H_{27}FN_3O_7S_2$: C, 49.02; H, 4.63; N, 7.15.
Found: C, 49.25; H, 4.89; N, 6.73.

Example 260

Synthesis of N-(4-Fluorobenzenesulfonyl)-L-(5,5-dimethyl)thiaprolyl-L-3-chloro-4-(thiomorpholin-4-ylcarbonyloxy)phenylalanine tert-Butyl Ester The title compound was prepared following the procedure described for the preparation of Example 82 and substitution of appropriate starting materials, mp. 111-114° C.

Physical data was as follows:
MS: +ESI [M+NH4]+719.
Anal. Calcd. for $C_{30}H_{37}ClFN_3O_7S$: C, 50.02; H, 5.46; N, 5.8.
Found: C, 50.23; H, 5.10; N, 5.50.

Example 261

Synthesis of N-(4-Fluorobenzenesulfonyl)-L-(5,5-dimethyl)thiaprolyl-L-3-chloro-4-(thiomorpholin-4-ylcarbonyloxy)phenylalanine Isopropyl Ester The title compound was prepared following the procedure described for the preparation of Example 82 and substitution of appropriate starting materials, mp. 77-81° C.
Physical data was as follows:
MS: [M+NH$_4$]+705.
Anal. Calcd. for $C_{29}H_{35}ClFN_3O_7S_3$: C, 50.61; H, 5.13; N, 6.1.
Found: C, 50.33; H, 5.07; N, 5.94.

Example 262

Synthesis of N-(4-Fluorobenzenesulfonyl)-L-(5,5-dimethyl)thiaprolyl-L-3-chloro-4-(N,N-dimethylcarbamyloxy)]phenylalanine Isopropyl Ester The title compound was prepared following the procedure described for the preparation of Example 2 and substitution-of-appropriate starting-materials, mp. 65-69° C.
Physical data was as follows:
MS: [M+NH$_4$]$^+$647.
Anal. Calcd. for $C_{27}H_{33}ClFN_3O_7S_2$: C, 51.46; H, 5.28; N, 6.4.
Found: C, 51.29; H, 5.19; N, 6.50.

Example 263

Synthesis of N-(Toluene-4-sulfonyl)-L-(5,5-dimethyl)thiaprolyl-L-3-chloro-4-(N,N-dimethylcarbamyloxy)phenylalanine Isopropyl Ester The title compound was prepared following the procedure described for the preparation of Example 2 and substitution of appropriate starting materials, mp. 68-72° C.
Physical data was as follows:
MS: [M+H]$^+$626.
Anal. Calcd. for $C_{28}H_{36}ClN_3O_7S_2$: C, 53.77; H, 5.80; N, 6.71. Found: C, 53.26; H, 5.8; N, 6.63.

Example 264

Synthesis of N-(4-Fluorobenzenesulfonyl)-L-(5,5-dimethyl)thiaprolyl-L-3-chloro-4-(4-methylpiperazin-1-ylcarbonyloxy)]phenylalanine Isopropyl Ester The title compound was prepared following the procedure described for the preparation of Example 4 and substitution of appropriate-starting materials:
Physical data was as follows: MS: [M+H]$^+$685.
Anal. Calcd. for $C_{30}H_{38}ClN_4O_7$: C, 52.59; H, 5.59; N, 8.18.
Found: C, 52.09; H, 5.48; N, 7.77.

Example 265

Synthesis of N-(Toluene-4-sulfonyl)-L-prolyl-L-3-chloro-4-(N,N-dimethylcarbamyloxy)]phenylalanine Isopropyl Ester The title compound was prepared following the procedure described for the preparation of Example 2 and substitution of appropriate starting materials.
Physical data was as follows:
MS: [M+H]$^+$580.
Anal. Calcd. for $C_{27}H_{34}ClN_3O_7S \cdot 0.5H_2O$: C, 55.04; H, 6.00; N, 7.13.
Found: C, 55.06; H, 5.71; N, 6.93.

Example 266

Synthesis of N-(4-Fluorobenzenesulfonyl)-L-(5,5-dimethyl)thiaprolyl-L-3-chloro-4-(4-(2'-pyridyl)-piperazin-1-ylcarbonyloxy)]phenylalanine Isopropyl Ester The title compound was prepared following the procedure described for the preparation of Example 4 and substitution of appropriate starting materials.
Physical data was as follows:
MS: [M+H]$^+$748.
Anal. Calcd. for $C_{34}H_{39}ClFN_5O_7S_2$: C, 54.57; H, 5.25; N, 9.3.
Found: C, 54.26; H, 5.10; N, 9.07.

Example 267

Synthesis of N-(4-Fluorobenzenesulfonyl)-L-(5,5-dimethyl)thiaprolyl-L-3-chloro-4-(4-(2'-pyridyl)-piperazin-1-ylcarbonyloxy)]phenylalanine tert-Butyl Ester The title compound was prepared following the procedure described for the preparation of Example 4 and substitution of appropriate starting materials, mp. 80-86° C.
Physical data was as follows:
MS: [M+H]$^+$ 762.
Anal. Calcd. for $C_{35}H_{41}ClFN_5O_7S_2$: C, 55.14; H, 5.42; N, 9.19.
Found: C, 54.67; H, 5.40; N, 8.69.

Example 268

Synthesis of N-(4-Nitrobenzenesulfonyl)-L-prolyl-L-4-(N,N-dimethylcarbamyloxy)phenylalanine Isopropyl Ester The title compound was prepared following the procedure described for the preparation of Example 2 and substitution of appropriate starting materials.
Physical data was as follows:
Anal. Calcd. for $C_{26}H_{32}N_4O_9S$: C, 54.16; H, 5.59; N, 9.72.
Found: C, 53.69; H, 5.24; N, 9.52.

Example 269

Synthesis of N-(4-Aminobenzenesulfonyl)-L-prolyl-L-4-(N,N-dimethylcarbamyloxy)phenylalanine Isopropyl Ester The title compound was prepared from the product of Example 268 using the procedure described in Method 4.
Physical data was as follows:
Anal. Calcd. for $C_{26}H_{34}N_4O_7S$: C, 57.13; H, 6.27; N, 10.25. Found: C, 56.30; H, 6.12; N, 10.05.

Example 270

Synthesis of N-(Toluene-4-sulfonyl)-L-prolyl-L-4-(thiomorpholin-4-ylcarbonyloxy)phenylalanine Isopropyl Ester The title compound was prepared following the procedure described for the preparation of Example 82 and substitution of appropriate starting materials.
Physical data was as follows:
Anal. Calcd. for $C_{29}H_{37}N_3O_7S_2$: C, 57.69; H, 6.18; N, 6.96.
Found: C, 57.36; H, 5.99; N, 6.76.

Example 271

Synthesis of N-(Toluene-4-sulfonyl)-L-prolyl-L-4-(4-phenylcarbamylpiperazin-1-ylcarbonyloxy)phenylalanine Isopropyl Ester The title compound was prepared following the procedure described for the preparation of Example 4 and substitution of appropriate starting materials.
NMR data was as follows:
$^1$H NMR (DMSO-d$_6$, 400 MHz): δ 8.62 (s, 1H); 8.11 (d, 1H); 7.73 (d, 2H); 7.45 (m, 4H); 7.26 (m, 3H); 7.04 (m, 2H); 6.95 (m, 1H); 6.25 (d, 1H); 4.90 (m, 1H); 4.50 (m, 1H); 4.11 (m, 1H); 3.6 (br, 4H); 3.4 (br, 4H); 3.10 (m, 2H); 3.00 (m, 1H); 2.40 (s, 3H); 1.60 (m, 3H); 1.40 (m, 1H); 1.18 (d, 3H); 1.12 (d, 3H).
IR (KBr, cm$^{-1}$) 3400-3500(br), 2950, 2900, 1725, 1650, 1540, 1450, 1240, 1210, 1000, 760, 675, 580, 540.
MS ((+)ESI, m/z (%)) 706 (100 [M+H]$^+$).
Anal. Calcd. for $C_{36}H_{43}N_5O_8S \cdot 0.35$ EtOAc: C, 60.98; H, 6.27; N, 9.51.
Found: C, 50.31; H, 6.16; N, 9.33.

Example 272

Synthesis of N-(Toluene-4-sulfonyl)-L-prolyl-L-4-(4-phenylcarbamylpiperazin-1-ylcarbonyloxy)phenylalanine The title compound was prepared from the product of Example 271 using the procedure described in Method 7.
NMR data was as follows:
$^1$H NMR (DMSO-d$_6$, 400 MHz): δ 12.8 (s, 1H); 8.62 (s, 1H); 8.11 (d, 1H); 7.73 (d, 2H), 7.45 (m, 4H); 7.26 (m, 3H); 7.04 (m, 2H); 6.95 (m, 1H); 6.25 (d, 1H); 4.50 (m, 1H); 4.11 (m, 1H); 3.6 (br, 4H); 3.4 (br, 4H); 3.10 (m, 2H); 3.00 (m, 1H); 2.40 (s, 3H); 1.60 (m, 3H); 1.40 (m, 1H).
IR (KBr, cm$^{-1}$) 3400, 1725, 1650, 1540, 1450, 1240, 1210, 1000, 760, 675, 580, 540.
MS ((−)ESI, m/z-(%)) 662 (100 [M−H]$^+$).

Example 273

Synthesis of N-(1-n-Butylpyrazole-4-sulfonyl)-L-(5,5-dimethyl)thiaprolyl-L-4-(N,N-dimethylcarbamyloxy)phenylalanine Isopropyl Ester The title compound was prepared following the procedure described for the preparation of Example 137 and substitution of appropriate starting materials.

NMR data was as follows:

$^1$H NMR (CDCl$_3$): δ 7.89 (s, 1H), 7.83 (s, 1H), 7.21 (d, 2H), 7.06 (d, 1H), 7.02 (d, 2H), 5.04 (sept, 1H), 4.89-4.82 (m, 1H), 4.57 (d, 1H), 4.41 (d, 1H), 4.16 (t, 2H), 3.78 (s, 1H), 3.14 (dd, 1H), 3.06 (dd, 1H), 3.09 (s, 3H), 3.00 (s, 3H), 1.85 (pent, 2H), 1.36-1.23 (m, 2H), 1.27 (s, 3H), 1.24 (d, 3H), 1.21 (d, 3H), 1.16 (s, 3H).

$^{13}$CNMR(CDCl$_3$): δ 170.4, 168.3, 154.9, 150.7, 139.2, 131.8, 130.3, 121.8, 117.0, 73.8, 69.6, 54.8, 53.2, 52.7, 50.6, 37.7, 36.6, 36.3, 31.8, 28.9, 24.0, 21.6, 21.5, 19.4, 13.3.

Example 274

Synthesis of N-(Toluene-4-sulfonyl)-L-prolyl-L-4-(pyridin-4-ylcarbonyl)piperazin-1-ylcarbonyloxy)phenylalanine Isopropyl Ester The title compound was prepared following the procedure described for the preparation of Example 4 and substitution of appropriate starting materials.

NMR data was as follows:
$^1$H NMR (DMSO-d$_6$, 400 MHz): δ 8.69 (dd, 2H), 8.28 (d, 1H); 7.71 (d, 2H); 7.43 (m, 4H); 7.26 (d, 2H); 7.04 (d, 2H); 4.86 (m, 1H); 4.42 (m, 1H); 4.05 (m, 1H); 3.4-3.8 (brm, 9H); 3.05 (m, 3H); 2.40 (s, 3H); 1.60 (m, 3H); 1.40 (m, 1H); 1.18 (d, 3H); 1.15 (d, 3H).

IR (KBr, cm$^{-1}$) 3400, 1725, 1650, 1510, 1200, 1160, 1100, 1010, 650, 600, 550.

MS ((+)ESI, m/z (%)) 692 (100 [M+H]$^+$).

Anal. Calcd. for C$_{35}$H$_{41}$N$_5$O$_9$S.0.75H$_2$O: C, 59.60; H, 6.07; N, 9.93 Found: C, 59.45; H, 5.86; N, 9.88.

Example 275

Synthesis of N-(Toluene-4-sulfonyl)-L-4-oxoprolyl-L-4-(N,N-dimethylcarbamyloxy)phenylalanine The title compound was prepared from the product of Example 164 using the procedure described in Method 11.
Physical data was as follows:
MS [(−)ESI] [M−H]) 516.

Synthesis of

N-(Toluene-4-sulfonyl)-L-trans-4-hydroxyprolyl-L-4-(N,N-dimethylcarbamyloxy)phenylalanine The title compound was prepared from the product of Example 165 using the procedure described in Method 11.
Physical data was as follows:
MS [(−)ESI] [M−H]) 518.

Example 277

Synthesis of N-(4-Cyanobenzenesulfonyl)-L-prolyl-L-4-(N,N-dimethylcarbamyloxy)phenylalanine Isopropyl Ester The title compound was prepared following the procedure described for the preparation of Example 2 and substitution of appropriate starting materials, mp. 166-167° C.

Example 278

Synthesis of N-(4-Aminobenzenesulfonyl)-L-prolyl-L-4-(N,N-dimethylcarbamyloxy)phenylalanine The title compound was prepared from the product of Example 107 using the procedure described in Method 11.
Physical data was as follows:
Anal. Calcd. For C$_{23}$H$_{28}$N$_4$O$_7$S: C, 47.34; H, 4.84; N, 9.60. Found: C, 47.57; H, 5.20; N, 8.75.

Example 279

Synthesis of N-(Toluene-4-sulfonyl)-L-4-oxoprolyl-L-4-(4-methylpiperazin-1-ylcarbonyloxy)phenylalanine tert-Butyl Ester Acetonitrile (3 mL) was cooled to −40° C. (CH$_3$CN/dry ice). Oxalyl chloride (0.10 mL) was added. N-(Toluene-4-sulfonyl)-L-4-hydroxyprolyl-L-4-(4-methylpiperazin-1-ylcarbonyloxy)phenylalanine tert-butyl ester (300 m-g) and dry DMSO (0.008 mL) were dissolved in acetonitrile (4 mL) and were added to the-above solution. The reaction was stirred at −40° C. for half an hour under dry conditions. Triethylamine (0.33 mL) was added to the solution. The dry ice bath was removed after 5 minutes. The reaction was stirred at room temperature for 1 hour. The solvent was evaporated in vacuo, and ethyl acetate (15 mL) was added. The mixture was washed with water (3×), then washed with brine. The solution was dried over MgSO$_4$. The solvent was evaporated in vacuo, and the residue was flushed on a silica gel column to give 150 mg of the title compound, mp. 84-85° C.

Example 280

Synthesis of N-(Toluene-4-sulfonyl)-L-prolyl-L4-[3-(hydroxymethyl)piperidin-1-ylcarbonyloxy]phenylalanine The title compound was prepared following the procedure described for the preparation of Example 4 and substitution of appropriate starting materials, mp. 84-85° C.

Example 281

Synthesis of N-(Toluene-4-sulfonyl)-L-(4,4-difluoro)prolyl-L-4-(N,N-dimethylcarbamyloxy)phenylalanine Isopropyl Ester The title compound was prepared following the procedure described for the preparation of Example 2 and substitution of appropriate starting materials.
Physical data was as follows:
MS: [(+)ESI], [M+NH$_4$]$^+$599.

Example 282

Synthesis of N-(Toluene-4-sulfonyl)-L-(4,4-difluoro)prolyl-L-4-(N,N-dimethylcarbamyloxy)phenylalanine The title compound was prepared from the product of Example 281 using the procedure described in Method 7.
Physical data was as follows:
MS: [(+)ESI], [M+NH$_4$]$^+$557.

Example 283

Synthesis of N-(Toluene-4-sulfonyl)-L-prolyl-L-(4-(4-benzoylpiperazin-1-ylcarbonyloxy)phenylalanine Isopropyl Ester The title compound was prepared following the procedure described for the preparation of Example 4 and substitution of appropriate starting materials.
NMR data was as follows:
$^1$H NMR (DMSO-d$_6$, 400 MHz): δ 8.27 (d, 1H); 7.69 (d, 2H); 7.45 (m, 7H); 7.24 9d, 2H); 7.02 (d, 2H); 4.86 (m, 1H);

4.42 (m, 1H); 4.07 (m, 1H); 3.65 (br s, 4H); 3.45 (br s, 4H); 3.35 (m, 1H); 3.05 (m, 3H); 2.38 (s, 3H); 1.60 (m, 3H); 1.40 (m, 1H); 1.18 (d, 3H); 1.11 (d, 3H).

IR (KBr, cm$^{-1}$) 3400, 1725, 1675, 1625, 1510, 1425, 1350, 1250, 1175, 1110, 1010, 700, 660, 590, 550.

MS ((+)ESI, m/z (%)) 708 (100 [M+NH$_2$]+).

Anal. Calcd. for $C_{36}H_{42}N_4O_8S \cdot 0.5H_2O$: C, 61.79; H, 6.19; N, 8.01.

Found: C, 61.64; H, 6.10; N, 7.72.

Example 284

Synthesis of N-(1-Methyl-1H-imidazole-4-sulfonyl)-L-prolyl-L-4-(N,N-dimethylcarbamyloxy)phenylalanine Isopropyl Ester The carbamate was prepared by treatment of 1-methylimidazole-4-sulfonyl-Pro-Try-iPr ester with 4-nitrophenyl chloroformate, followed by addition of dimethylamine (triethylamine, methylene chloride, 0° C., stirred at room temperature overnight.) The crude product was purified by flash chromatography (silica, 95:3:2 EtOAc:EtOH:Et$_3$N), followed by recrystallization from EtOAc. A white solid was obtained, mp 162-164° C. (8.7 g, 66%).

Physical data was as follows:

Anal. Calcd. for $C_{24}H_{33}N_5O_7S$: C, 53.82; H, 6.21; N, 13.08.

Found: C, 53.47; H, 6.13; N, 12.96.

Example 286

Synthesis of N-(Toluene-4-sulfonyl)-L-4-(thiomorpholin-4-ylcarbonyloxy)prolyl-L-4-(thiomorpholin-4-ylcarbonyloxy)phenylalanine The title compound was prepared from the product of Example 285 using the procedure described in Method 11, mp. 116-118° C.

Example 287

Synthesis of N-(4-Cyanobenzenesulfonyl)-L-prolyl-L-4-(thiomorpholin-4-ylcarbonyloxy)phenylalanine Isopropyl Ester The title compound was prepared following the procedure described for the preparation of Example 4 and substitution of appropriate starting materials, mp. 70-71° C.

Example 288

Synthesis of N-(4-Amidinobenzenesulfonyl)-L-prolyl-L4-(N,N-dimethylcarbamyloxy)phenylalanine Methyl Ester Methanol (dry) was cooled to 0° C. HCl was bubbled in the solution for 15 minutes to make a saturated solution. Example 277 was added and the reaction mixture was stirred at 0° C. for 30 minutes then at room temperature for 24 hours. The solvent was evaporated. NH$_3$ in methanol (2M, 5 mL) was added. The reaction was stirred at room temperature for 24 hours. The solvent was evaporated. The residue was purified by reverse phase HPLC in CH$_3$CN:H$_2$O (20:80). At a retention time of 12.45 minutes, the product was isolated and freeze-dried to provide the title compound.

NMR data was as follows:

$^1$H NMR-(in DMSO) multiplet at 1.47-1.55 ppm (1H), 1.63-1.72 ppm (3H's), singlet at 2.87 ppm (3H's), singlet at 3.02 ppm (3H's), multiplet at 3.05-3.10 ppm (2H's), multiplet at 3.17-3.22 ppm (1H), multiplet at 3.37-3.42 ppm (1H), singlet at 3.62 ppm (3H's), multiplet at 4.21-4.23 ppm (1H), quartet at 4.48-4.56 ppm (1H), doublet at 7.00-7.03 ppm (2H's), doublet at 7.23-7.26 ppm (2H's), a broad peak at 7.20-7.50 ppm, doublet at 8.02-8.03 ppm (4H's), doublet at 8.48-8.52 ppm (1H).

Example 289

Synthesis of N-(Toluene-4-sulfonyl)-L-4-hydroxyprolyl-L-4-(thiomorpholin-4-ylcarbonyloxy)phenylalanine tert-Butyl Ester The title compound was prepared following the procedure described for the preparation of Example 4 and substitution of appropriate starting materials, mp. 80-82° C.

Example 290

Synthesis of N-(Toluene-4-sulfonyl)-L-4-hydroxyprolyl-L4-(thiomorpholin-4-ylcarbonyloxy)phenylalanine N-(Toluene-4-sulfonyl)-L-4-hydroxyprolyl-L-4-(thiomorpholin-4-ylcarbonyloxy)phenylalanine tert-butyl ester (160 mg) was dissolved in formic acid (7 mL). The reaction was stirred at room temperature for 6 hours. The solvent was evaporated and the residue purified using reverse phase HPLC in 20:80 CH$_3$CN/water. At a retention time of 5.85 minutes, 50 mg of the title compound was obtained, mp. 170-172° C.

Example 291

Synthesis of N-(Toluene-4-sulfonyl)-L-prolyl-L-(4-benzoylpiperazin-1-ylcarbonyloxy)phenylalanine The title compound was prepared from the product of Example 283 using the procedure described in Method 11.

NMR data was as follows:

$^1$H NMR (DMSO-d$_6$, 400 MHz): δ 12.8 (s, 1H); 8.27 (d, 1H); 7.69 (d, 2H); 7.45 (m, 7H); 7.24 (d, 2H); 7.02 (d, 2H); 4.42 (m, 1H); 4.07 (m, 1H); 3.65 (br s, 4H); 3.45 (br s, 4H); 3.35 (m, 1H); 3.05 (m, 3H); 2.38 (s, 3H); 1.60 (m, 3H); 1.40 (m, 1H).

IR (KBr, cm$^{-1}$) 3400, 1725, 1675, 1625, 1510, 1425, 1350, 1260, 1175, 1110, 1010, 700, 660, 590, 550.

MS ((+)ESI, m/z (%)) 666 (100 [M+NH$_4$]$^+$).

Anal. Calcd. for $C_{33}H_{36}N_4O_8S \cdot 0.66H_2O$: C, 60.00; H, 5.69; N, 8.48 Found: C, 60.36; H, 5.70; N, 7.81.

Example 292

Synthesis of N-(4-Amidinobenzenesulfonyl)-L-prolyl-L-4-(thiomorpholin-4-ylcarbonyloxy)phenylalanine Methyl Ester The title compound was prepared following the procedure described for the preparation of Examples 287 and 288.

Physical data was as follows:

MS: [(+)ESI] [M+H] 604.

Example 293

Synthesis of N-(3-Fluorobenzenesulfonyl)-L-prolyl-L-4-(N,N-dimethylcarbonyloxy)phenylalanine The title compound was prepared from the product of Example 166 using the procedure described in Method 11, mp. 82-83° C.

Example 294

Synthesis of N-(Toluene-4-sulfonyl)-L-prolyl-L-4-[N-methyl-N-(2-(N'-methyl-N'-toluenesulfonyl-amino)ethyl)carbamyloxy]phenylalanine Isopropyl Ester The title compound was prepared following the procedure described for the preparation of Example 4 and substitution of appropriate starting materials.
NMR data was as follows:
$^1$H NMR (DMSO-$d_6$, 400 MHz): δ 8.27 (d, 1H); 7.71 (d, 2H); 7.69 (d, 2H); 7.40 (m, 4H); 7.24 (d, 2H); 6.99 (d, 2H); 4.86 (m, 1H); 4.43 (m, 1H); 4.06 (m, 1H); 3.51 (m, 1H); 3.2-3.35 (m, 3H); 2.9-3.2 (overlapping m, 7H); 2.67 (d, 3H); 2.38 (s, 6H); 1.60 (m, 3H); 1.40 (m, 1H); 1.20 (d, 3H); 1.15 (d, 3H).
IR (KBr, cm$^{-1}$) 3400, 2975, 2950, 1725, 1680, 1510, 1450, 1400, 1280, 1225, 1150, 1110, 800, 730, 675, 575, 550.
MS ((+)ESI, m/z (%)) 760 (100 [M+NH$_4$]$^+$).
Anal. Calcd. for $C_{36}H_{46}N_4O_9S_2$: C, 58.20; H, 6.24; N, 7.54.
Found: C, 57.90; H, 6.30; N, 7.34.

Example 295

Synthesis of N-(Toluene-4-sulfonyl)-L-prolyl-L-4-[N-(2-(N'-phenylaminocarbonyloxy)ethyl)carbamyloxy)]phenylalanine Isopropyl Ester The title compound was prepared following the procedure described for the preparation of Example 4 and substitution of appropriate starting materials.
NMR data was as follows:
$^1$H NMR (DMSO-$d_6$, 400 MHz): δ 9.67 (s, 1H); 8.27 (d, 1H); 7.72 (d, 2H); 7.47 (d, 2H); 7.42 (d, 2H); 7.24 (m, 4H); 6.98 (m, 3H); 4.87 (m, 1 h); 4.45 (m, 1H); 4.18 (m, 2H); 4.05 (m, 1H); 3.4 (m, 3H); 3.05 (m, 3H) 2.40 (s, 3H); 1.6 (m, 3H); 1.40 (m, 1H); 1.2 (d, 3H); 1.15 (d, 3H).
IR (KBr, cm$^{-1}$) 3350, 2950, 1725, 1675, 1600, 1550, 1500, 1325, 1200, 1150, 1100, 650, 575, 525.
MS ((+)ESI, m/z (%)) 698 (100 [M+NH$_4$]$^+$).
Anal. Calcd. for $C_{34}H_{40}N_4O_9S.0.21$ EtOAc. $0.5H_2O$: C, 59.08; H, 6.07; N, 7.91.
Found: C, 59.08; H, 6.02; N, 7.80.

Example 296

Synthesis of N-(4-Fluorobenzenesulfonyl)-L-4-(trans-hydroxy)prolyl-L-4-(N,N-dimethylcarbamyloxy)phenylalanine Isopropyl Ester The title compound was prepared following the procedure described in Example 2 and substitution of appropriate starting materials.

Physical data was as follows:
MS: [(+)ESI], [M+NH$_4$] 583.

Example 297

Synthesis of N-(4-Fluorobenzenesulfonyl)-L-4-(trans-hydroxy)prolyl-L-4(N,N-dimethylcarbamyloxy)phenylalanine tert-Butyl Ester The title compound was prepared following the procedure described in Example 2 and substitution of appropriate starting materials.
Physical data was as follows:
MS: [(+)ESI], [M+NH$_4$] 597.

Example 298

Synthesis of N-(4-Amidinobenzenesulfonyl)-L-prolyl-L-4-(N,N-dimethylcarbamyloxy)phenylalanine The title compound was prepared from the product of Example 288 using the procedure described in Method 5, mp. 130-132° C.

Example 299

Synthesis of piperazine-1,4-dicarboxylic Acid Bis-{4-[(2S)-2-tert-butoxycarbonyl-2-((4R)-5,5-dimethyl-3-(toluene-4-sulfonyl)thiazolidine-4-carboxamido)ethyl]phenyl} Ester The title compound was prepared following the procedure described in Example 4, except that 0.5 equivalents of piperazine were used.
Physical data was as follows:
Anal. Calcd. for $C_{58}H_{74}N_6O_{14}S_4$: C, 57.69; H, 6.18; N, 6.96.
Found: C, 58.01; H, 6.07; N, 6.68.

Example 300

Synthesis of piperazine-1,4-dicarboxylic Acid Bis-{4-[(2S)-2-carboxy-2-((4R)-5,5-dimethyl-3-(toluene-4-sulfonyl)thiazolidine-4-carboxamido)ethyl]phenyl} Ester The title compound was prepared by hydrolysis of the di-t-butyl ester from Example 299 with formic acid to give a white foam (300 mg, quantitative).
Physical data was as follows:
Anal. Calcd. for $C_{50}H_{58}N_6O_{14}S_4$: C, 54.83; H, 5.34; N, 7.67 Found: C, 55.10; H, 5.57; N, 7.37.

Other compounds of Formulae I and Ia prepared by the methods described above include those set forth in Examples 301-370 in Table 11 below.

TABLE 11

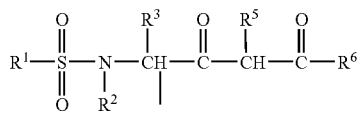

| Ex. No. | R$^1$ | R$^2$ | R$^3$ | R$^5$ | R$^6$ |
|---|---|---|---|---|---|
| 301 | p-CH$_3$-ψ- | R$^2$/R$^3$ = cyclic —CH$_2$CH$_2$—NH—CH$_2$— (L-piperazinyl) | | p-[(CH$_3$)$_2$NC(O)O—]benzyl- | —OC(CH$_3$)$_3$ |

TABLE 11-continued $$R^1-\overset{\overset{O}{\|}}{\underset{\underset{O}{\|}}{S}}-\underset{R^2}{N}-\overset{R^3}{\underset{|}{CH}}-\overset{O}{\overset{\|}{C}}-\overset{R^5}{\underset{|}{CH}}-\overset{O}{\overset{\|}{C}}-R^6$$

| Ex. No. | R¹ | R² | R³ | R⁵ | R⁶ |
|---|---|---|---|---|---|
| 302 | p-F-ψ- | R²/R³ = cyclic —CH₂—S—C(CH₃)₂— (L-5,5-dimeethylthiazolidin-4-yl) | | p-[(2-(hydroxymeethyl)pyrrolidin-1-yl-C(O)O—]-benzyl- | —OC(CH₃)₃ |
| 303 | p-F-ψ- | R²/R³ = cyclic —CH₂—S—C(CH₃)₂— (L-5,5-dimethylthiazolidin-4-yl) | | p-[(2-(hydroxymethyl)pyrrolidin-1-yl-C(O)O—]-benzyl- | —OH |
| 304 | p-CH₃-ψ- | R²/R³ = cyclic 3 carbon atoms (L-pyrrolidinyl) | | p-[(2-(CH₃OC(O)-)-pyrrolidin-1-yl)-C(O)O—] benzyl- | —OC(CH₃)₃ |
| 305 | p-F-ψ- | R²/R³ = cyclic —CH₂—S—C(CH₃)₂— (L-5,5-dimethylthiazolidin-4-yl) | | 3-chloro-4-[(thiomorpholin-4-yl)-C(O)O—] benzyl- | —OH |
| 306 | p-F-ψ- | R²/R³ = cyclic —CH₂—S—C(CH₃)₂— (L-5,5-dimethylthiazolidin-4-yl) | | p-[(4-(pyridin-2-yl)piperazin-1-yl)-C(O)O—] benzyl- | —OH |
| 307 | p-F-ψ- | R²/R³ = cyclic —CH₂—S—C(CH₃)₂— (L-5,5-dimethylthiazolidin-4-yl) | | p-[(4-(pyridin-2-yl)piperazin-1-yl)-C(O)O—] benzyl- | —OC(CH₃)₃ |
| 308 | p-CH₃-ψ- | R²/R³ '2 cyclic —CH₂CH(OH)CH₂— (L-4-hydroxypyrrolidinyl) | | p-[(thiomorpholin-4-yl)-C(O)O—]benzyl- | —OC(CH₃)₃ |
| 309 | p-CH₃-ψ- | R²/R³ = cyclic 3 carbon atoms (L-pyrrolidinyl) | | p-[(CH₃)₂NC(O)O—]benzyl- | —O(CH₂CH₂O)₂CH₃ |
| 310 | p-F-ψ- | R²/R³ = cyclic —CH₂—S—C(CH₃)₂— (L-5,5-dimeethylthiazolidin-4-yl) | | p-[(4-(pyrimidin-2-yl)piperazin-1-yl)-C(O)O—]benzyl- | —OC(CH₃)₃ |
| 311 | p-F-ψ- | R²/R³ = cyclic —CH₂—S—C(CH₃)₂— (L-5,5-dimethylthiazolidin-4-yl) | | 3-fluoro-4-[(CH₃)₂NC(O)O—]-benzyl- | —OCH(CH₃)₂ |
| 312 | p-CH₃-ψ- | R²/R³ = cyclic —CH₂—CH₂N— (—SO₂CH₃)—CH₂— (L-4-methanesulfonyl-piperazinyl) | | p-[(CH₃)₂NC(O)O—]benzyl- | —OC(CH₃)₃ |
| 313 | R¹/R² = 1,1-dioxo-2,3-dihydro-3,3-dimethyl-1,2-benzoisothiazol-2-yl- | | H | p-[(CH₃)₂NC(O)O—]benzyl- | —OH |
| 314 | R¹/R² = N-2,10-camphorsultamyl- | | H | p-[(CH₃)₂NC(O)O—]benzyl- | —OC(CH₃)₃ |
| 315 | R¹/R² = N-2,10-camphorsultamyl- | | H | p-[(CH₃)₂NC(O)O—]benzyl- | —OH |
| 316 | R¹/R² = N-2,10-camphorsultamyl- | | H | 3-chloro-4-[(CH₃)₂NC(O)O—]-benzyl- | —OCH(CH₃)₂ |
| 317 | p-Br-ψ- | R²/R³ = cyclic —CH₂—S—C(CH₃)₂— (L-5,5- | | p-[(CH₃)₂NC(O)O—]benzyl- | —OC(CH₃)₃ |

TABLE 11-continued $$R^1-\overset{\overset{O}{\|}}{\underset{\underset{O}{\|}}{S}}-\underset{R^2}{N}-\overset{R^3}{\underset{|}{CH}}-\overset{O}{\overset{\|}{C}}-\overset{R^5}{\underset{|}{CH}}-\overset{O}{\overset{\|}{C}}-R^6$$

| Ex. No. | R¹ | R² | R³ | R⁵ | R⁶ |
|---|---|---|---|---|---|
| 318 | p-Br-ψ- | R²/R³ = cyclic —CH₂—S—C(CH₃)₂— (L-5,5-dimethylthiazolidin-4-yl) | | p-[(CH₃)₂NC(O)O—]benzyl- | —OH |
| 319 | p-CH₃-ψ- | R²/R³ = cyclic —CH₂—CH(OH)—CH₂— (L-4-4 hydroxypyrrolidinyl) | | p-[(4-methylpiperazin-1-yl)-C(O)O—]benzyl- | —OH |
| 320 | p-F-ψ- | R²/R³ = cyclic —CH₂—S—C(CH₃)₂— (L-5,5-dimethylthiazolidin-4-yl) | | p-[(4-pyrimidin-2-yl)piperazin-1-yl)-C(O)O—]benzyl- | —OH |
| 321 | p-F-ψ- | R²/R³ = cyclic —CH₂—S—C(CH₃)₂— (L-5,5-dimeethylthiazolidin-4-yl) | | p-[4-(pyridin-2-yl)piperazin-1-yl)C(O)O—]benzyl- | —OCH(CH₃)₂ |
| 322 | p-F-ψ- | R²/R³ = cyclic —CH₂—CH₂—S— (thiazolidin-2-yl) | | p-[(CH₃)₂NC(O)O—]benzyl- | —OH |
| 323 | p-F-ψ- | R²/R³ = cyclic —CH₂—CH₂—S— (thiazolidin-2-yl) | | p-[(CH₃)₂NC(O)O—]benzyl- | —OC(CH₃)₃ |
| 324 | p-CH₃-ψ- | R²/R³ = cyclic —CH₂—C(O)—CH₂— (L-4-oxopyrrolidinyl) | | p-[(thiomorphnolin-4-yl)C(O)O—]benzyl- | —OH |
| 325 | p-CH₃-ψ- | R²/R³ = cyclic —CH₂—C(O)—CH₂— (L-4-oxopyrrolidinyl) | | p-[(4-methylpiperazin-1-yl)-C(O)O—]benzyl- | —OH |
| 326 | p-F-ψ- | R²/R³ = cyclic —CH₂—CH₂—S— (thiazolidin-2-yl) | | p-[(4-(pyridin-2-yl)piperazin-1-yl)-C(O)O—]benzyl- | —OH |
| 327 | p-NO₂-ψ- | R²/R³ = cyclic 3 carbon atoms (L-pyrrolidinyl) | | p-[(4-(pyridin-2-yl)piperazin-1-yl)-C(O)O—]benzyl- | —OC(CH₃)₃ |
| 328 | p-F-ψ- | R²/R³ = cyclic —CH₂—CH₂—S— (thiazolidin-2-yl) | | p-[(4-(pyridin-2-yl)piperazin-1-yl)-C(O)O—]benzyl- | —OC(CH₃)₃ |
| 329 | p-Br-ψ- | R²/R³ = cyclic —CH₂—S—C(CH₃)₂— (L-5,5-dimethylthiazoliddin-4-yl) | | p-[(4-(pyridin-2-yl)piperazin-1-yl)-C(O)O—]benzyl- | —OH |
| 330 | p-CH₃-ψ- | R²/R³ = cyclic 3 carbon atoms (L-pyrrolidinyl) | | p-[(4-(ψNHC(S)piperazin-1-yl)-C(O)O—]benzyl- | —OCH(CH₃)₂ |
| 331 | p-F-ψ- | R²/R³ = cyclic —CH₂—CH₂—S— (thiazolidin-2-yl) | | p-[(4-CH₃-homopiperazin-1-yl)-C(O)O—]benzyl- | —OC(CH₃)₃ |
| 332 | p-CH₃-ψ- | R²/R³ = cyclic —CH₂CH(—OSO₂CH₃)—CH₂— (L-4-methasulfoxy-pyrrolidinyl) | | p-[(CH₃)₂NC(O)O—]benzyl- | —OC(CH₃)₃ |
| 333 | p-H₂NC(O)-ψ- | R²/R³ = cyclic 3 carbon atoms (L-pyrrolidinyl) | | p-[(CH₃)₂NC(O)O—]benzyl- | —OH |
| 334 | p-H₂NC(O)-ψ- | R²/R³ = cyclic 3 carbon atoms (L-pyrrolidinyl) | | p-[(thiomorpholin-4-yl)C(O)O—]benzyl- | —OH |
| 335 | p-H₂NC(=N)-ψ- | R²/R³ = cyclic 3 carbon atoms (L-pyrrolidinyl) | | p-[(thiomorpholin-4-yl)C(O)O—]benzyl- | —OH |
| 336 | p-NO₂-ψ- | R²/R³ = cyclic 3 carbon atoms (L-pyrrolidinyl) | | p-[(4-(pyridin-02-yl)piperazin-1-yl)-C(O)O—]benzyl- | —OH |

TABLE 11-continued $$R^1-\underset{\underset{O}{\overset{O}{\|}}}{\overset{O}{\underset{\|}{S}}}-\underset{R^2}{N}-\underset{}{\overset{R^3}{\underset{|}{CH}}}-\overset{O}{\underset{}{\overset{\|}{C}}}-\overset{R^5}{\underset{|}{CH}}-\overset{O}{\underset{}{\overset{\|}{C}}}-R^6$$

| Ex. No. | R¹ | R² | R³ | R⁵ | R⁶ |
|---|---|---|---|---|---|
| 337 | p-F-ψ- | R²/R³ = cyclic —CH₂—S—C(CH₃)₂— (L-5,5-dimethylthiazolidin-4-yl) | | 3-chloro-4-[(4-pyridin-2-yl)piperazin-1-yl)C(O)O—]-benzyl- | —OCH₂CH₃ |
| 338 | p-F-ψ- | R²/R³ = cyclic —CH₂—S—C(CH₃)₂— (L-5,5-dimethylthiazolidin-4-yl) | | 3-chloro-4-[(4-pyridin-2-yl)piperazin-1-yl)C(O)O—]-benzyl- | —OH |
| 339 | p-F-ψ- | R²/R³ = cyclic —CH₂—CH₂—S— (thiazolidin-2-yl) | | p-[(4-CH₃-homopiperazin-1-yl-C(O)O—]benzyl- | —OH |
| 340 | 1-methylpyrazol-4-yl- | R²/R³ = cyclic —CH₂—S—C(CH₃)₂— (L-5,5-dimethylthiazolidin-4-yl) | | 3-chloro-4-[(CH₃)₂NC(O)O—]benzyl- | —OCH(CH₃)₂ |
| 341 | 1-methylimidazol-4-yl- | R²/R³ = cyclic 3 carbon atoms (L-pyrrolidinyl) | | p-[(4-(pyridin-2-yl)piperazin-1-yl)C(O)O—]benzyl- | —OCH(CH₃)₂ |
| 342 | 1-methylimidazol-4-yl- | R²/R³ = cyclic 3 carbon atoms (L-pyrrolidinyl) | | p-[(4-(pyridin-2-yl)piperazin-1-yl)C(O)O—benzyl- | —OC(CH₃)₃ |
| 343 | p-CH₃-ψ- | R²/R³ = cyclic 3 carbon atoms (L-pyrrolidinyl) | | p-[(4-(pyridin-2-yl)piperazin-1-yl)C(O)O—]benzyl- | —OH |
| 344 | p-CH₃-ψ- | R²/R³ = cyclic 3 carbon atoms (L-pyrrolidinyl) | | p-[(4-(pyridin-2-yl)piperazin-1-yl)C(O)O—]benzyl- | —OC(CH₃)₃ |
| 345 | p-CH₃-ψ- | R²/R³ = cyclic 3 carbon atoms (L-pyrrolidinyl) | | p-[(4-(pyridin-2-yl)piperazin-1-yl)-C(O)O—]benzyl- | —OCH(CH₃)₂ |
| 346 | p-F-ψ- | R²/R³ = cyclic 3 carbon atoms (L-pyrrolidinyl) | | p-[(4-(pyridin-2-yl)piperazin-1-yl)C(O)O—]benzyl- | —OCH(CH₃)₂ |
| 347 | p-F-ψ- | R²/R³ = cyclic 3 carbon atoms (L-pyrrolidinyl) | | p-[(4-(pyridin-2-yl)piperazin-1-yl)C(O)O—]benzyl- | —OC(CH₃)₃ |
| 348 | p-CH₃-ψ- | R²/R³ = cyclic —CH₂CH₂N(—SO₂—CH₃)CH₂— (4-methansulfonyl-piperazin-2-yl) | | p-[(CH₃)₂NC(O)O—]benzyl- | —OH |
| 349 | p-CH₃-ψ- | R²/R³ = cyclic —CH₂CH(—OSO₂—CH₃)CH₂— (L-4-methansulfoxy-pyrrolidinyl) | | p-[(CH₃)₂NC(O)O—]benzyl- | —OH |
| 350 | CH₃— | —CH₂ψ | H | p-[(CH₃)₂NC(O)O—]benzyl- | —OC(CH₃)₃ |
| 351 | p-Br-ψ- | R²/R³ = cyclic —CH₂—S—C(CH₃)₂— (L-5,5-dimeethylthiazolidin-4-yl) | | p-[(4-pyridin-2-yl)piperazin-1-yl)C(O)O—]benzyl- | —OC(CH₃)₃ |
| 352 | p-CF₃O-ψ- | R²/R³ = cyclic —CH₂—S—C(CH₃)₂— (L-5,5-dimethylthiazolidin-4-yl) | | p-[(CH₃)₂NC(O)O—]benzyl- | —OH |
| 353 | p-CF₃O-ψ- | R²/R³ = cyclic —CH₂—S—C(CH₃)₂— (L-5,5-dimethylthiazolidin-4-yl) | | p-[(CH₃)₂NC(O)O—]benzyl- | —OC(CH₃)₃ |
| 354 | p-CF₃O-ψ- | R²/R³ = cyclic —CH₂—S—C(CH₃)₂— (L-5,5-dimethylthiazolidin-4-yl) | | p-[(4-(pyridin-2-yl)piperazin-1-yl)C(O)O—]benzyl- | —OC(CH₃)₃ |

TABLE 11-continued $$R^1-\underset{\underset{O}{\|}}{\overset{\overset{O}{\|}}{S}}-\underset{R^2}{N}-\underset{\underset{}{}}{CH}-\overset{R^3}{\underset{}{C}}-\overset{O}{\underset{}{\|}}-\underset{}{CH}-\overset{R^5}{\underset{}{C}}-\overset{O}{\underset{}{\|}}-R^6$$

| Ex. No. | R¹ | R² | R³ | R⁵ | R⁶ |
|---|---|---|---|---|---|
| 355 | p-F-ψ- | R²/R³ = cyclic 3 carbon atoms (L-pyrrolidinyl) | | p-[(4-(pyridin-2-yl)piperazin-1-yl)C(O)O—]benzyl- | —OH |
| 356 | p-F-ψ- | R²/R³ = ccyclic —CH₂CH(OH)CH₂— (L-4-hydroxypyrrolidinyl) | | p-[(4-(pyridin-2-yl)piperazin-1-yl)C(O)O—]benzyl- | —OH |
| 357 | p-CF₃O-ψ- | R²/R³ = cyclic —CH₂—S—C(CH₃)₂— (L-5,5-dimethylthiazolidin-4-yl) | | p-[(4-(pyridin-2-yl)piperazin-1-yl)C(O)O—]benzyl- | —OH |
| 358 | 1-methylimidazol-4-yl- | R²/R³ = cyclic 3 carbon atoms (L-pyrrolidinyl) | | 3-chloro-4-[(CH₃)₂NC(O)O—]benzyl- | —OH |
| 359 | 1-methylimidazol-4-yl- | R²/R³ = cyclic 3 carbon atoms (L-pyrrolidinyl) | | 3-chloro-4-[(CH₃)₂NC(O)O—]-benzyl- | —OCH(CH₃)₂ |
| 360 | 1-methylimidazol-4-yl- | R²/R³ = cyclic 3 carbon atoms (L-pyrrolidinyl) | | p-[(4-(pyridin-2-yl)piperazin-01-yl)(-C(O)O—[benzyl- | —OH |
| 361 | 1-methylimidazol-4-yl- | R²/R³ = cyclicc —CH₂—S—C(CH₃)₂— (L-5,5-dimethylthiazolidin-4-yl) | | p-[(4-(pyridin-2-yl)piperazin-1-yl)C(O)O—]benzyl- | —OH |
| 362 | 1-methylpyrazol-4-yl- | R²/R³ = cyclic 3 carbon atoms (L-pyrrolidinyl) | | p-[(4-pyridin-2-yl)piperazin-1-yl)C(O)O—]benzyl- | —OH |
| 363 | 1-methylpyrazol-4-yl- | R²/R³ = cyclic 3 carbon atoms (L-pyrrolidinyl) | | p-[(4-(pyridin-2-yl)piperazin-1-yl)C(O)O—]benzyl- | —OCH(CH₃)₂ |
| 364 | 1-methylpyrazol-4-yl- | R²/R³ = cyclic 3 carbon atoms (L-pyrrolidinyl) | | p-[(4-(pyridin-2-yl)piperazin-1-yl)C(O)O—]benzyl- | —OC(CH₃)₃ |
| 365 | 1-methylpyrazol-4-yl- | R²/R³ = cyclic —CH₂—S—C(CH₃)₂— (L-5,5-dimethylthiazolidin-4-yl) | | p-[(4-(pyridin-2-yl)piperazin-1-yl)C(O)O—]benzyl- | —OC(CH₃)₃ |
| 366 | 1-methylpyrazol-4-yl- | R²/R³ = cyclic 3 carbon atoms (L-pyrrolidinyl) | | 3-chloro-4-[(4-(pyridin-2-yl)piperazin-1-yl)C(O)O—]benzyl- | —OCH(CH₃)₂ |
| 367 | 1-methylpyrazol-4-yl- | R²/R³ = ccyclic —CH₂—S—C(CH₃)₂— (L-5,5-dimethylthiazolidin-4-yl) | | p-[(CH₃)₂NC(O)O—]benzyl- | —OCH₂CH₂Oψ |
| 368 | 1-methylpyrazol-4-yl- | R²/R³ = cyclic —CH₂—S—C(CH₃)₂— (L-5,5-dimethylthiazolidin-4-yl) | | 3-chloro-4-[(4-pyridin-2-yl)piperazin-1-yl)C(O)O—]-benzyl- | —OH |
| 369 | 1-methylpyrazol-4-yl- | R²/R³ = cyclic —CH₂—S—C(CH₃)₂— (L-5,5-dimethylthiazolidin-4-yl) | | 3-chloro-4-[(4-pyridin-2-yl)piperazin-1-yl)C(O)O—]-benzyl- | —OCH₂CH₃ |
| 370 | 1,5-dimethyl-3-chloropyrazol-4-yl- | R²/R³ = cyclic —CH₂—S—C(CH₃)₂— (L-5,5-dimethylthiazolidin-4-yl) | | p-[4-[5-CF₃-pyridin-2-yl)piperazin-1-yl)-C(O)O—]benzyl- | —OH |

In addition, Examples 319, 324, 325, 332, 333, 334, 335 and 349 in Table 11 are exemplified as follows:

Example 319

Synthesis of N-(Toluene-4-sulfonyl)-L-(4-hydroxy) prolyl-L-4-(4-methylpiperazin-1-ylcarbonyloxy) phenylalanine The starting N-(toluene-4-sulfonyl)-L-(4-hydroxy)prolyl-L-4-(4-methylpiperazin-1-ylcarbonyloxy)phenylalanine tert-butyl ester (300 mg) was dissolved in formic acid (15 mL). The reaction was stirred at room temperature for 72 hours. The solvent was evaporated and the residue was purified using HPLC, reverse phase, 20-80% $CH_3CN$/water. At a retention time of 10.75 minutes, 82 mg of the title compound was obtained, mp: 128-130° C.

Example 324

Synthesis of N-(Toluene-4-sulfonyl)-L-(4-oxo)prolyl-L-4-(thiomorpholin-4-ylcarbonyloxy)phenylalanine The starting N-(toluene-4-sulfonyl)-L-(4-oxo)prolyl-L-4-(thiomorpholin-4-ylcarbonyloxy)phenylalanine tert-butyl ester (130 mg) was dissolved in formic acid (7 mL). The reaction was stirred at room temperature for 6 hours. The solvent was evaporated in vacuo to give 150 mg of the desired product, mp: 111-112° C.

Example 325

Synthesis of N-(Toluene-4-sulfonyl)-L-(4-oxo)prolyl-L-4-(4-methylpiperazin-1-ylcarbonyloxy)phenylalanine The starting N-(toluene-4-sulfonyl)-L-(4-oxo)prolyl-L-4-(4-methylpiperazin-1-ylcarbonyloxy)phenylalanine tert-butyl ester (150 mg) was dissolved in formic acid (7 mL). The reaction was stirred at room temperature for 6 hours. The solvent was evaporated in vacuo, and the residue was purified using HPLC, reverse phase, 20-80% $CH_3CH$/water. The retention time was 10.34 minutes. The product was freeze dried to yield 82 mg of the title compound, mp: 99-101° C.

Example 332

Synthesis of N-(Toluene-4-sulfonyl)-L-(4-methanesulfonyloxy)prolyl-L-4-(N,N-dimethylcarbamyloxy) phenylalanine tert-Butyl Ester The starting N-(toluene-4-sulfonyl)-L-(4-hydroxy)prolyl-L-4-(N,N-dimethylcarbamyloxy)phenylalanine tert-butyl ester (300 mg) and methylsulfonyl chloride was dissolved in THF (7 mL) at 0° C. in an ice bath. Triethylamine (0.21 mL) was added. The ice bath was removed after 10 minutes. The reaction mixture was stirred at room temperature for 24 hours. Ethyl acetate (20 mL) as added. The mixture was washed with citric acid (5%, 20 mL, 2×), and washed with saturated $NaHCO_3$ solution (20 mL), then with brine. The solution was dried over $MgSO_4$. The solvent was evaporated, and the residue was flushed on a silica gel column. The solvent was evaporated in vacuo to give 300 mg of the desired product, mp: 73-74° C.

Example 333

Synthesis of N-(4-Aminobenzenesulfonyl)-L-prolyl-L-4-(N,N-dimethylcarbamyloxy)phenylalanine The starting N-(4-aminobenzenesulfonyl)-L-prolyl-L-4-(N,N-dimethylcarbamyloxy)phenylalanine methyl ester (300 mg) and LiOH solution (2M, 0.6 mL) were added to methanol (6 mL). The reaction was stirred at room temperature for 7 hours. The solvent was evaporated in vacuo, and the residue was purified using HPLC, reverse phase, 20-80% $CH_3CN$/water. At a retention time of 12.11 minutes, 27 mg of the desired product were obtained, mp: 130-132° C.

Example 334

Synthesis of N-(4-Aminocarbonylbenzenesulfonyl)-L-prolyl-L-4-(thiomorpholin-4-ylcarbonyloxy)phenylalanine The starting N-(4-aminocarbonylbenzenesulfonyl)-L-prolyl-L-4-(thiomorpholin-4-ylcarbonyloxy)phenylalanine methyl ester (300 mg) and LiOH solution (2M, 0.5 mL) were added to methanol (6 mL). The reaction was stirred at room temperature for 8 hours. The solvent was evaporated in vacuo, and the residue purified using HPLC, reverse phase, 20-80% $CH_3CN$/water. At a retention time of 12.69 minutes, 20 mg of the desired product was obtained, mp: 123-125° C.

Example 335

Synthesis of N-(4-Amidinobenzenesulfonyl)-L-prolyl-L-4-(thiomorpholin-4-ylcarbonyloxy)phenylalanine The starting N-(4-amidinobenzenesulfonyl)-L-prolyl-L-4-(thiomorpholin-4-ylcarbonyloxy)phenylalanine methyl ester (300 mg) and LiOH solution (2M, 0.5 mL) were added to methanol (6 mL). The reaction was stirred at room temperature for 8 hours. The solvent was evaporated in vacuo, and the residue was purified using HPLC, reverse phase, 20-80% $CH_3CN$/water. At a retention time of 11.78 minutes, 25 mg of the desired product were obtained, mp: 123-125° C.

Example 349

Synthesis of N-(Toluene-4-sulfonyl)-L-(4-methanesulfonyloxy)prolyl-L-4-(N,N-dimethylcarbamyloxy) phenylalanine The starting N-(toluene-4-sulfonyl)-L-(4-methanesulfonyloxy)prolyl-L-4-(N,N-dimethylcarbamyloxy)phenylalanine tert-butyl ester (200 mg) was dissolved in formic acid (5 mL). The reaction mixture was stirred at room temperature for 6 hours. The solvent was evaporated in vacuo to provide the desired product (195 mg), mp: 83-84° C.

Example 371

Synthesis of N-(Toluene-4-sulfonyl)-L-prolyl-4-α-methylbenzyloxy)-L-phenylalanine N-(Toluene-4-sulfonyl)-L-prolyl-L-tyrosine methyl ester (785 mg, 1.89 mmol) was dissolved in DMF (20 mL) at room temperature. To this was added $K_2CO_3$ (1.1 eq, 281 mg) and 1-bromoethyl benzene (1.1 eq, 284 µL). The reaction was stirred for 12 hours at room temperature. Ethyl acetate (100 mL) was added, and the organic layer washed several times with brine (5×50 mL). The organic layer was dried over $MgSO_4$. Upon filtration and evaporation of the solvents under reduced pressure, an oil was isolated. The crude material was purified by elution on silica gel (EtOAc/hexanes (1:4)). The desired material was isolated in 32% yield (330 mg, 0.6 mmol). The methyl ester (330 mg. 0.6 mmol) was then converted to the corresponding acid upon treatment with NaOH (1.1 eq, 27 mg), in $MeOH:H_2O$ (1:1) (15 mL), for 4 hours at room temperature. EtOAc was added as well as water. The aqueous layer was collected and acidified with 1N HCl to pH 2.5, and reextracted with EtOAc. The organic layer was dried over MgSO$_4$. Upon filtration and evaporation of the solvents under reduced pressure, a foam was isolated in quantitative yields.

NMR data was as follows:
$^1$H NMR (300 MHz, CDCl$_3$): δ=7.71 (bd, 2H), 7.34 (m, 7H), 7.20 (m, 1H), 7.01 (m, 2H), 6.80 (d, 2H, J=8.37 Hz), 5.27 (m, 1H), 4.75 (m, 1H), 4.04 (m, 1H), 3.23-2.93 (m, 4H), 2.42 (s, 3H), 1.85 (m, 1H), 1.60 (d, 3H, J=6.09 Hz), 1.36-1.26 (m, 3H).
$^{13}$C NMR (75 MHz, CDCl$_3$): δ=174.74, 172.22, 157.53, 145.00, 143.77, 133.42, 130.76, 130.58, 129.14, 128.60, 128.48, 127.94, 126.15, 116.57, 76.39, 62.73, 53.90, 50.09, 37.09, 25.07, 24.52, 22.17.

Mass Spectroscopy: (FAB) 537 (M+H).

Example 372

Synthesis of N-(Toluene-4-sulfonyl)-L-prolyl-4-(2-carboxyphenoxy)-L-phenylalanine N-(Toluene-4-sulfonyl)-L-prolyl-L-tyrosine methyl ester (2.14 g, 5.16 mmol) was added to a suspension of sodium hydride, 60% in oil (1.1 eq., 228 mg) in xylenes (50 mL) at 0° C. The reaction mixture was stirred for 5 minutes and cuprous bromide dimethyl sulfide complex (1.4 eq., 1.48 g) was added. The reaction mixture was stirred at 23° C. for 0.5 hr. To this was added sodium 2-iodobenzoate (1.5 eq., 8.06 mmol), and the reaction mixture was refluxed for 12 hours. EtOAc (100 mL) was added, and the organic layer washed with NH$_4$Cl, 10% HCl, and brine, then dried over MgSO$_4$. The crude material was eluted on column chromatography (silica gel), with CHCl$_3$:MeOH (9:1), and isolated as an oil. The acid was prepared by treatment with NaOH (1.1 eq), in MeOH:H$_2$O (1:1) for 4 hours at room temperature. The diacid was isolated as a foam.

NMR data was as follows:
$^1$H NMR (300 MHz, CDCl$_3$): δ=7.71 (m, 2H), 7.29 (m, 4H), 7.19 (m, 4H), 6.72 (m, 1H), 4.84 (m, 1H), 4.13 (m, 1H), 3.39 (m, 1H), 3.11 (m, 3H), 2.43 (s, 3H), 1.89 (m, 1H), 1.48 (m, 3H).
$^{13}$C NMR (75 MHz, CDCl$_3$): δ=172.67, 157.84, 155.89, 155.04, 145.17, 133.61, 133.19, 133.08, 131.69, 131.02, 130.64, 128.42, 127.87, 124.24, 120.04, 119.61, 116.12, 62.81, 50.31, 37.28, 30.69, 24.81, 22.15.

Mass Spectroscopy: (FAB) 553 (M+H).

Example 373

Synthesis of N-(Toluene-4-sulfonyl)-L-prolyl-O-(benzyl)-L-tyrosine

N-(Toluene-4-sulfonyl)-L-Pro-OH was treated with (COCl)$_2$ and DMF in CH$_2$Cl$_2$ to give, after evaporation, N-(Toluene-4-sulfonyl)-L-Pro-Cl. This product was treated with L-Tyr(Bn)-OH and NaOH in THF and H$_2$O, to give, after acidification, extraction, drying with MgSO$_4$, and evaporation the title compound as a clear oil.

NMR data was as follows:
$^1$H NMR (DMSO-d$_6$, 300 MHz): δ=8.04 (d, J=8.2, 1H), 7.70 (d, J=8.1, 2H), 7.42-7.21 (m, 6H), 7.15 (d, J=8.5, 2H), 6.90 (d, J=8.5, 2H), 5.04 (s, 2H), 4.49-4.42 (m, 1H), 4.13-4.09 (m, 1H), 3.33-3.27 (m, 2H), 3.10-2.89 (m, 3H), 2.38 (s, 3H), 1.60-1.35 (m, 4H).
$^{13}$C NMR (DMSO-d$_6$, 75 MHz): δ=172.63, 170.8, 157.0, 143.6, 137.2, 133.8, 130.3, 129.8, 129.4, 128.9, 128.4, 127.6, 125.3, 114.4, 69.1, 61.3, 53.4, 49.0, 35.8, 30.4, 23.8, 21.0.

Mass Spectroscopy: (+FAB, 3-nitrobenzyl alcohol) 523 (M+H).

Example 374

Synthesis of N-(Toluene-4-sulfonyl)-L-prolyl-4-(1-H, 2-oxo-3-methyltetrahydropyrimidin-1-yl)-L-phenylalanine The title compound was prepared from the corresponding t-butyl ester using the procedure described in Method 11.

NMR data was as follows:
$^1$H NMR (CDCl$_3$): δ=7.73 (d, 2H), 7.58 (d, 1H), 7.34 (d, 2H), 7.21 (d, 2H), 7.17 (d, 2H), 4.79 (q, 1H), 4.15-4.11 (m, 1H), 3.68-3.63 (m, 2H), 3.48-3.39 (m, 3H), 3.27 (dd, 1H), 3.17 (dd, 1H), 3.15-3.07 (m, 1H), 2.99 (s, 3H), 2.43 (s, 3H), 2.16-2.08 (m, 2H), 2.00-1.98 (m, 1H).
$^{13}$C NMR (CDCl$_3$): δ=173.4, 172.2, 164.2, 156.4, 144.4, 142.5, 134.1, 133.0, 130.2, 130.0, 127.9, 126.2, 62.1, 53.4, 49.5, 48.9, 47.9, 36.5, 35.9, 30.2, 24.2, 22.0, 21.4.

Example 375

Synthesis of N-(Toluene-4-sulfonyl)-L-prolyl-4-(2-methoxyphenyl)-L-phenylalanine The title compound was prepared from the corresponding t-butyl ester using the procedure described in Method 11.

NMR data was as follows:
$^1$H NMR (CD$_3$OD): δ=7.70 (m, 2H), 7.36 (m, 4H), 7.22 (m, 4H), 6.98 (m, 2H), 4.75 (m, 1H), 4.10 (m, 1H), 3.71 (s, 3H), 3.29 (m, 2H), 3.11 (m, 2H), 2.39 (s, 3H), 1.75 (m, 1H), 1.53 (m, 3H).
$^{13}$C NMR(CD$_3$OD): δ=174.4, 174.2, 158.1, 145.9, 138.9, 136.7, 135.1, 131.2, 130.9, 130.8, 130.2, 129.9, 129.1, 122.0, 112.6, 63.3, 55.9, 54.6, 50.5, 37.9, 31.5, 25.2, 21.4.

Example 376

Synthesis of N-(Toiuene-4-sulfonyl)-L-prolyl-4-(2-methoxyphenyl)-L-phenylalanine The title compound was prepared from the corresponding t-butyl ester using the procedure described in Method 11.

NMR data was as follows:
$^1$H NMR (CDCl$_3$): δ 8.41 (d, 1H), 8.21 (s, 1H), 8.03 (d, 1H), 7.98 (s, 1H), 7.74 (d, 2H), 7.39 (d, 1H), 7.33 (d, 2H), 4.72-4.68 (m, 1H), 4.17-4.13 (m, 1H), 3.54-3.34 (m, 3H), 3.20-3.12 (m, 1H), 2.82 (s, 6H)m 2.43 (s, 3H), 2.09-2.04 (m, 1H), 1.79-1.59 (m, 3H).
$^{13}$C NMR (CDCl$_3$): δ=173.7, 171.8, 154.5, 147.2, 144.4, 137.8, 135.5, 133.2, 130.1, 127.9, 126.4, 62.2, 53.0, 49.5, 38.5, 36.0, 30.3, 24.4, 21.4.

Example 377

Synthesis of N-(Toluene-4-sulfonyl)-L-prolyl-4-(2,4,5-trioxo-3-(3-chlorophenyl)-tetrahydroimidazol-1-yl)-L-phenylalanine benzyl ester The compound was prepared by treatment of N-(toluene-4-sulfonyl)-L-prolyl-4-[(3-chlorophenyl ureido)-tetrahydroimidazol-1-yl]-L-phenylalanine isopropyl ester with oxalyl chloride in methylene chloride. The crude product was purified by flash chromatography (silica, 3:2 Hex: EtOAc) to afford a white solid. (0.410 g, 50%).

MS ((+)ESI, m/z (%) 746 (100[M+H]+) (746/748 1Cl)

Example 378

Synthesis of N-(Phenyl-sulfonyl)-D-prolyl-L-4-(2,6-dimethoxyphenyl)phenylalanine The title compound was prepared by coupling of 2,6-dimethoxyphenylboronic acid and 4'-iodophenylalanine derivates to provide dimethoxybiphenylalanines such as the title compound following procedures outlined in Hagmann et al., *Bioorganic & Medicinal Chemistry Letters*, 2001; 11(20): 2709-2713; Kamenecka et al., *Bioorganic & Medicinal Chemistry Letters*, 2002; 12(16): 2205-2208; and Doherty et al., *Bioorganic & Medicinal Chemistry Letters*, 2003; 13(11): 1891-1895.

Example 379

Synthesis of N-(3,5-dichlorophenyl-sulfonyl)-D-prolyl-L-4-[4-(methylcarbonyl aminobutyl)-2, 5-Dioxo-imidazolidin-1-yl]phenylalanine The title compound was prepared following procedures outlined in WO 01/54690.

Example 380

Synthesis of N-(2,6-dichlorophenyl-carbonyl)-L-4-(2,6-dimethoxyphenyl)phenylalanine The title compound was prepared by coupling of 2,6-dimethoxyphenylboronic acid and 4'-iodophenylalanine derivates to provide dimethoxybiphenylalanines such as the title compound following procedures outlined in WO 99/36393 and Sircar et al., *Bioorganic & Medicinal Chemistry*, 2002; 10(6): 2051-2066.

Example 381

Synthesis of N—[N-(3-pyridinesulfonyl)-L-3,3-dimethyl-4-thiaprolyl]-O-[1-methylpiperazin-4-ylcarbonyl]-L-tyrosine isopropyl ester 3-Pyridinesulfonyl Chloride
The free base of the title compound may be prepared from 3-pyridinesulfonic acid (Aldrich) by a published procedure: Corey et al., *J. Org. Chem.* 1989, 54(2): 389. Alternatively, the hydrochloride of the title compound may be prepared from 3-pyridinesulfonic acid (Aldrich) by published procedures: Crowell et al., *J. Med. Chem.* 1989, 32(11): 2436; Karaman et al., *J. Am. Chem. Soc.* 1992, 114(12): 4889.

L-3,3-Dimethyl-4-thiaproline
The title compound may be prepared from L-penicillamine (Aldrich) by published procedures: Samanen et al., *J. Med. Chem.* 1989, 32(2): 466; Nagasawa et al., *J. Med. Chem.* 1984, 27(5): 591.

N-(3-pyridinesulfonyl)-L-3,3-dimethyl-4-thiaproline
A pH=7.4 buffer was prepared by dissolving disodium hydrogen phosphate (43.2 g, 0.304 mol) and potassium dihydrogen phosphate (11.8 g, 0.0870 mol) in $H_2O$ to give a volume of 1.0 L. To a 0° C. solution of L-3,3-dimethyl-4-thiaproline (25.4 g, 0.157 mol) in 700 mL pH=7.4 buffer was added with stirring a solution of 3-pyridinesulfonyl chloride (28.0 g, 0.157 mol) in 300 mL $CH_2Cl_2$. The mixture was stirred for 24 h while warming to room temperature, and was acidified to pH=2 by addition of 3 M $H_2SO_4$, precipitating a yellow solid. The yellow solid was isolated by filtration of both phases, and the $CH_2Cl_2$ layer was separated and evaporated to afford additional yellow solid. The combined yellow solids were stirred in 700 mL $H_2O$ for 1 h, to dissolve associated inorganic salts, and isolated again by filtration. The two aqueous layers were combined and extracted with EtOAc (3×500 mL). The EtOAc layers were washed with brine, treated with sodium sulfate, filtered, and evaporated to afford additional yellow solid. All aliquots of yellow solid were combined to afford 36.1 g (76%) N-(3-pyridinesulfonyl)-L-3,3-dimethyl-4-thiaproline.

N-[N-(3-pyridinesulfonyl)-L-3,3-dimethyl-4-thiaprolyl]-L-tyrosine isopropyl ester
1-(3-Dimethylaminopropyl)-3-ethylcarbodiimide hydrochloride (4.83 g, 0.0253 mol) was added to a 0° C. solution of N-(3-pyridinesulfonyl)-L-3,3-dimethyl-4-thiaproline (6.37 g, 0.0211 mol), L-tyrosine isopropyl ester hydrochloride (5.48 g, 0.0211 mol), 1-hydroxybenzotriazole (5.69 g, 0.0421 mol), and 4-methylmorpholine (2.32 mL, 2.13 g, 0.0211 mol) dissolved in 125 mL DMF. The mixture was stirred for 16 h while warming to room temperature, and 200 mL EtOAc and 200 mL $H_2O$ were added. The mixture was shaken, and the aqueous layer was separated, and the organic layer was washed with 0.2 M citric acid (2×100 mL), $H_2O$ (2×100 mL), sat. $NaHCO_3$ (2×100 mL), $H_2O$ (2×100 mL), and brine (2×100 mL). The organic layer was treated with sodium sulfate, filtered, and evaporated to afford 9.40 g (86%) N-[N-(3-pyridinesulfonyl)-L-3,3-dimethyl-4-thiaprolyl]-L-tyrosine isopropyl ester as a yellow foam. $^1H$ NMR ($CDCl_3$, 300 MHz) δ 9.08 (bs, 1H), 8.86 (bs, 1H), 8.16 (dt, $J_d$=8.1 Hz, $J_t$=2.0 Hz, 1H), 7.51 (dd, J=8.0 Hz, J=4.6), 7.07 (d, J=8.1 Hz, 2H), 6.87 (d, J=8.1 Hz, 1H), 6.74 (d, J=8.1 Hz, 2H), 5.96 (bs, 1H), 5.06 (sept, J=6.3, 1H), 4.83 (dt, $J_d$=6.0 Hz, $J_t$=7.8 Hz, 1H), 4.57 (d, J=9.3 Hz, 1H), 4.46 (d, J=9.3 Hz, 1H), 3.91 (s, 1H), 3.09 (dd, J=14.1 Hz, J=5.4 Hz, 1H), 2.98 (dd, J=14.1 Hz, J=7.5 Hz, 1H), 1.25 (t, J=6.6 Hz, 6H), 1.18 (s, 3H), 1.13 (s, 3H). $^{13}C$ NMR ($CDCl_3$, 75 MHz) δ 170.5, 168.0, 155.2, 154.2, 148.6, 135.9, 130.7, 127.6, 124.1, 115.5, 105.5, 73.7, 69.7, 54.7, 53.4, 50.5, 37.5, 29.2, 23.7, 21.62, 21.55.

N-[N-(3-pyridinesulfonyl)-L-3,3-dimethyl-4-thiaprolyl]-O-[1-methylpiperazin-4-ylcarbonyl]-L-tyrosine isopropyl ester N-[N-(3-pyridinesulfonyl)-L-3,3-dimethyl-4-thiaprolyl]-L-tyrosine isopropyl ester (1.51 g, 2.89 mmol) and 4-nitrophenyl chloroformate (0.58 g, 2.89 mmol) were dissolved in 40 mL $CH_2Cl_2$, and the solution was stirred for 15 min while cooling in a −15° C. slurry of 4:1 $H_2O$/EtOH and dry ice. To the solution was added $Et_3N$ (1.00 mL, 0.73 g, 7.23 mol) with stirring over 2 min, and the solution was stirred for 1 h at −15° C. To the resulting suspension was added 1-methylpiperazine (0.32 mL, 0.289 g, 2.89 mmol) with stirring over 1 min, and the mixture was stirred for 16 h while warming to room temperature. The mixture was diluted with 40 mL hexanes, and washed with 10% (w/v) $K_2CO_3$ (4×50 mL) until no yellow color (4-nitrophenol) was seen in the aqueous layer. The organic layer was washed with brine (75 mL), treated with sodium sulfate, filtered, and evaporated to give a light yellow residue. The residue was purified by chromatography on silica gel using 70:25:5 $CH_2Cl_2$/EtOAc/EtOH to afford 1.53 g (84%) N-[N-(3-pyridinesulfonyl)-L-3,3-dimethyl-4-thiaprolyl]-O-[1-methylpiperazin-4-ylcarbonyl]-L-tyrosine isopropyl ester as a colorless foam. $^1H$ NMR ($CDCl_3$, 300 MHz) δ 9.09 (d, J=2.1 Hz, 1H), 8.87 (dd, J=4.9 Hz, J=1.6 Hz, 1H), 8.16 (dt, $J_d$=8.4 Hz, $J_t$=2.0 Hz, 1H), 7.51 (dd, J=8.2 Hz, J=4.9 Hz, 1H), 7.21 (d, J=8.4 Hz, 2H), 7.02 (d, J=8.4 Hz, 2H), 6.89 (d, J=7.8 Hz, 1H), 5.05 (sept, J=6.4 Hz, 1H), 4.84 (q, J=7.0 Hz, 1H), 6.59 (d, J=9.9 Hz, 1H), 4.47 (d, J=9.9 Hz, 1H), 3.90 (s, 1H), 3.67 (bs, 2H), 3.58 (bs, 2H), 3.18-3.03 (m, 2H), 2.45 (t, J=10.2 Hz, 4H), 2.34 (s, 3H), 1.26 (d, J=6.0 Hz, 3H), 1.23 (d, J=6.6 Hz, 3H), 1.20 (s, 3H), 1.17 (s, 3H). $^{13}C$ NMR (CDCl$_3$, 75 MHz) δ 170.4, 167.8, 154.3, 153.7, 150.6, 148.7, 135.8, 133.1, 133.0, 130.4, 133.0, 121.8, 73.7, 69.7, 54.8, 54.6, 54.5, 50.5, 46.1, 44.3, 43.8, 37.6, 29.1, 23.8, 21.6, 21.5.

Synthesis of Compounds of Formulae III-IX

The following Methods may be used to prepare the compounds of Formulae III-IX.

Method A

Methyl Ester Preparation Procedure

Amino acid methyl esters can be prepared using the method of Brenner and Huber *Helv. Chim. Acta* 1953, 36, 1109.

Method B

BOP Coupling Procedure

The desired dipeptide ester was prepared by the reaction of a carboxylic acid (1 equivalent) with the appropriate amino acid ester or amino acid ester hydrochloride (1 equivalent), benzotriazol-1-yloxy-tris(dimethylamino)phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method C

Hydrogenation Procedure I

Hydrogenation was performed using 10% palladium on carbon (10% by weight) in methanol at 30 psi overnight. The mixture was filtered through a pad of Celite and the filtrate concentrated to yield the desired compound.

Method D

Hydrolysis Procedure I

To a chilled (0° C.) THF/H$_2$O solution (2:1, 5-10 mL) of the appropriate ester was added LiOH (or NaOH) (0.95 equivalents). The temperature was maintained at 0° C. and the reaction was complete in 1-3 hours. The reaction mixture was extracted with ethyl acetate and the aqueous phase was lyophilized resulting in the desired carboxylate salt.

Method E

Ester Hydrolysis Procedure II

To a chilled (0° C.) THF/H$_2$O solution (2:1, 5-10 mL) of the appropriate ester was added LiOH (1.1 equivalents). The temperature was maintained at 0° C. and the reaction was complete in 1-3 hours. The reaction mixture was concentrated and the residue was taken up into H$_2$O and the pH adjusted to 2-3 with aqueous HCl. The product was extracted with ethyl acetate and the combined organic phase was washed with brine, dried over MgSO$_4$, filtered and concentrated to yield the desired acid.

Method F

Ester Hydrolysis Procedure III

The appropriate ester was dissolved in dioxane/H$_2$O (1:1) and 0.9 equivalents of 0.5 N NaOH was added. The reaction was stirred for 3-16 hours and then concentrated. The resulting residue was dissolved in H$_2$O and extracted with ethyl acetate. The aqueous phase was lyophilized to yield the desired carboxylate sodium salt.

Method G

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in Et$_2$O and reconcentrated. This procedure was repeated and the resulting solid was placed under high vacuum overnight.

Method H tert-Butyl Ester Hydrolysis Procedure I

The tert-butyl ester was dissolved in CH$_2$Cl$_2$ and treated with TFA. The reaction was complete in 1-3 hr at which time the reaction mixture was concentrated and the residue dissolved in H$_2$O and lyophilized to yield the desired acid.

Method I

EDC Coupling Procedure I

To a CH$_2$Cl$_2$ solution (5-20 mL) of a carboxylic acid (1 equivalent), the appropriate amino acid ester hydrochloride (1 equivalent), N-methylmorpholine (1.1-2.2 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was poured into H$_2$O and the organic phase was washed with sat. NaHCO$_3$, brine, dried (MgSO$_4$ or Na$_2$SO$_4$), filtered and concentrated. The crude product was purified by column chromatography.

Method J

EDC Coupling Procedure II

To a DMF solution (5-20 mL) of a carboxylic acid (1 equivalent), the appropriated amino acid ester hydrochloride (1 equivalent), Et$_3$N (1.1 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was partitioned between EtOAc and H$_2$O and the organic phase washed with 0.2 N citric acid, H$_2$O, sat. NaHCO$_3$, brine, dried (MgSO$_4$ or Na$_2$SO$_4$), filtered and concentrated. The crude product was purified by column chromatography or preparative TLC.

Method K tert-Butyl Ester Hydrolysis Procedure II

The tert-butyl ester was dissolved in CH$_2$Cl$_2$ (5 mL) and treated with TFA (5 mL). The reaction was complete in 1-3 hours at which time the reaction mixture was concentrated and the residue dissolved in H₂O and concentrated. The residue was redissolved in H₂O and lyophilized to yield the desired product.

Method L

Carbamate Formation Procedure I

Into a reaction vial were combined 15.2 mmol, 1.0 eq. of the starting hydroxy compound (typically a tyrosine derivative) and 1.86 g (15.2 mmol, 1.0 eq) DMAP. Methylene chloride (50 mL), triethylamine (2.12 mL, 1.54 g, 15.2 mmol, 1.0 eq), and dimethylcarbamyl chloride (1.68 mL, 1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The work-up of the reaction solution was as follows: 50 mL EtOAc and 50 mL hexanes was added to the reaction mixture, and the resulting mixture was washed with 0.5 M citric acid (3×50 mL), water (2×50 mL), 0% $K_2CO_3$ (2×50 mL), and sat. NaCl (1×50 mL); dried with $MgSO_4$, filtered and evaporated to afford the desired compound.

Method M

Carbamate Formation Procedure II

Into a reaction vial were combined 84.34 mmol (1.0 eq) of the starting hydroxy compound (typically a tyrosine derivative) and 17.0 g (84.34 mmol, 1.0 eq) 4-nitrophenyl, chloroformate. Methylene chloride (700 mL) was added and the vial was capped with a septum. A nitrogen line was attached and the vial was immersed in a 4:1 water/ethanol dry ice slurry with stirring to cool to −15° C. Triethylamine (29.38 mL, 21.33 g, 210.81 mmol, 2.5 eq) was added over five minutes with stirring and the stirring was continued at −10 to−15° C. for 1 h. N-Methyl piperazine (9.35 mL, 8.45 g, 84.34 mmol, 1.0 eq) was added over three minutes with stirring and stirring was continued overnight while warming to room temperature. The reaction mixture was diluted with 700 mL hexanes and the resulting mixture was washed repeatedly with 10% $K_2CO_3$, until no yellow color (from 4-nitrophenol) is observed in the aqueous layer. The mixture was then washed with sat. NaCl, dried over anhydrous $MgSO_4$, filtered and evaporated. The residue was dissolved in 500 mL of ethanol and evaporated to remove triethylamine. The residue was again dissolved in 500 mL of ethanol and evaporated to remove triethylamine. The residue was then dissolved in 400 mL of ethanol and 600 mL of water was added with stirring to precipitate a solid or oil. If an oil if formed, the oil is stirred vigorously to induce it to solidify. The solid is then isolated by filtration. Dissolution, precipitation, and filtration are repeated once and the resulting solid is rinsed with water to remove traces of yellow color. The solid is then subjected to high vacuum until the mass remains constant thereby affording the desired carbamyloxy compound.

Method N

Preparation of 5-Iodo-4(3H)-pyrimidinone

The procedure of Sakamoto et. al. (Chem. Pharm. Bull. 1986, 34(7), 2719-2724) was used to convert 4(3H)-pyrimidinone into 5-iodo-4(3H)-pyrimidinone, which was of sufficient purity for conversion to 4-chloro-5-iodopyrimidine.

Method O

Preparation of 4-Chloro-5-iodopyrimidine

5-Iodo-4(3H)-pyrimidinone (1 eq.) was suspended in toluene to which was added $POCl_3$ (2.0 eq.). The reaction mixture was heated to reflux for 3 hours, and then cooled and concentrated. The residue was suspended in water, adjusted to pH=7 by addition of 4N sodium hydroxide, and extracted with ethyl acetate. The organic extracts were washed with brine, dried ($MgSO_4$), filtered and stripped to give a red oil. The crude product was dissolved in methanol and silica gel was added. Following concentration, the coated silica gel was loaded onto a plug of silica gel and elution with ethyl acetate/hexanes yielded the title compound.

Method P

Preparation of N-(5-Iodopyrimidin-4-yl)-L-4-(N,N-dimethylcarbamyloxy)phenylalanine tert-Butyl Ester A solution 4-chloro-5-iodopyrimidine (1.0 eq.), L-4-(N,N-dimethylcarbamyloxy)-phenylalanine tert-butyl ester (1.0 eq), and N,N-diisoproylethyl amine (2.0 eq) in tetrahydrofuran was heated at reflux for 16 hours. The reaction mixture was then cooled and diluted with water and ethyl acetate. The organic phase was washed with 0.2 N citric acid, water, saturated $NaHCO_3$, brine, dried ($MgSO_4$), filtered and concentrated. The residue was purified by silica gel chromatography using ethyl acetate/hexanes to afford the title compound.

Method Q

Suzuki Coupling Procedure I

To an ethyleneglycol dimethyl ether solution of tetrakis (triphenylphosphine)palladium (0.04 eq) was added N-(5-iodopyrimidin-4-yl)-L-4-(N,N-dimethylcarbamyloxy)phenylalanine tert-butyl ester (1.0 eq.). After stirring for approximately ten minutes a boronic acid or ester (1.2 eq) and 2M $Na_2CO_3$ (2.0 eq) were added, and the reaction flask was evacuated and then flushed with nitrogen gas. The reaction was heated at reflux from three to sixteen hours. The reaction mixture was then cooled, diluted with water and ethyl acetate, and the organic phase was washed with 0.2 N citric acid, water, saturated $NaHCO_3$, brine, dried ($MgSO_4$), filtered and concentrated. Alternatively, the cooled reaction mixture was diluted with ethyl acetate and washed with water, saturated $NaHCO_3$, dried ($MgSO_4$), filtered and concentrated. Either column chromatography or preparative thin layer chromatography on silica gel using ethyl acetate/hexanes afforded the desired product.

Method R

Suzuki Coupling Procedure II

To a dimethylformamide solution of tetrakis(triphenylphosphine)-palladium (0.02-0.05 eq) was added N-(5-iodopyrimidin-4-yl)-L-4-(N,N dimethylcarbamyloxy)phenylalanine tert-butyl ester (1.0 eq.). After stirring for approximately ten minutes, the boronic acid (1.1-4.0 eq) and $K_3PO_4$ (1.5-2.0 eq) were added, and the reaction was heated at 100° C. for three to sixteen hours. The reaction mixture was then cooled, diluted with water and ethyl acetate, and the organic phase was washed with 0.2 N citric acid, water, saturated $NaHCO_3$, brine, dried ($MgSO_4$), filtered and concen-

Method S

Suzuki Coupling Procedure III

An ethyleneglycol dimethyl ether/2M $Na_2CO_3$ (1:1 by volume) solution of tetrakis(triphenylphosphine)palladium (0.04 eq), N-(5-iodopyrimidin-4-yl)-L-4-(N,N-dimethylcarbamyloxy)phenylalanine tert-butyl ester (1.0 eq.), the boronic acid (1.1 eq) and lithium chloride (3.0 eq) was heated to reflux for approximately six hours. The cooled reaction mixture was diluted with ethyl acetate and washed with water, brine, dried ($MgSO_4$), filtered and concentrated. The residue was purified by silica gel column chromatography using ethyl acetate/hexanes to afford the desired product.

Method T

Suzuki Coupling Procedure IV

An ethyleneglycol dimethyl ether/2M $Na_2CO_3$, (1:1 by volume) solution of tetrakis(triphenylphosphine)palladium (0.05 eq), N-(5-iodopyrimidin-4-yl)-L-4-(N,N-dimethylcarbamyloxy)phenylalanine tert-butyl ester (1.0 eq.), the boronic acid (1.5 eq) and tri-o-tolylphosphine (0.1 eq) was heated to reflux for approximately three hours. The cooled reaction mixture was diluted with ethyl acetate and water and washed with water, brine, dried ($MgSO_4$), filtered and concentrated. The residue was purified by preparative thin layer chromatography on silica gel using ethyl acetate/hexanes to afford the desired product.

Method U

Heck Reaction Procedure I

A dimethylformamide solution of N-(5-iodopyrimidin-4-yl)-L-4-(N,N-dimethylcarbamyloxy)phenylalanine tert-butyl ester (1.0 eq.), N,N-dimethylacrylamide (2.0 eq), and triethylamine (6.0 eq) was degassed with nitrogen and then dichlorobis-(triphenylphosphine)palladium was added. The reaction was warmed to 90° C. under a stream of nitrogen for 16 hours. The cooled reaction mixture was diluted with ethyl acetate and water and washed with water, brine, dried ($MgSO_4$), filtered and concentrated. The residue was purified by column chromatography on silica gel using ethyl acetate/hexanes followed by preparative thin layer chromatography on silica gel using ethyl acetate/hexanes to afford the desired product.

Method V

Hydrogenation Procedure II

N-(5-(2-N,N-dimethylcarbamylethyl)pyrimidin-4-yl)-L-4-(N,N-dimethylcarbamyloxy)-phenylalanine tert-butyl ester was dissolved in ethanol to which was added 10% palladium on carbon. The reaction mixture was hydrogenated at 35 psi hydrogen for approximately five hours. The reaction mixture was filtered through a pad of Celite, and the filtrate was concentrated. The residue was purified by preparative thin layer chromatography on silica gel using methanol/dichloromethane to afford the desired product.

Method W

Heck Reaction Procedure II

To a tetrahydrofuran solution of N-(5-iodopyrimidin-4-yl)-L-4-(N,N-dimethylcarbamyloxy)phenylalanine tert-butyl ester (1.0 eq) dichlorobis(triphenylphosphine)palladium, triethylamine (0.05 eq) and triphenylphosphine (0.025 eq) was added phenylacetylene (1.5 eq) and triethylamine (1.5 eq). After twenty minutes, copper (I) iodide (0.012 eq) was added, and the resulting mixture was stirred overnight at room temperature. The reaction mixture was then diluted with ethyl acetate and water and washed with 0.2 N citric acid, water, saturated $NaHCO_3$, brine, dried ($MgSO_4$), filtered and concentrated. The residue was chromatographed on a silica gel column using ethyl acetate/hexanes. $^1H$ NMR analysis showed that the desired product to be contaminated with the iodopyrimidine starting material. However, the product was used without further purification.

Method X

Hydrogenation Procedure III

Crude N-(5-(2-phenylethynyl)pyrimidin-4-yl)-L-4-(N,N-dimethylcarbamyloxy)phenylalanine tert-butyl ester-was dissolved in ethanol to which was added 10% palladium on carbon and sodium acetate (3.0 eq). The reaction mixture was hydrogenated at 40 psi hydrogen for approximately three hours, then filtered through a pad of Celite, and the filtrate concentrated. The residue was washed with 0.2 N citric acid, water, saturated $NaHCO_3$, brine, dried ($MgSO_4$), filtered and concentrated. Silica gel column chromatography using ethyl acetate/hexanes yielded the desired product.

Method Y

Preparation of N-(6-Chloropyrimidin-4-yl)-L-4-(N,N-dimethylcarbamyloxy)phenylalanine tert-Butyl Ester A solution 4,6-dichloropyrimidine (1.2 eq), L-4-(N,N-dimethylcarbamyloxy)-phenylalanine tert-butyl ester (1.0 eq), and triethylamine (1.05 eq) in ethanol was heated at reflux for 16 hours. The reaction mixture was cooled and concentrated, and the residue was taken-up in water and ethyl acetate. The organic phase was washed with 0.2 N citric acid, water, saturated $NaHCO_3$, brine, dried ($MgSO_4$), filtered and concentrated. The residue was purified by silica gel chromatography using ethyl acetate/hexanes to afford the title compound.

Method Z

Suzuki Coupling Procedure V

An ethyleneglycol dimethyl ether solution of tetrakis(triphenylphosphine)palladium (0.12 eq), N-(6-chloropyrimidin-4-yl)-L-4-(N,N-dimethylcarbamyloxy)phenylalanine tert-butyl ester (1.0 eq.) and triphenylphosphine (0.05 eq) was stirred for approximately ten minutes. The boronic acid or ester (1.2-2.5 eq) and 2M $Na_2CO_3$ (2.0 eq) were added, and the reaction was heated at 90° C. for 16 to 72 hours. The reaction mixture was cooled and concentrated, and the residue was taken up in water and ethyl acetate. The organic phase was washed with 0.2 N citric acid, water, saturated $NaHCO_3$, brine, dried ($MgSO_4$), filtered and concentrated.

The residue was purified by preparative thin layer chromatography on silica gel using ethyl acetate/hexanes to afford the desired product.

Method AA

Preparation of N-(6-CN-Alkylamino)pyrimidin-4-yl)-L-4-(N,N-dimethylcarbamyloxy)phenylalanine tert-Butyl Ester A mixture of N-(6-chloropyrimidin-4-yl)-L-4-(N,N-dimethylcarbamyloxy)phenylalanine tert-butyl ester (1.0 eq) and an alkylamine (10.0 eq) was heated in a sealed tube at 120° C. for 16 hours. The reaction mixture was cooled and diluted with ethyl acetate. The organic portion was washed with 0.2 N citric acid, water, saturated $NaHCO_3$, brine, dried ($MgSO_4$), filtered and concentrated. The residue was purified by silica gel chromatography using ethyl acetate/hexanes to afford the desired compound.

Method BB

Preparation of 4-N-Alkylamino-5-bromo-2-chloropyrimidine

A methanol solution of 5-bromo-2,4-dichloropyrimidine (1.0 eq), the alkylamine (1.05 eq, typically L-4-(N,N-dimethylcarbamyloxy)phenylalanine tert-butyl ester), and N,N-diisoproylethylamine (5.0 eq) was heated to 40° C. for 16 hours. The reaction mixture was then concentrated, and the residue was taken up in ethyl acetate. The organic portion was washed with 0.2 N citric acid, water, saturated $NaHCO_3$, brine, dried ($MgSO_4$), filtered and concentrated. The crude material was purified by silica gel chromatography using ethyl acetate/hexanes to afford the desired compound.

Method CC

Preparation of 4-N-Alkylamino-5-bromo-2-N-alkylaminopyrimidine

An isopropanol solution of the 4-N-alkylamino-5-bromo-2-chloropyrimidine (1.0 eq) and an alkylamine (5.0 eq) was heated in sealed tube at 130° C. for 3-5 hours. The reaction mixture was then cooled and washed with 0.2 N citric acid, water, saturated $NaHCO_3$, brine, dried ($MgSO_4$), filtered and concentrated. The crude material was purified by silica gel chromatography using ethyl acetate/hexanes to afford the desired compound.

Method DD

4-N-Alkylamino-5-bromo-2-N-alkylaminopyrimidine Suzuki Coupling Procedure

To an ethyleneglycol dimethyl ether solution of tetrakis(triphenylphosphine)palladium (0.04 eq) was added an 4-N-alkylamino-5-bromo-2-N-alkylaminopyrimidine (1.0 eq.). After stirring for approximately ten minutes, the boronic acid or ester (1.2 eq) and 2M $Na_2CO_3$ (2.0 eq) was added, and the reaction flask was evacuated and then flushed with nitrogen gas. The reaction was heated at reflux for three to four hours. The reaction mixture was then cooled and diluted with water and ethyl acetate, and the organic phase was washed with 0.2 N citric acid, water, saturated $NaHCO_3$, brine, dried ($MgSO_4$), filtered and concentrated. The residue was purified by either silica gel column or preparative thin layer chromatography using ethyl acetate/hexanes to afford the desired product.

Method EE

Preparation of N-tert-Butoxycarbonyl-4-Iodo-L-phenylalanine Methyl Ester

The title compound was prepared from 4-iodo-L-phenylalanine by standard conditions described by Bodanszky and Bodanszky in *The Practice of Peptide Synthesis*; Springer-Verlag: Berlin, 1984.

Method FF

Preparation of N-tert-Butoxycarbonyl-4-(2,6-dimethoxyphenyl)-L-phenylalanine Methyl Ester To a dimethylformamide solution of tetrakis(triphenylphosphine)palladium (0.02-0.05 eq) was added N-tert-butoxycarbonyl-4-(2,6-dimethoxyphenyl)-L-phenylalanine methyl ester (1.0 eq.). After stirring for approximately ten minutes, 2,6-dimethoxyphenyl boronic acid (1.1 eq) and $K_3PO_4$ (2.0 eq) were added, and the reaction was heated at 100° C. for sixteen hours. The reaction mixture was then cooled, diluted with water and ethyl acetate, and the organic phase was washed with 0.2 N citric acid, water, saturated $NaHCO_3$, brine, dried ($MgSO_4$), filtered and concentrated. Column chromatography on silica gel using ethyl acetate/hexanes afforded the desired product.

Method GG

Preparation of 4-(2,6-Dimethoxyphenyl)-L-phenyalanine Methyl Ester Trifluoroacetic Acid Salt A methylene chloride solution of N-tert-butoxycarbonyl-4-(2,6-dimethoxyphenyl)-L-phenylalanine methyl ester was treated with trifluoroacetic acid for six hours at room temperature. Concentration of the volatiles yielded the title compound.

Method HH tert-Butyl Ester Cleavage Procedure III

A methylene chloride solution of the appropriate tert-butyl ester was treated with trifluoroacetic acid at room temperature. After 2-3 hours the volatiles were evaporated, and the residue was treated again with methylene chloride and trifluoroacetic acid. After 2-3 hours the volatiles were evaporated again to yield the desired compound.

Method II

Preparation of N-(5-Allylpyrimidin-4-yl)-L-4-(N,N-dimethyl-carbamyloxy)phenylalanine tert-Butyl Ester N-(5-Iodo-pyrimidin-4-yl)-L-4-(N,N-dimethyl-carbamyloxy)phenylalanine tert-butyl ester (1.0 eq) was dissolved in dry DMF, with allyltributylstannane (1.1 eq), bis(triphenylphosphine)palladium dichloride (0.03 eq) and LiCl (3.0eq). The reaction mixture was flushed under nitrogen, and

Method JJ

Preparation of N-[5-propylpyrimidin-4-yl]-L-4-(N,N-dimethyl-carbamyloxy)phenylalanine tert-Butyl Ester N-(5-Allylpyrimidin-4-yl)-L-4-(N,N-dimethylcarbamyloxy)phenylalanine tert-butyl ester was dissolved in methanol and treated with a catalytic amount of 10% palladium on carbon. The mixture was shaken under 10 psi hydrogen gas for 3 hours. Upon filtration though a pad of Celite, and evaporation of the solvent under reduced pressure, the desired material was isolated as a foam.

Method KK

Preparation of N-(5-propylpyrimidin-4-yl)-L-4-(N,N-dimethyl-carbamyloxy)phenylalanine N-(5-Propylpyrimidin-4-yl)-L-4-(N,N-dimethylcarbamyloxy)-phenylalanine tert-butyl ester was treated with neat trifluoroacetic acid, and the mixture was stirred for 5 h at room temperature. Upon evaporation of the solvent under reduced pressure, the desired material was isolated as a foam.

Method LL

Preparation of Dimethyl 2-Alkylmalonate

To a suspension of sodium hydride 60% dispersion in mineral oil (1.1 eq) in anhydrous THF was added slowly with stirring dimethyl malonate (1.1 eq), causing the evolution of gas. To the resulting solution was added a bromoalkane, iodoalkane, or trifluoromethanesulfonyloxyalkane (1.0 eq), and the mixture was heated to 50° C. for 48 h, at which point TLC indicated consumption of the bromoalkane, iodoalkane, or trifluoromethanesulfonyloxyalkane. The mixture was diluted with diethyl ether and washed with 70% saturated sodium chloride. The organic extracts were treated with anhydrous magnesium sulfate, filtered, and evaporated to afford a dimethyl 2-alkylmalonate of sufficient purity for immediate conversion to a 5-alkyl-4,6-dihydroxypyrimidine.

Method MM

Preparation of Diethyl 2-Alkylidenylmalonate

Procedure B (p. 2759) of Houve and Winberg (J. Org. Chem. 1980, 45(14), 2754-2763) was employed to react diethyl malonate with a ketone or an aldehyde to afford a diethyl 2-alkylidenylmalonate of sufficient purity for immediate conversion to a diethyl 2-alkylmalonate.

Method NN

Preparation of Diethyl 2-Alkylmalonate

A diethyl 2-alkylidenylmalonate and an equal mass 10% palladium on carbon were suspended in ethanol. The mixture was shaken under 55 psi hydrogen gas for 24 h, at which point TLC indicated consumption of the diethyl 2-alkylidenylmalonate. The mixture was filtered through Celite and evaporated to afford a diethyl 2-alkylmalonate of sufficient purity for immediate conversion to a 5-alkyl-4,6-dihydroxypyrimidine.

Method OO

Preparation of 5-Alkyl-4,6-dihydroxypyrimidine

To a diethyl 2-alkylmalonate or a dimethyl 2-alkylmalonate (1.0 eq) was added formamidine acetate (1.0 eq) and 25% sodium methoxide in methanol (3.3 eq). The resulting slurry was stirred vigorously and heated to 60° C. for 4 h, and then allowed to cool. The slurry was diluted with water, and acidified to pH=2 by addition of HCl. The resulting precipitate was collected by filtration, washed with water, and dried under vacuum, to afford a 5-alkyl-4,6-dihydroxypyrimidine of sufficient purity for immediate conversion to a 5-alkyl-4,6-dichloropyrimidine.

Method PP

Preparation of 5-Alkoxy-4-hydroxypyrimidine

The method (p. 308) of Anderson et al. (Org. Proc. Res. Devel. 1997, 1, 300-310) was employed to react a methyl alkoxyacetate, sodium methoxide, ethyl formate, and formamidine acetate to afford a 5-alkoxy-4-hydroxypyrimidine of sufficient purity for immediate conversion to a 5-alkoxy-4-chloropyrimidine.

Method QQ

Preparation of 5-Alkyl-4,6-dichloropyrimidine or 5-Alkoxy-4-chloropyrimidine

To a 5-alkyl-4,6-dihydroxypyrimidine or a 5-alkoxy-4-hydroxypyrimidine (1.0 eq) were added phosphorus oxychloride (15.0 eq) and N,N-dimethylaniline (1.0 eq), and the mixture was heated to 100° C. for 3 h, and then allowed to cool. The resulting solution was poured onto ice, and the mixture was extracted with dichloromethane. The organic extracts were treated with anhydrous magnesium sulfate, filtered, and evaporated to afford a 5-alkyl-4,6-dichloropyrimidine or a 5-alkoxy-4-chloropyrimidine of sufficient purity for immediate conversion to a 5-alkyl-4-N-alkylamino-6-chloropyrimidine or a 5-alkoxy-4-N-alkylaminopyrimidine.

Method RR

Preparation of 5-Alkyl-4-N-alkylamino-6-chloropyrimidine or 5-Alkoxy-4-N-alkylaminopyrimidine To a solution of a 5-alkyl-4,6-dichloropyrimidine or a 5-alkoxy-4-chloropyrimidine (1.0 eq) in ethanol were added an alkyl amine (1.2 eq, typically L-4-(N,N-dimethylcarbamyloxy)-phenylalanine tert-butyl ester) and diisopropylethylamine (2.0 eq). The mixture was sealed in a pressure tube and heated to 120° C. for 48 h, at which point TLC indicated consumption of the 5-alkyl-4,6-dichloropyrimidine or the 5-alkoxy-4-chloropyrimidine. The mixture was evaporated, and the residue was partitioned between ethyl acetate and pH=4.5 citrate buffer. The organic extracts were washed with saturated sodium chloride, treated with anhydrous magnesium sulfate, filtered, and evaporated. The residue was

Method SS

Preparation of 5-Alkyl-4-N-alkylaminopyrimidine (Procedure I)

A suspension of 5-alkyl-4-N-alkylamino-6-chloropyrimidine (1.0 eq), and an equal mass 10% palladium on carbon, and sodium bicarbonate (5.0 eq) in methanol was shaken under 55 psi hydrogen gas for 16 h, at which point TLC indicated consumption of the 5-alkyl-4-N-alkylamino-6-chloropyrimidine. The mixture was filtered through Celite and evaporated to give a residue, which was partitioned between ethyl acetate and 70% saturated sodium chloride. The organic extracts were treated with anhydrous magnesium sulfate, filtered, and evaporated. The residue was purified by chromatography on silica gel using ethyl acetate and hexanes to afford a pure 5-alkyl-4-N-alkylaminopyrimidine.

Method TT

Preparation of 5-Alkyl-4-N-alkylaminopyrimidine (Procedure II)

A suspension of 5-alkyl-4-N-alkylamino-6-chloropyrimidine (1.0 eq), sodium acetate (10.0 eq), and zinc powder (20.0 eq) in a 9:1 mixture of acetic acid and water was stirred vigorously at 40° C. for 72 h, at which point TLC indicated partial consumption of the 5-alkyl-4-N-alkylamino-6-chloropyrimidine. The supernatant solution was decanted from remaining zinc and evaporated. The residue was partitioned between ethyl acetate and saturated sodium bicarbonate, and the organic extracts were treated with anhydrous magnesium sulfate, filtered, and evaporated. The residue was purified by chromatography on silica gel using ethyl acetate and hexanes to afford a pure 5-alkyl-4-N-alkylaminopyrimidine.

Method UU

Preparation of N-Benzyloxycarbonyl-L-Tyrosine tert-Butyl Ester

To a 0° C. suspension of L-tyrosine tert-butyl ester (Bachem, 1.0 eq) and sodium bicarbonate (2.0 eq) in a 1:1 mixture of THF and water was added slowly with stirring benzyl chloroformate (1.1 eq). After the addition, the mixture was stirred at 0° C. for 3 h and at room temperature for 24 h. The mixture was diluted with diethyl ether, and the aqueous layer was separated. The organic extracts were washed with saturated sodium chloride, treated with anhydrous magnesium sulfate, filtered, and evaporated to afford N-benzyloxycarbonyl-L-tyrosine tert-butyl ester of sufficient purity for immediate conversion of the tyrosine hydroxyl into a carbamate.

Method VV

Preparation of N-Benzyloxycarbonyl-L-4-(N,N-Dimethylcarbamyloxy)phenylalanine tert-Butyl Ester A mixture of N-benzyloxycarbonyl-L-tyrosine tert-butyl ester (1.0 eq), 4-dimethylaminopyridine (1.0 eq), triethylamine (1.5 eq), dimethylcarbamylchloride (1.2 eq), and dichloromethane was heated to 37° C. for 16 h. The mixture was diluted with additional dichloromethane and washed sequentially with 1.0 M potassium bisulfate, water, saturated sodium bicarbonate, and saturated sodium chloride. The organic extracts were treated with anhydrous magnesium sulfate, filtered, and evaporated to afford N-benzyloxycarbonyl-L-4-(N,N-dimethylcarbamyloxy)phenylalanine tert-butyl ester as a white solid of sufficient purity for immediate conversion to L-4-(N,N-dimethylcarbamyloxy)phenylalanine tert-butyl ester.

Method WW

Preparation of L-4-(N,N-Dimethylcarbamyloxy)phenylalanine tert-Butyl Ester

A suspension of N-benzyloxycarbonyl-L-4-(N,N-dimethylcarbamyloxy)phenylalanine tert-butyl ester and an equal mass of 10% palladium on carbon in methanol was shaken under 55 psi hydrogen gas for 1 h, at which point TLC indicated consumption of the N-benzyloxycarbonyl-L-4-(N,N-dimethylcarbamyloxy)phenylalanine tert-butyl ester. The mixture was filtered through Celite and evaporated to afford L-4-(N,N-dimethylcarbamyloxy)-phenylalanine tert-butyl ester of sufficient purity for immediate use in reactions with chloropyrimidines.

Method XX

Preparation of N-Benzyloxycarbonyl-L-4-(4-methylpiperazin-1-ylcarbonyloxy)phenylalanine tert-Butyl Ester To a stirred solution maintained at 0° C. of N-benzyloxycarbonyl-L-tyrosine tert-butyl ester (1.0 eq) and triethylamine (2.5 eq) in dichloromethane was added 4-nitrophenyl chloroformate (1.0 eq). The mixture was stirred for 30 min at 0° C., and then 1-methylpiperazine (1.5 eq) was added, and then the mixture was stirred for 2 h while warming to room temperature. The mixture was diluted with ethyl acetate and washed five times with 10% potassium carbonate and once with saturated sodium chloride. The organic extracts were treated with anhydrous magnesium sulfate, filtered, and evaporated to afford N-benzyloxycarbonyl-L-4-(4-methylpiperazin-1-ylcarbonyloxy)phenylalanine tert-butyl ester of sufficient purity for immediate conversion to L-4-(4-methylpiperazin-1-ylcarbonyloxy)phenylalanine tert-butyl ester.

Method YY

Preparation of L-4-(4-Methylpiperazin-1-ylcarbonyloxy)phenylalanine tert-Butyl Ester A suspension of N-benzyloxycarbonyl-L-4-(4-methylpiperazin-1-ylcarbonyloxy)-phenylalanine tert-butyl ester and an equal mass of 10% palladium on carbon in methanol was shaken under 55 psi hydrogen gas for 1 h, at which point TLC indicated consumption of N-benzyloxycarbonyl-L-4-(4-methylpiperazin-1-ylcarbonyloxy)phenylalanine tert-butyl ester. The mixture was filtered through Celite and evaporated to afford L-4-(4-methylpiperazin-1-ylcarbonyloxy)phenylalanine tert-butyl ester of sufficient purity for immediate use in reactions with chloropyrimidines.

Method ZZ tert-Butyl Ester Cleavage Procedure IV

The tert-butyl ester was dissolved in 96% formic acid and heated to 40° C. for 16 h, at which point TLC indicated consumption of the tert-butyl ester. The mixture was evaporated under a stream of air to give a residue, which was stored under high vacuum for 72 h to afford the pure carboxylic acid.

Method AAA

Preparation of 2,4-Dichloro-5-nitropyrimidine

5-Nitrouracil was treated with phosphorus oxychloride and N,N-dimethylaniline, according to the procedure of Whittaker (J. Chem. Soc. 1951, 1565), to give 2,4-dichloro-5-nitropyrimidine as an orange oil, which was used without distillation immediately in the next step.

Method BBB

Preparation of N-(2-Chloro-5-nitropyrimidin-4-yl)-L-4-(N,N-dimethylcarbamyloxy)phenylalanine tert-Butyl Ester To a stirred solution of L-4-(N,N-dimethylcarbamyloxy) phenylalanine tert-butyl ester (6.38 g, 20.69 mmol) and N,N-diisopropylethylamine (5.40 mL, 4.01 g, 31.03 mmol) in 70 mL $CH_2Cl_2$ at 0° C., was added a solution of 2,4-dichloro-5-nitropyrimidine (3.25 g, 20.69 mmol) in 70 mL of $CH_2Cl_2$, at such a rate the temperature did not exceed 110C. After the addition, the mixture was stirred at 0-10° C. for 15 minutes, at which point TLC indicated conversion of 2,4-dichloro-5-nitropyrimidine. To the mixture were added 100 mL 1 $\underline{M}$ $KHSO_4$ and 200 mL diethyl ether. The organic layer was separated, washed ($H_2O$, sat. $NaHCO_3$, and sat. NaCl), dried ($MgSO_4$), filtered, and evaporated to give N-(2-chloro-5-nitropyrimidin-4-yl)-L-4-(N,N-dimethylcarbamyloxy)phenylalanine tert-butyl ester (9.52 g, 20.45 mmol, 99%) as an orange oil, which was used immediately in the next step.

Method CCC

Preparation of N-(5-Aminopyrimidin-4-yl)-L-4-(N,N-dimethylcarbamyloxy)phenylalanine tert-Butyl Ester A mixture of N-(2-chloro-5-nitropyrimidin-4-yl)-L-4-(N,N-dimethylcarbamyloxy)-phenylalanine tert-butyl ester (9.52 g, 20.45 mmol), Degussa-type 20% palladium on carbon (9.52 g), $NaHCO_3$ (8.59 g, 102.2 mmol), and 165 mL MeOH was shaken under 55 psi $H_2$ for 16 h, at which point TLC indicated conversion of N-(2-chloro-5-nitropyrimidin-4-yl)-L-4-(N,N-dimethylcarbamyloxy)phenylalanine tert-butyl ester into a single product. The mixture was filtered through Celite, and the filtrate was evaporated to give a residue, which was dissolved by addition of 1.50 mL EtOAc and 75 mL $H_2O$. The organic layer was separated, washed (sat. NaCl), dried ($MgSO_4$), filtered, and evaporated to give N-(5-aminopyrimidin-4-yl)-L-4-(N,N-dimethylcarbamyloxy) phenylalanine tert-butyl ester (7.14 g, 17.79 mmol, 87%) as an orange solid, which was used immediately in the next step.

Method DDD

Preparation of N-(5-(N-4-Toluenesulfonylamino) pyrimidin-4-yl)-L-4-(N,N-dimethylcarbamyloxy) phenylalanine tert-Butyl Ester To a stirred solution of N-(5-aminopyrimidin-4-yl)-L-4-(N,N-dimethylcarbamyloxy)-phenylalanine tert-butyl ester (1.00 g, 2.49 mmol) in 10 mL anhydrous pyridine at 0° C., was added in portions 4-toluenesulfonylchloride (0.474 g, 2.49 mmol). After the addition, the resulting red solution was stirred at 0° C. for 3 h, at which point TLC indicated nearly complete conversion of N-(5-aminopyrimidin-4-yl)-L-4-(N,N-dimethylcarbamyloxy)phenylalanine tert-butyl ester. To the mixture was added 3-dimethylaminopropylamine (0.325 mL, 0.264 g, 2.49 mmol), and the mixture was stirred for 30 min while warming to room temperature. The mixture was poured into 100 mL 1 $\underline{M}$ $KHSO_4$, and extracted with 150 mL EtOAc. The organic layer was washed (2×1 $\underline{M}$ $KHSO_4$, $H_2O$, sat. $NaHCO_3$, sat. NaCl), dried ($MgSO_4$), filtered, and evaporated to give a brown residue, which was purified by flash chromatography using EtOAc/hexanes on silica gel, to give N-(5-(N-4-toluenesulfonylamino)pyrimidin-4-yl)-L-4-(N,N-dimethylcarbamyloxy)phenylalanine tert-butyl ester (1.01 g, 1.81 mmol, 73%) as a clear oil.

Method EEE

Preparation of N-(5-(N-Methyl-N-4-toluenesulfonylamino)pyrimidin-4-yl)-L-4-(N,N-dimethylcarbamyloxy)phenylalanine tert-Butyl Ester To a stirred two-phase mixture of 45 mL 1 M NaOH and 25 mL diethyl ether at 0° C., was added in portions 1-methyl-3-nitro-1-nitrosoguanidine (1.33 g, 9.05 mmol). After stirring for 25 min, at which point evolution of $N_2$ had subsided, the bright yellow solution of diazomethane in diethyl ether was transferred by pipette to a stirred solution of N-(5-(N-4-toluenesulfonylamino)pyrimidin-4-yl)-L-4-(N,N-dimethylcarbamyloxy)phenylalanine tert-butyl ester (1.01 g, 1.81 mmol) in 15 mL diethyl ether and 15 mL $CH_2Cl_2$ at 0° C. After stirring for 15 min, at which point TLC indicated complete conversion of N-(5-(N-4-toluenesulfonylamino)pyrimidin-4-yl)-L-4-(N,N-dimethylcarbamyloxy)phenylalanine tert-butyl ester, excess AcOH was added to destroy unreacted diazomethane. The mixture was diluted with 100 mL diethyl ether, washed (2×sat. $NaHCO_3$, sat. NaCl), dried ($MgSO_4$), filtered and evaporated to give a yellow residue, which was purified by flash chromatography using EtOAc/hexanes on silica gel, to give N-(5-(N-methyl-N-4-toluenesulfonylamino)pyrimidin-4-yl)-L-4-(N,N-dimethylcarbamyloxy) phenylalanine tert-butyl ester (0.846 g, 1.48 mmol, 82%) as a clear oil.

Method FFF

Preparation of Diethyl 2-(N,N-Dialkylamino)malonate

The appropriate amine (1.0 eq) was added to a 0° C. solution of diethyl bromomalonate (1.0 eq) and N,N-diisopropylethyl amine (1.1 eq) in ethanol. The mixture was stirred and allowed to warm room temperature. After 16 hours, the reaction mixture was concentrated and the residue was suspended in ethyl acetate and sat. $NaHCO_3$. The organic portion was washed with sat $NaHCO_3$, brine, dried ($MgSO_4$) filtered and concentrated to yield the diethyl 2-(N,N-dialkylamino)malonate, of sufficient purity for immediate conversion to a 5-(N,N-dialkylamino)-4,6-dihydroxypyrimidine.

Method GGG

Preparation of 5-(N,N-Dialkylamino)-4,6-dihydroxypyrimidine

A suspension of a diethyl 2-(N,N-dialkylamino)malonate (1.0 eq), formamidine acetate (1.10 eq.) and 25% sodium methoxide in methanol (3.3 eq) was heated to 65° C. for 3.5 hours. The reaction mixture was cooled and diluted with water. The mixture was acidified to pH=4.5 by addition of dilute HCl. The resulting precipitate was collected by filtration, washed with water, and dried under vacuum to afford a 5-(N,N-dialkylamino)-4,6-dihydroxypyrimidine of sufficient purity for immediate conversion to a 5-(N,N-dialkylamino)-4,6-dichloropyrimidine. Alternatively, the acidified solution was evaporated to give a solid residue, which was extracted with boiling ethanol. The ethanol extracts were filtered and concentrated to give a residue, which was recrystallized from isopropyl alcohol to afford a 5-(N,N-dialkylamino)-4,6-dihydroxypyrimidine of sufficient purity for immediate conversion to a 5-(N,N-dialkylamino)-4,6-dichloropyrimidine.

Method HHH

Preparation of 5-(NAN-Dialkylamino)-4,6-dichloropyrimidine

A 5-(N,N-dialkylamino)-4,6-dihydroxypyrimidine (1.0 eq) was suspended in $POCl_3$ (15.0 eq), and the mixture was heated to reflux for 16 hours. Then the mixture was cooled and carefully poured into a suspension of ethyl ether and aqueous $K_2CO_3$. The organic portion was washed with brine, dried ($MgSO_4$), filtered and concentrated to yield a 5-(N,N-dialkylamino)-4,6-dichloro-pyrimidine of sufficient purity for immediate reaction with alkylamines.

Method III

Preparation of 4-(N-Alkylamino)-5-(N,N-dialkylamino)-6-chloropyrimidine

A 5-(N,N-dialkylamino)-4,6-dichloropyrimidine (1.0 eq), L-4-(N,N-dimethylcarbamyloxy)phenylalanine tert-butyl ester (1.5 eq) and N,N-diisopropyl ethylamine (1.5 eq) were dissolved in ethanol and heated to 120° C. in a sealed tube for 72 h. The cooled reaction mixture was concentrated, and the residue dissolved in ethyl acetate. The ethyl acetate solution was washed with 0.2 N citric acid, water, saturated $NaHCO_3$, brine, dried ($MgSO_4$), filtered and concentrated. The residue was purified by silica gel chromatography using ethyl acetate/hexanes to afford the 4-(N-alkylamino)-5-(N,N-dialkylamino)-6-chloropyrimidine.

Method JJJ

Preparation of 4-(N-Alkylamino)-5-(N,N-dialkylamino)pyrimidine

A 4-(N-Alkylamino)-5-(N,N-dialkylamino)-6-chloropyrimidine (1.0 eq), an equal mass of 10% palladium on carbon, and $NaHCO_3$ (5.0 eq) were suspended in methanol. The reaction mixture was hydrogenated at 45 psi hydrogen for 16 hours and then filtered through a pad of Celite. The filtrate was concentrated, and the residue was dissolved in ethyl acetate. The ethyl acetate solution was washed with water, brine, dried ($MgSO_4$), filtered and concentrated to yield an oil. The oil was purified by column chromatorgraphy on silica gel using ethyl actate and hexanes to afford a pure 4-(N-alkylamino)-5-(N,N-dialkylamino)pyrimidine.

Method KKK

Suzuki Coupling Procedure V

To an ethyleneglycol dimethyl ether solution of tetrakis (triphenylphosphine) palladium (0.04 eq) was added N-(5-bromo-2-chloro-pyrimidin-4-yl)-L-4-(N,N-dimethylcarbamyloxy)phenylalanine tert-butyl ester (1.5 eq.). After stirring for approximately ten minutes o-tolylboronic acid (1.5 eq) and 2M $Na_2CO_3$ (2.0 eq) were added, and the reaction flask was evacuated and flushed with nitrogen gas. The reaction was heated tp reflux for four hours. The reaction mixture was then cooled and diluted with water and methylene chloride. The organic phase was separataed and washed with brine, dried ($MgSO_4$), filtered and concentrated. The residue was purified by silica gel chromatography using ethyl acetate/hexanes to afford the desired product.

Method LLL

Preparation of L-Phenylalanine Isopropyl Ester Hydrochloride or L-Tyrosine Isopropyl Ester Hydrochloride Excess HCl gas was added with stirring to a suspension of L-phenylalanine or L-tyrosine in excess isopropanol. The mixture was heated to reflux for 16 h, and then the volatiles were evaporated under vacuum to give L-phenylalanine isopropyl ester hydrochloride or L-tyrosine isopropyl ester hydrochloride of sufficient purity for immediate use.

Method MMM

Bromopyrimidine Debromination Procedure

The bromopyrimidine was dissolved in isopropyl alcohol to which was added 10% palladium on carbon. The reaction was hydrogenated at 45 psi hydrogen. Filtration and concentration of the filtrate yielded the desired dehalogenated pyrimidine.

Method NNN

Preparation of 2-Isopropropoxypyrimidine

A 2-chloropyrimidine was dissolved in isopropyl alcohol to which was added diisopropylamine. The reaction was heated in a sealed tube for ten days at 130° C. The cooled reaction mixture was concentrated, and the product purified via silica gel column chromatography to yield the 2-isopropoxypyrimidine.

Method OOO

Heck Reaction Procedure III

To a dioxane/triethylamine (1:1 by volume) solution of the N-(5-iodopyridin-4-yl)-L-4-(N,N-dimethylcarbamyloxy) phenylalanine isopropyl ester (1.0 eq), triphenylphosphine (0.05 eq), copper (I) iodide (0.2 eq) was added phenylacetylene (4.0 eq). After flushing the solution for ten minutes with nitrogen gas, dichlorobis(triphenylphosphine)palladium (0.10 eq) was added, and the resulting reaction mixture heated to 50° C. for 16 hours. The reaction mixture was then diluted with ethyl acetate and water, and the organic portion was washed with 0.2 N citric acid, water, saturated $NaHCO_3$, brine, dried ($MgSO_4$), filtered and concentrated. The residue was chromatographed on a silica gel column using ethyl acetate/hexanes to afford the desired product.

Method PPP

Preparation of N-[5-(Phenyl)pyrimidin-4-yl]-L-4-(N N-dimethylcarbamyloxy)phenylalanine tert-Butyl Ester N-[5-iodopyrimidin-4-yl]-L-4-(N,N-dimethylcarbamyloxy)phenylalanine tert-butyl ester (123 mg, 0.2 mmol) was diluted in dry DMF (5 mL) under nitrogen with KOAc (3.0 eq, 73 mg), bis(pinacolato)diboron (1.1 eq, 63 mg), and a catalytic amount of [1,1'-bis(diphenylphosphino)-ferrocene] dichloropalladium (II) complex with dichloromethane (1:1). The reaction was heated for 2 hours at 100° C. To this was added, K3PO4 (2.0 eq, 105 mg), iodobenzene (2.0 eq, 0.056 mL) and an additional catalytic amount of [1,1'bis(diphenylphosphino)-ferrocene]dichloropalladium (II) complex with dichloromethane (1:1). The reaction mixture was stirred overnight at 100° C. EtOAc was added and the organic layer washed with brine, dried over MgSO4. Upon filtration, and evaporation of the solvent under reduced pressure, the crude material was eluted on column chromatography (silica gel) with EtOAc/hexanes 1:1. The desired material was isolated in good yields.

Method QQQ

Preparation of 2-Amino-3-Chloropyrazine

A mixture of 2,3-dichloropyrazine (Lancaster) and ammonium hydroxide was heated in a sealed tube at 100° C. for 24 h resulting in a white precipitate. The precipitate was collected by filtration and dried under vacuum to afford 2-amino-3-chloropyrazine of sufficient purity for immediate conversion to 2-chloro-3-nitropyrazine.

Method RRR

Preparation of 2-Chloro-3-Nitropyrazine

The method (p. 1638) of Hartman et al. (*J. Med. Chem.* 1984, 27(12), 1634-1639) was employed to convert 2-amino-3-chloropyrazine into 2-chloro-3-nitropyrazine of sufficient purity for immediate use.

Method SSS

Preparation of 4-Alkylamino-2-dialkylamino-5-nitropyrimidine

A solution of 1.0 eq 4-alkylamino-2-chloro-5-nitropyrimidine and 5.0 eq dialkylamine in THF was allowed to stand for 16 h. The mixture was diluted with ethyl acetate and then washed with pH=4.5 citrate buffer and saturated sodium chloride. The organic extracts were treated with anhydrous magnesium sulfate, filtered, and evaporated to give a residue, which was purified by chromatography on silica gel using ethyl acetate and hexanes.

Method TTT

Preparation of L-4-(2,6-Dimethoxyphenyl)phenylalanine Methyl Ester

To a stirred solution (DMF, 66 mL) of N-Boc-L-(p-iodo) phenylalanine methyl ester (13.2 g, 32.7 mmol) prepared according to the procedure of Schwabacher et al., *J. Org. Chem.* 1994, 59, 4206-4210) was added $Pd(PPh_3)_4$ (0.03 eq, 1.13 g, 1 mmol). The solution was stirred for 10 min and then 2,6-dimethoxyboronic acid (1.2 eq, 7.1 g, 39 mmol) and $K_3PO_4$ (1.5 eq, 10.4 g, 49 mmol) were added. The reaction flask was evacuated and flushed with nitrogen. This process was repeated twice and the reaction mixture was then heated to 100° C. under a stream of nitrogen for about 3.5 h at which time TLC showed the reaction to be complete (4.5:1 hexanes: EtOAc, $R_f$=0.2, UV active). The reaction mixture was cooled and partitioned between water and ethyl acetate (200 mL each). The organic portion was washed with 0.2N citric acid (3×100 mL), brine (1×100 mL), dried ($MgSO_4$), filtered and stripped to a thick reddish oil, about 13 g. The resulting product was chromatographed on silica gel eluting with 4.5:1 hexanes/EtOAc, $R_f$=0.2. The combined fractions were stripped and treated with methanol saturated with HCl to yield the title intermediate as the hydrochloride salt.

Example 382

Synthesis of N-(2-Chloro-5-nitropyrimidin-4-yl)-L-4-(N,N-dimethylcarbamyloxy)phenylalanine Step A—Preparation of 2,4-Dichloro-5-nitropyrimidine 5-Nitrouracil (Aldrich Chemical Company) was treated with phosphorous oxychloride and N,N-dimethylaniline according to the procedure described in Whittaker, *J. Chem. Soc.* 1951, 1565, to give 2,4-dichloro-5-nitropyrimidine as an orange oil which was used without distillation immediately in the next step.

Step B—Preparation of N-(2-Chloro-5-nitropyrimidin-4-yl)-L-4-(N,N-dimethylcarbamyloxy)phenylalanine tert-Butyl Ester To a stirred solution of L-4-(N,N-dimethylcarbamyloxy) phenylalanine tert-butyl ester (6.38 g, 2069 mol) and N,N-diisopropylethylamine (5.40 mL, 4.01 g, 31.03 mol.) in 70 mL $CH_2Cl_2$ at 0° C., was added a solution of 2,4-dichloro-5-nitropyrimidine (3.25 g, 20.69 mol.) in 70 mL $CH_2Cl_2$ at such a rate that the temperature did not exceed 10° C. After the addition, the mixture was stirred at 0-101C for 15 minutes, at which point TLC indicated conversion of the starting materials. To the mixture were added 100 mL 1 M KHSO4 and 200 mL diethyl ether. The organic layer was separated, washed ($H_2O$, sat. $NaHCO_3$, and sat. NaCl), dried ($MgSO_4$), filtered, and evaporated to give the title compound (9.52 g, 2045 mol., 99%) as an orange oil.

Step C—Preparation of N-(2-Chloro-5-nitropyrimidin-4-yl)-L-4-(N,N-dimethylcarbamyloxy)phenylalanine The title compound was prepared by hydrolysis of the product from Step B using the procedure of Example 386.

Example 383

Synthesis of N-[5-(N-4-Toluenesulfonylamino)pyrimidin-4-yl]-L-4-(N,N-dimethylcarbamyloxy)phenylalanine tert-Butyl Ester Step A—Preparation of N-(5-Aminopyrimidin-4-yl)-L-4-(N,N-dimethylcarbamyloxy)phenylalanine tert-Butyl Ester A mixture of N-(2-chloro-5-nitropyrimidin-4-yl)-L-4-(N,N-dimethylcarbamyloxy)phenylalanine tert-butyl ester (9.52 g, 20.45 mol), Degussa-type 20% palladium on carbon (9.52 g), NaHCO$_3$ (8.59 g, 102.2 mol), and 165 mL MeOH was shaken under 55 psi for 16 h, at which point TLC indicated conversion of the starting material into a single product. The mixture was filtered through Celite, and the filtrate was evaporated to give a residue, which was dissolved by addition of 150 mL EtOAc and 75 mL H$_2$O. The organic layer was separated, washed (sat. NaCl), dried (MgSO$_4$), filtered, and evaporated to give the title intermediate (7.14 g, 17.79 mol, 87%) as an orange solid, which was used immediately in the next step.

Step B—Preparation of N-[5-(N-4-Toluenesulfonylamino)pyrimidin-4-yl]-L-4-(N,N-dimethylcarbamyloxy)phenylalanine tert-Butyl Ester To a stirred solution of the product from Step A (100 g, 2.49 mol) in 10 mL anhydrous pyridine at 0° C., was added in portions 4-toluenesulfonyl chloride (0.474 g, 2.49 mol). After the addition, the resulting red solution was stirred at 0° C. for 3 h, at which point TLC indicated nearly complete conversion of the starting material. To the mixture was added 3-dimethylaminopropylamine (0.325 mL, 0.264 g, 2.49 mol), and the mixture was stirred for 30 min while warming to room temperature. The mixture was poured into 100 mL 1 M KHSO4, and extracted with 150 mL EtOAc. The organic layer was washed (2×1 M KHSO$_4$, H$_2$O, sat. NaHCO$_3$, sat. NaCl), dried (MgSO$_4$), filtered, and evaporated to give a brown residue, which was purified by flash chromatography using EtOAc/hexanes on silica gel, to give the title compound (1.01 g, 1.81 mol., 73%) as a clear oil.

Example 384

Synthesis of N-[5-(N-4-Toluenesulfonylamino)pyrimidin-4-yl]-L-4-(N,N-dimethylcarbamyloxy)phenylalanine The title compound was prepared by hydrolysis of N-[5-(N-4-toluenesulfonylamino)pyrimidin-4-yl]-L-4-(N,N-dimethylcarbamyloxy)-phenylalanine tert-butyl ester using the procedure of Example 386.

Example 385

Synthesis of N-[5-(N-Methyl-N-4-toluenesulfonylamino)pyrimidin-4-yl]-L-4-(N,N-dimethylcarbamyloxy)phenylalanine tert-Butyl Ester To a stirred two-phase mixture of 45 mL 1 M NaOH and 25 mL diethyl ether at 0° C., was added in portions 1-methyl-3-nitro-1-nitrosoguanidine (1.33 g, 9.05 mol). After stirring for 25 min, at which point evolution of N$_2$ had subsided, the bright yellow solution of diazomethane in diethyl ether was transferred by pipette to a stirred solution of the product of Example 383 (1.01 g, 1.81 mol) in 15 mL diethyl ether and 15 mL CH$_2$Cl$_2$ at 0° C. After stirring for 15 min, at which point TLC indicated complete conversion of the starting material, excess AcOH was added to destroy unreacted diazomethane. The mixture was diluted with 100 mL diethyl ether, washed (2×sat. NaHCO$_3$, sat. NaCl), dried (MgSO$_4$), filtered and evaporated to give a yellow residue, which was purified by flash chromatography using EtOAc/hexanes on silica gel, to give the title compound (0.846 g, 1.48 mol, 82%) as a clear oil.

Example 386

Synthesis of N-[5-(N-Methyl-N-4-toluenesulfonylamino)pyrimidin-4-yl]-L-4-(N,N-dimethylcarbamyloxy)phenylalanine The product of Example 385 (0.400 g, 0.700 mol) was dissolved in 8 mL 96% formic acid, and the mixture was heated to 40° C. for 16 h, at which point TLC indicated conversion of the starting material. Most of the formic acid was evaporated under a stream of N$_2$, and then the residue was placed under high vacuum for 48 h to give the title compound (0.382 g, 0.700 mol, 100%) as a clear oil.

Physical data were as follows:
$^1$H NMR (CD$_3$OD): δ=8.33 (bs, 1H), 8.07 (bs, 1H), 7.64 (d, J=8.1 Hz, 2H), 7.42 (d, J=8.1 Hz, 2H), 7.36 (bs, 1H), 7.29 (bs, 2H), 6.99 (d, J=7.5 Hz, 2H), 5.07-4.96 (m, 1H), 3.42-3.31 (m, 1H), 3.25-3.15 (m, 1H), 3.08 (s, 3H), 3.05 (bs, 3H), 2.96 (s, 3H), 2.44 (s, 3H).
$^{13}$C NMR (CD$_3$OD): δ=174.7, 174.6, 164.6, 157.8, 156.8, 152.9., 152.1, 146.5, 135.4, 135.1, 131.7, 131.3, 129.4, 123.2, 122.9, 55.8, 38.2, 37.1, 36.8, 36.7, 21.5.

Using the appropriate starting materials and reagents, the following additional compounds were prepared:

N-[5-(N,N-Di-4-toluenesulfonylamino)pyrimidin-4-yl]-L-4-(N,N-dimethylcarbamyloxy)phenylalanine (Example 387);

N-[5-[N-(1-NA-Methylpyrazol-4-ylsulfonyl)-N-methylamino]pyrimidin-4-yl]-L-4-(N,N-dimethylcarbamyloxy)phenylalanine (Example 388);

N-[5-(N-Methyl-N-4-toluenesulfonylamino)pyrimidin-4-yl]-L-4-(N,N-dimethylcarbamyloxy)phenylalanine isopropyl ester (Example 389);

N-[5-(N-Methyl-N-3-pyridylsulfonylamino)pyrimidin-4-yl]-L-4-(N,N-dimethylcarbamyloxy)phenylalanine tert-butyl ester (Example 390).

Example 391

Synthesis of N-(5-(N-Methyl-N-(1-butylpyrazol-4-yl)sulfonylamino)pyrimidin-4-yl)-L4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 5-Nitrouracil (Aldrich) was converted via Method AAA into 2,4-dichloro-5-nitropyrimidine. L-4-(N,N-Dimethylcarbamyloxy)-phenylalanine tert-butyl ester and 2,4-dichloro-5-nitropyrimidine were coupled via Method BBB, and the product of this coupling was sequentially converted via Methods CCC, DDD (using 1-butyl-4-chlorosulfonylpyrazole), EEE and ZZ to give the title compound.

Physical data were as follows:
$^1$H NMR (CD$_3$OD): δ=8.35 (s, 1H), 8.14 (s, 1H), 7.76 (s, 1H), 7.61 (bs, 1H), 7.23 (bs, 2H), 6.98 (d, 2H), 5.01-4.94 (m, 1H), 4.19 (t, 2H), 3.40-3.28 (m, 1H), 3.26-3.14 (m, 1H), 3.09 (s, 3H), 3.06 (bs, 3H), 2.96 (s, 3H), 1.84 (pent., 2H), 1.29 (sext., 2H), 0.945 (t, 3H).

Example 392

Synthesis of N-(5-(2,4-Dimethoxypyrimidin-5-yl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-dimethylcarbamyloxy)phenylalanine tert-butyl ester and 4-chloro-5-iodopyrimidine were coupled via Method P, and the coupled product was reacted with 2,4-dimethoxypyrimidin-5-yl boronic acid (Frontier Scientific, Inc.) via Method S. The product of this coupling was converted via Method KK to give the title compound.

Example 393

Synthesis of N-(5-(2,6-Difluorophenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with 2,6-difluorophenyl boronic acid (Lancaster Synthesis) via Method R. The product of this coupling was converted via Method HH to give the title compound.

Example 394

Synthesis of N-(5-(2-Hydroxymethylphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-dimethylcarbamyloxy)phenylalanine tert-butyl ester and 4-chloro-5-iodopyrimidine were coupled via Method P, and the coupled product was reacted with 2-(hydroxymethyl)phenyl boronic acid (Lancaster Synthesis) via Method Q. The product of this coupling was converted via Method HH to give the title compound.

Example 395

Synthesis of N-(2-(N-Cyclohexylamino)-5-(2-tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with cyclohexylamine (Aldrich) via Method CC to give a product that was coupled with o-tolyl boronic acid (Aldrich) via Method DD. The product of this coupling was converted via Method ZZ to give the title compound.

Physical data were as follows:

$^1$H NMR (CDCl$_3$): δ=9.68 (s, 1H), 7.3-6.8 (m, 9H), 6.35 (m, 1H), 4.73(m, 1H), 3.81 (bs, 1H), 3.6-3.0 (m, 2H), 3.09 (s, 3H), 3.0 (s, 3H), 2.18 (s, 1.5H), 1.94 (s, 1.5H), 2.1-1.1 (m, 10H).

$^{13}$C NMR (CDCl$_3$): δ=176.11, 175.94, 160.05, 159.79, 154.76, 153.58, 150.05, 150.01, 139.26, 137.84, 137.63, 134.29, 134.15, 130.66, 130.36, 130.11, 129.14, 126.70, 126.41, 121.25, 109.57, 109.39, 56.84, 56.35, 50.15, 36.55, 36.32, 32.34, 31.99, 25.41, 24.86, 19.48, 19.27.

Example 396

Synthesis of N-(2-(N-Methyl-N(1-methylpiperidin-4-yl)amino)-5-(2-tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with 1-methyl-4-(N-methylamino)piperidine (Aldrich) via Method CC to give a product that was coupled with o-tolyl boronic acid (Aldrich) via Method DD. The product of this coupling was converted via Method ZZ to give the title compound.

Physical data were as follows:

$^1$H NMR (CDCl$_3$): δ=8.82 (s, 2H), 8.43 (s, 1H), 7.62 (s, 1H), 7.30-6.90 (m, 8H), 5.42 (br, 1H), 4.66 (br, 2H), 3.60-2.8 (m, 15H), 2.66 (bs, 3H), 2.32 (br, 2H), 2.18 (s, 1.5H), 1.82 (brs, 3.5H).

Example 397

Synthesis of N-(2-(N-Ethyl-N-isopropylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-ethyl-N-isopropylamine (Aldrich) via Method CC to give a product that was coupled with o-tolyl boronic acid (Aldrich) via Method DD. The product of this coupling was converted via Method ZZ to give the title compound.

Physical data were as follows:

$^1$H NMR (CDCl$_3$): δ=8.0-6.5 (br, 1H), 7.66 (s, 0.5H), 7.62 (s, 0.5H), 7.3-6.8 (m, 8H), 6.2 (m, 1H), 4.86 (br, 1H), 4.70 (m, 1H), 3.70-3.08 (m, 4H), 3.09 (s, 3H), 3.0 (s, 3H), 2.14 (bs, 1.5H), 1.92 (bs, 1.5H), 1.4-0.9 (br, 9H).

$^{13}$C NMR (CDCl$_3$): δ=174.38, 174.19, 159.44, 159.16, 155.24, 154.68, 152.39, 150.02, 141.63, 137.77, 137.56, 134.30, 134.09, 130.79, 130.66, 130.54, 130.46, 130.41, 130.33, 130.08, 129.07, 126.54, 126.45, 126.38, 121.21, 121.16, 110.27, 110.01, 56.77, 56.36, 47.59, 36.80, 36.55, 36.32, 20.27, 20.18, 19.57, 19.38, 14.51.

Example 398

Synthesis of N-(5-(2,4-6-Trimethylphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with 2,4,6-trimethylphenyl boronic acid (Frontier Scientific, Inc) via Method R. The product of this coupling was converted via Method HH to give the title compound.

Physical data were as follows:
$^1$H NMR (CD$_3$OD): δ=8.68 (d, 1H), 7.95 (d, 1H), 7.10 (d, 2H), 7.09-6.95(m, 2H), 6.94-6.91 (m, 2H), 5.32-5.27 (m, 1H), 3.42-3.36 (m, 1H), 3.15-3.09 (m, 4H), 2.97 (s, 3H), 2.33 (s, 3H), 2.04 (s, 3H), 1.84 (s, 3H).
$^{13}$CNMR(CD$_3$OD): δ=172.9, 163.5, 161.5, 161.0, 156.7, 152.0, 151.9, 142.6, 141.5, 138.9, 138.6, 135.3, 131.2, 130.4, 130.3, 126.5, 123.0, 120.3, 56.4, 36.7, 36.6, 36.5, 21.2, 19.9, 19.7.

Example 399

Synthesis of N-(5-Isopropylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Diethyl 2-isopropylmalonate (Aldrich) was sequentially converted via Methods OO and QQ into 4,6-dichloro-5-isopropylpyrimidine. L-4-(N,N-Dimethylcarbamyloxy)phenylalanine tert-butyl ester and 4,6-dichloro-5-isopropylpyrimidine were coupled via Method RR, and the product of this coupling was sequentially converted via Methods SS and ZZ to give the title compound.

Physical data were as follows:
$^1$H NMR (CD$_3$OD): δ=8.44 (bs, 1H), 7.94 (bs, 1H), 7.22 (d, 2H), 6.94 (d, 2H), 5.12 (dd, 1H), 3.46 (dd, 1H), 3.19 (dd, 1H), 3.07 (s, 3H), 2.95 (s, 3H), 3.00-2.88 (m, 1H), 1.25 (d, 3H), 1.13 (d, 3H).
$^{13}$C NMR (CD$_3$OD): δ=175.60, 165.74, 163.78, 156.91, 152.38, 151.85, 141.88, 136.30, 131.43, 126.17, 122.87, 57.84, 37.48, 36.81, 36.64, 26.63, 21.09, 20.94.

Example 400

Synthesis of N-(2-(N-Methyl-N-butylamino)-5-(2-tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-butylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=12.5-11.4 (br, 1H), 7.6 (s, 0.5H), 7.58 (s, 0.5H), 7.3-6.8 (m, 8H), 6.3 (m, 1H), 4.7 (m, 1H), 3.7-2.9 (m, 4H), 3.08 (s, 3H), 3.01 (s, 6H), 2.13 (s, 1.5H), 1.91 (s, 1.5H), 1.57 (bs, 2H), 1.33 (m, 2H), 0.96 (t, 3H).
$^{13}$C NMR (CDCl$_3$): δ=174.21, 174.06, 159.37, 159.22, 154.69, 153.52, 169.99, 141.87, 137.77, 137.54, 134.43, 130.78, 130.59, 130.10, 128.98, 126.51, 126.32, 121.17, 121.11, 110.20, 109.96, 56.82, 56.43, 50.03, 36.54, 36.32, 35.91, 29.27, 19.89, 19.52, 19.35, 13.84.

Example 401

Synthesis of N-(2-(N-Ethyl-N-propylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-ethyl-N-propylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=11.0-9.5 (br, 1H), 7.66 (s, 0.5H), 7.64 (s, 0.5H), 7.4-6.8 (m, 8H), 6.28 (m, 1H), 4.65 (m, 1H), 3.70-2.80 (m, 6H), 3.09 (s, 3H), 3.01 (s, 3H), 3.01 (s, 3H), 2.2 (s, 1.5H), 1.85 (s, 1.5H), 1.58 (bs, 2H), 1.05 (bs, 3H), 0.85 (bs, 3H).
$^{13}$C NMR (CDCl$_3$): δ=174.26, 174.11, 159.36, 159.11, 154.70, 153.07, 149.96, 142.43, 137.80, 137.56, 134.54, 134.37, 130.84, 130.74, 130.57, 130.14, 128.86, 126.47, 126.29, 121.10, 121.06, 110.01, 109.71, 56.86, 56.49, 49.62, 63.20, 36.55, 36.32, 20.87, 19.61, 19.41, 12.63, 11.03.

Example 402

Synthesis of N-(2-(N,N-Diethylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N,N-diethylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=12.2 (br, 1H), 7.63 (s, 0.5H), 7.60 (s, 0.5H), 7.40-6.80 (m, 8H), 6.28 (m, 1H), 4.70 (m, 1H), 3.80-2.90 (m, 6H), 3.06 (s, 3H), 2.98(s, 3H), 2.13 (s, 1.5H), 1.92 (s, 1.5H), 0.90 (s, 6H).
$^{13}$C NMR (CDCl$_3$): δ=174.34, 174.15, 159.4, 159.1, 154.70, 152.66, 169.97, 142.06, 137.76, 137.55, 134.44, 134.27, 130.81, 130.57, 130.10, 128.95, 126.48, 126.32, 121.14, 121.08, 110.08, 109.80, 56.78, 56.37, 42.77, 36.53, 36.31, 19.57, 19.38, 12.77.

Example 403

Synthesis of N-(2-(N-Methyl-N-ethylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-ethylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=12.5 (br, 2H), 8.23 (s, 1H), 7.50 (s, 0.5H), 7.44(s, 0.5H), 7.30-6.80 (m, 8H), 6.10 (m, 1H), 4.75 (m, 4H), —3.58 (bs, 2H), 3.30 (m, 1H), 3.00 (m, 1H), 3.08 (s, 3H), 3.00 (s, 3H), 2.93(s, 3H), 2.08 (s, 1.5H), 1.92 (s, 1.5H), 1.50 (s, 3H).
$^{13}$C NMR (CDCl$_3$): δ=174.63, 174.34, 165.72, 159.96, 159.72, 154.88, 152.62, 150.49, 150.45, 140.64, 137.90, 137.81, 133.83, 133.65, 131.03, 130.95, 130.85, 130.63, 130.10, 130.04, 129.76, 129.62, 126.88, 126.72, 121.70, 121.61, 110.69, 110.46, 56.65, 56.11, 45.16, 36.57, 36.35, 35.17, 19.38, 19.17, 11.96.

Example 404

Synthesis of N-(5-Benzyloxypyrimidin-4-yl)-L-phenylalanine

Methyl 2-benzyloxyacetate (Aldrich) was sequentially converted via Methods PP and QQ into 4-chloro-5-benzyloxypyrimidine. L-4-phenylalanine tert-butyl ester (Bachem) and 4-chloro-5-benzyloxypyrimidine were coupled via Method RR, and the product of this coupling was converted via Method ZZ to give the title compound.

Physical data were as follows:
$^1$H NMR (CD$_3$OD): δ=8.54 (s; formate), 8.03 (s, 1H), 7.67 (s, 1H), 7.37-7.31(m, 5H), 7.17-7.12 (m, 5H), 5.11 (s, 2H), 4.78-4.75 (m, 1H), 3.35-3.11 (m, 2H).
$^{13}$C NMR (CD$_3$OD): δ=159.07, 143.16, 132.35, 130.64, 124.52, 123.94, 123.83, 123.59, 123.11, 122.00, 99.47, 66.28, 50.32, 32.05.

Example 405

Synthesis of N-(5-Benzyloxypyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Methyl 2-benzyloxyacetate (Aldrich) was sequentially converted via Methods PP and QQ into 4-chloro-5-benzyloxypyrimidine. L-4-(N,N-Dimethylcarbamyloxy)phenylalanine tert-butyl ester and 4-chloro-5-benzyloxypyrimidine were coupled via Method RR, and the product of this coupling was converted via Method ZZ to give the title compound.

Example 406

Synthesis of N-(5-(N-Methyl-N-4-toluenesulfonylamino)pyrimidin-4-yl)-L-phenylalanine 5-Nitrouracil (Aldrich) was converted via Method AAA into 2,4-dichloro-5-nitropyrimidine. L-4-Phenylalanine tert-butyl ester (Bachem) and 2,4-dichloro-5-nitropyrimidine were coupled via Method BBB, and the product of this coupling was sequentially converted via Methods CCC, DDD, EEE and ZZ to give the title compound.

Example 407

Synthesis of N-(5-(N-Methyl-N-3-pyridinesulfonylamino)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 5-Nitrouracil (Aldrich) was converted via Method AAA into 2,4-dichloro-5-nitropyrimidine. L-4-(N,N-Dimethylcarbamyloxy)-phenylalanine tert-butyl ester and 2,4-dichloro-5-nitropyrimidine were coupled via Method BBB, and the product of this coupling was sequentially converted via Methods CCC, DDD (using 3-chlorosulfonylpyridine), EEE and ZZ to give the title compound.

Physical data were as follows:
$^1$H NMR (CD$_3$OD): δ=8.90 (d, 1H), 8.85 (d, 1H), 8.36 (s, 1H), 8.15 (d, 1H), 7.64 (dd, 1H), 7.53 (bs, 1H), 7.27 (bs, 2H), 6.99 (d, 2H), 5.04-4.87 (m, 1H), 3.40-3.28 (m, 1H), 3.26-3.16 (m, 1H), 3.13 (bs, 3H), 3.09 (s, 3H), 2.97 (s, 3H).

Example 408

Synthesis of N-(S-Phenylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with phenyl boronic acid (Aldrich) via Method S. The product of this coupling was converted via Method HH to give the title compound.

Physical data were as follows:
$^1$H NMR (CD$_3$OD): δ=8.62 (s, 1H), 8.04 (s, 1H), 7.53-7.51 (m, 3H), 7.30-7.27 (m, 2H), 7.17-7.15 (m, 2H), 7.00-6.97 (m, 2H), 5.27-5.22 (m, 1H), 3.45-3.39 (m, 1H), 3.16-3.08 (m, 4H), 2.96 (s, 3H).
$^{13}$C NMR(CD$_3$OD): δ=173.8, 163.7, 157.5, 152.8, 152.3, 142.4, 135.9, 132.2, 132.1, 131.8, 130.7, 123.9, 122.4, 57.7, 37.7, 37.5.

Example 409

Synthesis of N-(3-(N-Methyl-N-4-toluenesulfonylamino)pyrazin-2-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 2,3-Dichloropyrazine (Lancaster) was converted via Method QQQ and RRR into 2-chloro-3-nitropyrazine. L-4-(N,N-Dimethylcarbamyloxy)phenylalanine tert-butyl ester and 2-chloro-3-nitropyrazine were coupled via Method BBB, and the product of this coupling was sequentially converted via Methods CCC, DDD, EEE and ZZ to give the title compound.

Physical data were as follows:

$^1$H NMR (CD$_3$OD): δ=8.07 (s, formate), 7.94 (d, 1H), 7.59 (d, 2H), 7.51 (d, 1H), 7.36 (d, 2H), 7.29 (d, 2H), 7.01 (d, 2H), 4.90 (m, 1H), 3.30-3.18 (m, 2H), 3.08 (s, 3H), 2.96 (s, 3H), 2.94 (s, 3H), 2.43 (s, 3H).

$^{13}$C NMR (CD$_3$OD): δ=177.07, 169.41, 158.64, 150.92, 147.23, 145.92, 139.97, 137.14, 133.12, 129.62, 128.90, 125.69, 124.67, 124.08, 116.86, 49.99, 31.67, 31.28, 30.77, 30.62, 15.46.

Example 410

Synthesis of N-(5-(2,2,2-Trifluoroethyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 1-Trifluoromethanesulfonyloxy-2,2,2-trifluoroethane was sequentially converted via Methods LL, OO and QQ into 4,6-dichloro-5-(2,2,2-trifluoroethyl)pyrimidine. L-4-(N,N-Dimethylcarbamyloxy)-phenylalanine tert-butyl ester and 4,6-dichloro-5-(2,2,2-trifluoroethyl)pyrimidine were coupled via Method RR, and the product of this coupling was sequentially converted via Methods SS and ZZ to give the title compound.

Physical data were as follows:

$^1$H NMR (CD$_3$OD): δ=8.41 (s, 1H), 8.09 (s, formate), 8.06 (s, 1H), 7.24 (d, 2H), 6.96 (d, 2H), 5.06 (m, 1H), 3.60-3.40 (m, 2H), 3.37-3.11 (m, 2H), 3.08 (s, 3H), 2.96 (s, 3H).

$^{13}$CNMR(CD$_3$OD): δ=169.35, 158.91, 156.43, 151.33, 150.97, 148.87, 145.76, 130.21, 125.27, 116.80, 50.80, 31.34, 30.75, 30.60, 26.65, 26.23.

Example 411

Synthesis of N-(5-(N-Methyl-N-3-pyridinesulfonylamino)pyrimidin-4-yl)-L-4-(4-methylpiperazin-1-ylcarbonyloxy)phenylalanine Isopropyl Ester L-Tyrosine (Aldrich) was sequentially converted via Methods LLL, UU, XX and YY into L-4-(4-methylpiperazin-1-ylcarbonyloxy)phenylalanine isopropyl ester. 5-Nitrouracil (Aldrich) was converted via Method AAA into 2,4-dichloro-5-nitropyrimidine. L-4-(4-Methylpiperazin-1-ylcarbonyloxy)phenylalanine isopropyl ester and 2,4-dichloro-5-nitropyrimidine were coupled via Method BBB, and the product of this coupling was sequentially converted via Methods CCC, DDD (using 3-chlorosulfonylpyridine) and EEE to give the title compound.

Example 412

Synthesis of N-(5-Benzylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Diethyl 2-benzylmalonate (Aldrich) was sequentially converted via Methods OO and QQ into 4,6-dichloro-5-benzylpyrimidine. L-4-(N,N-Dimethylcarbamyloxy)phenylalanine tert-butyl ester and 4,6-dichloro-5-benzylpyrimidine were coupled via Method RR, and the product of this coupling was sequentially converted via Methods SS and ZZ to give the title compound.

Physical data were as follows:

$^1$H NMR (CD$_3$OD): δ=8.41 (s, 1H), 8.13 (s, formate), 7.80 (s, 1H) 7.34-7.19 (m, 3H), 7.17 (d, 2H), 7.00 (d, 2H), 6.85 (d, 2H), 5.01 (m, 1H), 3.82 (m, 2H), 3.09 (s, 3H), 3.09-2.97 (m, 2H), 2.97 (s, 3H).

$^{13}$CNMR(CD$_3$OD): δ=159.31, 156.23, 150.88, 148.07, 145.70, 141.38, 131.56, 129.81, 125.30, 124.21, 124.01, 122.37, 116.81, 51.35, 31.68, 30.78, 30.61, 28.28.

Example 413

Synthesis of N-(5-(N-Methyl-N-3-pyridinesulfonylamino)pyrimidin-4-yl)-L4-(4-methylpiperazin-1-ylcarbonyloxy)phenylalanine tert-Butyl Ester L-Tyrosine tert-butyl ester (Bachem) was sequentially converted via Methods UU, XX and YY into L-4-(4-methylpiperazin-1-ylcarbonyloxy)phenylalanine tert-butyl ester. 5-Nitrouracil (Aldrich) was converted via Method AAA into 2,4-dichloro-5-nitropyrimidine. L-4-(4-Methylpiperazin-1-ylcarbonyloxy)phenylalanine tert-butyl ester and 2,4-dichloro-5-nitropyrimidine were coupled via Method BBB, and the product of this coupling was sequentially converted via Methods CCC, DDD (using 3-chlorosulfonylpyridine) and EEE to give the title compound.

Example 414

Synthesis of N-(5-(2-Trifluoromethylphenyl)pyrimidin-4-yl)-L-4-(N,N-dimethylcarbamyloxy)phenylalanine L-Tyrosine tert-butyl ester (Bachem) was sequentially converted via UU, VV and WW into L-4-(N,N-dimethylcarbamyloxy)phenylalanine tert-butyl ester. 4(3H)-Pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with 2-trifluoromethylphenyl boronic acid (Aldrich) via Method Q. The product of this coupling was converted via Method HH to give the title compound.

Physical data were as follows:

$^1$H NMR (CD$_3$OD): δ=8.51 (s, 1H), 7.84-7.49 (m, 2H), 7.71-7.63 (m, 2H), 7.37 (d, 1H), 7.11-6.97 (m, 4H), 6.88 (d, 1H), 4.99 (s, 1H), 3.37-3.19 (m, 1H), 3.14-3.02 (m, 4H), 2.97 (s, 3H).

$^{13}$C NMR (CD$_3$OD): δ=175.7, 175.5, 165.6, 161.9, 161.7, 158.6, 157.6, 157.5, 153.3, 153.1, 152.6, 152.5, 136.4, 136.2, 135.0, 134.9, 134.5, 133.1, 132.2, 131.9, 131.7, 128.9, 128.7, 127.8, 124.3, 123.6.

Example 415

Synthesis of N-(5-(2-N,N-Dimethylcarbamylethyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with dimethylacrylamide (Aldrich) via Method U. The product of this reaction which was sequentially converted via Methods V and HH to give the title compound.

Physical data were as follows:
$^1$H NMR (CD$_3$OD): δ=8.56 (s, 1H), 8.06 (s, 1H), 7.32 (d, 2H), 7.01 (d, 2H), 5.35-5.30 (m, 1H), 3.56-3.49 (m, 1H), 3.23-3.18 (m, 1H), 3.11 (s, 3H), 3.02 (s, 3H), 2.99 (s, 3H), 2.97 (s, 3H), 2.88 (t, 2H), 2.65 (t, 2H).
$^{13}$CNMR(CD$_3$OD): δ=174.5, 174.2, 152.7, 151.6, 142.6, 136.5, 132.0, 123.8, 121.0, 57.8, 38.4, 37.9, 37.5, 36.9, 32.2, 24.6.

Example 416

Synthesis of N-(5-(N-Methyl-N-3-(1-methylpyrazole)sulfonylamino)pyrimidin-4-yl)-L-4-(N,N-dimethylcarbamyloxy)phenylalanine Isopropyl Ester L-Tyrosine (Aldrich) was sequentially converted via Methods LLL, UU, VV and WW into L-4-(N,N-dimethylcarbamyloxy)phenylalanine isopropyl ester. 5-Nitrouracil (Aldrich) was converted via Method AAA into 2,4-dichloro-5-nitropyrimidine. L-4-(N,N-Dimethylcarbamyloxy)-phenylalanine isopropyl ester and 2,4-dichloro-5-nitropyrimidine were coupled via Method BBB, and the product of this coupling was sequentially converted via Methods CCC, DDD (using 1-methyl-3-chlorosulfonylpyrazole) and EEE to give the title compound.

Physical data were as follows:
$^1$H NMR (CDCl$_3$) δ=8.47 (s, 1H), 7.76 (s, 1H), 7.68 (bs, 2H), 7.19 (m, 2H), 7.04 (d, 2H), 6.17 (d, 1H), 5.03 (m, 2H), 3.95 (s, 3H), 3.31-3.12 (m, 2H), 3.08 (s, 3H), 3.06 (s, 3H), 2.99 (s, 3H), 1.24 (d, 3H), 1.21 (d, 3H).

Example 417

Synthesis of N-(6-Phenylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 4,6-dichloropyrimidine (Aldrich) were coupled via Method Y and the coupled product was reacted with phenyl boronic acid (Aldrich) via Method Z. The product of this coupling was converted via Method HH to give the title compound.

Physical data were as follows:
$^1$H NMR (CD$_3$OD): δ=8.65 (s, 1H), 7.82-7.79 (m, 2H), 7.77-7.62 (m, 3H), 7.31 (d, 2H), 7.06-7.01 (m, 4H), 5.32-5.28 (m, 1H), 3.50-3.44 (m, 1H), 3.20-3.06 (m, 4H), 2.99 (s, 3H).
$^{13}$CNMR(CD$_3$OD): δ=173.9, 165.7, 157.6, 154.9, 154.3, 152.8, 135.8, 134.6, 132.3, 132.2, 131.7, 129.2, 123.8, 104.6, 57.8, 38.8, 37.7, 37.5.

Example 418

Synthesis of N-(6-(2-Trifluoromethylphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 4,6-dichloropyrimidine (Aldrich) were coupled via Method Y and the coupled product was reacted with 2-trifluoromethylphenyl boronic acid (Aldrich) via Method Z. The product of this coupling was converted via Method HH to give the title compound.

Physical data were as follows:
$^1$H NMR (CD$_3$OD): δ=8.46 (s, 1H), 7.95-7.82 (m, 1H), 7.73-7.67 (m, 2H), 7.50-7.48 (m, 1H), 7.29 (d, 2H), 7.03 (d, 2H), 6.65 (s, 1H), 5.05 (s, 1H), 3.39 (m, 1H), 3.16-3.12 (m, 4H), 3.00 (s, 3H).
$^{13}$CNMR(CD$_3$OD): δ=176.0, 164.3, 158.8, 157.7, 152.6, 136.6, 139.0, 132.9, 132.1, 131.4, 130.1, 129.7, 128.2, 128.2, 123.6, 38.8, 37.7, 37.5.

Example 419

Synthesis of N-(6-(2-Hydroxymethylphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 4,6-dichloropyrimidine (Aldrich) were coupled via Method Y and the coupled product was reacted with 2-(hydroxymethyl)phenyl boronic acid (Lancaster Synthesis) via Method Z. The product of this coupling was converted via Method HH to give the title compound.

Physical data were as follows:
$^1$H NMR (CD$_3$OD): δ=8.48 (s, 1H), 8.09 (s, 1H), 7.61-7.44 (m, 4H), 7.29 (d, 2H), 7.02 (d, 2H), 6.71 (s, 1H), 5.27 (s, 2H), 5.10-5.02 (m, 1H), 3.42-3.41 (m, 1H), 3.16-3.12 (m, 4H), 2.99 (s, 3H).
$^{13}$C NMR (CD$_3$OD): δ=175.7, 165.6, 164.7, 158.0, 157.6, 152.6, 141.6, 138.5, 136.7, 135.8, 132.2, 131.9, 131.7, 131.4, 131.3, 123.7, 64.9, 64.3, 38.9, 37.7, 37.5.

Example 420

Synthesis of N-(5-Cyclohexylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Cyclohexanone (Aldrich) was sequentially converted via Methods MM, NN, OO and QQ into 4,6-dichloro-5-cyclohexylpyrimidine. L-4-(N,N-Dimethylcarbamyloxy)phenylalanine tert-butyl ester and 4,6-dichloro-5-cyclohexylpyrimidine were coupled via Method RR, and the product of this coupling was sequentially converted via Methods SS and ZZ to give the title compound.

Physical data were as follows:
$^1$H NMR (CD$_3$OD): δ=8.41 (bs, 1H), 7.89 (bs, 1H), 7.21 (d, 2H), 6.94 (d, 2H), 5.12 (dd, 1H), 3.47 (dd, 1H), 3.19 (dd, 1H), 3.06 (s, 3H), 2.95 (s, 3H), 3.0 (m, 1H), 2.88-2.57 (bs, 1H), 2.5 (bs, 1H), 1.95-1.67(m, 1H).
$^{13}$CNMR(CD$_3$OD): δ=175.68, 165.82, 156.87, 152.10, 151.88, 141.96, 136.30, 131.44, 125.38, 122.89, 57.86, 37.44, 36.81, 36.64, 36.30, 32.65, 32.13, 27.29, 27.25, 26.95.

Example 421

Synthesis of N-(2-(N-Methyl-N-2-furanmethylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methylfurfurylamine (Salor) via Method CC to give a product that was coupled with o-tolyl boronic acid (Aldrich) via Method DD. The product of this coupling was converted via Method ZZ to give the title compound.

Physical data were as follows:
$^1$H NMR (CD$_3$OD): δ=7.43-7.35 (m, 2H), 7.35-7.2 (m, 2H), 7.2-7.0 (m, 4H), 7.0-6.9 (m, 2H), 6.42 (d, 1H), 6.39 (d, 1H), 4.85 (m, 1H), 3.3-3.1 (m, 7H), 3.09 (s, 3H), 2.98 (s, 3H), 2.16 (s, 3H), 1.89 (s, 3H).

Example 422

Synthesis of N-(2-(N-Methyl-N-4-chlorophenylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-4-chloroaniline (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CD$_3$OD): δ=8.17 (s, 1H), 7.56-7.34 (m, 8H), 7.1-6.97 (m, 4H), 3.50 (m, 2H), 3.13 (s, 3H), 2.1 (s, 3H), 2.17 (s, 3H), 1.94 (s, 3H).

Example 423

Synthesis of N-(5-(3-Thienyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with 3-thiophenyl boronic acid (Frontier Scientific, Inc.) via Method S. The product of this coupling was converted via Method KK to give the title compound.

Physical data were as follows:
$^1$H NMR (CD$_3$OD): δ=8.62 (s, 1H), 8.13 (s, 1H), 7.62 (m, 1H), 7.59 (m, 1H), 7.20 (d, 2H), 7.09 (d, 1H), 7.01 (d, 2H), 3.47-3.13 (m, 2H), 3.13 (s, 3H), 2.97 (s, 3H).
$^{13}$C NMR (CD$_3$OD): δ=173.22, 162.83, 156.84, 152.17, 151.43, 141.46, 135.22, 131.54, 131.35, 129.96, 127.99, 127.90, 123.24, 117.13, 56.87, 36.82, 36.64.

Example 424

Synthesis of N-(5-(2-Thienyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine. L-4-(N,N-dimethylcarbamyloxy)phenylalanine tert-butyl ester and 4-chloro-5-iodopyrimidine were coupled via Method P, and the coupled product was reacted with 2-thiophenyl boronic acid (Frontier Scientific, Inc.) via Method S. The product of this coupling was converted via Method KK to give the title compound.

Physical data were as follows:
$^1$H NMR (CD$_3$OD): δ=8.10 (s, 1H), 7.67 (s, 1H), 7.19 (d, 1H), 6.73 (m, 4H), 6.49 (m, 2H), 4.80 (m, 1H), 2.89 (m, 1H), 2.70 (m, 1H), 2.60 (s, 3H), 2.45 (s, 3H).
$^{13}$C NMR (CD$_3$OD): δ=173.07, 162.72, 156.80, 152.13, 151.74, 142.30, 135.07, 131.58, 131.14, 130.69, 130.38, 129.92, 123.19, 115.18, 56.94, 36.87, 36.81, 36.62, 28.74.

Example 425

Synthesis of N-(2-(N-Methyl-N-2-hydroxyethylamino)-5-(2-fluorophenyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with 2-(N-methylamino)ethanol (Aldrich) via Method CC to give a product that was coupled with 2-fluorophenyl boronic acid (Aldrich) via Method DD. The product of this coupling was converted via Method KK to give the title compound.

Example 426

Synthesis of N-(5-(Piperidin-1-yl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Piperidine (Aldrich) was sequentially converted via Methods FFF, GGG and HHH into 4,6-dichloro-5-piperidin-1-ylpyrimidine. L-4-(N,N-Dimethylcarbamyloxy)phenylalanine tert-butyl ester and 4,6-dichloro-5-piperidin-1-ylpyrimidine were coupled via Method III, and the product of this coupling was sequentially converted via Methods JJJ and ZZ into the title compound.

Example 427

Synthesis of N-(5-(1-Propylbutyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4-Heptanone (Aldrich) was sequentially converted via Methods MM, NN, OO and QQ into 4,6-dichloro-5-(1-propylbutyl)pyrimidine. L-4-(N,N-Dimethylcarbamyloxy)phenylalanine tert-butyl ester and 4,6-dichloro-5-(1-propylbutyl)pyrimidine were coupled via Method RR, and the product of this coupling was sequentially converted via Methods SS and ZZ to give the title compound.

Example 428

Synthesis of N-(2-(N-Methyl-N-cyclobutylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via

Example 429

Synthesis of N-(2-(N,N-Bis-(2-hydroxyethyl)amino) pyrimidin-4-yl)-L-4-(N,N-dimethylcarbamyloxy) phenylalanine A byproduct was isolated by chromatography of the crude product of Example 430, and the byproduct was converted via Method KK into the title compound.
Physical data were as follows:
$^1$H NMR (CD$_3$OD): δ=7.59 (d, 1H), 7.25 (d, 2H), 7.02 (d, 2H), 6.18 (d, 1H), 3.76 (brs, 8H), 2.97 (s, 8H).
$^{13}$C NMR (CD$_3$OD): δ=174.1, 163.7, 155, 152, 142.1, 135.2, 131.3, 123.7, 99, 60.5, 56.8, 53.2, 37.5, 36.8, 36.6.

Example 430

Synthesis of N-(2-(N,N-bis-(2-Hydroxyethyl) amino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with diethanolamine (Aldrich) via Method CC to give a product that was coupled with o-tolyl boronic acid (Aldrich) via Method DD. The product of this coupling was converted via Method KK to give the title compound.
Physical data were as follows:
$^1$H NMR (CD$_3$OD): δ=7.48-7.31 (m, 5H), 7.15-6.98 (m, 4H), 4.9 (m, 1H), 4.63 (m, 1H), 3.83 (d, 8H), 3.1 (s, 8H), 1.9 (d, 3H).
$^{13}$CNMR(CD$_3$OD): δ=173.8, 162.3, 154.6, 152.6, 140.9, 139.6, 139.4, 135.9, 135.8, 132.2, 132.0, 131.4, 131.2, 131.1, 128, 123.2, 123.1, 66.8, 60.6, 56.9, 56.4, 53.2, 52.8, 36.8, 36.6, 36.3, 19.5.

Example 431

Synthesis of N-(2-(N-Methyl-N-phenylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methylaniline (Aldrich) via Method CC to give a product that was coupled with o-tolyl boronic acid (Aldrich) via Method DD. The product of this coupling was converted via Method ZZ to give the title compound.
Physical data were as follows:
$^1$H NMR (CD$_3$OD): δ=7.57-6.99 (m, 14H), 4.99 (m, 1H), 3.49 (s, 3H), 3.11 (m, 5H), 2.98 (s, 3H), 2.16 (s, 3H).

$^{13}$CNMR(CD$_3$OD): δ=183.07, 173.72, 173.49, 162.55, 156.82, 153.97, 152.07, 142.25, 141.06, 140.91, 139.53, 139.40, 135.50, 135.39, 132.21, 132.16, 132.05, 131.52, 131.31, 130.53, 128.44, 128.11, 128.00, 123.13, 123.04, 113.18, 56.95, 56.49, 40.02, 39.96, 37.14, 36.83, 36.65, 19.56, 19.47.

Example 432

Synthesis of N-(2-(Isopropoxy)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this coupling was sequentially converted via Methods NNN, DD (using o-tolyl boronic acid, Aldrich) and ZZ to give the title compound.
Physical data were as follows:
$^1$H NMR (CDCl$_3$): δ=7.77 (bs, 1H), 7.40-6.8 (m, 9H), 6.43 (d, 0.5H) 6.27 (d, 0.5H), 6.78 (m, 1H), 6.16 (m, 1H), 3.09 (s, 3H), 3.00 (s, 3H), 3.40-2.80 (m, 4H), 2.20 (s, 1.5H), 1.94 (s, 1.5H), 1.23 (m, 6H).
$^{13}$CNMR(CDCl$_3$): δ=176.28, 176.15, 160.03, 159.78, 154.77, 153.65, 150.01, 169.97, 139.20, 137.81, 137.64, 134.39, 134.25, 130.71, 130.47, 130.12, 129.15, 126.69, 126.46, 121.24, 121.18, 109.56, 56.81, 56.34, 63.19, 36.90, 36.56, 36.32, 22.19, 21.99, 21.95, 19.51, 19.27.

Example 433

Synthesis of N-(2-(N-Methyl-N-3-methylbutylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methylN-isoamylamine (Pfaltz-Bauer) via Method CC to give a product that was coupled with o-tolyl boronic acid (Aldrich) via Method DD. The product of this coupling was converted via Method ZZ to give the title compound.
Physical data were as follows:
$^1$H NMR (CDCl$_3$): δ=7.6 (s, 0.5H), 7.56 (s, 0.5H), 7.30-6.80 (m, 8H) 6.30(bm, 1H), 7.00-6.00 (br, 1H), 4.63 (m, 1H), 3.09 (s, 3H), 3.01 (s, 6H), 3.80-2.80 (m, 4H), 2.13 (s, 1.5H), 1.90 (s, 1.5H), 1.61 (m, 1H—), 1.51 (bs, 2H), 0.96 (d, 6H).
$^{13}$C NMR (CDCl$_3$): δ=174.03, 173.87, 159.28, 159.04, 154.71, 153.67, 150.00, 142.10, 137.81, 137.53, 134.39, 134.22, 130.78, 130.58, 130.13, 128.96, 126.52, 126.30, 121.19, 121.13, 110.11, 109.91, 56.80, 56.40, 48.75, 36.55, 36.33, 35.80, 25.92, 22.54, 22.48, 19.53, 19.34.

Example 434

Synthesis of N-(2-(N-Methylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=10.0-8.0 (br, 1H), 9.42 (bs, 1H), 8.24 (s, 1H), 7.4-6.8 (m, 10H), 5.93 (m, 1H), 4.85 (m, 1H), 3.2-2.8 (m, 1H), 3.37 (m, 1H), 3.12 (s, 1.5H), 3.11 (s, 1.5H), 3.03 (s, 1.5H), 3.02 (s, 1.5H), 2.95 (s, 3H), 2.13 (s, 1.5H), 1.83 (s, 1.5H).

Example 435

Synthesis of N-(2-(2-tolyl)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with o-tolyl boronic acid (Aldrich) via Method KKK. The product of this coupling was converted via Method ZZ to give the title compound.

Physical data were as follows:
$^1$H NMR (CDCl$_3$): δ=8.14 (d, 1H), 7.68 (d, 1H)-7.4-6.8 (m, 12H), 5.42(m, 1H), 4.94 (m, 1H), 3.11 (s, 3H), 3.02 (s, 3H), 3.4-2.8 (m, 2H), 2.49 (s, 3H), 2.11 (s, 1.5H), 1.91 (s, 1.5H).

Example 436

Synthesis of N-(2-(N-Methyl-N-2-hydroxyethylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with 2-(methylamino)-ethanol (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CD$_3$OD): δ=7.4-6.94 (m, 4H), 4.82 (m, 1H), 3.8 (brs, 4H), 3.23/3.26 (s, rotamers, 3H), 2.98/3.7 (s, rotamers, 6H), 1.93/2.14 (s, rotamers, 3H).

Example 437

Synthesis of N-(2-(N-Methyl-N-2-methylpropylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl isobutylamine. (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=10.5-9.8 (br, 1H), 7.63 (d, 1H), 7.3-6.8 (m, 8H), 6.35(m, 1H), 4.65 (m, 1H), 3.6-2.8 (m, 4H), 3.08 (s, 3H), 3.01 (s, 6H), 2.13(s, 1.5H), 2.06 (bs, 1H), 1.25 (s, 1.5H), 0.9 (s, 6H).
$^{13}$CNMR(CDCl$_3$): δ=174.13, 173.97, 159.17, 158.9, 154.7, 153.99, 149.96, 142.00, 137.76, 137.53, 134.50, 134.33, 130.80, 130.58, 130.15, 128.95, 126.51, 126.30, 121.15, 121.11, 110.25, 109.99, 57.46, 56.90, 56.51, 36.89, 36.55, 36.32, 27.08, 19.87, 19.53, 19.38.

Example 438

Synthesis of N-(2-(N-Methyl-N-propylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-propylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=10.5-9.5 (br, 1H), 7.6 (d, 1H), 7.38-6.7 (m, 8H), 6.3 (m, 1H), 4.7 (m, 1H), 3.7-3.0 (m, 4H), 3.09 (s, 3H), 3.01 (s, 6H), 2.13 (s, 1.5H), 1.92 (s, 1.5H), 1.59 (bs, 2H), 0.89 (bs, 3H).
$^{13}$C NMR (CDCl$_3$): δ=174.22, 174.06, 159.26, 159.0, 154.7, 153.76, 149.97, 142.22, 137.78, 137.53, 134.53, 134.36, 130.80, 130.73, 130.51, 130.12, 128.93, 126.50, 126.30, 121.16, 121.10, 110.13, 109.87, 56.90, 56.52, 51.72, 36.55, 36.33, 35.96, 20.45, 19.56, 19.37, 11.06.

Example 439

Synthesis of N-(2-(N,N-Dimethylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N,N-dimethylamine (Aldrich) via Method CC to give a product that was coupled with o-tolylboronic acid (Aldrich) via Method DD. The product of this coupling was converted via Method ZZ to give the title compound.

Physical data were as follows:
$^1$H NMR (CDCl$_3$): δ=11.0-9.5 (br, 1H), 7.62 (d, 1H), 7.3-6.8 (m, 8H), 6.22(m, 1H), 4.72 (m, 1H), 3.5-3.0 (m, 2H), 3.8 (s, 6H), 3.01 (s, 3H), 2.12 (s, 1.5H), 1.94 (s, 1.5H).
$^{13}$C NMR (CDCl$_3$): δ=174.49, 174.3, 159.4, 158.93, 154.72, 149.93, 140.30, 137.75, 137.60, 134.67, 134.50, 130.92, 130.80, 130.51, 130.11, 128.87, 126.48, 126.32, 121.15, 121.08, 109.87, 109.69, 56.86, 56.49, 37.51, 36.87, 36.55, 36.34, 19.50, 19.38.

Example 440

Synthesis of N-(2-(N-Methyl-N-cyclohexylamino)-5-(3-pyridyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-cyclohexylamine (Aldrich) via Method CC to give a product that was coupled with 3-pyridyl boronic acid 1,3-propanediol cyclic ester (Lancaster Synthesis) via Method DD. The product of this coupling was converted via Method HH to give the title compound.

Physical data were as follows:
$^1$H NMR (CD$_3$OD): δ=8.83-8.78 (m, 1H), 8.56 (brs, 1H), 8.09-7.95 (m, 2H), 7.76-7.73 (m, 1H), 7.22 (d, 2H), 7.06 (d, 2H), 4.85 (m, 1H), 3.45-3.38 (m, 1H), 3.18-3.11 (m, 4H), 3.06 (s, 3H), 2.99 (sm, overlapping 4H), 1.92 (m, 2H), 1.76-1.57 (m, 8H).
$^{13}$C NMR (CD$_3$OD): δ=173.7, 161.5, 161.4, 160.9, 157.0, 152.0, 146.0, 145.7, 145.6, 143.3, 136.0, 132.2, 131.3, 128.1, 123.4, 107.8, 57.8, 57.4, 36.8, 36.6, 36.1, 30.6, 30.0, 26.4, 26.2.

Example 441

Synthesis of N-(5-(2-phenyl-2,2-difluoroethyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 1-Trifluoromethanesulfonyloxy-2,2-difluoro-2-phenylethane was sequentially converted via Methods LL, OO and QQ into 4,6-dichloro-5-(2,2-difluoro-2-phenylethyl)pyrimidine. L-4-(N,N-Dimethylcarbamyloxy)-phenylalanine tert-butyl ester and 4,6-dichloro-5-(2,2-difluoro-2-phenylethyl)pyrimidine were coupled via Method RR, and the product of this coupling was sequentially converted via Methods TT and ZZ to give the title compound.

Physical data were as follows:
$^1$H NMR (CD$_3$OD): δ=8.37 (s, 1H), 7.79 (s, 1H), 7.44 (s, 5H), 7.25 (d, 2H), 6.98 (d, 2H), 5.07 (dd, 1H), 3.62-3.32 (m, 3H), 3.14 (dd, 1H) 3.08 (s, 3H), 2.96 (s, 3H).

Example 442

Synthesis of N-(5-(2-phenyl-2,2-difluoroethyl)-6-chloropyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 1-Trifluoromethanesulfonyloxy-2,2-difluoro-2-phenylethane was sequentially converted via Methods LL, OO and QQ into 4,6-dichloro-5-(2,2-difluoro-2-phenylethyl)pyrimidine. L-4-(N,N-Dimethylcarbamyloxy)-phenylalanine tert-butyl ester and 4,6-dichloro-5-(2,2-difluoro-2-phenylethyl)pyrimidine were coupled via Method RR, and the product of this coupling was converted via Method ZZ to give the title compound.

Physical data were as follows:
$^1$H NMR (CD$_3$OD): δ=8.18 (s, 1H), 7.42-7.41 (m, 5H), 7.26 (d, 2H), 7.0 (d, 2H), 5.03 (dd, 1H), 3.72-3.45 (m, 2H), 3.34 (dd, 1H), 3.19 (dd, 1H), 3.08 (s, 3H), 2.96 (s, 3H).

Example 443

Synthesis of N-(5-(2-phenylethyl)pyrimidin-4-yl)-L-4-(N,N-dimethylcarbamyloxy)phenylalanine 4(3H)-Pyrimidinone (Aldrich) was sequentially converted via Methods N and O into 4-chloro-5-iodopyrimidine. L-Phenylalanine tert-butyl ester-hydrochloride (Bachem) and 4-chloro-5-iodopyrimidine were coupled via Method P. The product of this reaction was converted via Method W to a product that was sequentially converted via Methods X and HH to give the title compound.

Physical data were as follows:
$^1$H NMR (CD$_3$OD): δ=8.55 (d, 1H), 7.64 (d, 1H), 7.35-7.19 (m, 8H), 7.01-6.98 (m, 2H), 5.46-5.41 (m, 1H), 5.34-3.60 (m, 1H), 3.29-3.23 (m, 1H), 2.94-2.75 (m, 4H).
$^{13}$C NMR (CD$_3$OD): δ=174.3, 164.3, 151.5, 141.8, 141.7, 139.2, 131.0, 130.6, 130.5, 130.4, 128.9, 128.4, 120.6, 57.8, 38.4, 34.0, 30.7.

Example 444

Synthesis of N-(2-(N-Methyl-N-cyclohexylamino)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-cyclohexylamine (Aldrich) via Method CC to give a product which was sequentially converted via Methods MMM and ZZ to give the title compound.

Physical data were as follows:
$^1$H NMR (CDCl$_3$): δ=11.20 (bs, 2H), 8.44 (s, 1H), 7.76 (bs, 1H), 7.50 (br, 1H), 7.18 (d, 2H), 6.96 (d, 2H), 5.91 (bs, 1H),'4.83 (bs, 1H), 4.53 (br, 1H), 3.20 (m, 2H), 3.08 (s, 3H), 2.98 (s, 6H), 2.00-1.00 (m, 10H). $^3$CNMR(CDCl$_3$): δ=176.18, 171.50, 167.75, 162.44, 156.31, 154.49, 151.52, 135.83, 131.61, 122.85, 58.04, 56.87, 38.02, 37.79, 31.16, 31.00, 26.68.

Example 445

Synthesis of N-(5-Propylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-dimethylcarbamyloxy)-phenylalanine tert-butyl ester and 4-chloro-5-iodopyrimidine were coupled via Method P, and the product of this coupling was sequentially converted via Methods II, JJ and KK to give the title compound.

Physical data were as follows:

$^1$H NMR (CD$_3$OD): δ=8.51 (s, 1H), 7.97 (s, 1H), 7.26 (d, 2H), 6.97 (d, 2H), 5.36 (m, 1H), 3.51 (m, 1H), 3.23 (m, 1H), 3.16 (s, 3H), 2.95 (s, 3H), 2.47 (m, 2H), 1.57 (m, 2H), 0.99 (m, 3H).

$^{13}$C NMR (CD$_3$OD): δ=173.48, 163.61, 151.97, 150.75, 140.68, 135.74, 133.14, 131.30, 123.02, 120.85, 56.96, 36.99, 36.76, 36.58, 29.87, 21.02, 13.67.

Example 446

Synthesis of N-(5-(2-Methoxyphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with 2-methoxyphenyl boronic acid (Lancaster Synthesis) via Method Q. The product of this coupling was converted via Method HH to give the title compound.

Physical data were as follows:

$^1$H NMR (CD$_3$OD): δ=8.64 (s, 1H), 8.05 (s, 1H), 7.61-7.55 (m, 1H), 7.27-7.13 (m, 5H), 6.99 (d, 2H), 5.36-5.32 (m, 1H), 3.73 (s, 3H), 3.46-3.40 (m, 1H), 4.20-3.13 (m, 4H), 3.02 (s, 3H).

$^{13}$CNMR(CD$_3$OD): δ=173.8, 163.5, 159.5, 157.5, 152.8, 152.1, 143.0, 135.9, 134.2, 133.9, 132.2, 123.8, 123.4, 120.5, 120.0, 113.7, 57.5, 57.1, 37.9, 37.7, 37.5.

Example 447

Synthesis of N-(5-(2-Fluorophenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with 2-fluorophenyl boronic acid (Lancaster Synthesis) via Method Q. The product of this coupling was converted via Method HH to give the title compound.

Example 448

Synthesis of N-(2-(N-Methyl-N-isopropylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-isopropylamine (Aldrich) via Method CC to give a product that was coupled with o-tolyl boronic acid (Aldrich) via Method DD. The product of this coupling was converted via Method ZZ to give the title compound.

Physical data were as follows:

$^1$H NMR (CDCl$_3$): δ=10.5-9.5 (br, 1H), 7.59 (d, 1H), 7.30-6.70 (m, 8H), 6.3 (m, 1H), 4.92 (bs, 1H), 4.7 (m, 1H), 3.50-3.0 (m, 2H), 3.08 (s, 3H), 3.00 (s, 3H), 2.83 (s, 3H), 2.13 (s, 1.5H), 1.93 (s, 1.5H) 1.15 (d, 6H).

$^{13}$CNMR(CDCl$_3$): δ=174.31, 174.15, 159.21, 158.95, 154.70, 153.41, 149.92, 141.98, 137.79, 137.56, 134.59, 134.41, 130.59, 130.17, 128.95, 126.51, 126.32, 121.15, 110.26, 110.02, 56.87, 56.50, 46.86, 36.82, 36.55, 36.31, 28.18, 19.50, 19.39.

Example 449

Synthesis of N-(2-(N-Isopropylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with isopropylamine (Aldrich) via Method CC to give a product that was coupled with o-tolyl boronic acid (Aldrich) via Method DD. The product of this coupling was converted via Method ZZ to give the title compound.

Physical data were as follows:

$^1$H NMR (CDCl$_3$): δ=9.57 (s, 1H), 8.31 (s, 1H), 7.40-6.80 (m, 8H), 6.19 (m, 1H), 4.79 (m, 1H), 4.15 (m, 1H), 3.4-3.0 (m, 2H), 3.10 (s, 3H), 3.01 (s, 3H), 2.16 (s, 1.5H), 1.41 (s, 1.5H), 1.24 (s, 6H).

$^{13}$C NMR (CDCl$_3$): δ=176.07, 175.8, 166.23, 160.23, 159.99, 154.79, 153.50, 158.06, 139.38, 137.86, 137.66, 134.10, 133.93, 130.77, 130.61, 130.26, 130.01, 129.25, 126.71, 126.50, 121.46, 121.36, 109.59, 109.37, 56.77, 56.22, 43.31, 36.57, 36.34, 22.12, 21.96, 19.47, 19.22.

Example 450

Synthesis of N-(5-(2-phenylethyl)pyrimidin-4-yl)-L-4-(N,N-dimethylcarbamyloxy)phenylalanine Isopropyl Ester L-Tyrosine was sequentially converted via Methods LLL, UU, VV and WW into L-4-(N,N-dimethylcarbamyloxy)phenylalanine isopropyl ester. 4(3H)-Pyrimidinone (Aldrich) was sequentially converted via Methods N and O to 4-chloro-5-iodopyrimidine. L-4-(N,N-Dimethylcarbamyloxy)phenylalanine isopropyl ester and 4-chloro-5-iodopyrimidine were coupled via Method P, and the coupled product was converted via Method OOO to a product, which was converted via Method X to give the title compound.

Physical data were as follows:

$^1$H NMR (CDCl$_3$): δ=8.50 (s, 1H), 7.91 (s, 1H), 7.31-7.20 (m, 3H), 7.42-7.00 (m, 6H), 5.19-5.17 (m, 1H), 5.08-5.02 (m, 2H), 3.23-3.17 (m, 2H), 3.06 (s, 3H), 2.99 (s, 3H), 2.83-2.78 (m, 2H), 2.65-2.60 (m, 2H), 1.75-1.23 (m, 6H).

$^{13}$C NMR (CDCl$_3$): δ=171.8, 159.2, 156.7, 153.5, 150.7, 140.5, 130.3, 128.7, 128.5, 126.4, 121.8, 117.1, 69.4, 54.2, 36.9, 36.6, 36.5, 33.6, 29.8, 21.7, 21.6.

Example 451

Synthesis of N-(3-(N-Methyl-N-4-toluenesulfonylamino)pyrazin-2-yl)-L-phenylalanine Isopropyl Ester L-Phenylalanine (Aldrich) was converted via Method LLL to L-phenylalanine isopropyl ester hydrochloride. 2,3-Dichloropyrazine (Lancaster) was converted via Method QQQ and RRR into 2-chloro-3-nitropyrazine. L-Phenylalanine isopropyl ester hydrochloride and 2-chloro-3-nitropyrazine were coupled via Method BBB, and the product of this coupling was sequentially converted via Methods CCC, DDD and EEE to give the title compound.

Physical data were as follows:
$^1$H NMR (CDCl$_3$): δ=7.91 (d, 1H), 7.59 (d, 2H), 7.51 (d, 1H), 7.31-7.23 (m, 7H), 6.08 (d, 1H), 5.01-4.97 (m, 1H), 4.92-4.89 (m, 1H) 3.24 (d, 2H), 2.97 (s, 3H), 2.43 (s, 3H), 1.21-1.12 (m, 6H).
$^{13}$C NMR (CDCl$_3$): δ=167.32, 147.440, 139.85, 137.38, 133.25, 131.98, 128.68, 126.17, 125.17, 125.06, 124.41, 124.11, 122.58, 64.38, 50.65, 33.49, 32.41, 17.16, 17.08, 17.03.

Example 452

Synthesis of N-(5-(2-phenylethyl)pyrimidin-4-yl)-L-phenylalanine Isopropyl Ester L-Phenylalanine isopropyl ester hydrochloride was prepared by Method LLL. 4(3H)-Pyrimidinone (Aldrich) was sequentially converted via Methods N and O to 4-chloro-5-iodopyrimidine. L-Phenylalanine isopropyl ester hydrochloride and 4-chloro-5-iodopyrimidine were coupled via Method P and the coupled product sequentially converted via Methods OOO and X to give the title compound.

Physical data were as follows:
$^1$H NMR (CDCl$_3$): δ=8.51 (s, 1H), 7.92 (s, 1H), 7.30-7.15 (m, 5H), 7.14-7.06 (m, 4H), 5.16 (m, 1H), 5.09-5.01 (m, 2H), 3.31-3.16 (m, 2H), 2.79-2.74 (m, 2H), 2.62-2.57 (m, 2H), 1.15-1.20 (m, 6H).
$^{13}$C NMR (CDCl$_3$): δ=171.7, 159.1, 156.7, 153.5, 140.5, 136.1, 129.4, 128.6, 128.5, 128.3, 127.1, 126.4, 117.0, 69.3, 54.2, 37.6, 33.7, 30.0, 21.7, 21.6.

Example 453

Synthesis of N-(5-(N-Methyl-N-3-pyridinesulfonylamino)pyrimidin-4-yl)-L-4-(4-methylpiperazin-1-ylcarbonyloxy)phenylalanine L-Tyrosine tert-butyl ester (Bachem) was sequentially converted via Methods UU, XX and YY into-L-4-(4-methylpiperazin-1-ylcarbonyloxy)-phenylalanine tert-butyl-ester. 5-Nitrouracil (Aldrich) was converted via Method AAA into 2,4-dichloro-5-nitropyrimidine. L-4-(4-Methylpiperazin-1-ylcarbonyloxy)phenylalanine tert-butyl ester and 2,4-dichloro-5-nitropyrimidine were coupled via Method BBB, and the product of this coupling was sequentially converted via Methods CCC, DDD (using 3-chlorosulfonylpyridine), EEE and ZZ to give the title compound.

Example 454

Synthesis of N-(2-(N-Methyl-N-cyclohexylamino)-5-(2-tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-cyclohexylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=10.0-9.08 (br, 1H), 7.55 (s, 0.5H), 7.52 (s, 0.5H), 7.20-6.31 (m, 8H), 6.36 (br, 1H), 4.69 (m, 2H), 3.40 (m, 1H), 3.15 (m, 1H), 3.06 (brs, 3H), 2.98 (brs, 3H), 2.84 (brs, 3H), 2.11 (s, 1.5H), 2.00-1.00 (brm, 11.5H).
$^{13}$C NMR (CDCl$_3$): δ=164.10, 159.20, 159.00, 154.79, 153.50, 150.03, 137.68, 137.48, 134.48, 130.66, 130.22, 129.01, 126.62, 126.40, 121.16, 110.20, 57.00, 56.58, 55.50, 36.62, 36.39, 29.91, 29.52, 25.41, 19.60, 19.65.

Example 455

Synthesis of N-5-(2-Tolyl)pyrimidin-4-yl)-L-4-(N,N-dimethylcarbamyloxy)phenylalanine Isopropyl Ester L-Tyrosine (Aldrich) was sequentially converted via Methods LLL, UU, VV and WW into L-4-(N,N-dimethylcarbamyloxy)phenylalanine isopropyl ester. 4(3H)-Pyrimidinone (Aldrich) was sequentially converted via Methods N and O into 4-chloro-5-iodopyrimidine. L-4-(N,N-dimethylcarbamyloxy)-phenylalanine-isopropyl ester and. 4-chloro-5-iodopyrimidine were coupled via Method P. The product of this coupling was reacted with o-tolyl boronic acid via Method Q to afford the title compound.

Physical data were as follows:
$^1$H NMR (CDCl$_3$): δ=8.58 (s, 1H), 7.99 (s, 1H), 7.76-7.33 (m, 3H), 7.13 (m, 0.5H), 7.03-6.95 (m, 4H), 4.97-4.87 (m, 3H), 3.08-2.99 (m, 8H), 2.09 (s, 2H), 1.92 (s, 1.5H), 1.24-1.12 (m, 6H).
$^{13}$C NMR (CDCl$_3$): δ=171.4, 171.2, 158.8, 158.5, 157.5, 154.7, 153.6, 153.5, 150.5, 137.1, 137.0, 132.9, 132.3, 132.5, 130.8, 130.7, 130.0, 129.8, 129.7, 128.9, 126.6, 126.5, 121.6, 119.5, 119.4, 69.0, 54.5, 54.0, 36.9, 36.8, 36.6, 36.4, 21.65 21.60, 19.3, 19.2.

Example 456

Synthesis of N-(5-(3-Nitrophenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with 3-nitrophenyl boronic acid (Aldrich) via Method T. The product of this coupling was converted via Method HH to give the title compound.

Physical data were as follows:
$^1$H NMR (CD$_3$OD): δ=8.67 (s, 1H), 8.41-8.38 (m, 1H), 8.28-8.27 (m, 1H), 8.17 (s, 1H), 7.82-7.77 (m, 1H), 7.67-7.65 (m, 1H), 7.20 (d, 2H), 7.02 (d, 2H), 5.33-5.28 (m, 1H), 3.47-3.411 (m, 1H), 3.12-3.04 (m, 4H), 2.97 (s, 3H).
$^{13}$CNMR(CD$_3$OD): δ=173.7, 163.6, 157.6, 152.8, 152.7, 151.2, 143.8, 137.4, 136.3, 134.2, 133.1, 132.2, 126.7, 126.3, 124.0, 120.3, 58.0, 37.7, 37.6, 37.5.

Example 457

Synthesis of N-(5-(3-Pyridyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with 3-pyridyl boronic acid 1,3-propanediol cyclic ester (Lancaster Synthesis) via Method Q. The product of this coupling was converted via Method HH to give the title compound.

Example 458

Synthesis of N-(5-(2-phenylethyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P. The product of this reaction was sequentially converted via Methods W, X, and HH to give the title compound.

Physical data were as follows:
$^1$H NMR (CD$_3$OD): δ=8.52 (s, 1H), 7.67 (s, 1H), 7.34-7.19 (m, 5H), 7.08-6.99 (m, 4H), 5.50-5.42 (m, 1H), 5.59-5.53 (m, 1H), 3.26-3.21 (m, 1H), 3.09 (s, 2H), 2.99 (s, 3H), 2.94-2.85 (m, 4H).
$^{13}$C NMR (CD$_3$OD): δ=174.2, 164.2, 157.5, 152.7, 151.4, 141.8, 141.7, 136.5, 132.0, 130.5, 130.4, 128.4, 123.8, 120.5, 57.8, 37.9, 37.6, 37.5, 34.1, 30.6.

Example 459

Synthesis of N-(2-N,N-Dimethylamino-5-(N-methyl-N-4-toluenesulfonylamino)pyrimidin-4-yl)-L-phenylalanine 5-Nitrouracil (Aldrich) was converted via Method AAA into 2,4-dichloro-5-nitropyrimidine. L-Phenylalanine tert-butyl ester (Bachem) and 2,4-dichloro-5-nitropyrimidine were coupled via Method BBB, and the product of this coupling was sequentially converted via Methods SSS (using dimethylamine), CCC, DDD, EEE and ZZ to give the title compound.

Physical data were as follows:
$^1$H NMR (CD$_3$OD): δ=8.15 (s, formate), 7.65 (m, 2H), 7.41 (d, 2H), 7.40-7.19 (m, 5H), 7.02-6.92-(m, 1H), 4.90 (m, 1H), 3.40-3.10 (m, 2H), 3.09-2.92(m, 9H), 2.43 (s, 3H).
$^{13}$C NMR (CD$_3$OD): δ=177.07, 159.64, 154.70, 152.25, 144.10, 141.97, 141.33, 140.25, 132.57, 129.02, 125.21, 124.82, 123.57, 123.42, 121.88, 107.64, 51.08, 33.71, 32.72, 31.76, 15.49.

Example 460

Synthesis of N-(5-(2-Tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with o-tolyl boronic acid (Aldrich) via Method Q. The product of this coupling was converted via Method HH to give the title compound.

Physical data were as follows:
$^1$H NMR (CD$_3$OD): δ=8.75-8.65 (d, 1H), 8.05-8.03 (d, 1H), 7.51-7.35 (m, 3H), 7.26-7.11 (m, 3H), 7.02-6.97 (m, 2H), 5.38-5.27 (m, 2H), 3.50-3.39 (m, 1H), 3.21-3.07 (m, 4H), 3.02 (s, 3H), 2.21-1.93 (s, 3H).
$^{13}$C NMR (CD$_3$OD): δ=173.8, 173.6, 164.0, 163.8, 157.5, 152.7, 152.6, 143.0, 142.8, 139.7, 139.5, 136.1, 135.9, 133.2, 133.0, 132.4, 132.2, 132.1, 131.9, 131.1, 129.0, 128.9, 123.8, 123.7, 122.2, 122.0, 57.6, 57.4, 37.8, 37.7, 37.5, 37.4, 20.3, 20.2.

Additionally, using the procedures described herein and the appropriate starting materials, the following additional compounds can be prepared:

N-(2-(N-methyl-N-cyclohexylamino)-5-(2-methoxyphenyl)pyrimidin-4-yl)-L-4-(2,6-dimethoxyphenyl)phenylalanine (Example 461), N-(2-(N-methyl-N-isopropylamino)-5-(2-fluorophenyl)pyrimidin-4-yl)-L-4-(2,6-dimethoxyphenyl)phenylalanine (Example 462), N-(2-(N-methyl-N-isopropylamino)-5-(2-fluorophenyl)pyrimidin-4-yl)-L-4-(2-methoxyphenyl)phenylalanine (Example 463), N-(2-(N-methyl-N-cyclohexylamino)-5-(2,6-difluorophenyl)pyrimidin-4-yl)-L-4-(2,6-difluorophenyl)phenylalanine (Example 464), N-(2-(N-methyl-N-cyclohexylamino)-5-(2-hydroxymethylphenyl)pyrimidin-4-yl)-L-4-(2,6-dimethoxyphenyl)phenylalanine (Example 465), N-(2-(N,N-bis-(2-hydroxyethyl)amino)-5-(2,4,6-trimethylphenyl)pyrimidin-4-yl)-L-4-(2,6-dimethoxyphenyl)phenylalanine (Example 466), N-(2-(N-methyl-N-cyclohexylamino)-5-(2-trifluoromethylphenyl)pyrimidin-4-yl)-L-4-(2-cyanophenyl)phenylalanine (Example 467), N-(2-(N-methyl-N-cyclohexylamino)-5-(3-thienyl)pyrimidin-4-yl)-L-4-(2,6-dimethoxyphenyl)phenylalanine (Example 468), N-(2-(N-methyl-N-cyclohexylamino)-5-(2-thienyl)pyrimidin-4-yl)-L-4-(4-trifluoromethylphenyl)phenylalanine (Example 469), N-(2-(N-methyl-N-cyclohexylamino)-5-(3-pyridyl)pyrimidin-4-yl)-L-4-(2,6-dimethoxyphenyl)phenylalanine (Example 470), N-(2-(N-methyl-N-cyclohexylamino)-5-(3-nitrophenyl)pyrimidin-4-yl)-L-4-(2,6-dimethoxyphenyl)phenylalanine (Example 471), N-(2-(N-methyl-N-cyclohexylamino)-5-(2,6-dichlorophenyl)pyrimidin-4-yl)-L-4-(2,6-dimethoxyphenyl)phenylalanine (Example 472), N-(2-(N-methyl-N-cyclohexylamino)-5-(4-pyridyl)pyrimidin-4-yl)-L-4-(3-hydroxymethylphenyl)phenylalanine (Example 473), N-(2-(N-ethyl-N-isopropylamino)-5-(2,6-dimethoxyphenyl)pyrimidin-4-yl)-L-4-(2,6-dimethoxyphenyl)phenylalanine (Example 474), N-(2-(N-methyl-N-cyclohexylamino)-5-(2,3-dichlorophenyl)pyrimidin-4-yl)-L-4-(2,6-dimethoxyphenyl)phenylalanine (Example 475), N-(2-(N-methyl-N-ethylamino)-5-(2,4,6-trimethylphenyl)pyrimidin-4-yl)-L-4-(2-cyanophenyl)phenylalanine (Example 476), N-(2-(N-methyl-N-isopropylamino)-5-(2,4,6-trimethylphenyl)pyrimidin-4-yl)-L-4-(3-pyridyl)phenylalanine (Example 477), N-(2-(N,N-bis-(2-hydroxyethyl)amino)-5-(2,4,6-trimethylphenyl)pyrimidin-4-yl)-L-4-(2-cyanophenyl)phenylalanine (Example 478), N-(2-(N-methyl-N-(1-methylpiperidin-4-yl)amino)-5-(2-cyanophenyl)pyrimidin-4-yl)-L-4-(2,6-difluorophenyl)phenylalanine (Example 479), N-(2-(N-ethyl-N-isopropylamino)-5-(2,4,6-trimethylphenyl)pyrimidin-4-yl)-L-4-(o-tolyl)phenylalanine (Example 480), N-(2-(N-methyl-N-4-chlorophenylamino)-5-(2,4,6-trimethylphenyl)pyrimidin-4-yl)-L-4-(2,6-dimethoxyphenyl)phenylalanine (Example 481), N-(5-(N-methyl-N-2-(phenyl)ethylamino)pyrimidin-4-yl)-L-4-(N,N-dimethylcarbamyloxy)phenylalanine (Example 482), N-(5-(N-methyl-N-hexylamino)pyrimidin-4-yl)-L-4-(N,N-dimethylcarbamyloxy)phenylalanine (Example 483), N-(5-(N-methyl-N-isopropylamino)pyrimidin-4-yl)-L-4-(N,N-dimethylcarbamyloxy)phenylalanine (Example 484), N-(5-(N-methyl-N-tert-butylamino)pyrimidin-4-yl)-L-4-(N,N-dimethylcarbamyloxy)phenylalanine (Example 485), N-(5-(N-ethyl-N-isopropylamino)pyrimidin-4-yl)-L-4-(N,N-dimethylcarbamyloxy)phenylalanine (Example 486), N-(5-(N-methyl-N-2-(4-pyridyl)ethyl-pyrimidin-4-yl)-L-4-(N,N-dimethylcarbamyloxy)phenylalanine (Example 487), N-(5-(N-methyl-N-2-(phenyl)ethylamino)pyrimidin-4-yl)-L-4-(4-(2,6-dimethoxyphenyl)phenylalanine (Example 488), N-(5-(N-methyl-N-hexylamino)pyrimidin-4-yl)-L-4-(2,6-dimethoxyphenyl)phenylalanine (Example 489), N-(5-(N-methyl-N-isopropylamino)pyrimidin-4-yl)-L-4-(2,6-dimethoxyphenyl)phenylalanine (Example 490), N-(5-(N-methyl-N-tert-butylamino)pyrimidin-4-yl)-L-4-(2,6-dimethoxyphenyl)phenylalanine (Example 491), N-(5-(N-ethyl-N-isopropylamino)pyrimidin-4-yl)-L-4-(2,6-dimethoxyphenyl)phenylalanine (Example 492), N-(5-(N-methyl-N-2-(4-pyridyl)ethyl-pyrimidin-4-yl)-L-4-(2,6-dimethoxyphenyl)phenylalanine (Example 493), N-(2-(N-methyl-N-cyclohexylamino)-5-ethylpyrimidin-4-yl)-L-4-(N,N-dimethylcarbamyloxy)phenylalanine (Example 494).

Example 495

Synthesis of N-(4-(N,N-Di-n-hexylamino)-1,1-dioxo-1,2,5-thiadiazol-3-yl)-L-tyrosine Step A: Preparation of 3,4-Diethyloxy-1-oxo-1,2,5-thiadiazole and 3,4-Diethyloxy-1,1-dioxo-1,2,5-thiadiazole The title intermediates were prepared according to the procedures described in R. Y. Wen et al, *J Org Chem.*, (1975) 40, 2743; and R. Y. Wen et al, *Org Prep Proceed.*, (1969) 1, 255.

Step B: Preparation of 4-(N,N-Di-n-hexylamino)-3-ethoxy-1,1-dioxo-1,2,5-thiadiazole Dihexylamine (90 mg, 0.48 mmol) was added to a solution of 3,4-diethyloxy-1,1-dioxo-1,2,5-thiadiazole (100 mg, 0.48 mmol) in ethanol (5 mL) and the reaction stirred overnight at room temperature. The solvent was removed under reduced pressure and the residue absorbed onto silica gel, and purified by flash column chromatography (silica, hexane:EtOAc 3:1) to yield the title intermediate (120 mg, 72%).

Physical data were as follows:
MS (EI, m/e) 345.

Step C: Preparation of N-(4-(N,N-Di-n-hexylamino)-1,1-dioxo-1,2,5-thiadiazol-3-yl)-L-tyrosine tert-Butyl Ester A solution of 4-(N,N-di-n-hexylamino)-3-ethoxy-1,1-dioxo-1,2,5-thiadiazole (400 mg, 1.02 mmol) and L-tyrosine t-butyl ester (261 mg, 1.1 mmol) in EtOH (10 mL) was stirred at room temperature for 36 hrs. The solvent was removed under reduced pressure residue purified by flash column chromatography (silica, hexane:EtOAc 3:1 then 1:1) to give the title compound as a white waxy solid (400 mg, 73%).

Physical data were as follows:
Anal. Calcd. for $C_{27}H_{44}N_4O_5S \cdot 0.55$EtOAc: C, 59.93; H, 8.34; N, 9.57.
Found: C, 59.84; H, 8.44; N, 9.62.

Step D: Preparation of N-(4-(N,N-Di-n-hexylamino)-1,1-dioxo-1,2,5-thiadiazol-3-yl)-L-tyrosine The compound from Step C (100 mg, 0.19 mmol) was dissolved in formic acid and the mixture stirred at room temperature for 36 hrs. Excess formic acid was removed under reduced pressure to yield the title compound as a white solid (90 mg, 98%).

Physical data were as follows:
Anal. Calcd. for $C_{23}H_{36}N_4O_5S$: C, 57.48; H, 7.55; N, 11.66.
Found: C, 57.04; H, 7.23; N, 11.38.

Example 496

Synthesis of N-(4-(N,N-Di-n-hexylamino)-1,1-dioxo-1,2,5-thiadiazol-3-yl)-L-4-(N,N-dimethylcarbamyloxy)phenylalanine Step A: Preparation of N-(4-(N,N-Di-n-hexylamino)-1,1-dioxo-1,2,5-thiadiazol-3-yl)-L-4-(N,N-dimethylcarbamyloxy)-phenylalanine tert-Butyl Ester N-(4-(N,N-Di-n-hexylamino)-1,1-dioxo-1,2,5-thiadiazol-3-yl)-L-tyrosine tert-butyl ester (180 mg, 0.34 mmol.) was dissolved in pyridine (5 ml). Dimethylcarbamoyl chloride (108 mg, 1 mmol) was added dropwise and the mixture stirred at room temperature overnight. Pyridine was removed under high vacuum (low water bath temperature), the residue absorbed onto silica gel and purified by flash column chromatography (silica, hexane:EtOAc 2:1) to yield the title compound (140 mg, 68%).

Step B: Preparation of N-(4-(N,N-Di-n-hexylamino)-1,1-dioxo-1,2,5-thiadiazol-3-yl)-L-4-(N,N-dimethylcarbamyloxy)-phenylalanine The compound from Step A (140 mg, 0.23 mmol) was dissolved in formic acid and the mixture stirred at room temperature overnight. Excess formic acid was removed under reduced pressure to yield the title compound as a white solid (110 mg, 87%).

Physical data were as follows:
Anal. Calcd. for $C_{26}H_{41}N_5O_6S$: C, 56.6; H, 7.49; N, 12.69.
Found: C, 56.67; H, 7.4; N, 12.46.

Example 497

Synthesis of N-(4-(N,N-Di-n-hexylamino)-1,1-dioxo-1,2,5-thiadiazol-3-yl)-L-4-(4-methylpiperazin-1-ylcarbonyloxy)phenylalanine Step A: Preparation of N-(4-(N,N-Di-n-hexylamino)-1,1-dioxo-1,2,5-thiadiazol-3-yl)-L-4-(4-methylpiperazin-1-ylcarbonyloxy)phenylalanine tert-Butyl Ester A solution of N-(4-(N,N-di-n-hexylamino)-1,1-dioxo-1,2,5-thiadiazol-3-yl)-L-tyrosine tert-butyl ester (500 mg, 0.93-mmol), and p-nitrophenyl chloroformate-(179 mg, 0.89 mmol) in dichloromethane (20 mL) was cooled to 0° C. under an argon atmosphere. Triethylamine (235 mg, 2.32 mmol) was added dropwise and the mixture stirred at 0° C. for 30 mins, then allowed to warm to room temperature for a further 40 mins. The mixture was recooled to 0° C. and N-methylpiperazine (90 mg, 0.89 mmol) added. The mixture was allowed to warm to room temperature and stirred for three hours. The mixture was diluted with diethyl ether (150 mL) and the organic solution washed with 10% potassium carbonate solution until no further yellow color was produced in the aqueous phase. The organic layer was separated, dried ($MgSO_4$) and the solvent removed under reduced pressure. The residue was purified by flash column chromatography (silica, EtOAc: MeOH:$Et_3N$ 94:5:1) to give the title compound as a pale yellow foam (310 mg, 50%).

Physical data were as follows:

Anal. Calcd. for $C_{33}H_{54}N_6O_6S$: C, 59.79; H, 8.21; N, 12.68. Found: C, 59.47; H, 8.25; N, 12.49

Step B: Preparation of N-(4-(N,N-Di-n-hexylamino)-1,1-dioxo-1,2,5-thiadiazol-3-yl)-L-4-(4-methylpiperazin-1-ylcarbonyloxy)phenylalanine The compound from Step A (200 mg, 0.3 mmol) was dissolved in formic acid (5 mL) and the mixture stirred at room temperature for 48 hrs. Excess formic acid was removed under reduced pressure and the residue recrystallized from EtOAc/MeOH to yield the title compound as an off-white solid (120 mg, 67%).

Physical data were as follows:

Anal. Calcd. for $C_{29}H_{46}N_6O_6S \cdot 0.75H_2O$: C, 56.15; H, 7.72; N. 13.55. Found: C, 56.1; H, 7.44; N, 13.46.

Example 498

Synthesis of N-[4-(2-(3-Methylphenylaminocarbonylamino)eth-1-ylamino)-1,1-dioxo-1,2,5-thiadiazol-3-yl]-L-4-(N,N-dimethylcarbamyloxy)phenylalanine Step A: Preparation of N-(4-Ethoxy-1,1-dioxo-1,2,5-thiadiazol-3-yl) L-tyrosine tert-Butyl Ester A solution of 3,4-diethyloxy-1,1-dioxo-1,2,5-thiadiazole (400 mg, 1.94 mmol) and L-y tyrosine e t-butyl ester (1.25 g, 5.2 mmol) in ethanol (25 mL) was stirred at room temperature-overnight. Solvent was removed under reduced pressure and the product used in further transformations without further purification (Yield 790 mg).

Step B: Preparation of 2-(3-Methylphenylaminocarbonylamino)eth-1-ylamine

N-Boc-Ethylene diamine (800 mg, 5 mmol) and m-tolyl isocyanate (665 mg, 5 mmol) were dissolved in acetonitrile and the mixture stirred at room temperature for 4 hrs. Solvent was removed under reduced pressure and the residue absorbed onto silica gel; prior to purification by flash column chromatography (silica, hexane:EtOAc 1:1) to yield the desired compound as a white solid (300 mg, 21%) (MS (+ESI, m/e) 294 (M+H)$^+$). The N-Boc protected compound (300 mg, 1.02 mmol) was dissolved in formic acid (10 ml) and the mixture stirred at room temperature overnight. Excess acid was removed to yield the formate salt of the title compound as a white foam (210 mg).

Step C: Preparation of N-[4-(2-(3-Methylphenylamino-carbonylamino)eth-1-ylamino)-1,1-dioxo-1,2,5-thiadiazol-3-yl]-L-tyrosine tert-Butyl Ester To a solution of N-(4-ethoxy-1,1-dioxo-1,2,5-thiadiazol-3-yl)-L-tyrosine tert-butyl ester from Step A (150 mg, 0.38 mmol) and the formate salt of 2-(3-methylphenylaminocarbonylamino)eth-1-ylamine from Step B (210 mg, 0.89 mmol) in ethanol (10 mL) was added triethylamine (133 mg, 1.44 mmol). The reaction was stirred at room temperature overnight.

Solvent was removed under reduced pressure and the residue purified by flash column chromatography (silica, 5% MeOH in EtOAc) to give the title compound (130 mg, 91%).

Physical data were as follows:

MS (+ESI, m/e) 545 (M+H)$^+$.

Step D: Preparation of N-[4-(2-(3-Methylphenylamino-carbonylamino)eth-1-ylamino)-1,1-dioxo-1,2,5-thiadiazol-3-yl]-L-4-(N,N-dimethylcarbamyloxy)phenylalanine tert-Butyl Ester The intermediate from Step C (130 mg, 0.24 mmol) was dissolved in pyridine (5 mL). Dimethylcarbamoyl chloride (77 mg, 0.72 mmol) was added dropwise and the mixture heated at 50° C. under an argon atmosphere overnight. Pyridine was removed under reduced pressure, the residue absorbed onto silica gel and purified by flash column chromatography (silica, hexane:EtOAc 1:2, then 0.5% MeOH in EtOAc) to yield the title compound-(140 mg, 93%).

Physical data were as follows:

MS (+ESI, m/e) 616 (M+H)$^+$.

Step E: Preparation of N-[4-(2-(3-Methylphenylamino-carbonylamino)eth-1-ylamino)-1,1-dioxo-1,2,5-thiadiazol-3-yl]-L-4-(N,N-dimethylcarbamyloxy)phenylalanine The compound from Step D (120 mg, 0.19 mmol) was dissolved in formic acid (10 mL) and the mixture stirred at room temperature for 36 hrs. Excess acid was removed to yield the title compound as a pale yellow foam (100 mg, 93%).

Physical data were as follows:

MS (+ESI, m/e) 560 (M+H)$^+$.

Example 499

Synthesis of N-(4-(N,N-Dimethylamino)-1-oxo-1,2,5-thiadiazol-3-yl)-L-4-(N,N-dimethylcarbamyloxy)phenylalanine tert-Butyl Ester Step A: Preparation of N-(4-Ethoxy-1-oxo-1,2,5-thiadiazol-3-yl)-L-tyrosine tert-Butyl Ester A solution of 3,4-diethoxy-1-oxo-1,2,5-thiadiazole (1 g, 0.52 mmol) and L-tyrosine t-butyl ester (1.25 g, 0.52 mmol) in ethanol (25 mL) was stirred at room temperature for 60 hr. Solvent was removed under reduced pressure and the residue purified by flash column chromatography (silica, hexane: EtOAc 1:1 to give the title intermediate (1.75 g, 88%).

Physical data were as follows:

MS (+ESI, m/e) 382 (M+H)$^+$.

Step B: Preparation of N-(4-Ethoxy-1-oxo-1,2,5-thiadiazol-3-yl)-L-4-(N,N-dimethylcarbamyloxy)phenylalanine tert-Butyl Ester The intermediate from Step A (400 mg, 1.05 mmol) was dissolved in pyridine (10 mL) and dimethylcarbamoyl chloride (338 mg, 3.15 µmmol) was added. The reaction was stirred at room temperature under an inert atmosphere overnight. TLC indicated large amounts of unreacted starting material so the mixture was heated at 50° C. for a further 48 hrs. Excess pyridine was removed under reduced pressure and the residue purified by flash column chromatography (silica, hexane:EtOAc 1:1 to give the title intermediate (280 mg, 59%).

Physical data were as follows:
MS (+ESI, m/e) 453 (M+H).

Step C: Preparation of N-(4-(N,N-Dimethylamino)-1-oxo-1,2,5-thiadiazol-3-yl)-L-4-(N,N-dimethylcarbamyloxy)phenylalanine tert-Butyl Ester A 2M solution of dimethylamine in THF (5 mL, 10 mmol) was added to a solution of the compound from Step B (180 mg, 0.35 mmol) in ethanol (10 mL). The reaction was stirred at room temperature overnight and solvent removed under reduced pressure. Residue was purified by flash column chromatography (silica, EtOAc:MeOH:Et$_3$N 90:10:1) to give the title compound as a white foam (140 mg, 88%).

Physical data were as follows:
Anal. Calcd. for C$_{220}$H$_{29}$N$_5$O$_5$S: C, 53.2; H, 6.47; N, 15.51. Found: C, 52.94; H, 6.18; N, 15.34.

Example 500

Synthesis of N-(5-(2,2,2-Trifluoroethyl)pyrimidin-4-yl)-L-4-(2,6-dimethoxyphenyl)phenylalanine Substituting L-4-(2,6-dimethoxyphenyl)phenylalanine methyl ester from Method TTT for L-4-(N,N-dimethylcarbamyloxy)phenylalanine tert-butyl ester and following the procedure described for the preparation of Example 410 yielded the title compound.

Physical data were as follows:
$^1$H NMR (CD$_3$OD): δ 8.41 (s, 1H), 8.05 (s, 1H), 7.24 (t, 1H), 7.2 (d, 2H), 7.1 (d, 2H), 6.67 (d, 2H), 5.1 (dd, 1H), 3.65 (s, 6H), 3.61-3.42 (m, 2H), 3.36 (dd, 1H), 3.2 (dd, 1H).
$^{13}$C NMR (CD$_3$OD): δ 175.8, 162.3, 159.2, 157.9, 155.8, 136.9, 134.4, 132.2, 130.0, 129.5, 127.4, 120.9, 109.6, 105.7, 56.8, 56.2, 37.9, 32.6.

Example 501

Synthesis of N-(2-(N-Cyclohexyl-N-methyl)-5-(2-tolyl)pyrimidin-4-yl)-L-4-(2,6-dimethoxyphenyl)phenylalanine Substituting-L-4-(2,6dimethoxyphenyl)phenylalanine methyl ester-from-Method TTT for L-4-(N,N-dimethylcarbamyloxy)phenylalanine tert-butyl ester and following the procedure described for the preparation of Example 395 yielded the title compound.

Physical data were as follows:
$^1$H NMR (CD$_3$OD): δ 7.37-7.19 (m, 5.5H), 7.09-7.02 (m, 4H), 6.94 (d, 0.5H), 6.68 (d, 2H), 4.79-4.74 (m, 0.5H), 4.69-4.65 (m.0.5H), 3.67 (s, 3H), 3.65 (s, 3H), 3.44-3.33 (m, 1H), 3.02-2.95 (m, 4H), 2.19 (s, 1.5H), 1.85-1.71 (m, 6.5H), 1.57 (m, 4H), 1.29-1.2 (br s, 1H).

Example 502

Synthesis of N-(5-(2-Fluorophenyl)pyrimidin-4-yl)-L-4-(2,6-dimethoxyphenyl)phenylalanine Substituting L-4-(2,6-dimethoxyphenyl)phenylalanine methyl ester from Method TTT for L-4-(N,N-dimethylcarbamyloxy)phenylalanine tert-butyl ester and following the procedure described for the preparation of Example 447 yielded the title compound.

Physical data were as follows:
$^1$H NMR (CD$_3$OD): δ 8.50 (s, 1H), 8.01 (s, 1H), 7.3-7.0 (m, 9H), 6.69 (d, 2H), 5.0 (m, 1H), 3.65 (s, 6H), 3.20-3.05 (m, 2H).
$^{13}$C NMR (CD$_3$OD): δ 153.2, 151.6, 147.1, 130.2, 128.6, 126.7, 126.6, 126.5, 126.4, 126.3, 123.9, 123.5, 123.2, 120.5, 120.4, 111.7, 111.4, 99.6, 59.3, 31.7.

Example 503

Synthesis of N-(2-(N-Methyl-N-propyl)-5-(2-tolyl)pyrimidin-4-yl)-L-4-(2,6-dimethoxyphenyl)phenylalanine Substituting L-4-(2,6-dimethoxyphenyl)phenylalanine methyl ester from Method TTT for L-4-(N,N-dimethylcarbamyloxy)phenylalanine tert-butyl ester and following the procedure described for the preparation of Example 438 yielded the title compound.

Physical data were as follows:
$^1$H NMR (CD$_3$OD): δ 10.30-8.80 (br, 1H), 7.68 (s, 0.5H), 7.63 (s, 0.5H), 7.40-6.60 (m, 1H), 6.15 (m, 1H), 4.70 (m, 1H), 3.68 (s, 3H), 3.66 (s, 3H), 3.80-3.00 (m, 4H), 3.07 (s, 3H), 2.12 (s, 1.5H), 2.08 (s, 1.5H), 1.61 (bs, 2H), 0.87 (bs, 3H).

Example 504

Synthesis of N-(3-chloropyrazin-2-yl)-L4-[1-(tert-butoxycarbonyl)piperidin-4-ylcarbonylamino]phenylalanine ethyl ester Step A: Preparation of N-(3-Chloropyrazin-2-yl)-L-4-nitrophenylalanine 4-Nitrophenylalanine (50 mm, 10.59 mg) were stirred in absolute ethanol containing 1.0 eq (1.26 g) of sodium metal. The reaction mixture was stripped to a brown solid and the sodium salt was taken up in 200 mL of butanol containing 1.0 eq (7.45 g) 2,3-dichloropyrazine. The reaction mixture was refluxed overnight and the solvent was then removed under reduced pressure. The residue was taken up in ethyl acetate and washed with water (I x), brine (I x), dried over Na$_2$SO$_4$, filtered and stripped to give 15.5 g of the title intermediate as a brown oil.

Physical data were as follows:
Analytical: MS: (+)FAB [M+H] @ M/Z 323 with 1 Cl.

Step B: Preparation of N-(3-Chloropyrazin-2-yl)-L-4-nitrophenylalanine Ethyl Ester The intermediate from Step A was suspended in 300,mL of absolute ethanol. The reaction flask was placed in an ice bath and cooled to 0° C. and HCl (g) was bubbled into reaction for 15 minutes. The gas tube was replaced with a drying tube and the reaction mixture was warmed to room temperature and stirred overnight. Ethanol was stripped off under reduced pressure to afford a dark brown residue which was taken up in ethyl acetate and washed with sat. NaHCO$_3$ (2×), H$_2$O (1×), brine (1×), dried over Na$_2$SO$_4$, filtered and stripped to afford 15 g of a dark brown oil. This oil (8.0 g) was chromatographed on a silica 60 column packed in methylene chloride to provide 1.5 g (20% yield) of the title intermediate.

Physical data were as follows:
Analytical: MS: EI M$^+$ @ M/Z 350 1 Cl present.

Step C: Preparation of N-(3-Chloropyrazin-2-yl)-L-4-aminophenylalanine Ethyl Ester The intermediate from Step B (0.75 g, 0.021 mol) was placed in a Paar hydrogenation bottle with 50 mL ethanol and 0.40 g of Pd/C catalyst. The bottle was placed on Paar shaker under 50 psi of H2 for 3 hrs. The reaction mixture was then fitered through a sintered glass funnel (F) and the filtered catalyst was washed with ethanol. The combined filtrates were stripped to a yellow oil and the oil was taken up in ethyl acetate. A yellow precipitate formed and was filtered off. The filterate was washed with NaHCO$_3$ soution (1×), H$_2$O (1×), brine (1×), dried over Na$_2$SO$_4$, filtered and stripped to afford the title intermediate as a yellow oil (0.340 g, 55% yield)

Step D: Preparation of N-(3-Chloropyrazin-2-yl)-L-4-[1-(tert-butoxycarbonyl)piperidin-4-ylcarbonylamino]phenylalanine Ethyl Ester N-Boc-piperidine 4-carboxylic acid (0.253 g, 1.0 eq., 0.0011 mol) was stirred in 30 mL methylene chloride and reaction mixture was cooled to 0° C. in ice bath. HOBt (0.224 g, 1.5 eq) was added and the mixture was stirred for 10 minutes then the intermediate from step C (1 eq., 0.32 g) was added. The reaction mixture was stirred for 5 minutes and then 1,3-dicyclohexylcarbodiimide (0.25 g, 1.1 eq) was added. The reaction mixture was warmed to room temperature and stirred overnight. The reaction was then filtered and the filtrate was stripped to give a yellow solid. The solid was taken up in ethyl acetate and filtered. The ethyl acetate solution was washed with 10% citric acid (1×), H₂O (1×), brine (1×), dried over Na₂SO₄, filtered and stripped to afford a yellow oil (0.630 g; MS: EI M+(M/Z 531 (1 chloro)). The yellow oil was chromatographed on a silica 60 column eluting with 3:1 hexane/ethyl acetate to afford 0.997 g of the title compound. This compound may also be used as an intermediate for other compounds of this invention.

Physical data were as follows:

Analytical: CHN: Theory (0.5H₂O): C, 57.71; H, 6.72; N, 12.9 Found: C, 57.79; H, 6.32; N, 12.78. MS: M+@ M/Z 531 (1 Chloro).

Synthesis of Compounds of Formulae X-XV

Compounds of Formulae X-XV may be prepared as illustrated in the scheme and described in the Examples, below:

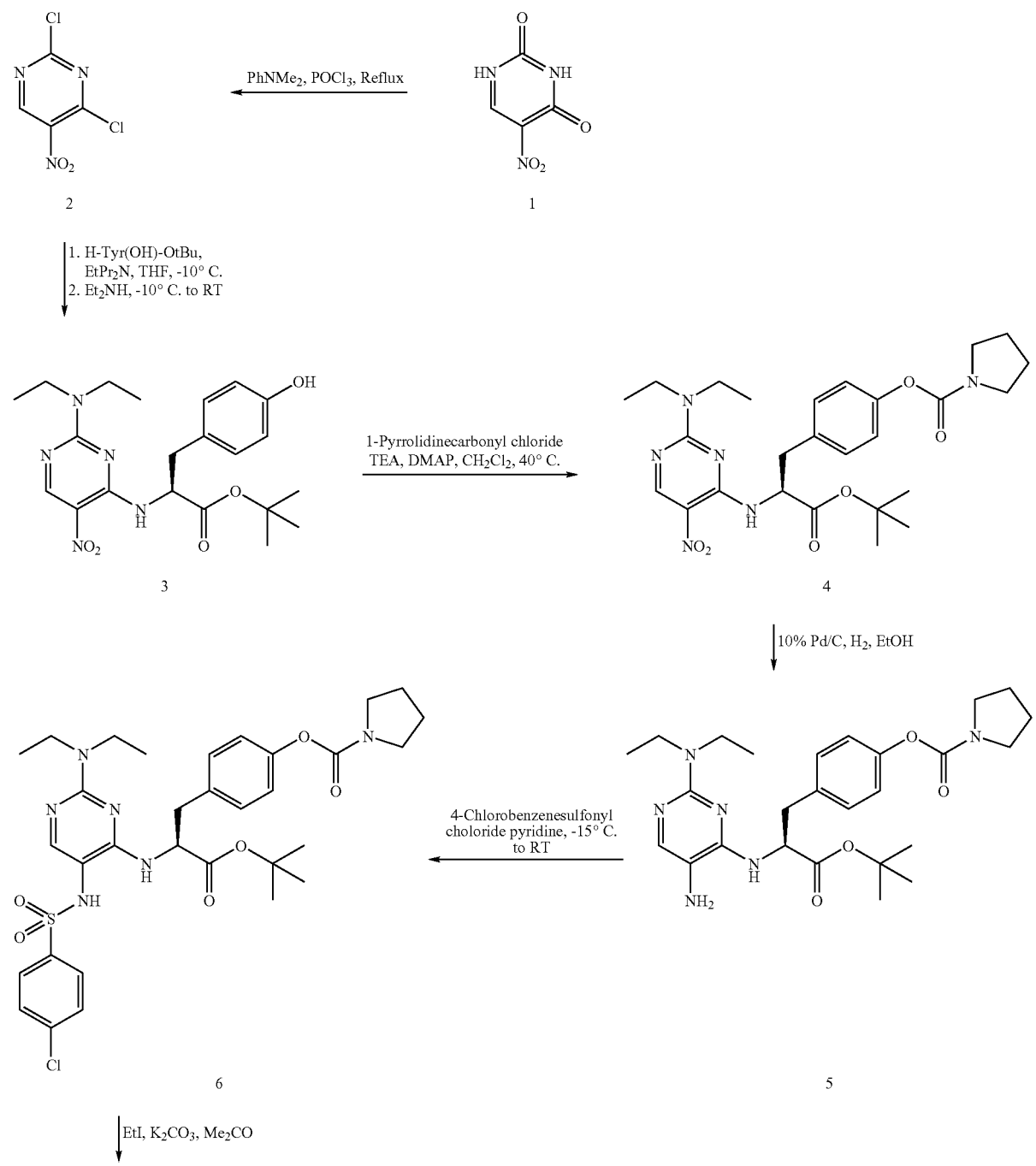

-continued

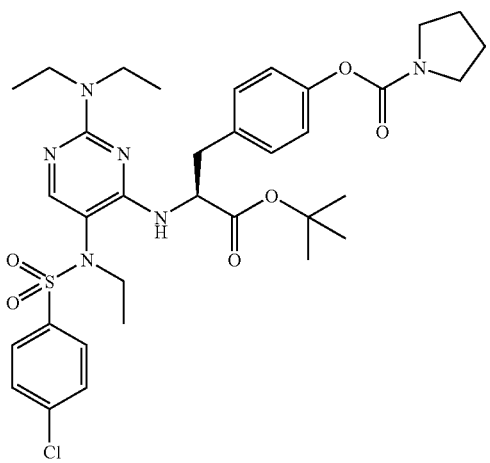 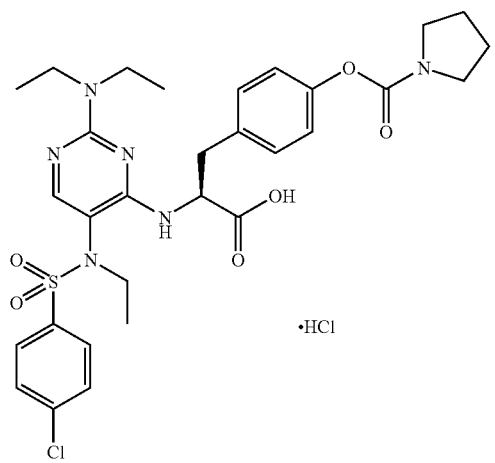

1. HCO₂H, 70° C.
2. 1 Eq. 1N HCl 7          8

Example 505

Preparation of N-(2-[N',N'-diethylamino]-5-[N'''-(4-chlorophenylsulfonyl)-N'⁹-ethylamino]pyrimidin-4-yl)-4'-(pyrrolidin-1-ylcarbonyloxy)-L-phenylalanine Step 1: Preparation of 2,4-Dichloro-5-nitropyrimidine (2). 5-Nitrouracil, (1), was treated with phosphorous oxychloride (POCl₃) and N,N-dimethylaniline (PhNMe₂), according to the procedure of Whittaker (J. Chem. Soc. 1951, 1565), to give compound 2. Compound 2 is also available from City Chemical (West Haven, Conn.).

Step 2: Preparation of N-(2-[N',N'-diethylamino]-5-nitropyrimidin-4-yl)-L-tyrosine tert-butyl ester (3). To a solution of L-tyrosine tert-butyl ester (H-Tyr(OH)-OtBu) (30.6 g, 0.129 mol) in THF (250 mL) at −10° C. was added 2,4-dichloro-5-nitropyrimidine (25 g, 0.129 mol), keeping the temperature below 5° C. during the addition. Once the addition was complete, N,N-diisopropylethylamine (EtiPr₂N) (33.7 mL, 0.194 mol) was added dropwise. After stirring for 1 h at −10° C., diethylamine (Et₂NH) (66.73 mL, 0.645 mol) was added slowly, and then the reaction mixture was warmed to room temperature overnight. The reaction mixture was diluted with diethyl ether (500 mL), and the organic layer was washed with 0.2 N citric acid (3×150 mL), water (1×150 mL), and 10% K₂CO₃ (3×150 mL). The organic phase was dried (Na₂SO₄), filtered, and concentrated in vacuo to yield a yellow residue. The residue was purified by flash chromatography (20% EtOAc/hexanes on silica gel) to yield 37.39 g (67%) of compound 3 as a yellow foam. $R_f$=0.21 (25% EtOAc/hexanes on silica gel).

Step 3: Preparation of N-(2-[N',N'-diethylamino]-5-nitropyrimidin-4-yl)-4'-(pyrrolidin-1-ylcarbonyloxy)-L-phenylalanine tert-butyl ester (4). To a solution of N-(2-[N',N'-diethylamino]-5-nitropyrimidin-4-yl)-L-tyrosine tert-butyl ester (37.39 g, 0.087 mol) in CH₂Cl₂ (150 mL) was added DMAP (10.59 g, 0.087 mol). After 5 minutes triethylamine (TEA) (18.19 mL, 0.131 mol) was added dropwise. 1-Pyrrolidinecarbamoyl chloride (14.42 mL, 0.131 mol) was added dropwise, and the reaction was heated to reflux (40° C.) overnight. The reaction mixture was concentrated in vacuo and taken up in EtOAc (300 mL). The organic phase was washed with 0.2 N citric acid (3×150 mL), water (1×150 mL), sat. NaHCO₃ (3×150 mL), brine (1×150 mL), dried (Na₂SO₄), filtered, and concentrated in vacuo to yield 43.07 g (94%) of compound 4 as a yellow solid. $R_f$=0.5 (50% EtOAc/hexanes on silica gel).

Step 4: Preparation of N-(2-[N',N'-diethylamino]-5-aminopyrimidin-4-yl)-4'-(pyrrolidin-1-ylcarbonyloxy)-L-phenylalanine tert-butyl ester (5). A mixture of N-(2-[N',N'-diethylamino]-5-nitropyrimidin-4-yl)-4'-(pyrrolidin-1-ylcarbonyloxy)-L-phenylalanine tert-butyl ester (43.07 g, 0.081 mol) and 10% Pd/C (4.3 g, 10 wt % Pd) in EtOH (200 mL) was shaken under 45 psi hydrogen until TLC (50% EtOAc/hexanes on silica gel) showed 100% conversion to product (48 hours). The reaction mixture was then filtered through a Celite plug and concentrated in vacuo to yield 40.29 g (100%) of compound 5 as a purple foam. $R_f$=0.11 (6:1 EtOAc/hexanes on silica gel).

Step 5: Preparation of N-(2-[N',N'-diethylamino]-5-[N'''-(4-chlorophenyl-sulfonyl)amino]pyrimidin-4-yl)-4'-(pyrrolidin-1-ylcarbonyloxy)-L-phenylalanine tert-butyl ester (6). A pyridine (160 mL) solution of N-(2-[N',N'-diethylamino]-5-aminopyrimidin-4-yl)-4'-(pyrrolidin-1-ylcarbonyloxy)-L-phenylalanine tert-butyl ester (40.29 g, 0.081 mol) was cooled to −20° C. with a dry ice/CH₃CN bath. The mixture stirred for 30 minutes, and then 4-chlorobenzenesulfonyl chloride (17.06 g, 0.081 mol) was added slowly. The reaction was stirred at −20° C. to −15° C. for 4 h and then allowed to warm to room temperature overnight. The reaction was diluted with EtOAc (400 mL), and the organic phase was washed with 0.2 N citric acid (3×150 mL), water (1×150 mL), sat. NaHCO₃ (3×150 mL), brine (1×150 mL), dried (Na₂SO₄), filtered, and concentrated in vacuo to yield a brown residue. The residue was purified by flash chromatography (50% EtOAc/hexanes on silica gel) to yield 43.49 g (80%) of compound 6 as a yellow foam. RF 0.35 (50% EtOAc/hexanes on silica gel).

Step 6: Preparation of N-(2-[N',N'-diethylamino]-5-[N'''-(4-chlorophenyl-sulfonyl)-N''-ethylamino]pyrimidin-4-yl)-4'-(pyrrolidin-1-ylcarbonyloxy)-L-phenylalanine tert-butyl ester (7). To a solution of N-(2-[N',N'-diethylamino]-5-[N'''-(4-chlorophenyl-sulfonyl)amino]pyrimidin-4-yl)-4'-(pyrrolidin-1-ylcarbonyloxy)-L-phenylalanine tert-butyl ester (42.92 g, 0.064 mol) in acetone (Me₂CO) (600 mL) was added K₂CO₃ (12.75 g, 0.096 mol), and the mixture was stirred for 1 h at room temperature. Iodoethane (EtI) (7.73 mL, 0.096 mol) was then added slowly, and the reaction mixture was stirred overnight at room temperature. The reaction mixture was concentrated in vacuo, and the residue was taken up in EtOAc (300 mL). The organic phase was washed with water (2×300 mL), brine (1×100 mL), dried (Na$_2$SO$_4$), filtered, and concentrated in vacuo. The residue was purified by flash chromatography (2:1 hexanes/EtOAc on silica gel) to yield 37.36 g (85%) of compound 7 as a white solid. R$_f$=0.53 (50% EtOAc/hexanes on silica gel).

Step 7: Preparation of N-(2-[N',N'-diethylamino]-5-[N''-(4-chlorophenylsulfonyl)-N'''-ethylamino]pyrimidin-4-yl)-4'-(pyrrolidin-1-ylcarbonyloxy)-L-phenylalanine hydrochloride (8). A formic acid (500 mL) solution of N-(2-[N',N'-diethylamino]-5-[N''-(4-chlorophenyl-sulfonyl)-N'''-ethylamino] pyrimidin-4-yl)-4'-(pyrrolidin-1-ylcarbonyloxy)-L-phenylalanine tert-butyl ester (36.21 g, 0.052 mol) was heated to 70° C. for 2 h and then concentrated in vacuo. The residue was dissolved again in formic acid (500 mL) and heated again at 70° C. for 2 h. The solution was reduced in volume by 80% and then treated with at least 1 eq. of 1.0 N HCl (52 mL, 0.052 mol) followed by distilled water (100 mL). The resulting heterogeneous mixture was concentrated in vacuo. Distilled water (100 mL) was added, and the heterogeneous mixture was concentrated in vacuo. The latter steps were repeated twice to yield a wet white product. This was dried by placing under high vacuum at 40° C. (7 days) to yield 32.8 g (93%) of compound 8, as a free-flowing white solid. R$_f$=0.25 (7/3 MeOH/H$_2$O+0.1% TFA, reverse phase).

$^1$H NMR (CD$_3$OD) δ 8.22 (bs, 1H), 7.82-7.79 (m, 1H), 7.64-7.60 (m, 2H), 7.36-7.33 (m, 1H), 7.22-7.13 (m, 2H), 7.07-6.98 (m, 2H), 4.91-4.90 (m, 1H), 4.80-4.79 (m, 1H), 4.12-4.10 (m, 1H), 3.87-3.75 (m, 1H), 3.55-3.53 (m, 4H), 3.41-3.40 (m, 3H), 3.26-3.19 (m, 2H), 2.03 (bs, 1H), 1.97-1.89 (m, 3H), 1.27-1.15 (m, 6H), 1.10-1.05 (t, 1.5H), 0.97-0.92 (t, 1.5H)

$^{13}$CNMR(CD$_3$OD) δ 175.8, 175.7, 166.5, 162.7, 162.2, 155.8, 155.7, 155.7, 152.6, 148.1, 147.7, 142.0, 138.5, 136.2, 132.6, 132.3, 131.9, 131.7, 123.7, 111.8, 111.5, 62.3, 57.8, 44.9, 38.7, 38.0, 27.4, 26.6, 15.3, 14.9, 14.7, 14.0, 13.9

Example 506

Preparation of N-(2-[N',N'-diethylamino]-5-[N''-(4-fluorophenylsulfonyl)-N'''-ethylamino]pyrimidin-4-yl)-4'-(pyrrolidin-1-ylcarbonyloxy)-L-phenylalanine Steps 1, 2, 3, 4, 6 and 7 were performed as for Example 505. Step 5 was performed using 4-fluorobenzenesulfonyl chloride in place of 4-chlorobenzenesulfonyl chloride.

$^1$H NMR (CD$_3$OD) δ 8.17 (bs, 1H), 7.90-7.87 (m, 2H), 7.40-7.34 (m, 2H), 7.20-7.16 (m, 1H), 7.08-7.00 (m, 3H), 5.52-5.51 (m, 1H), 4.96-4.93 (m, 2H), 5.78-5.70 (m, 1H), 3.85-3.75 (m, 1H), 3.59-3.53 (m, 4H), 4.47-4.43 (m, 2H), 3.44-3.24 (m, 2H), 2.02-1.94 (m, 3H), 1.24-1.16 (m, 6H), 1.10-1.05 (t, 1.5H), 0.99-0.94 (t, 1.5H)

$^{13}$C NMR (CD$_3$OD) δ 133.0, 132.9, 132.5, 132.2, 123.7, 123.6, 118.6, 57.1, 44.3, 38.3, 27.3, 26.6, 14.7, 14.1

MS m/z 629.5 (MH+)

Example 507

Preparation of N-(2-[N',N'-diethylamino]-5-[N''-(4-fluorophenylsulfonyl)-N'''-methylamino]pyrimidin-4-yl)-4'-(pyrrolidin-1-ylcarbonyloxy)-L-phenylalanine Steps 1, 2, 3, 4, 5 and 7 were performed as for Example 506. Step 6 was performed using dimethyl sulfate in place of ethyl iodide.

$^1$H NMR (CD$_3$OD) δ 8.16 (bs, 1H), 7.89-7.88 (m, 1H), 7.39-7.35 (m, 3H), 7.20-7.13 (m, 1H), 7.05-7.00 (m, 2H), 4.85-4.84 (m, 1H), 4.14-4.12 (m, 1H), 3.59-3.54 (m, 5H), 3.45-3.44 (m, 2H), 3.45-3.33 (m, 3H), 3.13-3.12 (m, 1H), 3.02-3.01 (m, 1H), 2.04-1.95 (m, 4H), 1.29-1.18 (m, 6H)

$^{13}$C NMR (CD$_3$OD) δ 176.5, 169.8, 166.9, 166.4, 156.2, 152.7, 151.8, 150.4, 136.8, 133.3, 133.2, 132.5, 123.7, 118.8, 118.5, 57.8, 57.1, 48.3, 44.5, 41.0, 38.8, 27.5, 26.7, 14.1

MS m/z 615.2 (MH+)

Example 508

Preparation of N-(2-[N',N'-diethylamino]-5-[N''-(4-chlorophenylsulfonyl)-N'''-methylamino]pyrimidin-4-yl)-4'-(pyrrolidin-1-ylcarbonyloxy)-L-phenylalanine Steps 1, 2, 3, 4, 5 and 7 were performed as for Example 505. Step 6 was performed using dimethyl sulfate in place of ethyl iodide.

$^1$H NMR (CD$_3$OD) δ 8.20 (bs, 1H), 7.83-7.80 (m, 2H), 7.67-7.64 (m, 2H), 7.37-7.34 (m, 1H), 7.21-7.18 (m, 1H), 7.10-7.03 (m, 2H), 4.88-4.87 (m, 1H), 4.13-4.10 (m, 1H), 3.55-3.45 (m, 6H), 3.42-3.40 (m, 2H), 3.24-3.23 (m, 2H), 3.11-3.10 (m, 1H), 3.02-3.01 (m, 1H), 2.04-2.03 (m, 1H), 1.98-1.90 (m, 3H), 1.28-1.18 (m, 6H)

$^{13}$C NMR (CD$_3$OD) δ 176.0, 166.4, 161.8, 155.9, 155.4, 152.6, 146.5, 142.2, 137.6, 137.4, 136.4, 132.5, 131.9, 123.7, 114.6, 62.4, 58.1, 57.7, 45.0, 40.8, 38.6, 38.3, 27.4, 26.6, 15.3, 13.9

Example 509

Preparation of N-(2-[N',N'-diethylamino]-5-[N''-(4-fluorophenylsulfonyl)-N'''-methylamino]pyrimidin-4-yl)-4'-(piperidin-1-ylcarbonyloxy)-L-phenylalanine Steps 1, 2, 4, 5, 6 and 7 were performed as for Example 507. Step 3 was performed using 1-piperidinecarbonyl chloride in place of 1-pyrrolidinecarbonyl chloride.

$^1$H NMR (CD$_3$OD) δ 8.16 (bs, 1H), 7.90-7.88 (m, 2H), 7.40-7.35 (m, 2H), 7.21-7.20 (m, 1H), 7.14-7.13 (m, 1H), 7.02-7.01 (m, 2H), 5.51 (bs, 1H), 4.83-4.77 (m, 1H), 3.64-3.53 (m, 6H), 3.34-3.33 (m, 2H), 3.20-3.17 (m, 1H), 3.12-3.11 (m, 2H), 3.02-3.01 (m, 1H), 1.68-1.65 (m, 6H), 1.19-1.17 (m, 6H) 3C NMR (CD$_3$OD) δ 185.0, 169.7, 166.3, 152.7, 136.6, 135.0, 133.2, 133.0, 132.5, 131.8, 126.3, 123.6, 121.7, 118.6, 118.3, 57.6, 54.5, 46.9, 44.3, 39.6, 38.7, 27.6, 25.9, 14.0

Example 510

Preparation of N-(2-[N',N'-diethylamino]-5-[N''-(4-fluorophenylsulfonyl)-N'''-ethylamino]pyrimidin-4-yl)-4'-(piperidin-1-ylcarbonyloxy)-L-phenylalanine Steps 1, 2, 4, 5, 6 and 7 were performed as for Example 506. Step 3 was performed using 1-piperidinecarbonyl chloride in place of 1-pyrrolidinecarbonyl chloride.

$^1$H NMR (CD$_3$OD) δ 8.17 (bs, 1H), 7.91-7.85 (m, 2H), 7.39-7.31 (m, 3H), 7.20-7.16 (m, 1H), 7.05-6.97 (m, 2H), 4.88-4.69 (m, 2H), 4.71-4.69 (m, 1H), 3.80-3.75 (m, 1H), 3.62-3.39 (m, 6H), 3.34-3.32 (m, 2H), 3.30-3.16 (m, 3H), 1.68-1.65 (m, 4H), 1.23-1.17 (m, 6H), 1.10-1.05 (t, 1.5H), 0.99-0.94 (t, 1.5H)

$^{13}$C NMR (CD$_3$OD) δ 199.9, 187.6, 183.1, 176.2, 169.7, 166.3, 163.0, 162.7, 153.9, 152.9, 136.5, 133.1, 133.0, 132.7, 132.4, 123.8, 118.8, 118.4, 111.1, 110.6, 102.8, 79.4, 57.3, 55.4, 44.4, 38.9, 38.4, 27.7, 26.1, 15.1, 14.8, 14.3, 14.2

Example 511

Preparation of N-(2-[N',N'-diethylamino]-5-[N"-(4-fluorophenylsulfonyl)-N"'-ethylamino]pyrimidin-4-yl)-4'-(azetidin-1-ylcarbonyloxy)-L-phenylalanine Steps 1, 2, 4, 5, 6 and 7 were performed as for Example 506. Step 3 was performed according to the following procedure.

$^1$H NMR (CD$_3$OD) δ 7.92-7.86 (m, 2H), 7.41-7.32 (m, 3H), 7.22 (d, 1H), 7.04-6.91 (m, 3H), 4.29-3.98 (m, 4H), 3.88-3.72 (m, 1H), 3.69-3.37 (m, 4H), 2.40-2.24 (m, 2H), 1.28-1.11 (m, 6H), 1.10-1.00 (t, 1.5H), 1.01-0.89 (t, 1.5H)

$^{13}$C NMR (CD$_3$OD) δ 174.2, 169.7, 166.4, 163.2, 162.8, 157.0, 153.3, 153.2, 152.4, 144.3, 143.8, 136.1, 135.6, 135.5, 133.2, 133.1, 132.5, 132.2, 123.7, 118.9, 118.6, 112.9, 112.6, 57.5, 38.1, 37.7, 17.4, 14.7, 14.5, 13.8, 13.7

MS m/z 615 (MH$^+$)

Alternative Preparation of N-(2-[N',N-diethylamino]-5-nitropyrimidin-4-yl)-4'-(azetidin-1-ylcarbonyloxy)-L-phenylalanine tert-butyl ester. To a −15° C. stirred solution of compound 3 (24.9 g, 0.0578 mol) and 4-nitrophenyl chloroformate (11.7 g, 0.0578 mmol) in CH$_2$Cl$_2$ (300 mL) was added triethylamine (24.2 mL, 0.173 mol), at a rate such that the temperature of the reaction mixture did not exceed −10° C. After stirring for 20 min, azetidine (3.30 g, 0.0578 mmol) was added dropwise, and the reaction mixtures was warmed to room temperature and stirred overnight. The reaction mixture was diluted with EtOAc (100 mL) and hexanes (100 mL), and then was extracted repeatedly with 10% aqueous K$_2$CO$_3$, until no yellow color (4-nitrophenol) was seen in the aqueous phase. The organic layer was washed with brine (75 mL), dried with MgSO$_4$, filtered, and evaporated to yield 28.5 g (96%) of N-(2-[N',N-diethylamino]-5-nitropyrimidin-4-yl)-4'-(azetidin-1-ylcarbonyloxy)-L-phenylalanine tert-butyl ester as a yellow solid, which was used without purification. Rf=0.17 (2:5 EtOAc/hexanes on silica gel).

Example 512

Preparation of N-(2-[N',N'-diethylamino]-5-[N"-(4-fluorophenylsulfonyl)-N"'-methylamino] pyrimidin-4-yl)-4'-(azetidin-1-ylcarbonyloxy)-L-phenylalanine Steps 1, 2, 3, 4, 5 and 7 were performed as for Example 511. Step 6 was performed using dimethyl sulfate in place of ethyl iodide.

$^1$H NMR (CD$_3$OD) δ 7.95-7.76 (m, 2H), 7.44-7.11 (m, 4H), 7.01-6.83 (m, 3H), 4.30-3.93 (m, 4H), 3.66-3.41 (m, 4H), 3.14-2.92 (m, 3H), 2.42-2.21 (m, 2H), 1.32-1.01 (m, 6H)

$^{13}$C NMR (CD$_3$OD) δ 152.3, 136.3, 133.4, 133.2, 132.4, 123.6, 118.8, 118.5, 38.2, 17.4, 13.8

MS m/z 601 (MH$^+$)

Example 513

Preparation of N-(2-[N',N'-diethylamino]-5-[N"-(4-chlorophenylsulfonyl)-N"'-methylamino]pyrimidin-4-yl)-4'-(azetidin-1-ylcarbonyloxy)-L-phenylalanine Steps 1, 2, 3, 4, 6 and 7 were performed as for Example 512. Step 5 was performed using 4-chlorobenzenesulfonyl chloride in place of 4-fluorobenzenesulfonyl chloride.

$^1$H NMR (CD$_3$OD) δ 7.83 (d, 2H), 7.67 (d, 2H), 7.36-7.18 (m, 2H), 7.06-6.86 (m, 3H), 4.29-3.97 (m, 4H), 3.66-3.34 (m, 5H), 3.15-2.95 (m, 4H), 2.41-2.22 (m, 2H) 1.26-1.06 (m, 6H)

$^{13}$C NMR (CD$_3$OD) δ 157.2, 153.0, 152.5, 142.9, 142.5, 136.4, 132.5, 132.1, 132.0, 123.8, 57.9, 52.2, 40.7, 38.0, 17.4, 13.6

MS m/z 617 (MH$^+$)

Example 514

Preparation of N-(2-[N',N'-diethylamino]-5-[N"-(4-chlorophenylsulfonyl)-N"'-ethylamino]pyrimidin-4-yl)-4'-(azetidin-1-ylcarbonyloxy)-L-phenylalanine Steps 1, 2, 3, 4, 6 and 7 were performed as for Example 511. Step 5 was performed using 4-chlorobenzenesulfonyl chloride in place of 4-fluorobenzenesulfonyl chloride.

$^1$H NMR (CD$_3$OD) δ 7.86-7.76 (m, 2H), 7.70-7.60 (m, 2H), 7.32 (bd, 1H), 7.21 (bd, 1H), 7.03-6.97 (m, 2H), 6.90 (bs, 1H), 4.29-4.00 (m, 4H), 3.89-3.72 (m, 1H), 3.70-3.36 (m, 5H), 3.28-3.10 (m, 2H), 2.42-2.24 (m, 2H), 1.28-1.13 (m, 6H), 1.11-1.02 (t, 1.5H), 1.01-0.90 (t, 1.5H)

MS m/z 631 (MH$^+$)

Example 515

Preparation of N-(2-[N',N'-diethylamino]-5-[N"-(2,4-difluorophenylsulfonyl)-N"'-methylamino]pyrimidin-4-yl)-4'-(pyrrolidin-1-ylcarbonyloxy)-L-phenylalanine Steps 1, 2, 3, 4, 6 and 7 were performed as for Example 507. Step 5 was performed using 2,4-difluorobenzenesulfonyl chloride in place of 4-fluorobenzenesulfonyl chloride.

$^1$H NMR (CDCl$_3$) δ 1.16 (bs, 6H), 1.93 (bs, 4H), 2.50-3.75 (m, 13H), 4.83 (bs, 1H), 6.60-7.40 (m, 7H), 7.60 (bs, 1H), 7.77 (m, 1H), 9.41 (bs, 1H)

Example 516

Preparation of N-(2-[N',N'-diethylamino]-5-[N"-(2,4-difluorophenylsulfonyl)-N"'-ethylamino]pyrimidin-4-yl)-4'-(pyrrolidin-1-ylcarbonyloxy)-L-phenylalanine Steps 1, 2, 3, 4, 6 and 7 were performed as for Example 506. Step 5 was performed using 2,4-difluorobenzenesulfonyl chloride in place of 4-fluorobenzensulfonyl chloride.

$^1$H NMR (CDCl$_3$) δ 0.91 (t, J=6.9, 1.8H), 1.12 (m, 7.2H), 1.92 (bs, 4H), 2.50-4.00 (m, 13H), 4.78 (m, 0.6H), 4.88 (m, 0.4H), 6.55 (d, J=6.9, 0.4H), 6.77 (d, J=6.3, 0.6H), 6.80-7.38 (m, 6H), 7.51 (s, 0.4H), 7.58 (s, 0.6H), 7.74 (m, 1H), 9.33 (m, 1H)

Example 517

Preparation of N-(2-[N',N'-diethylamino]-5-[N"-(2,4-difluorophenylsulfonyl)-N"'-methylamino]pyrimidin-4-yl)-4'-(azetidin-1-ylcarbonyloxy)-L-phenylalanine Steps 1, 2, 4, 5, 6 and 7 were performed as for Example 515. Step 3 was performed as for Example 511.

$^1$H NMR (CDCl$_3$) δ 1.14 (T, J=6.6, 6H), 2.32 (m, 2H), 2.50-3.80 (m, 9H), 4.13 (m, 4H), 4.62 (m, 0.6H), 4.81 (m, 0.4H), 5.81 (bd, 0.6H), 5.90 (bd, 0.4H), 6.90-7.40 (m, 7H), 7.77 (m, 1H)

MS m/z 619.2 (MH$^+$)

Example 518

Preparation of N-(2-[N',N'-diethylamino]-5-[N"-(2,4-difluorophenylsulfonyl)-N"-ethylamino]pyrimidin-4-yl)-4'-(azetidin-1-ylcarbonyloxy)-L-phenylalanine Steps 1, 2, 4, 5, 6 and 7 were performed as for Example 516. Step 3 was performed as for Example 511.

$^1$H NMR (CDCl$_3$) δ 0.89 (t, J=6.7, 1.8H), 1.16 (m, 7.2H), 2.28 (m, 2H), 3.00-4.00 (m, 8H), 4.09 (bs, 4H), 4.79 (m, 0.6H), 4.88 (m, 0.4H), 6.80-7.30 (m, 7H), 7.57 (s, 0.4H), 7.62 (s, 0.6H), 7.75 (m, 1H), 11.9 (bs, 1H)

MS m/z 633.2 (MH$^+$)

Example 519

Preparation of N-(2-[N',N'-diethylamino]-5-[N"-(4-fluorophenylsulfonyl)-N"-propargylamino]pyrimidin-4-yl)-4'-(pyrrolidin-1-ylcarbonyloxy)-L-phenylalanine Steps 1, 2, 3, 4, 5 and 7 were performed as for Example 506. Step 6 was performed using propargyl bromide in place of ethyl iodide.

$^1$H NMR (CDCl$_3$) δ 1.18 (m, 6H), 1.93 (bs, 4H), 2.37 (s, 1H), 3.00-3.70 (m, 10H), 3.80 (d, J=21.3, 0.6H), 3.98 (d, J=18.3, 0.4H), 4.51 (m, 1H), 4.88 (m, 1H), 6.75-7.35 (m, 7H), 7.58 (s, 0.6H), 7.63 (s, 0.4H), 7.86 (m, 2H), 9.71 (bs, 1H)

Example 520

Preparation of N-(2-[N',N'-diethylamino]-5-[N"-(2,4-difluorophenylsulfonyl)-N"-propargylamino]pyrimidin-4-yl)-4'-(pyrrolidin-1-ylcarbonyloxy)-L-phenylalanine Steps 1, 2, 3, 4, 5 and 7 were performed as for Example 515. Step 6 was performed using propargyl bromide in place of dimethyl sulfate.

$^1$H NMR (CDCl$_3$) δ 1.17 (m, 6H), 1.94 (m, 4H), 2.40 (m, 1H), 3.00-3.75 (m, 10H), 3.99 (d, J=18.0, 0.6H), 4.18 (d, J=18.0, 0.4H), 4.50 (m, 1H), 4.90 (m, 1H), 6.75-7.35 (m, 7H), 7.81 (m, 2H), 10.0 (bs, 1H)

Example 521

Preparation of N-(2-[N',N'-diethylamino]-5-[N"-(2,4-difluorophenylsulfonyl)-N"-propargylamino]pyrimidin-4-yl)-4'-(azetidin-1-ylcarbonyloxy)-L-phenylalanine Steps 1, 2, 4, 5, 6 and 7 were performed as for Example 520. Step 3 was performed as for Example 511.

$^1$H NMR (CDCl$_3$) δ 1.18 (m, 6H), 2.34 (m, 3H), 3.00-3.75 (m, 6H), 3.80-4.25 (m, 5H), 4.47 (m, 1H), 4.89 (m, 1H), 6.75-7.35 (m, 7H), 7.79 (m, 2H), 10.3 (bs, 1H)

MS m/z 643.2 (MH$^+$)

Example 522

Preparation of N-(2-[N',N'-diethylamino]-5-[N"-(4-fluorophenylsulfonyl)-N"-propargylamino]pyrimidin-4-yl)-4'-(azetidin-1-ylcarbonyloxy)-L-phenylalanine Steps 1, 2, 3, 4, 5 and 7 were performed as for Example 511. Step 6 was performed using propargyl bromide in place of ethyl iodide.

$^1$H NMR (CDCl$_3$) δ 1.25 (m, 6H), 2.28 (m, 3H), 3.00-3.75 (m, 6H), 3.80-4.25 (m, 5H), 4.47 (m, 1H), 4.89 (m, 1H), 6.75-7.35 (m, 7H), 7.57 (s, 0.6H), 7.62 (s, 0.4H), 7.79 (m, 2H), 10.6 (bs, 1H)

MS m/z 625.2 (MH$^+$)

Example 523

Preparation of N-(2-[N',N'-diethylamino]-5-[N"-(4-chlorophenylsulfonyl)-N"-propargylamino]pyrimidin-4-yl)-4'-(pyrrolidin-1-ylcarbonyloxy)-L-phenylalanine Steps 1, 2, 3, 4, 5 and 7 were performed as for Example 505. Step 6 was performed using propargyl bromide in place of ethyl iodide.

$^1$H NMR (CD$_3$OD) δ 8.13 (s, 1H), 7.86-7.82 (m, 2H), 7.62-7.58 (m, 2H), 7.32-7.28 (m, 2H), 7.19-7.17 (m, 1H), 7.04-6.98 (m, 2H), 4.83-4.5 (m, 2H), 4.12-3.82 (m, 1H), 3.63-3.37 (m, 8H), 3.27-3.08 (m, 2H), 2.72 (bs, 1H), 2.04-1.86 (m, 4H), 1.24-1.07 (m, 6H)

$^{13}$C NMR (CD$_3$OD) δ 177.2, 176.5, 162.7, 156.7, 155.7, 154.5, 153.2, 142.6, 140.3, 137.4, 137.3, 133.1, 132.9, 132.8, 132.7, 132.2, 132.1, 124.3, 111.3, 80.5, 80.3, 77.7, 58.2, 57.7, 44.9, 43.4, 28.1, 27.3, 14.8, 14.7

MS m/z 655 (MH$^+$)

Synthesis of Compounds of Formulae XVI-XXI

Compounds of Formulae XVI-XXI may be prepared as described in the Examples below:

Example 524

Preparation of 2-{2-diethylamino-5-[(4-fluorobenzenesulfonyl)methylamino] pyrimidin-4-ylamino}-3-(4-dimethylcarbamoyloxyphenyl)propionic acid General. Flash chromatography was performed using a Biotage Flash 75L, using 800 g KP-Sil silica cartridges (32-63 μM, 60 angstrom, 500-550 m$^2$/g). Rfs are reported for analytical thin layer chromatography, using EM Science Silica Gel F(254) 250 μM thick plates for normal phase, and Watman MKCl 8F 200 μM thick plates for reverse phase.

Step 1: Preparation of 2,4-Dichloro-5-nitropyrimidine. 5-Nitrouracil, was treated with phosphorous oxychloride and N,N-dimethylaniline, according to the procedure of Whittaker (J. Chem. Soc. 1951, 1565), to give the title compound, which is also available from City Chemical (West Haven, Conn.).

Step 2: Preparation of 2-(2-diethylamino-5-nitropyrimidin-4-ylamino)-3-(4-hydroxyphenyl)propionic acid, t-butyl ester. To a solution of 2-amino-3-(4-hydroxyphenyl)propionic acid, (30.6 g, 0.129 mol) in THF (250 mL) at −10C was added 2,4-Dichloro-5-nitropyrimidine (25 g, 0.129 mol), keeping the temperature below 5° C. during the addition. Once the addition was complete, N,N-diisopropylethylamine (33.7 mL, 0.194 mol) was added dropwise. After stirring for 1 h at −10° C, diethylamine (66.73 mL, 0.645 mol) was added slowly, and then the reaction mixture was warmed to room temperature overnight. The reaction mixture was diluted with diethyl ether (500 mL), and the organic layer was washed with 0.2 N citric acid (3×150 mL), water (1×150 mL); and 10% K$_2$CO$_3$ (3×0.150 mL). The organic phase was dried (Na$_2$SO$_4$), filtered, and concentrated in vacuo to yield a yellow residue. The residue was purified by flash chromatography (20% EtOAc/hexanes on silica gel) to yield 37.39 g (67%) the title compound as a yellow foam. R$_f$=0.21 (25% EtOAc/hexanes on silica gel).

Step 3: Preparation of 2-(2-diethylamino-5-nitropyrimidin-4-ylamino)-3-(4-dimethylcarbamoyloxyphenyl)propionic acid t-butyl ester. To a solution of 2-(2-diethylamino-5-nitropyrimidin-4-ylamino)-3-(4-hydroxy-phenyl)propionic acid t-butyl ester (31.80 g, 0.074 mol) in CH$_2$Cl$_2$ (600 mL) was added DMAP (9.00 g, 0.074 mol). After 5 minutes triethylamine (10.23 mL, 0.074 mol) was added dropwise. N,N- dimethylcarbamyl chloride (13.83 mL, 0.110 mol) was added dropwise, and the reaction was heated to reflux overnight. The reaction mixture was concentrated in vacuo and taken up in EtOAc (1 L). The organic phase was washed with 0.5 M citric acid (3×250 mL), sat. NaHCO$_3$ (3×250 mL), brine (1×250 mL), dried (MgSO$_4$), filtered, and concentrated in vacuo to yield 37.0 g (99%) the title compound as a white solid.

Step 4: Preparation of 2-(2-diethylamino-5-aminopyrimidin-4-ylamino)-3-(4-dimethylcarbamoyloxyphenyl)propionic acid t-butyl ester. A mixture of 2-(2-diethylamino-5-nitropyrimidin-4-ylamino)-3-(4-dimethylcarbamoyl-oxyphenyl) propionic acid t-butyl ester (37.0 g, 0.073 mol) and 10% Pd/C (3.8 g, 10 wt % Pd) in EtOH (250 mL) was shaken under 60 psi hydrogen until TLC (50% EtOAc/hexanes on silica gel) showed 100% conversion to product (48 hours). The reaction mixture was then filtered through a Celite plug and concentrated in vacuo to yield 32.0 g (92%) the title compound as a violet foam.

Step 5: Preparation of 2-{2-diethylamino-5-[(4-fluorobenzenesulfonyl) amino]-pyrimidin-4-ylamino}-3-(4-dimethylcarbamoyloxyphenyl) propionic acid t-butyl ester. A pyridine (120 mL) solution of 2-(2-diethylamino-5-aminopyrimidin-4-ylamino)-3-(4-dimethylcarbamoyloxy-phenyl)propionic acid t-butyl ester (32.0 g, 0.067 mol) was cooled to –20° C. with a dry ice/CH$_3$CN bath. The mixture stirred for 30 minutes, and then p-fluorobenzenesulfonyl chloride (13.18 g, 0.067 mol) was added slowly. The reaction was stirred at –20° C. for 4.5 hrs, and then 3-dimethylaminopropyl amine (8.52 mL, 0.067 mol) was added, and then the mixture was allowed to warm to room temperature overnight. The reaction was concentrated in vacuo. The residue was taken up in EtOAc (1 L), and the organic phase was washed with 0.5 M citric acid (3×900 mL), water (1×900 mL), sat. NaHCO$_3$ (3×900 mL), brine (1×900 mL), dried (MgSO$_4$), filtered, and concentrated in vacuo to yield a brown residue. The residue was purified by flash chromatography (50% EtOAc/hexanes on silica gel) to yield 33.04 g (77%) the title compound as a yellow foam. RF 0.54 (3:2 EtOAc/hexanes on silica gel).

Step 6: Preparation of 2-{2-diethylamino-5-[(4-fluorobenzenesulfonyl) methylamino]-pyrimidin-4-ylamino}-3-(4-dimethylcarbamoyloxyphenyl) propionic acid t-butyl ester. To a solution of 2-{2-diethylamino-5-[(4-fluorobenzenesulfonyl)amino]-pyrimidin-4-ylamino}-3-(4-dimethyl-carbamoyloxyphenyl)propionic acid t-butyl ester (33.04 g, 0.052 mol) in acetone (510 mL) was added K$_2$CO$_3$ (8.69 g, 0.063 mol), and the mixture was stirred for 10 min at room temperature. Dimethyl sulfate (5.95 mL, 0.063 mol) was then added slowly, and the reaction mixture was stirred overnight at room temperature. The reaction mixture was concentrated in vacuo, and the residue was taken up in EtOAc (600 mL). The organic phase was washed with water (2×400 mL), brine (2×400 mL), dried MgSO$_4$, filtered, and concentrated in vacuo. The residue was purified by flash chromatography (2:1 hexanes/EtOAc on silica gel) to yield 28.69 g (85%) the title compound as a white solid.

Step 7: Preparation of 2-{2-diethylamino-5-[(4-fluorobenzenesulfonyl) methylamino]pyrimidin-4-ylamino}-3-(4-dimethylcarbamoyloxyphenyl) propionic acid hydrochloride. A formic acid (500 mL) solution of 2-{2-diethylamino-5-[(4-fluorobenzenesulfonyl) methylamino]-pyrimidin-4-ylamino}-3-(4-dimethylcarbamoyloxyphenyl) propionic acid t-butyl ester (28.69 g, 0.044 mol) was heated to 70° C. for 2 h, and then concentrated in vacuo. The residue was dissolved again in formic acid (500 mL), and then heated again at 70° C. for 2 h, and then concentrated again in vacuo. The residue was dissolved again in formic acid (500 mL), and then heated again at 70° C. for 1 h. The solution was reduced in volume by 90%, and then treated with 1.0 M HCl (44 mL, 0.044 mol) and distilled water (490 mL). The resulting homogeneous solution was concentrated in vacuo, and then distilled water (100 mL) was added, and the homogenous solution was lyophilized over 14 days to yield 26.76 g (96%) the title compound, as a white solid.

$^1$H NMR (CD$_3$OD) δ 7.96-7.92 (m, 2H), 7.45-7.25 (m, 4H), 7.06-6.95 (m, 3H), 5.00-4.93 (m, 1H), 3.55-3.40 (m, 5H), 3.34-3.20 (m, 2H), 3.15-3.05 (m, 5H), 3.07-3.00 (m, 3H), 1.22 (bs, 6H)

$^{13}$CNMR(CD$_3$OD)δ 171.6, 168.3, 154.5, 144.4, 137.9, 135.1, 135.0, 134.1, 125.5, 120.6, 120.3, 39.6, 39.2, 39.1, 15.2

MS m/z 589 (MH+)

Example 525

Preparation of 2-{2-diethylamino-5-[(4-chlorobenzenesulfonyl)methylamino] pyrimidin-4-ylamino}-3-(4-dimethylcarbamoyloxyphenyl)propionic acid Steps 1, 2, 3, 4, 6 and 7 were performed as for Example 524. Step 5 was performed using 4-chlorobenzenesulfonyl chloride in place of 4-fluorobenzenesulfonyl chloride.

$^1$H NMR (CD$_3$OD) δ 7.88-7.85 (m, 2H), 7.72-7.69 (m, 2H), 7.39-7.25 (m, 2H), 7.14-6.92 (m, 3H), 5.00-4.85 (m, 1H), 3.60-3.50 (m, 1H), 3.37-3.28 (m, 6H), 3.15-3.07 (m, 6H), 3.01 (bs, 3H), 1.22 (bs, 6H)

$^{13}$C NMR (CD$_3$OD) δ 208.6, 145.3, 134.9, 128.8, 124.9, 124.5, 124.4, 116.3, 50.2, 30.4, 30.0, 6.0

MS m/z 605 (MH$^+$)

Example 526

Preparation of 2-{2-diethylamino-5-[(3,4-difluorobenzenesulfonyl) methylamino]pyrimidin-4-ylamino}-3-(4-dimethylcarbamoyloxyphenyl) propionic acid Steps 1, 2, 3, 4, 6 and 7 were performed as for Example 524. Step 5 was performed using 3,4-difluorobenzenesulfonyl chloride in place of 4-fluorobenzenesulfonyl chloride.

$^1$H NMR (CD$_3$OD) δ 7.84-7.77 (m, 1H), 7.67 (bs, 1H), 7.58-7.53 (m, 1H), 7.37-7.34 (m, 1H), 7.22-7.18 (m, 1H), 7.08-7.02 (m, 3H), 4.83-4.76 (m, 1H), 3.55-3.54 (m, 4H), 3.35-3.33 (m, 1H), 3.23-3.12 (m, 6H), 3.03-2.99 (m, 3H), 1.19 (bs, 6H)

$^{13}$C NMR (CD$_3$OD) δ 178.3, 177.8, 163.2, 162.6, 159.3, 159.1, 155.9, 155.7, 154.3, 153.0, 152.5, 152.4, 138.4, 138.1, 134.0, 129.5, 125.3, 122.4, 122.2, 121.7, 121.4, 115.3, 59.3, 46.0, 42.4, 41.9, 40.4, 39.9, 39.2, 39.1, 15.76

MS m/z 607.2 (MH$^+$)

Example 527

Preparation of 2-{2-diethylamino-5-[(3,4-dichlorobenzenesulfonyl) methylamino]pyrimidin-4-ylamino}-3-(4-dimethylcarbamoyloxyphenyl) propionic acid Steps 1, 2, 3, 4, 6 and 7 were performed as for Example 524. Step 5 was performed using 3,4-dichlorobenzenesulfonyl chloride in place of 4-fluorobenzenesulfonyl chloride.

$^1$H NMR (CD$_3$OD) δ 8.00-7.98 (m, 1H), 7.83-7.74 (m, 2H), 7.37-7.34 (m, 1H), 7.21-7.20 (m, 1H), 7.10-7.02 (m, 3H), 4.85-4.83 (m, 1H), 3.55-3.53 (m, 2H), 3.35-3.33 (m, 1H), 3.21-3.12 (m, 6H), 3.04-2.99 (m, 6H), 1.19 (bs, 6H)

$^{13}$C NMR (CD$_3$OD) δ 176.4, 166.2, 161.7, 161.2, 158.0, 157.8, 152.8, 151.5, 150.5, 140.2, 139.8, 139.5, 136.8, 135.8, 133.9, 132.6, 132.0, 129.8, 123.8, 113.7, 113.4, 57.8, 44.6, 40.8, 40.4, 38.7, 38.3, 37.7, 37.5, 14.1

MS m/z 639.1 (MH+)

Example 528

Preparation of 2-{2-diethylamino-5-[(benzenesulfonyl)methylamino]pyrimidin-4-ylamino}-3-(4-dimethylcarbamoyloxyphenyl)propionic acid Steps 1, 2, 3, 4, 6 and 7 were performed as for Example 524. Step 5 was performed using benzenesulfonyl chloride in place of 4-fluorobenzenesulfonyl chloride.

$^1$H NMR (CD$_3$OD) δ 8.14 (bs, 1H), (7.85-7.84 (m, 1H), 7.8-7.78 (m, 1H), 7.69-7.66(m, 2H), 7.40-7.37 (m, 1H), 7.21-7.195 (m, 1H), 7.04-7.03 (m, 2H), 7.95-7.90 (m, 1H), 5.52 (bs, 1H), 3.54-3.53 (m, 2H), 3.36-3.33 (m, 6H), 3.13-3.12 (m, 3H), 3.01-3.00 (m, 3H), 1.20-1.17 (m, 6H)

$^{13}$CNMR(CD$_3$OD)δ 165.9, 152.8, 136.7, 135.8, 132.6, 131.6, 130.2, 123.8, 44.7, 37.5, 14.0

MS m/z 571.2 (MH$^+$)

Example 529

Preparation of 2-{2-diethylamino-5-[(2-fluorobenzenesulfonyl)methylamino] pyrimidin-4-ylamino}-3-(4-dimethylcarbamoyloxyphenyl)propionic acid Steps 1, 2, 3, 4, 6 and 7 were performed as for Example 524. Step 5 was performed using 2-fluorobenzenesulfonyl chloride in place of 4-fluorobenzenesulfonyl chloride.

$^1$H NMR (CD$_3$OD) δ 8.31 (bs, 1H), 7.94-7.85 (m, 2H), 7.57-7.44 (m, 3H), 7.34-7.30 (m, 1H), 7.15-7.12 (m, 2H), 5.00-4.85 (m, 1H), 3.63-3.62 (m, 4H), 3.50-3.42 (m, 1H), 3.34-3.30 (m, 4H), 3.29-3.22 (m, 4H), 3.11-3.10 (m, 2H), 1.28 (bs, 6H)

$^{13}$C NMR (CD$_3$OD) δ 176.5, 166.4, 163.1, 160.4, 159.7, 157.7, 152.8, 151.5, 150.7, 138.5, 138.3, 136.7, 133.7, 132.5, 132.2, 127.1, 123.7, 119.9, 119.6, 113.4, 57.8, 44.6, 40.6, 39.0, 38.4, 37.7, 37.5, 14.1

Example 530

Preparation of 2-{2-diethylamino-5-[(3-fluorobenzenesulfonyl) methylamino]pyrimidin-4-ylamino}-3-(4-dimethylcarbamoyloxyphenyl) propionic acid Steps 1, 2, 3, 4, 6 and 7 were performed as for Example 524. Step 5 was performed using 3-fluorobenzenesulfonyl chloride in place of 4-fluorobenzenesulfonyl chloride.

$^1$H NMR (CD$_3$OD) δ 8.15-8.12 (bs, 1H), 7.72-7.68 (m, 1H), 7.63-7.60 (m, 1H), 7.53-7.52 (m, 1H), 7.38-7.35 (m, 1H), 7.21-7.20 (m, 1H), 7.10-6.99 (m, 3H), 4:87-4.86 (m, 1H), 3.54-3.53 (m, 4H), 3.35-3.34 (m, 3H), 3.15-3.12 (m, 4H), 3.05-3.00 (m, 4H), 1.20 (bs, 6H)

$^{13}$CNMR(CD$_3$OD) 8166.1, 153.1, 136.9, 134.1, 132.8, 126.5, 124.1, 123.2, 122.9, 117.7, 117.4, 103.4, 45.0, 38.0, 14.3

MS m/z 589.2 (MH$^+$)

Example 531

Preparation of 2-{2-diethylamino-5-[(4-fluorobenzenesulfonyl) isopropylamino]pyrimidin-4-ylamino}-3-(4-dimethylcarbamoyloxyphenyl) propionic acid Steps 1, 2 and 3 were performed as for Example 524. Thereafter, Steps 4 and 6 were accomplished in one pot, according to the following procedure. Thereafter, Steps 5 and 7 were performed as for Example 524.

$^1$H NMR (CD$_3$OD) δ 8.20-8.16 (m, 1H), 7.95-7.84 (m, 2H), 7.36-7.25 (m, 3H), 7.24-7.15 (m, 3H), 7.07-6.98 (m, 3H), 5.07-5.05 (m, 1H), 4.90-4.86 (m, 1H), 4.65-4.62 (m, 1H), 4.49-4.41 (m, 1H), 3.63-3.56 (m, 3H), 3.38-3.31 (m, 2H), 3.27-3.11 (m, 2H), 3.00-2.99 (m, 3H), 1.27-1.21 (m, 6H), 1.05-0.99 (m, 6H)

$^{13}$C NMR (CD$_3$OD) δ 175.8, 175.5, 169.6, 166.3, 165.9, 163.5, 163.4, 157.7, 153.0, 152.9, 152.3, 138.1, 136.4, 136.1, 133.1, 133.0, 133.0, 132.9, 132.7, 132.3, 123.8, 118.8, 118.7, 118.5, 118.4, 107.5, 57.6, 57.2, 54.7, 44.7, 38.7, 38.1, 37.6, 37.5, 23.0, 22.9, 22.2, 22.0, 14.1, 14.0

Alternative one-pot procedure for the preparation of 2-(2-diethylamino-5-isopropylaminopyrimidin-4-yl)-3-(4-dimethylcarbamoyloxyphenyl) propionic acid t-butyl ester: A mixture of 2-(2-diethylamino-5-nitropyrimidin-4-ylamino)-3-(4-dimethylcarbamoyloxyphenyl)propionic acid t-butyl ester (5.0 g, 0.010 mol), glacial acetic acid (10 drops), acetone (2.19 mL, 0.030 mol), and platinum oxide (0.250 g, 5 wt %) in EtOH (15 mL) was hydrogenated at 45 psi hydrogen until TLC (50% EtOAc/hexanes) showed 100% conversion to product (20 hours). The reaction mixture was then filtered through a Celite plug and concentrated in vacuo to yield a brown residue. The residue was purified by flash chromatography (4:1 EtOAc/hexanes) to yield 3.54 g (70%) 9 as a purple foam.

Example 532

Preparation of 2-{2-diethylamino-5-[(4-fluorobenzenesulfonyl)ethylamino]pyrimidin-4-ylamino}-3-(4-dimethylcarbamoyloxyphenyl)propionic acid Steps 1, 2, 3, 4, 5 and 7 were performed as for Example 524. Step 6 was performed using ethyl iodide in place of dimethyl sulfate.

$^1$H NMR (CDCl$_3$) δ 0.89 (t, J=7.2, 1.8H), 1.06 (t, J=7.1, 1.2H), 1.10-1.30 (m, 6H), 2.97 (s, 3H), 3.05 (s, 3H), 3.10-3.90 (m, 8H), 4.82 (q, J=5.4, 0.6H), 4:91 (q, J=6.1, 0.4H), 6.80-7.45 (m, 8H), 7.77 (m, 2H), 12.44 (bs, 1H)

MS m/z 603.3 (MH$^+$)

Example 533

Preparation of 2-{2-diethylamino-5-[(3,4-difluorobenzenesulfonyl) isopropylamino]pyrimidin-4-ylamino}-3-(4-dimethylcarbamoyloxyphenyl) propionic acid Steps 1, 2, 3, 4, 6 and 7 were performed as for Example 531. Step 5 was performed using 3,4-difluorobenzenesulfonyl chloride in place of 4-fluorobenzenesulfonyl chloride.

$^1$H NMR (CD$_3$OD) δ 8.20-8.19 (m, 1H), 7.84-7.78 (m, 1H), 7.70-7.64 (m, 1H), 7.54-7.48 (m, 1H), 7.39-7.31 (m, 1H), 7.20-7.17 (m, 1H), 7.05-6.96 (m, 2H), 4.91-4.89 (m, 1H), 4.70-4.68 (m, 1H), 4.48-4.41 (m, 2H), 3.60-3.58 (m, 3H), 3.34-3.33 (m, 1H), 3.27-3.20 (m, 1H), 3.09-3.08 (m, 2H), 2.98-2.97 (m, 2H), 1.28-1.19 (m, 6H), 1.06-0.98 (m, 6H), 0.83-0.81 (m, 1H)

$^{13}$C NMR (CD$_3$OD) δ 177.6, 177.2, 167.9, 164.9, 164.8, 159.2, 159.1, 155.7, 154.5, 154.4, 152.4, 152.3, 140.4, 140.3, 137.8, 134.3, 133.9, 129.3, 129.2, 125.4, 122.6, 122.5, 122.4, 122.2, 121.5, 121.2, 109.1, 59.5, 59.1, 56.7, 56.6, 46.4, 46.3, 39.6, 39.3, 39.2, 24.7, 24.5, 23.9, 23.6, 15.7, 15.6

Example 534

Preparation of 2-{2-diethylamino-5-[(4-chlorobenzenesulfonyl) isopropylamino]pyrimidin-4-ylamino}-3-(4-dimethylcarbamoyloxyphenyl) propionic acid Steps 1, 2, 3, 4, 6 and 7 were performed as for Example 531. Step 5 was performed using 4-chlorobenzenesulfonyl chloride in place of 4-fluorobenzenesulfonyl chloride.

$^1$H NMR (CD$_3$OD) δ 8.18-8.17 (m, 1H), 7.85-7.78 (m, 1H), 7.62-7.58 (m, 1H), 7.38-7.35 (m, 1H), 7.34-7.24 (m, 1H), 7.17-7.16 (m, 1H), 7.10-7.05 (m, 2H), 7.04-6.98 (m, 2H), 4.98-4.87 (m, 1H), 4.73-4.68 (m, 1H), 4.55-4.38 (m, 2H), 3.70-3.52 (m, 3H), 3.40-3.30 (m, 1H), 3.28-3.18 (m, 1H), 3.17-3.08 (m, 2H), 3.05-2.98 (m, 2H), 1.25-1.20 (m, 6H), 1.04-0.96 (m, 6H), 0.80-0.77 (m, 1H)

$^{13}$C NMR (CD$_3$OD) δ 175.7, 175.5, 166.2, 165.8, 169.6, 163.5, 163.4, 157.6, 152.9, 152.8, 138.0, 136.3, 136.1, 133.1, 133.0, 132.9, 132.7, 132.2, 123.8, 118.8, 118.6, 118.5, 118.5, 118.3, 107.5, 57.6, 57.2, 54.7, 44.6, 38.6, 38.1, 37.6, 37.5, 22.9, 22.8, 22.2, 21.9, 14.1, 13.9

Example 535

Preparation of 2-{2-diethylamino-5-[(3,4-difluorobenzenesulfonyl) ethylamino]pyrimidin-4-ylamino}-3-(4-dimethylcarbamoyloxyphenyl) propionic acid Steps 1, 2, 3, 4, 6 and 7 were performed as for Example 532. Step 5 was performed using 3,4-difluorobenzenesulfonyl chloride in place of 4-fluorobenzenesulfonyl chloride.

$^1$H NMR (CD$_3$OD) δ 8.15-8.14 (m, 1H), 7.80-7.75 (m, 1H), 7.73-7.62 (m, 1H), 7.60-7.49 (m, 1H), 7.30-7.18 (m, 1H), 7.16-7.00 (m, 2H), 5.58-5.50'(m, 1H), 4.90-4.83 (m, 1H), 5.78-5.70 (m, 1H), 3.85-3.75 (m, 1H), 3.65-3.54 (m, 3H), 3.40-3.23 (m, 5H), 3.18-3.10 (m, 3H), 3.05-2.98 (m, 3H), 1.25-1.15 (m, 3H), 1.18-1.05 (t, 1.5H), 1.02-1.00 (t, 1.5H)

$^{13}$C NMR (CD$_3$OD) δ 165.8, 152.7, 145.7, 136.4, 136.3, 132.5, 132.2, 127.5, 123.6, 120.7, 120.4, 81.4, 57.0, 44.3, 38.5, 38.1, 37.4, 14.9, 14.6, 14.1, 14.0

MS m/z 621.5 (MH$^+$)

Example 536

Preparation of 2-{2-diethylamino-5-[(4-chlorobenzenesulfonyl)ethylamino] pyrimidin-4-ylamino}-3-(4-dimethylcarbamoyloxyphenyl)propionic acid Steps 1, 2, 3, 4, 6 and 7 were performed as for Example 532. Step-5 was performed using 4-chlorobenzenensulfonyl chloride in place of 4-fluorobenzenesulfonyl chloride.

$^1$H NMR (CD$_3$OD) δ 8.15-8.14 (m, 1H), 7.84-7.79 (m, 1H), 7.67-7.61 (m, 1H), 7.37-7.33 (m, 1H), 7.22-7.18 (m, 1H), 7.14-7.13 (m, 1H), 7.06-7.00 (m, 3H), 4.80-4.75 (m, 1H), 4.18-4.10 (m, 1H), 3.65-3.30 (m, 3H), 3.28-3.20 (m, 3H), 3.18-3.08 (m, 2H), 3.03-2.98 (m, 2H), 2.05-2.04 (m, 1H), 1.30-1.16 (m, 9H), 1.10-1.08 (t, 1.5H), 0.99-0.95 (t, 1.5H)

$^{13}$CNMR(CD$_3$OD)δ 176.2, 176.1, 166.7, 162.7, 162.3, 157.6, 152.9, 142.0, 138.8, 136.5, 132.8, 132.5, 132.0, 131.8, 123.8, 111.7, 111.4, 57.9, 57.8, 44.9, 38.9, 38.3, 37.8, 37.7, 15.1, 14.9, 14.3, 14.2

MS m/z 619.4 (MH$^+$)

Example 537

Preparation of 2-{2-diethylamino-5-[(4-fluorobenzenesulfonyl) cylclopropylmethylamino]pyrimidin-4-ylamino}-3-(4-dimethylcarbamoyl-oxyphenyl)propionic acid Steps 1, 2, 3, 4, 5 and 7 were performed as for Example 524. Step 6 was performed using bromomethylcyclopropane and cesium carbonate in place of dimethyl sulfate and potassium carbonate.

$^1$H NMR (CDCl$_3$) δ −0.2-0.2 (m, 2.4H), 0.2-0.45 (m, 1.6H), 0.54 (m, 0.6H), 0.85 (m, 0.4H), 1.00-1.40 (m, 6H), 2.80-3.80 (m, 14H), 4.79 (q, J=5.5, 0.6H), 4.91 (q, J=6.3, 0.4H), 6.70-7.40 (m, 8H), 7.77 (m, 2H), 10.26 (bs, 1H)

MS m/z 629.2 (MH$^+$)

Example 538

Preparation of 2-{2-diethylamino-5-[(3,5-difluorobenzenesulfonyl) methylamino]pyrimidin-4-ylamino}-3-(4-dimethylcarbamoyloxypheyl) propionic acid Steps 1, 2, 3, 4, 6 and 7 were performed as for Example 524. Step 5 was performed using 3,5-difluorobenzenesulfonyl chloride in place of 4-fluorobenzenesulfonyl chloride.

$^1$H NMR (CD$_3$OD) δ 7.68-7.67 (m, 1H), 7.67-7.56 (m, 2H), 7.42-7.40 (m, 2H), 7.31-7.30 (m, 1H), 7.26-7.23 (m, 2H), 5.20-4.90 (m, 1H), 4.35-4.33 (m, 1H), 3.78-3.74 (m, 4H), 3.57-3.54 (2H), 3.38-3.33 (m, 2H), 3.26-3.21 (m, 2H), 2.41-2.39 (m, 2H), 2.26-2.25 (m, 2H), $^{13}$C NMR (CD$_3$OD) δ 162.5, 162.3, 159.2, 159.0, 148.0, 146.1, 132.2, 127.8, 127.7, 127.6, 118.9, 109.1, 109.0, 108.7, 108.6, 106.2, 105.8, 52.5, 39.6, 34.1, 32.9, 9.5

Example 539

Preparation of 2-{2-diethylamino-5-[(3,5-difluorobenzenesulfonyl) ethylamino]pyrimidin-4-ylamino}-3-(4-dimethylcarbamoyloxyphenyl) propionic acid Steps 1, 2, 3, 4, 5 and 7 were performed as-for Example 538. Step 6 was performed using ethyl iodide in place of dimethyl sulfate.

$^1$H NMR (CD$_3$OD) δ 7.45-7.43 (m, 1H), 7.42-7.18 (m, 2H), 7.21-7.16 (m, 2H), 7.07-7.06 (m, 1H), 7.04-6.97 (m, 2H), 5.51 (bs, 1H), 4.86-4.82 (m, 1H), 4.72-4.66 (m, 1H), 3.84-3.77 (m, 1H), 3.59-3.50 (m, 3H), 3.34-3.31 (m, 2H), 3.12-3.10 (m, 3H), 2.99-2.96 (m, 3H), 1.22-1.14 (m, 9H), 1.10-1.05 (t, 1.5H), 0.97-0.95 (t, 1.5H)

¹³C NMR (CD₃OD) δ 159.9, 150.9, 150.1, 134.0, 130.0, 129.7, 121.2, 107.9, 86.7, 42.0, 41.9, 36.3, 35.2, 35.1, 12.8, 12.5, 11.9, 11.8,

Example 540

Preparation of 2-{2-diethylamino-5-[(2,4-difluorobenzenesulfonyl) methylamino]pyrimidin-4-ylamino}-3-(4-dimethylcarbamoyloxyphenyl) propionic acid Steps 1, 2, 3, 4, 6 and 7 were performed as for Example 524. Step 5 was performed using 2,4-difluorobenzenesulfonyl chloride in place of 4-fluorobenzenesulfonyl chloride.

¹H NMR (CD₃OD) δ 8.16-8.11 (m, 1H), 7.59-7.56 (m, 2H), 7.48-7.45 (m, 2H), 7.26-7.24 (m, 3H), 5.21-5.16 (m, 1H), 3.79-3.77 (m, 4H), 3.57-3.54 (m, 3H), 3.48-3.46 (m, 2H), 3.44-3.34 (m, 3H), 3.22-3.21 (m, 3H), 1.45-1.44 (m, 6H)

¹³CNMR(CDCl)δ 180.2, 170.3, 166.6, 150.3, 129.0, 128.9, 128.7, 125.9, 125.4, 117.5, 117.4, 116.5, 114.8, 107.7, 107.4, 95.5, 90.8, 68.0, 65.1, 55.7, 50.8, 37.6, 36.4, 31.9, 31.7, 31.6, 13.2, 9.4, 8.3, 7.8

Example 541

Preparation of 2-{2-diethylamino-5-[(2,4-difluorobenzenesulfonyl) ethylamino] pyrimidin-4-ylamino}-3-(4-dimethylcarbamoyloxyphenyl) propionic acid Steps 1, 2, 3, 4, 5 and 7 were performed as for Example 540. Step 6 was performed using ethyl iodide in place of dimethyl sulfate.

¹H NMR (CD₃OD) δ 8.15 (bs, 1H), 7.91-7.76 (m, 1H), 7.32-7.30 (m, 2H), 7.20-7.19 (m, 2H), 7.04-7.00 (m, 2H), 4.84-4.83 (m, 1H), 4.74-4.67 (m, 1H), 4.14-4.07 (m, 1H), 3.92-3.82 (m, 1H), 3.51-3.49 (m, 3H), 3.34-3.31 (m, 3H), 3.12-2.99 (m, 2H), 2.98-2.97 (m, 2H), 2.03-2.02 (m, 1H), 1.26-1.17 (m, 6H), 1.10-1.06 (t, 1.5H), 1.03-0.98 (t, 1.5H)

¹³C NMR (CD₃OD) δ 173.6, 173.3, 171.4, 167.7, 164.3, 161.2, 159.9, 159.3, 157.1, 156.7, 155.2, 152.4, 151.0, 150.3, 134.0, 133.3, 133.1, 132.9, 130.0, 123.2, 122.9, 122.8, 121.3, 121.2, 112.0, 111.8, 111.6, 111.5, 107.7, 107.2, 106.0, 105.9, 105.6, 105.2, 60.0, 54.8, 42.0, 36.5, 35.9, 35.3, 35.1, 19.3, 13.0, 12.9, 12.7, 11.9, 11.8

Example 542

Preparation of 2-{2-diethylamino-5-[(3,5-dichlorobenzenesulfonyl) methylamino] pyrimidin-4-ylamino}-3-(4-dimethylcarbamoyloxyphenyl) propionic acid Steps 1, 2, 3, 4, 6 and 7 were performed as for Example 524. Step 5 was performed using 3,5-dichlorobenzenesulfonyl chloride in place of 4-fluorobenzenesulfonyl chloride.

¹H NMR (CD₃OD) δ 7.84-7.82 (m, 1H), 7.76-7.75 (m, 3H), 7.34-7.32 (m, 1H), 7.19-7.10 (m, 1H), 7.03-7.00 (m, 2H), 5.50 (bs, 1H), 4.83-4.82 (m, 1H), 4.74-7.73 (m, 1H), 3.55-3.38 (m, 4H), 3.34-3.32 (m, 2H), 3.15-3.11 (m, 4H), 3.02-2.99 (m, 3H), 1.18-1.15 (m, 6H

¹³CNMR(CD₃OD)δ 157.1, 155.2, 150.1, 149.7, 140.1, 135.9, 134.3, 132.9, 130.0, 129.9, 126.0, 121.2, 110.7, 55.2, 54.8, 42.0, 38.5, 38.1, 36.5, 35.9, 35.2, 35.1, 11.9

MS m/z 639.1 (MH⁺)

Example 543

Preparation of 2-{2-diethylamino-5-[(3,5-dichlorobenzenesulfonyl) ethylamino] pyrimidin-4-ylamino}-3-(4-dimethylcarbamoyloxyphenyl) propionic acid Steps 1, 2, 3, 4, 5 and 7 were performed as for Example 542. Step 6 was performed using ethyl iodide in place of dimethyl sulfate.

¹H NMR (CD₃OD) δ 8.15 (bs, 1H), 7.84-7.84-7.79 (m, 1H), 7.76-7.74 (m, 2H), 7.33-7.30 (m, 1H), 7.22-7.11 (m, 2H), 7.04-6.98 (m, 1H), 5.51 (bs, 1H), 4.86-4.82 (m, 1H), 4.72-4.67 (m, 1H), 3.77-3.75 (m, 1H), 3.60-3.50 (m, 3H), 3.34-3.29 (m, 2H), 3.27-3.22 (m, 2H), –3.12-3.11 (m, 2H), 2.99-2.98 (m, 2H), 1.23-1.14 (m, 6H), 1.10-1.05 (t, 1.5H), 0.99-0.94 (t, 1.5H)

¹³C NMR (CD₃OD) δ 173.6, 173.4, 163.7, 159.9, 159.3, 157.3, 156.8, 155.2, 155.1, 152.1, 150.8, 150.2, 141.4, 141.2, 135.9, 134.0, 132.7, 130.0, 129.7, 125.8, 125.7, 121.3, 121.2, 107.9, 107.4, 54.8, 54.7, 42.0, 36.4, 35.8, 35.3, 35.1, 12.8, 12.5, 11.9, 11.8

MS m/z 653.2 (MH+)

Example 544

Preparation of 2-{2-diethylamino-5-[(4-fluorobenzenesulfonyl)-n-propylamino] pyrimidin-4-ylamino}-3-(4-dimethylcarbamoyloxyphenyl) propionic acid Steps 1, 2, 3, 4, 5 and 7 were performed as for Example 524. Step 6 was performed using 1-propyl iodide in place of dimethyl sulfate.

¹H NMR (CDCl₃) δ 0.75 (m, 3H), 1.00-1.50 (m, 8H), 3.00 (s, 3H), 3.08 (s, 3H), 3.20-3.70 (m, 8H), 4.79 (q, J=6.3, 0.6H), 4.91 (q, J=6.6, 0.4H), 5.73 (bs, 0.6H), 5.92 (bs, 0.4H), 6.90-7.45 (m, 7H), 7.76 (m, 2H)

MS m/z 617.2 (MH⁺)

Example 545

Preparation of 2-{2-diethylamino-5-[(4-fluorobenzenesulfonyl)allylamino] pyrimidin-4-ylamino}-3-(4-dimethylcarbamoyloxyphenyl)propionic acid Steps 1, 2, 3, 4, 5 and 7 were performed as for Example 524. Step 6 was performed using allyl bromide in place of dimethyl sulfate.

¹H NMR (CDCl₃) δ 1.20 (m, 6H), 2.98 (s, 3H), 3.06 (s, 3H), 3.10-4.30 (m, 8H), 4.75-4.95 (m, 1H), 5.07 (m, 2H), 5.48 (m, 0.6H), 5.67 (m, 0.4H), 6.90-7.45 (m, 8H), 7.76 (m, 2H), 11.07 (bs, 1H)

MS m/z 615.2 (MH⁺)

Example 546

Preparation of 2-{2-diethylamino-5-[(4-fluorobenzenesulfonyl)isobotylamino] pyrimidin-4-ylamino}-3-(4-dimethylcarbamoyloxyphenyl)propionic acid Steps 1, 2, 3, 4, 5 and 7 were performed as for Example 524. Step 6 was performed using isobutyl iodide in place of dimethyl sulfate.

MS m/z 631.2 (MH$^+$)

Example 547

Preparation of 2-{2-diethylamino-5-[(4-fluorobenzenesulfonyl)-n-butylamino] pyrimidin-4-ylamino}-3-(4-dimethylcarbamoyloxyphenyl)propionic acid Steps 1, 2, 3, 4, 5 and 7 were performed as for Example 524. Step 6 was performed using 1-butyl iodide in place of dimethyl sulfate.

$^1$H NMR (CDCl$_3$) δ 0.82 (q, J=7.1, 3H), 1.05-1.40 (m, 101H), 3.01 (s, 3H), 3.10 (s, 3H), 3.15-3.80 (m, 8H), 4.75 (q, J=6.3, 0.6H), 4.91 (q, J=5.9, 0.4H), 5.79 (d, J=5.4, 0.6H), 5.91 (d, J=6.6, 0.4H), 7.00-7.40 (m, 7H), 7.77 (m, 2H)

Example 548

Preparation of 2-{2-diethylamino-5-[(2,5-difluorobenzenesulfonyl) methylamino] pyrimidin-4-ylamino}-3-(4-dimethylcarbamoyloxyphenyl) propionic acid Steps 1, 2, 3, 4, 6 and 7 were performed as for Example 524. Step 5 was performed using 2,6-difluorobenzenesulfonyl chloride in place of 4-fluorobenzenesulfonyl chloride.

$^1$H NMR (CD$_3$OD) δ 8.38-8.37 (m, 1H), 7.99-7.95 (m, 1H), 7.55-7.54 (m, 2H), 7.50-7.42 (m, 2H), 7.27-7.22 (m, 2H), 5.08-5.06 (m, 1H), 3.76-3.74 (m, 4H), 3.59-3.54 (m, 3H), 3.49-3.42 (m, 4H), 3.36-3.34 (m, 2H), 3.23-3.21 (m, 2H), 1.40 (bs, 6H)

$^{13}$C NMR (CD$_3$OD) δ 161.4, 159.2, 155.8, 153.1, 148.1, 147.1, 133.6, 132.0, 127.8, 119.0, 111.1, 110.8, 110.7, 108.5, 105.8, 94.8, 86.4, 66.7, 54.0, 52.8, 39.7, 35.8, 34.2, 33.7, 32.9, 32.8, 9.4

Example 549

Preparation of 2-{2-diethylamino-5-[(2,3-difluorobenzenesulfonyl) ethylamino]pyrimidin-4-ylamino}-3-(4-dimethylcarbamoyloxyphenyl) propionic acid Steps 1, 2, 3, 4, 6 and 7 were performed as for Example 524. Step 5 was performed using 2,3-difluorobenzenesulfonyl chloride in place of 4-fluorobenzenesulfonyl chloride. 2,3-Difluorobenzenesulfonyl chloride was prepared by the following procedure.

$^1$H NMR (CD$_3$OD) δ 8.32 (bs, 1H), 7.90-7.80 (m, 2H), 7.59-7.48 (m, 3H), 7.27-7.23 (m, 2H), 5.09-5.08 (m, 1H), 3.77-3.70 (m, 4H), 3.60-3.51. (m, 3H), 3.50-3.42 (m, 2H), 3.39-3.31 n (m, 3H), 3.32-3.18 (m, 2H), 1.43-1.41 (m, 6H)

$^{13}$C NMR (CD$_3$OD) δ 170.4, 160.8, 158.1, 156.1, 153.0, 151.6, 150.5, 148.9, 148.2, 147.3, 147.2, 143.9, 143.5, 142.6, 141.1, 140.9, 131.8, 127.7, 125.1, 123.8, 120.8, 120.6, 119.2, 40.5, 35.7, 33.4, 32.9, 32.7, 9.0

Preparation of 2,3-Difluorobenzenesulfonyl Chloride. The following procedure was executed using two flasks. In the first flask, 2,3-difluoroaniline (2.0 g, 0.015 mol) was dissolved in concentrated HCl (15.9 mL), and the resulting solution was cooled to −5° C., using an ice/NaCl bath. A solution of sodium nitrite (1.18 g, 0.017 mol) in distilled water (13.6 mL) was added in portions with stirring, while maintaining the temperature below 0° C., and the mixture was stirred for 10 min. In the second flask, thionyl chloride (5.08 mL, 0.069 mol) was added dropwise to distilled water (30.6 mL), which had been pre-cooled to −5° C., using an ice/NaCl bath. The resulting solution was allowed to warm to room temperature, and then Cu(I)Cl (0.08 g, 0.77 mmol) was added, and then the reaction mixture was re-cooled to −5° C. With continued cooling and stirring, the contents of the first flask were added in 2 mL portions to the contents of the second flask, and the mixture was stirred for 30 min, during which time a precipitate formed. The precipitate was isolated by filtration, rinsed with cold water, and stored under vacuum to give 3.25 g (98%) 10 as a white solid.

Example 550

Preparation of 2-{2-Diethylamino-5-[(4-fluorobenzenesulfonyl) propargylamino]pyrimidin-4-ylamino}-3-(4-dimethylcarbamoyloxyphenyl) propionic acid Steps 1, 2, 3, 4, 5 and 7 were performed as for Example 524. Step 6 was performed using propargyl bromide in place of dimethyl sulfate.

$^1$H NMR (CDCl$_3$) δ 1.15 (m, 6H), 2.27 (d, J=2.1, 1H), 2.97 (s, 3H), 3.06 (s, 3H), 3.10-3.70 (m, 6H), 3.75 (dd, J=17.7, 2.0, 0.6H), 3.95 (dd, J=18.1, 2.0, 0.4H), 4.51 (dd, J=19.5, 2.2, 0.6H), 4.54 (dd, J=18.1, 2.2, 0.4H), 4.79 (q; J=5.9, 0.6H), 4.88 (q, J=6.6, 0.4H), 6.42 (bd, 0.4H), 6.65 (bs, 0.6H), 6.85-7.30 (m, 6H), 7.52 (s, 0.6H), 7.56 (s, 0.4H), 7.85 (m, 2H), 8.20 (bs, 1H)

MS m/z 613.2 (MH$^+$)

Example 551

Preparation of 2-{2-Diethylamino-5-[(2,4-difluorobenzenesulfonyl)propargylamino]pyrimidin-4-ylamino}-3-(4-dimethylcarbamoyloxyphenyl)propionic acid Steps 1, 2, 3, 4, 5 and 7 were performed as for Example 540. Step 6 was performed using propargyl bromide in place of dimethyl sulfate.

$^1$H NMR (CDCl$_3$) δ 1.16 (q, J=7.5, 6H), 2.27 (m, 1H), 2.99 (s, 3H), 3.09 (s, 3H), 3.10-3.70 (m, 6H), 4.04 (dd, J=17.7, 2.4, 0.6H), 4.24 (dd, J=17.9, 2.2, 0.4H), 4.47 (m, 1H), 4.81 (q, J=5.9, 0.6H), 4.89 (q, J=6.3, 0.4H), 6.27 (d, J=7.5, 0.4H), 6.41 (d, J=5.7, 0.6H), 6.90-7.10 (m, 4H), 7.16 (d, J=8.3, 1H), 7.28 (d, J=8.3, 1H), 7.55 (bs, 1H), 7.66 (s, 0.6H), 7.67 (s, 0.4H), 7.81 (m, 1H)

Example 552

Preparation of 2-{2-diethylamino-5-[(4-fluorobenzenesulfonyl)-(2,2,2-trifluoroethyl)amino]pyrimidin-4-ylamino}-3-(4-dimethylcarbamoyl-oxyphenyl)propionic acid Steps 1, 2, 3, 4, 5 and 7 were performed as for Example 524. Step 6 was performed using 2,2,2-trifluoroethyl triflate and cesium carbonate in place of dimethyl sulfate and potassium carbonate.

$^1$H NMR (CDCl$_3$) δ 1.14 (m, 6H—)-2.98 (s, 3H), 3.06 (s, 3H), 3.10-4.20 (m, 8H), 4.80 (q, J=5.9, 0.6H), 4.87 (q, J=6.2, 0.4H), 6.09 (d, J=5.9, 0.4H), 6.18 (bd, 0.6H), 6.80-7.50 (m, 7H), 7.55 (bs, 1H), 7.77 (m, 2H)

MS m/z 657.2 (MH$^+$)

Synthesis of Compounds of PEG Derivatives

The following methods may be used to prepare the compounds of this invention. In one method outlined in Scheme 16 below is illustrative of such preparation.

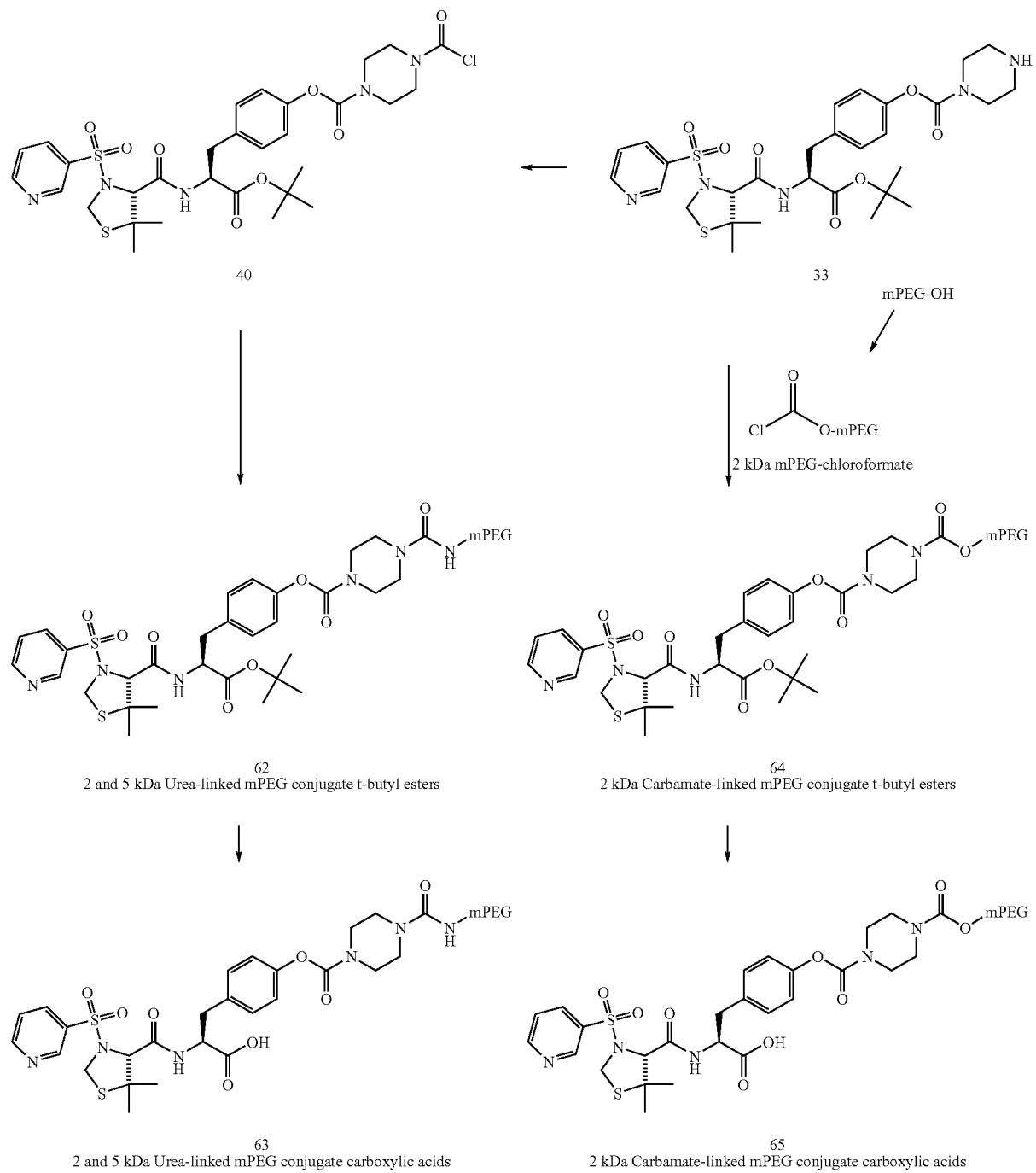

Scheme 16

40

33 mPEG-OH 2 kDa mPEG-chloroformate 62
2 and 5 kDa Urea-linked mPEG conjugate t-butyl esters 64
2 kDa Carbamate-linked mPEG conjugate t-butyl esters 63
2 and 5 kDa Urea-linked mPEG conjugate carboxylic acids 65
2 kDa Carbamate-linked mPEG conjugate carboxylic acids The following Examples describe methods for preparing the compounds shown in 5Scheme 6 and Scheme 16 above. Unless otherwise indicated some or all of the following HPLC methods were used in the preparation of the following exemplary compounds.

Method A1: Samples of conjugates of more than 100 mg were purified using reverse phase HPLC on a Phenomenex Luna C18(2), 5 μm column 250 mm×21.2 mm with a Varian UV detector, using a gradient of 40-60% ACN+0.1% TFA in 100 min at 15 mL/min.

Method B1: Samples of conjugates of more than 100 mg but less than 500 mg were purified using reverse phase HPLC on a Phenomenex Luna C18(2), 10 μm column 250 mm×50 mm with a Varian UV detector using a gradient of 40-60% ACN+0.1%. TFA in 100 min at 60 mL/min.

Method C1: The purity of conjugates was confirmed using reverse phase HPLC on a Luna 3 μm C18(2) column (30×4.6 mm) with a Sedex 75 (35° C., gain=5) evaporative light scattering detector, using a gradient of 20-70% ACN w/0.1% TFA at a flow rate of 1.5 mL/min.

Example 553

Preparation of 2 kDa urea-linked mPEG conjugate carboxylic acid

Step 1: Preparation of compound 29

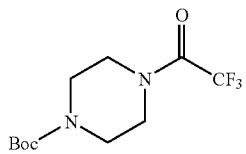

Compound 25 (20 g, 0.11 mol) (as shown in Scheme 6 above) was dissolved in $CH_2Cl_2$ (500 mL) under $N_2$. The reaction mixture was cooled to 0° C. Triethylamine (18.12 mL, 0.13 mol) was added, followed by trifluoroacetic anhydride (18.14 mL, 0.13 mol) in portions. The reaction was allowed to warm to room temperature overnight. The reaction mixture was concentrated in vacuo and the residue was taken up in ethyl acetate (200 mL). The organic phase was washed with $H_2O$, sat. $NaHCO_3$, brine, dried over $Na_2SO_4$, filtered, and concentrated in vacuo to yield 29.73 g (96%) of the title compound, 29, as a yellow solid.

$^1$H NMR (CDCl$_3$) δ 3.64-3.60 (m, 2H), 3.55-3.53 (m, 2H), 3.49-3.45 (m, 4H), 1.44 (s, 9H).

$^{13}$C NMR (CDCl$_3$) δ 155.7 ($J_{C-F}$=36 Hz), 154.3, 116.4 ($J_{C-F}$=288 Hz), 80.8, 45.7, 43.3, 28.3.

Step 2: Preparation of compound 30

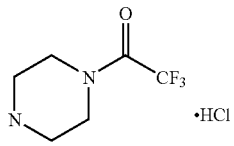

Compound 29 (29.26 g, 0.10 mol) was added in portions to a 500 mL flask containing a solution of 4N HCl in dioxane (200 mL) at 0° C. The reaction was stirred in ice bath for 4 hours when TLC (3:1 hexanes:ethyl acetate) showed 100% conversion to product. The reaction mixture was concentrated in vacuo and treated with ethyl ether (500 mL). The product was filtered and dried to yield 22.53 g (99%) compound 30 as a white mono-hydrochloride salt.

$^1$H NMR (DMSO-d$_6$) δ 3.82-3.79 (m, 4H), 3.53 (s, 1H), 3.18-3.16 (m, 4H).

$^{13}$C NMR (DMSO-d$_6$) δ 154.3 ($J_{C-F}$=35 Hz), 115.9 ($J_{C-F}$=289 Hz), 66.1, 42.0, 41.9, 41.5.

Step 3: Preparation of compound 31

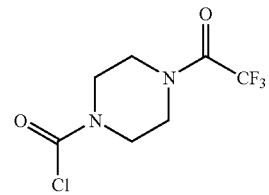

A 250 mL flask was charged with compound 30 (1.0 g, 4.6 mmol), $CH_2Cl_2$ (40 mL), and sat. $NaHCO_3$ (40 mL). The reaction mixture was stirred vigorously at 0° C. for 15 minutes. Stirring was ceased and the layers were allowed to separate. A 2.0 M solution of phosgene in toluene (9 mL, 18 mmol) was added to the reaction mixture which was stirred vigorously for 30 minutes, while maintaining temperature at 0° C. The layers were separated and the aqueous phase was washed with $CH_2Cl_2$ (15 mL). The combined organic layers were washed with brine, dried over $Na_2SO_4$, filtered, and concentrated in vacuo. The residue was taken up in $CH_2Cl_2$ and concentrated in vacuo again to yield 1.04 g (92%) compound 31 as a white solid.

MS(PI-FAB) 245, (M+H)$^+$.

$^1$H NMR (CDCl$_3$) δ 3.80-3.68 (m, 8H).

$^{13}$C NMR (CDCl$_3$) δ 155.9 ($J_{C-F}$=37 Hz), 148.7 ($J_{C-F}$=12 Hz), 116.3 ($J_{C-F}$=289 Hz), 48.3, 47.8, 45.7, 45.3, 45.1, 42.9, 42.7.

Step 4: Preparation of Compound 32

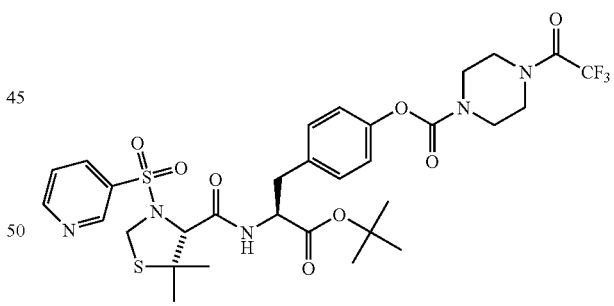

A 25 mL flask was charged with compound 24 (5.97 g, 0.011 mol), DMAP (1.34 g, 0.011 mol), and $CH_2Cl_2$ (22 mL). Triethylamine (2.4 mL, 0.017 mol) was added followed by compound 31 (4.2 g, 0.017 mol). The reaction mixture was heated at reflux for 20 hours. The reaction mixture was concentrated in vacuo and the residue was taken up in ethyl acetate. The organic phase was washed with sat. $NaHCO_3$, $H_2O$, brine, dried over $Na_2SO_4$, filtered, and concentrated in vacuo to yield 9.31 g (115%) pink foam. The crude material was purified by flash chromatography (gradient of 50% ethyl acetate/hexanes to 75% ethyl acetate/hexanes) to yield 6.1 g (76%) compound 32 as a pale pink foam. $R_f$=0.14 (1:1 hexanes:ethyl acetate).

MS(PI-FAB) 730, (M+H)+.

1H NMR (CDCl3) δ 9.08-9.07 (m, 1H), 8.87-8.85 (m, 1H), 8.16-8.14 (m, 1H), 7.52-7.48 (m, 1H), 7.25-7.22 (d, 2H), 7.03-7.00 (d, 2H), 6.91-6.88 (d, 1H), 4.78-4.70 (q, 1H), 4.60-4.44 (dd, 2H), 3.88 (s, 1H), 3.75-3.60 (m, 8H), 3.09-3.06 (m, 2H), 1.42 (s, 9H), 1.18 (s, 3H), 1.16 (s, 3H).

Step 5: Preparation of Compound 33

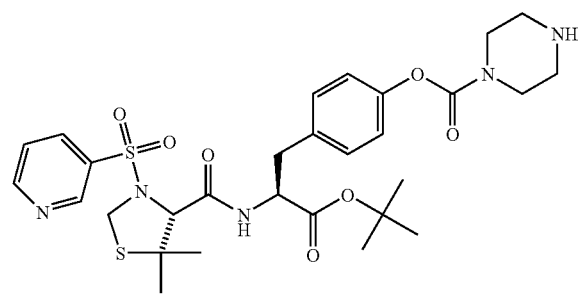

To a solution of compound 32 (6.11 g, 8.4 mmol) dissolved in MeOH (90 mL) was added a solution of potassium carbonate (5.79 g, 42 mmol) in H2O (10 mL). The reaction was stirred at room temperature for 15 minutes and then concentrated in vacuo. The residue was filtered and washed with copious amounts of H2O to yield 4.65 g (88%) compound 33 as a white solid. $R_f$=0.08 (5% MeOH/CH2Cl2).

MS(PI-FAB) 634, (M+H)+.

1H NMR (CDCl3) δ 9.09-9.08 (m, 1H), 8.87-8.85 (m, 1H), 8.16-8.14 (m, 1H), 7.52-7.48 (m, 1H), 7.23-7.20 (d, 2H), 7.03-7.00 (d, 2H), 6.91-6.88 (d, 1H), 4.78-4.70 (q, 1H), 4.59-4.46 (dd, 2H), 3.89 (s, 1H), 3.65-3.50 (m, 4H), 3.09-3.06 (m, 2H), 2.92-2.88 (m, 4H), 1.43 (s, 9H), 1.19 (s, 3H), 1.17 (s, 3H).

13C NMR (CDCl3) δ 170.1, 167.9, 154.5, 153.9, 150.7, 148.8, 136.0, 133.4, 133.2, 130.6, 124.1, 121.9, 83.0, 73.9, 55.0, 53.7, 50.7, 46.0, 45.7, 45.0, 37.9, 29.3, 28.0, 24.0.

Step 6: Preparation of Compound 40

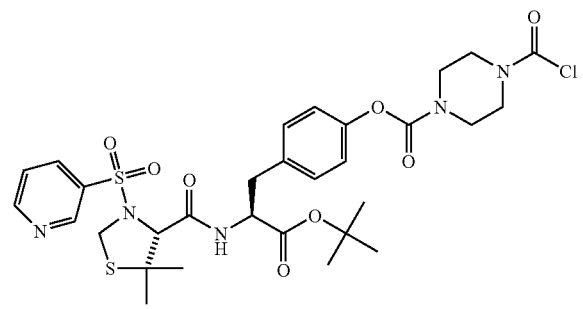

A 250 mL flask was charged with compound 33 (2.5 g, 3.9 mmol), CH2Cl2 (40 mL), and sat. NaHCO3 (40 mL). The reaction mixture was stirred vigorously at 0° C. for 15 minutes. Stirring was ceased and the layers were allowed to separate. A 2.0 M solution of phosgene in toluene (7.9 mL, 16 mmol) was quickly added to the reaction mixture which was stirred vigorously for 60 minutes maintaining the temperature at 0° C. The layers were separated and the aqueous phase was washed with CH2Cl2 (30 mL). The combined organic layers were washed with 0.2 N citric acid, brine, dried over Na2SO4, filtered, and concentrated in vacuo to yield 2.76 g (100%) white foam. The crude material was purified through a silica plug, eluting with 100% ethyl acetate, to yield 2.15 g (78%) compound 40 as a white foam. RF 0.43 (3:1 ethyl acetate: hexanes).

1H NMR (CDCl3) δ 9.09-9.08 (m, 1H), 8.87-8.85 (m, 1H), 8.16-8.14 (d, 1H), 7.52-7.48 (m, 1H), 7.25-7.22 (d, 2H), 7.03-7.01 (d, 2H), 6.90-6.88 (d, 1H), 4.78-4.70 (q, 1H), 4.60-4.45 (dd, 2H), 3.88 (s, 1H), 3.79-3.65 (m, 8H), 3.10-3.07 (m, 2H), 1.43 (s, 9H), 1.18 (s, 3H), 1.17 (s, 3H).

13CNMR(CDCl3)δ 169.9, 167.9, 154.1, 153.6, 150.2, 148.5, 136.1, 133.8, 130.6, 124.2, 121.7, 82.9, 73.7, 54.8, 53.8, 50.6, 48.3, 45.8, 37.7, 29.2, 27.9, 23.9.

Step 7: Preparation 2 kDa Urea-Linked mPEG Conjugate t-butyl ester

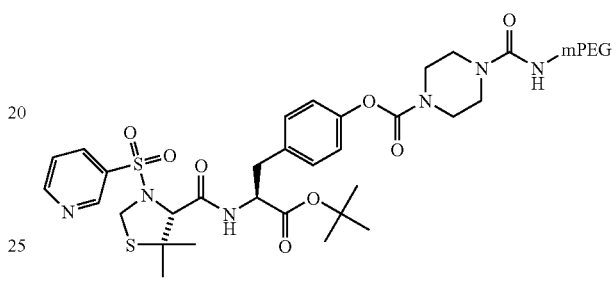

The 2 kilodalton mPEG-amine (192 mg, 0.09 mmol) and DMAP (11 mg, 0.09 mmol) were dissolved in CH2Cl2 (0.6 mL). Triethylamine (19.5 µL, 0.14 mmol) was added, followed by compound 40 (100 mg, 0.14 mmol). The reaction mixture was heated to reflux for 20 hours. The reaction was concentrated in vacuo and the residue was taken up in MeOH (25 mL). 2% cross-linked polystyrene sulfonic acid resin (300 mg) was added and reaction vessel was swirled for 2 hours. The mixture was then filtered and concentrated in vacuo to yield 182 mg (~50%) of a beige solid which was purified by HPLC Method B1 yielding 50.7 mg 2 kDa mPEG conjugate t-butyl ester as a white wax. $R_f$ 0.12 (5% MeOH/CH2Cl2). HPLC Method C1 determined conjugate to be >99% pure with no remaining compound 33 or mPEG-amine (retention time=1.924).

1H NMR (CDCl3) δ 8.21-8.18 (d, 1H), 7.23-7.21 (d, 2H), 7.03-7.00 (d, 2H), 6.91-6.88 (d, 1H), 4.76-4.73 (q, 1H), 4.60-4.46 (dd, 2H), 3.91-3.86 (m, 3H), 3.64 (bs, 184H), 3.37 (s, 3H), 3.09-3.06 (m, 3H), 1.43 (s, 9H), 1.20 (s, 3H), 1.17 (s, 3H).

Step 8: Preparation 2 kDa Urea-Linked mPEG Conjugate carboxylic acid

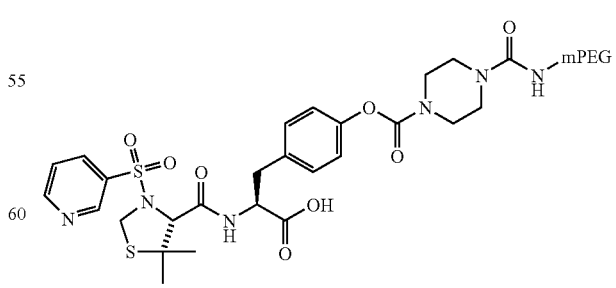

The 2 kDa urea-linked mPEG conjugate t-butyl ester (94 mg, 0.04 mmol) was dissolved in formic acid (5 mL) and heated at 40° C. for 48 hours. The reaction was concentrated in vacuo to yield 88 mg (100%) beige gel, which was purified by HPLC Method A1 to yield 53.7 mg (~60%) of the free carboxylic acid as a white wax. $R_f$ 0.45 (7/3 MeOH:H$_2$O+ 0.1% TFA; C-18 Reverse Phase). HPLC Method C1 determined conjugate to be >99% pure (retention time=2.188)

$^1$H NMR (CDCl$_3$) δ 9.07 (bs, 1H), 8.86-8.85 (m, 1H), 8.23-8.20 (d, 1H), 7.59-7.55 (m, 1H), 7.26-7.21 (d, 2H), 7.02-6.96 (m, 2H), 4.82-4.80 (m, 1H), 4.60-4.49 (dd, 2H), 3.99 (s, 1H), 3.62 (bs, 184H), 3.37 (s, 3H), 3.15-3.13 (m, 2H), 1.25 (s, 3H), 1.23 (s, 3H).

Example 554

Preparation of 5 kDa urea-linked mPEG conjugate carboxylic acid

The 5 kDa urea-linked mPEG conjugate t-butyl ester was prepared in the same manner as the 2 kDa conjugate above, using a 5 kDa mPEG-amine, and yielded 476 mg (~90%) white solid. The crude material (200 mg, 0.04 mmol) was deprotected in the same manner as above yielding 182 mg (100%) beige gum. This was purified by HPLC Method B1, yielding 74.5 mg of the 5 kDa urea-linked mPEG conjugate carboxylic acid as a white powder. RF 0.16 (7/3 MeOH:H$_2$O+ 0.1% TFA; C-18 Reverse Phase). HPLC Method C1 determined conjugate to be >99% pure (retention time=2.260).

$^1$H NMR (CDCl$_3$) δ 9.07 (bs, 1H), 8.86-8.85 (m, 1H), 8.17-8.15 (d, 1H), 7.54-7.50 (m, 1H), 7.26-7.22 (d, 2H), 7.03-7.00 (d, 2H), 6.95-6.93 (d, 1H), 5.46 (bs, 1H), 4.83-4.81 (m, 1H), 4.60-4.46 (dd, 2H), 3.93 (s, 1H), 3.64 (bs, 490H), 3.37 (s, 3H), 3.16 (m, 3H), 1.22 (s, 6H).

Example 555

Preparation of 2 kDa carbamate-linked mPEG conjugate t-butyl ester

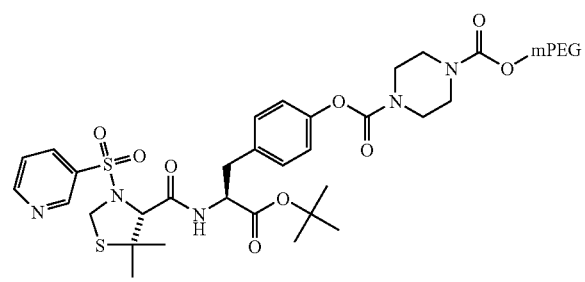

The carbamate linked conjugates were prepared based on a method modified from International Patent Publication Number WO 92/16555. Thus, a 2 kDa mPEG-alcohol (500 mg, 0.25 mmol) was dried by azeotropic distillation in toluene (5 mL). The solution was S5 cooled to room temperature and CH$_2$Cl$_2$ (5 mL) was added, followed by a 2.0 M solution of phosgene in toluene (0.38 mL, 0.75 mmol). The reaction was stirred at room temperature for 18 hours and then concentrated in vacuo to yield 500 mg (100%) of the 2 kDa mPEG chloroformate as a white solid. A solution of compound 33 (317 mg, 0.5 mmol) in CH$_2$Cl$_2$ (3 mL) was added to the 2 k')a mPEG chloroformate (500 mg, 0.25 mmol) dissolved in CH$_2$Cl$_2$ (2 mL). Triethylamine (35 μL, 0.25 mmol) was added and reaction was stirred at room temperature for 30 minutes. The reaction mixture was concentrated in vacuo and the residue was taken up in MeOH (10 mL). 2% cross-linked polystyrene sulfonic acid resin (750 mg) was added and the reaction vessel was swirled for 2 hours. The mixture was then filtered and concentrated in vacuo to yield 470 mg (75%) of the 2kDa carbamate-linked mPEG conjugate t-butyl ester as a white solid. HPLC Method C1 shows >96% pure (retention time=2.639).

Example 556

Preparation of 2 kDa carbamate-linked mPEG conjugate carboxylic acid

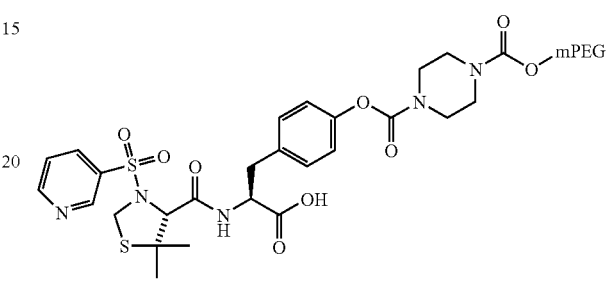

The crude 2 kDa carbamate-linked mPEG conjugate t-butyl ester (250 mg, 0.1 mmol) was dissolved in formic acid (5 mL) and heated at 40° C. for 48 hours. The reaction was concentrated in vacuo to yield 280 mg (100%) of the 2 kDa carbamate-linked mPEG conjugate carboxylic acid as a beige gel.

Biological Examples

Example A

In vitro Assay For Determining Binding of Candidate Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive binding assays). This assay is sensitive to IC$_{50}$ values as low as about 1 nM.

The activity of $\alpha_4\beta_1$ integrin was measured by the interaction of soluble VCAM-1 with Jurkat cells (e.g., American Type Culture Collection Nos. TIB 152, TIB 153, and CRL 8163), a human T-cell line which expresses high levels of $\alpha_4\beta_1$ integrin. VCAM-1 interacts with the cell surface in an $\alpha_4\beta_1$ integrin-dependent fashion (Yednock et al., *J. Bio. Chem.*, 1995, 270:28740).

Recombinant soluble VCAM-1 was expressed as a chimeric fusion protein containing the seven extracellular domains of VCAM-1 on the N-terminus and the human IgG heavy chain constant region on the C-terminus. The VCAM-1 fusion protein was made and purified by the manner described by Yednock, supra. Jurkat cells were grown in RPMI 1640 supplemented with 10% fetal bovine serum, penicillin, streptomycin and glutamine as described by Yednock, supra. Jurkat cells were incubated with 1.5 mM MnCl$_2$ and 5 μg/mL 15/7 antibody for 30 minutes on ice. Mn$^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock et al., supra. Antibodies similar to the 15/7 antibody have been prepared by other investigators (Luque et al., 1996, *J. Bio. Chem.*, 271:11067) and may be used in this assay.

Cells were then incubated for 30 minutes at room temperature with candidate compounds, in various concentrations ranging from 66 μg/mL to 0.01 μg/mL using a standard 5-point serial dilution. 15 μL soluble recombinant VCAM-1 fusion protein was then added to Jurkat cells and incubated for 30 minutes on ice. (Yednock et al., supra.). Cells were then washed two times and resuspended in PE-conjugated goat F(ab')$_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock et al., supra.

Compounds having an IC$_{50}$ of less than about 15 μM possess binding affinity to $\alpha_4\beta_1$.

When tested-in this assay, the compounds. (or the corresponding-carboxylic acids of the ester compounds, i.e., the prodrugs) have an IC$_{50}$ of 15 μM or less.

Example B

Adjuvant-Induced Arthritis in Rats

Adjuvant induced arthritis ("AIA") is an animal model useful in the study of rheumatoid arthritis (RA), which is induced by injecting *M. tuberculosis* in the base of the tail of Lewis rats. Between 10 and 15 days following injection, animals develop a severe, progressive arthritis.

Generally, compounds are tested for their ability to alter hind paw swelling and bone damage resulting from adjuvant-induced edema in rats. To quantitate the inhibition of hind paw swelling resulting from AIA, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, Arth. Rheum., 20, 1135-1141 (1977).

Using an animal model of RA, such as AIA, enables one to study the cellular events involved in the early stages of the disease. CD44 expression on macrophages and lymphocytes is up-regulated during the early development of adjuvant arthritis, whereas LFA-1 expression is up-regulated later in the development of the disease. Understanding the interactions between adhesion molecules and endothelium at the earliest stages of adjuvant arthritis could lead to significant advances in the methods used in the treatment of RA.

Example C

Anti-alpha 4-integrin antibodies for prophylactic, semi-therapeutic and therapeutic treatment A murine collagen-induced arthritis (CIA) model was used to examine the pharmacological effect of anti-alpha4-integrin antibodies prophylactically, semi-therapeutically and therapeutically. Dosing of the antibody was begun on day 20 for the prophylactic animals. Dosing for the semi-therapeutic animals was started when 10% of the mice cohort had a clinical score of 1. Therapeutic dosing started when the mice with CIA had a clinical score of 1. The results seen with the treatment of the CIA mice is seen in FIG. 1. These results indicate that blockade of the alpha 4-integrin ameliorates disease severity and suggest that alpha-4 integrins (VLA-4 and LPAM-1) play an important role in CIA and may constitute a valid target for RA.

Example D

The effect of anti-alpha 4, anti-α4β7 and anti-VCAM-1 antibodies on CIA Animals

Peripheral blood leucocytes (PBLs) from mice treated with anti-alpha4, anti-α4β7 and anti-VCAM 1 antibodies were collected at 4, 12 and 24 hours after antibody dosing. Cells were stained with goat anti-rat antibodies to confirm antibodies in circulation. Anti-α4β7 and anti-VCAM1 antibodies had minimal effect on disease severity in the murine CIA models (FIG. 2). In contrast, mice treated with anti-alpha-4 antibody had reduced severity of disease. These results demonstrated that VLA-4, not LPAM-1 or CAM-1 are involved in cell trafficking in CIA. Individual clinical scores on day 21 are shown in FIG. 3.

Example E

Effect of the compound of Formula P in vivo in CIA Animal Model

The effect of the compound of Formula P was evaluated in a therapeutica CIA model. It was demonstrated to have no effect on disease progression in spite of average blood levels of 1 μg/mL at 16 hours after dosing. 100 DBA/1LacJ male mice, ages 6-8 weeks were obtained from Jackson Laboratories. The mice were immunized at Day 0 as follows: 100 μg bovine type II collagen (Chondrex) in Complete Freund's adjuvant (CFA, Sigma) were injected into the mice. At Day 21, another 100 μg bovine type II collagen (Chondrex) in Incomplete Freund's Adjuvant (IFA, Sigma) was injected into the mice. Treatment with the compound began when the animals had the disease (i.e., 100% therapeutic).

TABLE 12

| Group | n | Substance | Dose |
|---|---|---|---|
| 1 | 15 | Untreated | — |
| 2 | 15 | 151246, 2% Tween/0/5% CMC | 100 mg/kg b.i.d. |
| 3 | 15 | 2% Tween/0.5% CMC | 5 ml/kg b.i.d. |
| 4 | 15 | PS/2 (anti-VLA-4) | 80 μg/100 μL/mouse i.p. every 2 days |
| 5 | 15 | Control, Rag IgG2b | 70 μg/100 L/mouse i.p. every 2 days |

The mice are scored daily after the boost. When a mouse showed symptoms it was assigned to a treatment group (therapeutic protocol). Treatment continued for 3 weeks of dosing. Dosing was every other day for the antibody group and control group. FIG. 4 shows the effect of anti-VLA-4 antibodies and the compound of Formula P on CIA animals.

Example F

The Effect of the Compounds of Formulae W and Y in AIA Rats

It has been shown that anti-alpha 4 integrin antibody treatment significantly reduced clinical and histological scores in an AIA model. The compound of Formula N at 30 mg/kg b.i.d. was shown to ameliorate clinical and histological scores in the AIA animal model. Thus, the compounds of Formulae W and Y were analyzed at 30 mg/kg, 10 mg/kg and 3 mg/kg amounts in CIA. The compound of Formula P was shown to ameliorate disease at all concentrations tested. PK results demonstrate that 12 hours after dosing, the levels of the compound of Formula P were above receptor saturation at all conetrations tested. In contrast, the compound of Formula N dose at 3 mg/kg had no effect on disease severity. Consistent with these results, the compound was present in the blood at 12 hours was below receptor saturation.

The AIA animal models were Lewis rats (weight of 175-200 g) immunized on day 0 by injection in the base of the tail with 0.1 mg *M. tuberculosis* in mineral oil with 12 hour dosing. There were 6 rats per group in the efficacy study. Paw swelling and erythema (indicators of induced condition) were measured daily and Basal paws selected for histological analysis at the end of the study. Plasma was collected at 4 and 12 hours for compound measurement. FIG. 5 shows the results obtained at the different doses for each of the compounds tested.

N nor Y had any impact on disease severity. At 12 hours, animals administered the compound of Formula P had blood levels of the compound that were above receptor saturation at all concentrations tests.

The results in FIG. 6 show the results for compounds. There were 8 rats per group in the efficacy study. Paw swelling and erythema were measured daily and the tarsal paws collected for histological analysis at the end of the study. Plasma which was heparinized was collected at 12 hours (i.e., the trough level) and at 4 horus after the last dose for compound measurement (FIG. 6).

Example H

Prophylactic Treatment of CIA Animals

In order to examine the role of VLA-4 in RA, two models have been evaluated: murine CIA (collagen-induced arthritis) and rat AIA (adjuvant-induced arthritis). Initial studies evaluated the effect of anti-α4-integrin antibodies on disease progression in both models.

TABLE 13

| Group | Group Description | Ab/vehicle | Route | Schedule | Dose | Dose Volume |
|---|---|---|---|---|---|---|
| 1 | Vehicle | Saline, pH 4.1 | s.c. | b.i.d. | n/a | 5 mL/kg |
| 2 | Compound of Formula N | Saline, pH 4.1 | s.c. | b.i.d. | 30 mg/kg | 5 mL/kg |
| 3 | Compound of Formula N | Saline, pH 4.1 | s.c. | b.i.d. | 10 mg/kg | 5 mL/kg |
| 4 | Compound of Formula N | Saline, pH 4.1 | s.c. | b.i.d. | 3 mg/kg | 5 mL/kg |
| 5 | Vehicle 2 | 2% Tween 80 + 0.5% CMC susp. | p.o. | b.i.d. | n/a | 5 mL/kg |
| 6 | Compound of Formula P | 2% Tween 80 + 0.5% CMC susp. | p.o. | b.i.d. | 30 mg/kg | 5 mL/kg |
| 7 | Compound of Formula P | 2% Tween 80 + 0.5% CMC susp. | p.o. | b.i.d. | 10 mg/kg | 5 mL/kg |
| 8 | Compound of Formula P | 2% Tween 80 + 0.5% CMC susp. | p.o. | b.i.d. | 3 mg/kg | 5 mL/kg |

Example G

Evaluation of Compounds in CIA Animal Model

Anti alpha-4 antibodies, and the compounds of Formulae W and Y were tested in the rat CIA model according to the methods shown in Table 14 below.

Prophylactic treatment with anti-α 4-integrin antibodies (PS/2) in the CIA model resulted in a 50% reduction of clinical scores (see FIG. 7 and Table 15 below). The results strongly suggest the VLA-4 pathway may play a role in CIA, but was somewhat offset the SD among mice/group was greater than desired. DBA/1LacJ mice, aged 8 weeks will be

TABLE 14

| Group | Group Description | AB/Vehicle | Route | Schedule | Dose | Dose Volume |
|---|---|---|---|---|---|---|
| 1 | Murine IgG1 | Mu anti-*E. tenella* | i.v. | Days (10-12 and 13-15) | 3 mg/kg | 5 mL/kg |
| 2 | Anti-VLA-4 Ab | GG5/3 | i.v. | Days (10-12 and 13-15) | 3 mg/kg | 5 mL/kg |
| 3 | Vehicle 1 | Saline, pH 4.1 | s.c. | b.i.d. | n/a | 5 mL/kg |
| 4 | Compound of Formula N | Saline, pH 4.1 | s.c. | b.i.d. | 30 mg/kg | 5 mL/kg |
| 5 | Compound of Formula N | Saline, pH 4.1 | s.c. | b.i.d. | 10 mg/kg | 5 mL/kg |
| 6 | Compound of Formula N | Saline, pH 4.1 | s.c. | b.i.d. | 3 mg/kg | 5 mL/kg |
| 7 | Vehicle 2 | 2% Tween 80 + 0.5% CMC susp. | p.o. | b.i.d. | n/a | 5 mL/kg |
| 8 | Compound of Formula P | 2% Tween 80 + 0.5% CMC susp. | p.o. | b.i.d. | 30 mg/kg | 5 mL/kg |
| 9 | Compound of Formula P | 2% Tween 80 + 0.5% CMC susp. | p.o. | b.i.d. | 10 mg/kg | 5 mL/kg |
| 10 | Compound of Formula P | 2% Tween 80 + 0.5% CMC susp. | p.o. | b.i.d. | mg/kg | 5 mL/kg |

Results indicated that anti-alpha-4 antibody treatment ameliorates disease. However, neither the compound of Formula N nor Y had any impact on disease severity. immunized with bovine collagen (100 μg/mice) in CFA and re-challenge on day 21 in IFA.

TABLE 15

| Group | Description | Antibody | Dose | n |
|---|---|---|---|---|
| 1 | Disease control | None | n/a | 10 |
| 2 | Anti-VLA-4 mAb | PS/2 (IgG2b) | 80 µg/mouse, 3X/week | 10 |
| 3 | Rat Ig | Rat anti-human creatinine kinase (IgG1) | 80 µg/mouse, 3X/week | 10 |
| 4 | Vehicle control, PBS | | 100 µL/mouse, 3X/week | 10 |

Antibody treatment started on day 20 and ended on day 42. Clinical evaluation: paw swelling. Where "n" is the number of animals in the group.

Example I

Therapeutic Treatment of AIA Animals with Anti-α4-integrin antibody

Therapeutic treatment with anti-α4-integrin antibody (GG5/3) in the AIA model resulted in significant reduction of joint and histological scores (FIGS. 8 and 9). These results indicate that in this model, blockade of α4-integrin significantly reduces disease severity, synovitis and mankin scores. No isotype antibody control was included in this experiment.

Lewis rats (animal weight is about 175 to about 200 g) were immunized on day 0 by injection in the base of the tail with 0.1 mg *M. tuberculosis* in mineral oil. Injections were performed as follows:

TABLE 16

| Group | Description | Antibody | Dose | N |
|---|---|---|---|---|
| 1 | Disease control | None | N/a | 5 |
| 2 | Anti-VLA-4 mAb | GG5/3 (IgG1), I.V. days 8, 11, 14 and 17 | 3 mg/kg | 5 |

N represents the number of animals in the group.

Clinical evaluation was performed by measuring paw erythema and swelling. Histological evaluation was performed by staining tarsal joints with hematoxylin/eosin and saffranin o-fast green stain.

Example J

Exposure, Potency and Specificity of Compounds in AIA Model

The compound of Tanabe is included as a comparative example and forms a positive control. The compound is depicted by E. Kudlacz et al., *Pharmacol. Exp. Ther.*, 301(2): 747-52 (2002) and below:

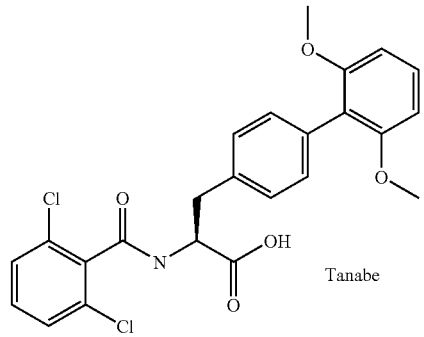

The goal of these studies was to evaluate the efficacy of selected VLA-4 small molecule antagonist in the AIA model. Compounds with different characteristics related to exposure (the compound of Formula M versus the compound of Formula N), potency (for example, the compound of Formula N versus the compound of Formula P) and/or specificity (for example, the compound of Formula N versus the compound of Tanabe) were assessed for their effect on disease.

Results indicate that the compounds of Formulae V and W ameloriate disease at the administered dose.

Lewis rats (animal weight is about 175 to about 200 g) were immunized on day 0 by injection in the base of the tail with 0.1 mg *M. tuberculosis* in mineral oil. Six rats ("n") per group for clinical and histological evaluation; 3 rats per group for clinical evaluation and "tissue distribution" determinations. Plasma collected twelve hr (trough) and four hr after last dosing for PK. Animals were dosed as shown in Table 17 below. The results are displayed in FIG. 10.

TABLE 17

| Group | Description | Ab/vehicle | Route | Schedule | Dose | Dose Voume | Efficacy | Exposure |
|---|---|---|---|---|---|---|---|---|
| 1 | Muring IgG1 | Mu anti-*E. tenella* | i.v. | Days 8, 11, 14 | 3 mg/kg | 5 ml/kg | N = 6 | N/A |
| 2 | Anti-VLA-4 Ab | GG5/3 | i.v. | Days 8, 11, 14 | 3 mg/kg | 5 ml/kg | N = 6 | N/A |
| 3 | Vehicle 1 | Saline, pH 4.1 | s.c. | b.i.d.* | N/A | 5 ml/kg | N = 6 | N/A |
| 4 | Compound of Formula N | Saline, pH 4.1 | s.c. | b.i.d.* | 30 mg/kg | 5 mg/kg | N = 6 | N = 3 |
| 5 | Vehicle 2 | 10% EtOH:90% corn oil | s.c. | b.i.d.* | N/A | 5 mg/kg | N = 6 | N = 3 |
| 6 | Compound of Formula N | 10% EtOH:90% corn oil | s.c. | b.i.d.* | 100 mg/kg | 5 mg/kg | N = 6 | N = 3 |

Example K

Potency and Specificity of Compounds in the AIA Model

The results indicate that all compounds tested ameloriate disease scores. The results are displayed in FIG. 11. The compounds of Formulae W and Y affected disease equally well in spite of their different potencies. Compounds with preferential selectivity for α4 μl ameloriate disease better than those with equal selectivity for α4β1 and α4β7.

Lewis rats (animal weight was about 175 to about 200 g) were immunized on day 0 by injection in the base of the tail with 0.1 mg *M. tuberculosis* in mineral oil. Six rats per group were evaluated for clinical and histological scores. Plasma was collected four hours after last dosing for PK.

TABLE 18

| Group | Description | Ab/vehicle | Route | Schedule | Dose | Dose volume | Efficacy |
|---|---|---|---|---|---|---|---|
| 1 | Vehicle | Saline, pH 4.1 | s.c. | b.i.d. | n/a | 5 mg/kg | N = 6 |
| 2 | Compound of Formula N | Saline, pH 4.1 | s.c. | b.i.d. | 30 mg/kg | 5 mg/kg | N = 6 |
| 3 | Vehicle 2 | 20% Tween 80 + 0.5% CMC susp. | p.o. | b.i.d. | n/a | 5 mg/kg | N = 6 |
| 4 | Compound of Formula P | 20% Tween 80 + 0.5% CMC susp. | p.o. | b.i.d. | 30 mg/kg | 5 mg/kg | N = 6 |
| 5 | Vehicle 3 | NaOH/dH$_2$O | p.o. | b.i.d. | n/a | 5 mg/kg | N = 6 |
| 6 | Compound of Formula O | NaOH/dH$_2$O | p.o. | b.i.d. | 100 mg/kg | 5 mg/kg | N = 6 |
| 7 | Compound of Tanabe | NaOH/dH$_2$O | s.c. | b.i.d. | 30 mg/kg | 5 mg/kg | N = 6 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the invention.

All references cited herein are herein incorporated by reference in their entirety for all purposes.

---

We claim:

1. A method for treating rheumatoid arthritis in a mammal in need thereof comprising administering in therapeutically effective amounts a combination therapy comprising methotrexate and a compound of Formula X below:

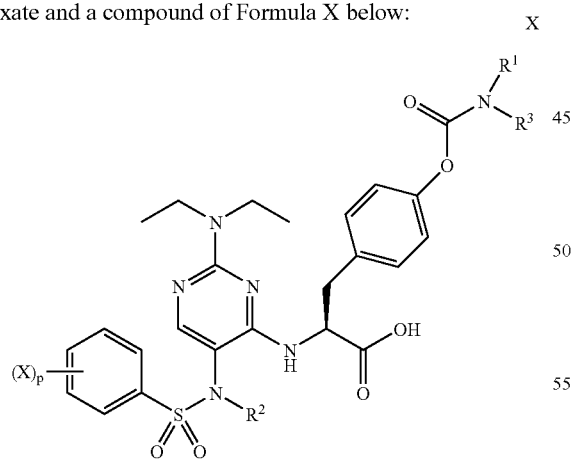

X wherein each X is independently fluoro, chloro or bromo;
p is an integer from 0 to 3;
$R^1$ and $R^3$ together with the nitrogen atom to which they are bound form an azetidinyl, pyrrolidinyl, pyrrolyl, 2,5-dihydopyrrol-1-yl, piperidinyl, or 1,2,3,6-tetrahydropyridin-1-yl;
$R^2$ is selected from the group consisting of lower alkyl, lower alkenyl, and lower alkylenecycloalkyl;
and pharmaceutically acceptable salts thereof.

2. A method for treating rheumatoid arthritis in a mammal in need thereof comprising administering in therapeutically effective amounts a combination therapy comprising methotrexate and a compound of Formula XI below:

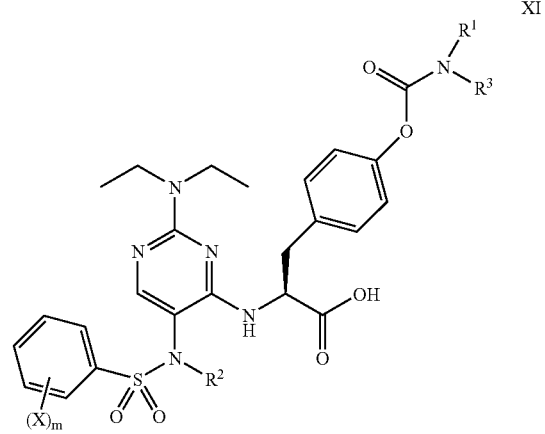

XI wherein each X is independently selected from the group consisting of fluoro and chloro;
m is an integer equal to 1 or 2;
$R^2$ is selected from the group consisting of lower alkyl, lower alkenyl, and lower alkylenecycloalkyl;
$R^1$ and $R^3$ together with the nitrogen atom to which they are bound form an azetidinyl, pyrrolidinyl, or piperidinyl group;
and pharmaceutically acceptable salts thereof.

3. A method for treating rheumatoid arthritis in a mammal in need thereof comprising administering in therapeutically effective amounts a combination therapy comprising methotrexate and a compound of Formula XII below:

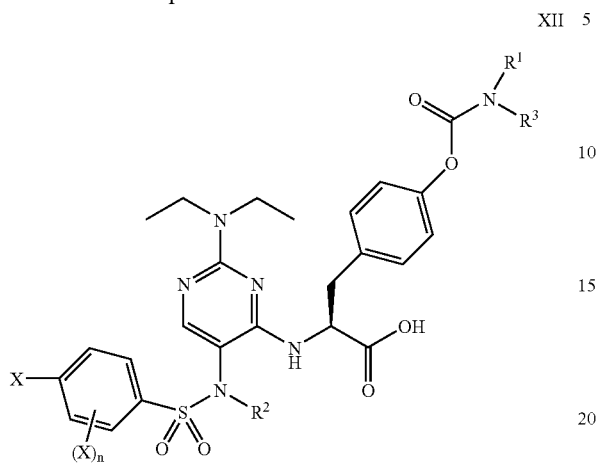

XII wherein each X is independently fluoro or chloro;

n is zero or one;

R² is —CH₂—R' where R' is selected from the group consisting of hydrogen, methyl or —CH=CH₂;

R¹ and R³ together with the nitrogen atom to which they are bound form an azetidinyl, pyrrolidinyl, or piperidinyl group;

and pharmaceutically acceptable salts thereof.

4. The method according to claim 3, wherein the compound of Formula XII is the compound of Formula P below:

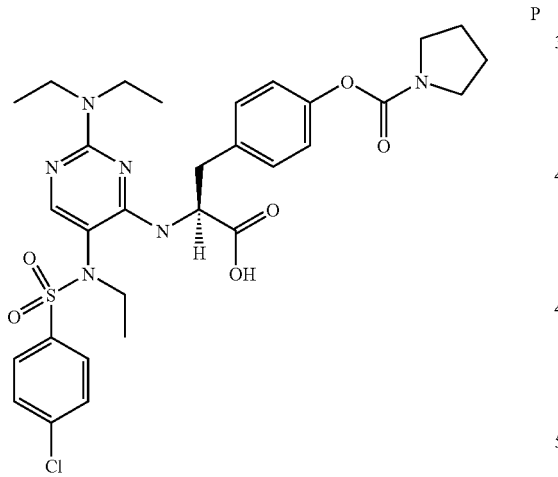

P

5. The method according to claim 1, wherein R¹ and R³ together with the nitrogen atom to which they are bound form an azetidinyl, pyrrolidinyl, or piperidinyl group.

6. The method according to any one of claims 1, 2, or 3, wherein R² is CH₃.

7. The method according to claim 3, wherein X is F or Cl and n is 0.

8. The method according to claim 1, wherein the compound of Formula X is selected from the group consisting of:

N-(2-[N',N'-diethylamino]-5-[N''-(4-chlorophenylsulfonyl)-N''-ethylamino]pyrimidin-4-yl)-4'-(pyrrolidin-1-ylcarbonyloxy)-L-phenylalanine;

N-(2-[N',N'-diethylamino]-5-[N''-(4-fluorophenylsulfonyl)-N''-ethylamino]pyrimidin-4-yl)-4'-(pyrrolidin-1-ylcarbonyloxy)-L-phenylalanine ELN;

N-(2-[N',N'-diethylamino]-5-[N''-(4-fluorophenylsulfonyl)-N''-methylamino]pyrimidin-4-yl)-4'-(pyrrolidin-1-ylcarbonyloxy)-L-phenylalanine;

N-(2-[N',N'-diethylamino]-5-[N''-(4-chlorophenylsulfonyl)-N''-methylamino]pyrimidin-4-yl)-4'-(pyrrolidin-1-ylcarbonyloxy)-L-phenylalanine;

N-(2-[N',N'-diethylamino]-5-[N''-(4-fluorophenylsulfonyl)-N''-methylamino]pyrimidin-4-yl)-4'-(piperidin-1-ylcarbonyloxy)-L-phenylalanine;

N-(2-[N',N'-diethylamino]-5-[N''(4-fluorophenylsulfonyl)-N''-ethylamino]pyrimidin-4-yl)-4'-(piperidin-1-ylcarbonyloxy)-L-phenylalanine;

N-(2-[N',N'-diethylamino]-5-[N''-(4-fluorophenylsulfonyl)-N''-ethylamino]pyrimidin-4-yl)-4'-(azetidin-1-ylcarbonyloxy)-L-phenylalanine;

N-(2-[N',N'-diethylamino]-5-[N''-(4-fluorophenylsulfonyl)-N''-methylamino]pyrimidin-4-yl)-4'-(azetidin-1-ylcarbonyloxy)-L-phenylalanine;

N-(2-[N',N'-diethylamino]-5-[N''-(4-chlorophenylsulfonyl)-N''-methylamino]pyrimidin-4-yl)-4'-(azetidin-1-ylcarbonyloxy)-L-phenylalanine;

N-(2-[N',N'-diethylamino]-5-[N''-(4-chlorophenylsulfonyl)-N''-ethylamino]pyrimidin-4-yl)-4'-(azetidin-1-ylcarbonyloxy)-L-phenylalanine;

N-(2-[N',N'-diethylamino]-5-[N''-(2,4-difluorophenylsulfonyl)-N''-methylamino]pyrimidin-4-yl)-4'-(pyrrolidin-1-ylcarbonyloxy)-L-phenylalanine;

N-(2-[N',N'-diethylamino]-5-[N''-(2,4-difluorophenylsulfonyl)-N''-ethylamino]pyrimidin-4-yl)-4'-(pyrrolidin-1-ylcarbonyloxy)-L-phenylalanine;

N-(2-[N',N'-diethylamino]-5-[N''-(2,4-difluorophenylsulfonyl)-N''-methylamino]pyrimidin-4-yl)-4'-(azetidin-1-ylcarbonyloxy)-L-phenylalanine;

N-(2-[N',N'-diethylamino]-5-[N''-(2,4-difluorophenylsulfonyl)-N''-ethylamino]pyrimidin-4-yl)-4'-(azetidin-1-ylcarbonyloxy)-L-phenylalanine; and pharmaceutically acceptable salts thereof.

9. A method for treating rheumatoid arthritis in a mammal in need thereof comprising administering in therapeutically effective amounts a combination therapy comprising methotrexate and a compound of Formula XIII below:

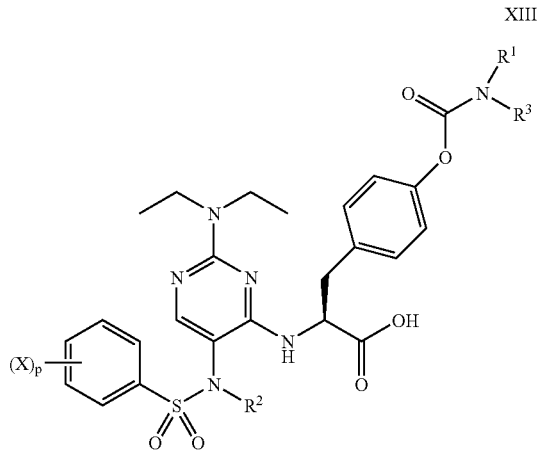

XIII wherein each X is independently fluoro, chloro or bromo;

p is an integer from 0 to 3;

R¹ and R³ together with the nitrogen atom to which they are bound form an azetidinyl, pyrrolidinyl, pyrrolyl, 2,5-dihydopyrrol-1-yl, piperidinyl, or 1,2,3,6-tetrahydropyridin-1-yl;

R² is lower alkynyl;

and pharmaceutically acceptable salts thereof.

10. A method for treating rheumatoid arthritis in a mammal in need thereof comprising administering in therapeutically effective amounts a combination therapy comprising methotrexate and a compound of Formula XIV below:

XIV

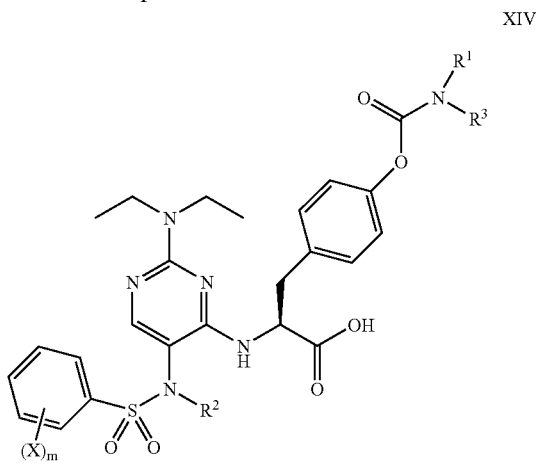

wherein each X is independently selected from the group consisting of fluoro and chloro;
m is an integer equal to 1 or 2;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

11. A method for treating rheumatoid arthritis in a mammal in need thereof comprising administering in therapeutically effective amounts a combination therapy comprising methotrexate and a compound of Formula XV below:

XV

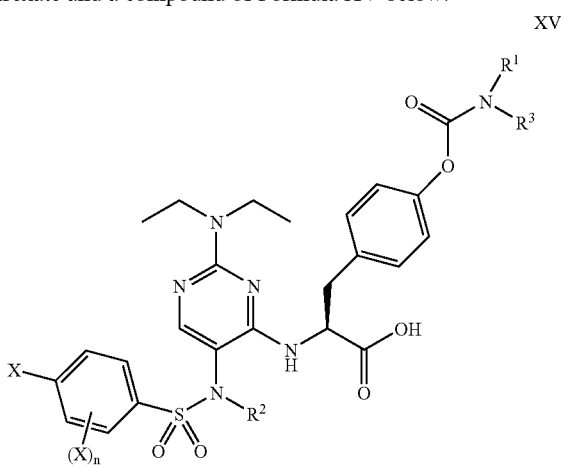

wherein each X is independently fluoro or chloro;
n is zero or one;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

12. The method according to claim 9, wherein $R^1$ and $R^3$ together with the nitrogen atom to which they are bound form an azetidinyl, pyrrolidinyl, or piperidinyl group.

13. The method according to any one of claims 9, 10, or 11, wherein $R^2$ is propargyl.

14. The method according to claim 12, wherein X is F or Cl and n is 0.

15. The method according to claim 12, wherein the compound of Formula XIII is the compound of Formula Q below:

Q

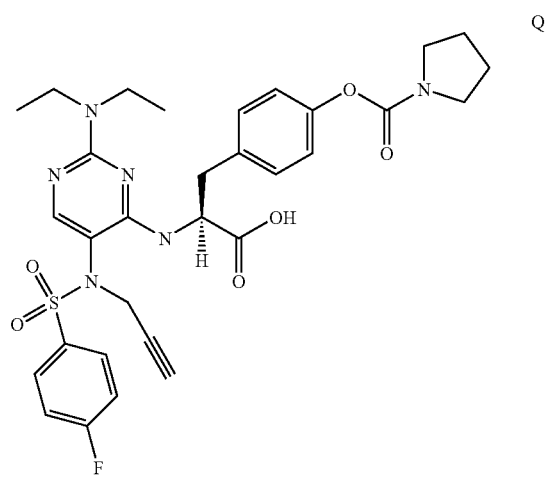

16. The method according to claim 9, wherein the compound of Formula XIII is selected from the group consisting of:
N-(2-[N',N'-diethylamino]-5-[N"-(4-fluorophenylsulfonyl)-N"-propargylamino]pyrimidin-4-yl)-4'-(pyrrolidin-1-ylcarbonyloxy)-L-phenylalanine;
N-(2-[N',N'-diethylamino]-5-[N"-(2,4-difluorophenylsulfonyl)-N"-propargylamino]pyrimidin-4-yl)-4'-(pyrrolidin-1-ylcarbonyloxy)-L-phenylalanine;
N-(2-[N',N'-diethylamino]-5-[N"-(2,4-difluorophenylsulfonyl)-N"-propargylamino]pyrimidin-4-yl)-4'-(azetidin-1-ylcarbonyloxy)-L-phenylalanine;
N-(2-[N',N'-diethylamino]-5-[N"-(4-fluorophenylsulfonyl)-N"-propargylamino]pyrimidin-4-yl)-4'-(azetidin-1-ylcarbonyloxy)-L-phenylalanine;
N-(2-[N',N'-diethylamino]-5-[N"-(4-chlorophenylsulfonyl)-N"-propargylamino]pyrimidin-4-yl)-4'-(pyrrolidin-1-ylcarbonyloxy)-L-phenylalanine; and
pharmaceutically acceptable salts thereof.

17. A regimen for the treatment of rheumatoid arthritis which comprises administering to a subject in need thereof about 2 mg to about 20 mg of methotrexate and about 0.01 mg/kg of body weight to about 100 mg/kg of body weight of a compound of formula X, wherein the amount of methotrexate administered per week does not exceed 20 mg, wherein the compound of formula X is as below:

X

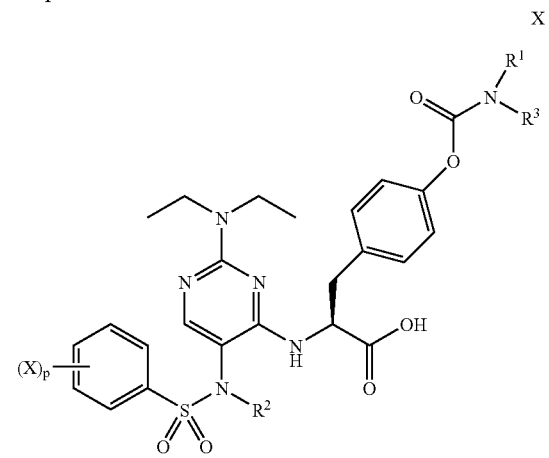

wherein each X is independently fluoro, chloro or bromo;
p is an integer from 0 to 3;
$R^1$ and $R^3$ together with the nitrogen atom to which they are bound form an azetidinyl, pyrrolidinyl, pyrrolyl, 2,5-dihydopyrrol-1-yl, piperidinyl, or 1,2,3,6-tetrahydropyridin-1-yl;

R² is selected from the group consisting of lower alkyl lower alkenyl, and lower alkylenecycloalkyl;
and pharmaceutically acceptable salts thereof.

18. A regimen for the treatment of rheumatoid arthritis which comprises administering to a subject in need thereof about 2 mg to about 20 mg of methotrexate and about 0.01 mg/kg of body weight to about 100 mg/kg of body weight of a compound of formula XIII, wherein the amount of methotrexate administered per week does not exceed 20 mg, wherein the compound of formula XIII is as below:

XIII

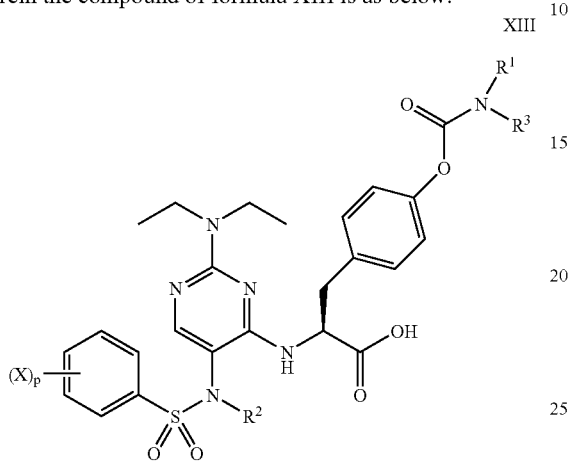

wherein each X is independently fluoro, chloro or bromo;
p is an integer from 0 to 3;
R¹ and R³ together with the nitrogen atom to which they are bound form an azetidinyl, pyrrolidinyl, pyrrolyl, 2,5-dihydopyrrol-1-yl, piperidinyl, or 1,2,3,6-tetrahydropyridin-1-yl;
R² is lower alkynyl;
and pharmaceutically acceptable salts thereof.

19. A regimen for the treatment of rheumatoid arthritis which comprises administering to a subject in need thereof about 2 mg to about 20 mg of methotrexate and about 0.01 mg/kg of body weight to about 100 mg/kg of body weight of a compound of formula XIV, wherein the amount of methotrexate administered per week does not exceed 20 mg, wherein the compound of formula XIV is as below:

XIV

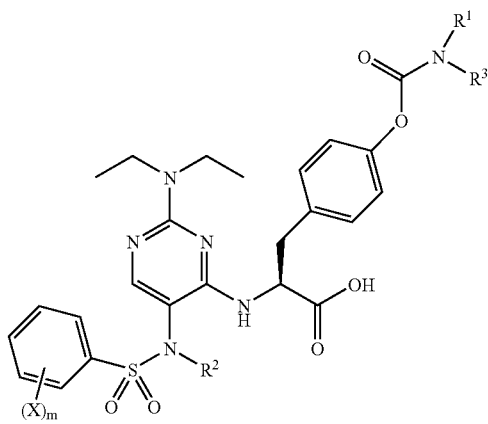

wherein each X is independently selected from the group consisting of fluoro and chloro;
m is an integer equal to 1 or 2;
R² is lower alkynyl;
R¹ and R³ together with the nitrogen atom to which they are bound form an azetidinyl, pyrrolidinyl, or piperidinyl group;
and pharmaceutically acceptable salts thereof.

* * * * *

UNITED STATES PATENT AND TRADEMARK OFFICE
CERTIFICATE OF CORRECTION

PATENT NO. : 7,605,166 B2  Page 1 of 1
APPLICATION NO. : 10/875282
DATED : October 20, 2009
INVENTOR(S) : Yednock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 830 days.

Signed and Sealed this

Fifth Day of October, 2010

David J. Kappos
*Director of the United States Patent and Trademark Office*